United States Patent
Chen et al.

(10) Patent No.: US 9,556,177 B2
(45) Date of Patent: Jan. 31, 2017

(54) SUBSTITUTED 1,3-THIAZOLES AS SYNTHETIC INTERMEDIATES FOR PREPARATION OF RAF KINASE INHIBITORS

(71) Applicants: Millennium Pharmaceuticals, Inc., Cambridge, MA (US); Sunesis Pharmaceuticals, Inc., South San Francisco, CA (US)

(72) Inventors: Weirong Chen, Waltham, MA (US); Benjamin Lane, Chelsea, MA (US); Hairuo Peng, Needham, MA (US)

(73) Assignees: Millennium Pharmaceuticals, Inc., Cambridge, MA (US); Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/444,007

(22) Filed: Jul. 28, 2014

(65) Prior Publication Data
US 2015/0080568 A1    Mar. 19, 2015

Related U.S. Application Data

(60) Division of application No. 13/657,506, filed on Oct. 22, 2012, now Pat. No. 8,802,657, which is a continuation of application No. 12/164,762, filed on Jun. 30, 2008, now Pat. No. 8,293,752.

(60) Provisional application No. 60/947,291, filed on Jun. 29, 2007.

(51) Int. Cl.
| | |
|---|---|
| C07D 277/20 | (2006.01) |
| C07D 213/61 | (2006.01) |
| C07D 487/04 | (2006.01) |
| C07D 401/12 | (2006.01) |
| C07D 401/14 | (2006.01) |
| C07D 403/12 | (2006.01) |
| C07D 413/14 | (2006.01) |
| C07D 417/12 | (2006.01) |
| C07D 417/14 | (2006.01) |
| C07D 471/04 | (2006.01) |
| C07D 473/00 | (2006.01) |

(52) U.S. Cl.
CPC ........... *C07D 487/04* (2013.01); *C07D 401/12* (2013.01); *C07D 401/14* (2013.01); *C07D 403/12* (2013.01); *C07D 413/14* (2013.01); *C07D 417/12* (2013.01); *C07D 417/14* (2013.01); *C07D 471/04* (2013.01); *C07D 473/00* (2013.01)

(58) Field of Classification Search
CPC ............................ C07D 213/61; C07D 277/20
USPC ........................................ 546/345; 548/202
See application file for complete search history.

(56) References Cited

U.S. PATENT DOCUMENTS

| | | | |
|---|---|---|---|
| 5,563,158 | A | 10/1996 | DeGrado et al. |
| 5,691,329 | A | 11/1997 | DeGrado et al. |
| 5,760,028 | A | 6/1998 | Jadhav et al. |
| 5,840,917 | A | 11/1998 | Oi et al. |
| 5,872,136 | A | 2/1999 | Anthony et al. |
| 5,877,182 | A | 3/1999 | Nargund et al. |
| 6,017,925 | A | 1/2000 | Duggan |
| 6,127,382 | A | 10/2000 | Beard et al. |
| 6,214,834 | B1 | 4/2001 | Jadhav et al. |
| 6,242,470 | B1 | 6/2001 | Baxter et al. |
| 6,284,757 | B1 | 9/2001 | Sanner |
| 6,288,078 | B1 | 9/2001 | Walsh et al. |
| 6,369,227 | B1 | 4/2002 | Lam et al. |
| 6,403,583 | B1 | 6/2002 | Lam et al. |
| 6,500,855 | B1 | 12/2002 | Lam et al. |
| 6,602,871 | B2 | 8/2003 | Lam et al. |
| 6,632,823 | B1 | 10/2003 | Vernier et al. |
| 8,293,752 | B2 | 10/2012 | Chen et al. |
| 8,802,657 | B2 | 8/2014 | Cossrow et al. |
| 2003/0119811 | A1 | 6/2003 | Liverton et al. |
| 2004/0014765 | A1 | 1/2004 | Boyle et al. |
| 2004/0048866 | A1 | 3/2004 | Kolasa et al. |
| 2004/0082627 | A1 | 4/2004 | Darrow et al. |
| 2004/0097531 | A1 | 5/2004 | Ledeboer et al. |
| 2004/0106631 | A1 | 6/2004 | Bernardelli et al. |
| 2005/0070538 | A1 | 3/2005 | Cheng et al. |
| 2005/0171105 | A1 | 8/2005 | Chopiuk et al. |
| 2005/0209249 | A1 | 9/2005 | Akritopoulou-Zanze et al. |
| 2006/0183747 | A1 | 8/2006 | Freyne et al. |

(Continued)

FOREIGN PATENT DOCUMENTS

| | | |
|---|---|---|
| CA | 02367051 A1 | 10/2000 |
| CA | 02471566 A1 | 7/2003 |
| CA | 02504153 A1 | 5/2004 |
| DE | 10328999 A1 | 1/2005 |
| EP | 0847992 A1 | 6/1998 |
| EP | 1547585 A1 | 6/2005 |
| EP | 1820795 A1 | 8/2007 |

(Continued)

OTHER PUBLICATIONS

U.S. Appl. No. 13/108,670, Crossrow et al.
(Continued)

*Primary Examiner* — Douglas M Willis
(74) *Attorney, Agent, or Firm* — Sterne, Kessler, Goldstein & Fox P.L.L.C.

(57) ABSTRACT

The present disclosure provides compounds having Formula II-vi-a:

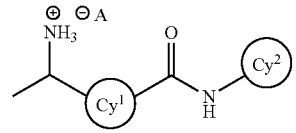

II-vi-a wherein $Cy^1$, $Cy^2$, and $A^-$ are defined as set forth in the specification. These compounds are synthetic intermediates used to prepare inhibitors of Raf protein kinase.

18 Claims, No Drawings

(56) References Cited

U.S. PATENT DOCUMENTS

| | | |
|---|---|---|
| 2006/0205721 A1 | 9/2006 | Edgard Freyne et al. |
| 2007/0015207 A1 | 1/2007 | Ludovici et al. |
| 2007/0197553 A1 | 8/2007 | Jaeschke et al. |
| 2007/0259849 A1 | 11/2007 | Aquila et al. |
| 2009/0005359 A1 | 1/2009 | Cossrow et al. |
| 2009/0036419 A1 | 2/2009 | Chen et al. |
| 2013/0065858 A1 | 3/2013 | Chen et al. |

FOREIGN PATENT DOCUMENTS

| | | |
|---|---|---|
| GB | 2361474 A | 10/2001 |
| JP | H11209366 A | 8/1999 |
| JP | 2004161716 A | 6/2004 |
| JP | 2004339159 A | 12/2004 |
| WO | WO-97/23480 A1 | 7/1997 |
| WO | WO-97/36901 A1 | 10/1997 |
| WO | WO-97/44337 A1 | 11/1997 |
| WO | WO-98/22460 A1 | 5/1998 |
| WO | WO-98/42323 A1 | 10/1998 |
| WO | WO-00/53602 A1 | 9/2000 |
| WO | WO-00/58300 A1 | 10/2000 |
| WO | WO-01/38309 A1 | 5/2001 |
| WO | WO-01/98294 A2 | 12/2001 |
| WO | WO-02/080928 A1 | 10/2002 |
| WO | WO-2005/066156 A1 | 7/2005 |
| WO | WO-2005/072733 A1 | 8/2005 |
| WO | WO-2005/082367 A1 | 9/2005 |
| WO | WO-2006/003378 A1 | 1/2006 |
| WO | WO-2006/040568 A1 | 4/2006 |
| WO | WO-2006/045010 A2 | 4/2006 |
| WO | WO-2006/065703 A1 | 6/2006 |
| WO | WO-2006/074057 A2 | 7/2006 |
| WO | WO-2006/120573 A2 | 11/2006 |
| WO | WO-2007/070398 A1 | 6/2007 |
| WO | WO-2007/079199 A2 | 7/2007 |
| WO | WO-2007/087429 A2 | 8/2007 |
| WO | WO-2007/087443 A2 | 8/2007 |
| WO | WO-2007/093542 A1 | 8/2007 |
| WO | WO-2008/063504 A2 | 5/2008 |
| WO | WO-2008/156869 A2 | 12/2008 |
| WO | WO-2010/078408 A1 | 7/2010 |

OTHER PUBLICATIONS

Frimurer, T.M. et al., A physicogenetic method assign ligand-binding relationships between 7TM receptors, Bioorganic and Medicinal Chemistry, 15:3707-3712 (2005).

International Search Report for PCT/US2008/068762, 2 pages (Feb. 5, 2009).

Plouvier, B. et al., Synthesis of two new thiazole-containing oligopeptides as potential DNA minor groove binding analogs of netropsin, Heterocycles, 32(4):693-701 (1991).

Smith, R.A. et al., Recent Advances in the Research and Development of RAF Kinase Inhibitors, Current Topics in Medicinal Chemistry, 6(11):1071-1089 (2006).

SUBSTITUTED 1,3-THIAZOLES AS SYNTHETIC INTERMEDIATES FOR PREPARATION OF RAF KINASE INHIBITORS

CROSS-REFERENCE TO RELATED APPLICATIONS

The present invention is a divisional application claiming priority to U.S. patent application Ser. No. 13/657,506, filed Oct. 22, 2012, which is a continuation of U.S. patent application Ser. No. 12/164,762, filed Jun. 30, 2008, now U.S. Pat. No. 8,293,752, which claims priority to U.S. provisional patent application Ser. No. 60/947,291, filed Jun. 29, 2007, the entirety of each of which is hereby incorporated herein by reference.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

Cancer results from the deregulation of the normal processes that control cell division, differentiation and apoptotic cell death. Protein kinases play a critical role in this regulatory process. A partial non-limiting list of such kinases includes ab1, ATK, bcr-ab1, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK4, flt-1, Fps, Frk, Fyn, Hck, IGF-1R, INS-R, Jak, KDR, Lck, Lyn, MEK, p38, PDGFR, PIK, PKC, PYK2, ros, tie$_2$, tie$_2$, TRK, Yes and Zap70. In mammalian biology, such protein kinases comprise mitogen activated protein kinase (MAPK) signalling pathways. MAPK signalling pathways are inappropriately activated by a variety of common disease-associated mechanisms such as mutation of ras genes and deregulation of growth factor receptors (Magnuson et al., Seminars in Cancer Biology; 1994 (5), 247-252).

Additionally, protein kinases have been implicated as targets in central nervous system disorders (such as Alzheimer's), inflammatory disorders (such as psoriasis, arthritis), bone diseases (such as osteoporosis), atherosclerosis, restenosis, thrombosis, metabolic disorders (such as diabetes) and infectious diseases (such as viral and fungal infections).

One of the most commonly studied pathways involving kinase regulation is intracellular signalling from cell surface receptors to the nucleus. One example of this pathway includes a cascade of kinases in which members of the Growth Factor receptor Tyrosine Kinases (such as EGF-R, PDGF-R, VEGF-R, IGF1-R, the Insulin receptor) deliver signals through phosphorylation to other kinases such as Src Tyrosine kinase, and the Raf, Mek and Erk serine/threonine kinase families. Each of these kinases is represented by several family members, which play related, but functionally distinct roles. The loss of regulation of the growth factor signalling pathway is a frequent occurrence in cancer as well as other disease states.

The signals mediated by kinases have also been shown to control growth, death and differentiation in the cell by regulating the processes of the cell cycle. Progression through the eukaryotic cell cycle is controlled by a family of kinases called cyclin dependent kinases (CDKs). The regulation of CDK activation is complex, but requires the association of the CDK with a member of the cyclin family of regulatory subunits. A further level of regulation occurs through both activating and inactivating phosphorylations of the CDK subunit. The coordinate activation and inactivation of different cyclin/CDK complexes is necessary for normal progression through the cell cycle. Both the critical G1-S and G2-M transitions are controlled by the activation of different cyclin/CDK activities. In G1, both cyclin D/CDK4 and cyclin E/CDK2 are thought to mediate the onset of S-phase. Progression through S-phase requires the activity of cyclin A/CDK2 whereas the activation of cyclin A/cdc2 (CDK1) and cyclin B/cdc2 are required for the onset of metaphase. It is not surprising, therefore, that the loss of control of CDK regulation is a frequent event in hyperproliferative diseases and cancer.

Raf protein kinases are key components of signal transduction pathways by which specific extracellular stimuli elicit precise cellular responses in mammalian cells. Activated cell surface receptors activate ras/rap proteins at the inner aspect of the plasma membrane which in turn recruit and activate Raf proteins. Activated Raf proteins phosphorylate and activate the intracellular protein kinases MEK1 and MEK2. In turn, activated MEKs catalyze phosphorylation and activation of p42/p44 mitogen-activated protein kinase (MAPK). Various cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g., histiocytic lymphoma, lung adenocarcinoma, small cell lung cancer, and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery, and/or during childbirth.

Accordingly, there is a great need to develop compounds useful as inhibitors of protein kinases. In particular, it would be desirable to develop compounds that are useful as Raf inhibitors.

BRIEF SUMMARY OF THE INVENTION

It has now been found that compounds of this invention, and pharmaceutically acceptable compositions thereof, are effective as inhibitors of one or more protein kinases. Such compounds are of formula I:

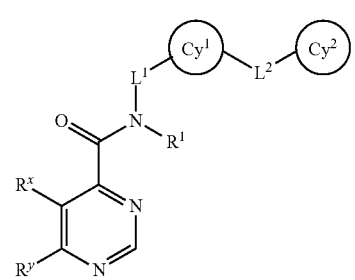

or a pharmaceutically acceptable salt thereof, wherein each of $R^x$, $R^y$, $R^1$, $L^1$, $L^2$, $Cy^1$, and $Cy^2$ are as defined in classes and subclasses herein, and pharmaceutical compositions thereof, as described generally and in subclasses herein, which compounds are useful as inhibitors of protein kinase (e.g., Raf), and thus are useful, for example, for the treatment of Raf-mediated diseases.

In certain other embodiments, the invention provides pharmaceutical compositions comprising a compound of the invention, wherein the compound is present in an amount effective to inhibit Raf activity. In certain other embodiments, the invention provides pharmaceutical compositions comprising a compound of the invention and optionally further comprising an additional therapeutic agent. In yet other embodiments, the additional therapeutic agent is an agent for the treatment of cancer.

In yet another aspect, the present invention provides methods for inhibiting kinase (e.g., Raf) activity in a patient or a biological sample, comprising administering to said patient, or contacting said biological sample with, an effective inhibitory amount of a compound of the invention. In still another aspect, the present invention provides methods for treating any disorder involving Raf activity, comprising administering to a subject in need thereof a therapeutically effective amount of a compound of the invention.

DETAILED DESCRIPTION OF CERTAIN EMBODIMENTS OF THE INVENTION

1. General Description of Compounds of the Invention

In certain embodiments, the present invention provides a compound of formula I:

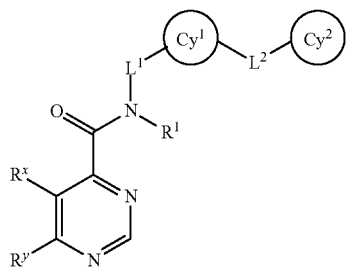

I or a pharmaceutically acceptable salt thereof, wherein:
$Cy^1$ is an optionally substituted phenyl or 5-6 membered saturated, partially unsaturated, or aromatic ring having 1-3 heteroatoms independently selected from nitrogen, oxygen, or sulfur;
$Cy^2$ is an optionally substituted 5-14 membered saturated, partially unsaturated, or aromatic monocyclic, bicyclic, or tricyclic ring having 0-4 heteroatoms, independently selected from nitrogen, oxygen, or sulfur;
$L^1$ is a direct bond or an optionally substituted, straight or branched $C_{1-6}$ alkylene chain;
$L^2$ is a direct bond, or is an optionally substituted, straight or branched $C_{1-6}$ alkylene chain wherein 1 or 2 methylene units of $L^2$ are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, or a 3-6 membered cycloalkylene;

each R is independently hydrogen or an optionally substituted $C_{1-6}$ aliphatic group;
$R^1$ is hydrogen or an optionally substituted $C_{1-6}$ aliphatic group;
each of $R^x$ and $R^y$ is independently selected from —$R^2$, -halo, —NO$_2$, —CN, —OR$^2$, —SR$^2$, —N(R$^2$)$_2$, —C(O)R$^2$, —CO$_2$R$^2$, —C(O)C(O)R$^2$, —C(O)CH$_2$C(O)R$^2$, —S(O)R$^2$, —S(O)$_2$R$^2$, —C(O)N(R$^2$)$_2$, —SO$_2$N(R$^2$)$_2$, —OC(O)R$^2$, —N(R$^2$)C(O)R$^2$, —N(R$^2$)N(R$^2$)$_2$, —N(R$^2$)—C(=NR$^2$)N(R$^2$)$_2$, —C(=NR$^2$)N(R$^2$)$_2$, —C=NOR$^2$, —N(R$^2$)C(O)N(R$^2$)$_2$, —N(R$^2$)SO$_2$N(R$^2$)$_2$, —N(R$^2$)SO$_2$R$^2$, or —OC(O)N(R$^2$)$_2$; and
each $R^2$ is independently hydrogen or an optionally substituted group selected from $C_{1-6}$ aliphatic, a $C_{6-10}$ monocyclic or bicyclic aryl ring, or a 5-10 membered saturated, partially unsaturated, or aromatic monocyclic or bicyclic ring having 1-4 heteroatoms independently selected from nitrogen, oxygen, or sulfur, or
two $R^2$ on the same nitrogen are taken together with the nitrogen to form an optionally substituted 5-8 membered saturated, partially unsaturated, or aromatic ring having 1-4 heteroatoms independently selected from nitrogen, oxygen, or sulfur.

Compounds of this invention include those generally set forth above and described specifically herein, and are illustrated in part by the various classes, subgenera and species disclosed herein. Additionally, the present invention provides pharmaceutically acceptable derivatives of the compounds of the invention, and methods of treating a subject using these compounds, pharmaceutical compositions thereof, or either of these in combination with one or more additional therapeutic agents.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various isomeric forms, e.g., stereoisomers and/or diastereomers. Thus, compounds of the invention and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein, may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl) alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl or tetrahydronaphthyl, where the radical or point of attachment is on the aliphatic ring.

As used herein, the term "cycloalkylene" refers to a bivalent cycloalkyl group. In certain embodiments, a cycloalkylene group is a 1,1-cycloalkylene group (i.e., a Spiro-fused ring). Exemplary 1,1-cycloalkylene groups include

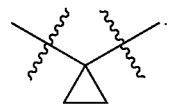

In other embodiments, a cycloalkylene group is a 1,2-cycloalkylene group or a 1,3-cycloalkylene group. Exemplary 1,2-cycloalkylene groups include

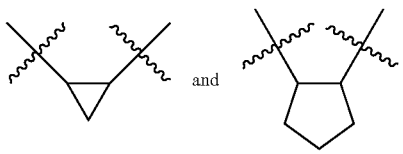

The term "alkyl," as used herein, refers to saturated, straight- or branched-chain hydrocarbon radicals derived from an aliphatic moiety containing between one and six carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, isobutyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 it electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As defined herein, an alkylene chain also can be optionally replaced by a functional group. An alkylene chain is "replaced" by a functional group when an internal methylene unit is replaced with the functional group. Examples of suitable "interrupting functional groups" are described in the specification and claims herein.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH═CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$—, SC(S)$SR°$; —$(CH_2)_{0-4}$ SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 4-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O (haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O (haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O (haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

3. Description of Exemplary Compounds

As defined generally above, each of R$^x$ and R$^y$ is independently selected from —R$^2$, -halo, —NO$_2$, —CN, —OR$^2$, —SR$^2$, —N(R$^2$)$_2$, —C(O)R$^2$, —CO$_2$R$^2$, —C(O)C(O)R$^2$, —C(O)CH$_2$C(O)R$^2$, —S(O)R$^2$, —S(O)$_2$R$^2$, —C(O)N(R$^2$)$_2$, —SO$_2$N(R$^2$)$_2$, —OC(O)R$^2$, —N(R$^2$)C(O)R$^2$, —N(R$^2$)N(R$^2$)$_2$, —N(R$^2$)—C(=NR$^2$)N(R$^2$)$_2$, —C(=NR$^2$)N(R$^2$)$_2$, —C=NOR$^2$, —N(R$^2$)C(O)N(R$^2$)$_2$, —N(R$^2$)SO$_2$N(R$^2$)$_2$, —N(R$^2$)SO$_2$R$^2$, or —OC(O)N(R$^2$)$_2$, wherein R$^2$ is as defined above and described herein.

In certain embodiments, each of R$^x$ and R$^y$ is independently selected from —R$^2$, halo, —OR$^2$, —N(R$^2$)$_2$, —OC(O)R$^2$, —N(R$^2$)C(O)R$^2$, —N(R$^2$)N(R$^2$)$_2$, —N(R$^2$)C(O)N(R$^2$)$_2$, —N(R$^2$)SO$_2$N(R$^2$)$_2$, —N(R$^2$)SO$_2$(R$^2$)$_2$, or —OC(O)N(R$^2$)$_2$; wherein R$^2$ is as defined above and described herein. In some embodiments, each of R$^x$ and R$^y$ is independently selected from —R$^2$, halo, —OR$^2$, and —N(R$^2$)$_2$. In other embodiments, each of R$^x$ and R$^y$ is independently hydrogen, halo, —OR$^2$, —N(R$^2$)$_2$, or an optionally substituted group selected from C$_{1-6}$ aliphatic or a 5-10 membered saturated, partially unsaturated, or aromatic monocyclic or bicyclic ring having 1-4 heteroatoms independently selected from nitrogen, oxygen, or sulfur.

In certain embodiments, R$^x$ is selected from —R$^2$, -halo, —CN, or —CO$_2$R$^2$.

In certain embodiments, R$^x$ is R$^2$ or halo. In some embodiments, R$^x$ is hydrogen, CN, an optionally substituted C$_{1-6}$ aliphatic group, or halo. In certain embodiments, R$^x$ is hydrogen. In certain embodiments, R$^x$ is fluoro, chloro or bromo. In other embodiments, R$^x$ is chloro.

In certain embodiments, R$^x$ is an optionally substituted C$_{1-6}$ aliphatic group. In some embodiments, R$^x$ is an optionally substituted C$_{1-6}$ alkyl group. In other embodiments, R$^x$ is an optionally substituted C$_{1-3}$ alkyl group. In certain embodiments, R$^x$ is an optionally substituted methyl, ethyl, n-propyl or isopropyl group. According to one embodiment, R$^x$ is an optionally substituted methyl group. According to another embodiment, one or more substituents present on the C$_{1-6}$ aliphatic, C$_{1-6}$ alkyl, C$_{1-3}$ alkyl, n-propyl, isopropyl, ethyl or methyl group include —N(R$^2$)$_2$, wherein R$^2$ is as defined above and described herein. In certain embodiments, R$^x$ is —CF$_3$.

Exemplary R$^x$ groups include those set forth in Tables 1, 3, 4, and 5 in the Examples section, infra.

In certain embodiments, $R^y$ is selected from —$R^2$, —$OR^2$, or —$N(R^2)_2$. In certain embodiments, $R^y$ is independently selected from hydrogen, —$OR^2$, —$N(R^2)_2$, or an optionally substituted group selected from $C_{1-6}$ aliphatic or a 5-10 membered saturated, partially unsaturated, or aromatic monocyclic or bicyclic ring having 1-4 heteroatoms independently selected from nitrogen, oxygen, or sulfur.

In certain embodiments, $R^y$ is hydrogen.

In some embodiments, $R^y$ is an optionally substituted $C_{1-6}$ aliphatic group. In other embodiments, $R^y$ is an optionally substituted $C_{2-6}$ aliphatic group. In certain embodiments, $R^y$ is an optionally substituted $C_{2-6}$ alkenyl group. In certain embodiments, $R^y$ is an optionally substituted $C_{2-6}$ alkynyl group. According to one embodiment, $R^y$ is an optionally substituted $C_{2-5}$ alkynyl group. According to another embodiment, substituents present on the $C_{1-6}$ aliphatic, $C_{2-6}$ aliphatic, $C_{2-6}$ alkenyl, $C_{2-6}$ alkynyl or $C_{2-5}$ alkynyl $R^y$ group include —$(CH_2)_{0-4}OR°$ or —$(CH_2)_{0-4}N(R°)_2$ groups, wherein $R°$ is as defined above and herein.

In certain embodiments, $R^y$ is an optionally substituted $C_{6-10}$ monocyclic or bicyclic aryl ring. In certain embodiments, $R^y$ is an optionally substituted $C_{8-10}$ bicyclic aryl ring. In some embodiments, $R^y$ is an optionally substituted phenyl ring.

According to one embodiment, $R^y$ is an optionally substituted 5-10 membered saturated monocyclic or bicyclic ring having 1-4 heteroatoms independently selected from nitrogen, oxygen, or sulfur. In certain embodiments, $R^y$ is an optionally substituted 5,6- or 6,6-fused saturated bicyclic ring having 1-4 heteroatoms independently selected from nitrogen, oxygen, or sulfur. In some embodiments, $R^y$ is an optionally substituted 5-6 membered saturated monocyclic ring having 1-4 heteroatoms independently selected from nitrogen, oxygen, or sulfur. In other embodiments, $R^y$ is an optionally substituted 5-6 membered saturated monocyclic ring having 1-2 heteroatoms independently selected from nitrogen, oxygen, or sulfur.

In certain embodiments, $R^y$ is an optionally substituted 5-membered saturated monocyclic ring having 1-2 heteroatoms independently selected from nitrogen, oxygen, or sulfur. In some embodiments, $R^y$ is an optionally substituted 5-membered saturated monocyclic ring having 2 heteroatoms independently selected from nitrogen, oxygen, or sulfur. In other embodiments, $R^y$ is an optionally substituted 5-membered saturated monocyclic ring having 2 heteroatoms independently selected from nitrogen or oxygen.

In certain embodiments, $R^y$ is an optionally substituted 6-membered saturated monocyclic ring having 1-2 heteroatoms independently selected from nitrogen, oxygen, or sulfur. In some embodiments, $R^y$ is an optionally substituted 6-membered saturated monocyclic ring having 2 heteroatoms independently selected from nitrogen, oxygen, or sulfur. In other embodiments, $R^y$ is an optionally substituted 6-membered saturated monocyclic ring having 2 heteroatoms independently selected from nitrogen or oxygen.

Exemplary $R^y$ groups include optionally substituted octahydroazocinyl, thiocyclopentanyl, thiocyclohexanyl, pyrrolidinyl, piperidinyl, piperazinyl, tetrahydrothiopyranyl, tetrahydrothiophenyl, dithiolanyl, tetrahydrofuranyl, tetrahydropyranyl, dioxanyl, thioxanyl, morpholinyl, oxathiolanyl, imidazolidinyl, oxathiolanyl, oxazolidinyl, or thiazolidinyl groups. In certain embodiments, $R^y$ is an optionally substituted imidazolidinyl, oxathiolanyl, oxazolidinyl, or thiazolidinyl group. In some embodiments, $R^y$ is an optionally substituted piperidinyl, piperazinyl, morpholinyl, or pyrrolidinyl group. In other embodiments, $R^y$ is an optionally substituted morpholinyl group.

In certain embodiments, $R^y$ is an optionally substituted 5-membered heteroaryl ring having 1-3 heteroatoms selected from nitrogen, oxygen, or sulfur. In some embodiments, $R^y$ is an optionally substituted 5-membered heteroaryl ring having 1-2 heteroatoms selected from nitrogen, oxygen, or sulfur. In other embodiments, $R^y$ is an optionally substituted 5-membered heteroaryl ring having 2 heteroatoms selected from nitrogen, oxygen, or sulfur. According to one aspect, $R^y$ is an optionally substituted 5-membered heteroaryl ring having 1 heteroatom selected from nitrogen, oxygen, or sulfur. In certain embodiments, $R^y$ is an optionally substituted 5-membered heteroaryl ring having 1 nitrogen atom, and an additional heteroatom selected from sulfur or oxygen. Exemplary $R^y$ groups include optionally substituted pyrrolyl, pyrazolyl, imidazolyl, triazolyl, tetrazolyl, thiophenyl, furanyl, thiazolyl, isothiazolyl, thiadiazolyl, oxazolyl, isoxazolyl, or oxadiaziolyl group.

In certain embodiments, $R^y$ is an optionally substituted 6-membered heteroaryl ring having 1-4 heteroatoms independently selected from nitrogen, oxygen, or sulfur. In some embodiments, $R^y$ is an optionally substituted 6-membered heteroaryl ring having 1-3 nitrogen atoms. In other embodiments, $R^y$ is an optionally substituted 6-membered heteroaryl ring having 1-2 nitrogen atoms. According to one aspect, $R^y$ is an optionally substituted 6-membered heteroaryl ring having 2 heteroatoms nitrogen atoms. Exemplary $R^y$ groups include an optionally substituted pyridinyl, pyrimidinyl, pyrazolyl, pyrazinyl, pyridazinyl, triazinyl, or tetrazinyl group. In certain embodiments, $R^y$ is an optionally substituted pyridinyl group.

In certain embodiments, $R^y$ is an optionally substituted 5-10 membered partially unsaturated monocyclic or bicyclic ring having 1-3 heteroatoms independently selected from nitrogen, oxygen, or sulfur. In some embodiments, $R^y$ is an optionally substituted 5-6 membered partially unsaturated monocyclic ring having 1-2 heteroatoms independently selected from nitrogen, oxygen, or sulfur. In other embodiments, $R^y$ is an optionally substituted tetrahydropyridinyl group.

In certain embodiments, $R^y$ is an optionally substituted 8-10 membered aromatic bicyclic heteroaryl ring having 1-4 heteroatoms independently selected from nitrogen, oxygen, or sulfur. In some embodiments, $R^y$ is an optionally substituted 5,6-fused heteroaryl ring having 1-4 heteroatoms independently selected from nitrogen, oxygen, or sulfur. In other embodiments, $R^y$ is an optionally substituted 5,6-fused heteroaryl ring having 1-2 heteroatoms independently selected from nitrogen, oxygen, or sulfur. In certain embodiments, $R^y$ is an optionally substituted 5,6-fused heteroaryl ring having 1 heteroatom independently selected from nitrogen, oxygen, or sulfur.

In certain embodiments, $R^y$ is an optionally substituted 6,6-fused heteroaryl ring having 1-4 heteroatoms independently selected from nitrogen, oxygen, or sulfur. In some embodiments, $R^y$ is an optionally substituted 6,6-fused heteroaryl ring having 1-2 heteroatoms independently selected from nitrogen, oxygen, or sulfur. In other embodiments, $R^y$ is an optionally substituted 6,6-fused heteroaryl ring having 1 heteroatom independently selected from nitrogen, oxygen, or sulfur. According to one aspect, $R^y$ is an optionally substituted 6,6-fused heteroaryl ring having 2 heteroatoms independently selected from nitrogen, oxygen, or sulfur. Exemplary $R^y$ groups include an optionally substituted benzofuranyl, thianaphthenyl, pyyrolizinyl, indolyl, quinolinyl, isoquinolinyl, benximidazolyl, imidazopyridinyl, purinyl, indazolyl, pyrrolopyridinyl, cinnolinyl, quinazolinyl, phthalazinyl, napthyridinyl, or quinoxalinyl group. In some embodiments, $R^y$ is a pyrrolylpyridinyl, imidazopyridinyl, or purinyl group. In other embodiments, Ry is a pyrrolylpyridinyl group.

In certain embodiments, $R^y$ is —$OR^2$, wherein $R^2$ is defined above and described herein. In certain embodiments, $R^y$ is —$OR^2$, wherein $R^2$ is hydrogen or an optionally substituted $C_{1-6}$ aliphatic group. In some embodiments, $R^y$ is —$OR^2$, wherein $R^2$ is an optionally substituted $C_{1-6}$ aliphatic group. In other embodiments, $R^y$ is —$OR^2$, wherein $R^2$ is an optionally substituted $C_{1-6}$ alkyl group. According to one aspect, $R^y$ is —$OR^2$, wherein $R^2$ is an optionally substituted $C_{1-3}$ alkyl group. In other embodiments, $R^y$ is —$OR^2$, wherein $R^2$ is an optionally substituted $C_{1-2}$ alkyl group. In some embodiments, $R^y$ is —$OCH_3$. In other embodiments, $R^y$ is —OH. In yet other embodiments, $R^y$ is —$OR^2$, wherein $R^2$ is —$(CH_2)_{0-3}CH_2N(R^\circ)_2$, and wherein each $R^\circ$ is defined and described herein.

In certain embodiments, $R^y$ is —$N(R^2)_2$, wherein $R^2$ is defined above and described herein. In other embodiments, $R^y$ is —$N(R^2)_2$, wherein each $R^2$ is independently hydrogen or an optionally substituted $C_{1-6}$ aliphatic group.

In certain embodiments, $R^y$ is —$NH_2$.

In certain embodiments, $R^y$ is —$NHR^2$, wherein $R^2$ is an optionally substituted $C_{1-6}$ aliphatic group. In some embodiments, $R^y$ is —$NHR^2$, wherein $R^2$ is an optionally substituted $C_{1-6}$ alkyl group. In other embodiments, $R^y$ is —$NHR^2$, wherein $R^2$ is an optionally substituted $C_{1-3}$ alkyl group. According to one aspect, $R^y$ is —$NHR^2$, wherein $R^2$ is an optionally substituted methyl or ethyl. Exemplary $R^y$ groups include —$NHCH_3$, —$NHCH_2CH_3$, —$NHCH_2CH_2CH_3$, —$NHCH(CH_3)_2$, or —$NH(C_3H_5)$, $NHCH_2CH_2CH_2OH$, and —$N(CH_2CH_2)_2O$, —$NHCH_2CH_2CH_2NH(CH_3)_2$.

In certain embodiments, $R^y$ is —$N(R^2)_2$, wherein each $R^2$ is independently hydrogen or an optionally substituted $C_{6-10}$ monocyclic or bicyclic aryl ring. In certain embodiments, $R^y$ is —$NHR^2$, wherein $R^2$ is an optionally substituted $C_{6-10}$ monocyclic or bicyclic aryl ring. In certain embodiments, $R^y$ is —$NHR^2$, wherein $R^2$ is an optionally substituted $C_6$ monocyclic aryl ring. In certain embodiments, $R^y$ is —$NHR^2$, wherein $R^2$ is an optionally substituted $C_{8-10}$ bicyclic aryl ring.

In certain embodiments, $R^y$ is —$NHR^2$, wherein $R^2$ is an optionally substituted 5-10 membered monocyclic or bicyclic heteroaryl ring having 1-4 heteroatoms independently selected from nitrogen, oxygen, or sulfur. In some embodiments, $R^y$ is —$NHR^2$, wherein $R^2$ is an optionally substituted 5-6 membered heteroaryl ring having 1-4 heteroatoms independently selected from nitrogen, oxygen, or sulfur. In other embodiments, $R^y$ is —$NHR^2$, wherein $R^2$ is an optionally substituted 5-6 membered heteroaryl ring having 1-2 heteroatoms independently selected from nitrogen, oxygen, or sulfur. In certain aspects, $R^y$ is —$NHR^2$, wherein $R^2$ is an optionally substituted 5-6 membered heteroaryl ring having 1-2 nitrogen atoms.

In certain embodiments, $R^y$ is —$NHR^2$, wherein $R^2$ is an optionally substituted 5 membered heteroaryl ring having 1-2 heteroatoms selected from nitrogen, oxygen, or sulfur. In some embodiments, $R^y$ is —$NHR^2$, wherein $R^2$ is an optionally substituted 5 membered heteroaryl ring having 2 heteroatoms selected from nitrogen, oxygen, or sulfur. In other embodiments, $R^y$ is —$NHR^2$, wherein $R^2$ is an optionally substituted 5 membered heteroaryl ring having 1 heteroatom selected from nitrogen, oxygen, or sulfur. In certain embodiments, $R^y$ is —$NHR^2$, wherein $R^2$ is an optionally substituted 5 membered heteroaryl ring having a nitrogen atom, and another heteroatom selected from sulfur or oxygen.

In certain embodiments, $R^y$ is —$NHR^2$, wherein $R^2$ is an optionally substituted 6 membered heteroaryl ring having 1-2 heteroatoms independently selected from nitrogen, oxygen, or sulfur. In certain embodiments, $R^y$ is —$NHR^2$, wherein $R^2$ is an optionally substituted 6 membered heteroaryl ring having 1 heteroatom independently selected from nitrogen, oxygen, or sulfur. In certain embodiments, $R^y$ is —$NHR^2$ wherein $R^2$ is an optionally substituted 6 membered heteroaryl ring having 2 heteroatoms independently selected from nitrogen, oxygen, or sulfur. In certain embodiments, $R^y$ is —$NHR^2$, wherein $R^2$ is an optionally substituted 6 membered heteroaryl ring having 1 heteroatom selected from nitrogen, and 1 heteroatom selected from sulfur or oxygen.

In certain embodiments, $R^y$ is —$NHR^2$, wherein $R^2$ is an optionally substituted 5,6-fused heteroaryl ring having 1-4 heteroatoms independently selected from nitrogen, oxygen, or sulfur. In some embodiments, $R^y$ is —$NHR^2$, wherein $R^2$ is an optionally substituted 5,6-fused heteroaryl ring having 1-2 heteroatoms independently selected from nitrogen, oxygen, or sulfur. In other embodiments, $R^y$ is —$NHR^2$, wherein $R^2$ is an optionally substituted 5,6-fused heteroaryl ring having 1 heteroatom independently selected from nitrogen, oxygen, or sulfur. In certain aspects, $R^y$ is —$NHR^2$, wherein $R^2$ is an optionally substituted 5,6-fused heteroaryl ring having 2 heteroatoms independently selected from nitrogen, oxygen, or sulfur.

In certain embodiments, $R^y$ is —$NHR^2$, wherein $R^2$ is an optionally substituted 6,6-fused heteroaryl ring having 1-4 heteroatoms independently selected from nitrogen, oxygen, or sulfur. In some embodiments, $R^y$ is —$NHR^2$, wherein $R^2$ is an optionally substituted 6,6-fused heteroaryl ring having 1-2 heteroatoms independently selected from nitrogen, oxygen, or sulfur. In other embodiments, $R^y$ is —$NHR^2$, wherein $R^2$ is an optionally substituted 6,6-fused heteroaryl ring having 1 heteroatom independently selected from nitrogen, oxygen, or sulfur. In certain aspects, $R^y$ is —$NHR^2$, wherein $R^2$ is an optionally substituted 6,6-fused heteroaryl ring having 2 heteroatoms independently selected from nitrogen, oxygen, or sulfur.

In certain embodiments, $R^y$ is —$NHR^2$, wherein $R^2$ is an optionally substituted pyrrolyl, pyrazolyl, imidazolyl, pyridinyl, pyrimidinyl, pyrazinyl, pyridazinyl, triazinyl, tetrazinyl, tetrazolyl, pyyrolizinyl, indolyl, quinolinyl, isoquinolinyl, benzidmidazolyl, pyrrolylpyridinyl, indazolyl, cinnolinyl, quinazolinyl, phthalazinyl, napthyridinyl, quinoxalinyl, thiophenyl, thiepinyl, thianaphthenyl, furanyl, benzofuranyl, thiazolyl, isothiazolyl, thiadiazolyl, oxazolyl, isoxazolyl, or oxadiaziolyl group. In other embodiments, $R^y$ is —$NHR^2$, wherein $R^2$ is an optionally substituted pyridinyl, thiazolyl, isothiazolyl, oxazolyl, or isoxazolyl group. In certain embodiments, $R^y$ is —$NHR^2$, wherein $R^2$ is an optionally substituted pyridinyl, thiazolyl or isoxazolyl group.

In certain embodiments, $R^y$ is —$N(R^2)_2$, wherein two $R^2$ groups on the same nitrogen are taken together with the nitrogen to form a 5-8 membered saturated, partially unsaturated, or aromatic mono- or bicyclic ring having 1-4 heteroatoms independently selected from nitrogen, oxygen, or sulfur. In some embodiments, $R^y$ is —$N(R^2)_2$, wherein two $R^2$ on the same nitrogen are taken together with the nitrogen to form an optionally substituted piperidinyl, piperazinyl, pyrrolidinyl, octahydroazocinyl or morpholinyl group. In other embodiments, $R^y$ is —$N(R^2)_2$, wherein two $R^2$ on the same nitrogen are taken together with the nitrogen to form an optionally substituted piperidinyl, piperazinyl, morpholinyl, or pyrrolidinyl group. In certain aspects, $R^y$ is —$N(R^2)_2$, wherein two $R^2$ on the same nitrogen are taken together with the nitrogen to form an optionally substituted morpholinyl group.

Exemplary $R^y$ groups include those set forth in the Examples section, infra.

In certain embodiments, $R^1$ is hydrogen. In other embodiments, $R^1$ is an optionally substituted $C_{1-6}$ aliphatic group. In certain embodiments, $R^1$ is an optionally substituted $C_{1-6}$ alkyl group. In some embodiments, $R^1$ is an optionally substituted $C_{1-3}$ alkyl group. In certain aspects, $R^1$ is an optionally substituted methyl or ethyl group. In certain embodiments, $R^1$ is an optionally substituted methyl group.

As defined above, $L^1$ is a direct bond or an optionally substituted, straight or branched $C_{1-6}$ alkylene chain. In some embodiments, $L^1$ is a direct bond. In certain embodiments, $L^1$ is an optionally substituted, straight or branched $C_{1-5}$ alkylene chain. In some embodiments, $L^1$ is an optionally substituted, straight or branched $C_{1-4}$ alkylene chain. In other embodiments, $L^1$ is an optionally substituted, straight or branched $C_{1-3}$ alkylene chain. According to some embodiments, $L^1$ is an optionally substituted, straight or branched $C_{1-2}$ alkylene chain.

In certain embodiments, $L^1$ is an optionally substituted, straight or branched $C_1$ alkylene chain. In some embodiments, $L^1$ is an optionally substituted, straight or branched $C_2$ alkylene chain. In other embodiments, $L^1$ is an optionally substituted, straight or branched $C_3$ alkylene chain. According to some embodiments, $L^1$ is an optionally substituted, straight or branched $C_4$ alkylene chain. In certain aspects, $L^1$ is an optionally substituted, straight or branched $C_5$ alkylene chain. In other aspects, $L^1$ is an optionally substituted, straight or branched $C_6$ alkylene chain.

In certain embodiments, $L^1$ is an optionally substituted, straight $C_{1-6}$ alkylene chain. In some embodiments, $L^1$ is a straight $C_{1-6}$ alkylene chain. In other embodiments, $L^1$ is an optionally substituted, branched $C_{1-6}$ alkylene chain. In certain aspects, $L^1$ is a branched $C_{1-6}$ alkylene chain. In certain embodiments, $L^1$ is —CH($C_{1-6}$alkyl)-, —CH($C_{1-5}$alkyl)-, —CH($C_{1-4}$ alkyl)-, —CH($C_{1-3}$alkyl)-, or —CH($C_{1-2}$alkyl)-. In certain embodiments, $L^1$ is —CH(CH$_3$)—. Exemplary $L^1$ groups include —CH$_2$—, —C(CH$_3$)$_2$—, —CH(CF$_3$)—, —CH(CHF$_2$)—, —CH(CH$_2$F)—, —CH(CH$_2$OH)—, —CH(CH$_2$NH$_2$)—, —CH(OCH$_3$)—, —CH(NHCH$_3$)—, —CH(N(CH$_3$)$_2$)—, —CH(SCH$_3$)—, —CH(=O)—, and —C(=CH$_2$)—.

Exemplary $L^1$ groups include those set forth in Tables 2, 3, 4, and 5 in the Examples section, infra.

As defined generally above, $Cy^1$ is an optionally substituted phenyl or an optionally substituted 5-6 membered saturated, partially unsaturated, or aromatic ring having 1-3 heteroatoms independently selected from nitrogen, oxygen, or sulfur. In some embodiments, $Cy^1$ is optionally substituted phenyl. In certain embodiments, $Cy^1$ is an optionally substituted 6 membered saturated, partially unsaturated, or aromatic ring having 1-3 heteroatoms independently selected from nitrogen, oxygen, or sulfur. In other embodiments, $Cy^1$ is an optionally substituted 5-membered saturated, partially unsaturated, or aromatic ring having 1-3 heteroatoms independently selected from nitrogen, oxygen, or sulfur. In certain aspects, $Cy^1$ is an optionally substituted 5-membered heteroaryl ring having 2 heteroatoms independently selected from nitrogen, oxygen, or sulfur. In other embodiments, $Cy^1$ is an optionally substituted 5-membered heteroaryl ring having 2 heteroatoms independently selected from nitrogen and oxygen. In some embodiments, $Cy^1$ is an optionally substituted 5-membered heteroaryl ring having 2 heteroatoms independently selected from nitrogen and sulfur.

Exemplary $Cy^1$ groups include an optionally substituted pyrrolyl, pyrazolyl, imidazolyl, triazolyl, tetrazolyl, thiophenyl, furanyl, thiazolyl, isothiazolyl, thiadiazolyl, oxazolyl, isoxazolyl, or oxadiaziolyl group. In certain embodiments, $Cy^1$ is an optionally substituted thiazolyl or isoxazolyl group. In other embodiments, $Cy^1$ is an optionally substituted thiazolyl group. In some embodiments, $Cy^1$ is an unsubstituted thiazolyl group. In certain aspects, $Cy^1$ is an optionally substituted isoxazolyl group. According to another aspect, $Cy^1$ is an unsubstituted isoxazolyl group.

In other embodiments, $Cy^1$ is an optionally substituted 5-6 membered saturated ring having 1-2 heteroatoms independently selected from nitrogen and oxygen. In certain embodiments, $Cy^1$ is optionally substituted piperidinyl or pyrrolidinyl.

In other embodiments, $Cy^1$ is an optionally substituted 6-membered saturated, partially unsaturated or aryl ring having 1-2 nitrogens. In certain embodiments, $Cy^1$ is an optionally substituted pyridine or pyrimidine ring.

Exemplary $Cy^1$ groups include those set forth in the Examples section, infra.

As defined generally above, $L^2$ is a direct bond, or is an optionally substituted, straight or branched $C_{1-6}$ alkylene chain wherein 1 or 2 methylene units of $L^2$ are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, or a 3-6 membered cycloalkylene. In certain embodiments, $L^2$ is a direct bond.

In certain embodiments, $L^2$ is an optionally substituted, straight or branched $C_{1-6}$ alkylene chain wherein 1 or 2 methylene units of $L^2$ are replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, or —C(O)O—; wherein each R is as defined above and described herein. In some embodiments, $L^2$ is an optionally substituted, straight or branched $C_{1-4}$ alkylene chain wherein 1 or 2 methylene units of $L^2$ are replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, or —C(O)O—. In other embodiments, $L^2$ is an optionally substituted, straight or branched $C_{1-2}$ alkylene chain wherein 1 methylene unit of $L^2$ is replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, or —C(O)O—. In certain aspects, $L^2$ is —O—, —S—, —N(R)—, —C(O)—, —C(O)N(R)—, —N(R)C(O)—, —SO$_2$—, —SO$_2$N(R)—, —N(R)SO$_2$—, —OC(O)—, or —C(O)O—. In other embodiments, $L^2$ is —C(O)N(R)—, —N(R)C(O)—, —SO$_2$N(R)—, —N(R)SO$_2$—, —OC(O)—, or —C(O)O—. In certain aspects, $L^2$ is —C(O)N(R)— or —N(R)C(O)—. In certain embodiments, $L^2$ is —C(O)N(H)— or —N(H)C(O)—. In certain embodiments, $L^2$ is —C(O)N(H)—.

Exemplary $L^2$ groups include those set forth in the Examples section, infra.

As defined generally above, $Cy^2$ is an optionally substituted 5-14 membered saturated, partially unsaturated, or aromatic monocyclic, bicyclic, or tricyclic ring having 0-4 heteroatoms, independently selected from nitrogen, oxygen, or sulfur.

In some embodiments, $Cy^2$ is optionally substituted phenyl.

In certain embodiments, $Cy^2$ is an optionally substituted 5-10 membered saturated, partially unsaturated, or aromatic monocyclic ring having 1-4 heteroatoms, independently selected from nitrogen, oxygen, or sulfur. In other embodiments, $Cy^2$ is an optionally substituted 5-6 membered saturated, partially unsaturated, or aromatic monocyclic ring having 1-4 heteroatoms, independently selected from nitrogen, oxygen, or sulfur.

In certain embodiments, $Cy^2$ is an optionally substituted 5-membered saturated, partially unsaturated, or aromatic monocyclic ring having 1-3 heteroatoms, independently selected from nitrogen, oxygen, or sulfur. In some embodiments, $Cy^2$ is an optionally substituted 5-membered saturated, partially unsaturated, or aromatic monocyclic ring having 1-2 heteroatoms, independently selected from nitrogen, oxygen, or sulfur. In other embodiments, $Cy^2$ is an optionally substituted 5-membered heteroaryl ring having 1-3 heteroatoms, independently selected from nitrogen, oxygen, or sulfur. In still other embodiments, $Cy^2$ is an optionally substituted 5-membered heteroaryl ring having 1-2 heteroatoms, independently selected from nitrogen. Exemplary $Cy^2$ groups include an optionally substituted pyrrolyl, pyrazolyl, imidazolyl, triazolyl, tetrazolyl, thiophenyl, furanyl, thiazolyl, isothiazolyl, thiadiazolyl, oxazolyl, isoxazolyl, or oxadiaziolyl group.

In certain embodiments, $Cy^2$ is an optionally substituted 6-membered saturated, partially unsaturated, or aromatic monocyclic ring having 1-4 heteroatoms, independently selected from nitrogen, oxygen, or sulfur. In some embodiments, $Cy^2$ is an optionally substituted 6-membered saturated, partially unsaturated, or aromatic monocyclic ring having 1-2 heteroatoms, independently selected from nitrogen, oxygen, or sulfur. In other embodiments, $Cy^2$ is an optionally substituted 6-membered heteroaryl ring having 1-4 nitrogen atoms. In certain aspects, $Cy^2$ is an optionally substituted 6-membered heteroaryl ring having 1-3 nitrogen atoms. In some embodiments, $Cy^2$ is an optionally substituted 6-membered heteroaryl ring having 1-2 nitrogen atoms. Exemplary $Cy^2$ groups include an optionally substituted pyridinyl, pyrimidinyl, pyrazinyl, pyridazinyl, triazinyl, or tetrazinyl group. In some embodiments, $Cy^2$ is an optionally substituted pyridinyl, pyrimidinyl or pyridazinyl group.

In certain embodiments, $Cy^2$ is an optionally substituted 8-10 membered saturated, partially unsaturated, or aromatic bicyclic ring having 1-4 heteroatoms, independently selected from nitrogen, oxygen, or sulfur. In some embodiments, $Cy^2$ is an optionally substituted 5,5-fused, 5,6-fused, or 6,6-fused saturated, partially unsaturated, or aromatic bicyclic ring having 1-4 heteroatoms, independently selected from nitrogen, oxygen, or sulfur. In other embodiments, $Cy^2$ is an optionally substituted 5,5-fused, 5,6-fused, or 6,6-fused heteroaryl ring having 1-4 heteroatoms, independently selected from nitrogen, oxygen, or sulfur. In certain aspects, $Cy^2$ is an optionally substituted 5,5-fused, 5,6-fused, or 6,6-fused heteroaryl ring having 1-4 nitrogen atoms. In other embodiments, $Cy^2$ is an optionally substituted 5,6-fused heteroaryl ring having 1-4 nitrogen atoms. Exemplary $Cy^2$ groups include an optionally substituted pyyrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphtheneyl, or benzofuranyl group. In certain aspects, $Cy^2$ is an optionally substituted benzimidazolyl, imidazopyridinyl or purinyl group.

In certain embodiments, $Cy^2$ is an optionally substituted 5-10 membered saturated, partially unsaturated, or aromatic monocyclic or bicyclic carbocyclic ring. In some embodiments, $Cy^2$ is an optionally substituted 5-10 membered saturated, partially unsaturated, or aromatic monocyclic or bicyclic carbocyclic ring. In other embodiments, $Cy^2$ is an optionally substituted 5-6 membered saturated, partially unsaturated, or aromatic monocyclic carbocyclic ring. In certain aspects, $Cy^2$ is an optionally substituted 5-membered saturated or partially unsaturated carbocyclic ring. According to one embodiment, $Cy^2$ is an optionally substituted 6 membered saturated, partially unsaturated, or aromatic ring. In still other embodiments, $Cy^2$ is an optionally substituted phenyl group.

In certain embodiments, $Cy^2$ is an optionally substituted 5,5-fused-, 5,6-fused, or 6,6-fused saturated, partially unsaturated, or aromatic bicyclic ring. In some embodiments, $Cy^2$ is an optionally substituted 5,5-fused, 5,6-fused, or 6,6-fused aromatic bicyclic ring. In other embodiments, $Cy^2$ is optionally substituted naphthalenyl, indanyl or indenyl group.

In certain embodiments, $Cy^2$, as described above and herein, is optionally substituted with one or more groups selected from —R°, -halo, —NO$_2$, —CN, —OR°, —SR°, N(R°)$_2$, —C(O)R°, —CO$_2$R°, —C(O)C(O)R°, —C(O)CH$_2$C(O)R°, —S(O)R°, —S(O)$_2$R°, —C(O)N(R°)$_2$, —SO$_2$N(R°)$_2$, —OC(O)R°, —N(R°)C(O)R°, —N(R°)N(R°)$_2$, —C=NN(R°)$_2$, —C=NOR°, —N(R°)C(O)N(R°)$_2$, —N(R°)SO$_2$N(R°)$_2$, —N(R°)SO$_2$R°, or —OC(O)N(R°)$_2$; wherein R° is as defined above and described herein. In other embodiments, $Cy^2$ is optionally substituted with $C_{1-6}$ aliphatic or halogen. In some embodiments, $Cy^2$ is optionally substituted with Cl, F, CF$_3$, or $C_{1-4}$ alkyl. Exemplary substituents on $Cy^2$ include methyl, tert-butyl, and 1-methylcyclopropyl. In other embodiments, $Cy^2$ is mono- or di-substituted. In certain aspects, $Cy^2$ is optionally substituted at the meta or the para position with any one of the above-mentioned substituents. In some embodiments, $Cy^2$ is substituted with R°, wherein R° is a 4-6-membered saturated, partially unsaturated, or aryl ring having 0-4 heteroatoms independently selected from nitrogen, oxygen, or sulfur, Exemplary $Cy^2$ groups include those set forth in Tables 2, 3, 4, and 5 in the Examples section, infra.

According to one aspect, the present invention provides a compound of formula II:

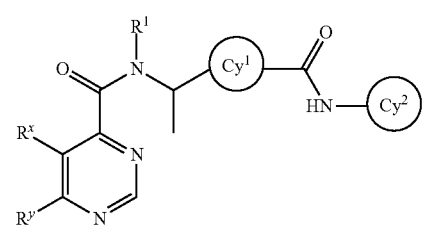

or a pharmaceutically acceptable salt thereof, wherein:
each of $R^1$, $R^x$, and $R^y$ is as defined above and described in classes and subclasses herein;
$Cy^1$ is an optionally substituted 5-membered saturated, partially unsaturated, or aromatic ring having 1-3 heteroatoms independently selected from nitrogen, oxygen, or sulfur; and Cy² is optionally substituted phenyl or an optionally substituted 6-membered aromatic ring having 1-3 nitrogen atoms.

According to another aspect, the present invention provides a compound of formula II':

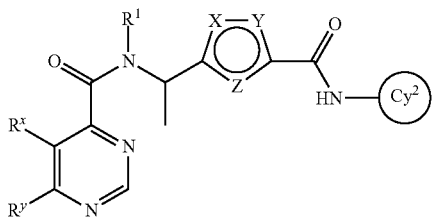

II' or a pharmaceutically acceptable salt thereof, wherein:
each of $R^1$, $R^x$, and $R^y$ is as defined above and described in classes and subclasses herein;
each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and
Cy² is optionally substituted phenyl or an optionally substituted 6-membered aromatic ring having 1-3 nitrogen atoms.

Yet another aspect of the present invention provides a compound of formulae II-a and II-b:

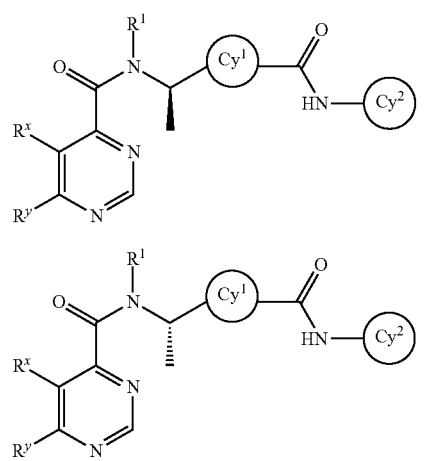

II-a

II-b or a pharmaceutically acceptable salt thereof, wherein:
each of $R^1$, $R^x$, and $R^y$ is as defined above and described in classes and subclasses herein;
Cy¹ is an optionally substituted 5-membered saturated, partially unsaturated, or aromatic ring having 1-3 heteroatoms independently selected from nitrogen, oxygen, or sulfur; and
Cy² is optionally substituted phenyl or an optionally substituted 6-membered aromatic ring having 1-3 nitrogen atoms.

In certain embodiments, the present invention provides a compound of formulae II-a' and II-b':

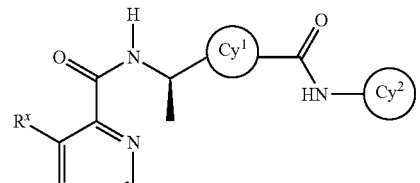

II-a'

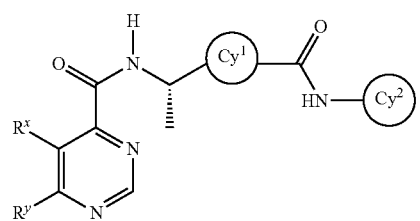

II-b' or a pharmaceutically acceptable salt thereof, wherein:
each of $R^x$, and $R^y$ is as defined above and described in classes and subclasses herein;
Cy¹ is an optionally substituted 5-membered saturated, partially unsaturated, or aromatic ring having 1-3 heteroatoms independently selected from nitrogen, oxygen, or sulfur; and
Cy² is optionally substituted phenyl or an optionally substituted 6-membered aromatic ring having 1-3 nitrogen atoms.

In certain embodiments, the present invention provides a compound of formula II-a or II-b wherein Cy¹ is a 5-membered heteroaryl ring having 1-3 heteroatoms independently selected from nitrogen, oxygen, or sulfur. Such compounds are represented by formulae II-c and II-d:

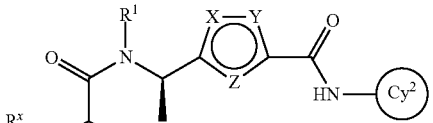

II-c

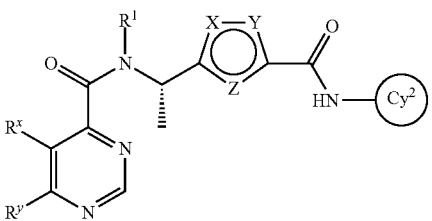

II-d or a pharmaceutically acceptable salt thereof, wherein:
each of $R^1$, $R^x$, and $R^y$ is as defined above and described in classes and subclasses herein;
each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and
Cy² is optionally substituted phenyl or an optionally substituted 6-membered aromatic ring having 1-3 nitrogen atoms.

According to another embodiment, the present invention provides a method for preparing a compound of formula II-a':

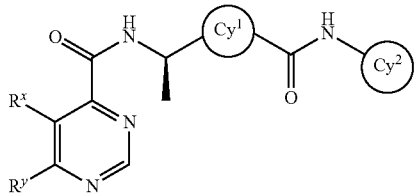

or a pharmaceutically acceptable salt thereof, wherein:

each of $R^x$ and $R^y$ is as defined above and described in classes and subclasses herein;

$Cy^1$ is an optionally substituted 5-membered saturated, partially unsaturated, or aromatic ring having 1-3 heteroatoms independently selected from nitrogen, oxygen, or sulfur; and $Cy^2$ is optionally substituted phenyl or an optionally substituted 6-membered aromatic ring having 1-3 nitrogen atoms, wherein said method comprises the steps depicted in Scheme II, below.

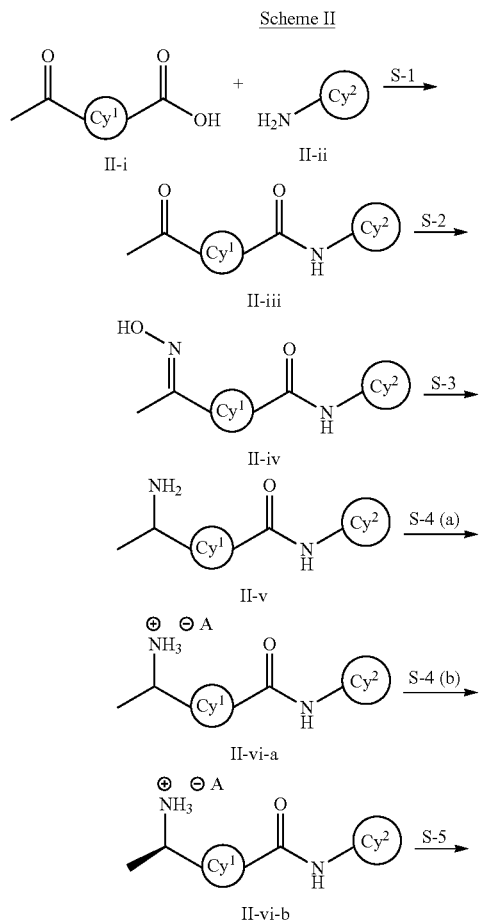

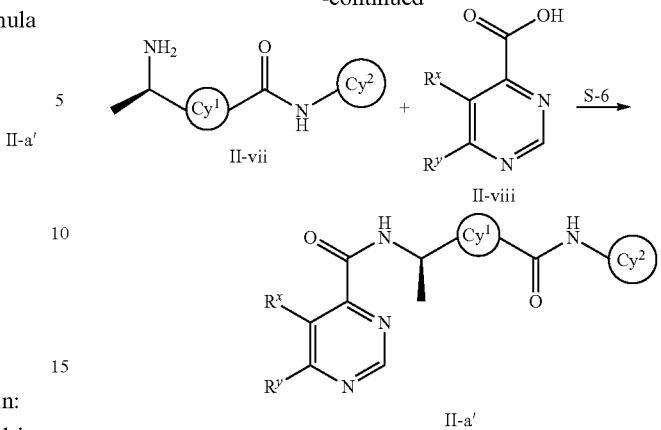

wherein each $Cy^1$ and $Cy^2$ is as defined above and described in classes and subclasses herein and $A^-$ is a suitable chiral anion.

At step S-1, above, a compound of formula II-i is coupled to a compound of formula II-ii. Such coupling of a carboxylic acid group with an amine can be performed using methods well known to one of ordinary skill in the art. In certain embodiments, the carboxylic acid moiety of formula II-i is activated prior to coupling. In some embodiments, the carboxylic acid moiety is converted to an acyl halide group prior to coupling. In another embodiment, the carboxylic acid moiety is treated with a suitable reagent to form the acyl chloride thereof which is then coupled to the amine moiety of compound to form a compound of formula II-iii. Such reagents for forming acyl halides are well known to one of ordinary skill in the art and include oxalyl chloride and thionyl chloride, to name a few. In certain embodiments, the acyl halide of formula II-iii can be used directly in step S-2 without isolation or purification.

At step S-2, the ketone moiety of formula II-iii is converted to the oxime moiety of formula II-iv. In some embodiments, the compound of formula II-iii is treated with hydroxylamine to form a compound of formula II-iv. In certain embodiments, the compound of formula II-iv is about 1:1 E:Z configuration with respect to the —C=N— bond. In some embodiments, the present invention provides a compound of formula II-iv that is at least about 50%, 60%, 70%, 80%, 85%, 90%, 95%, 97%, 98%, 99%, or 100% in the E configuration with respect to the —C=N— bond. In certain embodiments, the present invention provides a compound of formula II-iv that is at least about 50%, 60%, 70%, 80%, 85%, 90%, 95%, 97%, 98%, 99%, or 100% in the Z configuration with respect to the —C=N— bond.

At step S-3, the oxime moiety of formula II-iv is converted to the amine group of formula II-v. In certain embodiments, the compound of formula II-iv is treated with zinc dust and acetic acid in an alcohol to form a compound of formula II-v. In certain embodiments, the alcohol is a $C_{4-6}$ alkanol. In some embodiments, the alcohol is 1-butanol or pentanol.

At step S-4 (a), the racemic compound II-v is treated with a chiral agent to form a diastereomeric salt of formula II-vi-a. In certain embodiments, the chiral acid has two carboxylate moieties as with, for example, tartaric acid or a derivative thereof. In some embodiments, the chiral acid is ditoluoyl tartaric acid. The term "chiral agent" means an enantiomerically enriched group which may be ionically or covalently bonded to the nitrogen of a compound of formula II-v to form II-vi-a. As used herein, the term "enantiomerically enriched", as used herein means that one enantiomer makes up at least 85% of the preparation. In certain embodiments, the term enantiomerically enriched means that at least 90% of the preparation is one of the enantiomers. In other embodiments, the term means that at least 95% of the preparation is one of the enantiomers.

Chiral agents that are ionically bonded to said nitrogen include, for example, chiral acids. When the chiral agent is a chiral acid, the acid forms a diastereomeric salt with the nitrogen. The resulting diastereomers are then separated by suitable physical means. Examples of chiral acids include, but are not limited to, tartaric acid and tartaric acid derivatives, mandelic acid, malic acid, camphorsulfonic acid, and Mosher's acid, among others. In certain embodiments, the chiral acid is ditoluoyl-D-tartaric acid. In other embodiments, the chiral acid is ditoluoyl-L-tartaric acid. Other chiral agents that may be covalently bonded to the nitrogen are known in the art. Exemplary chiral acids include camphorsulfonic acid (−); tartaric acid (+); malic acid (−); N-acetyl-L-leucine (−); di-toluloyl-L-tartaric acid (−); deoxycholic acid (+); quinic acid (−); camphoric acid (+); N—BOC-alanine (−); tartaric acid (−); di-toluloyl-D-tartaric acid (+); camphorsulfonic acid (+); dibenzoyl-D-tartaric acid (+); L(+)citramalic; S-acetyl mandelic acid (+); and BOC-isoleucine(+).

At step S-4 (b), a diastereomeric salt of formula II-vi-b is obtained via suitable physical means, In some embodiments, "suitable physical means" refers to preferential crystallization, trituration, or slurry of a diastereomeric salt formed at step S-4 (a) above. In certain embodiments, a diastereomeric salt of formula II-vi-b is obtained via slurry. In other embodiments, the crystallization is achieved from a protic solvent. In still other embodiments, the protic solvent is an alcohol. It will be appreciated that the crystallization may be achieved using a single protic solvent or a combination of one or more protic solvents. Such solvents and solvent mixtures are well known to one of ordinary skill in the art and include, for example, one or more straight or branched alkyl alcohols. In certain embodiments, the crystallization is achieved from isopropyl alcohol and water.

At step S-4(a), a chiral acid is added to a compound of formula II-v to form a compound of formula II-vi-a. In certain embodiments, an equimolar amount of chiral acid is added. In other embodiments, a substoichiometric amount of chiral acid is added. In some embodiments, about 0.5 to about 0.75 molar equivalents of chiral acid are added. As used herein, the term "substoichiometric amount" denotes that the chiral acid is used in less than 1 mole equivalent relative to the compound of formula II-v.

In certain embodiments, the diastereomeric salt of formula II-vi comprises an equimolar amount of chiral acid and amine. In other embodiments, the diastereomeric salt of formula II-vi comprises a substoichiometric amount of chiral acid. In some embodiments, the diastereomeric salt of formula II-vi is a dihydrate.

It should be readily apparent to those skilled in the art that enantiomeric enrichment of one enantiomer in compound II-vi-b (ie resulting from preferential crystallization, trituration, or reslurry) causes an enantiomeric enrichment in the mother liquor of the other enantiomeric form. Therefore, according to another embodiment, the invention relates to a method of enhancing the percent enantiomeric excess ("% ee") of a racemic compound of formula II-vi-a or enantiomerically enriched compound of formula II-vi-b.

At step S-5, the diastereomeric salt of formula VI-vi-b is treated with a suitable base obtain a compound of formula II-vii. Free bases according to the invention are also prepared, for example, by contacting a compound of formula VI-vi-b with a suitable base in the presence of a solvent suitable for free base formation. In certain embodiments, the suitable solvent is one or more polar aprotic solvent optionally mixed with a protic solvent. In some embodiments, the suitable solvent is an ether mixed with an alcohol. In other embodiments, the suitable solvent is tert-butylmethyl ether and methanol or tert-butylmethyl ether and acetone. Such suitable bases include strong inorganic bases, i.e., those that completely dissociate in water under formation of hydroxide anion. Exemplary suitable bases include metal hydroxides, including sodium hydroxide and potassium hydroxide. In some embodiments, the base is a carbonate base, e.g. sodium bicarbonate.

At step S-6, a compound of formula II-vii is coupled with a compound of formula II-viii to form a compound of formula II-a. Such coupling reactions are well known in the art. In certain embodiments, the coupling is achieved with a suitable coupling reagent. Such reagents are well known in the art and include, for example, DCC, HATU, and EDC, among others. In other embodiments, the carboxylic acid moiety is activated for use in the coupling reaction. Such activation includes formation of an acyl halide, use of a Mukaiyama reagent, and the like. These methods, and others, are known to one of ordinary skill in the art, e.g., see, "Advanced Organic Chemistry," Jerry March, 5$^{th}$ Ed., pp. 351-357, John Wiley and Sons, N.Y.

According to another embodiment, the present invention provides a method for preparing a compound of formula II-a':

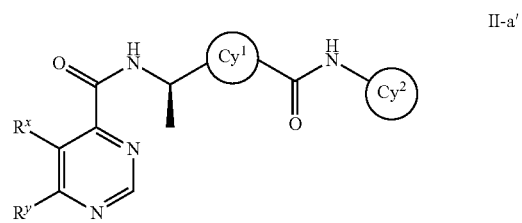

II-a' or a pharmaceutically acceptable salt thereof, wherein:
each of $R^x$ and $R^y$ is as defined above and described in classes and subclasses herein;
$Cy^1$ is an optionally substituted 5-membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms,
comprising the step of coupling a compound of formula II-viii:

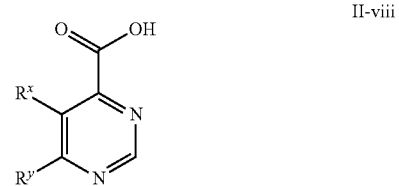

II-viii wherein each of $R^x$ and $R^y$ is as defined above and described in classes and subclasses herein;
with a compound of formula II-vii:

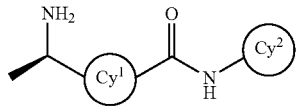

wherein:
$Cy^1$ is an optionally substituted 5-membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms,
to form the compound of formula II-a'.

In certain embodiments, the compound of formula II-vii:

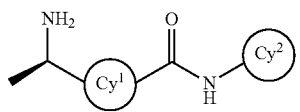

wherein:
$Cy^1$ is an optionally substituted 5-membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms,
is prepared from a compound of formula II-vi-b:

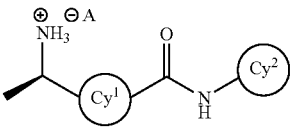

wherein $A^-$ is a suitable chiral anion,
comprising the step of treating the compound of formula II-vi-b with a suitable base to form a compound of formula II-vii.

In certain embodiments, the compound of formula II-vi-b:

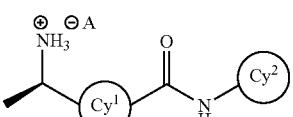

wherein:
$A^-$ is a suitable chiral anion;
$Cy^1$ is an optionally substituted 5-membered saturated, partially unsaturated, or aromatic ring having 1-3 heteroatoms independently selected from nitrogen, oxygen, or sulfur; and $Cy^2$ is optionally substituted phenyl or an optionally substituted 6-membered aromatic ring having 1-3 nitrogen atoms,
is prepared from a compound of formula II-v:

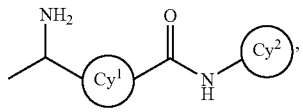

comprising the steps of:
(a) treating the compound of formula II-v with a chiral agent to form a compound of formula II-vi-a:

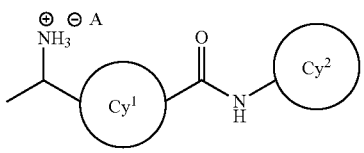

and
(b) separating the resulting diastereomers by suitable physical means to obtain a compound of formula II-vi-b.

In certain embodiments, the compound of formula II-v:

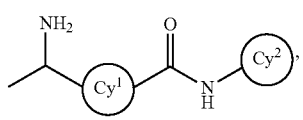

wherein:
$Cy^1$ is an optionally substituted 5-membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms,
is prepared from a compound of formula II-iv:

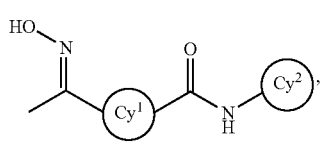

comprising the step of converting the oxime moiety of formula II-iv to the amine group of formula II-v.

In some embodiments, the present invention provides a method for preparing a compound of formula II-iv:

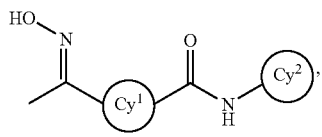

wherein:
Cy¹ is an optionally substituted 5-membered saturated, partially unsaturated, or aromatic ring having 1-3 heteroatoms independently selected from nitrogen, oxygen, or sulfur; and
Cy² is optionally substituted phenyl or an optionally substituted 6-membered aromatic ring having 1-3 nitrogen atoms, comprising the step of treating a compound of formula II-iii:

II-iii with hydroxylamine to form the compound of formula II-iv.

In certain embodiments, the compound of formula II-iii:

II-iiii wherein:
Cy¹ is an optionally substituted 5-membered saturated, partially unsaturated, or aromatic ring having 1-3 heteroatoms independently selected from nitrogen, oxygen, or sulfur; and
Cy² is optionally substituted phenyl or an optionally substituted 6-membered aromatic ring having 1-3 nitrogen atoms, is prepared by coupling a compound of formula II-i:

II-i wherein Cy¹ is an optionally substituted 5-membered saturated, partially unsaturated, or aromatic ring having 1-3 heteroatoms independently selected from nitrogen, oxygen, or sulfur, with a compound of formula II-ii:

II-ii wherein Cy² is optionally substituted phenyl or an optionally substituted 6-membered aromatic ring having 1-3 nitrogen atoms.

In certain embodiments, the present invention provides a compound of formula II-vi-a or II-vi-b:

II-vi-a

II-vi-b wherein each of Cy¹, Cy² and A⁻ is as defined herein.

In some embodiments, the present invention provides a compound of formula II-iv:

II-iv wherein each of Cy¹ and Cy² is as defined herein.

According to another aspect, the present invention provides a compound of formula III:

III or a pharmaceutically acceptable salt thereof, wherein:
each of $R^1$, $R^x$, and $R^y$ is as defined above and described in classes and subclasses herein;
Cy¹ is an optionally substituted 5-membered saturated, partially unsaturated, or aromatic ring having 1-3 heteroatoms independently selected from nitrogen, oxygen, or sulfur; and
Cy² is an optionally substituted 8-10 membered saturated, partially unsaturated, or aromatic bicyclic ring having 1-4 heteroatoms, independently selected from nitrogen, oxygen, or sulfur.

According to certain embodiments, the present invention provides a compound of formula III':

III' or a pharmaceutically acceptable salt thereof, wherein:

each of $R^1$, $R^x$, and $R^y$ is as defined above and described in classes and subclasses herein;

each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and $Cy^2$ is optionally substituted phenyl or an optionally substituted 6-membered aromatic ring having 1-3 nitrogen atoms.

In certain aspects, the present invention provides a compound of formulae III-a and III-b:

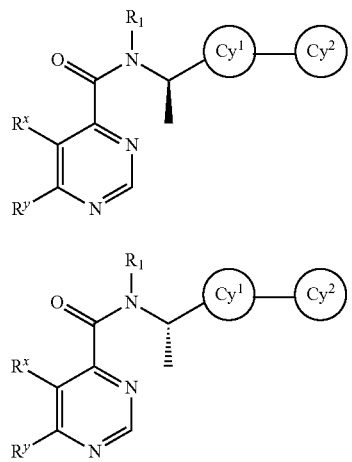

III-a

III-b or a pharmaceutically acceptable salt thereof, wherein:

each of $R^1$, $R^x$, and $R^y$ is as defined above and described in classes and subclasses herein;

$Cy^1$ is an optionally substituted 5-membered saturated, partially unsaturated, or aromatic ring having 1-3 heteroatoms independently selected from nitrogen, oxygen, or sulfur; and $Cy^2$ is an optionally substituted 8-10 membered saturated, partially unsaturated, or aromatic bicyclic ring having 1-4 heteroatoms, independently selected from nitrogen, oxygen, or sulfur.

In certain embodiments, the present invention provides a compound of formula III-a or III-b wherein $Cy^1$ is a 5-membered heteroaryl ring having 1-3 heteroatoms independently selected from nitrogen, oxygen, or sulfur. Such compounds are represented by formulae III-c and III-d:

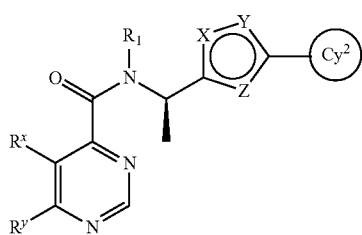

III-c

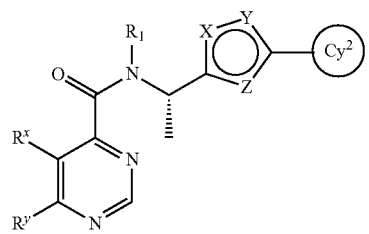

III-d or a pharmaceutically acceptable salt thereof, wherein:

each of $R^1$, $R^x$, and $R^y$ is as defined above and described in classes and subclasses herein;

each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and $Cy^2$ is optionally substituted phenyl or an optionally substituted 6-membered aromatic ring having 1-3 nitrogen atoms.

In certain embodiments, each of $R^1$, $R^x$, $R^y$, $L^1$, $L^2$, $Cy^1$, and $Cy^2$ is selected from those groups depicted in Tables 1-5, infra.

According to one aspect, the present invention provides a compound of formula IV:

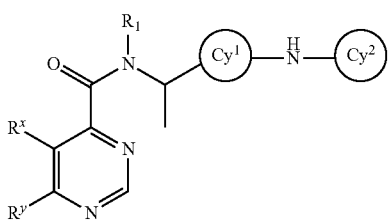

IV or a pharmaceutically acceptable salt thereof, wherein:

each of $R^1$, $R^x$, and $R^y$ is as defined above and described in classes and subclasses herein;

$Cy^1$ is an optionally substituted 5-6 membered saturated, partially unsaturated, or aromatic ring having 1-3 heteroatoms independently selected from nitrogen, oxygen, or sulfur; and $Cy^2$ is optionally substituted phenyl or an optionally substituted 6-membered aromatic ring having 1-3 nitrogen atoms.

Yet another aspect of the present invention provides a compound of formulae IV-a and IV-b:

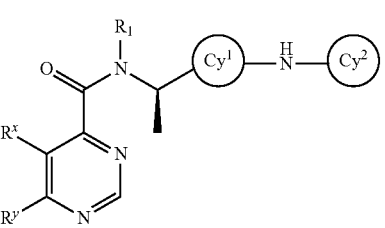

IV-a

-continued

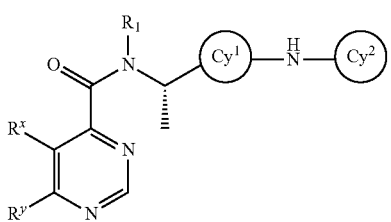

IV-b or a pharmaceutically acceptable salt thereof, wherein:
each of $R^1$, $R^x$, and $R^y$ is as defined above and described in classes and subclasses herein;
$Cy^1$ is an optionally substituted 5-6 membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms.

In certain embodiments, the present invention provides a compound of formula IV, IV-a, or IV-b wherein $Cy^1$ is a 5-membered heteroaryl ring having 1-3 heteroatoms independently selected from nitrogen, oxygen, or sulfur.

Exemplary compounds of the present invention are set forth in the Examples at Tables 3, 4, and 5, infra. In certain embodiments, the present invention provides a compound selected from those set forth in Table 3, or a pharmaceutically acceptable salt thereof. In some embodiments, the present invention provides a compound selected from those set forth in Table 4, or a pharmaceutically acceptable salt thereof. In other embodiments, the present invention provides a compound selected from those set forth in Table 5, or a pharmaceutically acceptable salt thereof 4. Uses, Formulation and Administration Pharmaceutically Acceptable Compositions As discussed above, the present invention provides compounds that are inhibitors of protein kinases (e.g., Raf kinase), and thus the present compounds are useful for the treatment of diseases, disorders, and conditions mediated by Raf kinase. In certain embodiments, the present invention provides a method for treating a Raf-mediated disorder. As used herein, the term "Raf-mediated disorder" includes diseases, disorders, and conditions mediated by Raf kinase. Such Raf-mediated disorders include melanoma, leukemia, or cancers such as colon, breast, gastric, ovarian, lung, brain, larynx, cervical, renal, lymphatic system, genitourinary tract (including bladder and prostate), stomach, bone, lymphoma, melanoma, glioma, papillary thyroid, neuroblastoma, and pancreatic cancer.

Raf-mediated disorders further include diseases afflicting mammals which are characterized by cellular proliferation. Such diseases include, for example, blood vessel proliferative disorders, fibrotic disorders, mesangial cell proliferative disorders, and metabolic diseases. Blood vessel proliferative disorders include, for example, arthritis and restenosis. Fibrotic disorders include, for example, hepatic cirrhosis and atherosclerosis. Mesangial cell proliferative disorders include, for example, glomerulonephritis, diabetic nephropathy, malignant nephrosclerosis, thrombotic microangiopathy syndromes, organ transplant rejection, and glomerulopathies. Metabolic disorders include, for example, psoriasis, diabetes mellitus, chronic wound healing, inflammation, and neurodegenerative diseases.

In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, pharmaceutically acceptable derivatives include, but are not limited to, pharmaceutically acceptable salts, esters, salts of such esters, or any other adducts or derivatives that, upon administration to a patient in need, are capable of providing, directly or indirectly, a compound as otherwise described herein, or a metabolite or residue thereof.

As used herein, the term "pharmaceutically acceptable salt" refers to those salts that are, within the scope of sound medical judgement, suitable for use in contact with the tissues of humans or animals without undue toxicity, irritation, allergic response, or the like, and are offer with a reasonable benefit/risk ratio. A "pharmaceutically acceptable salt" means any at least substantially non-toxic salt or salt of an ester of a compound of this invention that, upon administration to a recipient, is capable of providing, either directly or indirectly, a compound of this invention or an inhibitorily active metabolite or residue thereof. As used herein, the term "inhibitory metabolite or residue thereof" means that a metabolite or residue thereof is also an inhibitor of a Raf kinase.

Pharmaceutically acceptable salts are well known in the art. For example, S. M. Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $-N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

According to the present invention, provided compounds may be assayed in any of the available assays known in the art for identifying compounds having kinase inhibitory activity. For example, the assay may be cellular or non-cellular, in vivo or in vitro, high- or low-throughput format, etc.

In certain exemplary embodiments, compounds of this invention were assayed for their ability to inhibit protein kinases, more specifically Raf.

Thus, in one aspect, compounds of this invention which are of particular interest include those which:
 are inhibitors of protein kinases;
 exhibit the ability to inhibit Raf kinase;
 are useful for treating mammals (e.g., humans) or animals suffering from an Raf-mediated disease or condition, and for helping to prevent or delay the onset of such a disease or condition;
 exhibit a favorable therapeutic profile (e.g., safety, efficacy, and stability).

In certain embodiments, compounds of the invention are Raf kinase inhibitors. In certain exemplary embodiments, compounds of the invention are Raf inhibitors. In certain exemplary embodiments, compounds of the invention have $^{Cell}IC_{50}$ values $\leq 100$ µM. In certain other embodiments, compounds of the invention have $^{Cell}IC_{50}$ values $\leq 75$ µM. In certain other embodiments, compounds of the invention have $^{Cell}IC_{50}$ values $\leq 50$ µM. In certain other embodiments, compounds of the invention have $^{Cell}IC_{50}$ values $\leq 25$ µM. In certain other embodiments, compounds of the invention have $^{Cell}IC_{50}$ values $\leq 10$ µM. In certain other embodiments, compounds of the invention have $^{Cell}IC_{50}$ values $\leq 7.5$ µM. In certain other embodiments, of the invention compounds have $^{Cell}IC_{50}$ values $\leq 5$ µM. In certain other embodiments, of the invention compounds have $^{Cell}IC_{50}$ values $\leq 2.5$ µM. In certain other embodiments, of the invention compounds have $^{Cell}IC_{50}$ values $\leq 1$ µM. In certain other embodiments, of the invention compounds have $^{Cell}IC_{50}$ values $\leq 800$ nM. In certain other embodiments, of the invention compounds have $^{Cell}IC_{50}$ values $\leq 600$ nM. In certain other embodiments, inventive compounds have $^{Cell}IC_{50}$ values $\leq 500$ nM. In certain other embodiments, compounds of the invention have $^{Cell}IC_{50}$ values $\leq 300$ nM. In certain other embodiments, compounds of the invention have $^{Cell}IC_{50}$ values $\leq 200$ nM. In certain other embodiments, of the invention compounds have $^{Cell}IC_{50}$ values $\leq 100$ nM.

In yet another aspect, a method for the treatment or lessening the severity of an Raf-mediated disease or condition is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a Raf-mediated disease or condition. The compounds and compositions, according to the method of the present invention, may be administered using any amount and any route of administration effective for treating or lessening the severity of a Raf-mediated disease or condition. The exact amount required will vary from subject to subject, depending on the species, age, and general condition of the subject, the severity of the infection, the particular agent, its mode of administration, and the like. In certain embodiments, compounds of the invention are formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds of the invention are Raf kinase inhibitors, and thus, without wishing to be bound by any particular theory, the compounds and compositions are particularly useful for treating or lessening the severity of a disease, condition, or disorder where activation of Raf kinase is implicated in the disease, condition, or disorder. When activation of Raf kinase is implicated in a particular disease, condition, or disorder, the disease, condition, or disorder may also be referred to as a "Raf-mediated disease". Accordingly, in another aspect, the present invention provides a method for treating or lessening the severity of a disease, condition, or disorder where activation of Raf kinase is implicated in the disease state.

The activity of a compound utilized in this invention as an Raf kinase inhibitor, may be assayed in vitro, in vivo, ex vivo, or in a cell line. In vitro assays include assays that determine inhibition of either the phosphorylation activity or ATPase activity of activated Raf. Alternate in vitro assays quantitate the ability of the inhibitor to bind to Raf. Inhibitor binding may be measured by radiolabelling the inhibitor (e.g., synthesizing the inhibitor to include a radioisotope) prior to binding, isolating the inhibitor/Raf, complex and determining the amount of radiolabel bound. Alternatively, inhibitor binding may be determined by running a competition experiment where new inhibitors are incubated with Raf bound to known radioligands.

The term "measurably inhibit", as used herein means a measurable change in Raf activity between a sample comprising said composition and a Raf kinase and an equivalent sample comprising Raf kinase in the absence of said composition.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, compound of the invention may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, other therapies, chemotherapeutic agents, or other anti-proliferative agents may be combined with the compounds of this invention to treat proliferative diseases and cancer. Examples of therapies or anticancer agents that may be used in combination with the inventive anticancer agents of the present invention include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs.

Examples of chemotherapeutic anticancer agents that may be used as second active agents in combination with compounds of the invention include, but are not limited to, alkylating agents (e.g. mechlorethamine, chlorambucil, cyclophosphamide, melphalan, ifosfamide), antimetabolites (e.g., methotrexate), purine antagonists and pyrimidine antagonists (e.g. 6-mercaptopurine, 5-fluorouracil, cytarabine, gemcitabine), spindle poisons (e.g., vinblastine, vincristine, vinorelbine, paclitaxel), podophyllotoxins (e.g., etoposide, irinotecan, topotecan), antibiotics (e.g., doxorubicin, daunorubicin, bleomycin, mitomycin), nitrosoureas (e.g., carmustine, lomustine), inorganic ions (e.g., platinum complexes such as cisplatin, carboplatin), enzymes (e.g., asparaginase), hormones (e.g., tamoxifen, leuprolide, flutamide, and megestrol), topoisomerase II inhibitors or poisons, EGFR (Her1, ErbB-1) inhibitors (e.g., gefitinib), antibodies (e.g., rituximab), IMIDs (e.g., thalidomide, lenalidomide), various targeted agents (e.g., HDAC inhibitors such as vorinostat, Bcl-2 inhibitors, VEGF inhibitors); proteasome inhibitors (e.g., bortezomib), cyclin-dependent kinase inhibitors, and dexamethasone.

For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix).

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory agents, including immunosuppressive agents, such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinson's agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from composition containing a compound of the invention, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting Raf activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Raf kinase activity in a biological sample is useful for a variety of purposes that are known to one of skill in the art. Examples of such purposes include, but are not limited to, blood transfusion, organ-transplantation, biological specimen storage, and biological assays.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Examples

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Synthesis of the Pyrimidine ("Left-Side") Groups

Scheme 1.

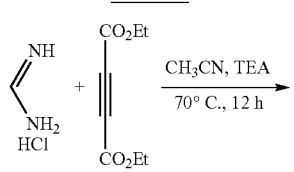

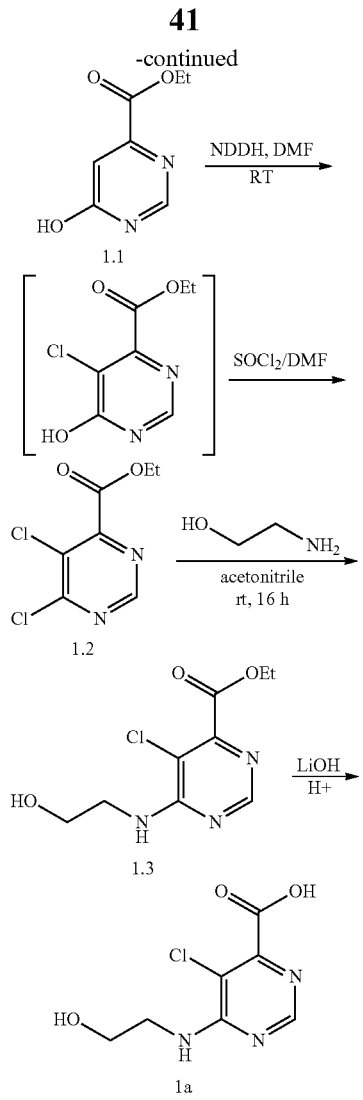

Synthesis of Compound 1.1.

To a stirred solution of diethyl acetylenedicarboxylate (20 g, 0.117 mol) and formamidine hydrochloride (9.4 g, 0.117 mol) in acetonitrile (400 mL) was added triethylamine (16.3 mL, 0.117 mol) dropwise at room temperature (RT) and the reaction mixture was heated at reflux for 16 hours (hr). The reaction mixture was cooled to 0° C. and the obtained solid was filtered and purified by silica gel column chromatography to furnish compound 1.1 (11 g, 55.6%). $^1$H NMR (200 MHz, DMSO-$d_6$): δ 12.7 (bs, 1H), 8.25 (s, 1H), 6.85 (s, 1H), 4.28 (q, J=7 Hz, 2H), 1.25 (t, J=7 Hz, 3H); LCMS: m/z 169 $[M+1]^+$.

Synthesis of Compound 1.2.

To a stirred solution of compound 1.1 (8 g, 0.047 mol) in DMF (22 mL) was added 1,3-dichloro-5,5-dimethyl hydantoin (NDDH; 5.6 g, 0.028 mol) in DMF (14.7 ml) and the reaction mixture stirred at RT for 1 hr. After complete consumption of the starting material was observed by TLC analysis, the reaction mixture was cooled to 0° C. and $SOCl_2$ (5.3 mL, 0.062) was added dropwise. After warming to RT and stirring for 1 hr, the reaction mixture was diluted with water (120 mL) and extracted with ether (3×200 mL). The combined organic layers were dried ($Na_2SO_4$), concentrated under reduced pressure and purified by column chromatography to give compound 1.2 (4.6 g, 40.7%). $^1$H NMR (200 MHz, DMSO-$d_6$): δ 9.15 (s, 1H), 4.42 (q, J=7 Hz, 2H), 1.41 (t, J=7 Hz, 3H). $^{13}$C NMR (125 MHz, DMSO-$d_6$): 162.293, 159.731, 156.087, 155.993, 126.329, 62.962 and 13.803. LCMS: m/z: m/z 221 $[M+1]^+$.

Synthesis of Compound 1.3.

To a stirred solution of compound 1.2 (500 mg, 0.0022 mol) in 1,4-dioxane (5 mL) was added ethanolamine (152 mg, 0.0024 mol) and the reaction mixture was stirred at RT overnight. The progress of the reaction was monitored by TLC. After consumption of the starting material, the reaction mixture was concentrated under reduced pressure and purified by column chromatography (5% MeOH/DCM) to give compound 1.3 (220 mg, 40%). $^1$H NMR (200 MHz, DMSO-$d_6$): δ 8.40 (s, 1H), 7.70 (bs, N—H), 4.78 (bs, O—H), 4.28 (q, J=7.4 Hz, 2H), 3.58-3.42 (m, 4H), 1.25 (t, J=7.4 Hz, 3H); LCMS: m/z 246 $[M+1]^+$.

Synthesis of Compound 1a.

To a solution of ester 1.3 in THF (10 equiv.) and water (30 equiv.) was added LiOH (2.0 equiv.). The reaction mixture was stirred at RT for 1-3 hr and monitored by LCMS. THF was removed under reduced pressure and the resulting aqueous solution was neutralized with 2 N HCl. Precipitates were collected and dried to give the corresponding acid. In cases where precipitation did not occur, the mixture was lyophilized to give a crude product which was used for coupling without further purification.

Compounds 1a-1t. Using different amines and compound 1.2, the following acids can be synthesized by the general method depicted in Scheme 1:

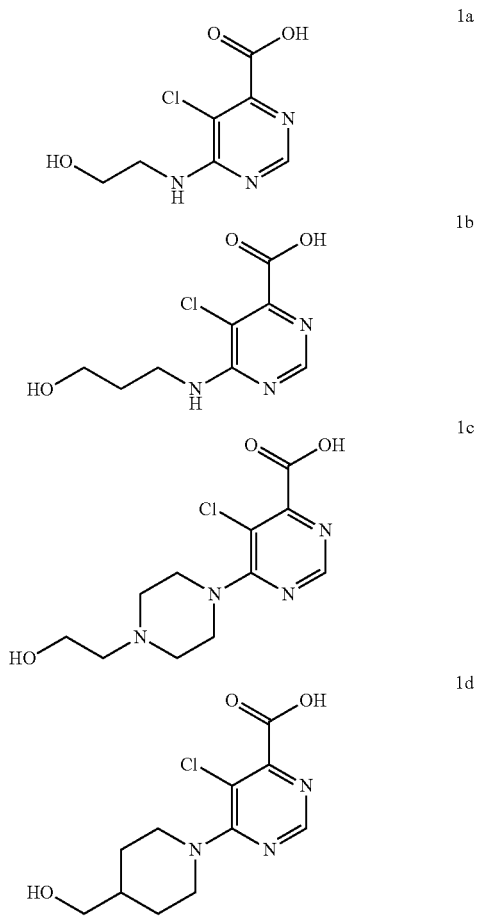

-continued
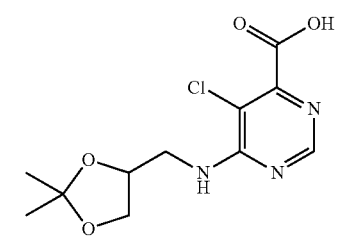 [SMILES: CC1(C)OCC(CNc2ncnc(C(=O)O)c2Cl)O1]
1e
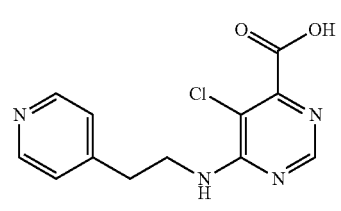 [SMILES: O=C(O)c1ncnc(NCCc2ccncc2)c1Cl]
1f
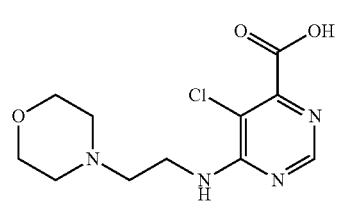 [SMILES: O=C(O)c1ncnc(NCCN2CCOCC2)c1Cl]
1g
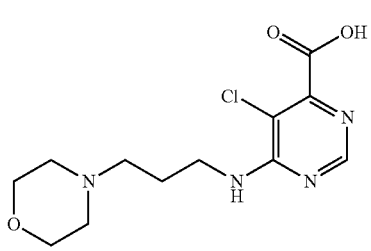 [SMILES: O=C(O)c1ncnc(NCCCN2CCOCC2)c1Cl]
1h
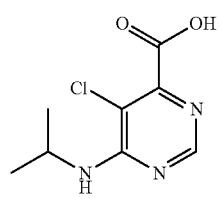
1i
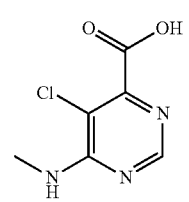
1j
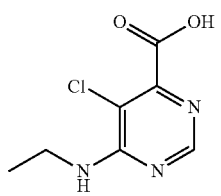
1k
-continued
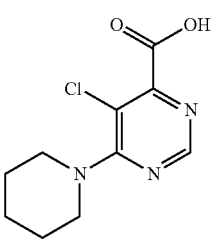 [SMILES: O=C(O)c1ncnc(N2CCCCC2)c1Cl]
1l
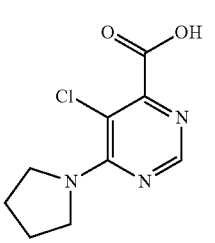 [SMILES: O=C(O)c1ncnc(N2CCCC2)c1Cl]
1m
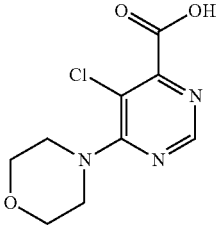 [SMILES: O=C(O)c1ncnc(N2CCOCC2)c1Cl]
1n
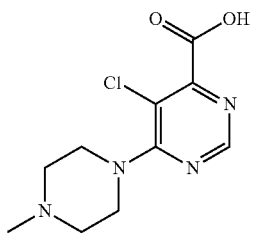 [SMILES: CN1CCN(c2ncnc(C(=O)O)c2Cl)CC1]
1o
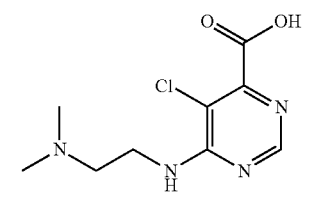 [SMILES: CN(C)CCNc1ncnc(C(=O)O)c1Cl]
1p
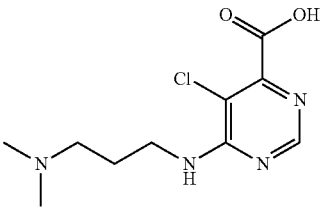 [SMILES: CN(C)CCCNc1ncnc(C(=O)O)c1Cl]
1q
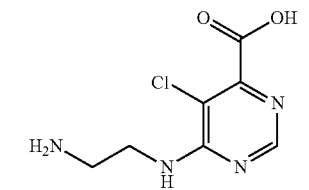 [SMILES: NCCNc1ncnc(C(=O)O)c1Cl]
1r -continued

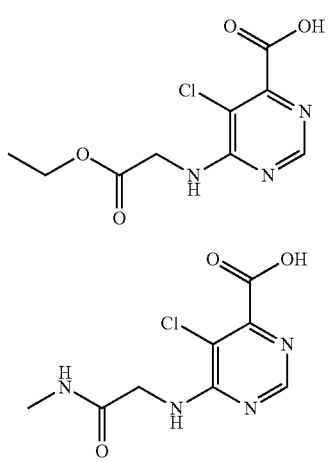

Scheme 2.

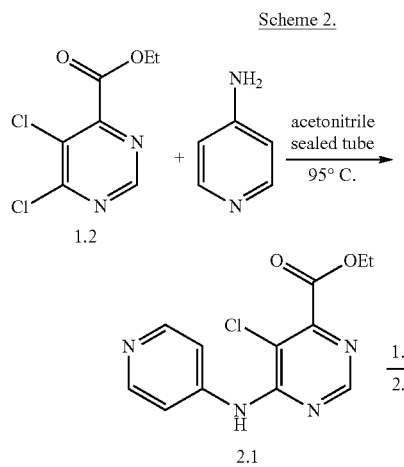

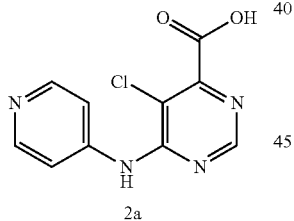

Synthesis of Compound 2.1.

A mixture of compound 1.2 (250 mg, 0.0011 mol) and 4-amino pyridine (106 mg, 0.0011 mol) in acetonitrile (2.5 mL) was stirred in a sealed tube at 95° C. for 3 hr. After the reaction was judged to be complete by TLC analysis, the reaction mixture was cooled to 0° C. The obtained solid was filtered and purified by column chromatography (50% ethyl acetate/hexane) to give compound 2.1 (100 mg, 33%). $^1$H NMR (500 MHz, CDCl$_3$): δ 8.78 (s, 1H), 8.57 (d, J=7.0 Hz, 2H), 7.70 (d, J=6.0 Hz, 2H), 7.60 (bs, N—H), 4.50 (q, J=7.0 Hz, 4H), 1.43 (t, J=7.0 Hz, 3H); LCMS: m/z 279 [M+1]$^+$.

Synthesis of Compound 2a.

Compound 2.1 was hydrolyzed as described for compound 1 to afford 2 which was used without further purification. $^1$H NMR (500 MHz, DMSO-d$_6$): δ 10.50 (bs, 1H), 8.88-8.36 (m, 5H). LCMS: 251 [M+1]$^+$.

Compounds 2a-2g. Using different anilines and compound 1.2, the following acids can be synthesized as by the general method depicted in Scheme 2:

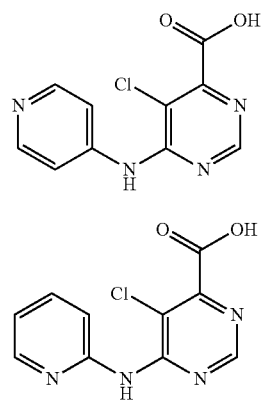

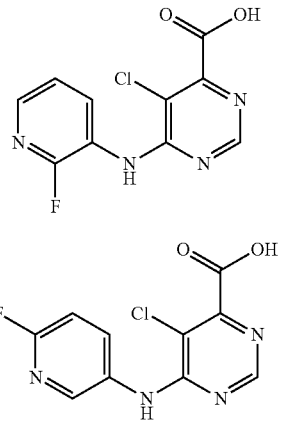

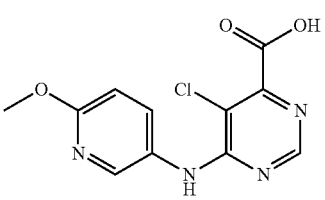 [SMILES: COc1ccc(Nc2ncnc(C(=O)O)c2Cl)cn1]

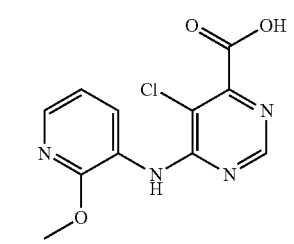 [SMILES: COc1ncccc1Nc1ncnc(C(=O)O)c1Cl]

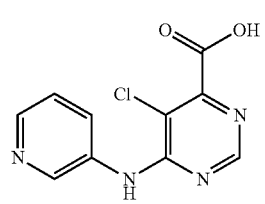 [SMILES: O=C(O)c1ncnc(Nc2cccnc2)c1Cl]

Scheme 3.

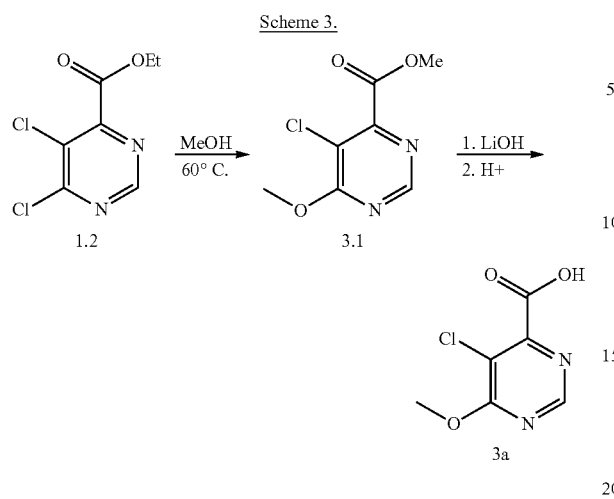

Synthesis of Compound 3.1.

A solution of compound 1.2 (250 mg, 0.00113 mol) in MeOH (5 mL) in a sealed tube was stirred at 60° C. overnight. After consumption of the starting material, MeOH was removed under reduced pressure. The obtained crude material was purified by column chromatography (30% ethyl acetate/hexanes) to give compound 3.1 (78 mg, 31%). $^1$H NMR (200 MHz, CD$_3$OD): δ 8.69 (s, 1H), 4.51 (s, 3H), 3.99 (s, 3H); LCMS: m/z 203 [M+1]$^+$.

Synthesis of Compound 3a.

Compound 3.1 was hydrolyzed as described for compound 1 to afford 3a as a crude product which was used without further purification. $^1$H NMR (200 MHz, DMSO-d$_6$): δ 8.58 (s, 1H), 3.98 (s, 3H); LCMS: 188 [M+1]$^+$.

Compounds 3a-3c. Using different alcohols and compound 1.2, the following acids can be synthesized as exemplified in Scheme 3:

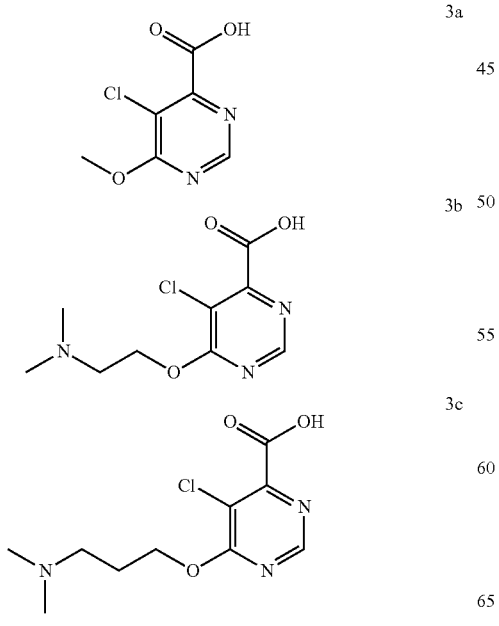

Scheme 4.

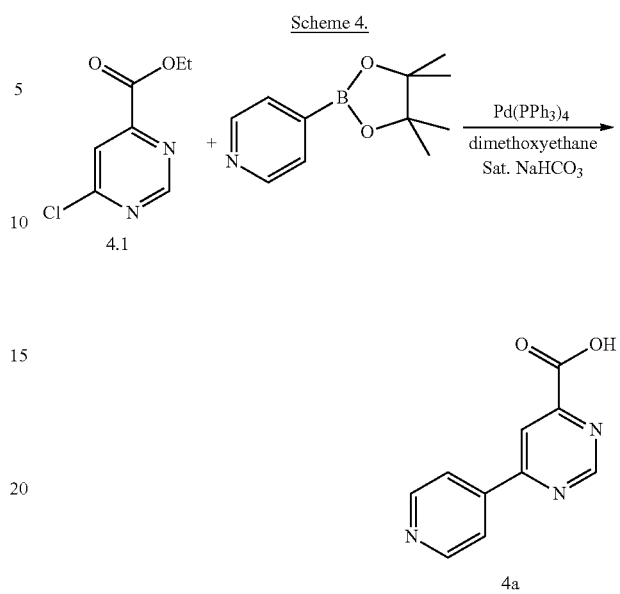

Synthesis of Compound 4.1 was synthesized using the approach shown in Scheme 1, except omitting the chlorination step using NDDH.

Synthesis of Compound 4a.

To a microwave vial was added 6-chloro-pyrimidine-4-carboxylic acid ethyl ester (250 mg, 0.0013 mol), 4-(4,4,5,5-tetramethyl-[1,3,2]dioxaborolan-2-yl)-pyridine (275 mg, 0.00134 mol), 1,2-dimethoxyethane (5.0 mL, 0.048 mol), saturated sodium bicarbonate solution (0.9 mL, 0.009 mol), and tetrakis(triphenylphosphine)palladium(0) (150 mg, 0.00013 mol). The vial was purged with nitrogen, and sealed with a rubber septum. The reaction mixture was heated in the microwave (300 watts, 110° C.) for 2 hr. LCMS indicated consumption of starting material. The major product was found to be the hydrolysis product [by LCMS (M+1=202)]. The reaction mixture was diluted with 50% MeOH/CH$_2$Cl$_2$ (20 mL), and filtered through Celite®. The filtrate was concentrated under reduced pressure and the resultant residue was triturated with water (3×20 mL). The aqueous mixture was collected and washed with ethyl acetate EtOAc (3×10 mL) to remove residual ligand. The solution was neutralized with 1N HCl and lyophilized to give acid 4 as a light purple powder (160 mg, 50%) which was used without further purification. LCMS: m/z 202 [M+1]$^+$.

Compounds 4a-4z. Using different boronic acids or esters, and compound 1.4, the following acids can be synthesized by the general method depicted in Scheme 4:

4b 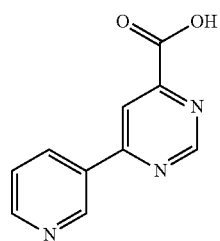 [SMILES: O=C(O)c1cc(-c2cccnc2)ncn1]
4c 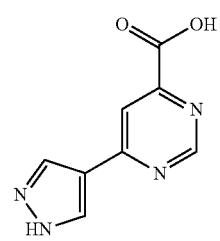 [SMILES: O=C(O)c1cc(-c2cn[nH]c2)ncn1]
4d 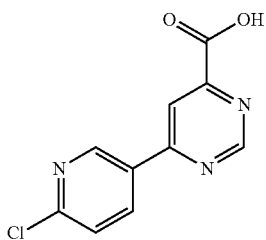 [SMILES: O=C(O)c1cc(-c2ccc(Cl)nc2)ncn1]
4e 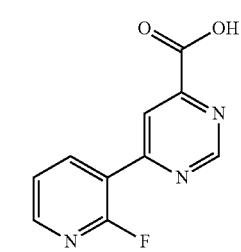 [SMILES: O=C(O)c1cc(-c2cccnc2F)ncn1]
4f 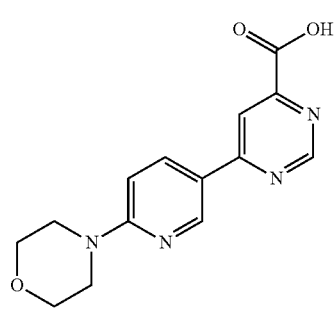 [SMILES: O=C(O)c1cc(-c2ccc(N3CCOCC3)nc2)ncn1]
4g 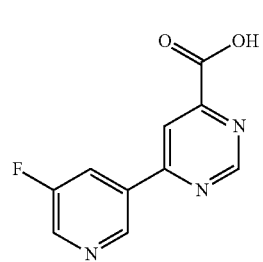
4h 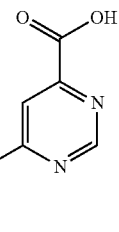
4i 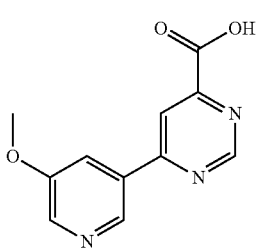 [SMILES: COc1cncc(-c2cc(C(=O)O)ncn2)c1]
4j 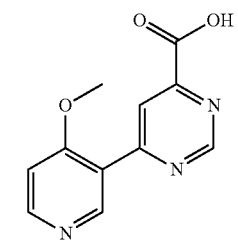 [SMILES: COc1ccncc1-c1cc(C(=O)O)ncn1]
4k 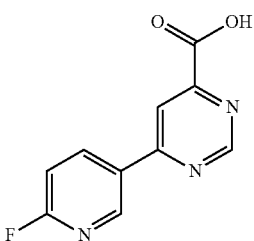 [SMILES: O=C(O)c1cc(-c2ccc(F)nc2)ncn1]
4l 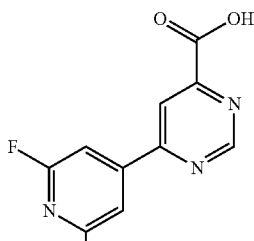
4m -continued
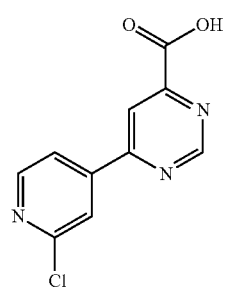 [SMILES: O=C(O)c1cc(-c2ccnc(Cl)c2)ncn1]
4n
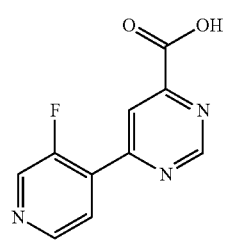 [SMILES: O=C(O)c1cc(-c2ccncc2F)ncn1]
4o
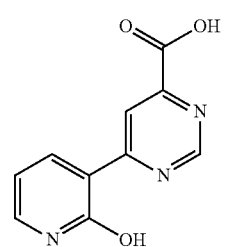 [SMILES: O=C(O)c1cc(-c2cccnc2O)ncn1]
4p
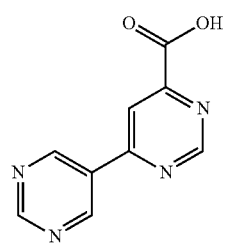 [SMILES: O=C(O)c1cc(-c2cncnc2)ncn1]
4q
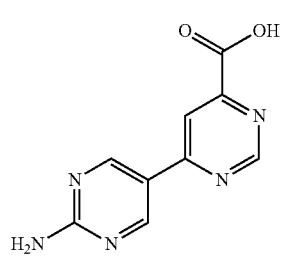 [SMILES: Nc1ccc(-c2cc(C(=O)O)ncn2)cn1]
4r
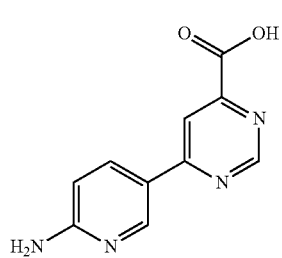
4s
-continued
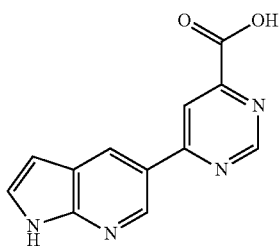 [SMILES: O=C(O)c1cc(-c2cnc3[nH]ccc3c2)ncn1]
4t
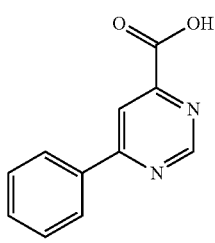 [SMILES: O=C(O)c1cc(-c2ccccc2)ncn1]
4u
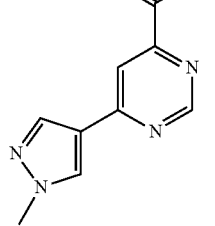
4v
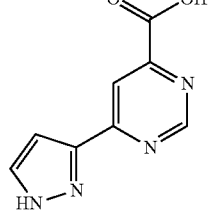
4w
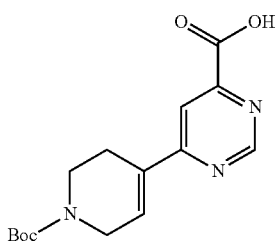
4z
Scheme 5.
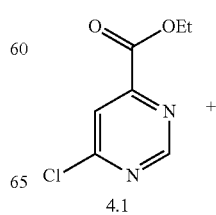
4.1

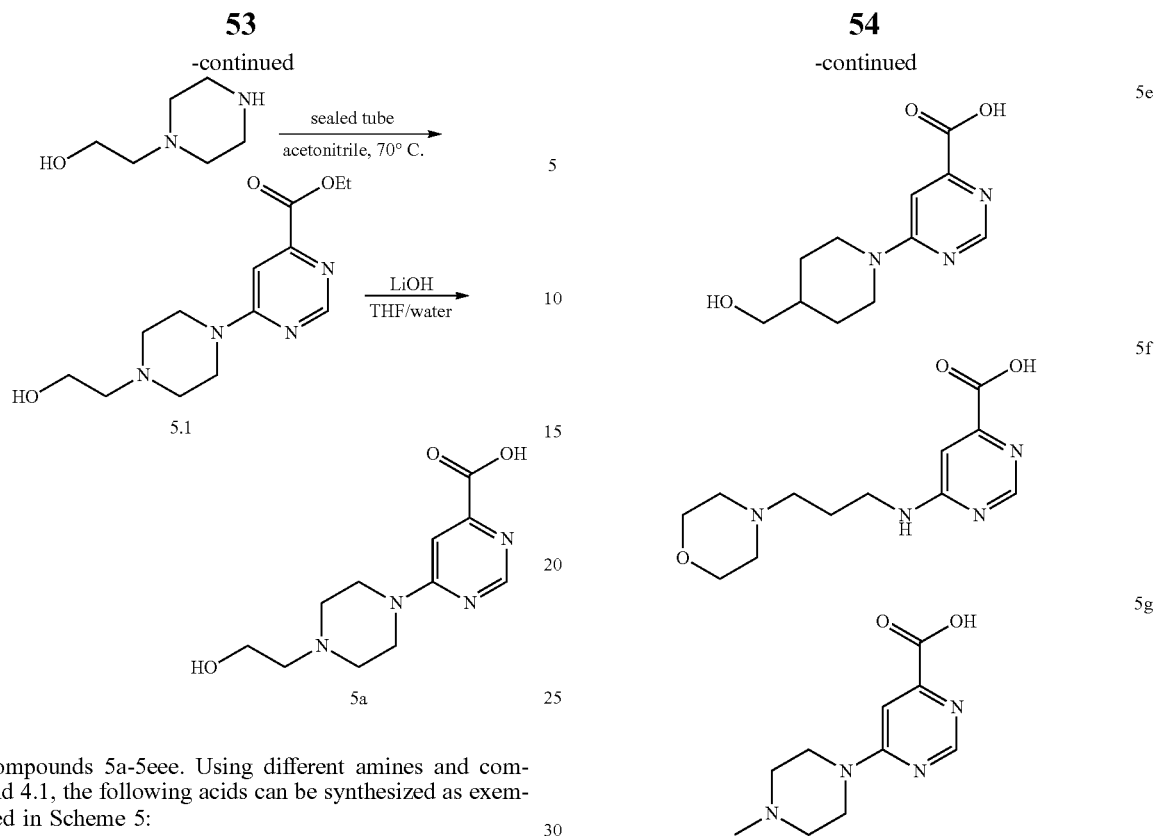
Compounds 5a-5eee. Using different amines and compound 4.1, the following acids can be synthesized as exemplified in Scheme 5:
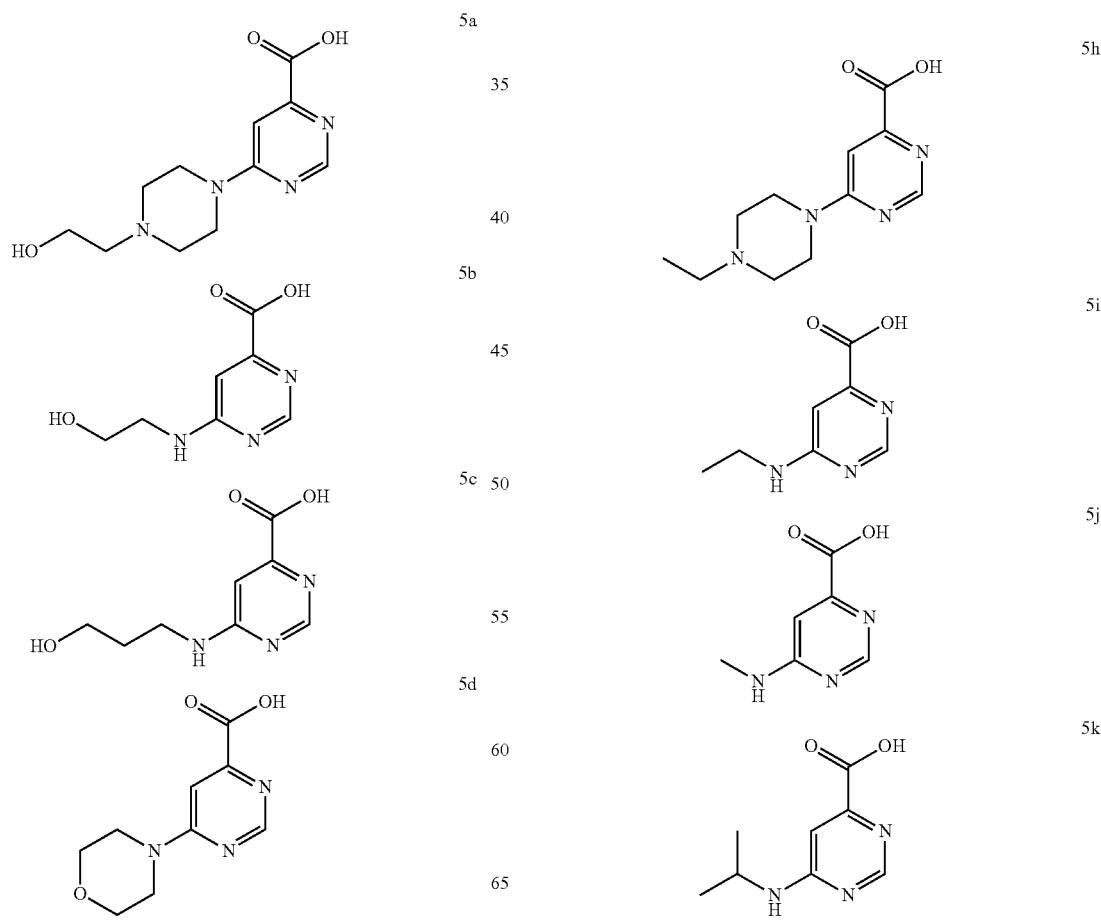

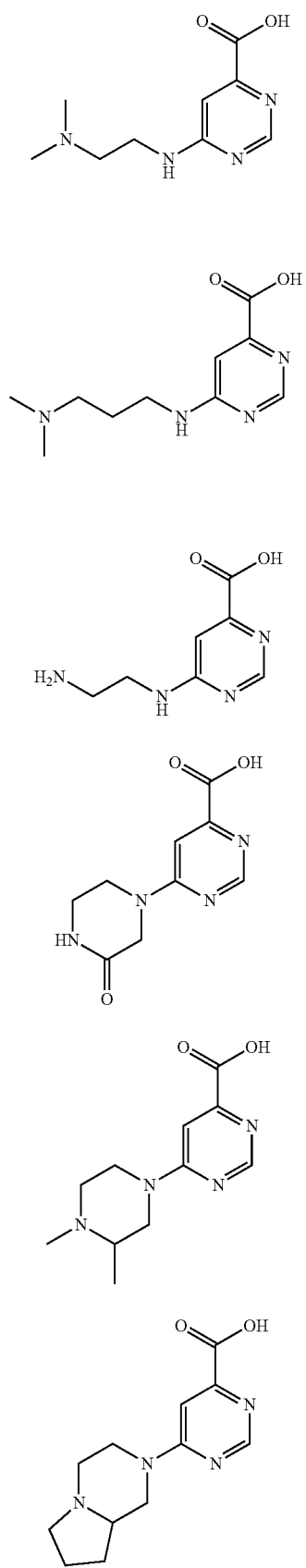
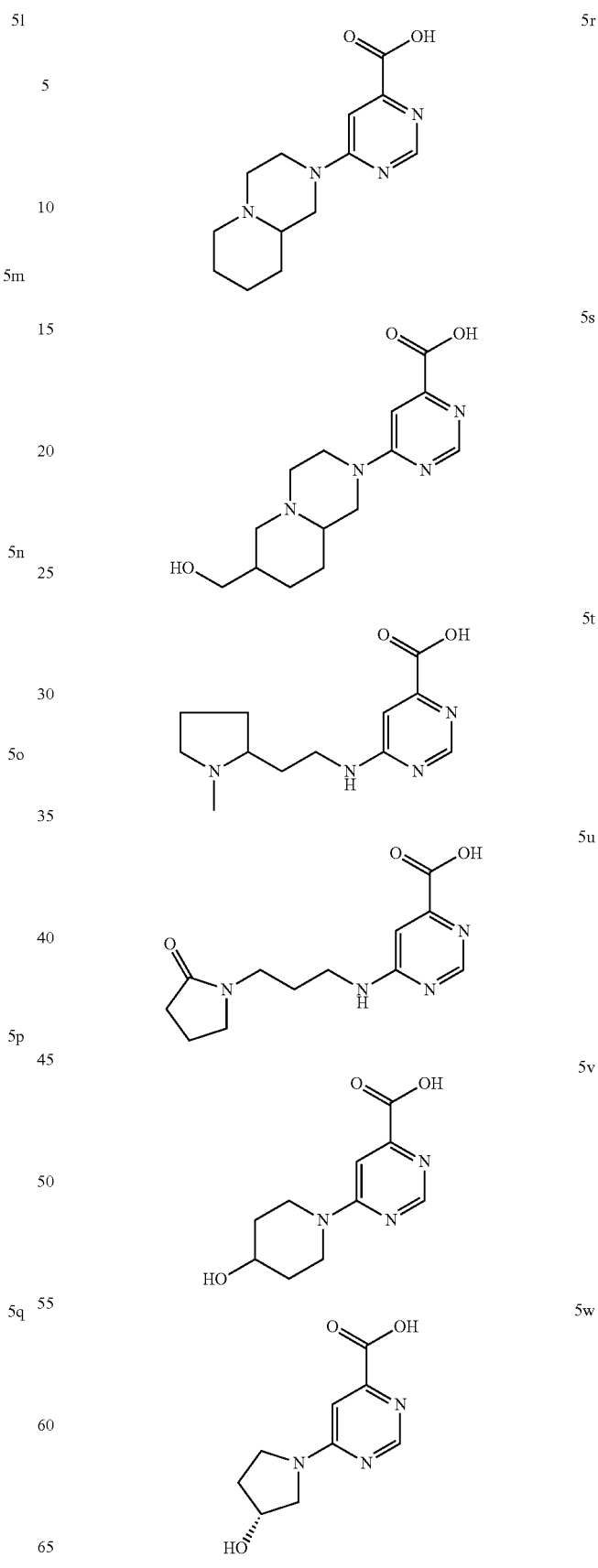

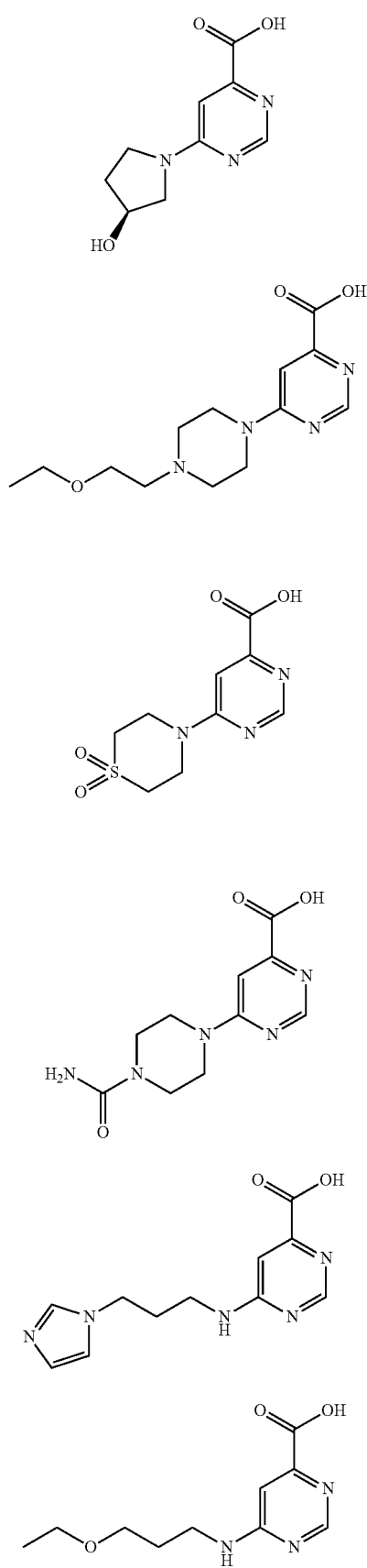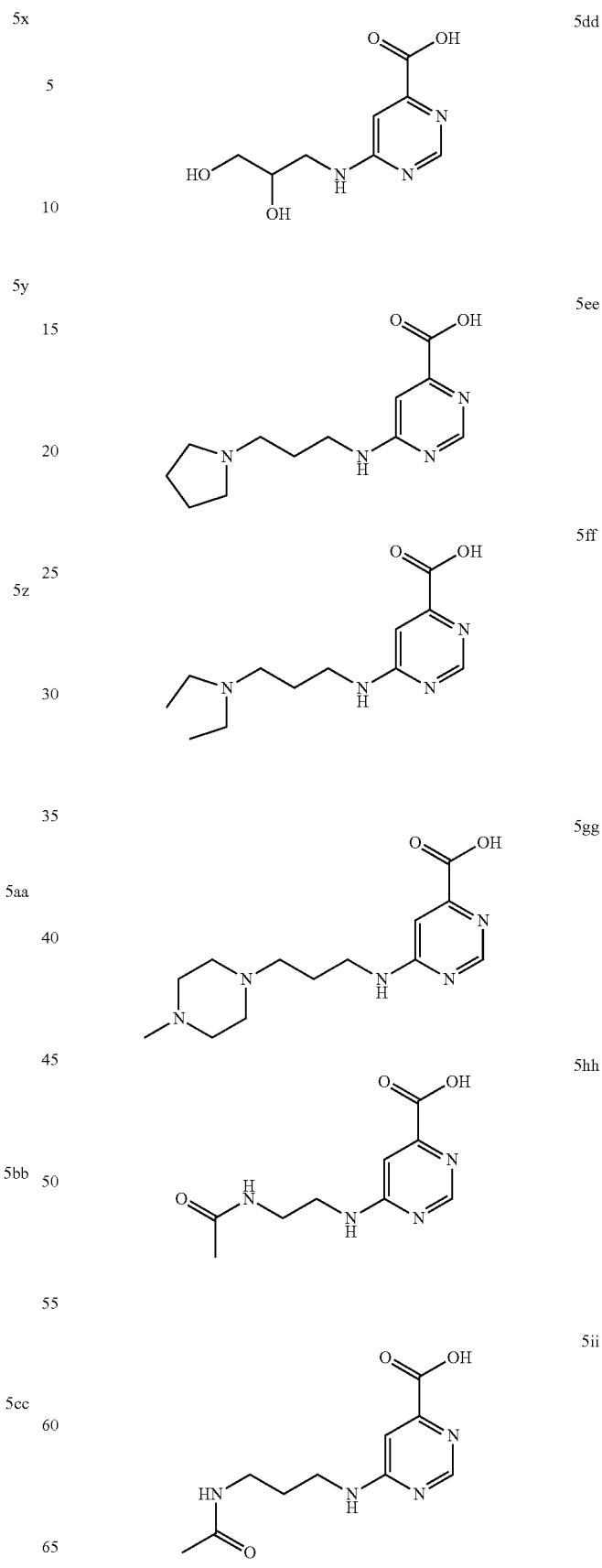

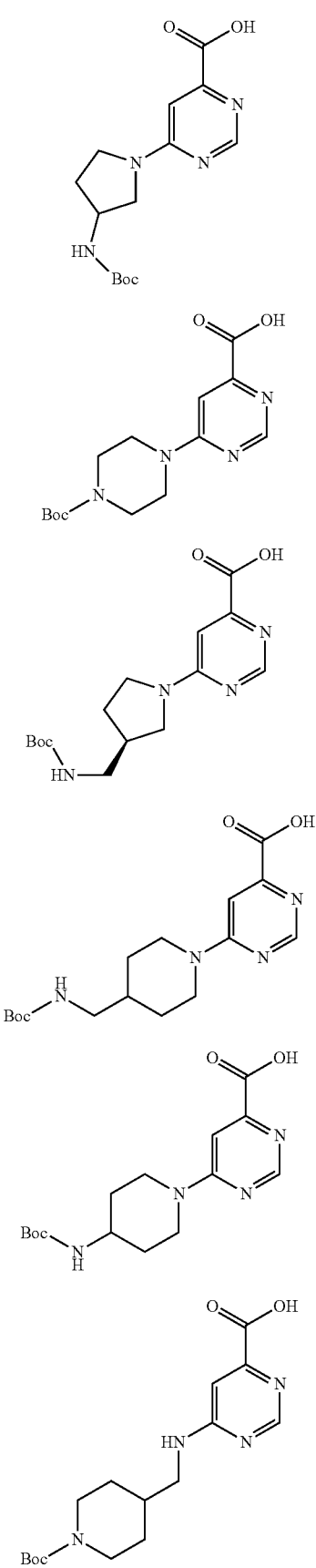

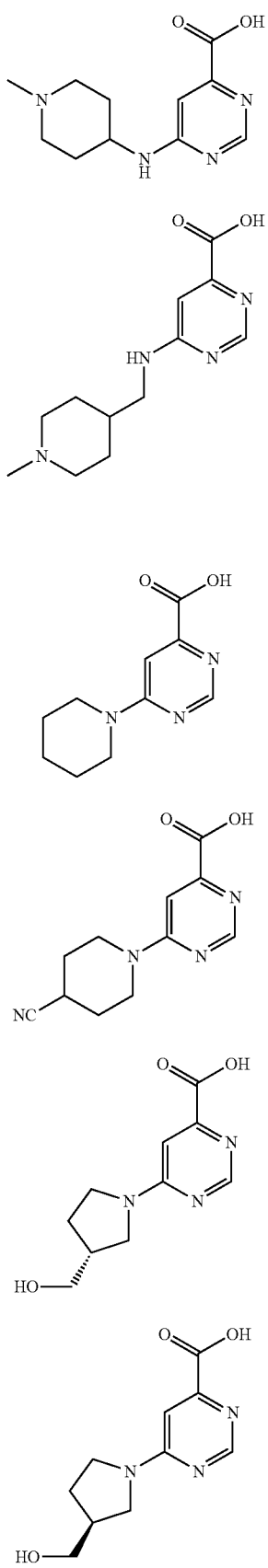
5xx
5yy
5zz
5aaa
5bbb
5ccc
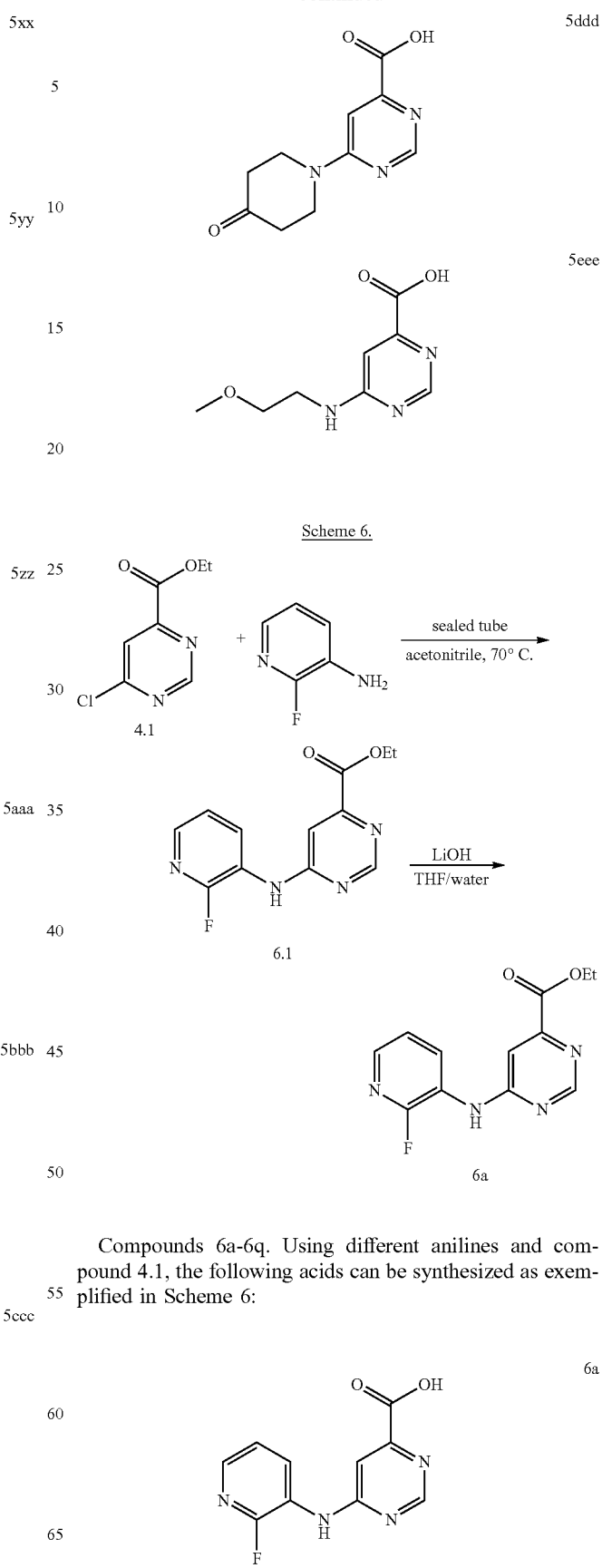
5ddd
5eee
Scheme 6.
Compounds 6a-6q. Using different anilines and compound 4.1, the following acids can be synthesized as exemplified in Scheme 6:
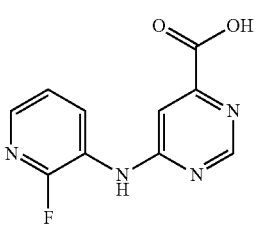
6a

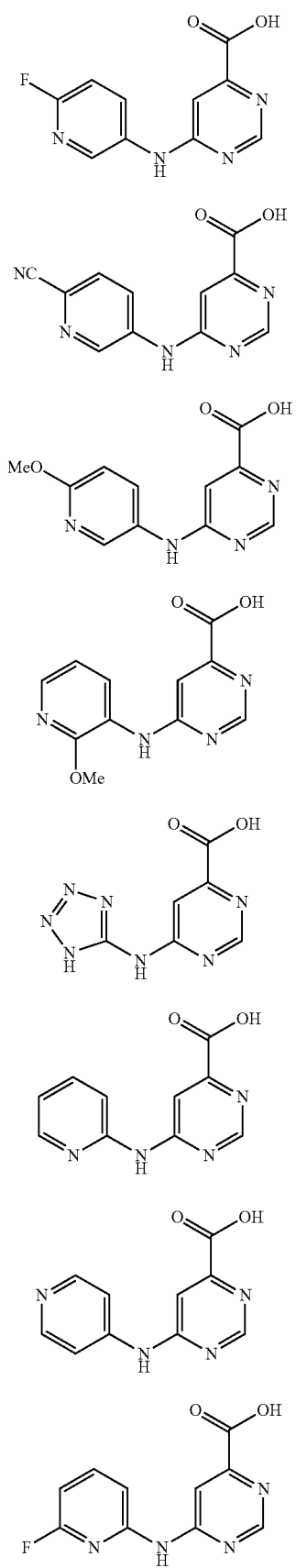
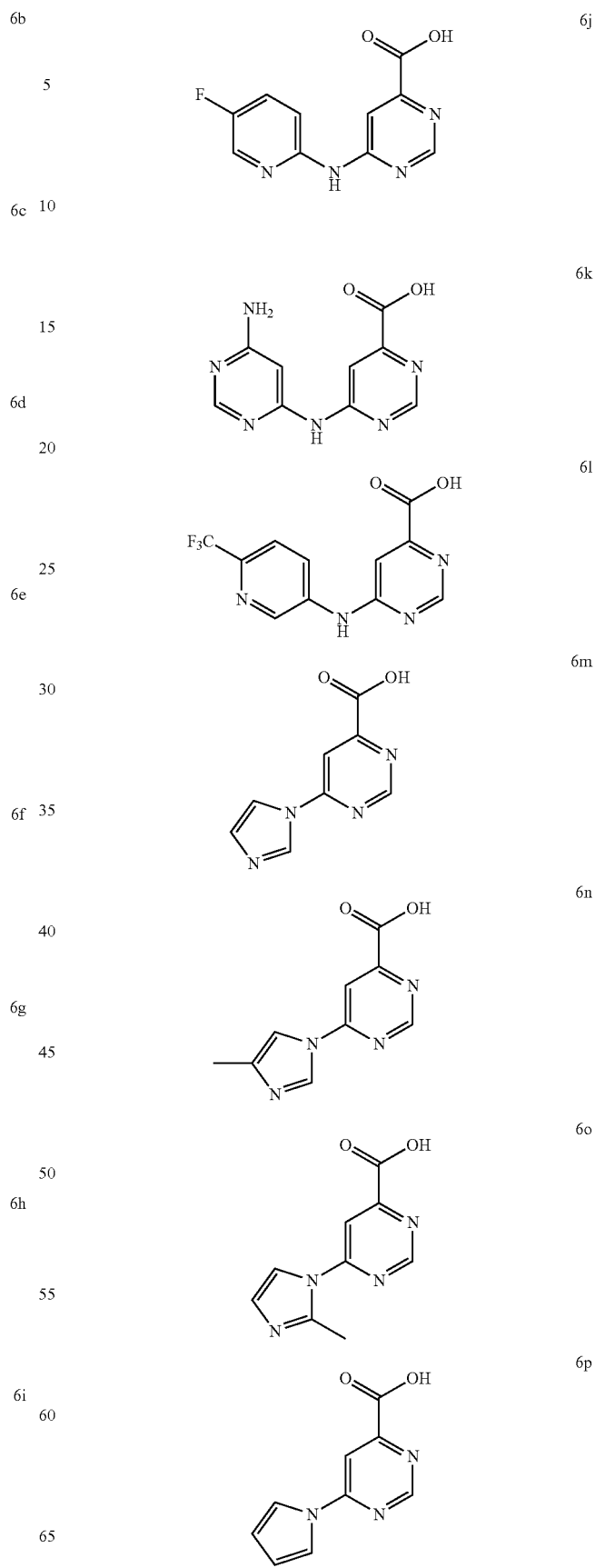

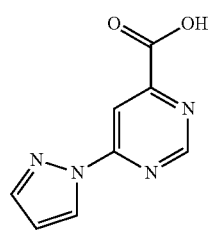

6q

Scheme 7.

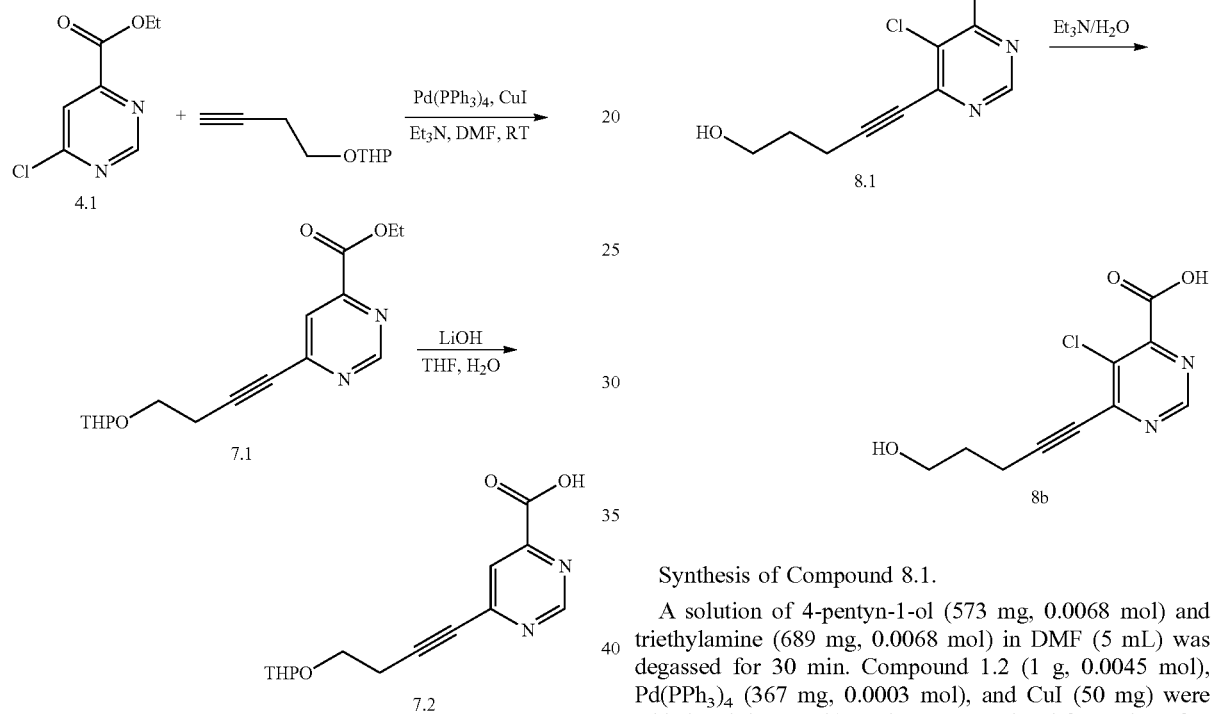

Scheme 8.

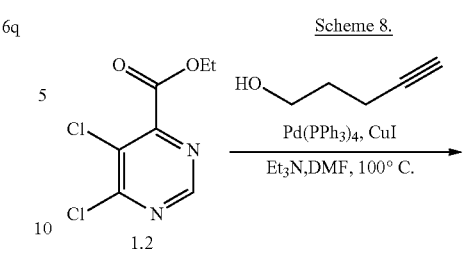

Synthesis of Compound 7.1.

A solution of THP-protected homopropargyl alcohol (500 mg, 0.00324 mol) and triethylamine (0.4 mL, 0.00324 mol) in DMF (5 mL) was degassed for 30 min. Compound 4.1 (600 mg, 0.00324 mol), Pd(PPh$_3$)$_4$ (260 mg, 0.0002 mol) and CuI (20 mg) were added and the reaction mixture was stirred at RT for 16 hr. The reaction mixture was diluted with water (100 mL) and extracted with EtOAc (3×50 mL). The combined organic layers were washed with cold water (100 mL), dried over Na$_2$SO$_4$, concentrated under reduced pressure and purified by column chromatography to give 7.1 (350 mg, 42%). $^1$H NMR (200 MHz, CDCl$_3$): δ 9.30 (s, 1H), 8.00 (s, 1H), 4.70 (t, J=2.2 Hz, 1H), 4.52 (q, J=7.2 Hz, 2H), 4.02-3.75 (m, 2H), 3.75-3.50 (m, 2H), 2.82 (t, J=6.8 Hz, 2H), 1.82-1.41 (m, 4H); LCMS: m/z 304 [M+1]$^+$.

Synthesis of Compound 7.2.

Compound 7.1 was hydrolyzed as described for compound 1 to afford 7.2 which was used without further purification. $^1$H NMR (200 MHz, DMSO-d$_6$): δ 9.07 (s, 1H), 7.67 (s, 1H), 4.66 (s, 1H), 3.79-3.56 (m, 4H). LCMS: m/z 276 [M+1]$^+$.

Synthesis of Compound 8.1.

A solution of 4-pentyn-1-ol (573 mg, 0.0068 mol) and triethylamine (689 mg, 0.0068 mol) in DMF (5 mL) was degassed for 30 min. Compound 1.2 (1 g, 0.0045 mol), Pd(PPh$_3$)$_4$ (367 mg, 0.0003 mol), and CuI (50 mg) were added and the reacti(on mixture was stirred for 20 hr. After consumption of the starting material, the reaction mixture was diluted with water (100 mL) and extracted with EtOAc (3×50 mL). The combined organic layers were washed with cold water (100 mL), dried over Na$_2$SO$_4$, concentrated under reduced pressure and purified by column chromatography (20% ethyl acetate/hexane) to give compound 8.1 (848 mg, 69%). $^1$H NMR (500 MHz, DMSO-d$_6$): δ 9.18 (s, 1H), 4.60 (t, J=5.5 Hz, O—H), 4.43 (q, J=7.5 Hz, 2H), 3.53 (t, J=6.5 Hz, 2H), 2.65 (t, J=6.5 Hz, 2H), 1.76-1.71 (m, 2H), 1.32 (t, J=7.5 Hz, 3H); LCMS: m/z 268.9 [M+1]$^+$.

Synthesis of Compound 8b.

To a suspension of compound 8.1 (50 mg, 0.0011 mol) in water (2 mL) was added triethylamine (56 mg, 0.0005 mol) and the reaction mixture was stirred at RT for 16 h. After completion of the starting material (by TLC), water was removed under reduced pressure and co-distilled with toluene (2×5 mL) to afford compound 8 (200 mg), which was used without any further purification.

Compounds 8a-8g. Using different propargyl alcohols and compound 4.1, the following acids can be synthesized as exemplified in Scheme 8.

Scheme 8
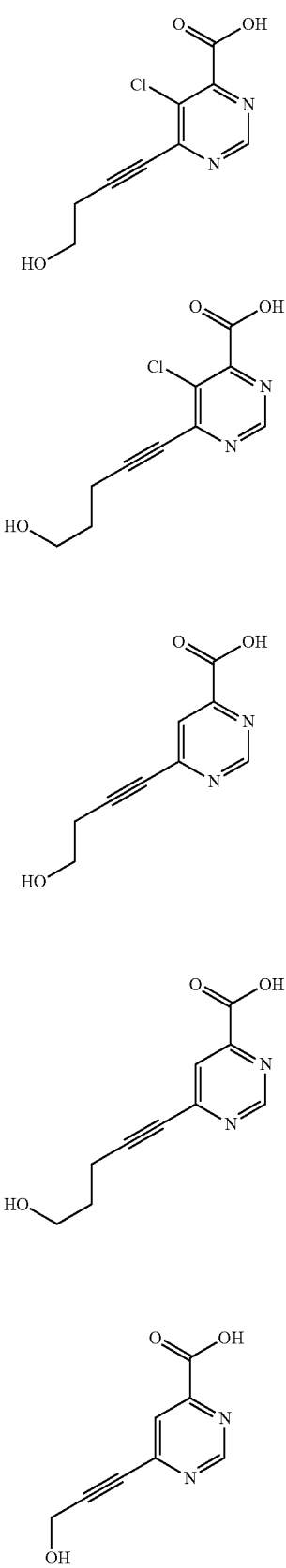
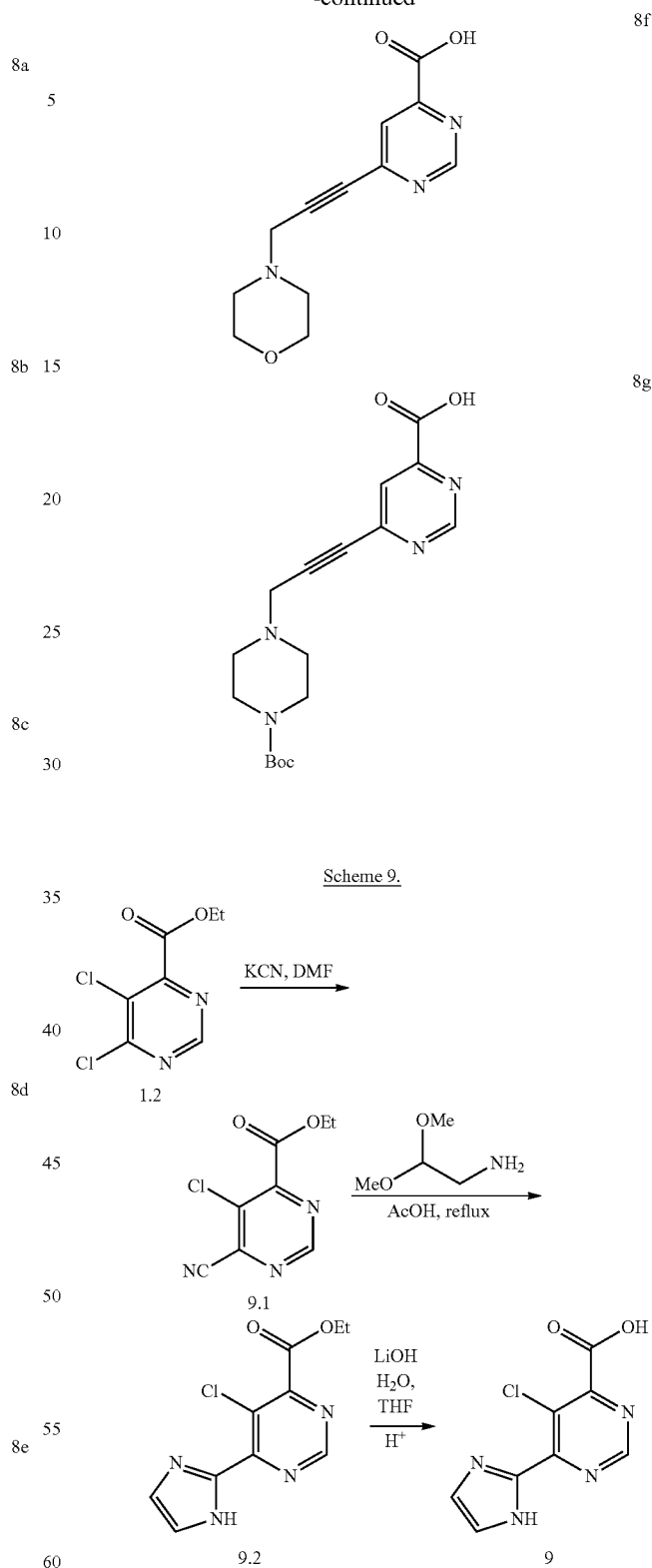
Synthesis of Compound 9.1.
To a solution of compound 1.2 (1250 mg, 0.00566 mol) in DMF (4 mL) was added potassium cyanide (520 mg, 0.0079 mol). The reaction mixture was stirred for 3 days. Additional KCN (360 mg) was added and the reaction mixture was stirred for another 24 hr. The mixture was diluted with EtOAc (150 mL) and washed with water (100 mL). The aqueous phase was extracted with EtOAc (100 mL). The organic phases were combined and washed with brine, dried over sodium sulfate and concentrated to give compound 9.1 (650 mg, 54%) as a dark brown oil. LCMS: m/z 212 [M+1]+.

Synthesis of Compound 9.2.

A vial was charged with compound 9.1 (35 mg, 0.00016 mol), acetic acid (0.7 mL, 0.01 mol), and aminoacetaldehyde dimethyl acetal (50 mg, 0.00047 mol). The reaction mixture was purged with nitrogen and stirred at 110° C. overnight. The solvent was removed and the crude product was purified on Gilson reverse phase HPLC to give compound 9.2 (15 mg, 38%) as a light brown oil. LCMS: m/z 253/255 [M+1/M+3]

Synthesis of Compound 9.

Compound 9.2 was hydrolyzed as described for compound 1 to give 9 which was used without further purification.

NaHCO$_3$ was added to the residue and the resultant neutral aqueous mixture was extracted with EtOAc (3×50 mL). The combined organic layers were dried over MgSO$_4$ and concentrated under reduced pressure. The crude material was purified by column chromatography (0-60% ethyl acetate/hexanes) to give compound 10.2 (0.6 g, 70%) as off-white crystals.

Synthesis of Compound 10.

Compound 10.2 was hydrolyzed as described for compound 1 to give acid 10, which was used without further purification. $^1$H NMR (400 MHz, Methanol-d$_4$): δ 8.21 (s, 1H); LCMS: 174 [M+1]+.

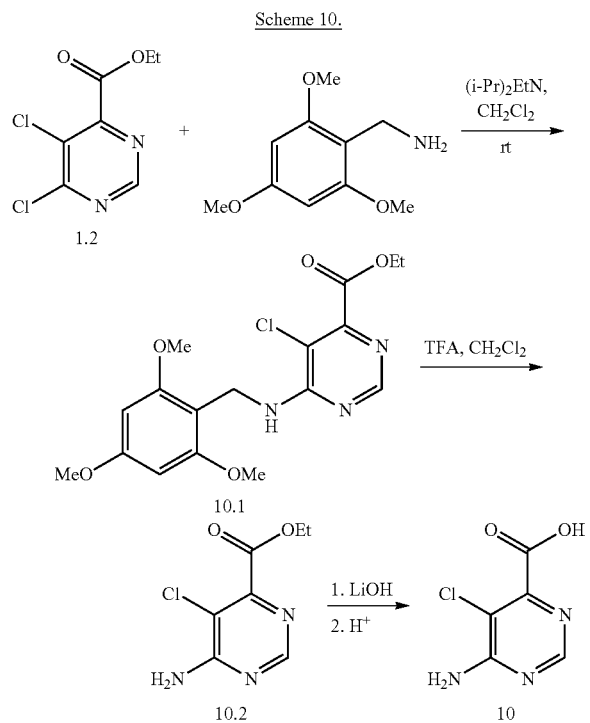

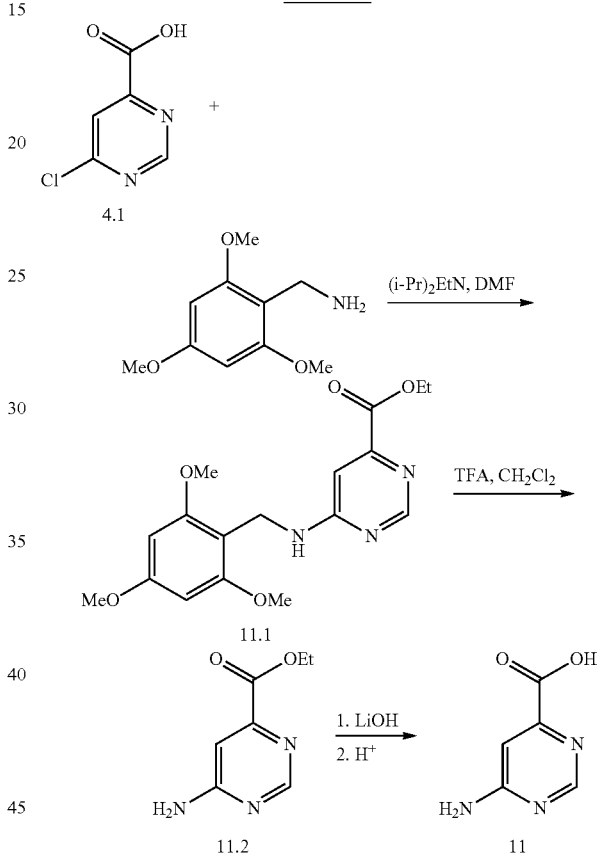

Synthesis of Compound 10.1.

To a solution of compound 1.2 (1.0 g, 0.0045 mol) in methylene chloride (6 mL) was added trimethoxybenzylamine hydrochloride (1.0 g, 0.0043 mol,) and diisopropylethylamine (1.5 mL, 0.0086 mol). The resulting mixture was stirred at RT for 3 hr. The reaction mixture was diluted with methylene chloride (80 mL) and washed 1 N HCl (2×) and brine (1×). The organic layer was dried over MgSO$_4$ and concentrated to give compound 10.1 (1.6 g, 99%) as a yellow solid which was used without further purification. LCMS: m/z 382 [M+1]+.

Synthesis of Compound 10.2.

To a stirred solution of compound 10.1 (1.6 g, 0.0042 mol) in DCM (5 mL) was added TFA (15 mL). The mixture was stirred at RT for 24 hr whereupon the solvent was removed under reduced pressure. Saturated aqueous Synthesis of Compound 11.

Using ester 4.1 as the starting material, compound 11 was synthesized according to scheme 11, following the procedure used for the synthesis of compound 10 (Scheme 10).

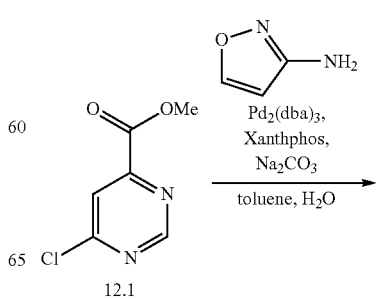

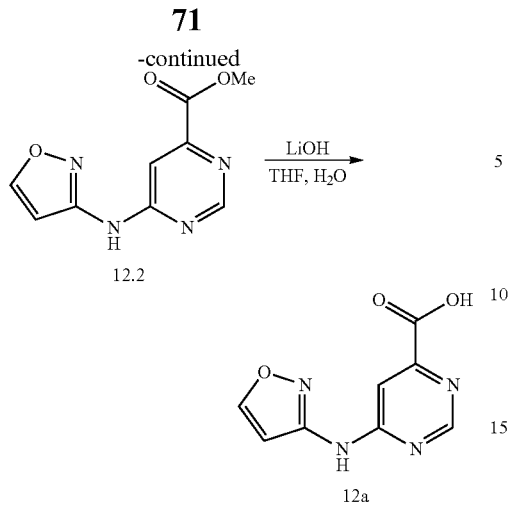

Synthesis of Compound 12.1:

Compound 12.1 was synthesized using a similar approach as for compound 4.1 (Scheme 4).

Synthesis of Compound 12.2.

To compound 12.1 (0.16 g, 0.91 mmol, 1.0 equiv), isoxazol-3-ylamine (92 mg, 1.1 mmol, 1.2 equiv), tris(dibenzylideneacetone)-dipalladium (21 mg, 0.023 mmol, 0.025 equiv), xantphos (39 mg, 0.068 mmol, 0.075 equiv), and Na$_2$CO$_3$ (133 mg, 1.4 mmol, 1.4 equiv) in toluene (3 mL) was added H$_2$O (16 μL, 0.91 mmol, 1.0 equiv). The reaction mixture was heated to 100° C. and stirred for 3 hr, whereupon it was cooled to RT. The mixture was filtered through Celite® and adsorbed onto SiO$_2$ gel. Purification by flash column chromatography (50-75-100% EtOAc/hexanes) afforded 12.2 (0.79 mg, 40%). LCMS: m/z: 221 [M+1]$^+$.

Synthesis of Compound 12a.

To a solution of ester 12.2 (79 mg, 0.36 mmol) in THF (1.5 mL) was added a solution of LiOH (17 mg, 0.72 mmol, 2.0 equiv) in H$_2$O (0.50 mL). The reaction mixture was stirred at RT for 18 hr. The reaction mixture was concentrated, and the residue was dissolved in MeOH (5 mL) and water (10 mL). The solution was frozen and lyophilized for 2 days to provide 12a (0.74 g, 100%, Li salt) as a white solid. LC-MS: m/z: 207 [M+1]$^+$.

Compounds 12a-12c. Using different aromatic amines and compound 12.1, the following acids can be synthesized as exemplified in Scheme 12:

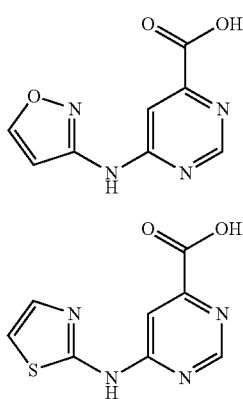

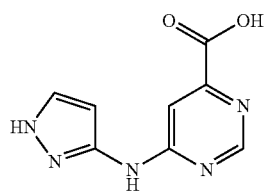

Scheme 13.

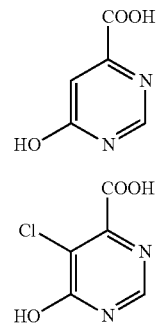

Compounds 13a and 13b can be synthesized by hydrolysis of compound 1.1 (Scheme 1) and by chlorination of compound 1.1 followed by hydrolysis.

Scheme 14-1.

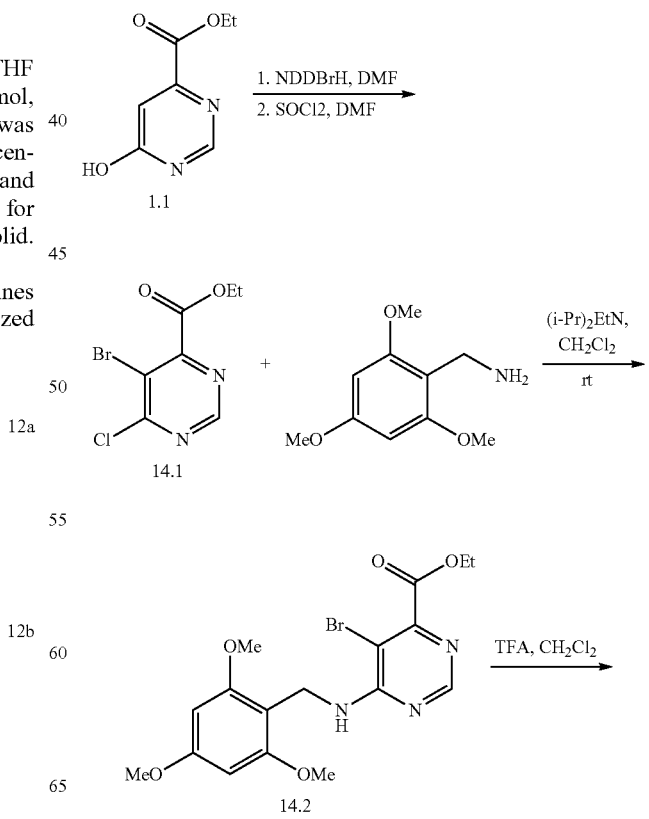

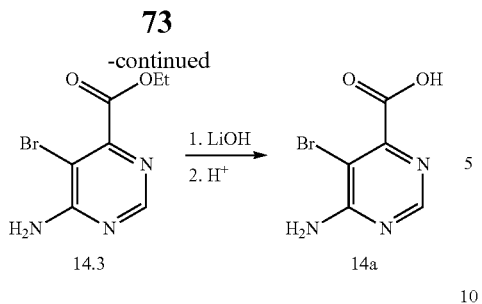

Synthesis of Compound 14a.

Using ester 1.1 as the starting material and 1,3-dibromo-5,5-N,N-dimethylhydantoin, compound 14a was synthesized according to Scheme 14-1 by following the procedure used for the synthesis of compound 10 (Scheme 10).

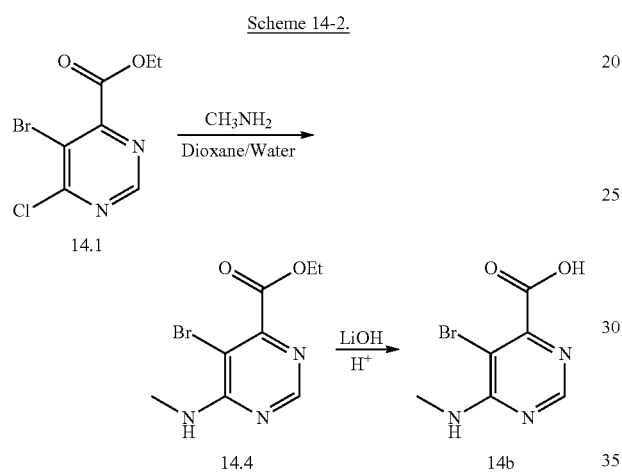

Compound 14.1.

Compound 14.1 was synthesized using a approach similar to that described in Scheme 10, except replacing the dichlorohydantoin reagent with a dibromohydantoin reagent for the first halogenation. $^1$H NMR (500 MHz, CDCl$_3$): δ 8.93 (s, 1H), 4.51 (q, J=7 Hz, 2H), 1.49 (t, J=7 Hz, 3H). LCMS: m/z 265 [M+1]$^+$.

Compound 14.4.

Aqueous methylamine (0.25 mL, 0.003 mol) was added to a solution of 13.1 (500 mg, 0.002 mol) in 1,4-dioxane (10 mL, 0.1 mol). The reaction mixture was stirred at RT for 18 hr. The solvent was removed in vacuo and the crude reaction mixture purified by reverse phase column chromatography to provide 14.4. (350 mg, 60%). $^1$H NMR (400 MHz, CDCl3): δ 8.56 (s, 1H), 5.89 (bs, N—H), 4.47 (q, J=7.3 Hz, 2H), 3.12 (d, J=4.8 Hz, 3H), 4.43 (t, J=4.8 Hz, 3H; LCMS: m/z 261 [M+1]$^+$.

Compound 14b.

Compound 14.4 (500 mg, 0.002 mol) was added to a mixture of tetrahydrofuran (2.22 mL, 0.0274 mol) and water (1.06 mL, 0.0592 mol) and the suspension stirred. Lithium hydroxide (130 mg, 0.0053 mol) was added and the reaction was stirred for 1.5 hr. The reaction mixture was then adjusted to pH 5 with 1N HCl. Solvent was removed in vacuo and the aqueous solution lyophilized to give the crude product 14.4 which was used without further purification. LCMS: m/z 233 [M$^+$+1]. $^1$H NMR (400 MHz, DMSO-d$_6$): δ 8.23 (s, 1H), 6.97 (m, 1H, NH), 2.85 (d, J=4.3 Hz, 3H). LCMS: m/z 233 [M+1]$^+$.

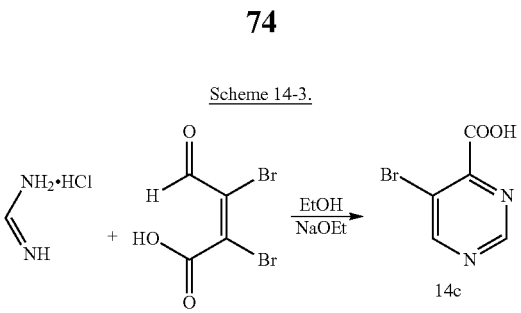

Compound 14c.

To a suspension of formamidine hydrochloride (30 g, 0.252 mole) in ethanol (150 ml) at 45° C. was added sodium ethoxide (prepared by dissolving Na (6.4 g, 0.282 mol) in ethanol (100 mL)) and mucobromic acid (25 g, 0.097 mol) in ethanol (50 mL). The two solutions were added simultaneously over 1 hr. After stirring the reaction mixture at 45-50° C. for 3 hr, the solvent was evaporated in vacuo and the residue was dissolved in ice water (100 mL). Decolorizing charcoal (2 g) was added and filtered. The filtrate was washed with ethyl acetate and aqueous layer was acidified with 12 N HCl. The aqueous layer was extracted with EtOAc (3×) and the combined organic layer was dried over anhydrous sodium sulfate. The solvent was evaporated and the residue was washed several times with ether to obtain 14c as a light brown solid (3.8 g, 9.25%). $^1$H NMR: (DMSO-d$_6$, 200 MHz) δ: 9.22 (s, 1H), 9.18 (s, 1H).

Compound 14d. Using different amines and compound 14.1, compound 14d is prepared as exemplified in Scheme 14.1.

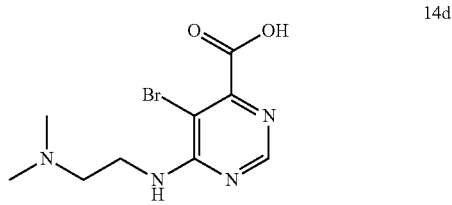

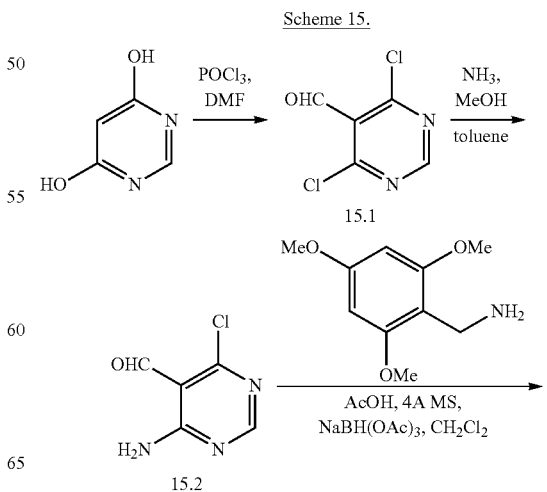

-continued

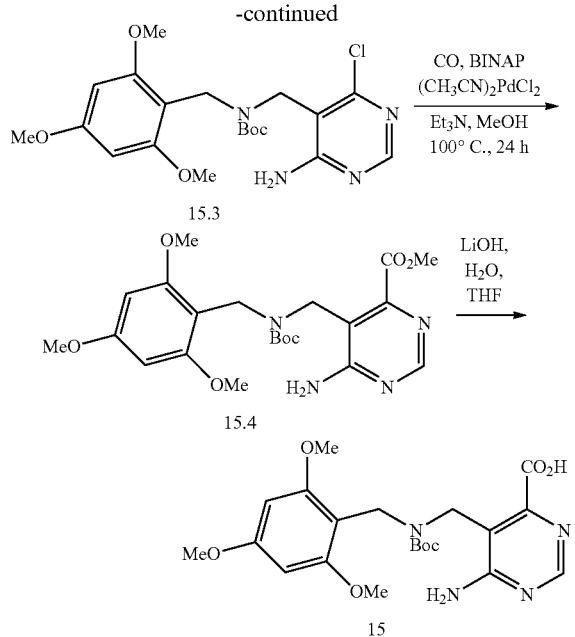

Synthesis of Compound 15.1.

To cooled (0° C.) phosphorus oxychloride (20.0 mL, 215 mmol, 4.8 equiv.) was added DMF (6.4 mL, 83 mmol, 1.9 equiv) dropwise over 3 min. The reaction mixture was stirred for fifteen min and the ice bath was removed. 4,6-Dihydroxypyrimidine (5.0 g, 44.6 mmol, 1.0 equiv.) was added and the reaction mixture was heated to 130° C. and stirred for 3.5 hr. The mixture was cooled to RT and concentrated. Ice was slowly added to the dark brown residue, followed by 600 mL of ice water. The aqueous mixture was extracted with diethyl ether (5×100 mL), and the organic extracts were washed with aqueous saturated NaHCO$_3$ (2×100 mL) and brine (100 mL), and dried over anhydrous sodium sulfate and concentrated in vacuo to provide Compound 15 (4.42 g, 57%) as a crude orange solid, which was used without further purification.

Synthesis of Compound 15.2.

To a solution of aldehyde 14.1 (1.50 g, 8.48 mmol, 1.0 equiv.) in toluene (18 mL) was added 7 M NH$_3$ in MeOH (1.8 mL, 12.7 mmol, 1.5 equiv.) and the reaction mixture was heated to 55° C. Additional NH$_3$ was added (7 M in MeOH, 3.5 mL, 24.5 mmol) over the next 4 hr, and then the reaction mixture was cooled to RT. Water (2 mL) was added and the resultant mixture was concentrated. The residue was dissolve in MeOH and adsorbed onto SiO$_2$ gel. Purification by flash column chromatography (20-25-33-40% EtOAc/hexanes) afforded 15.2 (0.88 g, 66%) as a beige solid. LCMS: m/z: 158 [M+1]$^+$.

Synthesis of Compound 15.3.

To a mixture of trimethoxybenzylamine (469 mg, 2.38 mmol, 1.0 equiv., HCl salt free based prior to use), 4 angstrom molecular sieves (290 mg), and aldehyde 15.2 (375 mg, 2.38 mmol, 1.0 equiv.) in dichloromethane (5 mL) was added acetic acid (0.14 mL, 2.43 mmol, 1.02 equiv.). After stirring for 3 hr at RT, sodium triacetoxyborohydride (757 mg, 3.57 mmol, 1.5 equiv.) was added and the reaction mixture was stirred at RT for 21.5 hr. The reaction mixture was diluted with dichloromethane (20 mL) and aqueous saturated NaHCO$_3$ (20 mL). The aqueous layer was extracted with dichloromethane (4×20 mL), and the combined organic extracts were washed with brine, dried over anhydrous sodium sulfate, and concentrated in vacuo. The resultant crude residue and Boc$_2$O (524 mg, 2.38 mmol, 1 equiv.) were dissolved in THF (10 mL), and pyridine (0.59 mL, 5.95 mmol, 2.5 equiv.) was added. After stirring at RT for 16.5 hr, the reaction mixture was diluted with water (25 mL), EtOAc (25 mL), and 1 N aqueous HCl (25 mL). The aqueous layer was extracted with EtOAc (4×30 mL). The combined organic extracts were washed with water (50 mL), 1 N aqueous HCl (50 mL), and brine (50 mL), dried over anhydrous sodium sulfate, and concentrated. Purification by flash column chromatography (50-60-66% EtOAc/hexanes) afforded compound 15.3 (403 mg, 39% over 2 steps) as a beige foam. LCMS: m/z: 439 [M+1]$^+$.

Synthesis of Compound 15.4.

A bomb was charged with chloride 15.3 (0.202 g, 0.46 mmol, 1.0 equiv.), bis(acetonitrile)dichloropalladium II (6 mg, 0.023 mmol, 0.05 equiv.), rac-BINAP (15 mg, 0.023 mmol, 0.05 equiv.), methanol (25 mL), and triethylamine (0.88 mL, 0.60 mmol, 1.3 equiv.). After purging and backfilling the bomb with CO (g) (3×, 50 psi), the bomb was pressurized to 50 psi CO. The reaction mixture was stirred at 100° C. for 22 hr, and then cooled to RT and the bomb was carefully vented. LC-MS analysis indicated incomplete conversion, so additional bis(acetonitrile)dichloropalladium II (18 mg, 0.069 mmol, 0.15 equiv.), rac-BINAP (44 mg, 0.069 mmol, 0.15 equiv.) and triethylamine (0.10 mL, 0.7 mmol) were added and the bomb was repressurized to 60 psi CO and heated to 105° C. The reaction mixture was stirred at 105° C. for 23 hr, then cooled to RT and the bomb was carefully vented. The reaction mixture was filtered through Celite and adsorbed onto SiO$_2$ gel. Purification by flash column chromatography (10-20-40-50-75-100% EtOAc/hexanes) afforded 15.4 (0.109 g, 51%) as a yellow foam. LCMS: m/z: 463 [M+1]$^+$.

Synthesis of Compound 15.

To a solution of ester 15.4 (0.103 g, 0.22 mmol) in THF (0.85 mL) was added a solution of LiOH (6 mg, 0.27 mmol, 1.2 equiv.) in H$_2$O (0.27 mL). The reaction mixture was stirred at RT for 18 hr. The reaction mixture was concentrated, and the residue was dissolved in MeOH (5 mL) and water (10 mL). The solution was frozen and lyophilized for 2 days to provide 15 (0.101 g, 100%, Li salt) as a pale yellow solid. LC-MS: m/z: 449 [M+1]$^+$.

Compounds 15a-15e. Using different amines and compound 15.2, the following acids can be synthesized as exemplified in Scheme 15:

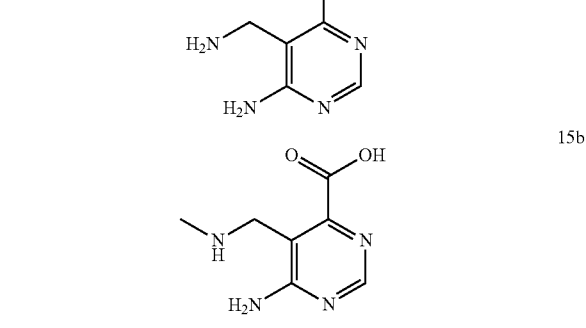

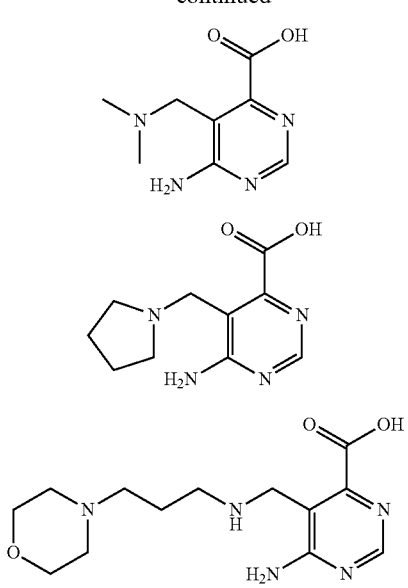

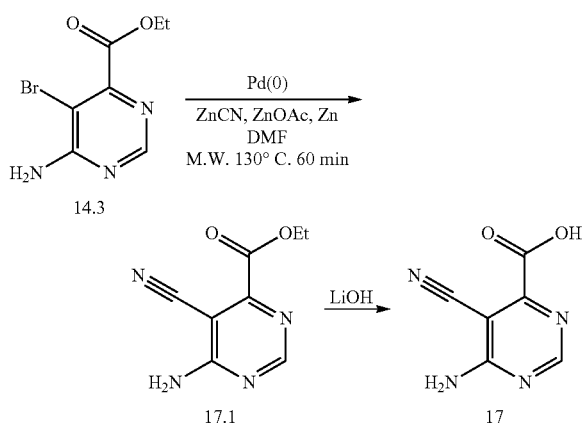

Compound 16 is commercially available and was used without additional purification.

Compound 17.1.

A 5 mL microwave vial was flushed with nitrogen gas. To the vial was added compound 14.3 (500 mg, 0.20 mmol), zinc cyanide (130 mg, 0.11 mmol), tris(dibenzylideneacetone)dipalladium(0) (20 mg, 0.002 mmol), 1,1'-bis-(diphenylphosphino)ferrocene (30 mg, 0.11 mmol), zinc acetate (20 mg, 0.009 mmol) and zinc (6 mg, 0.009 mmol). N,N-Dimethylformamide (2.3 mL, 2.9 mmol) was added and the reaction capped and flushed with nitrogen gas (3×). The reaction mixture was heated in a microwave reactor at 130° C. for 1 hr. The solvent was removed in vacuo and the residue added to 5 mL of 5% NaHCO₃ and extracted with EtOAc (3×). The organic layers were combined and washed with brine. The solvent was removed in vacuo and the crude product was used in subsequent reactions without further purification. LCMS: m/z 193.07 [M+1]⁺.

Compound 17.

Compound 17 was obtained from 17.1 using the hydrolysis procedure outlined in Scheme 1 (1.3 to 1a). LCMS: m/z 165.16 [M+1]⁺.

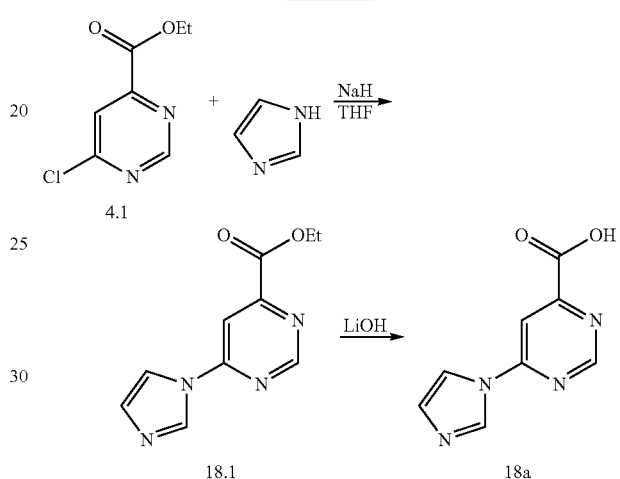

Synthesis of Compound 18.1.

To the suspension of NaH (70 mg, 60% NaH in paraffin oil, 0.00295 mol) in THF (5 mL) was added imidazole (201 mg, 0.00295 mol) at 0° C. and stirred for 30 min. Compound 4.1 (500 mg, 0.0026 mol) was added at 0° C. and the reaction mixture was heated at 60° C. for 18 hr. The reaction mixture was quenched with ice water (2 mL) and extracted with EtOAc (3×20 mL). The combined organic layers were dried over Na₂SO₄ and concentrated under reduced pressure. The crude material was purified by flash column chromatography to give 18.1 (300 mg, 52%).

Synthesis of Compound 18a.

Compound 18.1 was hydrolyzed as described for compound 1 to give 18a which was used without further purification Compounds 18a-18l.

Using different heterocycles or alcohols and compound 4.1, the following acids can be synthesized as exemplified in Scheme 18:

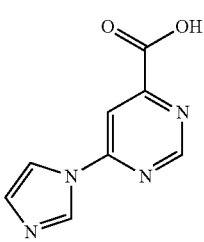

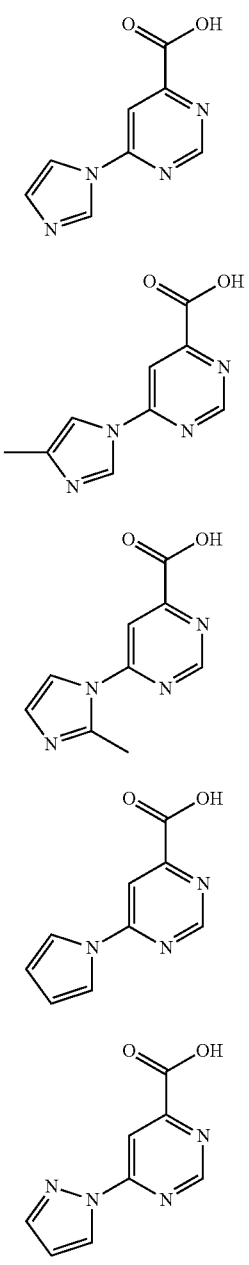
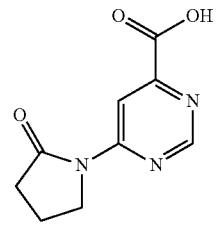
18b
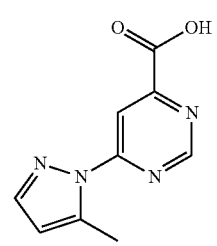
18h
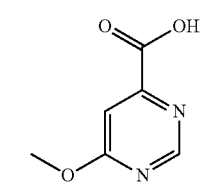
18i
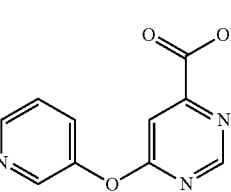
18j
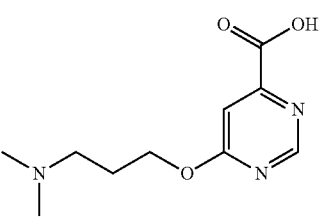
18k
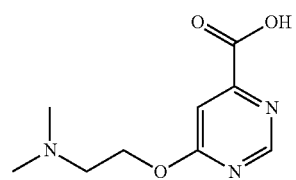
18l
Scheme 19.1
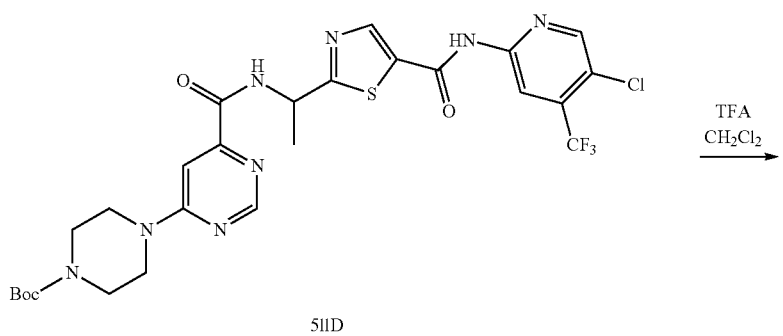
5llD

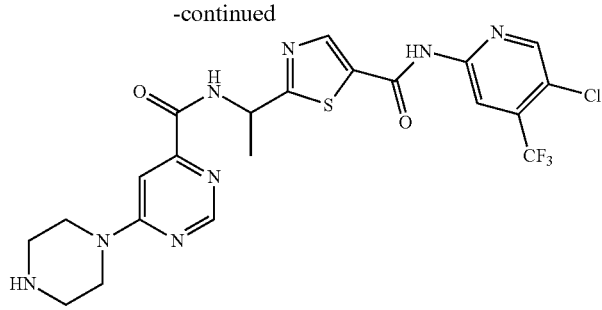
19llD
Synthesis of Compounds 19llD-19rrD.
Compounds 19llD-19rrD were prepared by TFA deprotection of the corresponding Boc protected amines 5llD-5rrD under standard TFA deprotection conditions.
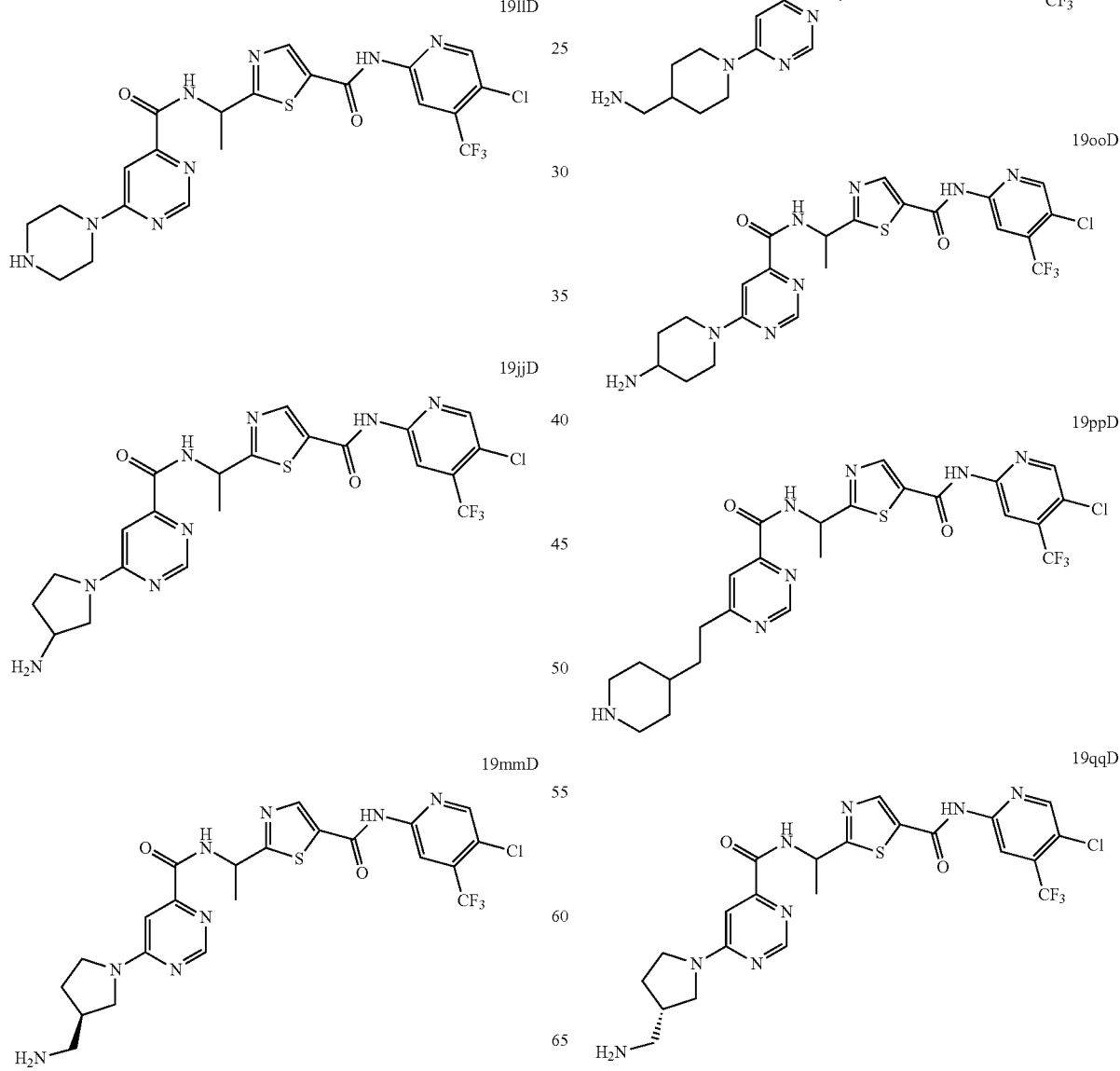

-continued

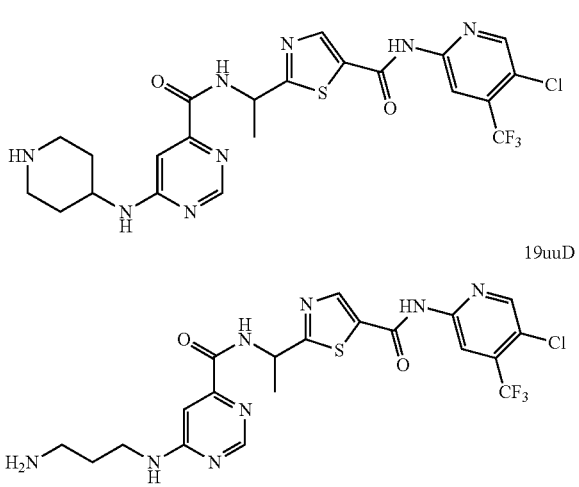

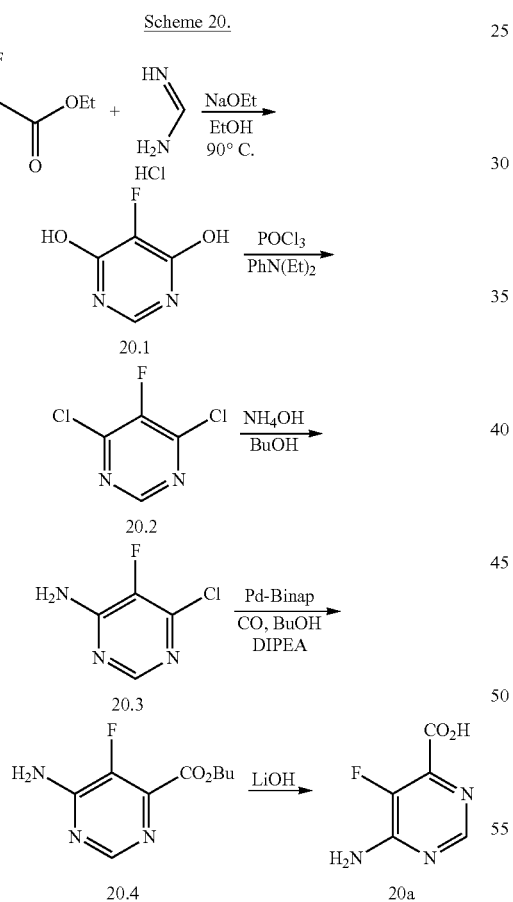

Scheme 20.

Synthesis of Compound 20.1.

To a stirred solution of NaOEt (2.7 g, 0.04 mol) in EtOH (40 mL) was added formamidine acetate (4.2 g, 0.04 mol), followed by addition of diethylfluoromalonate in ethanol (10 mL) at 0° C. The reaction mixture was stirred at 90° C. overnight. Ethanol was removed under reduced pressure and the reaction mixture was acidified with conc. HCl to pH 1. The resulting solid was filtered and dried under vacuum to afford 20.1 (crude, 750 mg, 52%). $^1$H-NMR (DMSO-$d_6$ 200 MHz): δ 12.40 (bs, 2H), 7.89 (s, 1H).

Synthesis of Compound 20.2.

A mixture of 20.1 (800 mg, 0.0062 mol) and N,N-diethylaniline in POCl$_3$ (3 mL) was refluxed at 100° C. overnight. The reaction mixture was poured into ice water and extracted with hexane (3×100 mL). The combined organic layers were washed with saturated NaHCO$_3$ and dried over Na$_2$SO$_4$. Hexane was removed under reduced pressure and the obtained crude material was purified by column chromatography to give 300 mg of 20.2 (30%). $^1$H-NMR (CDCl$_3$ 200 MHz): δ 8.61 (s, 1H); m/z: 167 [M+1]$^+$.

Synthesis of Compound 20.3.

To a stirred solution of 20.2 (120 mg, 0.000722 mol) in n-butanol (0.5 mL) was added NH$_4$OH (1 mL). The reaction mixture was heated at 90° C. for 2.5 hr in a sealed tube. The reaction mixture was cooled to 0° C., and the resulting solid was filtered and dried under vacuum to give 20.3 (60 mg, 57%). $^1$H-NMR (DMSO-$d_6$ 500 MHz): δ 8.03 (s, 1H), 7.60 (s, 2H); m/z: 148 [M+1]$^+$.

Synthesis of Compound 20.4.

To a stirred solution of 20.3 (150 mg, 0.00102 mol) in n-butanol (2 ml) and acetonitrile (2 mL) was added DIPEA (0.2 ml, 0.0013 mol), [2,2'-bis(diphenylphospino)-1,1'-binaphthyl]palladium (II) chloride (41 mg, 0.000051 mol) in a steel bomb was stirred at 100° C. under CO (100 psi) overnight. The progress of the reaction was monitored by TLC. After completion of the reaction, solvents were removed under reduced pressure and the obtained crude material was purified by column chromatography to give 20.4 (95 mg, 44%). $^1$H-NMR (DMSO-d6 500 MHz): δ 8.21 (s, 1H), 7.64 (s, 2H), 4.29 (t, J=6.5 Hz, 2H), 1.67 (m, 2H), 1.41 (m, 2H), 0.923 (t, J=7.5 Hz, 3H); m/z: 214 [M+1]$^+$.

Synthesis of Compound 20a.

To the stirred solution of 20.4 (120 mg, 0.000563 mol) in THF (1 mL) and water (1 mL) was added LiOH (25 mg, 0.000619 mol) at 0° C. The reaction mixture was stirred at RT for 2 hr. The reaction mixture was concentrated under reduced pressure to give 110 mg of 20a (crude) as a Li salt. $^1$H-NMR (DMSO-$d_6$ 500 MHz): δ 7.96 (s, 1H), 6.91 (s, 2H); m/z: 158 [M+1]$^+$.

Compounds 20a-20b. Using different amines and compound 20.2, the following acids can be synthesized as exemplified in Scheme 20.

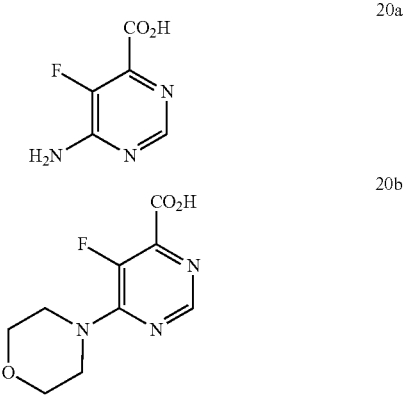

Scheme 21.

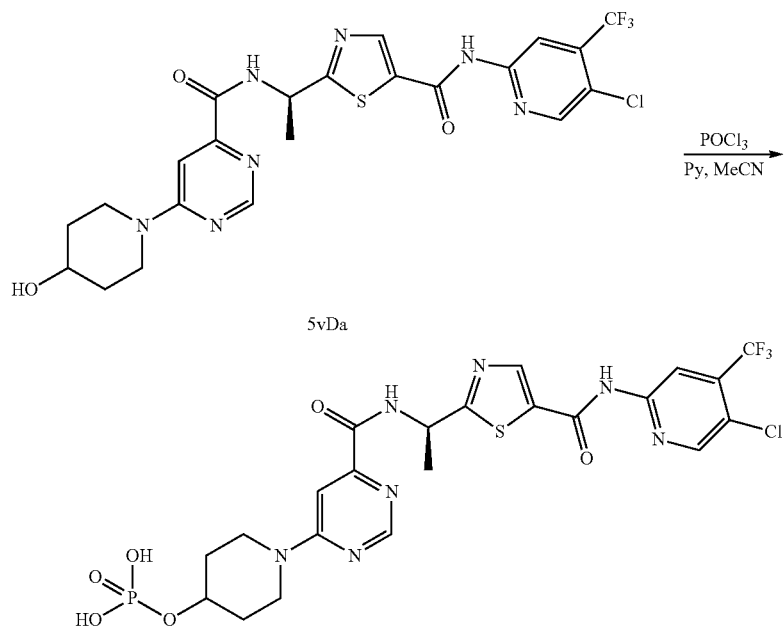

Synthesis of Compound 21.

To a solution of 5vDa (56 mg, 0.10 mmol) in acetonitrile (1 mL, 20 mmol) in a sealed microwave tube under nitrogen atmosphere was added phosphoryl chloride (37 μL, 0.40 mmol), followed by pyridine (8.1 μL, 0.10 mmol). The reaction mixture was stirred at RT overnight. Next morning, the tube was heated at 80° C. under microwave irradiation for 10 min. The reaction was quenched by addition of water. The mixture was diluted with DMSO, purified by reverse phase preperatory HPLC (acetonitrile 10-90%, buffed with TFA), and lyophilized to afford 36 mg (yield 57%) of 21 as a white solid.

Scheme 22.

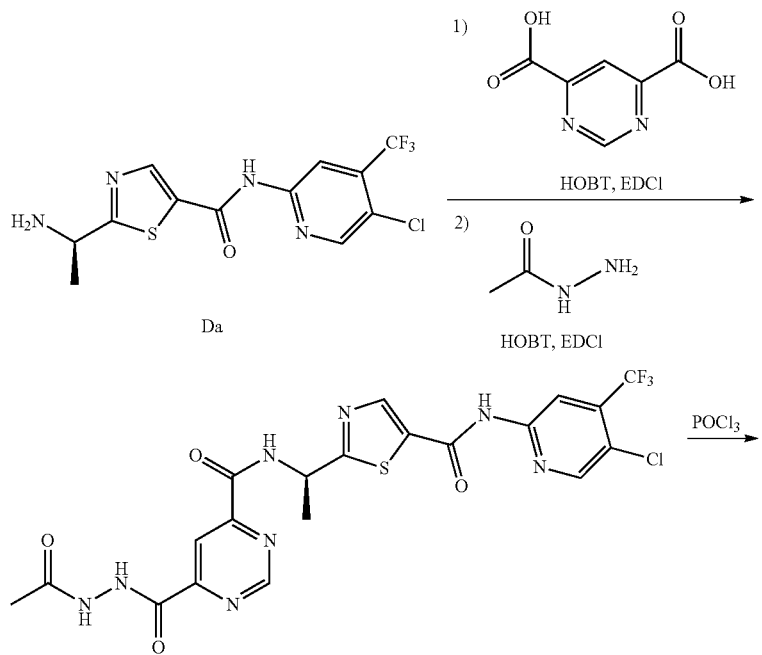

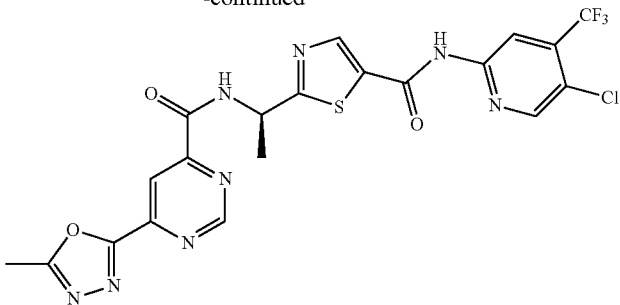

22

Synthesis of Compound 22.1.

To a mixture of pyrimidine-4,6-dicarboxylic acid (34 mg, 0.20 mmol) in DMF (3 mL, 40 mmol), cooled with ice-bath, was added 1-hydroxybenzotriazole (200 mg, 0.15 mmol), N-(3-dimethylaminopropyl)-N'-ethylcarbodiimide hydrochloride (48 mg, 0.25 mmol) and 4-methylmorpholine (16 µL, 0.15 mmol). The mixture was stirred at 0° C. for 30 min. Compound Da (70 mg, 0.20 mmol) was added, and stirred in the cold bath (allow the ice to melt) for 2 hr. LC-MS showed the desired mono-amide intermediate, along with di-amide byproduct. To the reaction mixture was added acetohydrazide (30 mg, 0.40 mmol), followed by an additional portion of N-(3-ddimethylaminopropyl)-N'-ethylcarbodiimide hydrochloride. The reaction mixture was stirred at RT over the weekend. The reaction mixture was concentrated in vacuo to remove most of DMF solvent, re-dissolved in DMSO/MeOH, purified by reverse phase HPLC (20-100%), and lyophilized to obtain 20 mg (20%) of 22.1 as a white solid

Synthesis of Compound 22.

A mixture of 22.1 (11 mg, 0.020 mmol) in phosphoryl chloride (250 µL, 2.7 mmol) was heated in a sealed tube in a 100° C. oil bath for 30 min. The reaction mixture was partitioned between EtOAc and aqueous saturated NaHCO₃. The organic phase was dried, filtered, and concentrated. The residue was purified by reverse phase HPLC (20-100% acetonitrile, TFA) to provide 5 mg (50%) of 22 as a pink solid.

Scheme 23.

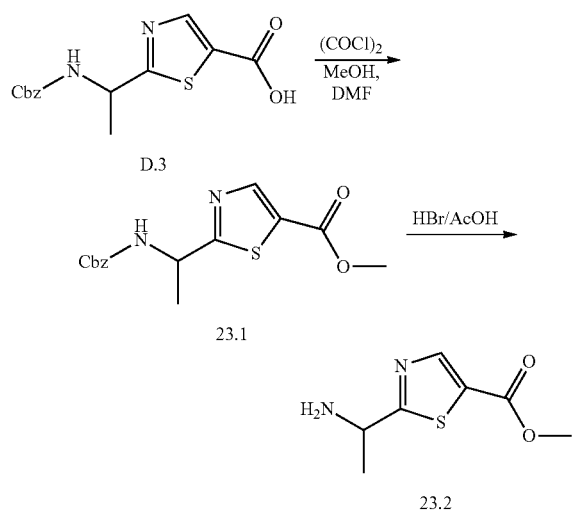

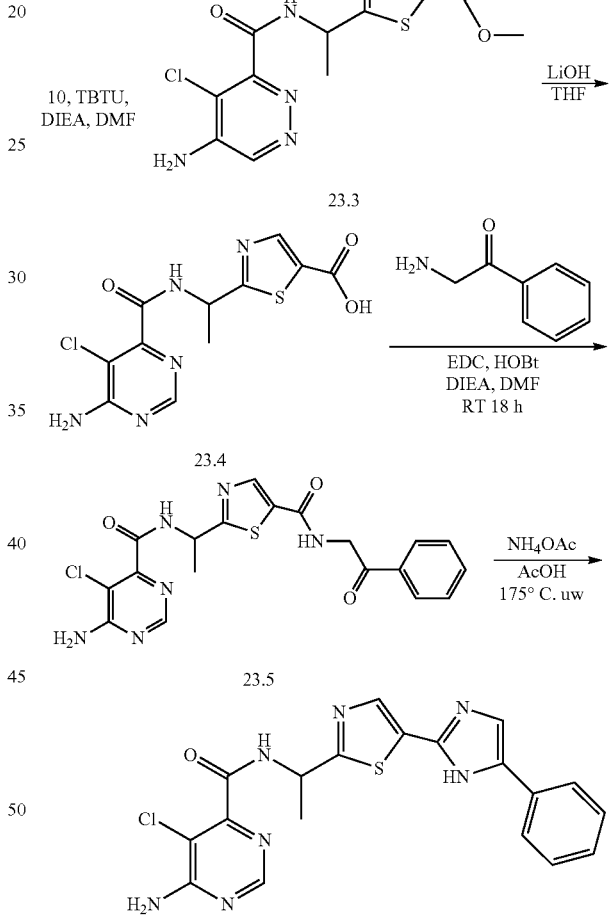

Synthesis of Compound 23.1.

In a 100 mL round-bottom flask D.3 (5.00 g, 0.0163 mole) and oxalyl chloride (1.52 mL, 0.0180 mole) were dissolved in acetonitrile (50.0 mL). The resulting solution evolved gas for 5 min. After 5 min, N,N-dimethylformamide (0.100 mL) was added dropwise at RT with much gas evolution. The reaction was allowed to stir at RT for 3 hr. Methanol (50.0 mL) was added in one portion and allowed to stir for an additional 2 hr. The solvent was then removed in vacuo. The resulting residue was then diluted with 250 mL of EtOAc and washed with 2×200 mL of sat NaHCO₃ 1×100 mL brine. The EtOAc layer was then dried over Na₂SO₄ and removed in vacuo. Yielded 5.00 g of 23.1, which was used without further purification. LCMS m/z 321 [M+1]⁺.

Synthesis of Compound 23.2.

In a 50 mL round-bottom flask 23.1 (5.00 g, 0.0156 mole) was taken up in HBr/AcOH (4.0 M, 10 mL). The resulting brown reaction mixture was allowed to stir at RT for 18 hr. After 18 hr the HBr/AcOH was removed in vacuo to yield a brown solid. The brown solid (HBr salt) was then titurated with CH₂Cl₂, which removed most of the brown color, yielding an off-white solid. The resulting solid was then taken up in 300 mL of EtOAc and washed with 75 mL of sat NaHCO₃ (2×) and 75 mL brine. The EtOAc was then dried over Na₂SO₄. The EtOAc was removed in vacuo to yield 1.70 g (0.0156 mol 59%) of the desired 23.2, which was used without further purification. LCMS m/z 187 [M+1]⁺.

Synthesis of Compound 23.3.

In a 100 mL round-bottom flask, 23.2 (1.21 g, 0.00697 mole), methyl 2-(1-aminoethyl)thiazole-5-carboxylate (1.30 g, 0.00697 mole), and TBTU (2.69 g, 0.00837 mole) were dissolved in N,N-dimethylformamide (25.0 mL, 0.323 mole) to which was added N,N-diisopropylethylamine (3.64 mL, 0.0209 mole). The resulting yellow brown solution was allowed to stir at RT for 3 hr. The reaction mixture was diluted with 250 mL EtOAc, washed with 75 mL satd. NaHCO₃ (2×), 75 mL of water, and 50 mL brine. The organic layer was dried over Na₂SO₄ and concentrated to a brown oil. The residue was purified by flash column chromatography (50% EtOAc/Hexanes gradient to 100% EtOAc) to yield 1.12 g (0.0070 47%) of desired product 23.3. LCMS m/z 342 [M+1]⁺.

Synthesis of Compound 23.4

In a 50 mL round-bottom flask, 23.3 (1.12 g, 0.00328 mol) was taken up in THF (20 mL, 0.2 mole) to which was added a solution of LiOH (0.08633 g, 0.003605 mole) in water (4 mL, 0.2 mole). The resulting reaction mixture was then allowed to stir at RT for 6 hr. The solvent was removed in vacuo and the resulting residue was taken up in 200 mL CH₂Cl₂ and then washed 50 mL sat NH₄Cl (2×) and brine to yield 0.653 g (0.0038 mole, 60%) of 23.4. LCMS m/z 327 [M+1]⁺.

Synthesis of Compound 23.5.

In a 25 mL round-bottom flask 23.4 (0.382 g, 0.00116 mole), 1-hydroxybenzotriazole (0.157 g, 0.00116 mole) and 2-amino-1-phenylethanone (0.200 g, 0.00116 mole) were taken up in DMF (5 mL, 0.06 mole), and to this was added N-(3-dimethylaminopropyl)-N'-ethylcarbodiimide hydrochloride (0.268 g, 0.00140 mole) and then N,N-diisopropylethylamine (0.203 mL, 0.00116 mole). The resulting cloudy solution was allowed to stir at RT for 3 hr. The reaction mixture was diluted with 100 mL EtOAc and washed with 50 mL Sat NaHCO₃ (2×) and brine. The organic layer was dried over Na₂SO₄, filtered, and concentration. The residue was dissolved in CH₂Cl₂ and eluted through a silica gel column with 90-100% EtOAc/hexanes to afford 270 mg of 23.5. LCMS m/z 446 [M+1]⁺.

Synthesis of Compound 23.

In a 5 mL microwave reaction vial 23.5 (0.100 g, 0.000225 mole) and ammonium acetate (0.173 g, 0.00225 mole) were taken up in acetic acid (4.0 mL, 0.070 mole). The vial was sealed and allowed to stir at RT for 5 min. The reaction was heated at 175° C. under microwave radiation for 15 min. The acetic acid was removed in vacuo to yield a slightly yellow oil. The oil was taken up in 100 mL of CH₂Cl₂ and washed with 50 mL of sat NaHCO₃. The organic layer was then washed with 50 mL NaHCO₃, 50 mL H₂O, and 35 mL brine. The organic layer was then dried over Na₂SO₄ and the solvent was removed in vacuo. The resulting slightly yellow oil was taken up in DMSO and purified by preparative HPLC (10%-90% CH₃CN/water 0.1% TFA acidic method) to yield 42 mg (0.00022 mol, 35%) of 23 as a TFA salt. LCMS m/z 427 [M+1]⁺.

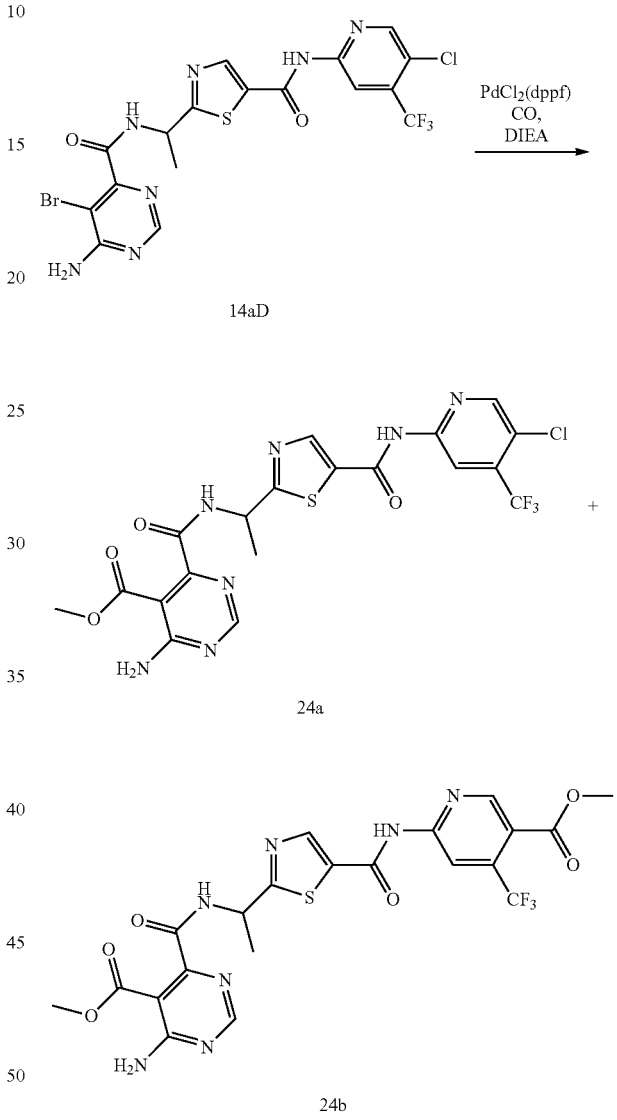

Scheme 24.

14aD

24a

24b

Synthesis of Compound 24a and 24b.

A solution of 14aD (200 mg, 0.0004 mole) and [1,1'-bis(diphenylphosphino)ferrocene]dichloropalladium(II) (10 mg, 0.00002 mol) in methanol (30 mL) was treated with N,N-diisopropylethylamine (75.90 μL, 0.0004358 mole). The mixture was then placed in the parr autoclave and flushed with CO. The autoclave was then charged with CO to 10 bar and heated to 100° C. for 16 hr. After cooling to RT, the mixture was filtered to remove any solid, and the resulting reddish brown solution was concentrated to a brown solid. The residue was purified via preparatory HPLC to afford 24a (22 mg, 11%) and 24b (2.8 mg, 1%). 24a: m/z 530 [M+1]. 24b: m/z 554 [M+1]⁺.

Scheme 25.

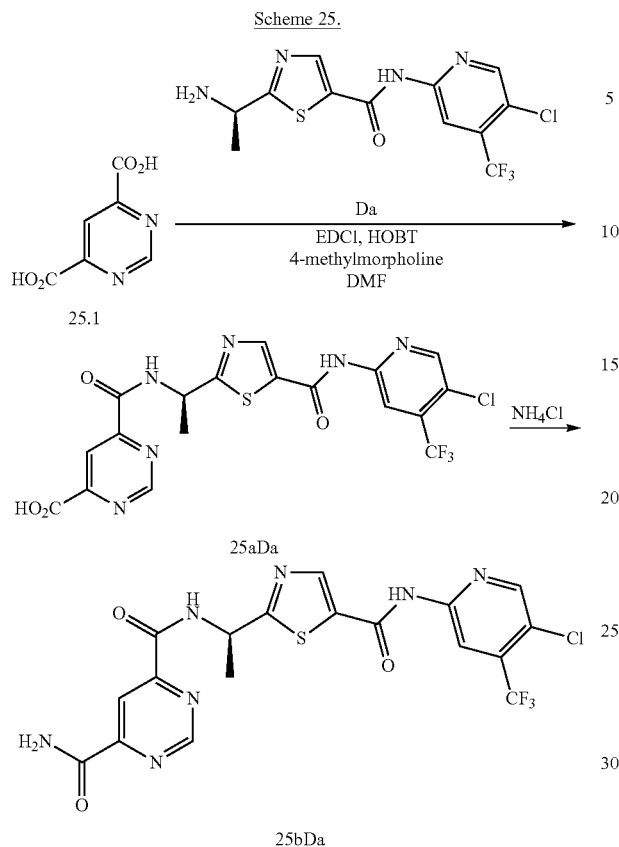

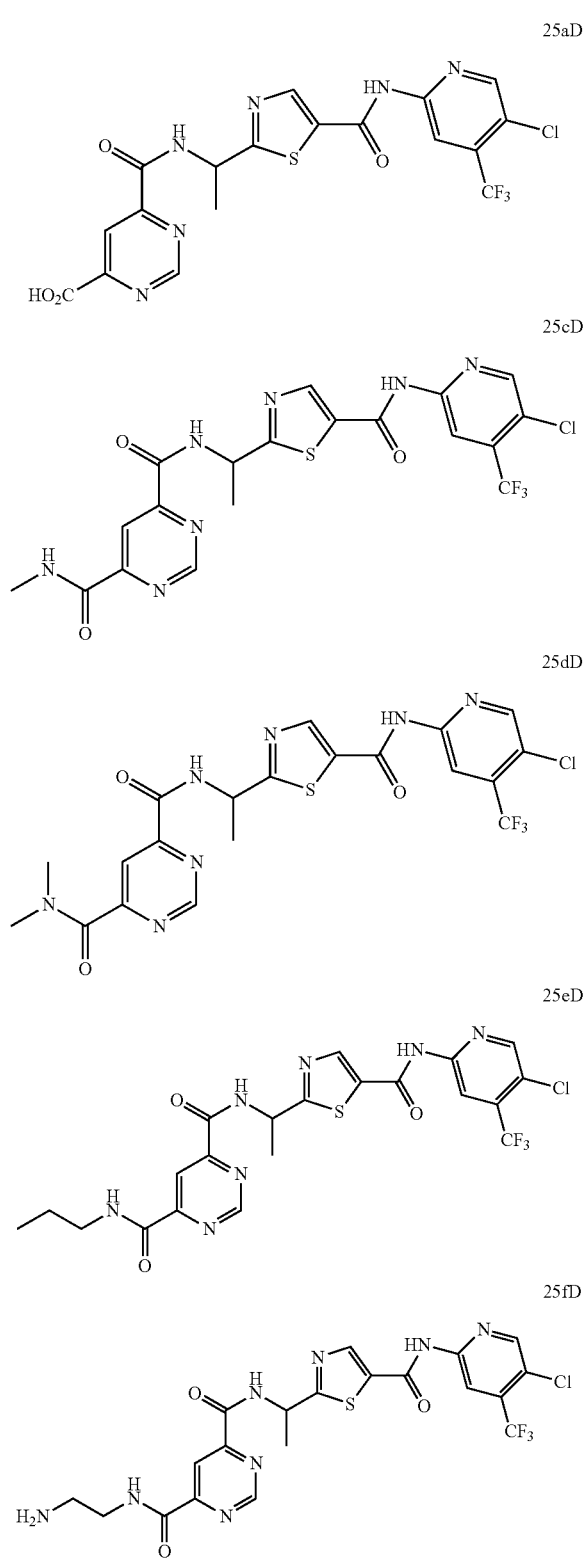

Synthesis of Compound 25aDa.

To a stirred solution of 25.1 (600 mg, 3.569 mmol) in DMF (50 mL) at 0° C. were added HOBT (361 mg, 2.676 mmol), EDCI (855 mg, 4.46 mmol) and NMM (288 mg, 2.854 mmol). After stirring for 30 min., Da (626 mg, 1.784 mmol) was added, and the reaction was stirred for 4 hr at 10-15° C. After completion, the reaction mixture was diluted with water (50 mL) and extracted twice with DCM (2×50 mL). The combined organic layer was dried over anhydrous $Na_2SO_4$ and concentrated. The residue was dissolved in water and acidified with 6 N HCl (pH=2-3). The solid obtained was filtered, washed with water, EtOAc (5 mL), and hexane, and dried under vacuum. The white solid obtained was codistilled twice with $CCl_4$ to obtain 25aDa (710 mg, 79.41%). $^1$H NMR (DMSO-d6, 500 MHz) δ: 14.0-14.4 (s, 1H, $D_2O$ exchangeable), 11.7 (s, 1H, $D_2O$ exchangeable), 9.95 (d, 1H, $D_2O$ exchangeable), 9.5 (s, 1H), 8.8 (2 s, 2H), 8.5 (s, 1H), 8.4 (s, 1H), 5.5 (m, 1H), 1.7 (d, 3H); m/z 501 [M+1]$^+$.

Synthesis of Compound 25bDa.

To a solution of compound 25aDa (100.0 mg, 0.1997 mmol) in DMF (4.0 mL) were added HOBT (200 mg, 0.15 mmol), EDCI (47.8 mg, 0.250 mmol), and 4-methylmorpholine (60 µL, 0.6 mmol). This resulting brown solution was then treated with ammonium chloride (21 mg, 0.40 mmol). After stirring for 4 hr, this mixture was purified via preparatory Gilson HPLC (flow rate 20, from 10% B (MeCN with 0.1% formic acid) to 95% B in 10 min), affording 25bDa as a white solid (19 mg, 19%). $^1$H NMR (400 MHz, DMSO-d6) δ=11.72 (br. s., 1H), 9.93 (d, J=8.6 Hz, 1H), 9.50 (s, 1H), 8.77 (s, 1H), 8.75 (s, 1H), 8.55 (s, 1H), 8.47 (s, 1H), 8.46-8.41 (m, 1H), 8.10 (s, 1H), 5.54-5.45 (m, 1H), 1.70 (d, J=7.1 Hz, 3H); m/z 500 [M+1]$^+$.

Compounds 25aD-25lD.

Using different amines and compound D, the following compounds were synthesized as exemplified in Scheme 25.

25gD
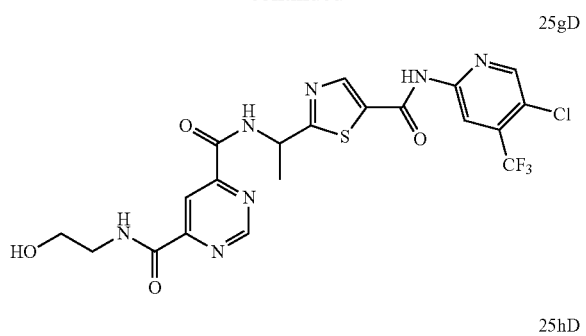
25hD
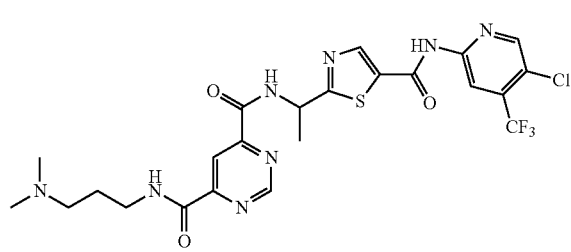
25iD
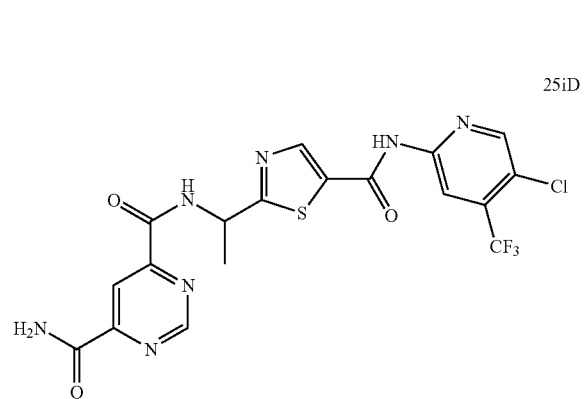
25jD
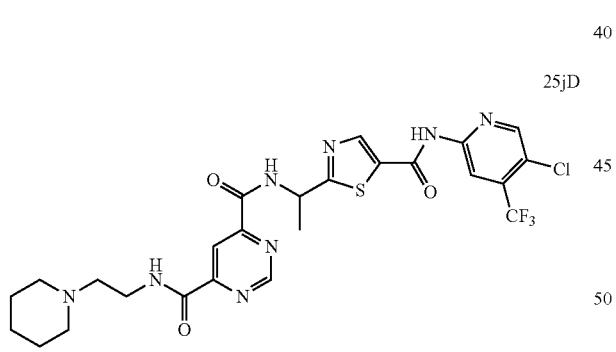
25kD
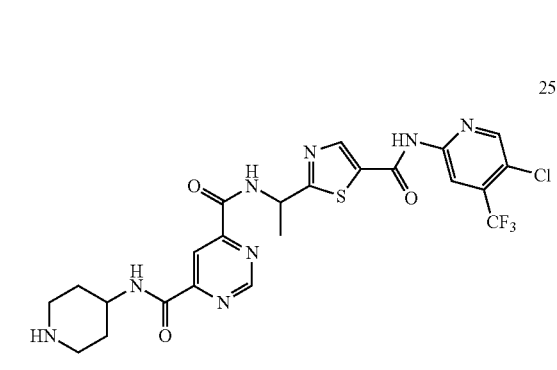
25lD
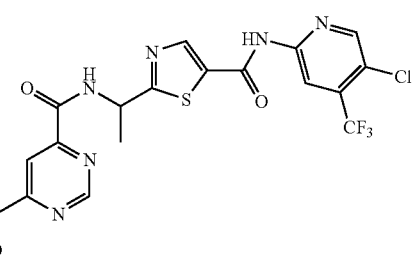
Compounds 25cDa, 25iDa, 25 kDa, 25lDa, 25 mDa, and 25nDa.
Using different amines and compound Da, the following compounds were synthesized as exemplified in Scheme 25.
25cDa
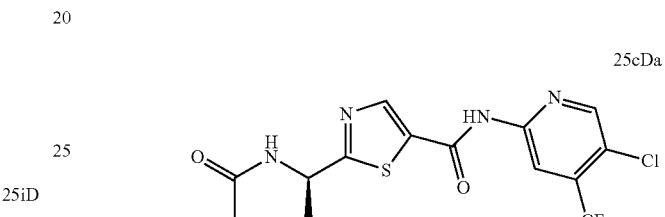
25iDa
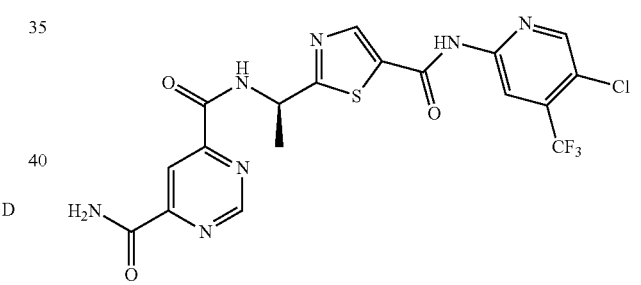
25lDa
25kDa
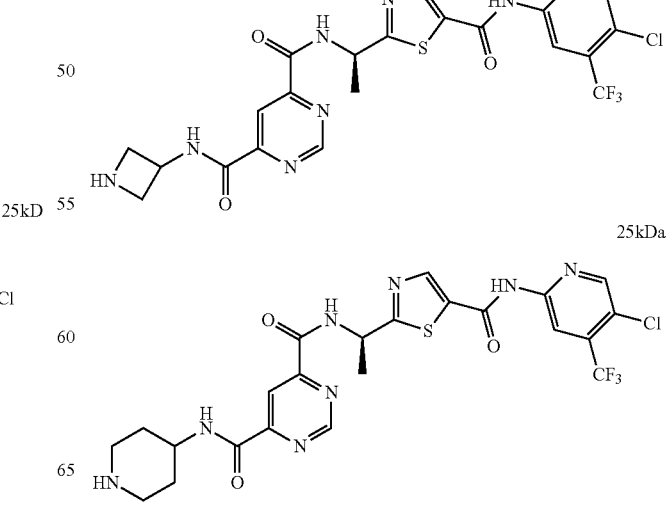

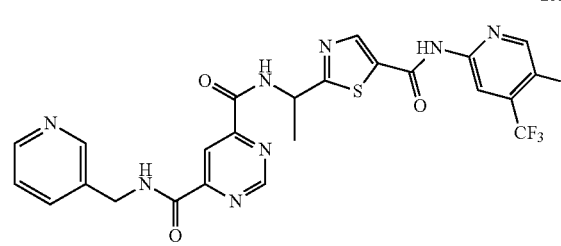
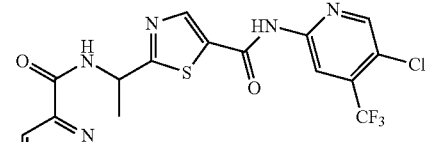
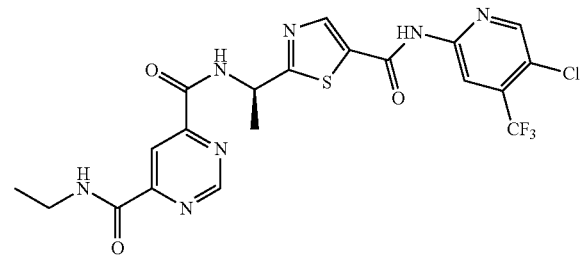
Scheme 26.
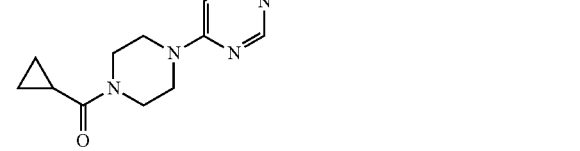
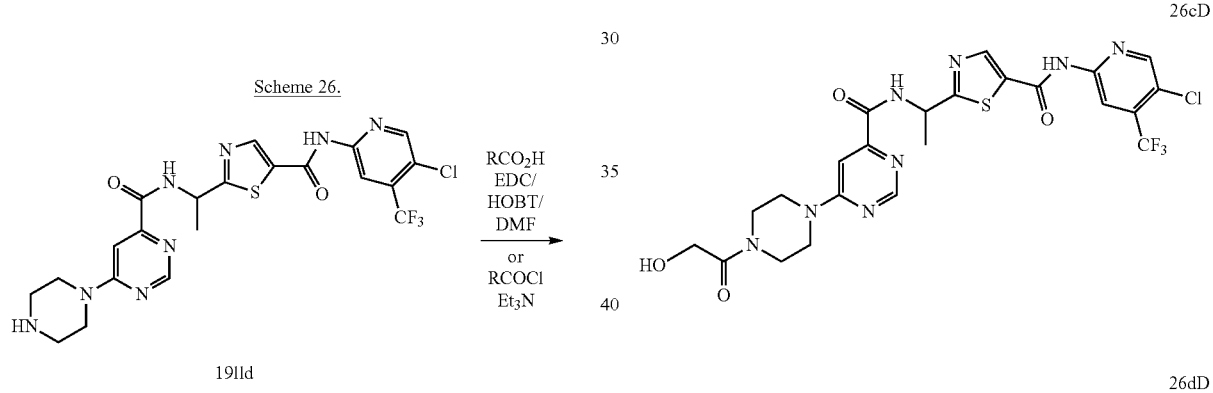
Synthesis of Compounds 26aD-26eD.
Compounds 26aD-26eD were prepared by coupling of the corresponding carboxylic acid or acid chloride with amine 19llD under standard acid coupling conditions.

Scheme 27.
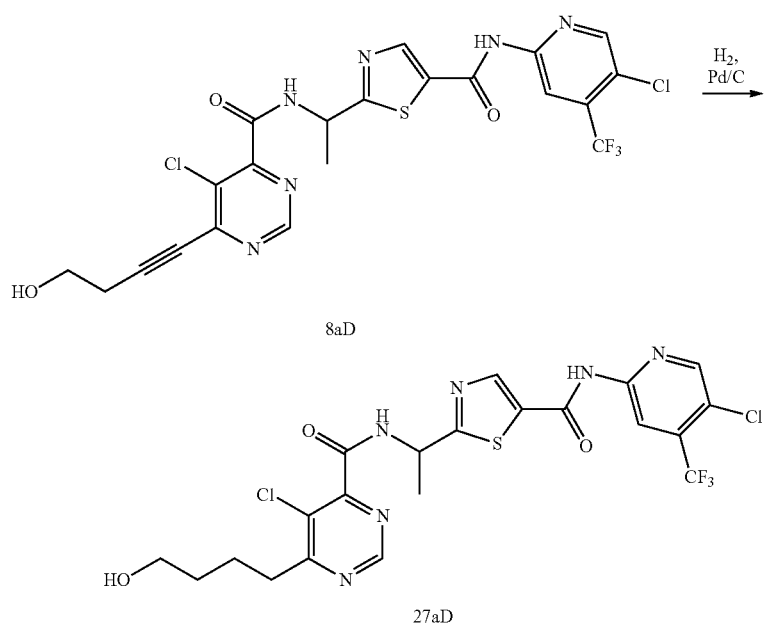
Synthesis of Compounds 27aD-26hD.
Compounds 27aD-27hD were prepared by hydrogenation of the corresponding alkynes under standard alkyne hydrogenation conditions.
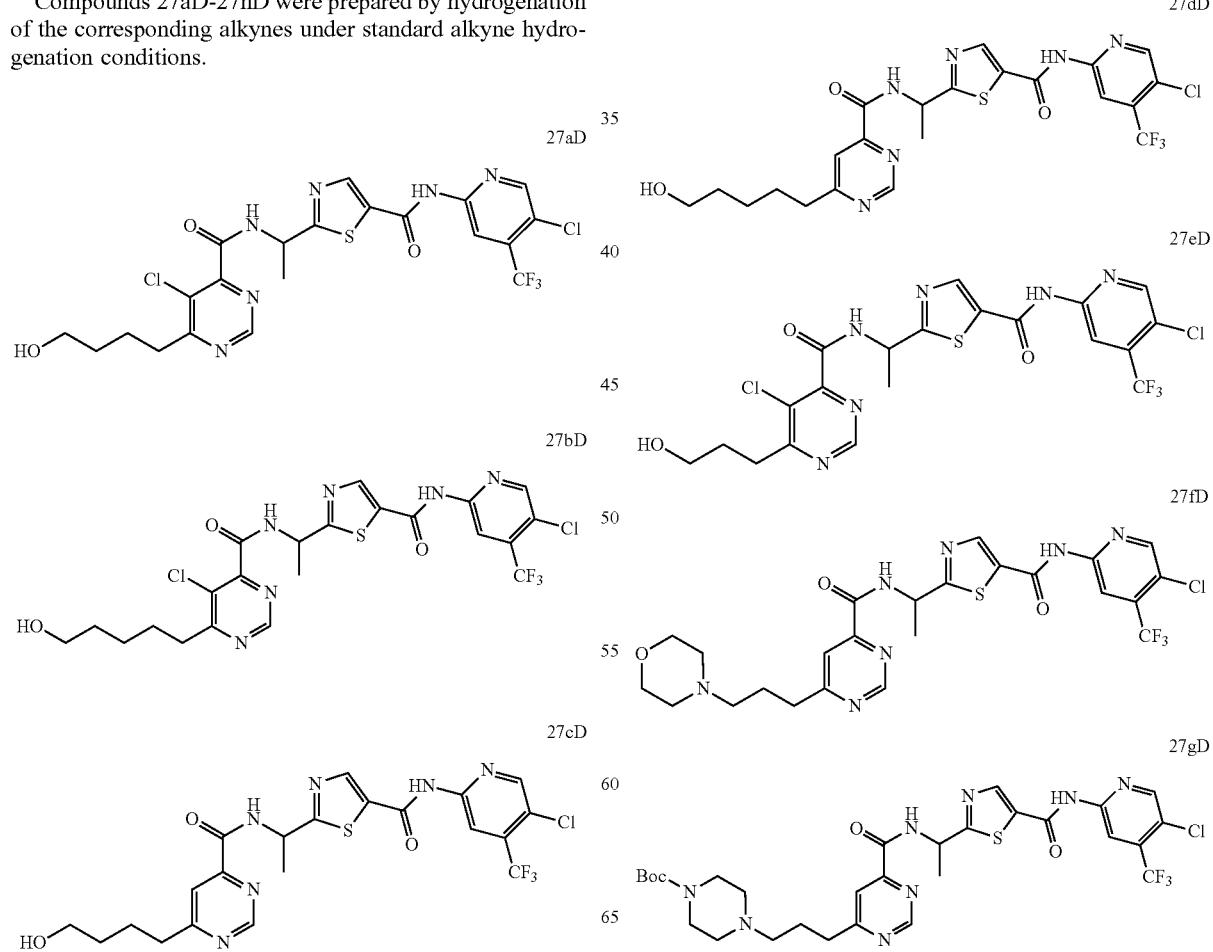

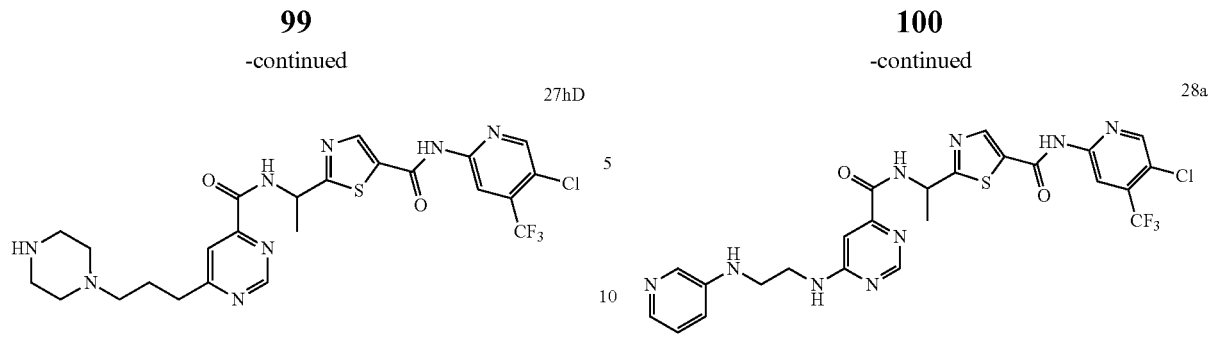
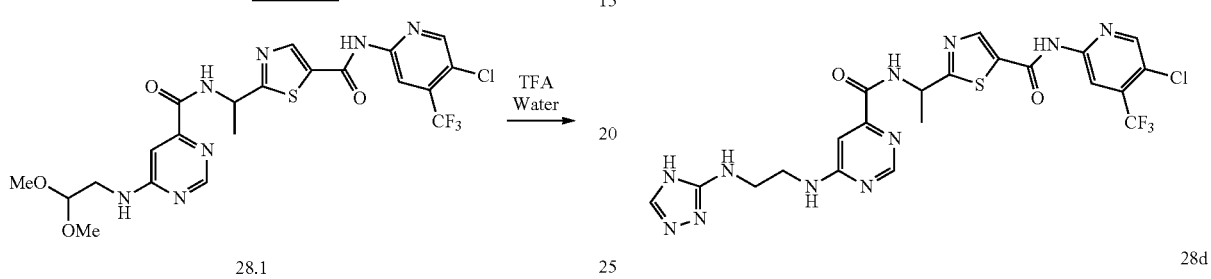
Scheme 28.
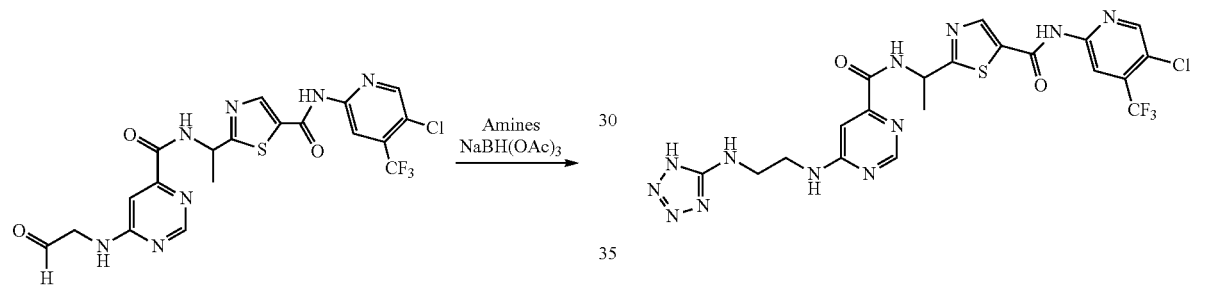
Synthesis of Compounds 28a-28m.
Compounds 28a-28m were prepared by reductive amination of different amines and compound 28.2 as exemplified in Scheme 28.
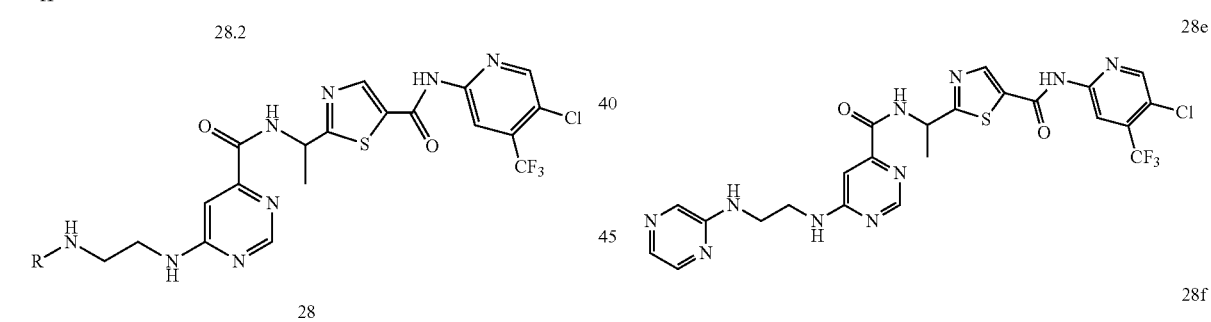
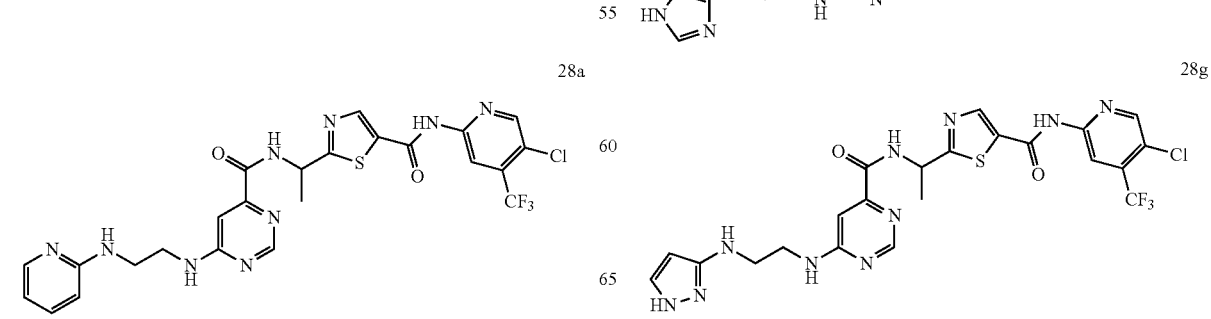

-continued

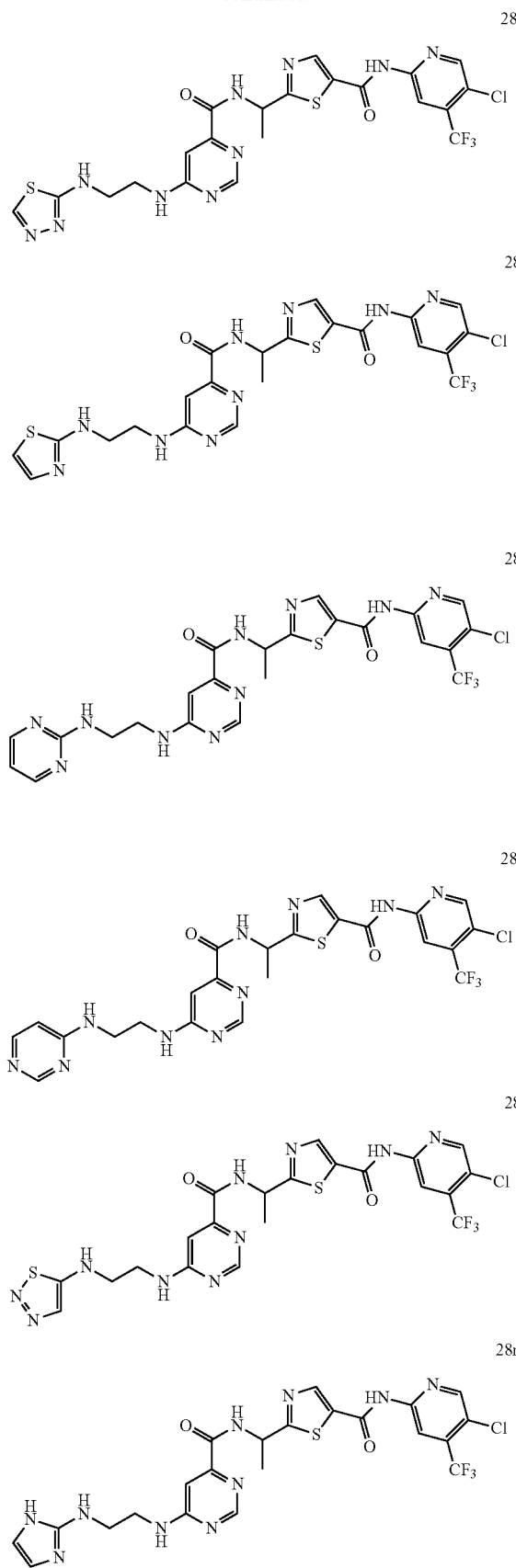

Scheme 29.

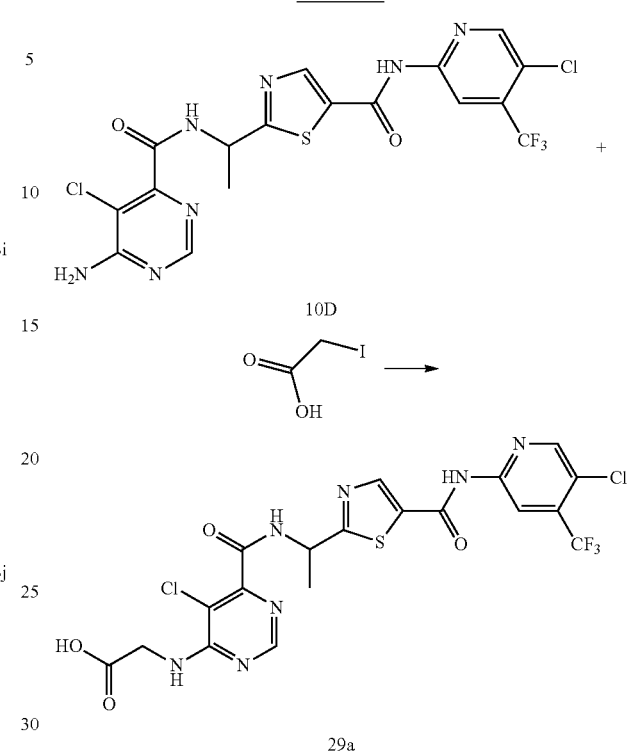

Synthesis of Compound 29a.

To a solution of 10D (30.0 mg, 0.059 mmol) in THF (5.00 mL) were added 1 M of potassium tert-butoxide in THF (0.071 mL, 0.07 mmol), 4-methylmorpholine (0.020 mL, 0.178 mmol) and iodoacetic acid (12.1 mg, 0.065 mmol). After stirring at 25° C. for 18 hr, the crude mixture was purified via preparatory reverse-phase HPLC, affording 29a as a white solid (20 mg, 60%). $^1$H NMR (400 MHz, DMSO-d$_6$) δ=11.77 (s, 1H), 9.58 (d, J=7.8 Hz, 1H), 8.78 (s, 1H), 8.76 (s, 1H), 8.58 (s, 1H), 8.47 (s, 1H), 8.06 (t, J=6.0 Hz, 1H), 5.40-5.31 (m, 1H), 4.07 (d, J=6.1 Hz, 2H), 1.59 (d, J=7.1 Hz, 3H); m/z 564 [M+1]$^+$.

Synthesis of Compound 29b.

Compound 29b was synthesized as exemplified in Scheme 29 substituting ethyl 2-bromoacetate for the iodoacetic acid.

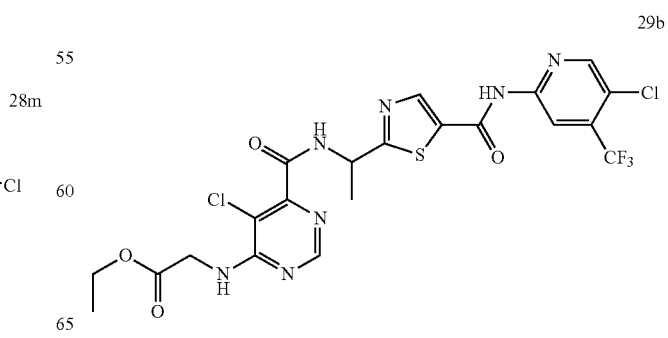

Scheme 30.

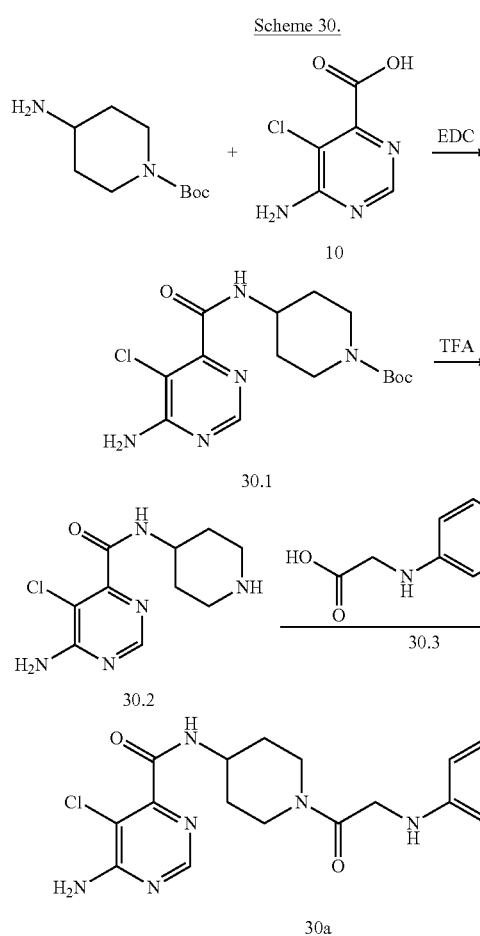

Synthesis of Compound 30.1.

A solution of tert-butyl 4-aminopiperidine-1-carboxylate (1 g, 0.0049 mol), 10 (868 mg, 0.0049 mol), EDCI (2.3 g, 0.0124 mol) and HOBT (269 mg, 0.0019 mol) in DMF (10 ml) was stirred at RT for 16 h. The reaction mixture was diluted with water (50 ml) and extracted with ethyl acetate (3×50 ml). The combined organic layers was washed with water (3×30 ml), dried over $Na_2SO_4$ and concentrated under reduced pressure. The resulting mixture was purified by column chromatography to give 30.1 (1.7 mg, 58%). $^1$H-NMR ($CDCl_3$ 500 MHz): δ 8.41 (s, 1H), 7.89 (bs, 1H), 5.65 (bs, 2N—H), 4.15 (m, 4H), 2.93 (m, 2H), 1.94 (m, 2H), 1.42 (s, 9H); m/z 356 [M+1]$^+$.

Synthesis of Compound 30.2.

To a stirred solution of 30.2 (600 mg, 0.0016 mol) in DCM (4 ml) and cooled to 0° C., then added TFA (4 ml). The reaction mixture was stirred at RT for 2 hr and then volatiles were removed under reduced pressure. The residue was co-distilled with toluene (2×10 ml) to afford 30.2 as light yellow solid (400 mg, 93%). $^1$H-NMR ($CD_3OD$, 500 MHz) δ 8.28 (s, 1H), 4.18 (t, 1H), 3.70 (dd, 2H), 3.21 (m, 2H), 2.25 (d, 2H), 1.85 (m, 2H); m/z 255.9 [M+1]$^+$.

Synthesis of Compound 30a.

A solution of 30.2 (100 mg, 0.00039 mol), 30.3 (86 mg, 0.00039 mol), EDCI (188 mg, 0.00098 mol), HOBT (23 mg, 0.00017 mol) and DIPEA (152 mg, 0.0011 mol) in DMF (3 ml) was stirred at RT for 16 hr. The reaction mixture was diluted with water (20 ml) and extracted with ethyl acetate (3×20 ml). The combined organic layers were washed with (2×10 ml), dried over $Na_2SO_4$ and concentrated under reduced pressure. The resulting mixture was purified by column chromatography to give 30a (60 mg, 33%). $^1$H-NMR (DMSO-d6, 500 MHz): δ 8.62 (d, J=7.5 Hz, 1H), 8.32 (s, 1H), 7.35 (dd, J=8, 1H), 6.95 (d, J=25 Hz, 2H), 6.82 (d, J=7.5 Hz, 1H); 6.18 (d, 1H), 4.25 (d, 1H), 4.0-0.8 (br, 4H), 3.15 (t, 1H), 2.93 (t, 1H), 1.92 (br, 2H), 1.6-1.49 (br, 2H); m/z 456.8 [M+1]$^+$.

Synthesis of Compound 30b-30c.

Compound 30b was prepared as exemplified in Scheme 30 utilizing tert-butyl 3-aminopyrrolidine-1-carboxylate. Compound 30c was prepared as exemplified in Scheme 31 utilizing tert-butyl 3-aminopiperidine-1-carboxylate.

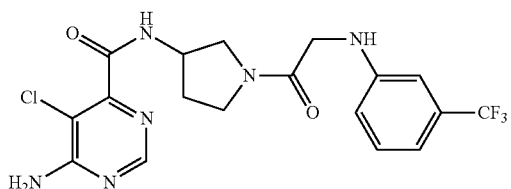

30b

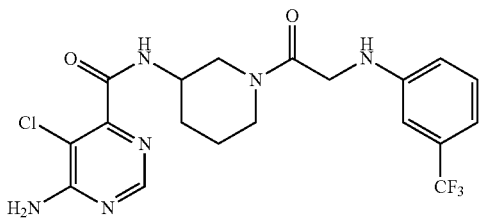

30c

Scheme 31.

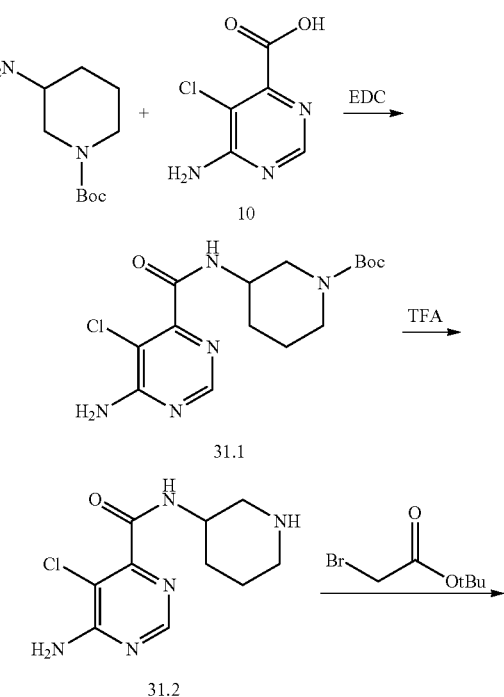

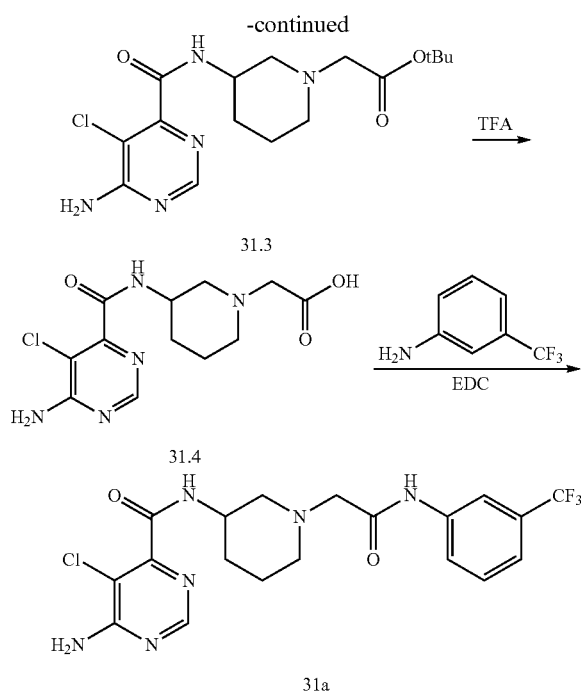

Synthesis of Compound 31.1.

The solution of tert-butyl 3-aminopiperidine-1-carboxylate (500 mg, 0.0024 mol), 10 (434 mg, 0.0024 mol), EDCI (1.2 g, 0.0062 mol) and HOBT (136 mg, 0.0009 mol) in DMF (5 ml) was stirred at RT for 16 hr. The reaction mixture was diluted with water (25 ml) and extracted with ethyl acetate (3×25 ml). The combined organic layers was washed with water (3×15 ml), dried over $Na_2SO_4$ and concentrated under reduced pressure. The resulting mixture was purified by column chromatography to give 31.1 (560 mg, 63%). $^1$H-NMR (DMSO-d6, 500 MHz): δ 8.45 (s, 1H), 8.25 (s, 1H), 7.90-7.20 (bs, 2N—H), 3.89-3.65 (m, 3H), 2.95-2.78 (m, 2H), 1.94-1.82 (m, 2H), 1.75-1.68 (m, 2H), 1.42 (s, 9H); m/z 355.9 $[M+1]^+$.

Synthesis of Compound 31.2.

To the stirred solution of 31.1 (560 mg, 0.0015 mol) in DCM (4 ml) at 0° C. was added TFA (3 ml). The reaction mixture was stirred at RT for 2 hr, DCM was removed under reduced pressure and the resulting crude material was co-distilled with toluene (2×10 ml) to obtain 31.2 (360 mg, 58%). $^1$H-NMR (DMSO-d6, 500 MHz): δ 8.45 (s, 1H), 8.25 (s, 1H), 7.9-7.2 (bs, 2N—H), 3.89-3.65 (m, 3H), 2.95-2.78 (m, 2H), 1.94-1.82 (m, 1H), 1.75-1.68 (m, 1H); m/z: 255.9 $[M+1]^+$.

Synthesis of Compound 31.3.

To a solution of 31.2 (100 mg, 0.0039 mol) in acetonitrile (5 ml) was added DIPEA (151 mg, 0.0011 mol), followed by tert-butyl bromoacetate (0.7 ml, 0.00047 mol) and stirred at RT for 6 hr. The reaction mixture was concentrated under reduced pressure and the resulting crude material was purified by column chromatography to give 31.3 (100 mg, 69%). $^1$H-NMR (DMSO-d6, 500 MHz): δ 8.41 (d, J=8.0 Hz, 1H), 8.28 (s, 1H), 7.60-7.50 (bs, 2N—H), 5.74 (s, 1H), 3.12 (s, 2H), 2.81 (d, J=8.5 Hz, 2H), 2.62-2.61 (m, 2H), 2.21-2.19 (m, 2H), 1.68-1.59 (m, 2H), 1.42 (s, 9H); m/z: 370 $[M+1]^+$.

Synthesis of Compound 31.4.

To the stirred solution of 31.3 (100 mg, 0.00022 mol) in DCM (2 ml) at 0° C. was added TFA (2 ml). The reaction mixture was stirred at RT for 2 hr and DCM was removed under reduced pressure. The resulting crude material was co-distilled with toluene (2×10 ml) to obtain 31.4 (crude 70 mg). $^1$H-NMR ($CD_3OD$, 500 MHz): δ 8.50 (s, 1H), 4.38-4.20 (m, 1H), 4.18 (s, 2H), 3.64-3.61 (m, 2H), 3.21-3.01 (m, 2H), 2.19-2.01 (m, 2H), 1.20-1.16 (m, 2H); m/z: 314 $[M+1]^+$.

Synthesis of Compound 31a.

The solution of 31.4 (100 mg, 0.00031 mol), 3-(trifluoromethyl) aniline (51 mg, 0.00031 mol), EDCI (152 mg, 0.00079 mol), HOBT (17 mg, 0.00012 mol) and DIPEA (50 mg, 0.00031 mol) in DMF (2 ml) was stirred at RT for 16 hr. The reaction mixture was diluted with water (20 ml) and extracted with ethyl acetate (3×20 ml). The combined organic layers were washed with water (2×10 ml), dried over $Na_2SO_4$ and concentrated under reduced pressure. The resulting mixture was purified by column chromatography to give 31a (29 mg, 25%). $^1$H-NMR (DMSO-d6, 500 MHz): δ 9.99 (s, 1H), 8.57 (d, J=8.0 Hz, 1H), 8.28 (s, 1H), 8.10 (s, 1H), 7.82 (d, J=7.5 Hz, 1H), 7.54-7.51 (m, 1H), 7.39 (d, J=7.5 Hz, 1H), 4.03-3.98 (m, 1H), 3.20-3.06 (m, 2H), 2.69 (d, J=9.5 Hz, 1H), 2.49-2.30 (m, 2H), 1.68-1.59 (m, 3H), 1.42-1.34 (m, 1H); m/z: 456.9 $[M+1]^+$.

Synthesis of Compound 31b.

Compound 31b was prepared as exemplified in Scheme 31 utilizing tert-butyl 3-aminopyrrolidine-1-carboxylate. Compound 31c was prepared as exemplified in Scheme 31 utilizing tert-butyl 4-aminopiperidine-1-carboxylate.

Scheme 31.

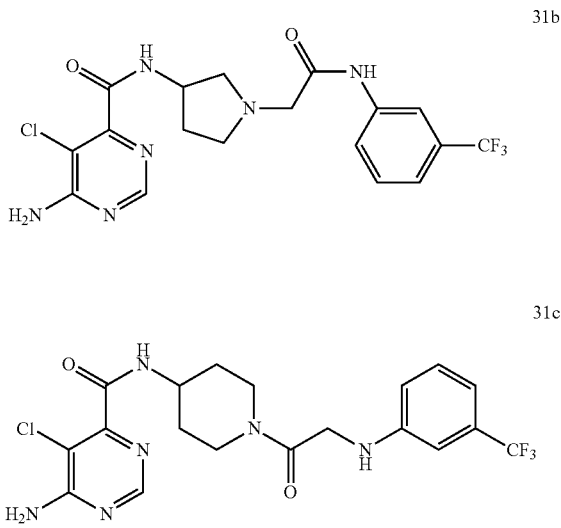

Scheme 32.

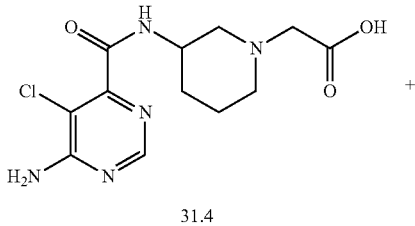

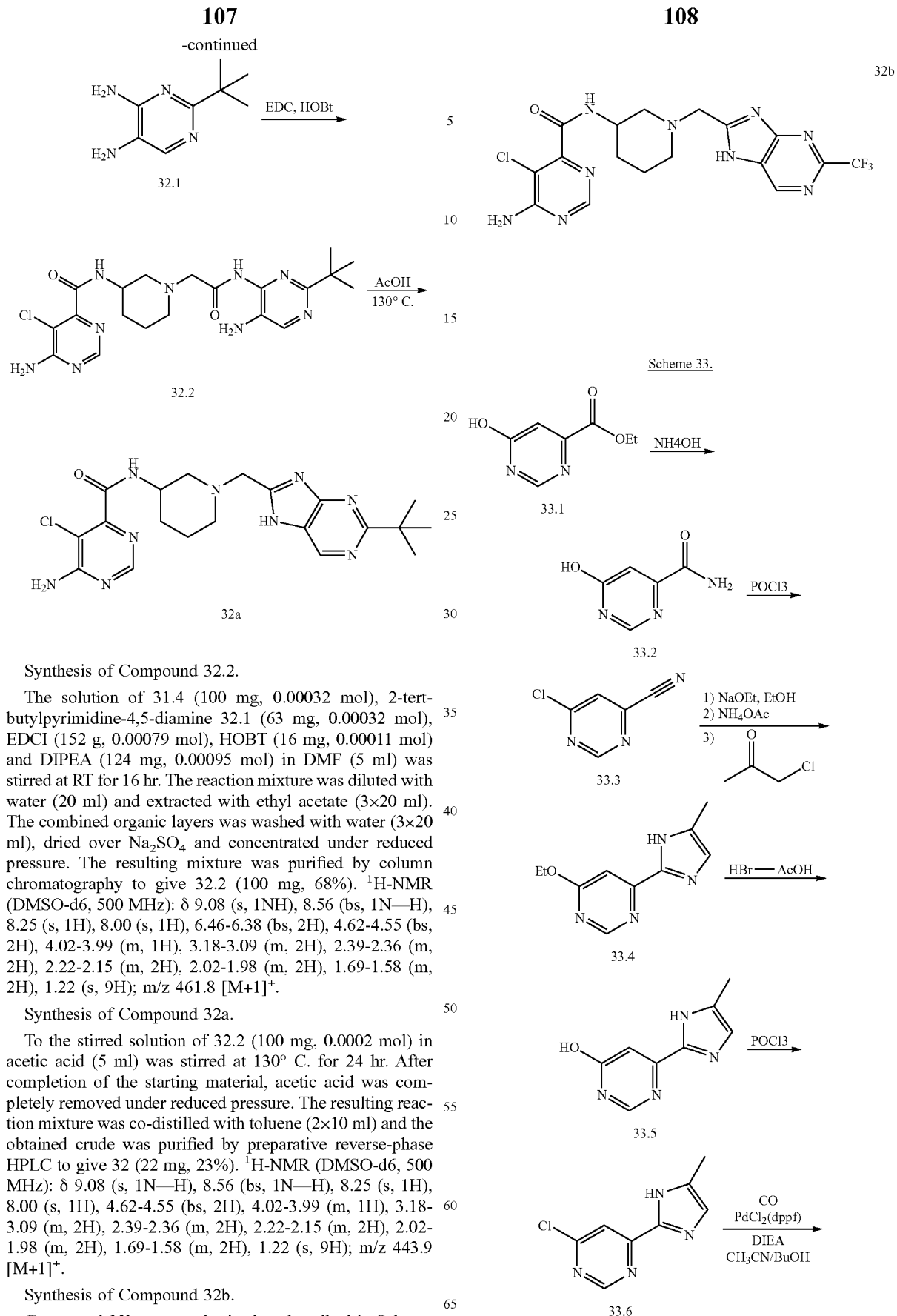

Synthesis of Compound 32.2.

The solution of 31.4 (100 mg, 0.00032 mol), 2-tert-butylpyrimidine-4,5-diamine 32.1 (63 mg, 0.00032 mol), EDCI (152 g, 0.00079 mol), HOBT (16 mg, 0.00011 mol) and DIPEA (124 mg, 0.00095 mol) in DMF (5 ml) was stirred at RT for 16 hr. The reaction mixture was diluted with water (20 ml) and extracted with ethyl acetate (3×20 ml). The combined organic layers was washed with water (3×20 ml), dried over $Na_2SO_4$ and concentrated under reduced pressure. The resulting mixture was purified by column chromatography to give 32.2 (100 mg, 68%). $^1$H-NMR (DMSO-d6, 500 MHz): δ 9.08 (s, 1NH), 8.56 (bs, 1N—H), 8.25 (s, 1H), 8.00 (s, 1H), 6.46-6.38 (bs, 2H), 4.62-4.55 (bs, 2H), 4.02-3.99 (m, 1H), 3.18-3.09 (m, 2H), 2.39-2.36 (m, 2H), 2.22-2.15 (m, 2H), 2.02-1.98 (m, 2H), 1.69-1.58 (m, 2H), 1.22 (s, 9H); m/z 461.8 [M+1]$^+$.

Synthesis of Compound 32a.

To the stirred solution of 32.2 (100 mg, 0.0002 mol) in acetic acid (5 ml) was stirred at 130° C. for 24 hr. After completion of the starting material, acetic acid was completely removed under reduced pressure. The resulting reaction mixture was co-distilled with toluene (2×10 ml) and the obtained crude was purified by preparative reverse-phase HPLC to give 32 (22 mg, 23%). $^1$H-NMR (DMSO-d6, 500 MHz): δ 9.08 (s, 1N—H), 8.56 (bs, 1N—H), 8.25 (s, 1H), 8.00 (s, 1H), 4.62-4.55 (bs, 2H), 4.02-3.99 (m, 1H), 3.18-3.09 (m, 2H), 2.39-2.36 (m, 2H), 2.22-2.15 (m, 2H), 2.02-1.98 (m, 2H), 1.69-1.58 (m, 2H), 1.22 (s, 9H); m/z 443.9 [M+1]$^+$.

Synthesis of Compound 32b.

Compound 32b was synthesized as described in Scheme 32 utilizing 2-trifluoromethylpyrimidine-4,5-diamine.

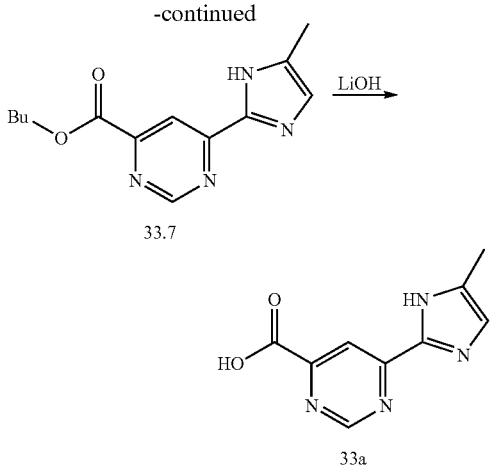

Synthesis of Compound 33.2.

Compound 33.1 (30 g, 178.5 mmol) was treated with ammonium hydroxide solution (300 mL) at 0° C. The reaction mixture was warmed to RT and stirred for 10 hr. After completion of the starting material (by TLC), the precipitated solid was filtered and dried under vacuum. The crude material was co-distilled with toluene to provide 33.2 (15 g, 60.43%) as brown color solid. $^1$H NMR (200 MHz, DMSO-d6) δ 11.6-11.0 (brs, 1H, D$_2$O exchangeable), 8.25 (s, 1H), 8.0-7.9 (brs, 1H, D$_2$O exchangeable), 7.9-7.8 (brs, 1H, D$_2$O exchangeable), 6.8 (s, 1H); m/z 140.0 [M+1]$^+$.

Synthesis of Compound 33.3.

A mixture of 33.2 (15 g, 107.9 mmol) in POCl$_3$ (105 mL, 7 volumes) was heated at reflux for 16 hr. After completion of the starting material (by TLC), the reaction mixture was cooled to RT, poured into ice cold water and neutralized with aqueous ammonium hydroxide solution. Aqueous layer was extracted with ethyl acetate (3×200 mL), and combined organic layers were dried over anhydrous Na$_2$SO$_4$ and evaporated under vacuum to afford crude compound. The crude compound was purified over silica gel column chromatography eluting with 10% ethyl acetate/hexane to afford 33.3 (9.8 g, 65.33%) as pale yellow syrup. $^1$H NMR (1H, 200 MHz, CDCl3): δ 9.15 (s, 1H), 7.75 (s, 1H).

Synthesis of Compound 33.4.

To a stirred solution of 33.3 (4 g, 28.77 mmol) in absolute ethanol (40 mL) was added freshly prepared NaOEt (5.86 g, 86.33 mmol) at RT and stirred for 3 hr. After complete consumption of the starting material (by TLC), the reaction mixture was diluted with absolute ethanol (40 mL), and treated with NH$_4$OAc (8.87 g, 115.08 mmol) at RT and continued stirring for overnight at RT. The reaction mixture was filtered and the filtrate was evaporated under reduced pressure and the residue was dissolved in absolute ethanol (120 mL). To this chloro-acetone (6.93 mL, 86.33 mmol) was added at RT and the reaction mixture was heated at reflux temperature for 16 hr. After completion of the starting material (by TLC), the volatiles were evaporated under reduced pressure. The resulting residue was dissolved in water and neutralized with saturated NaHCO$_3$ solution. The aqueous layer was extracted ethyl acetate (2×100 mL). The combined organic extracts were dried over anhydrous Na$_2$SO$_4$ and concentrated under vacuum. The crude material was purified by column chromatography eluting with 40% EtOAc/hexane to obtain 33.4 (300 mg, 6.97%) as brown color solid. $^1$H NMR (200 MHz, CDCl3) δ 10.3-10.0 (brs, 1H, D$_2$O exchangeable), 8.65 (s, 1H), 7.41 (2 s, 1H), 6.95 (2 s, 1H), 4.6-4.4 (q, 2H), 2.4 (d, 3H), 1.41 (t, 3H); m/z 205.0 [M+1]$^+$.

Synthesis of Compound 33.5.

A mixture of 33.4 (300 mg, 1.47 mmol) in HBr-acetic acid (10 mL) was stirred at reflux temperature for 4 hr under inert atmosphere. After completion of the starting material (by TLC), the solvent was evaporated under reduced pressure to afford crude compound. The crude compound was dissolved in water; aqueous layer was washed with ethyl acetate (30 mL). The aqueous layer was evaporated under reduced pressure and to the crude compound was dried with toluene (co-distilled) to obtain 33.5 (200 mg, 77.51%) as brown colored solid. $^1$H NMR (1H, 200 MHz, DMSO-d6): δ 8.15 (s, 1H), 6.80 (s, 1H), 6.50 (s, 1H), 2.18 (s, 3H); m/z 177.0 [M+1]$^+$.

Synthesis of Compound 33.6.

A mixture of 33.5 (0.2 g, 1.13 mmol) in POCl$_3$ (10 mL) was heated at reflux temperature for 4 hr under inert atmosphere. After completion of the starting precursor (by TLC), reaction mixture was poured into ice water and neutralized to pH 7 using NaHCO$_3$. The aqueous layer was extracted with EtOAc (2×50 mL). The combined organic extracts were dried over anhydrous Na$_2$SO$_4$ and evaporated under reduced pressure to provide 33.6 (0.15 g, 68%) as a brown colored solid. $^1$H NMR (200 MHz, DMSO-d6) δ 9.18 (s, 1H), 8.60 (s, 1H), 7.41 (s, 1H), 2.31 (s, 3H); m/z 194.9 [M+1]$^+$.

Synthesis of Compound 33.7.

To a stirred solution of 33.6 (0.3 g, 1.54 mmol) in acetonitrile (9.0 mL) and n-BuOH (9.0 mL) in steel bomb was added dppf-PdCl$_2$ (0.15 g) followed by N-ethyldiisopropylamine (0.4 mL, 2.3 mmol) at RT under inert atmosphere. The steel bomb was filled with carbon monoxide (120 psi) and heated at 65° C. for 16 hr. After consumption of the starting material (by TLC), the reaction mixture was filtered through a pad of celite. The filtrate was evaporated under reduced pressure to obtain a crude material that was purified over silica gel column chromatography eluting with 30% EtOAc/hexane to afford 33.7 (mixture of two isomers) (0.2 g, 49%) as light brown color solid. $^1$H NMR (200 MHz, CDCl$_3$) δ 10.4-10.2 (brs, 1H), 9.12 (2 s, 1H), 8.62 (2 s, 1H), 7.01 (d, 1H), 4.42 (t, 2H), 2.38 (d, 3H), 1.81-1.72 (m, 2H), 1.61-1.40 (m, 2H), 1.02 (t, 3H); m/z 260.9 [M+1]$^+$.

Synthesis of Compound 33a.

To a stirred solution of 33.7 (0.2 g, 0.76 mmol) in THF (1.5 mL) was added LiOH solution (1M in H$_2$O) (0.769 mL, 0.76 mmol) at RT under inert atmosphere and the resulting mixture was stirred for 2 hr at RT. After complete consumption of starting precursor (by TLC), the volatiles were evaporated under vacuum and crude material was dissolved in water (10 mL). Aqueous layer was washed with EtOAc (10 mL) and acidified with 2N HCl at 0° C. The precipitated solid was filtered, washed with hexane (10 mL) and dried under vacuum to provide 33.7 (0.15 g, 96%) as a yellow colored solid. $^1$H NMR (500 MHz, DMSO-d6) δ 14.20-13.91 (brs, 1H, D$_2$O exchangeable), 9.38 (s, 1H), 8.45 (s, 1H), 7.22 (s, 1H), 2.21 (s, 3H); m/z 205.0 [M+1]$^+$.

Compounds 33a-33b.

Using 4-chloro-6-(5-(trifluoromethyl)-1H-imidazol-2-yl) pyrimidine (See WO2007076473 and WO2007076474), compound 33b was synthesized as exemplified in Scheme 33.

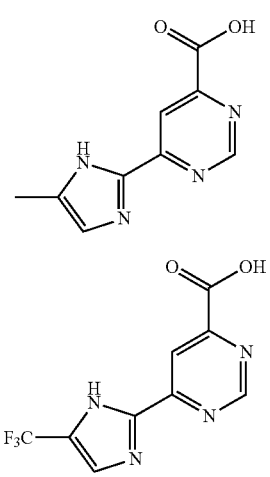

33a

33b

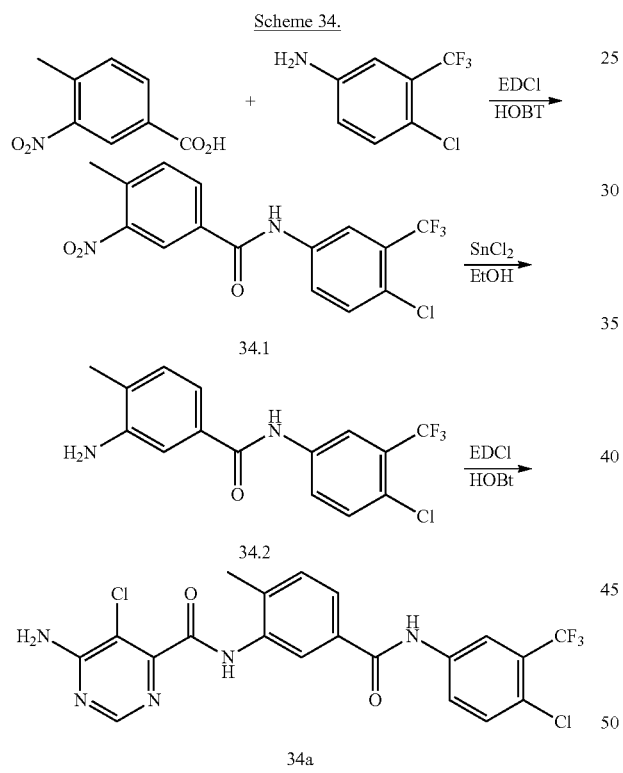

Scheme 34.

34.1

34.2

34a

Synthesis of Compound 34.1.

To a stirred solution of 4-methyl-3-nitrobenzoic acid (500 mg, 2.76 mmol) in DMF (10 mL), HOBT (560 mg, 4.14 mmol), EDCI (794 mg, 4.14 mmol) and 4-chloro-3-trifluoromethyl-aniline (540 mg, 2.76 mmol) were added at 0° C., and the reaction mixture was stirred for 6 hr at room temperature. The reaction mixture was diluted with water (50 mL) and extracted with EtOAc (2×50 mL). The combined organic layers was washed with water, dried over anhydrous $Na_2SO_4$ and concentrated under reduced pressure. The residue was purified by column chromatography ($SiO_2$, 100% Hexane then gradient to 12% EtOAC/hexane) to afford compound 34.2 (700 mg, 70.7%) as light yellow solid. $^1H$ NMR (DMSO-D6, 200 MHz) δ 10.8 (s, 1H, $D_2O$ exchangeable), 8.6 (s, 1H), 8.5 (s, 1H), 8.2-8.3 (d, 1H), 8.1-8.2 (d, 1H), 7.6-7.8 (m, 2H), 2.6 (s, 3H); LCMS m/z 358.9 $[M+1]^+$.

Synthesis of Compound 34.2.

To a stirred solution of 34.1 (550 mg, 1.553 mmol) in ethanol (50 mL) at room temperature, tin(II)chloride (1.38 g, 6.133 mmol) was added and the reaction mixture was refluxed for 2 hr. The solvent was concentrated under vacuum. The residue was dissolved in EtOAc, washed with 2N NaOH and brine, dried over anhydrous $Na_2SO_4$, and concentrated to afford 34.2 (400 mg, 79.36%) as a yellow solid. $^1H$ NMR (DMSO-D6, 200 MHz) δ 10.2 (s, 1H, $D_2O$ exchangeable), 8.4 (s, 1H), 8.05-8.15 (d, 1H), 7.6-7.65 (d, 1H), 7.2 (s, 1H), 7.1 (s, 1H), 5.05 (s, 2H, $D_2O$ exchangeable), 2.1 (s, 3H); LCMS m/z 328.9 $[M^+1]^+$.

Synthesis of Compound 34a.

To a stirred solution of 34.2 (250 mg, 0.76 mmol) in DMF (10 mL), HOBT (154 mg, 1.14 mmol), EDCI (218 mg, 1.14 mmol) and compound 10 (132 mg, 0.76 mmol) were added at 0° C. and stirred for 8 hr at room temperature. After completion, the reaction mixture was diluted with water (50 mL) and extracted with twice with EtOAc (2×50 mL). The combined organic layers were washed with water, dried over anhydrous $Na_2SO_4$, and concentrated. The crude compound obtained was purified by column chromatography ($SiO_2$, 100% DCM then gradient to 2% MeOH/DCM) to afford 34a (300 mg, 81.52%) as off white solid. $^1H$ NMR (DMSO-D6, 500 MHz) δ 10.6 (s, 1H, $D^2O$ exchangeable), 10.3 (s, 1H, D2O exchangeable), 8.4 (2 s, 2H), 8.15 (m, 2H), 7.8 (m, 1H), 7.75 (m, 1H), 7.5 (m, 1H), 2.3 (s, 3H); LCMS m/z 484.26 $[M+1]^+$.

Compounds 34a-34h.

Using different amines, the following compounds can be synthesized as exemplified in Scheme 34:

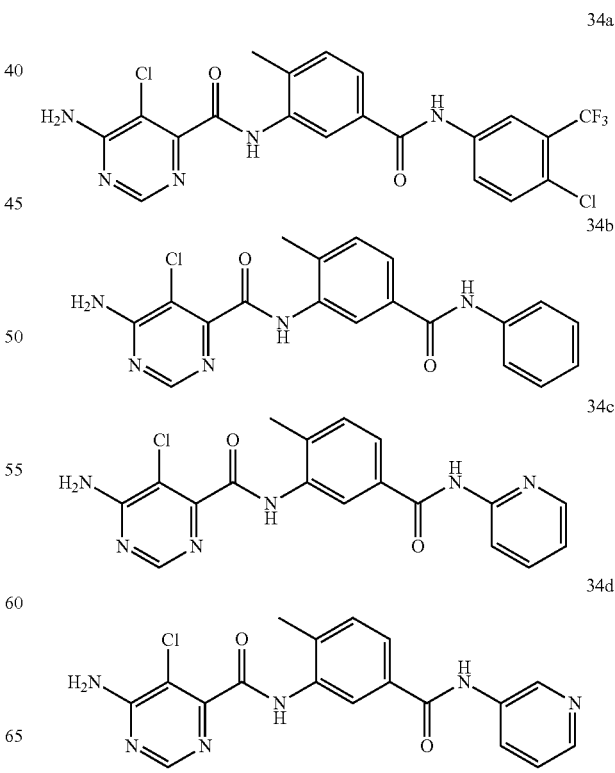

34a

34b

34c

34d

-continued

34e
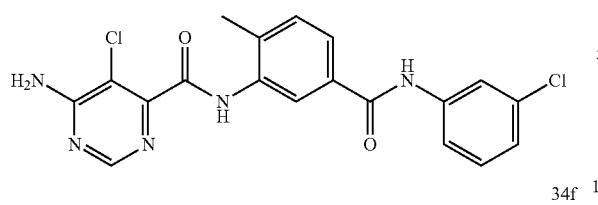

34f
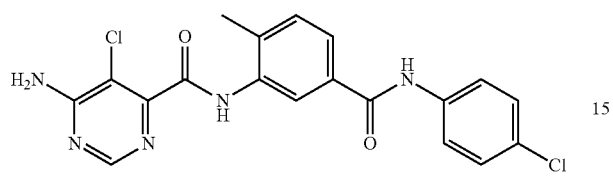

34g
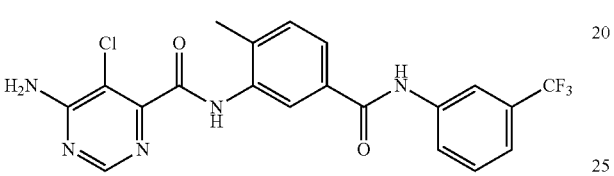

34h
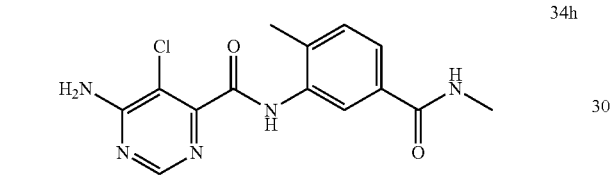

Compounds 34i.

Using 4-methyl-3-nitro-aniline and 4-chloro-3-trifluoromethyl-benzoic acid, the following compounds can be synthesized as exemplified in Scheme 34.

34i
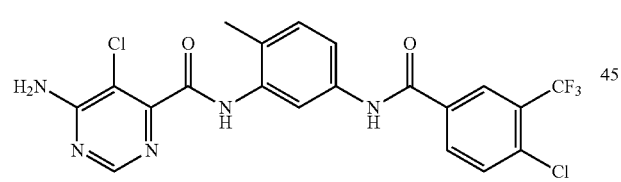

Compounds 34j-34k.

Using compound O.7 or N.6, the following compounds can be synthesized as exemplified in Scheme 34 and Schemes O and N.

34j
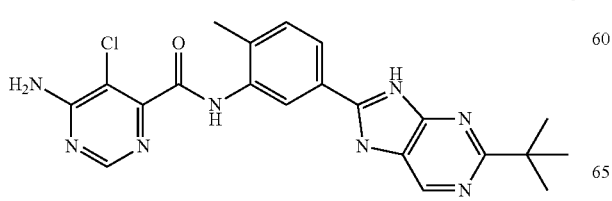

34k
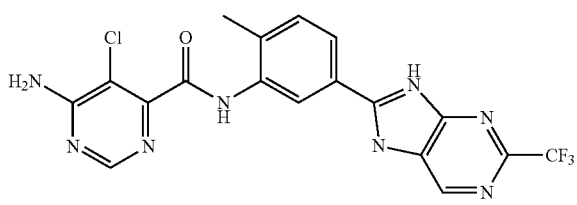

In certain embodiments, the compound of formula

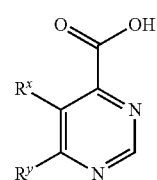

for use in preparing compounds of the present invention is selected from those set forth in Table 1, below.

TABLE 1

| Exemplary | 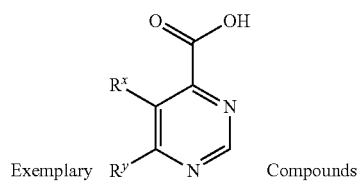 | Compounds |
|---|---|---|
| | 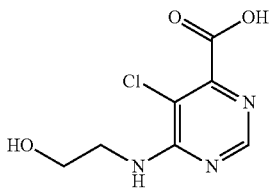 | 1a |
| | 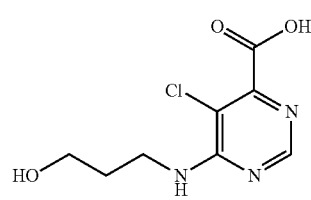 | 1b |
| | 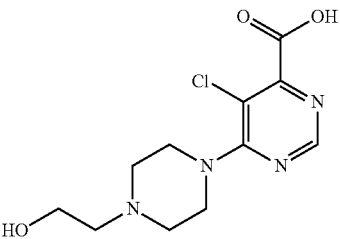 | 1c |

TABLE 1-continued
Exemplary Compounds
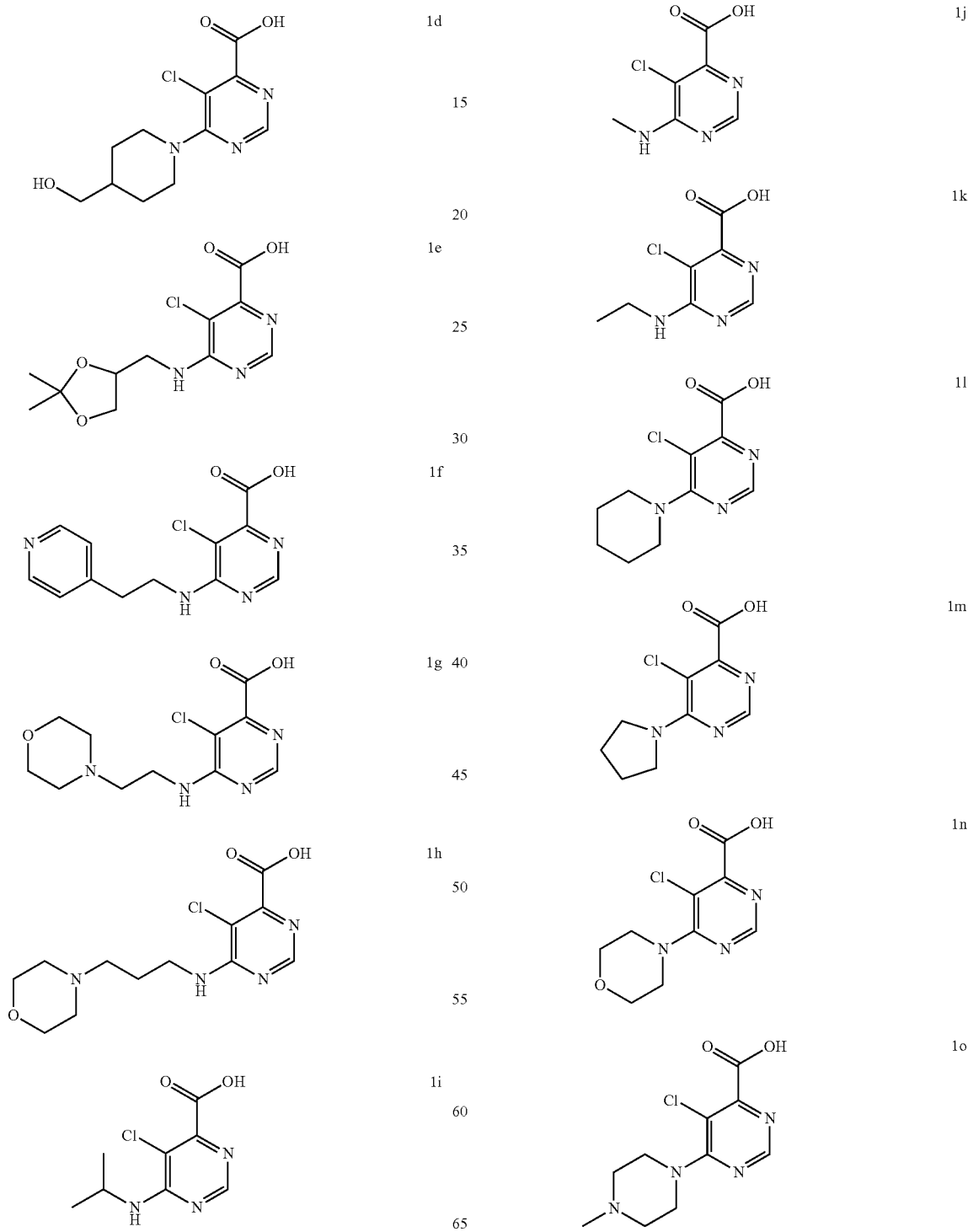

TABLE 1-continued
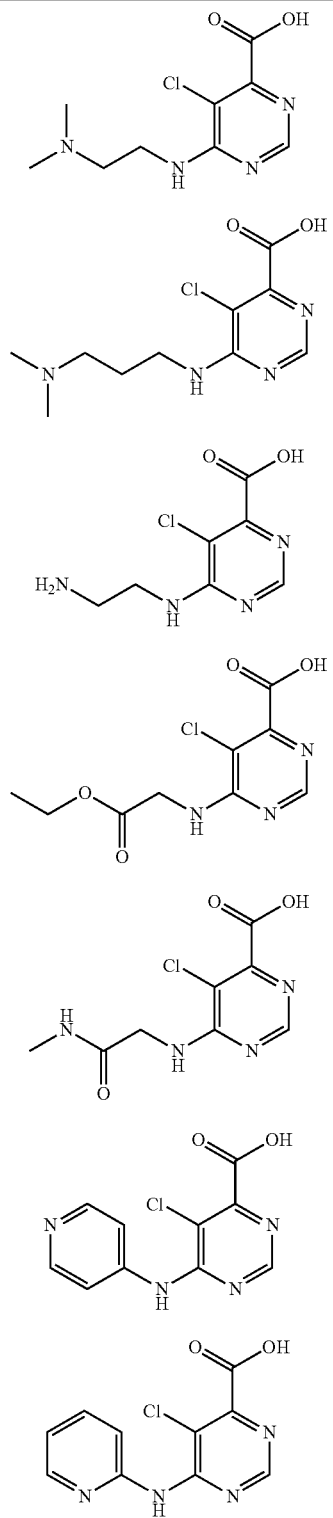
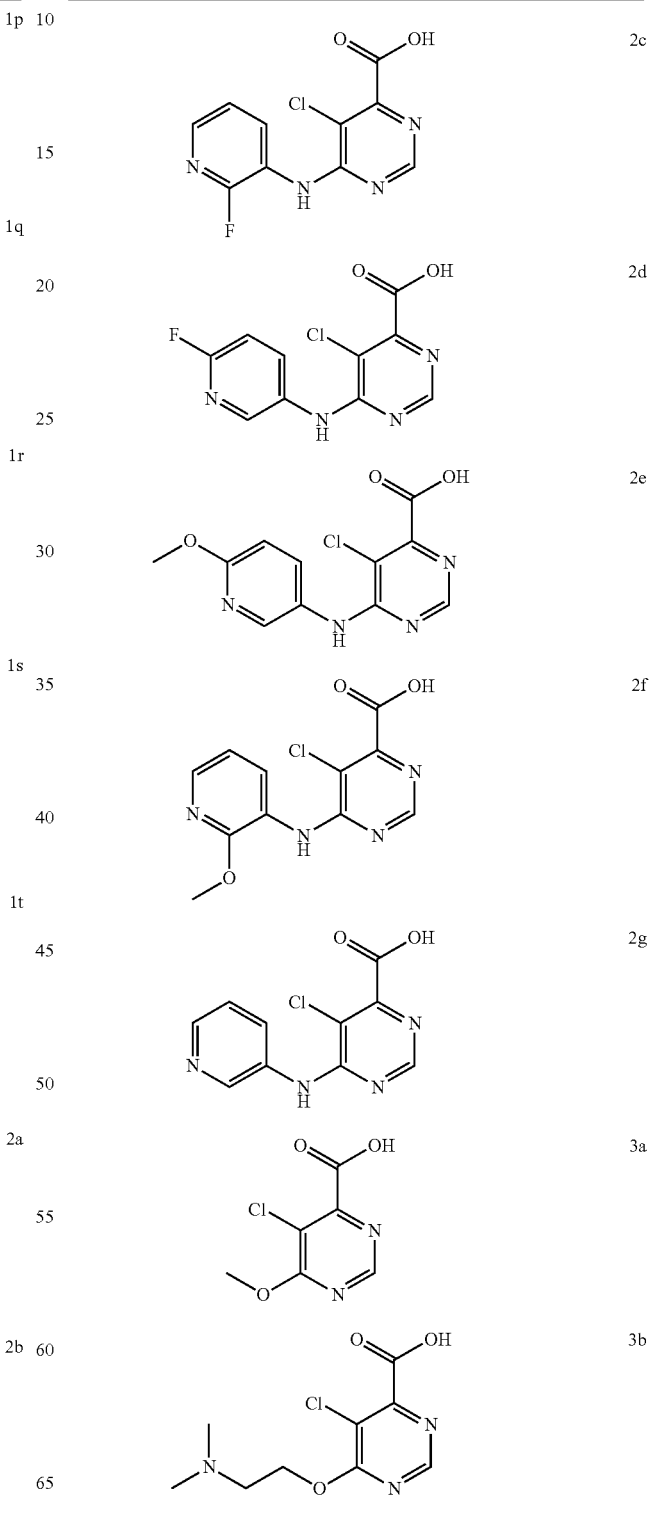

TABLE 1-continued
| Exemplary | Compounds |
|---|---|
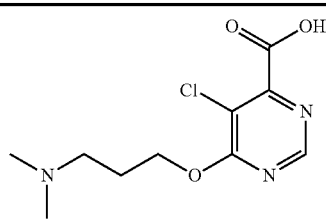  3c
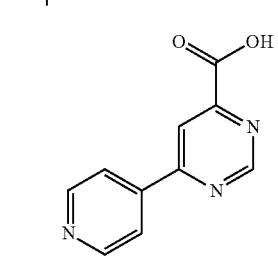  4a
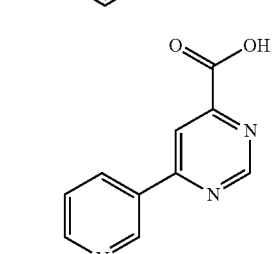  4b
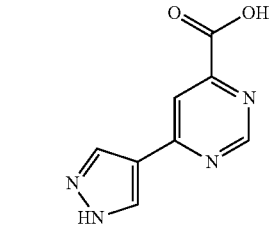  4c
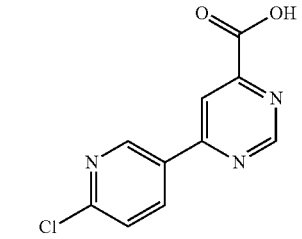  4d
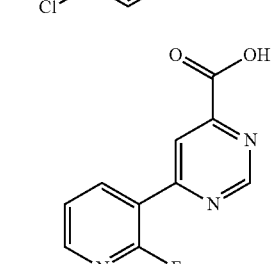  4e
TABLE 1-continued
| Exemplary | Compounds |
|---|---|
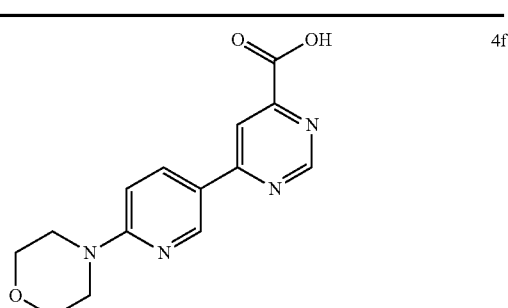  4f
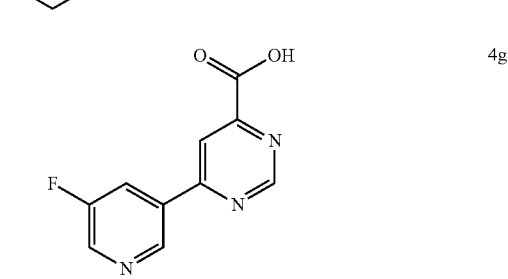  4g
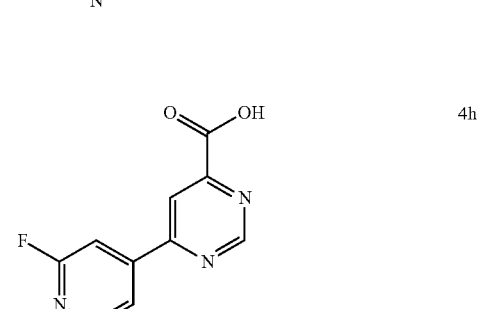  4h
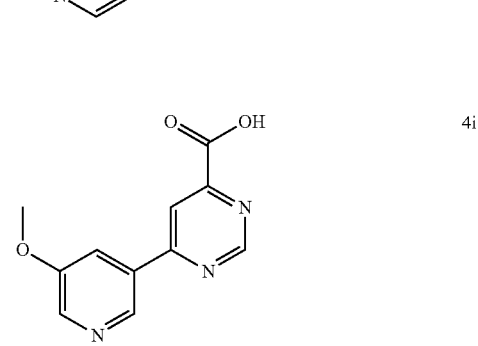  4i
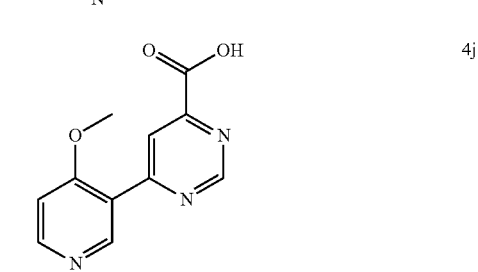  4j TABLE 1-continued
Exemplary Compounds
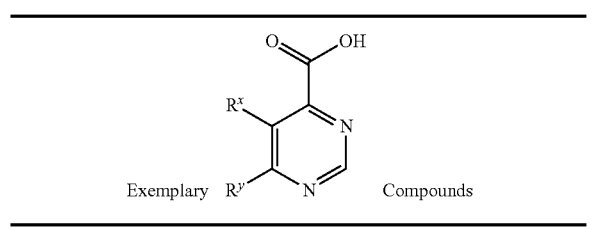
| | |
|---|---|
| 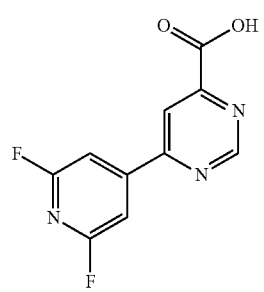 | 4k |
| 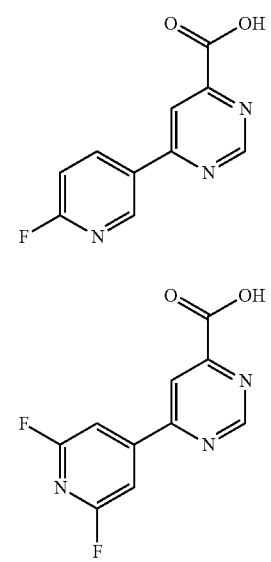 | 4l |
| 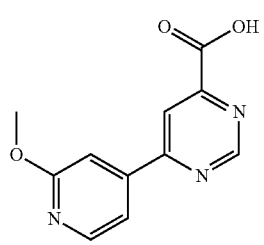 | 4m |
| 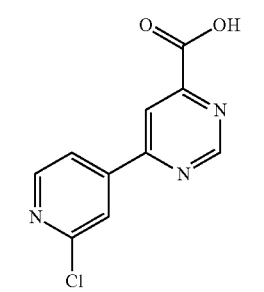 | 4n |
| 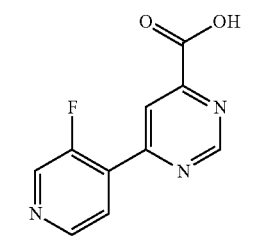 | 4o |
TABLE 1-continued
Exemplary Compounds
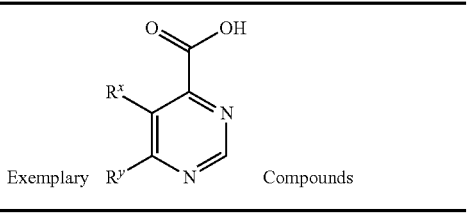
| | |
|---|---|
| 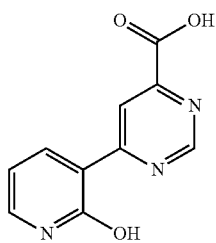 | 4p |
| 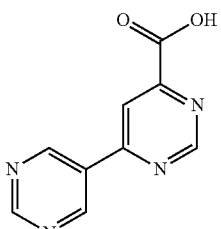 | 4q |
| 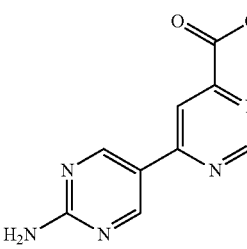 | 4r |
| 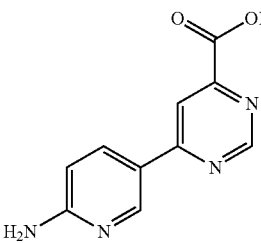 | 4s |
| | 4t |

TABLE 1-continued
Exemplary Compounds
| | |
|---|---|
| 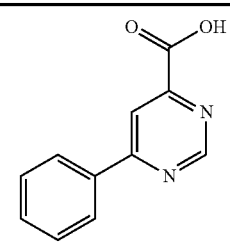 4u | 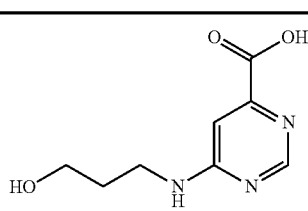 5c |
| 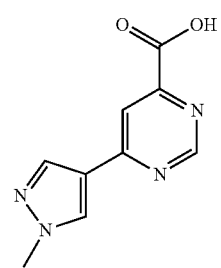 4v | 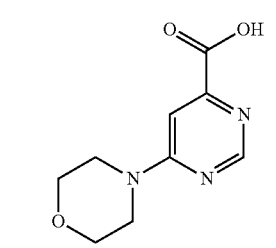 5d |
| 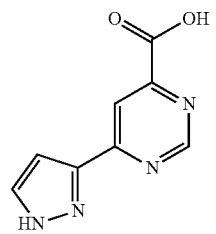 [SMILES: O=C(O)c1cc(-c2cc[nH]n2)ncn1] 4w | 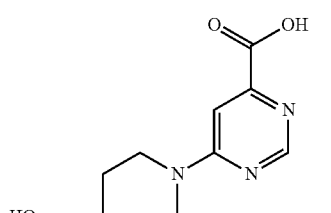 5e |
| 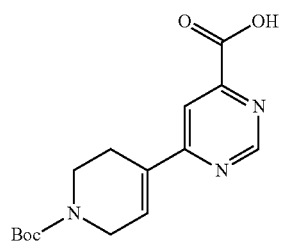 [SMILES: CC(C)(C)OC(=O)N1CC=C(c2cc(C(=O)O)ncn2)CC1] 4z | 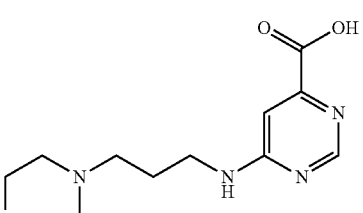 5f |
| 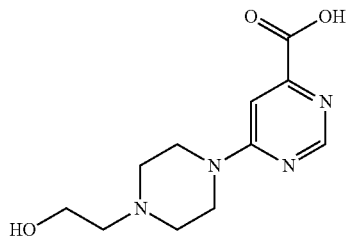 [SMILES: O=C(O)c1cc(N2CCN(CCO)CC2)ncn1] 5a | 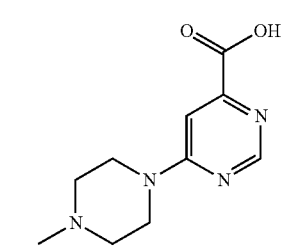 5g |
| 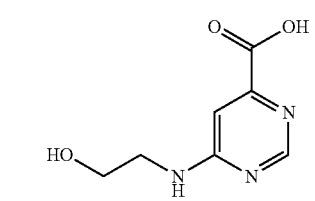 [SMILES: O=C(O)c1cc(NCCO)ncn1] 5b | 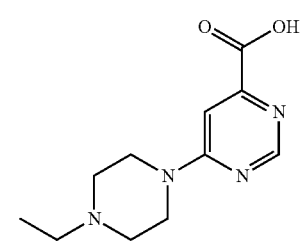 [SMILES: CCN1CCN(c2cc(C(=O)O)ncn2)CC1] 5h |

TABLE 1-continued
Exemplary Compounds
| | |
|---|---|
| 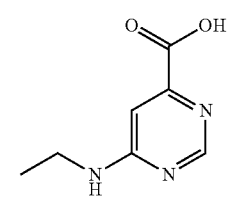 | 5i |
| 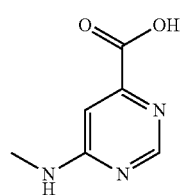 | 5j |
| 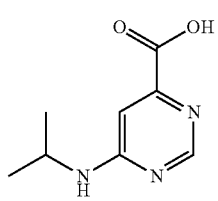 | 5k |
| 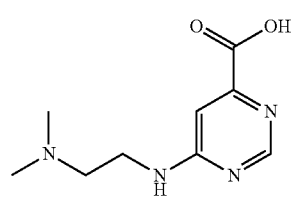 | 5l |
| 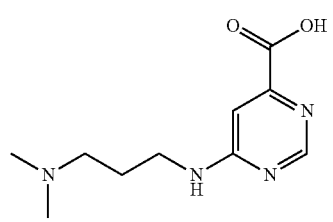 [SMILES: CN(C)CCCNc1cc(C(=O)O)ncn1] | 5m |
| 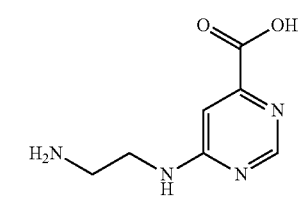 [SMILES: NCCNc1cc(C(=O)O)ncn1] | 5n |
TABLE 1-continued
Exemplary Compounds
| | |
|---|---|
| 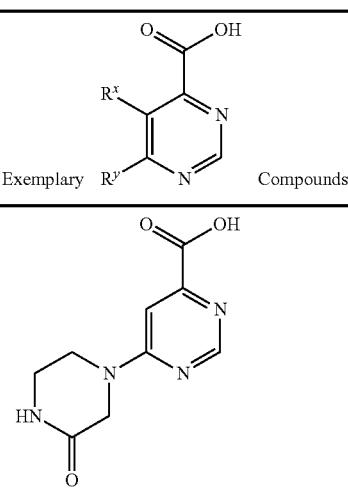 | 5o |
| 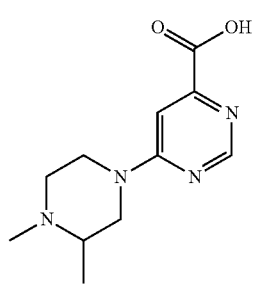 [SMILES: CC1CN(c2cc(C(=O)O)ncn2)CCN1C] | 5p |
| 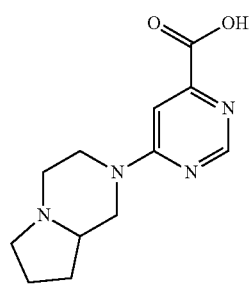 [SMILES: O=C(O)c1cc(N2CCN3CCCC3C2)ncn1] | 5q |
| 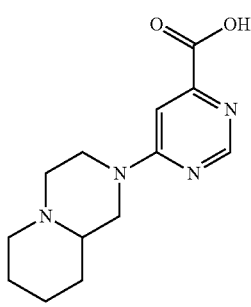 [SMILES: O=C(O)c1cc(N2CCN3CCCCC3C2)ncn1] | 5r |
| 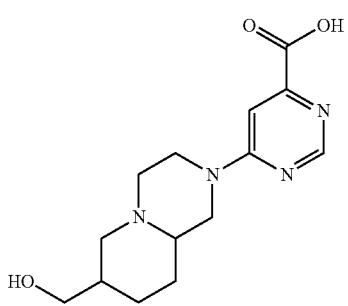 [SMILES: O=C(O)c1cc(N2CCN3CC(CO)CCC3C2)ncn1] | 5s |

TABLE 1-continued
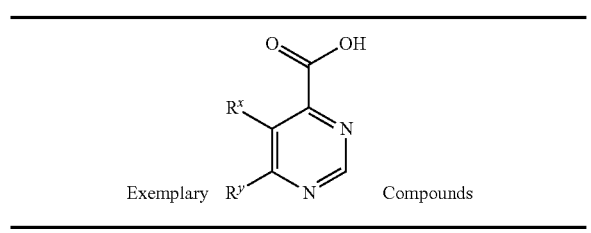
Exemplary Compounds
| | |
|---|---|
| 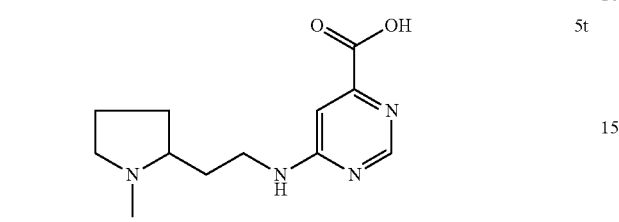 | 5t |
| 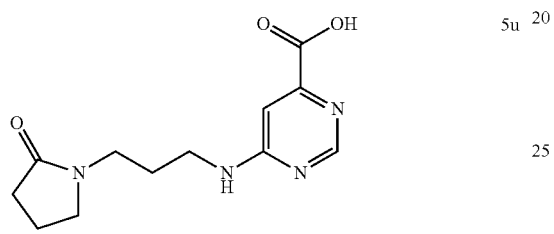 | 5u |
| 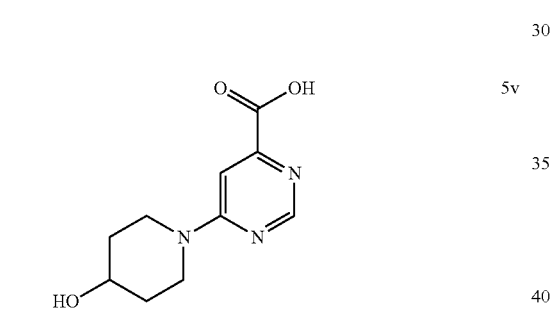 | 5v |
| 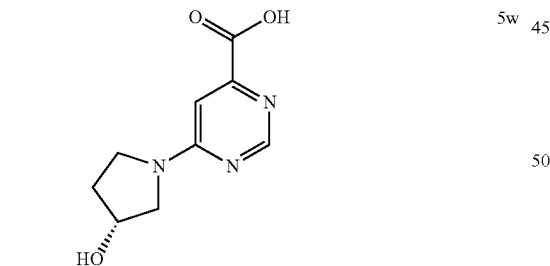 | 5w |
| 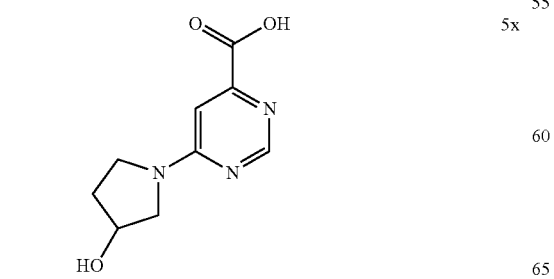 | 5x |
TABLE 1-continued
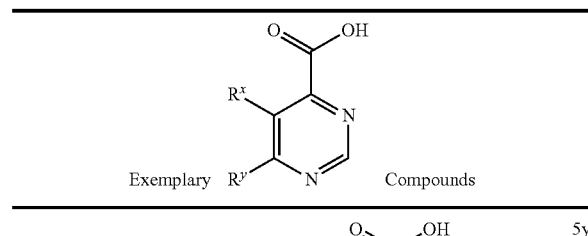
Exemplary Compounds
| | |
|---|---|
| 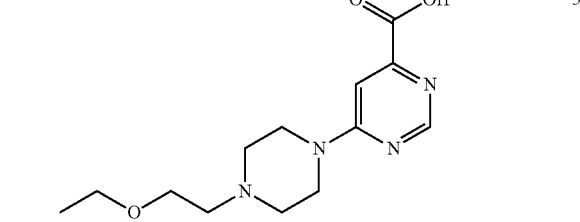 | 5y |
| 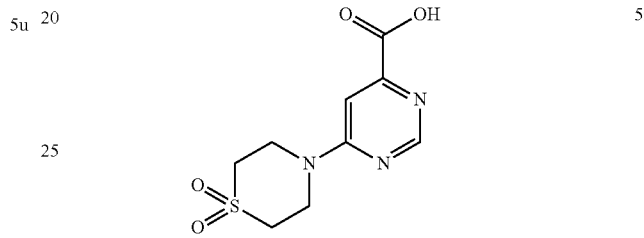 | 5z |
| 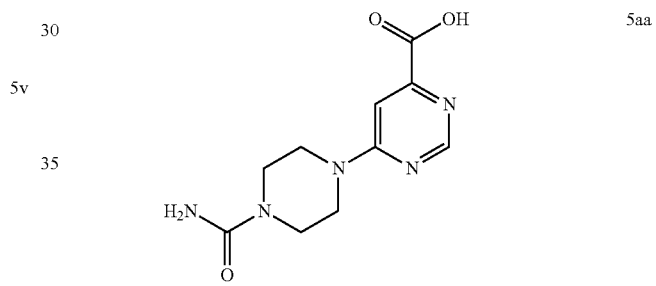 | 5aa |
| 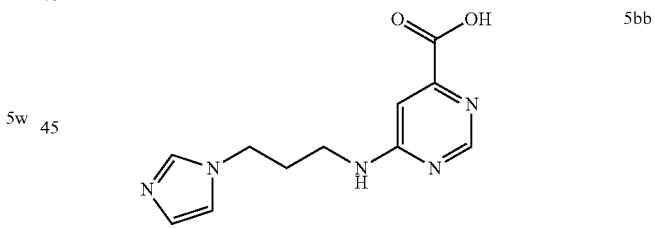 | 5bb |
| 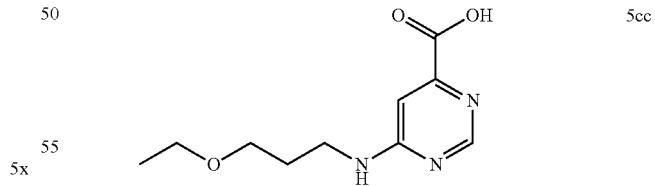 | 5cc |
| 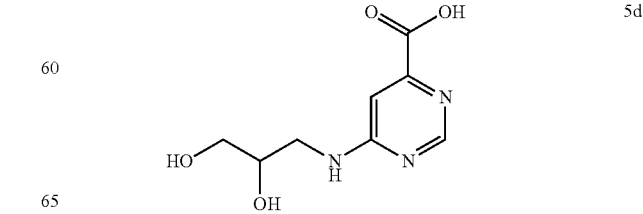 | 5dd |

TABLE 1-continued
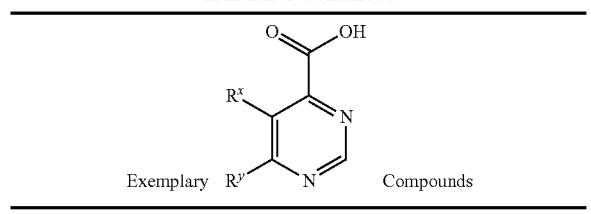
Exemplary Compounds
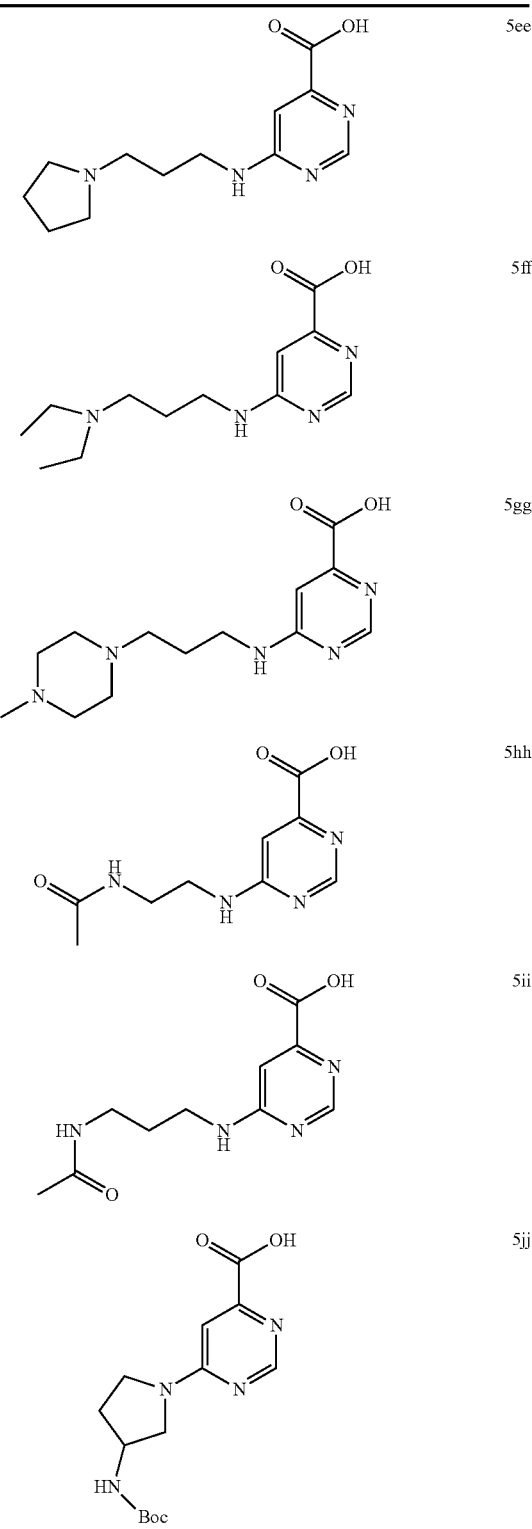
TABLE 1-continued
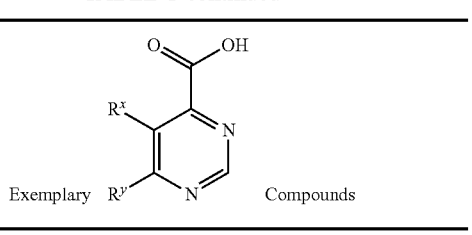
Exemplary Compounds
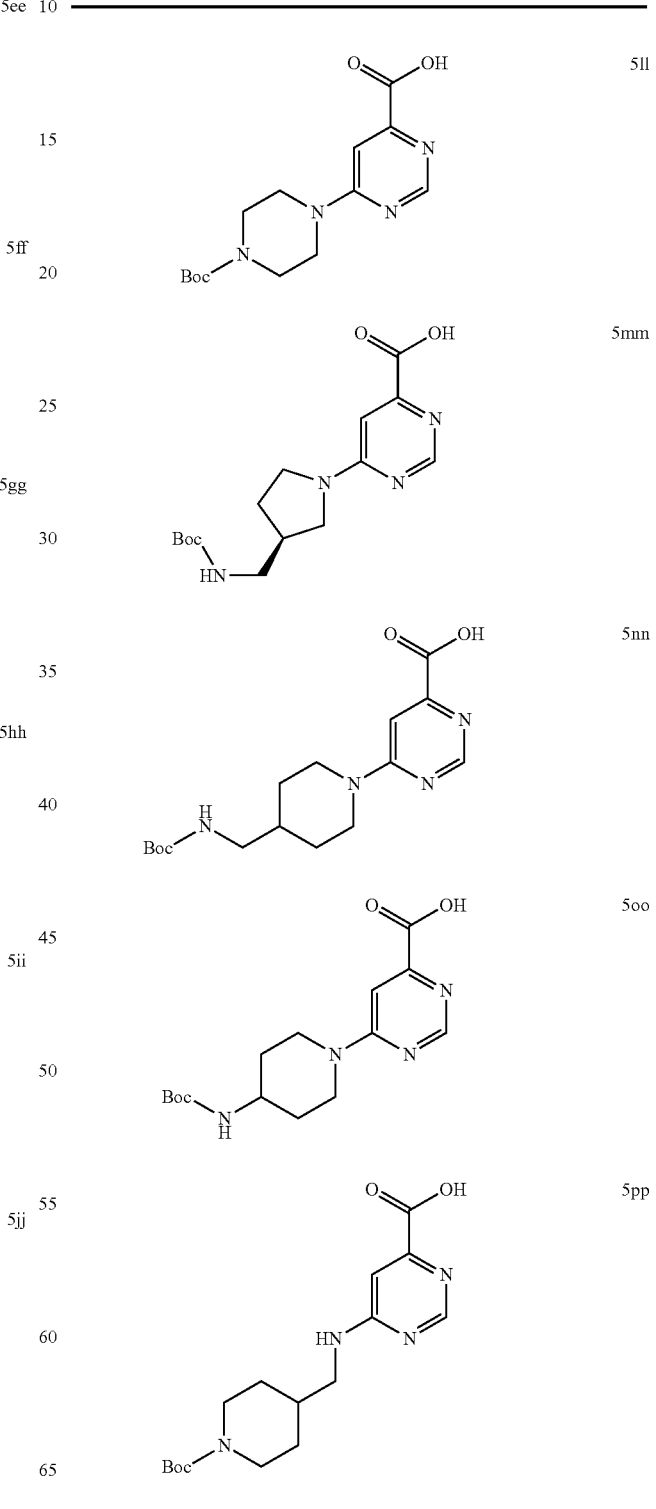

TABLE 1-continued
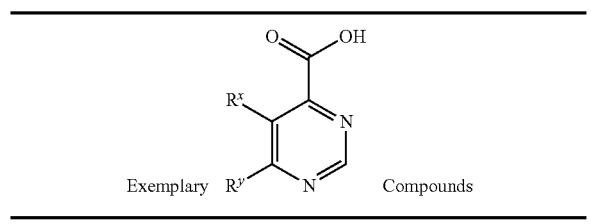
Exemplary Compounds
| | |
|---|---|
| 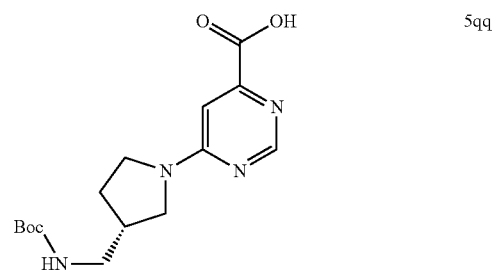 | 5qq |
| 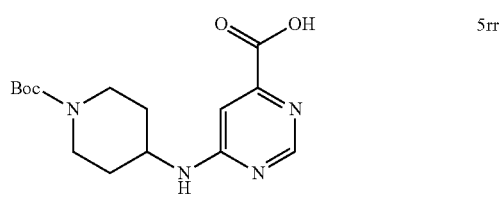 | 5rr |
| 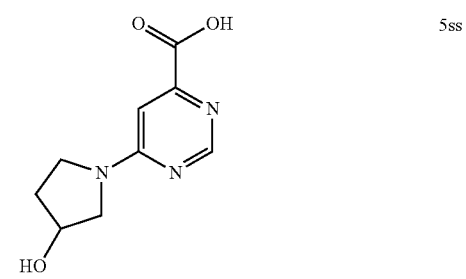 | 5ss |
| 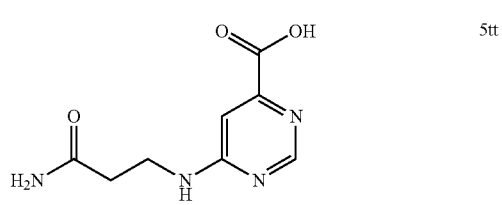 | 5tt |
| 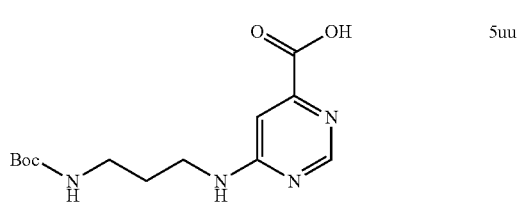 | 5uu |
| 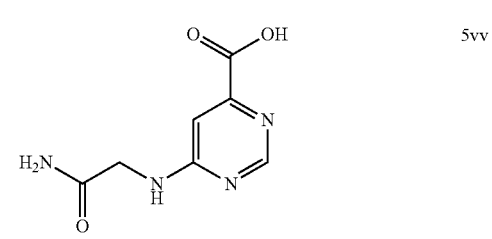 | 5vv |
TABLE 1-continued
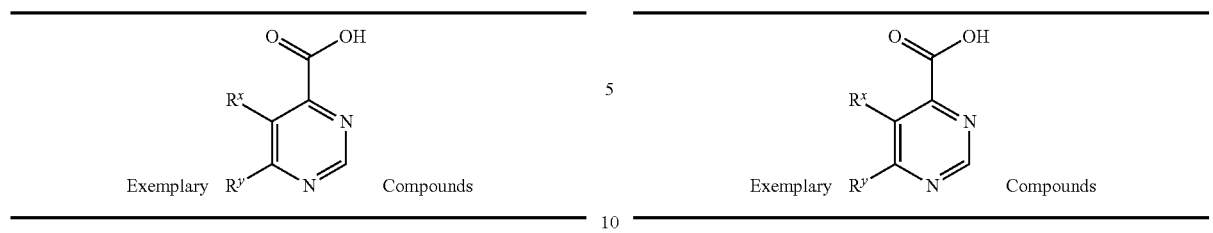
Exemplary Compounds
| | |
|---|---|
| 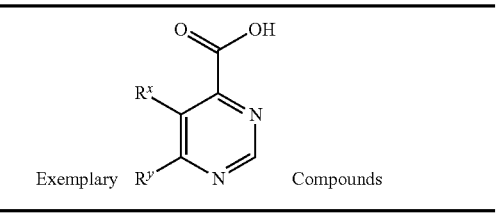 | 5ww |
| 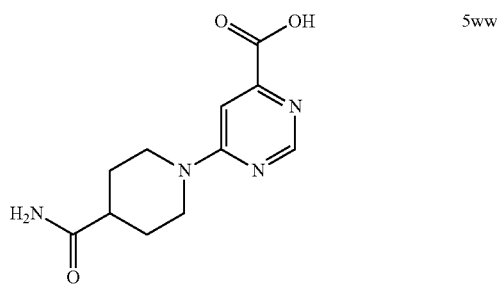 | 5xx |
| 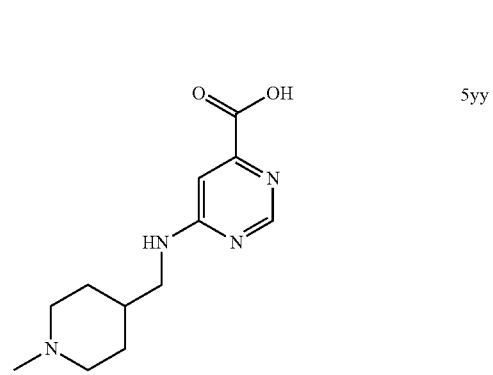 | 5yy |
| 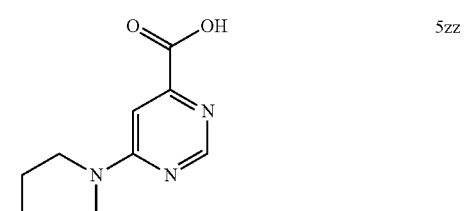 | 5zz |
| 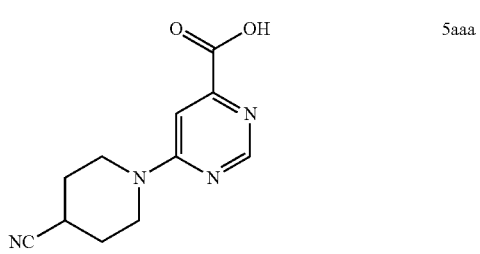 | 5aaa |

TABLE 1-continued

Exemplary Compounds

| Compound |
|---|
| 5bbb |
| 5ccc |
| 5ddd |
| 5eee |
| 6a |
| 6b |
| 6c |
| 6d |
| 6e |
| 6f |
| 6g |
| 6h |
| 6i |

TABLE 1-continued
Exemplary Compounds
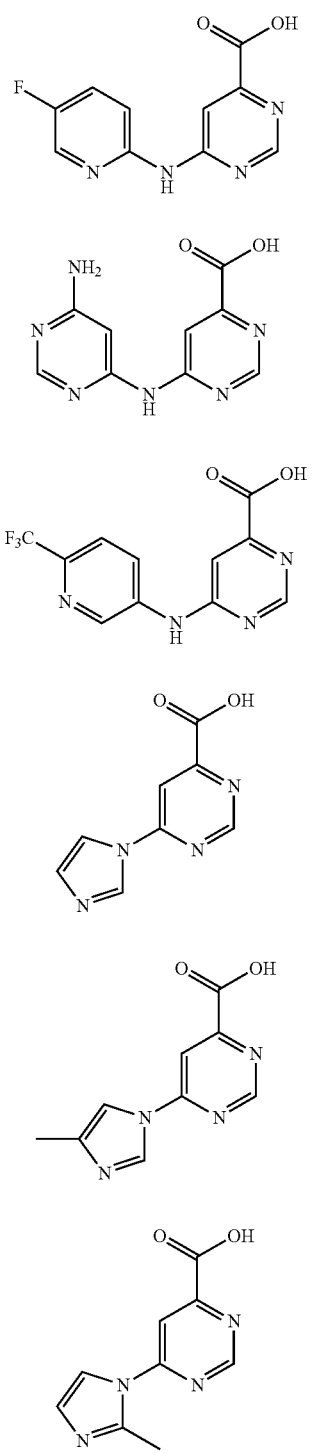
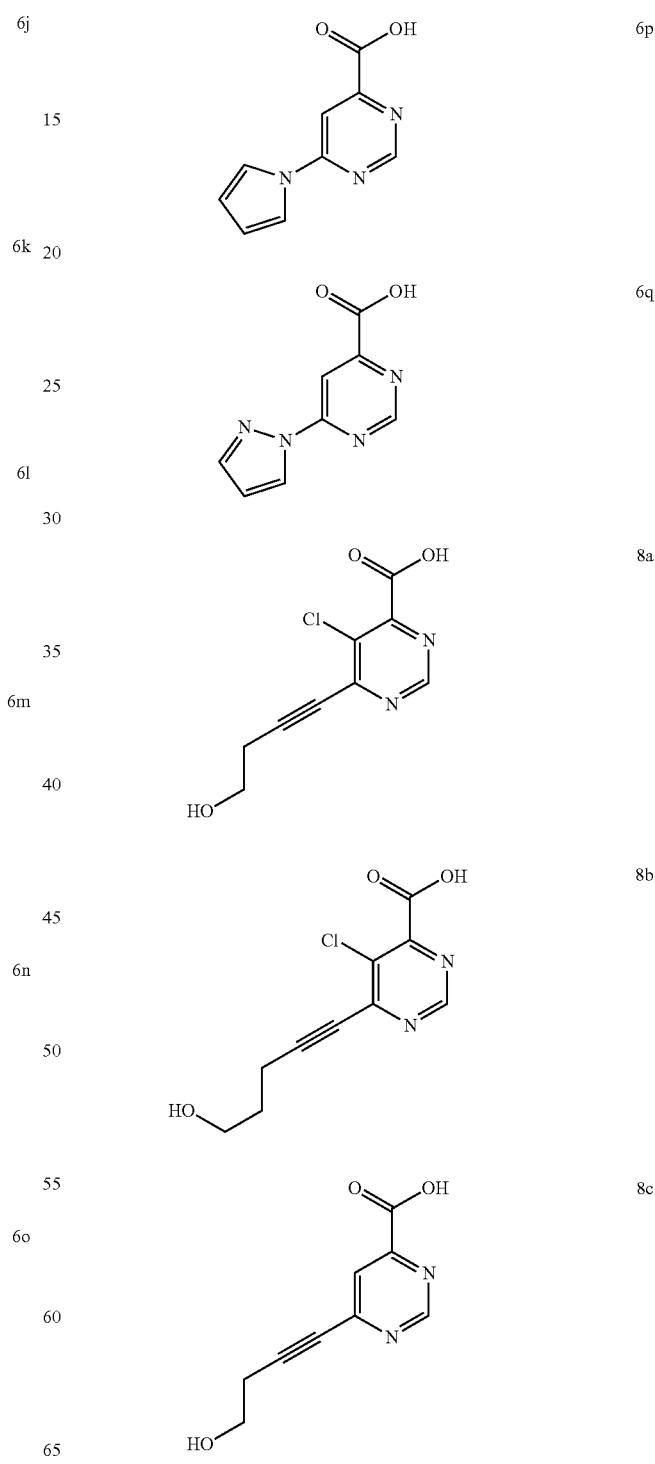

TABLE 1-continued
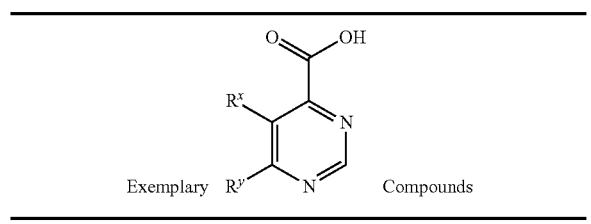
Exemplary Compounds
| | |
|---|---|
| 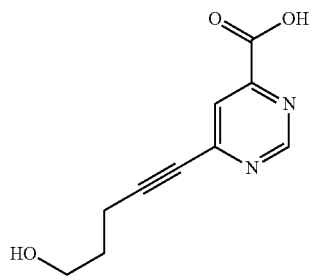 [SMILES: O=C(O)c1cc(C#CCCCO)ncn1] | 8d |
| 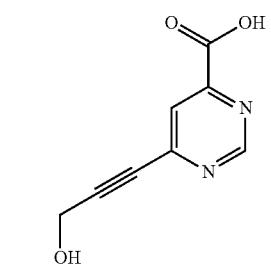 [SMILES: O=C(O)c1cc(C#CCO)ncn1] | 8e |
| 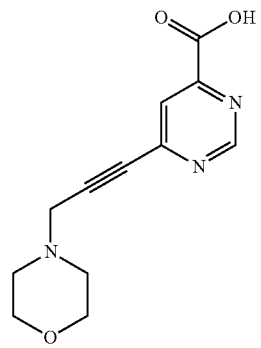 [SMILES: O=C(O)c1cc(C#CCN2CCOCC2)ncn1] | 8f |
| 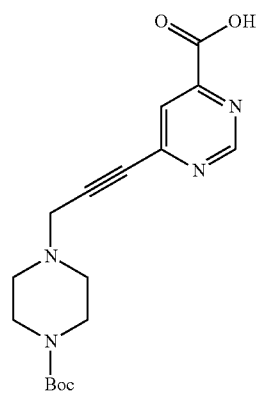 [SMILES: CC(C)(C)OC(=O)N1CCN(CC#Cc2cc(C(=O)O)ncn2)CC1] | 8g |
TABLE 1-continued
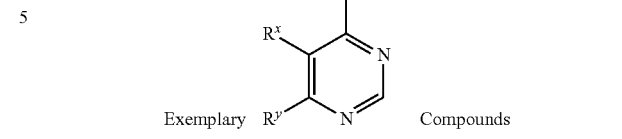
Exemplary Compounds
| | |
|---|---|
| 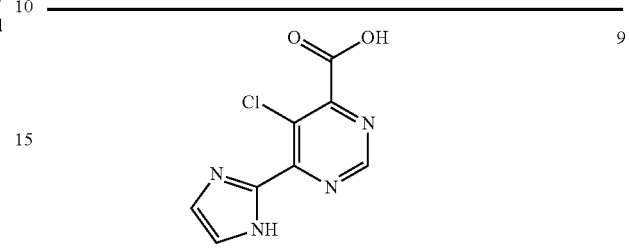 | 9 |
| 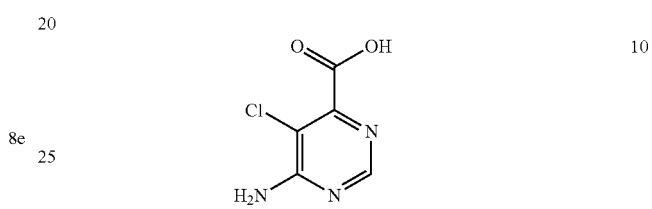 | 10 |
| 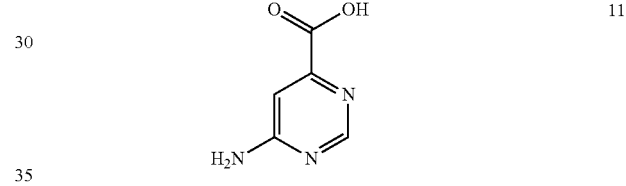 | 11 |
| 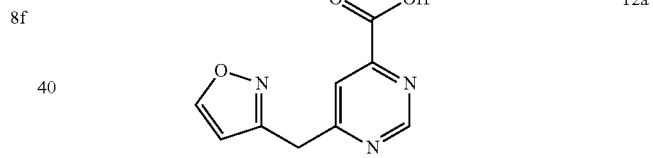 | 12a |
| 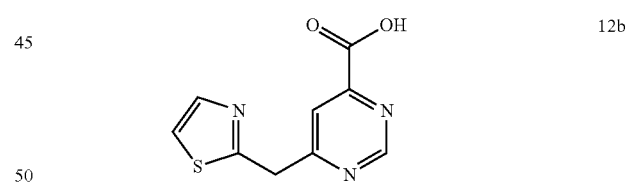 | 12b |
| 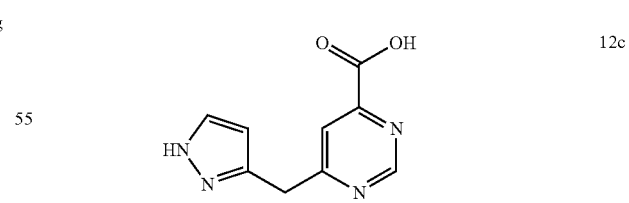 | 12c |
| 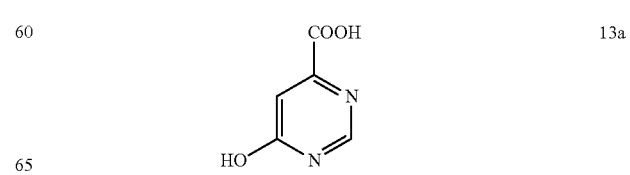 | 13a |

TABLE 1-continued
Exemplary Compounds
| | |
|---|---|
| 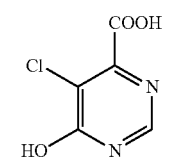 13b | 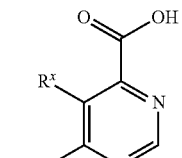 15c |
| 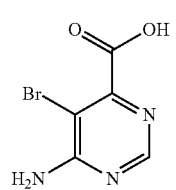 14a | 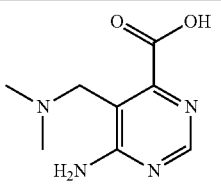 15d |
|  14b | 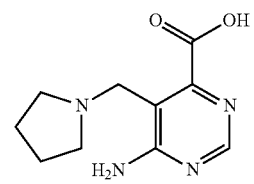 15e |
| 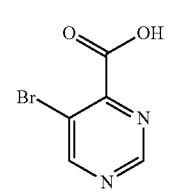 14c | 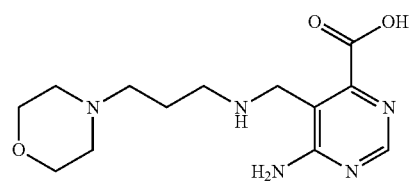 [SMILES: Nc1ncnc(C(=O)O)c1CNCCCN1CCOCC1] 16 |
| 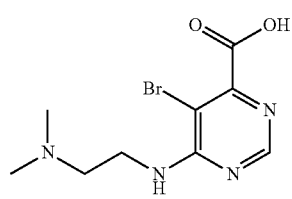 14d | 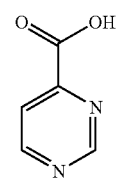 17 |
| 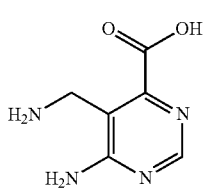 15a | 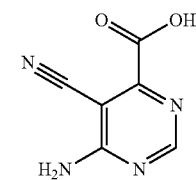 18a |
| 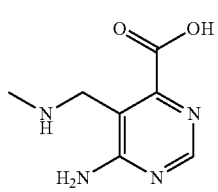 15b | 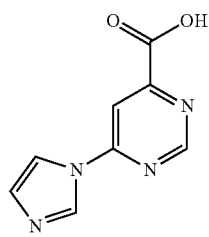 [SMILES: O=C(O)c1cc(-n2ccnc2)ncn1] 18b |
| | 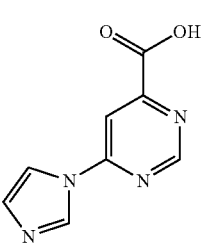 [SMILES: O=C(O)c1cc(-n2ccnc2)ncn1] |

TABLE 1-continued

Exemplary Compounds

| Compound | |
|---|---|
| 18c | 6-(4-methylimidazol-1-yl)pyrimidine-4-carboxylic acid |
| 18d | 6-(2-methylimidazol-1-yl)pyrimidine-4-carboxylic acid |
| 18e | 6-(pyrrol-1-yl)pyrimidine-4-carboxylic acid |
| 18f | 6-(pyrazol-1-yl)pyrimidine-4-carboxylic acid |
| 18g | 6-(2-oxopyrrolidin-1-yl)pyrimidine-4-carboxylic acid |
| 18h | 6-(5-methylpyrazol-1-yl)pyrimidine-4-carboxylic acid |
| 18i | 6-methoxypyrimidine-4-carboxylic acid |
| 18j | 6-(pyridin-3-yloxy)pyrimidine-4-carboxylic acid |
| 18k | 6-(3-(dimethylamino)propoxy)pyrimidine-4-carboxylic acid |
| 18l | 6-(2-(dimethylamino)ethoxy)pyrimidine-4-carboxylic acid |
| 20a | 6-amino-5-fluoropyrimidine-4-carboxylic acid |
| 20b | 5-fluoro-6-morpholinopyrimidine-4-carboxylic acid |
| 33a | 6-(4-methyl-1H-imidazol-2-yl)pyrimidine-4-carboxylic acid |

143

TABLE 1-continued

Exemplary Compounds

| | |
|---|---|
| (structure with R$^x$, R$^y$, pyrimidine-COOH) | |
| (structure with F$_3$C-imidazole-pyrimidine-COOH) | 33b |

Synthesis of -L$^1$-Cy$^1$-L$^2$-Cy$^2$ Moieties (1) Thiazole Condensation and the organic layer was washed with sat. NaHCO$_3$ (2 mL). The aqueous layer was again extracted with EtOAc (2×5 mL). The combined organic extracts were again washed with sat. NaHCO$_3$ (3×5 mL), dried (Na$_2$SO$_4$) and concentrated under reduced pressure to furnish compound A.2 as a light yellow solid (0.42 g, 79%). $^1$H NMR: (CDCl$_3$-DMSO-d$_6$, 200 MHz) δ: 7.4 (s, 5H), 6.4 (1H, D$_2$O exchangeable), 5.2 (s, 2H), 4.2 (d, 2H, J=5 Hz); LCMS: m/z 224.9 [M+1]$^+$.

Synthesis of Compound A.3.

Ethyl chloroacetate (50 g, 0.409 mol) and ethyl formate (30.3 g, 0.409 mol) were taken in anhydrous toluene (500 mL) and cooled to 0° C. NaOEt (33 g, 0.485 mol) was added portion wise. The reaction mixture was stirred at 0° C. for 5 hr and then at RT for 12 hr. The reaction mixture was quenched with water (250 mL) and washed with Et$_2$O (2×250 mL). The aqueous layer was cooled to 0° C. and acidified to pH 4 using 5N HCl. The aqueous layer was extracted with Et$_2$O (3×300 mL). The combined organic layers were dried (Na$_2$SO$_4$) and concentrated under reduced pressure to obtain compound A.3 as light brown oil (54 g, 88%), which was used without further purification.

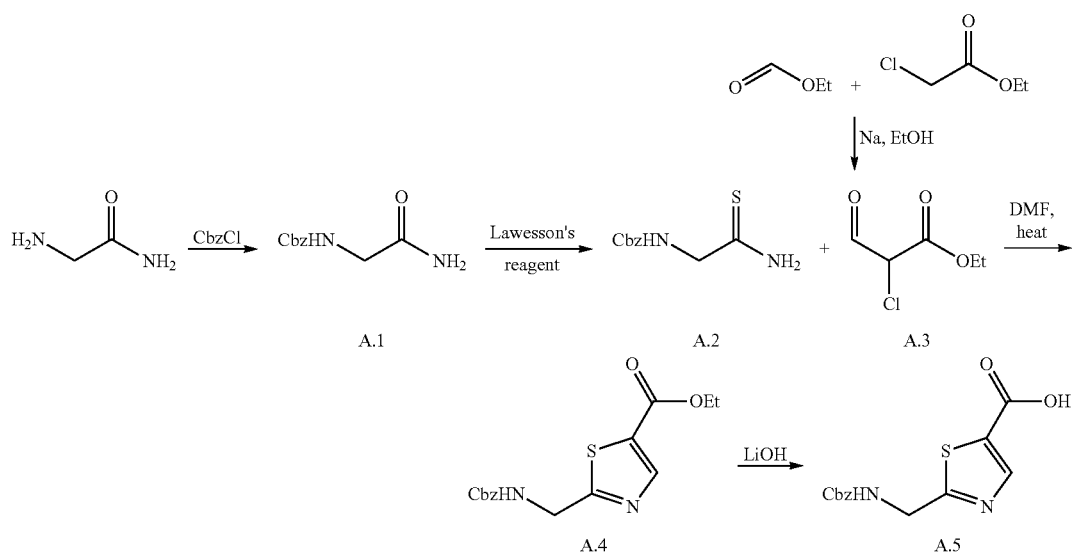

Scheme A-1.

Synthesis of Compound A.1.

To an ice cold solution of 2-amino-acetamide (100 g, 0.90 mol) in water/dioxane (1200 mL, 1:1), CbzCl (130 mL, 0.90 mol) was added slowly. The reaction was brought to RT and stirred at RT for 12 hr. Dioxane was removed under reduced pressure and the reaction mixture was filtered and air-dried to obtain compound A.1 as a white solid (167.0 g, 88%). $^1$H NMR: (CDCl$_3$-DMSO-d$_6$, 200 MHz) δ: 7.4 (s, 5H), 6.8 (1H, D$_2$O exchangeable), 6.2 (1H, D$_2$O exchangeable), 6.1 (1H, D$_2$O exchangeable), 5.1 (s, 2H), 3.8 (d, 2H, J=5 Hz); LCMS: m/z 209.3 [M+1]$^+$.

Synthesis of Compound A.2.

To a solution of compound A.1 (0.5 g, 0.0024 mol) in dioxane (7 mL) was added Lawesson's reagent (0.5 g, 0.0013 mol). The reaction was heated at 60° C. for 30-45 min. The reaction was brought to RT and stirred for an additional 4 hr. Dioxane was removed under reduced pressure. The reaction mixture was diluted with EtOAc (3 mL)

Synthesis of Compound A.4.

To a solution of aldehyde A.3 (54 g, 0.36 mol) in anhydrous DMF (42 mL), was added a solution of compound A.2 (40.3 g, 0.18 mol) in anhydrous DMF (320 mL). The reaction was heated at 50° C. for 3 days. The mixture was cooled to 0° C., and Et$_2$O (390 mL) followed by sat. NaHCO$_3$ solution (200 mL) were added slowly. After separation of the phases, the aqueous layer was extracted with Et$_2$O (2×300 mL). The combined organic extracts were washed with sat. NaHCO$_3$ (3×500 mL), dried (Na$_2$SO$_4$) and concentrated under reduced pressure to give crude material as thick brown oil, which was purified by column chromatography (EtOAc/hexanes) to give compound A.4 as a brown solid (22 g, 19%). $^1$H NMR: (CDCl$_3$, 200 MHz) δ: 8.3 (s, 1H), 7.4 (s, 5H), 5.6 (brs, 1H), 5.2 (s, 2H), 4.7 (d, 2H, J=5 Hz), 4.4 (m, 2H), 1.4 (m, 3H); LCMS: m/z 320.9 [M+1]$^+$.

Synthesis of Compound A.5.

To an ice-cold solution of compound A.4 (10 g, 0.0311 mol) in THF/H$_2$O (80 mL, 1:1) was added LiOH (2.6 g, 0.062 mol). The reaction was stirred for 3 hr, whereupon THF was removed under reduced pressure and the aqueous layer was extracted with Et$_2$O (2×50 mL). The aqueous layer was cooled to 0° C. and acidified with 3N HCl (20 mL) during which solid precipitated out. The solid was filtered, washed with water (2×100 mL) and dried to give compound A.5 as a white solid (7 g, 77%). $^1$H NMR: (CDCl$_3$-DMSO-d$_6$) δ 8.2 (s, 1H), 7.4 (s, 5H), (brs, 1H), 5.2 (s, 2H), 4.8 (d, 2H, J=4 Hz); $^{13}$C NMR: (DMSO-d$_6$, 60 MHz): 176.33, 162.04, 156.39, 147.62, 136.78, 130.25, 128.3, 127.7, 65.9, 42.71, 40.34; LCMS: m/z 292.8 [M+1]$^+$.

(2) Oxalyl Chloride Coupling

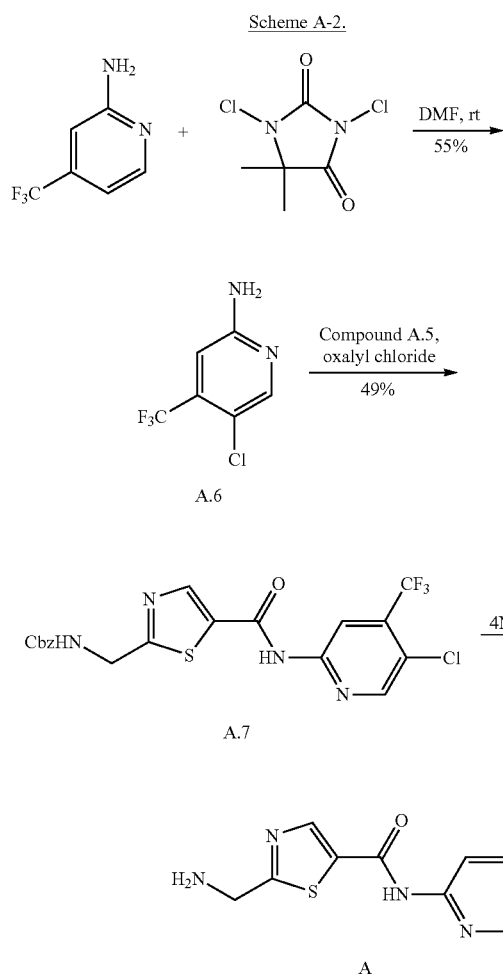

Synthesis of Compound A.6.

To a solution of 2-amino-4-trifluoropyridine (2.00 g, 0.0123 mol) in DMF (4 mL, 0.05 mol) was added a solution of 1,3-dichloro-5,5-dimethylhydantoin (1.4 g, 0.0074 mol) in DMF (4 mL) dropwise. The reaction was stirred at RT for 2 hr, whereupon the reaction mixture was diluted with ether (80 mL) and washed with water (10 mL). The organic phase was dried and concentrated to give the crude product, which was purified on combiflash (0-20% EtOAc/Hexanes) to give compound A.6 as light yellow oil. (65% yield); $^1$H NMR: (DMSO-d$_6$) δ 8.16 (s, 1H), 6.87 (s, 1H), 6.76 (brs, 1H); LCMS: m/z 197 [M+1]$^+$.

Synthesis of Compound A.7.

A 20 mL vial was charged with compound A.5 (191.8 mg, 0.0006561 mol), methylene chloride (3.0 mL), a 2.0 M solution of oxalyl chloride in methylene chloride (390 µL) and DMF (10.0 µL, 0.000129 mol). The reaction mixture was stirred for 15 minutes at rt, then concentrated in vacuo and the resultant residue was taken up in acetonitrile (3.0 mL). To this solution was added a solution of compound A.6 (129 mg, 0.000656 mol) and pyridine (0.5 mL, 0.006 mol) in acetonitrile (1.5 mL). The reaction mixture was stirred at RT overnight. The solvent was removed under reduced pressure, and the residue was purified by combiflash (0-30% EtOAc/CH$_2$Cl$_2$) to give compound A.7 in 49% yield. LCMS: m/z 471 [M+1]$^+$.

Synthesis of Compound A.

A vial was charged with compound A.7 (1.0E2 mg, 0.00021 mol), acetic acid (1.0 mL, 0.018 mol) and hydrogen bromide (300 µL, 4 M/acetic acid). The reaction mixture was stirred at RT for 2 h. The reaction mixture was diluted with methanol and concentrated under reduced pressure. The residue was diluted with aqueous NaHCO$_3$ and ethyl acetate. After separation of the phases, the organic layer was washed with aqueous NaHCO$_3$ and brine, dried over sodium sulfate, and concentrated to give compound A as a light brown solid (73% yield), which was used without further purification. $^1$H NMR (300 MHz, DMSO-d$_6$): δ 8.85 (s, 1H), 8.79 (s, 1H), 8.57 (s, 1H), 4.48 (brs, 2H). LCMS: m/z 337 [M+1]$^+$.

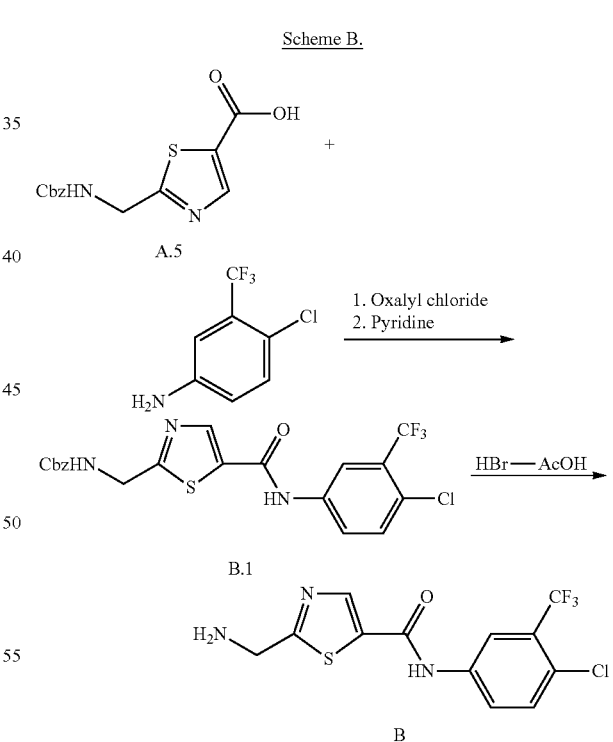

Synthesis of Compound B.

Compound A.5 was coupled to 4-chloro-3-trifluoromethyl-phenylamine and deprotected according to procedures described in Scheme A.2. $^1$H NMR (400 MHz, CDCl$_3$): δ 8.40 (s, 1H), 8.21 (d, J=2.6 Hz, 1H), 7.96 (dd, J$^1$=8.7 Hz, J$^2$=2.6, 1 H), 7.60 (d, J=8.7 Hz, 1H), 4.48 (brs, 2H); LCMS: m/z 336 [M+1]$^+$.

Scheme C.

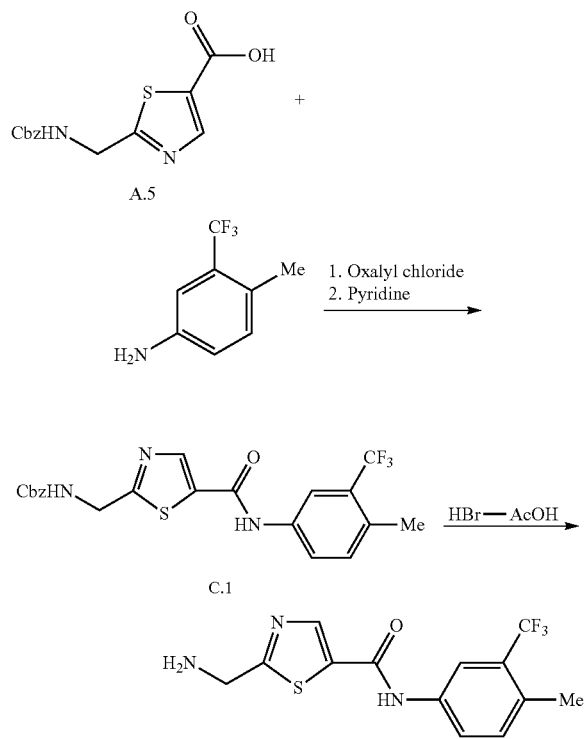

Synthesis of Compound C:

Compound A.5 was coupled to 4-methyl-3-trifluoromethyl-phenylamine and deprotected according to procedures described in Scheme A.2. Compound C.1. $^1$H NMR: (MeOD-$d_4$, 400 MHz) δ: 8.3 (s, 1H), 7.9 (s, 1H), 7.7 (d, 1H, J=8 Hz), 7.3-7.2 (m, 8H), 5.0 (s, 2H), 4.5 (s, 2H), 2.4 (s, 3H); LCMS: m/z 450.1 [M+1]$^+$. $R_f$=0.2 (50% EtOAc/hexanes). Compound C. LCMS: m/z 316.1 [M+1]$^+$.

Scheme D.

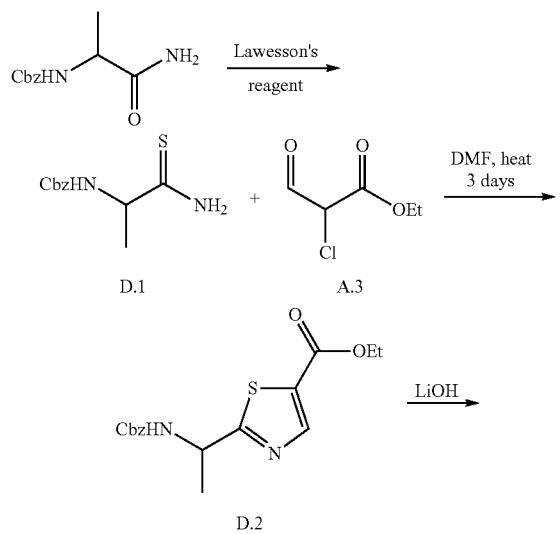

As shown in Scheme D, using Z-alanine-NH$_2$ as starting material, compound D was synthesized following the same procedures as previously detailed in Methods 3 and 4, Schemes A-1 and A-2.

Synthesis of Compound D.1.

To a solution of Z-alanine-NH$_2$ (5 g, 22.5 mmol) in dioxane (100 mL) was added Lawesson's reagent (5.4 g, 13.5 mmol). The reaction was heated at 60° C. overnight. The solvent was removed under reduced pressure, the resulting residue was diluted with a 1:1 mixture of saturated aqueous NaHCO$_3$:H$_2$O (100 mL), and extracted with ethyl acetate (3×100 mL). The combined extracts were washed with brine (100 mL), dried over anhydrous sodium sulfate, and concentrated in vacuo. Purification by flash column chromatography (10-60% EtOAc/hexanes) afforded compound D.1 (4.7 g, 90%) as a white solid. LCMS: m/z: 239 [M+1]$^+$.

Synthesis of Compound D.2.

Compound D.1 was condensed with compound A.3 according to the procedure described previously (Scheme A-1) to afford compound D.2 (50% yield) as a light yellow solid. ¹H NMR (CDCl₃, 200 MHz): δ 8.3 (s, 1H), 7.3-7.5 (m, 5H), 5.4-5.5 (m, 1H), 5.1 (m, 2H), 4.3-4.4 (m, 2H), 1.6-1.7 (d, 2H), 1.3-1.4 (t, 3H); LCMS: m/z 335 [M+1]⁺.

Synthesis of Compound D.3.

Hydrolysis of compound D.2 according to the procedure described previously (Scheme A-1) afford compound D.3 (83.5% yield) as a white solid. ¹H NMR (CDCl₃, 200 MHz): δ 8.2 (s, 1H), 7.2-7.4 (m, 5H), 5.1 (m, 2H), 4.8-4.9 (m, 1H), 1.3-1.5 (d, 2H); ¹³C NMR (75 MHz, DMSO-d6): δ 181.12, 162.22, 155.81, 147.85, 136.89, 130.05, 128.46, 128.0, 127.89, 65.86, 20.47; LCMS: m/z 307 [M+1]⁺.

Synthesis of Compound D.4.

Compound D.3 was coupled to compound A.6 according to the procedure described previously (Scheme A-2) to afford compound D.4 (60% yield). ¹H NMR (CDCl₃, 200 MHz): δ 8.6 (s, 1H), 8.4 (s, 2H, 1H D₂O exchangeable), 8.2 (s, 1H), 7.2 (s, 5H), 5.4-5.5 (m, 1H), 5.1 (s, 2H), 5.1 (s, 2H), 1.7 (d, J=7 Hz, 3H); LCMS: m/z 484.9 [M+1]⁺.

Synthesis of Compound D.

Compound D.4 was deprotected according to the procedure described previously (Scheme A-2) to afford compound D (85% yield). ¹H NMR (400 MHz, DMSO-d₆): δ 8.77 (s, 1H), 8.70 (s, 1H), 8.59 (s, 1H), 4.22 (q, J=7.0 Hz, 1H), 1.39 (d, J=7.0 Hz, 2H); LCMS: m/z 351 [M+1]⁺.

Synthesis of Compound Da and Compound Db.

Compound D was separated by preparative chiral HPLC, using CHIRALCEL OJ column and hexane/IPA/EtOH (80:15:5) as the mobile phase to afford compound Da and compound Db.

Scheme D'.

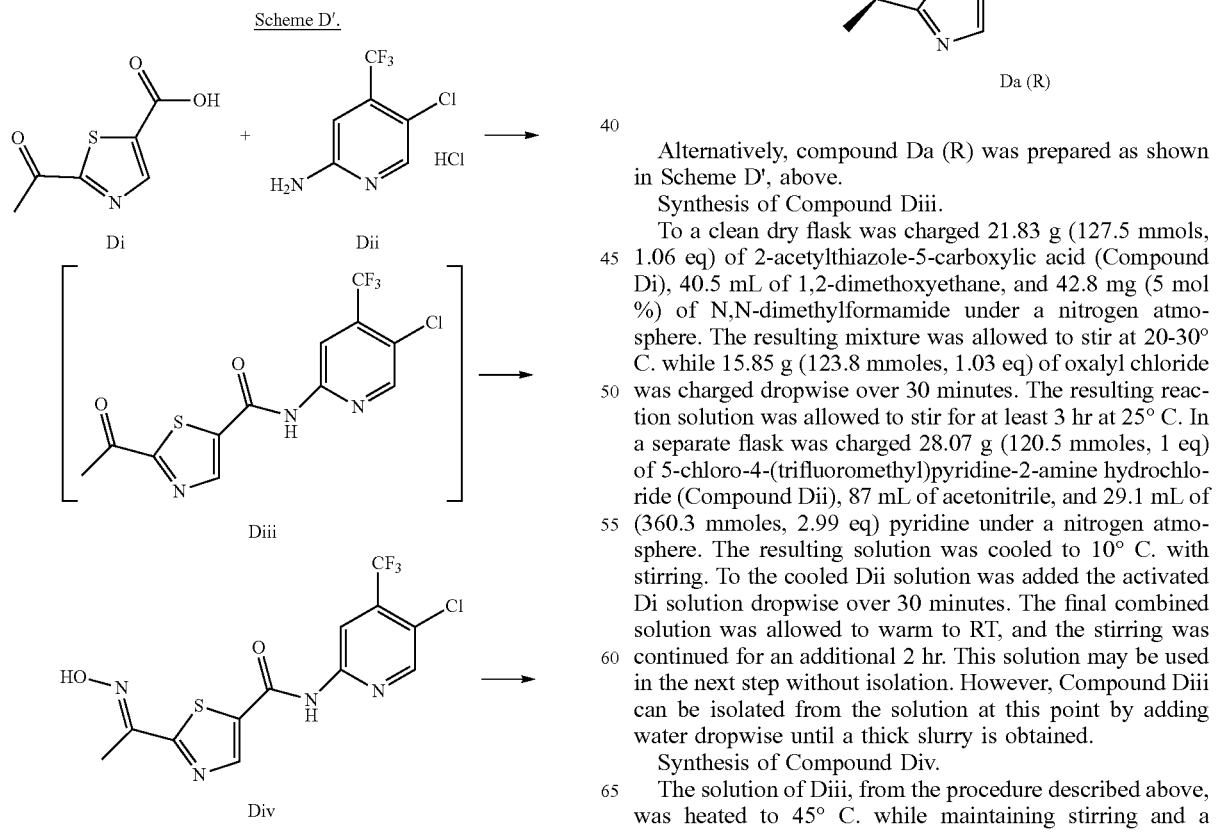

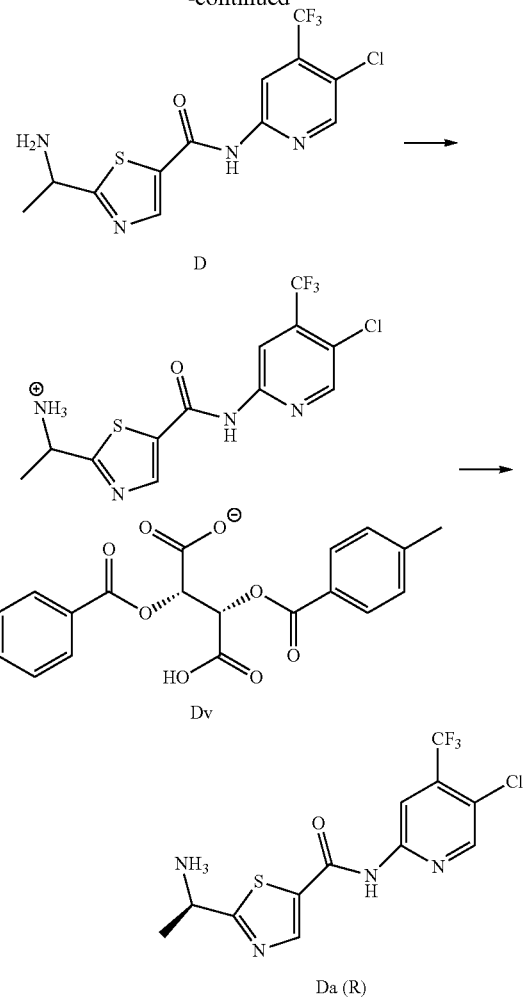

Alternatively, compound Da (R) was prepared as shown in Scheme D', above.

Synthesis of Compound Diii.

To a clean dry flask was charged 21.83 g (127.5 mmols, 1.06 eq) of 2-acetylthiazole-5-carboxylic acid (Compound Di), 40.5 mL of 1,2-dimethoxyethane, and 42.8 mg (5 mol %) of N,N-dimethylformamide under a nitrogen atmosphere. The resulting mixture was allowed to stir at 20-30° C. while 15.85 g (123.8 mmoles, 1.03 eq) of oxalyl chloride was charged dropwise over 30 minutes. The resulting reaction solution was allowed to stir for at least 3 hr at 25° C. In a separate flask was charged 28.07 g (120.5 mmoles, 1 eq) of 5-chloro-4-(trifluoromethyl)pyridine-2-amine hydrochloride (Compound Dii), 87 mL of acetonitrile, and 29.1 mL of (360.3 mmoles, 2.99 eq) pyridine under a nitrogen atmosphere. The resulting solution was cooled to 10° C. with stirring. To the cooled Dii solution was added the activated Di solution dropwise over 30 minutes. The final combined solution was allowed to warm to RT, and the stirring was continued for an additional 2 hr. This solution may be used in the next step without isolation. However, Compound Diii can be isolated from the solution at this point by adding water dropwise until a thick slurry is obtained.

Synthesis of Compound Div.

The solution of Diii, from the procedure described above, was heated to 45° C. while maintaining stirring and a nitrogen atmosphere. To the heated solution was added 9.30 g of NH$_2$OH dropwise over 5 minutes. After the addition was complete, stirring was continued at 45° C. for an additional 4 hr. The reaction solution was then heated to 60° C. and 215 mL of water was added over the course of 1 hr. The resulting slurry was cooled to RT and filtered to collect the solids. The filter cake was washed with 25% v/v acetonitrile/water, then water, and dried to constant weight at ambient temperature. A total of 44.26 g of compound Div was produced in 98% yield. Mass spectra showed a molecular ion (M+1) of 365.01.

Synthesis of Compound D.

To a clean dry flask was charged 11.5 g (31.5 mmoles, 1 eq) of compound Div, 4.6 g (70.3 mmoles, 2.23 eq) of zinc dust, 35 mL of water, and 57 mL of 1-butanol under a nitrogen atmosphere. While stirring vigorously, the resulting mixture was cooled to 0-5° C. To the cold mixture was charged 10.8 mL (188.7 mmoles, 6 eq) of acetic acid dropwise, while maintaining the internal reaction temperature of <10° C. Once the addition is complete, the reaction was allowed to warm to 30° C., and the stirring was continued for an additional 3-4 hr. After aging the reaction solution, the contents of the flask were cooled to ~5° C., and 56 mL of NH$_4$OH was added dropwise while maintaining an internal temperature <10° C. The biphasic mixture was warmed to 35° C. and the aqueous phase was removed. The organic layer was washed once more with a mixture of 24 mL of NH$_4$OH and 24 mL of water at 35° C. The aqueous phase was removed and the 16 mL of heptane was added to the organic layer. The organic solution was then washed with a solution of 1.15 g of EDTA in 50 mL of water at 35° C. The aqueous phase was removed, and the organic phase, at 35° C., was filtered through a 4-5.5 micron filter funnel into a separate clean dry flask. To the filtered solution was added 215 mL of heptane at ambient temperature with stirring over the course of 1 hr. The slurry was cooled to 0-5° C. and held with stirring for an additional 3 hr. The solids were collected by filtration and washed with 35 mL of heptane in 2 portions. The wet solids were dried at 50° C. under high vacuum for 30 hr. Compound D, 8.52 g, was isolated as a pale pink solid in a 77% yield. The mass spectrum showed a molecular ion of 351.35 [M+1]$^+$.

Synthesis of Compound Dv.

To a clean dry flask was charged 80 g (228 mmoles, 1 eq) of Compound D, 263 g of 2-propanol, and 263 mL of water under a nitrogen atmosphere. The resulting mixture was heated to 53° C. and stirred until all the solids dissolved. In a separate clean dry flask was charged 59.2 g (153 mmoles, 0.67 eq) of D-ditoluoyl tartaric acid, 481 g of 2-propanol, and 206 g of water under a nitrogen atmosphere. The tartaric acid solution was stirred until all the solids dissolved at ambient temperature, and then added to the Compound D solution through a coarse filter funnel at such a rate to maintain the internal temperature of the Compound D solution at 45-53° C. The coarse filter funnel was washed with an additional 40 mL of a 3:1 2-propanol:water solution. Immediately following the funnel wash, the stirring of combined solutions was stopped, and the contents of the flask were held at 45° C. for 9 hr. After aging, the reaction mixture was cooled to 20° C., and the stirring was resumed. The contents of the flask were held at 20° C. with stirring for approximately 12 hr. The solids were then collected by filtration, and the wet solids were washed with 80 mL of a cold 2-propanol:water (3:1) solution in 2 portions. The wet solids were then dried at 50° C. under vacuum to constant weight. A total of 74.2 g of Compound Dv was obtained in a 88% yield.

The stereochemical purity of Compound Dv was further enhanced by the following procedure. To a clean dry flask was charged 66.5 g (90 mmoles, 1 eq) of Compound Dv, 335 g of water, and 1330 g of 2-propanol under a nitrogen atmosphere. With stirring, the contents of the flask were heated to 60° C., and held at that temperature for 1 hr. After aging, the stirring was stopped, and the contents of the flask were cooled to 0° C. over 4 hr. During this cooling period, the stirring was started and stopped after approximately 20 seconds 5 times over evenly spaced intervals. The contents of the flask were held at 0° C. for 2 hr without stirring. After aging, the solids were collected by filtration. The wet solids were dried at 50° C. under vacuum to constant weight. A total of 53.8 g of Compound Dv was obtained in a 81% yield. Mass spectral analysis (positive mode) showed a molecular ion of 351.43 [M+1]$^+$.

Synthesis of Compound Da (R).

To a clean dry flask was charged 156 g (217 mmoles, 1 eq) of Compound Dv, 1560 mL of methyl tert-butyl ether, and 780 mL of methanol under a nitrogen atmosphere. The contents of the flask were then stirred at ambient temperature, and a solution of 250 g (1110 mmoles, 5.26 eq) of sodium bicarbonate in 2340 mL of water was added slowly to maintain the internal temperature of ≤30° C. The resulting mixture was stirred for an additional hr at 30° C. After aging, the stirring was stopped and the organic and aqueous layers were allowed to separate. The aqueous layer was removed, and the organic layer was concentrated under vacuum to obtain a thick slurry. To the slurry was added 1000 mL of heptane, and the resulting mixture was cooled to 0-5° C. The solids were collected from the cold solution by filtration. The wet solids were then dried at 50° C. under vacuum to constant weight. A total of 68.7 g of Compound Da was obtained in a 92% yield. Mass spectral analysis showed a molecular ion of 351.35 [M+1]$^+$.

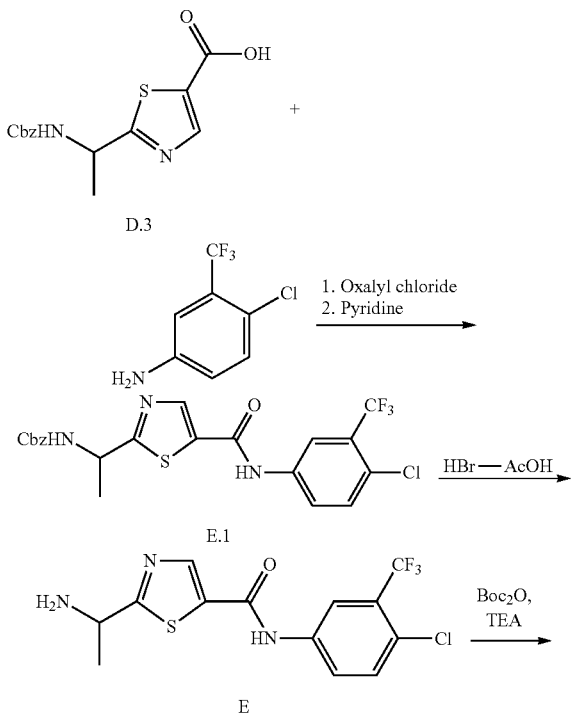

Scheme E.

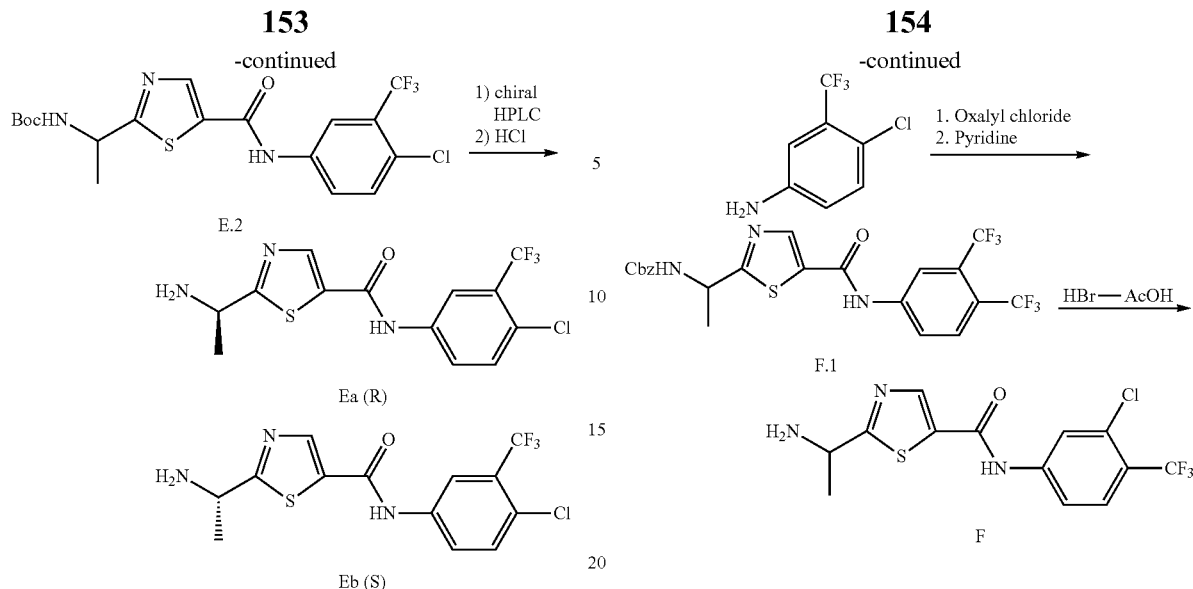

Synthesis of Compound E.

Compound D.3 was coupled to 4-chloro-3-trifluorom-ethyl-phenylamine and deprotected according to procedures described in Scheme A-2. $^1$H NMR (400 MHz, DMSO-$d_6$): δ 11.54 (s, 1H), 9.06 (s, 1H), 8.92 (br. s, 3H), 8.30 (d, J=Hz, 1H), 8.05 (dd, J=8.8, 2 Hz, 1H), 7.86 (d, J=8.8 Hz, 1H), 4.91 (quintet, J=6 Hz, 1H), 1.65 (d, J=6.8 Hz, 3H). LCMS: m/z 350 [M+1]$^+$.

Synthesis of Compound E.2.

To a flask containing compound E (10.3 mg, 0.0294 mmol) was added a solution of carbonic acid di-tert-butyl ester (17.6 mg, 0.0799 mmol) in $CH_2Cl_2$ (0.6 mL) at RT. Triethylamine (8 μL) was added and the reaction was stirred at RT overnight. Water and ethyl acetate were added to the reaction mixtures and the layers were separated. The aqueous layer was extracted once more with ethyl acetate. The combined organic layers were dried over anhydrous sodium sulfate and concentrated in vacuo. Purification by column chromatography (EtOAc/Hexanes) afforded compound E.2 as a white solid (8.2 mg, 62%). Rf=0.1 (100% EtOAc); LCMS: m/z: 450 [M+1]$^+$.

Synthesis of Compound Ea and Eb.

Compound E.2 was separated by preparative chiral HPLC, using CHIRALPAK AD column and hexanes/EtOH (85:15) as the mobile phase. The compounds were deprotected by treatment with 4M-hydrochloric acid in dioxane at RT to afford compound Ea and compound Eb. LCMS: m/z: 350 [M+1]$^+$.

Scheme F.

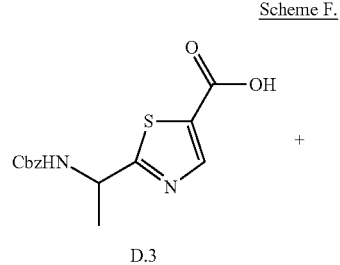

Synthesis of Compound F.

Compound D.3 was coupled to 3-chloro-4-trifluorom-ethyl-phenylamine and deprotected according to the procedures described in Scheme A.2. $^1$H NMR (400 MHz, DMSO-$d_6$): δ 11.38 (s, 1H), 8.96 (s, 1H), 8.87 (br. s, 3H), 8.42 (d, J=2.4 Hz, 1H), 8.18 (dd, J=9, 2.6 Hz, 1H), 7.73 (d, J=9 Hz, 1H), 4.91 (br. s, 1H), 1.65 (d, J=6.8 Hz, 3H); LCMS: m/z 350 [M+1]$^+$.

Scheme G.

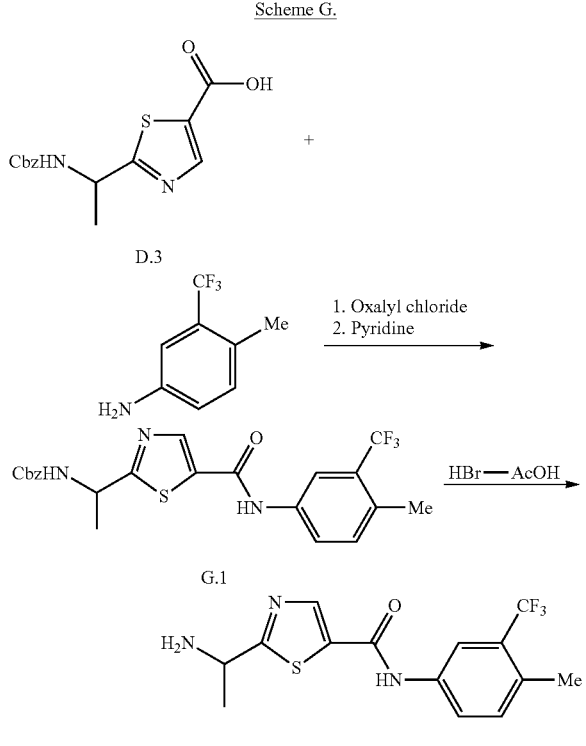

Synthesis of Compound G:

Compound D.3 was coupled to 3-methyl-4-trifluorom-ethyl-phenylamine and deprotected according to the procedures described in Scheme A-2. Compound G.1. $^1$H NMR: (MeOD-$d_4$, 400 MHz) δ: 8.3 (s, 1H), 7.9 (s, 1H), 7.7 (d, 1H, J=8 Hz), 7.3-7.2 (m, 8H), 5.0 (s, 2H), 5.0-4.9 (m, 1H), 2.4

(s, 3H), 1.49 (d, 1H, J=4 Hz); LCMS: m/z 464.1 [M+1]'; R$_f$=0.5 (50% EtOAc/hexanes). Compound G. LCMS: m/z 330.1 [M+1]$^+$.

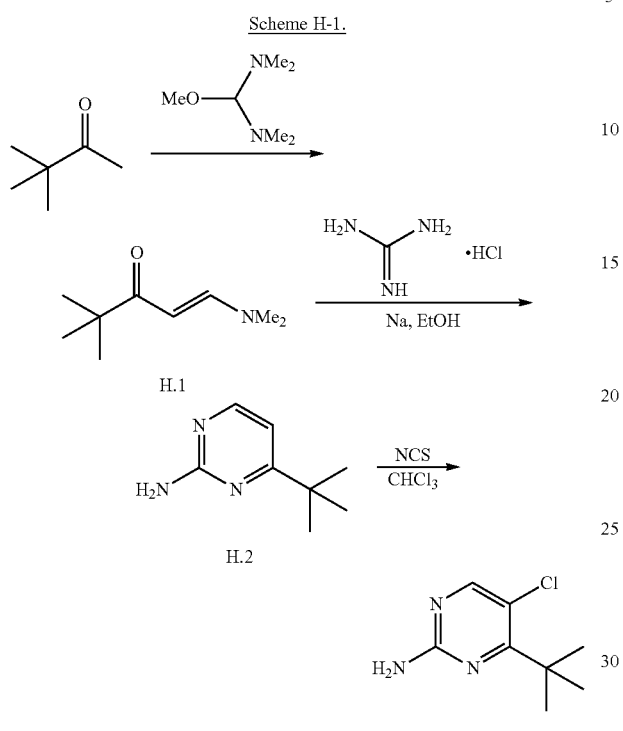

Synthesis of Compound H.1.

In a 50 mL round-bottomed flask, pinacolone (6.2 mL, 50.0 mmol) and methoxy-bis(dimethylamino)methane (10 mL) were heated at 110° C. under nitrogen. After 18 hr, the solvent was removed under reduced pressure. The crude product was purified by flash chromatography (hexanes/EtOAc=1:1→1:3) to afford compound H.1 (5.94 g, 77%) as a yellow oil which solidified upon standing. $^1$H NMR (400 MHz, CDCl$_3$): δ 7.56 (d, J=12.7 Hz, 1H), 5.20 (d, J=12.7 Hz, 1H), 2.92 (br s, 6H), 1.11 (s, 9H); LCMS: m/z 156 [M+1]$^+$.

Synthesis of Compound H.2.

To a solution of Na (74 mg, 3.22 mmol) in EtOH (21 mL) was added guanidine hydrochloride (308 mg, 3.22 mmol). The resultant suspension was stirred at RT, and after 30 min, a solution of compound H.1 (500 mg, 3.22 mmol) in EtOH (2.1 mL) was added. The reaction was refluxed overnight under nitrogen. After 20 hr, the solvent was removed under reduced pressure. To the residue was added Et$_2$O and H$_2$O. The aqueous layer was extracted three times with Et$_2$O. The combined organic layers were washed with brine, dried over anhydrous sodium sulfate, filtered, and concentrated. The crude product was purified by flash chromatography (hexanes/EtOAc=1:1→1:3) to afford 379 mg (78%) of compound H.2. Rf=0.3 (50% EtOAc/hexanes); $^1$H NMR (400 MHz, MeOD-d$_4$): δ 8.11 (d, J=5.38 Hz, 1H), 6.69 (d, J=5.38 Hz, 1H), 1.27 (s, 9H); LCMS: m/z 152 [M+1]$^+$.

Synthesis of Compound H.3.

A solution of compound H.2 (200 mg, 1.32 mmol) and N-chlorosuccinimide (185 mg, 1.39 mmol) in chloroform (3.4 mL) was refluxed. After 1.5 hr, sat. aq. NaHCO$_3$ and EtOAc were added. The aqueous layer was extracted three times with EtOAc. The combined organic layers were washed with brine, dried over anhydrous sodium sulfate, filtered, and concentrated. The crude product was purified by flash chromatography (hexanes/EtOAc=5:1→3:1) to afford 200 mg (81%) of compound H.3 as a white solid. $^1$H NMR (400 MHz, MeOD-d$_4$): δ 8.02 (s, 1H), 1.40 (s, 9H); LCMS: m/z 186 [M+1]$^+$.

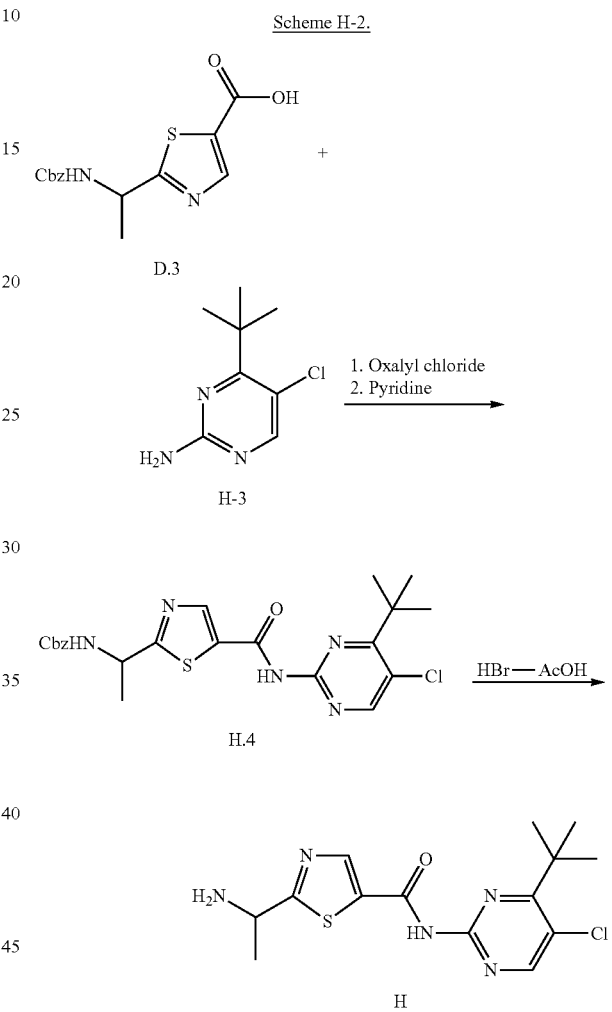

Synthesis of Compound H.

Compound D.3 was coupled to 4-tert-butyl-5-chloropyrimidin-2-ylamine and deprotected according to procedures described in Scheme A-2. Rf=0.2 (5% MeOH/EtOAc); LCMS: m/z 340 [M+1]$^+$.

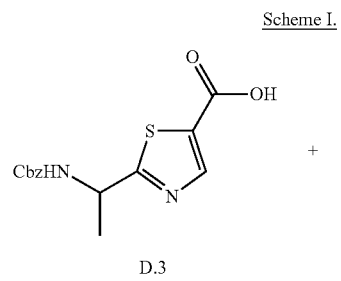

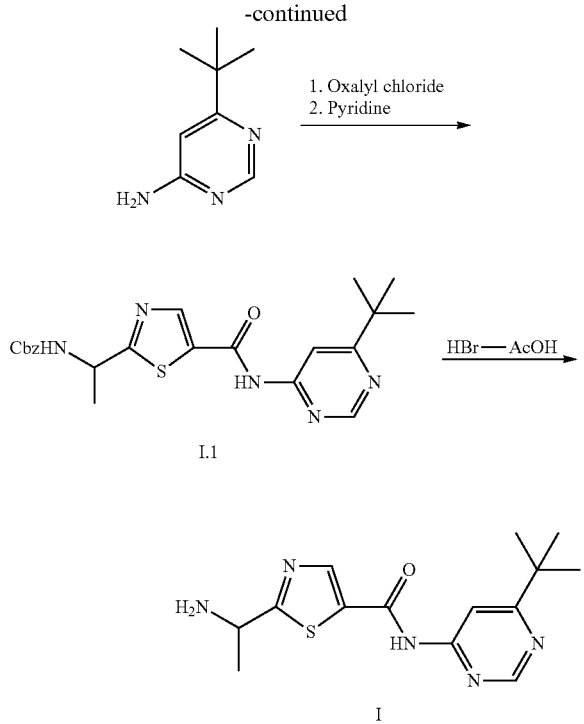

Synthesis of Compound I.

Compound D.3 was coupled to 6-tert-butyl-pyrimidin-4-ylamine and deprotected according to procedures described in Scheme A-2. Rf=0.1 (5% MeOH/EtOAc); LCMS: m/z 306 [M+1]$^+$.

Scheme J-1.

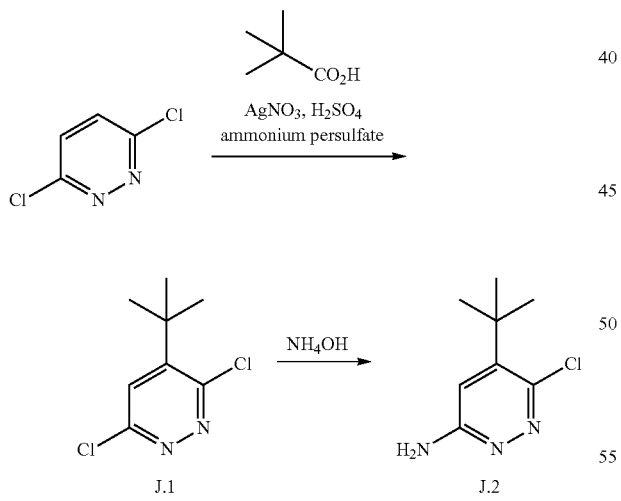

Synthesis of Compound J.1.

A flask was charged with 3,6-dichloropyridazine (1.49 g, 0.01 mol, 1.0 equiv), silver nitrate (0.17 g, 0.001 mol, 0.1 equiv), water (30 mL), pivalic acid (3.57 g, 0.035 mol, 3.5 equiv), and sulfuric acid (1.6 mL, 0.03 mol, 3.0 equiv). The mixture was heated to 70° C. and a solution of ammonium persulfate (2.28 g, 0.01 mol, 1.0 equiv) in water (10 mL) was added dropwise over ten minutes. The reaction was stirred at 70° C. for one hr and then cooled to RT. The reaction mixture was poured into ice water and then adjusted to pH 8 with aqueous ammonium hydroxide. The aqueous mixture was extracted with $CH_2Cl_2$ (2×250 mL). The combined organic extracts were filtered through a cotton plug, washed with aqueous 1 N NaOH (70 mL), dried over anhydrous $MgSO_4$ and concentrated under reduced pressure. Purification by flash column chromatography (20% EtOAc/hexanes) afforded the title compound (1.32 g, 64%) as a white solid. $^1$H NMR: (CDCl$_3$, 400 MHz) δ: 7.5 (s, 1H), 1.5 (s, 9H); R$_f$=0.5 (80% EtOAc/hexanes).

Synthesis of Compound J.2.

To a solution of compound J.1 (1.32 g, 0.006 mol) in EtOH (1 mL) was added 50% aqueous ammonium hydroxide (10 mL). The reaction mixture was stirred at 140° C. for 19 hr, then additional aqueous ammonium hydroxide (10 mL) was added and the mixture was stirred at 130° C. for one hr. After cooling to rt, the reaction mixture was concentrated under reduced pressure and the resultant residue was suspended in water. The solid was filtered, washed with water and Et$_2$O, and dried to afford compound J.2 as a peach solid (0.27 g, 23%). $^1$H NMR: (CDCl$_3$) δ 7.01 (s, 1H), 1.5 (s, 9H); LCMS: m/z 186.1 [M+1]$^+$.

Scheme J-2.

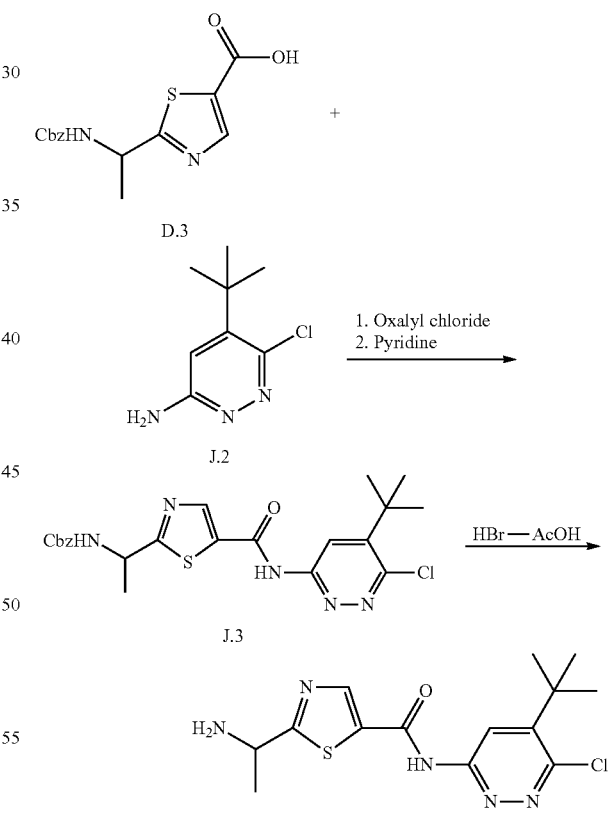

Synthesis of Compound J:

Compound D.3 was coupled to compound J.2, 5-tert-butyl-6-chloro-pyridazin-3-ylamine, and deprotected according to procedures described in Scheme A-2. Compound J.3. LCMS: m/z 474.1 [M+1]$^+$; R$_f$=0.4 (50% EtOAc/hexanes). Compound J. LCMS: m/z 340.1 [M+1]$^+$.

Scheme K.

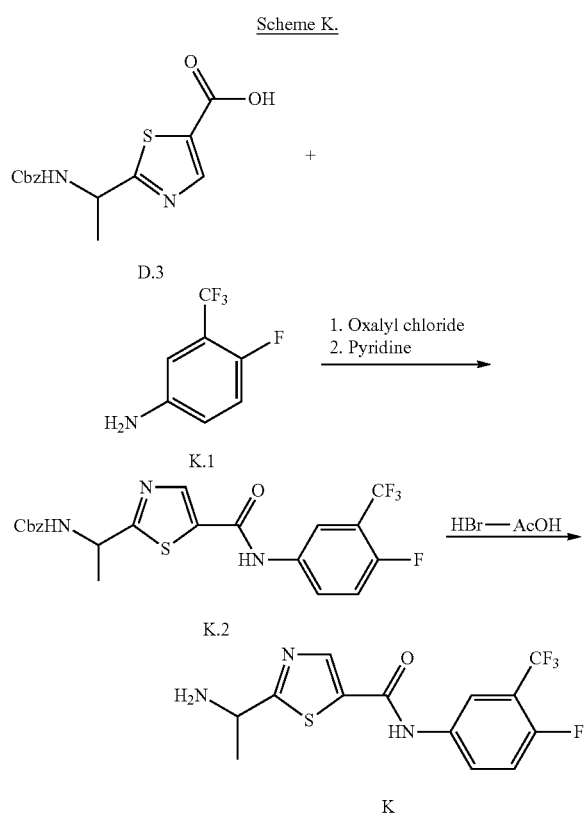

Synthesis of Compound K:

Compound D.3 was coupled to compound K.1, 4-fluoro-3-trifluoromethyl-phenylamine, and deprotected according to procedures described in Scheme A.2. Compound K.2. Rf=0.2 (50% EtOAc/hexanes); LCMS: m/z 468 [M+1]$^+$. Compound K. Rf=0.1 (100% EtOAc); LCMS: m/z 334 [M+1]$^+$.

(3) Isoxazole Synthesis

Scheme L-1.

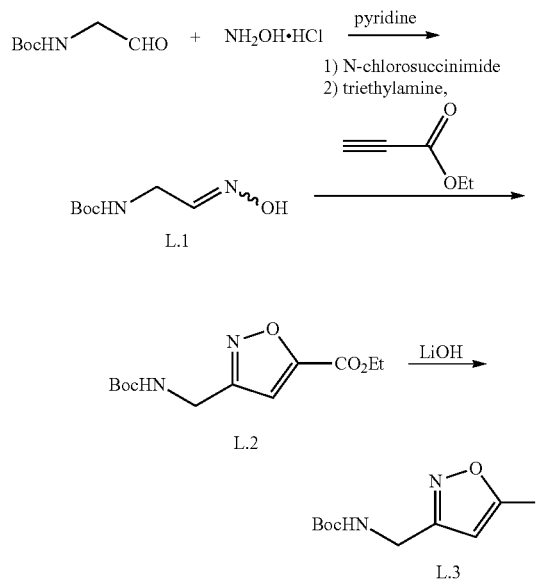

Synthesis of Compound L.1.

(2-Oxo-ethyl)-carbamic acid tert-butyl ester (1.0 g, 6.28 mmol), hydroxylamine hydrochloride (647 mg, 9.31 mmol) and pyridine (5 mL) were dissolved in methanol (40 mL) and the reaction was stirred at RT overnight. Solvent was removed at reduced pressure and the reaction was partitioned between chloroform and water. The aqueous layer was extracted with chloroform (2×). The combined organic layers were dried over anhydrous sodium sulfate. Removal of solvent under reduced pressure afforded crude L.1 which was used without further purification.

Synthesis of Compound L.2.

To a solution of L.1 (~1.2 g, ~6.28 mmol) in DMF (35 mL) was added N-chlorosuccinimide (1.05 g, 7.86 mmol) at RT. The reaction mixture was heated at 60° C. for one hr. The reaction mixture was cooled to 0° C. and propynoic acid ethyl ester (1.8 mL, 17.8 mmol) was added. Triethylamine (1.06 mL, 7.61 mmol) in DMF (8 mL) was added dropwise over 30 minutes. The reaction mixture was slowly allowed to warm to RT. The reaction mixture was diluted with ethyl acetate and water. The layers were separated and the aqueous layer was extracted with ethyl acetate (2×). The combined organic layers were washed with water followed by brine and dried over anhydrous sodium sulfate. After removal of the solvent under reduced pressure the crude material was purified by silica gel column chromatography (ethyl acetate/hexane) to afford L.2 (1.68 g, 86%). $^1$H NMR (400 MHz, CDCl$_3$): δ 6.93 (s, 1H), 5.02 (br, 1H), 4.42 (s, 2H), 4.41 (q, 2H, J=6.9 Hz), 1.45 (s, 9H), 1.39 (t, 3H, J=6.9 Hz); LCMS: m/z 271 [M+1]$^+$.

Synthesis of Compound L.3.

Compound L.2 (1.68 g, 6.22 mmol) was dissolved in THF (20 mL) at 0° C. Aqueous lithium hydroxide (1M-solution, 6.5 mL, 6.5 mmol) was added and the reaction was stirred for one hr. THF was removed under reduced pressure and the reaction mixture was washed with hexanes. The reaction mixture was acidified using 3N-hydrochloric acid and extracted with chloroform (3×). The combined organic layers were dried over anhydrous sodium sulfate. Upon removal of solvent under reduced pressure, crude L.3 was obtained (743 mg, 49%) which was used without further purification. LCMS: m/z 243 [M+1]$^+$.

(4) HATU Coupling

Scheme L-2.

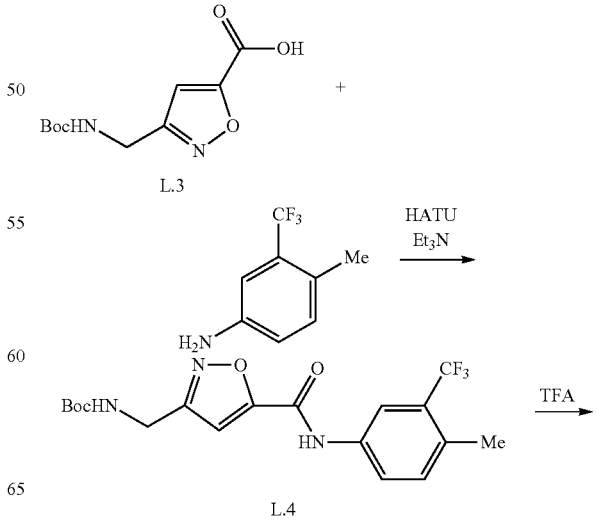

-continued

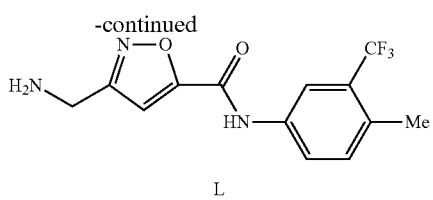

L

Synthesis of Compound L.4.

Compound L.3 (51.0 mg, 0.211 mmol) and 4-methyl-3-trifluoromethyl-phenylamine (33 µL, 0.230 mmol) were dissolved in DMF (1 mL) at RT. HATU (98.0 mg, 0.258 mmol) and triethylamine (74 µL, 0.531 mmol) were added and the reaction mixture was stirred at RT overnight. Ethyl acetate and water were added to the reaction mixture and the layers were separated. The aqueous layer was extracted with ethyl acetate (2×) and the combined layers were dried over anhydrous sodium sulfate. Upon removal of the solvent under reduced pressure, the crude L.4 was obtained as a white solid, which was used without further purification. LCMS: m/z 400 [M+1]+.

Synthesis of Compound L.

Compound L.4 (<0.211 mmol) was dissolved in 20% TFA in dichloromethane (1 mL) at 0° C. The reaction was allowed to warm to RT over one hr. Benzene was added and the solvents were removed under reduced pressure. The reaction mixture was dissolved in dichloromethane and saturated sodium bicarbonate solution was added. After separation of the phases, the aqueous layer was extracted with dichloromethane (2×). The combined organic layers were dried over anhydrous sodium sulfate. The solvent was removed under reduced pressure and the crude L obtained was used without further purification. LCMS: m/z 300 [M+1]+.

Scheme M-1.

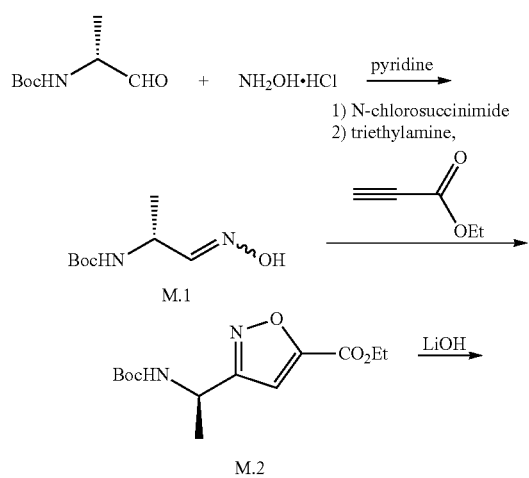

Synthesis of Compound M.2 and Compound M.3:

As shown in Scheme M-1, using (1R)-(1-methyl-2-oxo-ethyl)-carbamic acid tert-butyl ester as starting material, compounds M.2 and M.3 were synthesized following the same procedures as previously detailed in Schemes L-1 and L-2. Compound M.2. This compound was prepared using a procedure described for compound L.2. $^1$H NMR (400 MHz, CDCl$_3$): δ 6.88 (s, 1H), 4.97 (br, 1H), 4.41 (q. 2H, J=7.4 Hz), 1.53 (d, 3H, J=4.9 Hz), 1.44 (s, 9H), 1.39 (t, 3H, J=7.4 Hz); LCMS: m/z 285 [M+1]+. Compound M.3. This compound was prepared using a procedure described for compound L.3 in scheme L-1 and the product was used without further purification. LCMS: m/z 225 [M+1]+.

Scheme M-2.

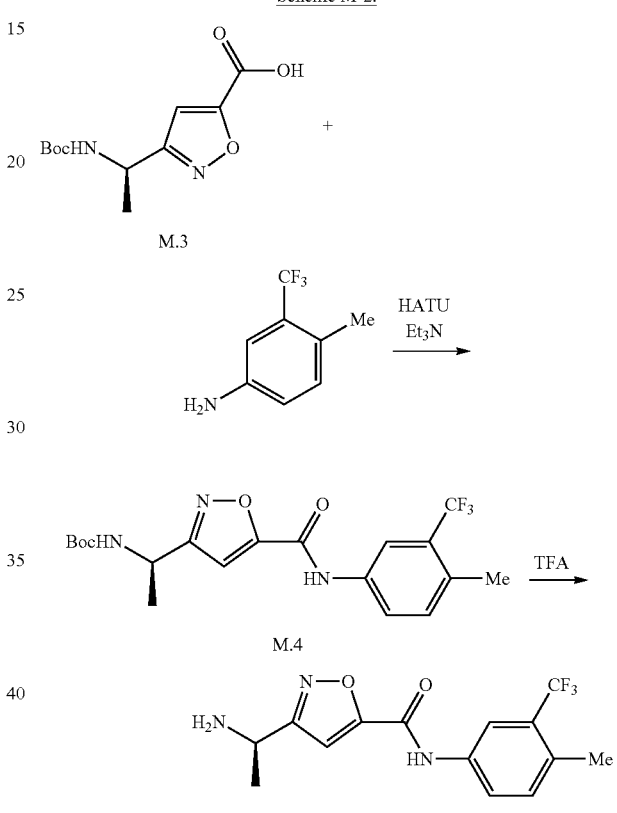

Synthesis of Compound Ma.

Compound M.3 was coupled to 4-methyl-3-trifluoromethyl-phenylamine and deprotected according to procedures described in Scheme L-2. LCMS: m/z 314 [M+1]+.

Scheme M-3.

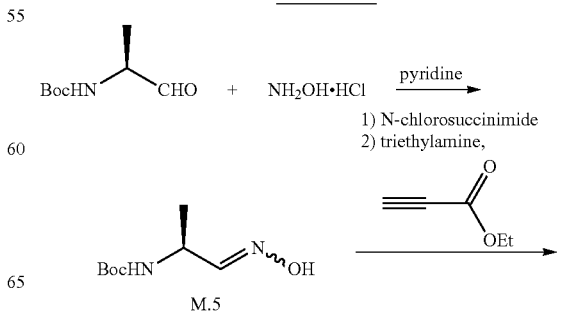

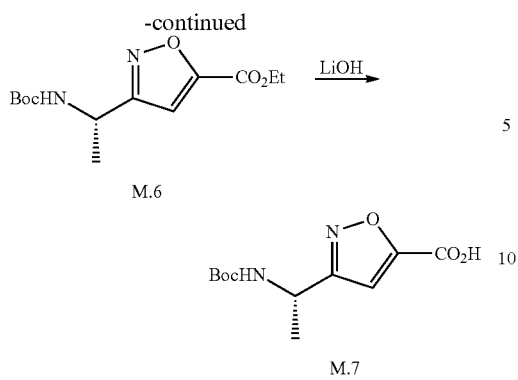

(5) Isoxazole Regioisomer Synthesis

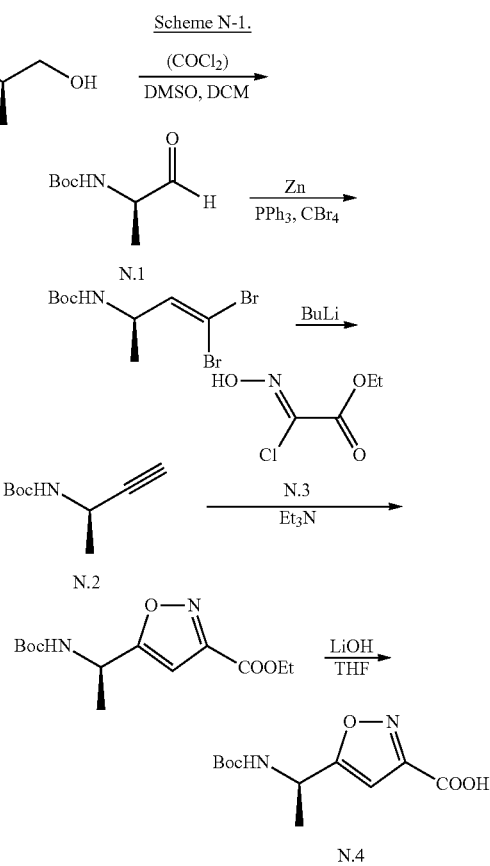

Synthesis of Compound M.6 and M.7:

As shown in Scheme M-3, using (1S)-(1-Methyl-2-oxo-ethyl)-carbamic acid tert-butyl ester as starting material, compound Mb was synthesized following the same procedures as previously detailed in Schemes L-1 and L-2. Compound M.6. This compound was prepared using the procedure described for compound L.2. $^1$H NMR (400 MHz, CDCl$_3$): δ 6.88 (s, 1H), 4.97 (br, 1H), 4.41 (q, 2H, J=7.4 Hz), 1.53 (d, 3H, J=4.9 Hz), 1.44 (s, 9H), 1.39 (t, 3H, J=7.4 Hz); LCMS: m/z 285 [M+1]$^+$. Compound M.7. This compound was prepared using the procedure described for compound L.3 in scheme L-1 and the product was used without further purification. LCMS: m/z 225 [M+1]$^+$.

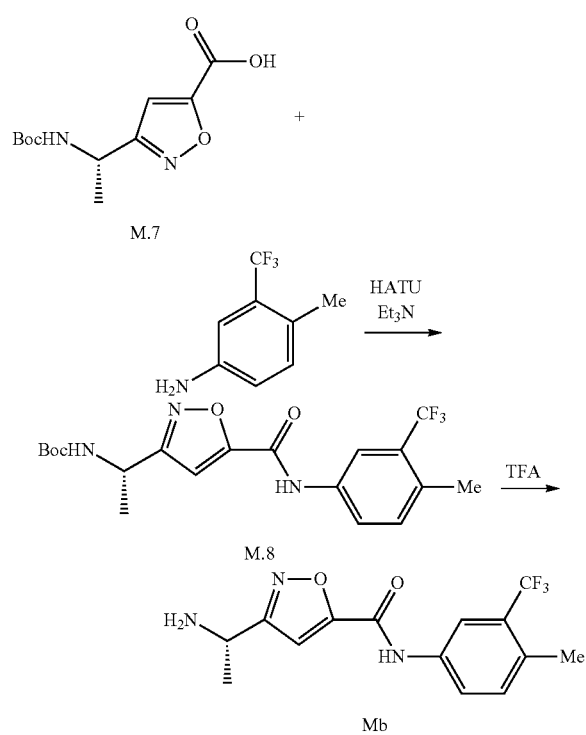

Synthesis of Compound Mb.

Compound M.7 was coupled to 4-methyl-3-trifluoromethyl-phenylamine and deprotected according to procedures described in Scheme L-2. LCMS: m/z 314 [M+1]$^+$.

Synthesis of Compound N.1.

To a cooled (−78° C.) solution of oxalyl chloride (90 mL, 1.03 mol) in CH$_2$Cl$_2$ was added dropwise a solution of DMSO (100 mL, 1.41 mol) in CH$_2$Cl$_2$. The mixture was stirred at −78° C. for 1 hr, and a solution of (R)-tert-butyl 1-hydroxypropan-2-ylcarbamate (90 g, 0.51 mol) in CH$_2$Cl$_2$ was added. After stirring for 3 hr, 500 mL of triethylamine was added and the reaction mixture was stirred for another 3 h at −78° C. The reaction was quenched with 1% HCl and the reaction mixture was warmed to RT. The organic layer was separated and the aqueous layer was extracted with CH$_2$Cl$_2$. The organic layer was washed with water, dried over MgSO$_4$, and evaporated to provide crude N.1, (R)-tert-butyl 1-oxopropan-2-ylcarbamate (76.0 g, 85.4%). $^1$H NMR (CDCl3) δ 9.56 (s, 1H), 4.23 (br s, 1H), 1.45 (s, 9H), 1.32 (s, 3H).

Synthesis of Compound N.2.

A solution of zinc (135 g, 2.08 mol), PPh$_3$ (545 g, 2.08 mol) and CBr$_4$ (682 g, 4.08 mol) in CH$_2$Cl$_2$ (2 L) was stirred at 0° C. for 1.5 hr. A solution of (R)-tert-butyl 1-oxopropan-2-ylcarbamate (114 g, 0.66 mol) in DCM was added in one portion, and the reaction mixture was stirred at 0° C. for another 3 hr. The mixture was quickly passed though a silica gel, and the solvent was evaporated to give the crude (R)-tert-butyl 4,4-dibromobut-3-en-2-ylcarbamate. To a cooled (−78° C.) solution of the crude compound (R)-tert-butyl 4,4-dibromobut-3-en-2-ylcarbamate in THF (2 L) was added dropwise 2.5 M BuLi (0.75 L, 1.88 mol) under nitrogen. The reaction was quenched with water and the organic layer was separated. The aqueous layer was extracted with ethyl acetate. The organic layers were combined, washed with water, dried over MgSO₄, filtered and concentrated to give the crude compound N.2, (R)-tert-butyl but-3-yn-2-ylcarbamate, which was used without further purification. ¹H NMR (CDCl₃) δ 4.47 (br s, 1H), 2.24 (s, 1H), 1.49 (s, 9H), 1.27 (s, 3H).

Synthesis of Compound N.4.

To a stirred solution of (R)-tert-butyl but-3-yn-2-ylcarbamate (262.5 g, 1.56 mol) and (Z)-ethyl 2-chloro-2-(hydroxyimino)acetate (78.2 g, 0.52 mol) in DMF (1 L) was added dropwise Et₃N (216 mL, 1.56 mol) at 90° C. The mixture was stirred for 5 hr, and then concentrated in vacuo. The residue was re-dissolved in ethyl acetate. The ethyl acetate solution was washed with water, dried over Na₂SO₄, and evaporated to provide the crude compound (R)-ethyl 5-(1-(tert-butoxycarbonylamino)ethyl)isoxazole-3-carboxylate. To a solution of (R)-ethyl 5-(1-(tert-butoxycarbonylamino)ethyl)isoxazole-3-carboxylate in THF (2 L) was added aqueous 2.5 N LiOH (1 L) at RT. The mixture was stirred for 1 hr, and then evaporated under reduced pressure to remove THF. The residue was partitioned between water (1 L) and ethyl acetate (0.5 L). The organic layer was separated and the aqueous layer was extracted with ethyl acetate twice. The aqueous layer was adjusted to pH 2 with 10% HCl and extracted with ethyl acetate (2×1 L). All the organic layers were combined, washed with water, dried over Na₂SO₄, filtered and concentrated under reduced pressure. The residue was dried under vacuum to give the crude product N.4, (R)-5-(1-(tert-butoxycarbonylamino)ethyl) isoxazole-3-carboxylic acid (55.2 g, 44.8%), which was used without further purification. ¹H NMR (CDCl₃) δ 6.57 (s, 1H), 4.12 (q, 1H), 1.56 (d, 3H), 1.37 (s, 9H).

Scheme N-2.

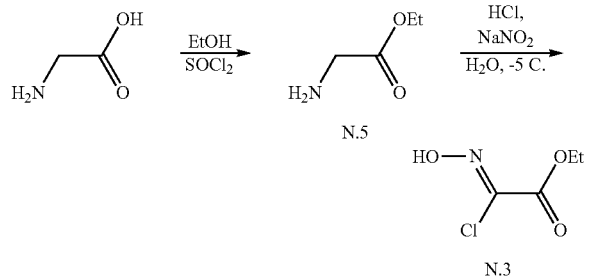

Synthesis of Compound N.5.

To a suspension of glycine (300 g, 4 mol) in ethanol (1500 mL) was added dropwise SOCl₂ at −5° C. After the addition was complete, the mixture was heated to reflux and stirred for 3 hr. The reaction mixture was cooled to 0° C., and methyl t-butyl ether (500 mL) was added. The resultant suspension was filtered and the filter cake was washed with methyl t-butyl ether and dried under vacuum to provide the pure compound N.5, ethyl 2-aminoacetate (482 g, 86.7%) as a white solid. ¹H NMR (D₂O) 84.21 (q, 2H), 3.84 (s, 2H), 1.21 (t, 3H).

Synthesis of Compound N.3.

To a solution of compound ethyl 2-aminoacetate (30.0 g, 0.24 mol) in water (50 mL) and 36% HCl (36 mL) was added dropwise a solution of NaNO₂ in water (100 mL) at −5° C. The reaction mixture was extracted with ethyl acetate. The organic layer was dried over MgSO4, filtered and concentrated to give compound N.3, (Z)-ethyl 2-chloro-2-(hydroxyimino)acetate (17.4 g, 42.1%). ¹H NMR (DMSO-d₆) δ 13.41 (s, 1H), 4.25 (q, 2H), 1.24 (t, 3H).

Scheme N-3.

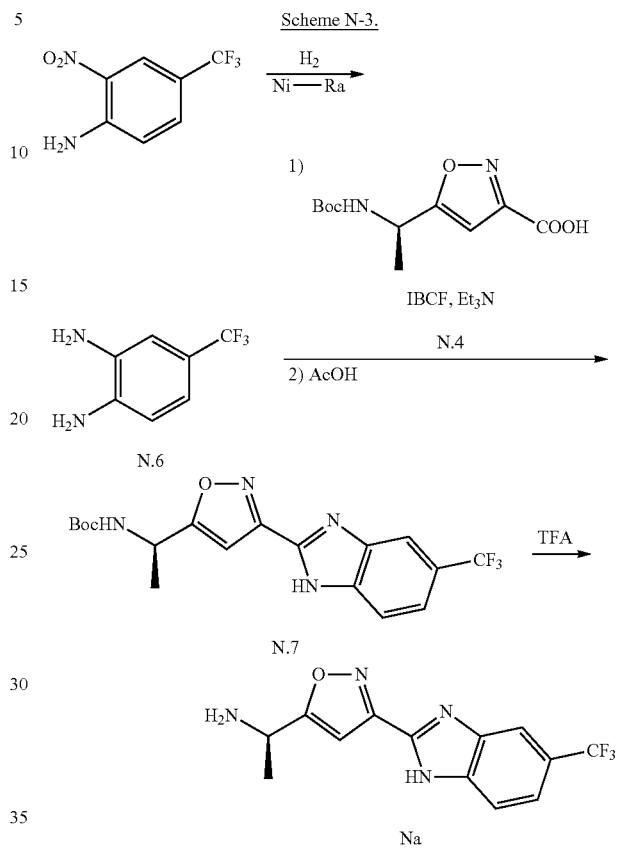

Synthesis of Compound N.6.

A mixture of 2-nitro-4-trifluoromethyl-phenylamine (240 g, 1.16 mol) and Raney Ni (10 g) in methanol (2400 mL) was stirred at RT under hydrogen (50 psi) overnight. The reaction mixture was filtered and concentrated to provide the compound N.6 (197.7 g, 96.4%). ¹H NMR (CDCl₃) δ 6.98 (d, 1H), 6.93 (s, 1H), 6.71 (d, 2H).

Synthesis of Compound N.7.

To a solution of (R)-5-(1-(tert-butoxycarbonylamino) ethyl)-isoxazole-3-carboxylic acid (55 g, 0.215 mol) and Et₃N (36 mL, 0.26 mol) in THF (2 L) was added dropwise isobutyl chloroformate (33 mL, 0.26 mol) at −20° C. The reaction mixture was stirred for 1 hr, and a solution of 4-(trifluoromethyl)benzene-1,2-diamine (45.4 g, 0.26 mol) in THF was added. After stirring for 2 h at −20° C., the mixture was allowed to warm up to RT and stirred for another 2 hr. Water was added to quench the reaction and the reaction mixture was evaporated under reduced pressure to remove THF. The aqueous layer was extracted with ethyl acetate (2×). The combined organic layers were washed with water, dried over Na₂SO₄, filtered and concentrated. The residue was re-dissolved in acetic acid (250 mL) and stirred for 2 hr at 90° C. The solution was concentrated under vacuum and partitioned with ethyl acetate and water. The organic layer was separated, washed with water, Na₂CO₃ solution and brine, dried over Na₂SO₄, filtered and concentrated. The crude product was purified by column chromatography to afford compound N.7, (R)-tert-butyl 1-(3-(6-(trifluoromethyl)-1H-benzo[d]imidazol-2-yl)isoxazol-5-yl)

ethylcarbamate (75.7 g, 88.8%). $^1$H NMR (DMSO-$d_6$) δ 7.8 (m, 4H), 6.9 (s, 1H), 4.91 (m, 1H), 1.46 (d, 3H), 1.39 (s, 9H).

Synthesis of Compound Na.

A mixture of (R)-tert-butyl 1-(3-(6-(trifluoromethyl)-1H-benzo[d]imidazol-2-yl)isoxazol-5-yl)ethylcarbamate (86.5 g, 0.22 mol) in TFA (300 mL) was stirred at RT for 2 hr. The reaction mixture was concentrated in vacuo and re-dissolved in ethyl acetate. The ethyl acetate solution was washed with $K_2CO_3$ and water, dried over $Na_2SO_4$, and concentrated. The crude product was purified by column chromatography to afford compound Na, (R)-1-(3-(6-(trifluoromethyl)-1H-benzo[d]imidazol-2-yl)isoxazol-5-yl)ethanamine (30.2 g, 46.7%). $^1$H NMR (DMSO-$d_6$) δ 7.98 (s, 1H), 7.78 (d, 1H), 7.56 (d, 1H), 6.94 (s, 1H), 4.16 (q, 1H), 1.36 (d, 3H).

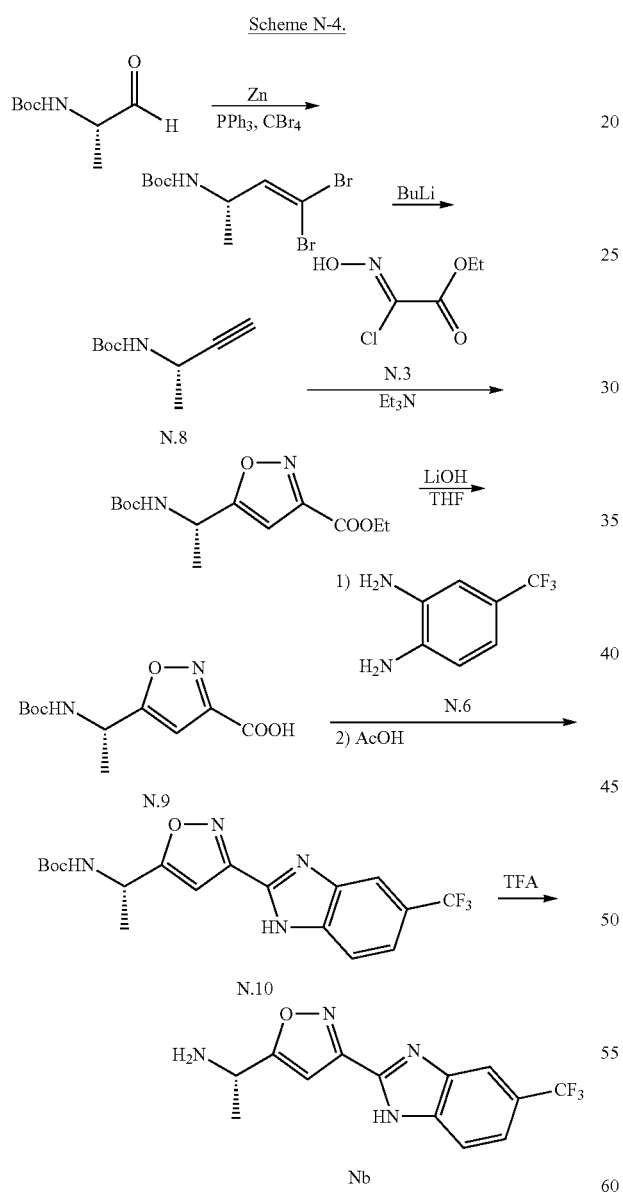

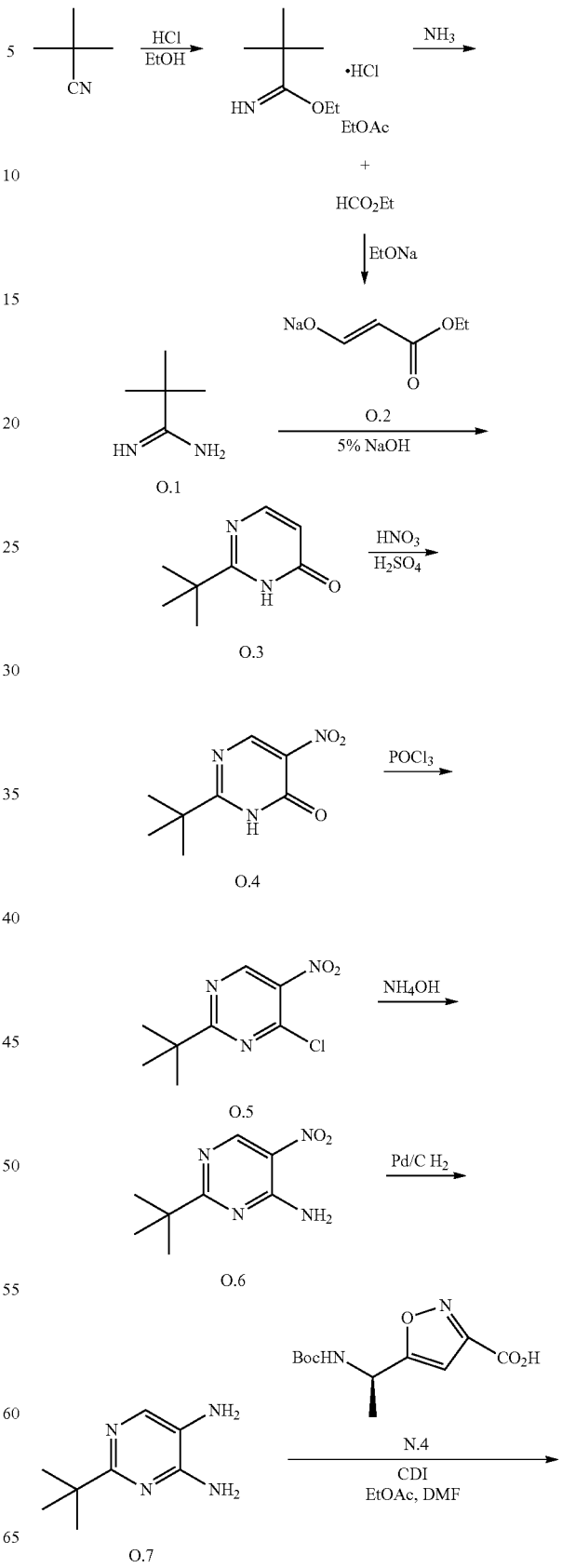

Synthesis of Compound Nb.

This compound was synthesized in the same manner as described for compound Na in schemes N-1~N-3 starting from (1S)-(1-methyl-2-oxo-ethyl)-carbamic acid tert-butyl ester. $^1$H NMR (DMSO-$d_6$) δ 7.98 (s, 1H), 7.78 (d, 1H), 7.56 (d, 1H), 6.94 (s, 1H), 4.16 (q, 1H), 1.36 (d, 3H).

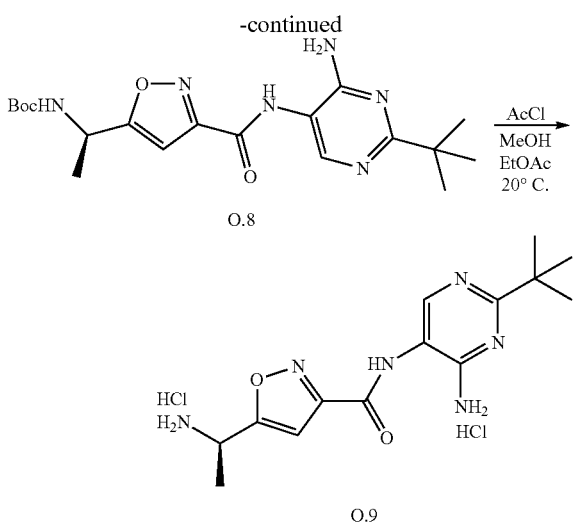

Synthesis of Compound O.1.

Pivalonitrile (13 g, 157 mmol) was dissolved in absolute ethanol (50 mL) and cooled in a salt-ice bath. HCl gas was bubbled through this solution for 1 h to saturate the solution. The reaction was warmed to RT. After 3 hr, the solvent was removed in vacuo to afford ethyl pivalimidate (16 g, 62%) as white solid. The crude ethyl pivalimidate (16 g, 97 mmol) was taken up in absolute ethanol (20 mL) and absolute ethanol saturated with ammonia (30 mL) was added. The reaction mixture was stirred at RT for 3 hr, whereupon ammonium chloride was filtered off and the salt washed with ethanol. The filtrate was concentrated in vacuo and the solid obtained was dried under vacuum to afford compound O.1, pivalimidamide (10 g, 76%). $^1$H NMR (DMSO-$d_6$, 200 MHz): δ 8.6 (br s, 1H), 1.2 (s, 9H); LCMS m/z 101 [M+1]$^+$.

Synthesis of Compound O.2.

Sodium metal (15 g, 0.65 moles) was added to dry toluene and the mixture was heated to 120° C. Ethanol (38 mL, 0.847 g) was added dropwise through an addition funnel, and the mixture was refluxed for 3 hr after the addition. The reaction was cooled to RT and dry ether (400 mL) was added. To the resultant suspension, a mixture of ethyl formate (45 mL, 75 mmol) and ethyl acetate (54.7 mL, 88 mmol) were added dropwise. The reaction was stirred at RT for 3 days. Solvent was evaporated and the obtained solid O.2, sodium (E)-3-ethoxy-3-oxoprop-1-en-1-olate (60 g, 67%), was used without further purification.

Synthesis of Compound O.3.

A mixture of O.1 (25 g, 182 mmol), O.2 (50 g, 363 mmol) and 5% aqueous sodium hydroxide (320 mL) was stirred at RT overnight. The reaction mixture was brought to pH ~5.0 with conc. HCl and the product was extracted with DCM (3×). The combined organic layers were dried (Na$_2$SO$_4$) and concentrated in vacuo. The resultant crude residue was purified by column chromatography to obtain compound O.3, 2-tert-butylpyrimidin-4(3H)-one, as a yellow solid (15 g, 54%). $^1$H NMR (CDCl$_3$, 200 MHz) δ: 12.2 (brs, D$_2$O exchangeable, 1H), 8.0 (d, J=6.9 Hz, 1H), 6.3 (d, J=6.9 Hz, 1H), 1.4 (s, 9H); LCMS: m/z 153 [M+1]$^+$.

Synthesis of Compound O.4.

Compound O.3 (10 g, 66 mmol) was taken up in concentrated sulfuric acid (64 mL) and heated to 110° C. To the reaction mixture at 110° C., concentrated nitric acid (64 mL) was added dropwise in four equal portions. After 70% conversion, the reaction mixture was poured into ice water and extracted (DCM). The organic layer was dried (Na$_2$SO$_4$) and concentrated in vacuo to afford compound O.4, 2-tert-butyl-5-nitropyrimidin-4(3H)-one, as a white solid (5.0 g, 39%). $^1$H NMR (CDCl$_3$, 200 MHz) δ: 12.0 (br s, 1H), 9.0 (s, 1H), 1.4 (s, 9H); LCMS m/z 198 [M+1]$^+$.

Synthesis of Compound O.5.

A solution of compound O.4 (12 g, 60.9 mmol) in phosphorus oxychloride (96 mL) was stirred at reflux for 5 hr. The reaction mixture was cooled to RT and the excess phosphorus oxychloride was concentrated in vacuo. The residue was added to ice-water and extracted into DCM. The organic layer was dried (Na$_2$SO$_4$) and removed invacuo to afford compound O.5, 2-tert-butyl-4-chloro-5-nitropyrimidine, as a brown liquid (12 g, 92%) which was used without further purification.

Synthesis of Compound O.6.

To a stirred solution of compound O.5 (12 g, 55.7 mmol) in methanol (96 mL) was added ammonium hydroxide solution (156 mL) at 0-5° C. The reaction was warmed to RT and stirred overnight. The mixture was concentrated in vacuo, and the residue was dissolved in water and extracted with DCM. The organic layer was dried (Na$_2$SO$_4$) and concentrated in vacuo to afford compound O.6, 2-tert-butyl-5-nitropyrimidin-4-amine, as a light green solid (8.4 g, 77%). $^1$H NMR (CDCl$_3$, 200 MHz) δ 9.2 (s, 1H), 7.8 (br. s, 1H), 6.0 (br. s, 1H), 1.38 (s, 9H); LCMS: m/z 197.0 [M+1]$^+$.

Synthesis of Compound O.7.

To a stirred solution of compound O.6 (8.0 g, 40 mmol) in methanol (200 mL) was added 10% palladium carbon (1.0 g). The reaction was stirred under an atmospheric pressure of hydrogen for 6 h at RT. The mixture was filtered through celite and the solution was concentrated in vacuo to afford compound O.7, 2-tert-butylpyrimidine-4,5-diamine, as an off-white solid (6.7 g, 98.96%). $^1$H NMR: (CDCl$_3$, 200 MHz) δ 7.8 (s, 1H), 4.7 (br. s, 2H), 3.0 (br. s, 2H), 1.35 (s, 9H); $^{13}$C NMR: (CDCl$_3$, 60 MHz) δ 167.9, 155.9, 138.4, 125.2, 38.9, 30.2; LCMS: m/z 167.1 [M+1]$^+$.

Synthesis of Compound O.8.

To a three-neck round-bottom flask equipped with a thermometer, a magnetic stirrer and a nitrogen inlet was added ethyl acetate (50.0 mL), and CDI (9.7 g, 59.9 mmol) at RT. To the resultant slurry was added a solution of compound N.4, 5-(1-tert-butoxycarbonylamino-ethyl)-isoxazole-3-carboxylic acid (15.7 g, 60 mmol) in ethyl acetate (80.0 mL) at RT over 1 hr. The clear solution was heated to 40° C. for additional 10 min. The reaction was cooled to RT and to it was added a solution of compound O.7 (10.0 g, 59.9 mmol) in DMF (20 mL) over 30 min. The reaction mixture was stirred at RT for an additional 5 hr, whereupon ethyl acetate (150 mL) was added. The mixture was washed with water (3×110 mL) and the organic layer was concentrated under reduced pressure to give compound O.8, (R)-tert-butyl 1-(3-(4-amino-2-tert-butylpyrimidin-5-ylcarbamoyl)isoxazol-5-yl)ethylcarbamate, as a glassy solid (25.7 g, 91.2%). $^1$H NMR (CDCl$_3$, 200 MHz) δ: 8.3 (s, 1H), 8.2 (s, 1H), 6.65 (s, 1H), 5.1-5.2 (m, 1H), 1.6 (d, 3H), 1.4 (s, 9H), 1.3 (s, 9H); LCMS: m/z 405.2 [M+1]$^+$.

Synthesis of Compound O.9.

To a three-neck round-bottom flask equipped with a thermometer, a magnetic stirrer and a nitrogen inlet was added compound O.8 (17.6 g, 37.4 mmol) and methanol (60.0 mL) at RT. To the resultant clear solution was then added acetyl chloride (16.5 mL, 232 mmol) while maintaining the reaction temperature below 40° C. The solution was stirred at RT for an additional 1 to 2 hr, whereupon ethyl acetate (95 mL) was added. The product started to crystallize from the reaction mixture and additional ethyl acetate (265 mL) was added over 1 hr. The resultant slurry was stirred for additional 1 h and filtered. The wet cake was washed with ethyl acetate (3×50 mL) and dried under vacuum to give compound O.9 (13.11 g, 92%) as a white solid. $^1$H NMR (DMSO-d$_6$, 400 MHz) δ 10.64 (s, 1H), 9.19 (br s, 3H), 8.83 (s, 1H), 7.17 (s, 1H), 4.83 (br. s, 1H), 1.64 (d, J=7 Hz, 3H), 1.41 (s, 9H); LCMS: m/z 305.3 [M+1]$^+$.

of hydrogen for 4 hr and filtered through Celite®. The filtrate was concentrated in vacuo to provide a residue which was purified by column chromatography (2% methanol/DCM) to obtain compound P.4 (2 g, 47.4%). $^1$H NMR: (CDCl$_3$, 200 MHz) δ 6.85 (d, J=8.5 Hz, 1H), 6.7-6.8 (brs, J=8.5 Hz, 1H), 4.1-4.3 (br s, 2H, NH), 3.1-3.3 (brs, 2H, NH), 1.4 (s, 3H), 1.0-1.1 (m, 2H), 0.6-0.8 (m, 2H); $^{13}$C NMR Scheme P-1.

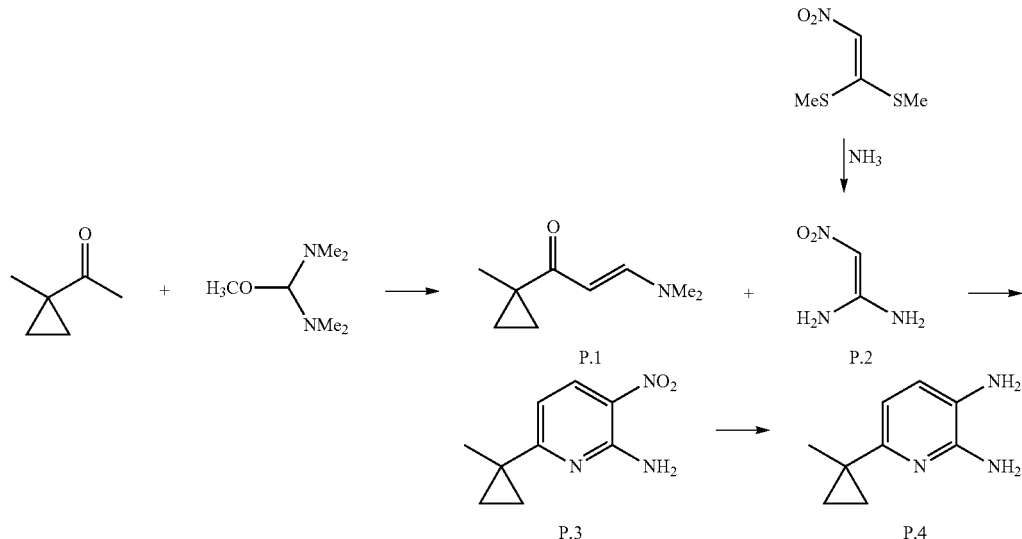

Synthesis of Compound P.1.

1-(1-methylcyclopropyl)ethanone (8 g, 81.5 mmol) and methoxybis(N,N-dimethyl)methane (14 g, 16.2 ml, 106.0 mmol) were heated at 110° C. for 18 hr. Excess methoxybis(N,N-dimethyl)methane was removed by concentration in vacuo to obtain compound P.1 as yellow crystals (11.1 g, 88.2%). $^1$H NMR (CDCl$_3$, 200 MHz) δ: 7.60 (d, J=11.3 Hz, 1H), 5.20 (d, J=11.3 Hz, 1H), 1.4 (s, 3H), 1.1-1.2 (m, 2H), 0.7-0.8 (m, 2H); LCMS: m/z 154.2 [M+1]$^+$.

Synthesis of Compound P.2.

In a 350 mL sealed flask (2-nitroethene-1,1-diyl)bis(methylsulfane) (15 g, 90 mmol) was dissolved in 7M ammonia in methanol (150 mL) and stirred at 50° C. overnight. After 18 hr, solvent was removed in vacuo and the solid obtained was washed with DCM to afford P.2 as an orange solid (7.2 g, 76.9%). $^1$H NMR (DMSO-D6, 200 MHz) δ: 6.6 (s, 1H).

Synthesis of Compound P.3.

Compound P.1 (8.0 g, 52.3 mmol) and compound P.2 (5.38 g, 52.3 mmol) were dissolved in AcOH:EtOH (1:4). The reaction mixture was heated at 100° C. for 16 hr, then cooled to RT and concentrated in vacuo. The resultant residue was dissolved in 1 M NaOH and extracted with ethyl acetate (3×). The combined organic layers were washed with brine, dried over anhydrous sodium sulfate and concentrated in vacuo. The crude product was purified by column chromatography (50-100% DCM/hexane) to afford compound P.3 (4.8 g, 47.6%). $^1$H NMR (CDCl$_3$, 200 MHz): δ 8.25 (d, J=8.5 Hz, 1H), 6.6-6.7 (d, J=8.5 Hz, 1H), 1.5 (s, 3H), 1.2-1.3 (m, 1H), 0.8-0.9 (m, 1H); LCMS: m/z 194.1 [M+1]$^+$.

Synthesis of Compound P.4.

Compound P.3 (5.0 g, 25.9 mmol) was dissolved in methanol (200 mL) and palladium/C (1.0 g) was added. The reaction mixture was stirred under an atmospheric pressure (CDCl3, 60 MHz): δ 154.03, 148.50, 125.75, 123.08, 111.17, 23.24, 19.65, 15.80; LCMS: m/z 164.2 [M+1]$^+$.

Scheme P-2.

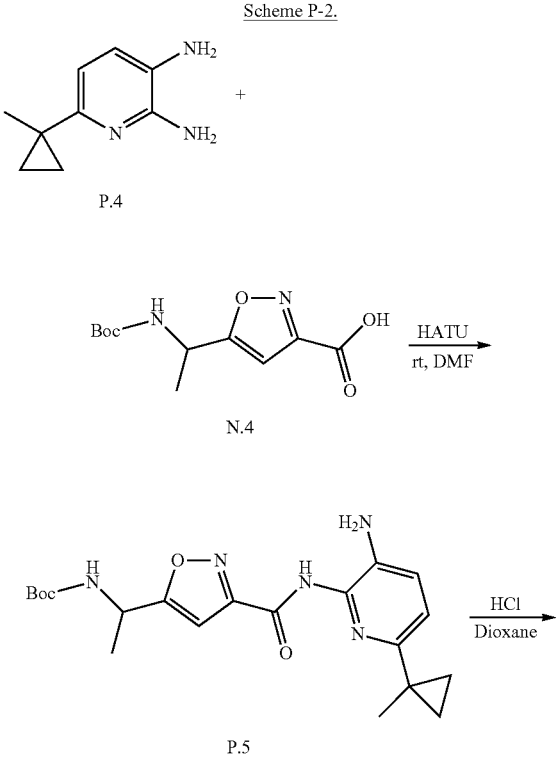

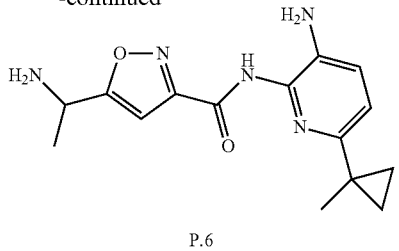

P.6

Synthesis of Compound P.5.

Compound N.4 (1 g, 0.004 mol) was dissolved in DMF (30 mL). Compound P.4 (0.64 g, 0.004 mol), HATU (2.4 g, 0.006 mol), and diisopropylethylamine (3.0 mL, 0.02 mol) were added and the reaction mixture was stirred at RT for 1 hr. Solvent was removed in vacuo and the crude reaction mixture was dissolved in EtOAc and washed with saturated aqueous NaHCO$_3$ (3×) and brine (1×). The organic layer was dried over anhydrous sodium sulfate and concentrated in vacuo. The crude product was purified by column chromatography (0-5% MeOH/DCM) to afford compound P.5 (1.28 g, 80%). $^1$H NMR (DMSO-d$_6$, 200 MHz): δ 9.89 (s, 1H, NH), 7.64 (d, J=7.6 Hz, 1H, NH), 7.39 (d, J=6.6 Hz, 1H) 6.62 (s, 1H), 6.59 (d, J=7.6 Hz, 1H), 5.64 (br s, 1H), 4.91-4.84 (m, 1H), 1.44 (s, 3H), 1.49-1.39 (m, 12H), 1.08 (dd, J=3.4 Hz, J=2.6 Hz, 2H), 0.68 (dd, J=3.4 Hz, J=2.6 Hz, 2H); LCMS: m/z 402.5 [M+1]$^+$.

Synthesis of Compound P.6.

A solution of compound P.5 (1.0 g, 0.0025 mol) in 4 N HCl/dioxane (5 mL) was stirred for 3 hr and concentrated in vacuo. The resultant residue (0.65 g, 86%) was used without further purification. LCMS: m/z 302.5 [M+1]$^+$.

were dissolved in DMF (1.5 mL) at rt. Triethylamine (106 µL, 0.761 mmol) was added and the reaction was stirred at RT overnight. The reaction mixture was diluted with ethyl acetate and water was added. The layers were separated and the aqueous layer was extracted twice more with ethyl acetate. The combined organic layers were dried over anhydrous sodium sulfate and concentrated under reduced pressure. The crude material was purified using silica gel column chromatography (ethyl acetate/hexanes) to afford the coupled product in quantitative yield. This compound was dissolved in acetic acid (1 mL) and the reaction was stirred at 80° C. for one hr. After cooling, acetic acid was removed under vacuum and the crude product was purified using silica gel column chromatography (ethyl acetate/hexanes) to afford compound Q.1 (85.4 mg, 73%). LCMS: m/z 383 [M+1]$^+$.

Synthesis of Compound Q.

Compound Q.1 (85.4 mg, 0.223 mmol) was dissolved in 20% TFA in dichloromethane (1 mL) at 0° C. and the reaction mixture was gradually warmed to RT over one hr. Benzene was added and the solvents were removed under reduced pressure. The resultant residue was dissolved in dichloromethane and saturated sodium bicarbonate solution was added. The layers were separated and the aqueous layer was extracted twice more with dichloromethane. The combined organic layers were dried over anhydrous sodium sulfate and concentrated under reduced pressure to afford compound Q which was used without further purification. LCMS: m/z 283 [M+1]$^+$.

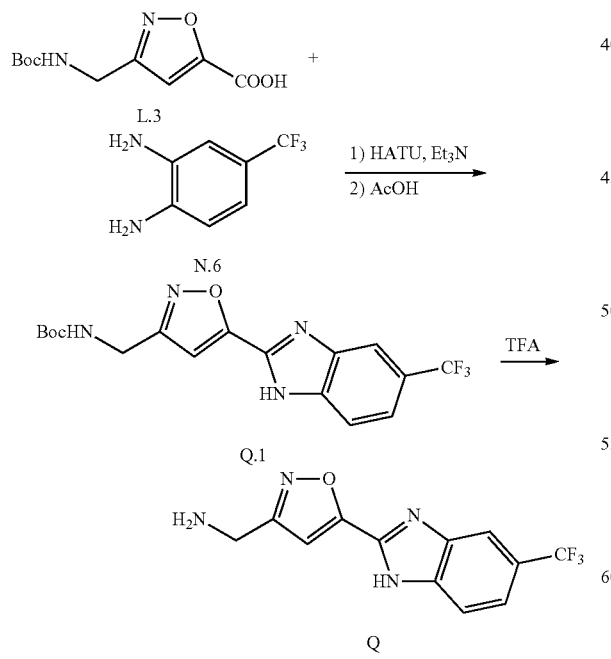

Scheme Q.

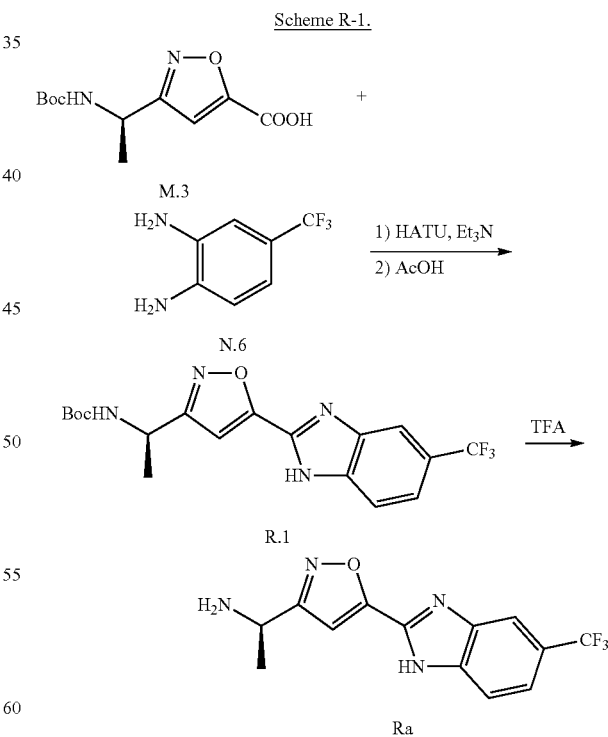

Scheme R-1.

Synthesis of Compound Q.1.

Compound L.3 (73.8 mg, 0.305 mmol), compound N.6 (59.5 mg, 0.338 mmol) and HATU (139.7 mg, 0.367 mmol)

Synthesis of Compound R.

This compound was synthesized in a similar manner as compound Q following Scheme Q using compound M.3 instead of L.3. LCMS: m/z 297 [M+1]$^+$.

Scheme R-2.

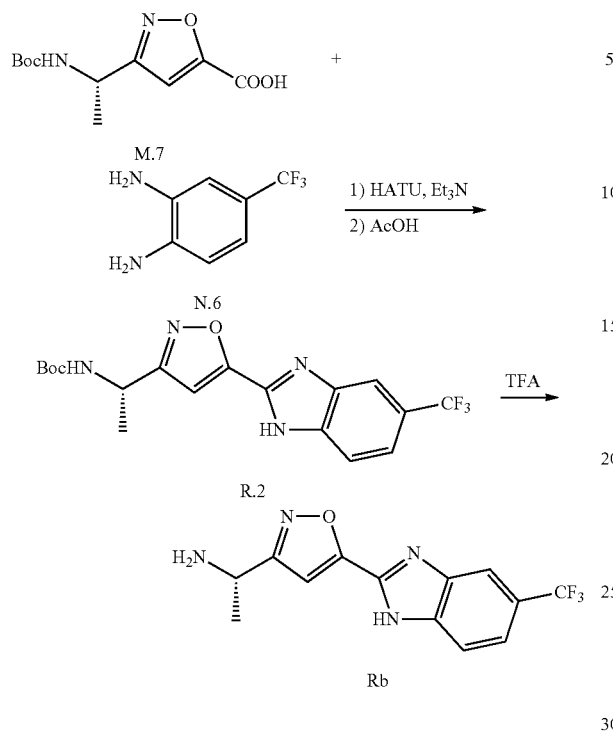

Synthesis of Compound Rb.

This compound was synthesized in a similar manner as compound Q following scheme Q using compound M.7 instead of L.3. LCMS: m/z 297 [M+1]$^+$.

Scheme S.

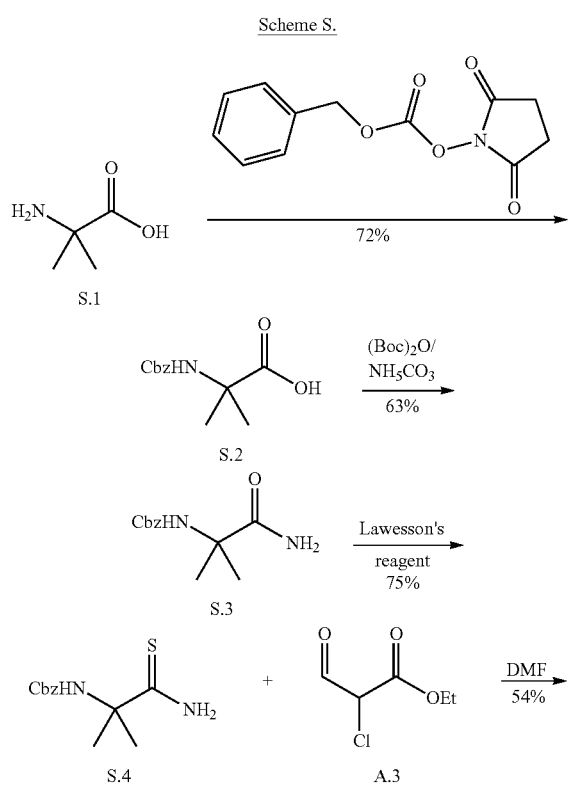

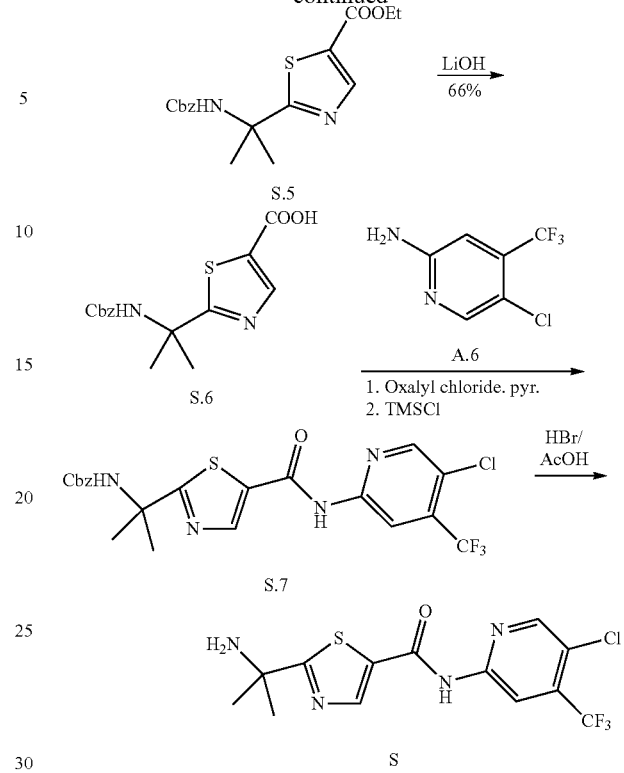

Synthesis of Compound S.2.

To S.1 (10 g, 0.0969 mol) in THF (60 ml) and water (60 mL) at 0° C. was added sodium bicarbonate (16.27 g, 0.193 mole) followed by N-(benzyloxy carbonyloxy) succinimide (60.37 g, 0.242 mol). The reaction mixture was stirred at RT for 12 hr. The THF was removed under vacuum and the aqueous phase was washed with ether (2×100 mL). The aqueous phase was cooled to 0° C. and acidified to pH=2 with 5N HCL (50 mL). The reaction mixture was extracted with ethyl acetate (2×100 mL); the combined organic layer was dried over sodium sulfate and concentrated under reduced pressure. The crude material was purified by column chromatography (1% MeOH in dichloromethane) to give S.2 (16 g, 72%). $^1$H NMR (CDCl$_3$, 200 MHz) δ 7.45-7.32 (m, 5H), 5.40 (bs, 1H,) 5.12 (s, 2H), 1.82 (s, 6H); LCMS: m/z 238 [M+1]$^+$.

Synthesis of Compound S.3.

To a suspension of S.2 (20 g, 0.0843 mol) in acetonitrile were added (400 mL), di-tert-butyl-dicarbonate (24 mL, 0.107 mol), ammonium bicarbonate (8 g, 0.101 mol) and pyridine (5.2 ml). The reaction mixture was stirred at RT for 3 h and then the acetonitrile was removed under reduced pressure. The reaction mixture was diluted with water (50 mL) and the resulting solid was removed by filtration. The solid was washed with water ad dried to afford S.3 (12 g, 63%) as a off-white solid. This material was used for the next reaction with out any further purification. $^1$H NMR (CDCl$_3$, 200 MHz) δ 7.41-7.38 (m, 5H), 6.30 (bs, 1H), 5.40 (bs, 2H), 5.15 (s, 2H), 1.78 (s, 6H); LCMS: m/z 236 [M+1]$^+$.

Synthesis of Compound S.4.

Lawessons reagent (10.28 g, 0.0254 mol) was added to a suspension of S.3 (10 g, 0.04237 mol) in dioxane (58 mL) at RT. The reaction mixture was heated at 60° C. for 30 minutes, cooled to RT and stirred for additional 1.5 hr. The resulting solution was concentrated under reduced pressure and the residue was diluted with saturated sodium bicarbonate (50 mL). The solid obtained was filtered, washed with water and dried under vacuum to afford an off-white solid S.4 (8.0 g, 75%) which was for the next step without further purification. ¹H NMR (CDCl₃, 200 MHz) δ 7.90 (bs, 1H) 7.72 (bs, 1H) 7.41-7.7.38 (m, 5H), 5.58 (bs, 1H), 5.12 (s, 2H), 1.72 (s, 6H). LCMS: m/z 253 [M+1]⁺.

Synthesis of Compound S.5.

A solution of A.3 (9.5 g, 0.0635 mol) in DMF (64 mL) was added to thioamide S.4 (8 g, 0.031 mol). The reaction mixture was stirred at 50° C. under nitrogen atmosphere overnight. After cooling to rt, ether (70 mL) was added. The solution was cooled to 0° C. and saturated sodium bicarbonate (30 mL) was added slowly. The reaction mixture was extracted with ether (2×50 mL); the combined organic layer was washed with saturated sodium bicarbonate (1×50 mL), dried over sodium sulfate and concentrated under vacuum to give a brown oil. Purification by column chromatography (20% ethyl acetate/hexane) provided compound S.5 (6 g, 54%) as a brown solid. ¹H NMR (CDCl₃ 200 MHz) δ 8.13 (s, 1H) 7.40-7.35 (m, 5H) 5.70 (bs, 1H), 5.10 (s, 2H), 4.35 (q, J=7.2 Hz, 2H) 1.80 (s, 6H), 1.37 (t, J=7.2 Hz, 3H). LCMS m/z: 349 [M+1]⁺.

Synthesis of Compound S.6.

To a 0° C. solution of S.5 (300 mg, 0.86 mmol) in THF (4 mL) and water (4 mL) was added lithium hydroxide (200 mg, 0.0258 mol) in water (1 mL). The reaction mixture was stirred at RT for 2.5 hr and then the solvent was removed under reduced pressure. The aq. layer was washed with ether (2×15 ml), cooled to 0° C. and acidified to pH 2 with 5N HCl. The obtained precipitate was filtered and dried to give S.6 (180 mg, 66%). ¹H NMR (DMSO-d₆, 200 MHz) δ 13.45 (bs, 1H), 8.20 (bs, 1H), 8.18 (s, 1H), 7.40-7.38 (m, 5H), 5.02 (s, 2H), 1.60 (s, 6H). LCMS m/z: 320.9 [M+1]⁺.

Synthesis of Compound S.7.

To a solution of S.6 (205 mg, 0.64 mmol) in methylene chloride (4 mL) at RT was added oxalyl chloride (160 μL, 0.0019 mol) followed by the addition of DMF (50 μL) and stirred at RT for 1 hr. Separately a solution of A.6 (132 mg, 0.000672 mol), acetonitrile (2 ml) and pyridine (520 μL, 0.0065 mol) was stirred at RT followed by the addition of chlorotrimethylsilane (100 μL, 0.0008 mol). The acid chloride was concentrated under reduced pressure to a tan solid and redissolved in acetonitrile (2 mL). To the acid chloride solution was added the activated aniline. After 3 hr, the reaction mixture was diluted with ethyl acetate (75 mL) and washed with dilute citric acid (50 mL), aqueous sodium bicarbonate (50 mL) and water. The organic layer was dried over sodium sulfate and concentrated to a residue which was purified by to give compound S.7. LCMS m/z: 498.95 [M+1]⁺.

Synthesis of Compound S.

To a solution of S.7 (80 mg, 0.16 mmol) in acetic acid (3 mL) was added 4M hydrogen bromide in acetic acid (1 mL, 0.004 mol) and stirred at RT for 4 hr. The reaction mixture was concentrated to a residue which was triturated with saturated sodium bicarbonate. The residue was dissolved in ethyl acetate and washed with saturated sodium bicarbonate. The organic layer was dried over sodium sulfate and concentrated to provide S. LCMS m/z: 364.97 [M+1]⁺.

Scheme T

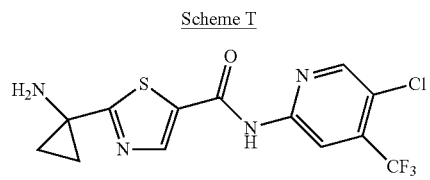 [SMILES: NC1(c2ncc(C(=O)Nc3cc(C(F)(F)F)c(Cl)cn3)s2)CC1]

Synthesis of Compound T.

The synthesis of T was accomplished following Scheme S substituting 1-amino-cyclopropanecarboxylic acid for 2-amino-2-methyl-propionic acid (S.1).

Scheme U.

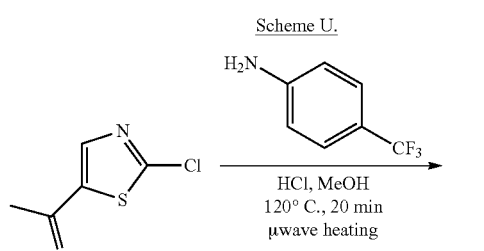

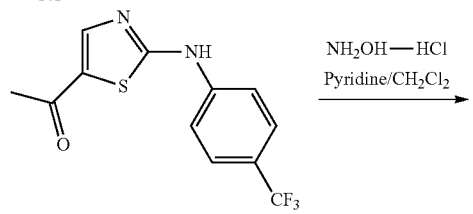

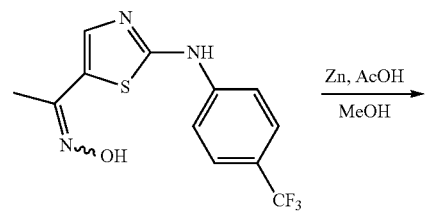

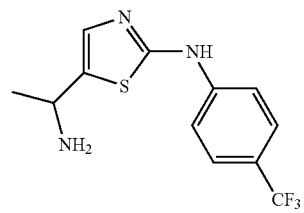

Synthesis of Compound U.2.

To a 2 mL reaction vial was charged with U.1 (50 mg, 0.2 mmol), 4-trifluoromethylbenzenamine (30 μL, 0.24 mmol), MeOH (500 μL) and 4 M of HCl in 1,4-dioxane (5 μL, 0.02 mmol). The mixture was heated in microwave oven for 20 min at 120° C. This crude mixture was purified via preparatory reverse-phase HPLC, affording U.2 (30 mg, 50%). ¹H NMR (DMSO-d6, 400 MHz) δ: 11.2 (br s, 1H), 8.2 (s, 1H), 7.8-7.9 (d, 2H), 7.7-7.8 (d, 2H), 2.4 (s, 3H); m/z 287 [M+1]⁺.

Synthesis of Compound U.3.

To a solution of U.2 (1.0 g, 3.49 mmol) in methanol (20 mL) at 0° C., were added pyridine (1.17 mL, 13.98 mmol)

and hydroxylamine hydrochloride (485 mg, 6.99 mmol). After stirring at RT overnight, methanol was removed and the residue was diluted with water. The formed solid was collected via filtration, affording compound U.3 (800 mg, 80%). $^1$H NMR (mixture of cis, trans isomers, DMSO-d6 200 MHz) δ: 11.4 and 11.1 (1H, —OH), 10.7-10.8 (br s, 1H), 7.8-7.9 (d, 2H), 7.8 and 7.6 (s, 1H), 7.6-7.7 (d, 2H), 2.1 and 2.2 (s, 3H); m/z 302 [M+1]$^+$.

Synthesis of Compound U.

To a mixture of U.3 (800 mg, 2.65 mmol) in 1:1 ethanol and acetic acid (30 mL) was added Zn powder (1 g, 15.9 mmol). After stirring overnight at RT, solvents were distilled off and residue was taken in water. The solution was basified with NH$_4$OH, extracted into EtOAc and concentrated. Crude compound was purified by column chromatography using DCM to 2-4% MeOH in DCM as elute to afford U as a brown color solid (500 mg, 65.61%). $^1$H NMR (DMSO-d$_6$, 200 MHz) δ: 10.4-10.6 (br s, 1H), 7.8-7.9 (d, 2H), 7.6-7.7 (d, 2H), 7.1 (s, 1H), 4.2-4.3 (m, 1H), 1.3-1.4 (d, 3H); m/z 288 [M+1]$^+$.

Synthesis of Compound Ua and Ub.

Preparatory chiral SFC of compound U (440 mg) on a Chiralpak AS-H (2×25 cm) with an eluant of 30% isopropanol (0.1% Et$_2$NH)/CO$_2$ at 100 bar at 60 mL/min and monitoring at 220 nM afforded and 206 mg of Ub (ee >99%) as the first eluting peak and 186 mg of Ua (ee >99%) as the second eluting peak.

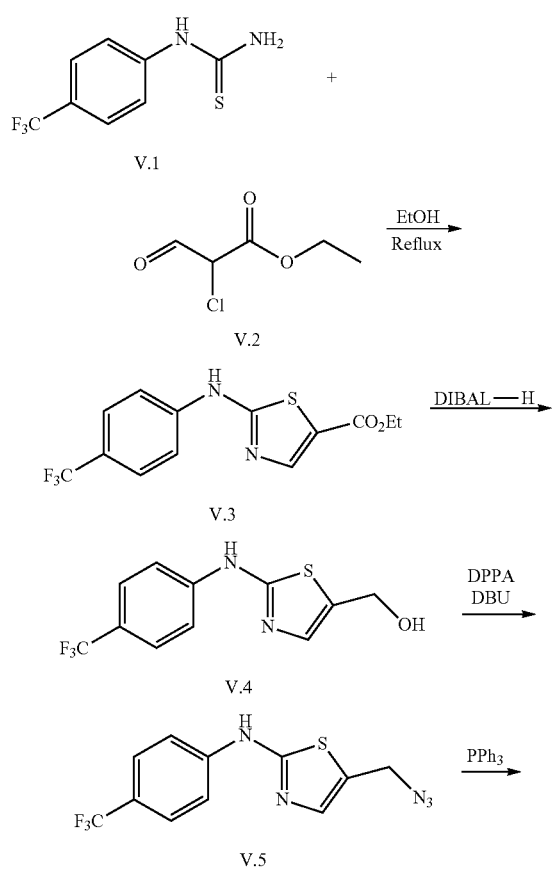

Scheme V.

Synthesis of Compound V.3.

A RT solution of V.1 (10 g, 45.45 mmol) in ethanol (100 mL) was treated with V.2 (10.26 g, 68.18 mmol, Plouvier, B.; Bailly, C.; Houssin, R.; Henichart, J. P. *Heterocycles* 1991, 32, 693-701), and the reaction mixture was heated at reflux for 16 hr. The ethanol solvent was distilled off and the residue was dissolved in EtOAc. The organic layer was washed with sodium bicarbonate solution, water, and brine, dried over anhydrous Na$_2$SO$_4$, filtered, and concentrated under vacuum. Purification by flash column chromatography (SiO$_2$, 100% hexane to 12% EtOAc-Hexane) afforded V.3 as a yellow solid (10 g, 69.63%). $^1$H NMR (CDCl$_3$, 200 MHz) δ 9.3-9.4 (br s, 1H, D$_2$O exchangeable), 8.0 (s, 1H), 7.6-7.7 (d, 2H), 7.3-7.4 (d, 2H), 4.2-4.4 (q, 2H), 1.3-1.4 (t, 3H); m/z: 317 [M+1].

Synthesis of Compound V.4.

A solution of V.3 (4 g, 12.65 mmol) in dry DCM (60 mL) was cooled to −78° C. under a N$_2$ atmosphere, and treated with DIBAL-H (38 mL, 1M solution in toluene, 38 mmol). The reaction was stirred at −78° C. for 2 hr, then quenched by addition of saturated NH$_4$Cl solution, and slowly warmed to RT. The reaction mixture was filtered through celite, and the filter cake was washed with DCM. The organic layer was separated and dried over anhydrous Na$_2$SO$_4$, filtered, and concentrated under vacuum. Purification by flash column chromatography (SiO$_2$, 100% hexanes to 25% ethyl acetate-Hexane) afforded V.4 as white solid (1.8 g, 52%). $^1$H NMR (DMSO-D$_6$, 200 MHz) δ: 10.5 (s, 1H, D$_2$O exchangeable), 7.7-7.8 (d, 2H), 7.5-7.6 (d, 2H), 7.1 (s, 1H), 5.3 (t, 1H, D$_2$O exchangeable), 4.5 (s, 2H); m/z: 274.9 [M+1]$^+$.

Synthesis of Compound V.5.

A solution of V.4 (1.8 g, 6.57 mmol) in toluene (30 mL) and THF (10 mL) was cooled in an ice bath at 0° C., and treated with diphenylphosphonic azide (2.835 g, 13.139 mmol) and DBU (2 g, 13.139 mmol). The reaction mixture was stirred overnight at RT. The mixture was concentrated under vacuum, and the residue was purified by flash column chromatography to obtain V.5 (1 g, 51%) as yellow solid. $^1$HNMR (1H, CDCl$_3$, 200 MHz) δ: 7.6-7.7 (d, 2H), 7.5-7.6 (d, 2H), 7.3 (s, 1H), 4.4 (s, 2H); m/z: 300 [M+1]$^+$.

Synthesis of Compound V.

A solution of SBN-69-5 (500 mg, 1.672 mmol) in THF (20 mL) and water (1 mL) was treated with triphenylphosphine (657 mg, 2.508 mmol). The mixture was stirred overnight at RT. Solvents were evaporated and the residue was purified by column chromatography (SiO$_2$, 100% DCM to 2.5% MeOH/DCM) to obtain the product as brown colour solid. (300 mg, 65.78%). $^1$HNMR: (1H, DMSO-D6, 200 MHz) δ: 10.4-10.6 (br s, 1H), 7.7-7.9 (d, 2H), 7.6-7.7 (d, 2H), 7.1 (s, 1H), 3.9 (s, 2H); m/z: 274 [M+1]$^+$.

Scheme W.

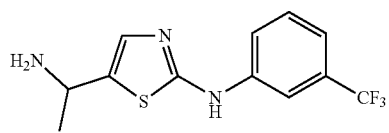

W

Synthesis of Compound W.

The synthesis of W was accomplished following Scheme U substituting 3-trifluoromethylaniline for 4-trifluoromethylaniline.

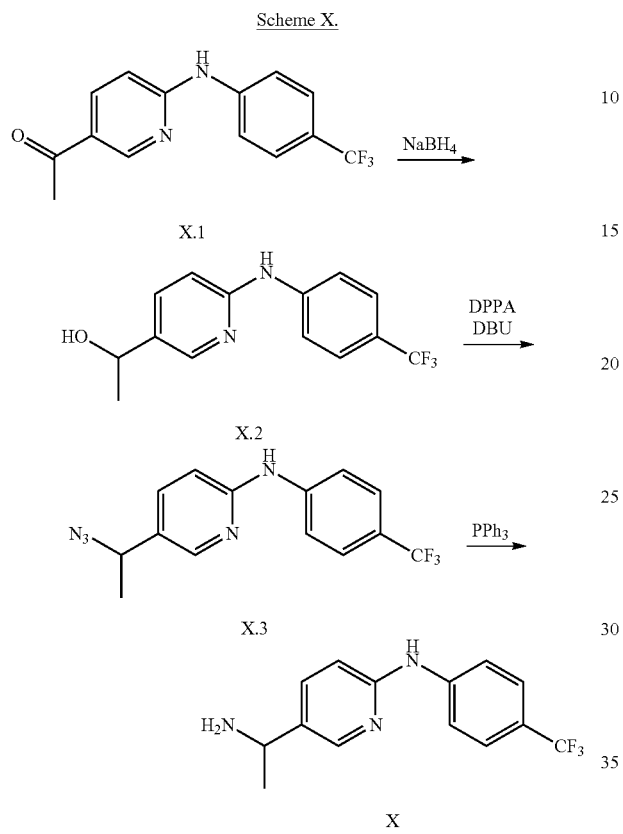

Synthesis of Compound X.1.

The synthesis of X.1 was accomplished following Scheme U substituting 1-(6-chloro-3-pyridinyl)-1-ethanone for 1-(2-chlorothiazol-5-yl)ethanone (U.1).

Synthesis of Compound X.2.

A suspension of X.1 (804 mg, 2.87 mmole) in 30 mL of ethanol was treated with sodium borohydride (0.217 g, 5.74 mmol), and the reaction mixture was stirred at RT for 16 hr. The mixture was concentrated to dryness and the residue was dissolved in EtOAc and H$_2$O. The organic layer was separated, dried over MgSO$_4$, filtered, and concentrated, absorbing onto 10 g SiO$_2$. Purification by flash column chromatography (40 g SiO2, 10% EtOAc/hexane for 5 min then gradient to 60% EtOAc/hexanes over 15 min) afforded 738 mg (91%) of X.2 as a clear oil that slowly solidified the a white solid. LCMS, m/z=284 [M+1]$^+$.

Synthesis of Compound X.3.

A solution of X.2 (738 mg, 2.61 mmol) in anhydrous DCM (10 mL) was and cooled in an ice bath, treated with diphenylphosphonic azide (0.817 mL, 3.79 mmol) in a dropwise fashion, and stirred for 15 min. 1,8-Diazabicyclo[5.4.0]undec-7-ene (0.567 mL, 3.79 mmol) was added in a dropwise fashion. The reaction mixture was stirred in the ice bath for 1 hr, warmed to RT and stirred for 16 hr. The reaction mixture was partitioned between EtOAc and H2O. The organic layer was dried over MgSO$_4$, filtered, and concentrated, absorbing onto 5 g SiO$_2$. Purification by flash column chromatography (40 g SiO$_2$, 5% EtOAc/hexane then gradient to 40% EtOAc/hexanes) yielded X.3 (464 mg, 58%) as a yellow viscous oil. LCMS m/z=292 [M+H].

Synthesis of Compound X.

A solution of X.3 (463 mg, 1.51 mmol) in THF (10 mL) and H$_2$O (3 mL) was treated with triphenylphosphine (0.593 g, 2.26 mmol) and was heated at 60° C. for 16 hr. The reaction mixture was cooled to RT, diluted with EtOAc and extracted with 1 N HCl (2×10 mL). The aqueous layer was made basic by addition of 10% NaOH and extracted with EtOAc (2×). The combined organic layers were dried over MgSO$_4$, filtered, and concentrated to obtain X (316 mg, 75%) as a viscous oil that solidified to a white solid upon standing. LCMS m/z=282 [M+H].

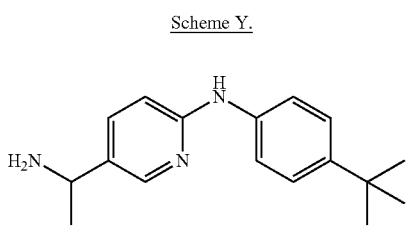

Synthesis of Compound Y.

The synthesis of Y was accomplished following Scheme X substituting 4-t-butyl-aniline for 4-trifluoromethylaniline.

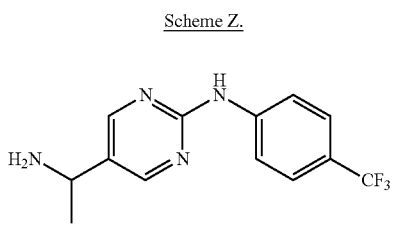

Synthesis of Compound Z.

The synthesis of Z was accomplished following Scheme U and X substituting 1-(2-chloropyrimidin-5-yl)ethanone (*Bioorg. Med.* Chem. 2005, 13, 3707) for 1-(2-chlorothiazol-5-yl)ethanone (U.1).

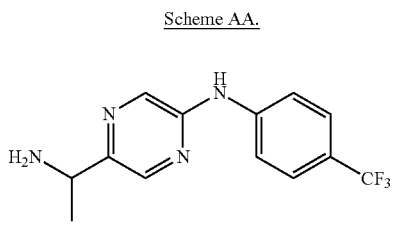

Synthesis of Compound AA.

The synthesis of AA was accomplished following Scheme U and X substituting 1-(2-chloropyrazin-5-yl)ethanone (*Bioorg. Med. Chem.* 2005, 13, 3707) for 1-(2-chlorothiazol-5-yl)ethanone (U.1).

Scheme BB.

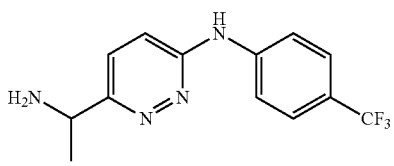 [SMILES: CC(N)c1ccc(Nc2ccc(C(F)(F)F)cc2)nn1]

BB

Synthesis of Compound BB.

The synthesis of BB was accomplished following Scheme U substituting 1-(2-chloropyridazin-5-yl)ethanone (*Bioorg. Med. Chem.* 2005, 13, 3707) for 1-(2-chlorothiazol-5-yl)ethanone (U.1).

Scheme CC.

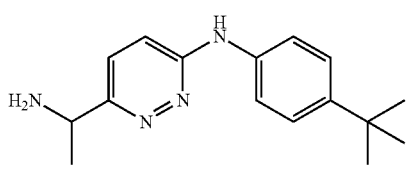 [SMILES: CC(N)c1ccc(Nc2ccc(C(C)(C)C)cc2)nn1]

CC

Synthesis of Compound CC.

The synthesis of CC was accomplished following Scheme U substituting 1-(2-chloropyridazin-5-yl)ethanone (*Bioorg. Med. Chem.* 2005, 13, 3707) for 1-(2-chlorothiazol-5-yl)ethanone (U.1) and 4-t-butylaniline for 4-trifluoromethylaniline.

Scheme DD.

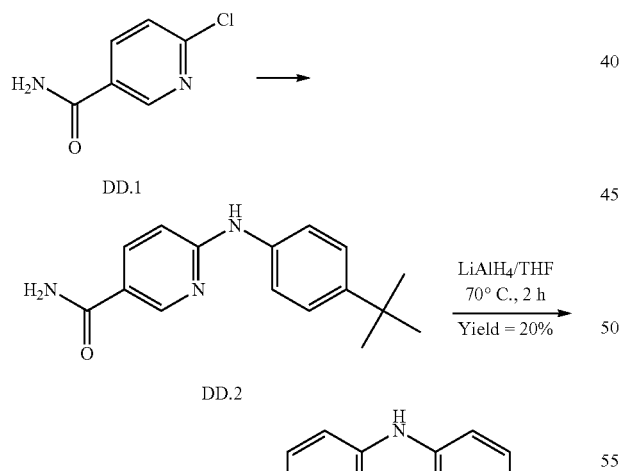

Synthesis of Compound DD.2.

Compound DD.2 was synthesized as described in Scheme U. m/z 270 [M+1]⁺.

Synthesis of Compound DD.

To a mixture of DD.2 (200 mg, 0.7 mmol) in THF (5 mL) was added lithium tetrahydroaluminate (90 mg, 2.0 mmol) and heated it at 70° C. for 2 hr. After cooling down to 25° C., the mixture was quenched with ice water, followed by added 1 N NaOH. The formed solid was removed via filtration, and the filtrate was concentrated and further purified via preparatory reverse-phase HPLC, affording DD (40 mg, 20%). m/z 256 [M+1]⁺.

Scheme EE.

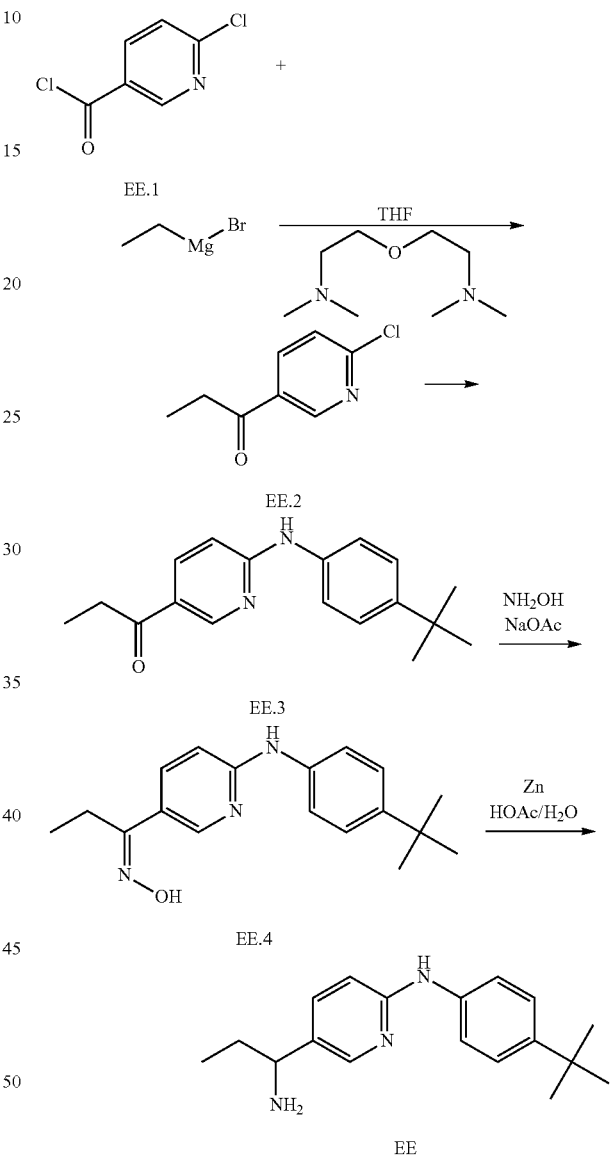

Synthesis of Compound EE.2.

To a solution (in a flame dried vial) of ethanamine, 2,2'-oxybis[N,N-dimethyl-(0.50 mL, 2.6 mmol) in tetrahydrofuran (7.0 mL) at 0° C., was added 1.0 M of ethylmagnesium bromide in tetrahydrofuran (2.6 mL, 2.6 mmol). After stirring at 0-5° C. for 15 min, this mixture was slowly added to a solution (in a flame dried vial) of EE.1 (350 mg, 2.0 mmol) in tetrahydrofuran (4.0 mL) at −60° C. over 10 min and the resulted mixture was further stirred at −60° C. for 8 min. The mixture was then quenched with aqueous ammonium chloride. The aqueous layer was extracted with EtOAc. The organic layer was concentrated to afford EE.2 as a white solid (250 mg, 74%). m/z 170 [M+1]⁺.

Synthesis of Compound EE.

Compound EE was synthesized as described in Scheme U. m/z 284 [M+1]+.

Scheme FF.

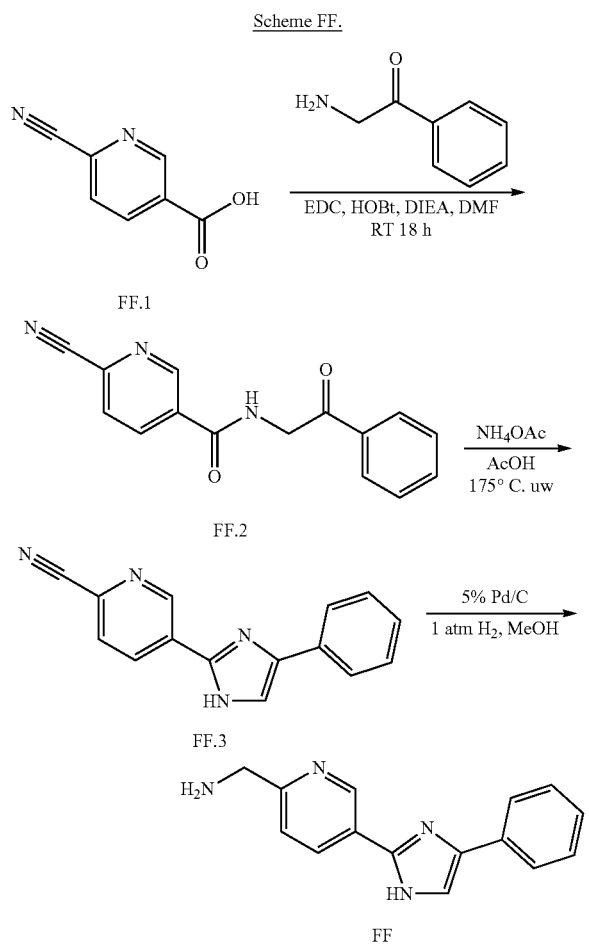

FF

Synthesis of Compound FF.2.

In a 50 mL round-bottom flask, FF.1 (0.949 g, 0.641 mmole), 2-amino-1-phenylethanone (1.10 g, 0.00641 mole), and 1-hydroxybenzotriazole (0.866 g, 0.641 mmole) were dissolved in DMF (20 mL). The mixture was treated with N-(3-dimethylaminopropyl)-N'-ethylcarbodiimide hydrochloride (1.474 g, 0.7691 mmole) and N,N-diisopropylethylamine (1.12 mL, 0.641 mmole). The yellow reaction mixture was allowed to stir at RT for 18 hr and then diluted with 200 mL of EtOAc. The organic layer was washed 2×50 mL of water. FF.2 precipitated as a white solid which was collected by filtration. The filtrate was washed with 50 mL brine, dried over $Na_2SO_4$, and concentrated. The combined solids were titurated with $Et_2O$ to yield 1.55 g (0.0064 mol, 91%) of FF.2.

Synthesis of Compound FF.3.

In a 20 mL microwave reaction vial FF.2 (1.5 g, 0.0565 mole) and ammonium acetate (0.262 g, 0.023 mole) were suspended in acetic acid (10.0 mL). The mixture was then stirred at RT for 1 hr before then heated at 175° C. for 15 min under microwave irradiation. The acetic acid was then removed in vacuo and the resulting residue was neutralized to pH 7 with $NaHCO_3$ sat (aq) 100 mL and solid in the presence of 200 mL of EtOAc. The aqueous layer was washed 2×75 mL EtOAc. The combined organic layers were dried over $Na_2SO_4$, filtered, and concentrated to yield an orange tar. Purification by flash column chromatography ($SiO_2$, 50% EtOAc/Hexanes gradient to 100% EtOAc) yielded 250 mg (18%) of FF.3.

Synthesis of Compound FF.

In a 5 mL microwave reaction vial FF.3 (0.250 g, 1.02 mmole) and 5% Pd/C (0.2 g) were taken up in methanol (4 mL). The reaction was stirred under a $H_2$ balloon at RT for 24 hr. The mixture was filtered through celite and concentration to yield 250 mg of FF.

Scheme GG.

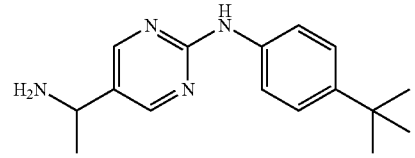 [SMILES: CC(N)c1cnc(Nc2ccc(C(C)(C)C)cc2)cn1]

GG

Synthesis of Compound GG.

The synthesis of GG was accomplished following Scheme U and Scheme X substituting 1-(2-chloropyrimidin-5-yl)ethanone (*Bioorg. Med. Chem.* 2005, 13, 3707) for 1-(2-chlorothiazol-5-yl)ethanone (U.1) and 4-t-butylaniline for 4-trifluoromethylaniline.

Scheme HH.

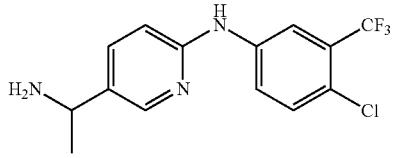 [SMILES: CC(N)c1ccc(Nc2ccc(Cl)c(C(F)(F)F)c2)nc1]

HH

Synthesis of Compound HH.

The synthesis of HH was accomplished following Scheme X substituting 4-chloro-3-trifluoromethylaniline for 4-trifluoromethylaniline. LCMS m/z=316 [M+1]+.

Scheme II.

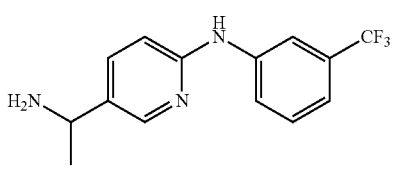 [SMILES: CC(N)c1ccc(Nc2cccc(C(F)(F)F)c2)nc1]

II

Synthesis of Compound II.

The synthesis of II was accomplished following Scheme X substituting 3-trifluoromethylaniline for 4-trifluoromethylaniline.

Synthesis of Compounds JJ-TT.

Compounds JJ-TT could be synthesized following Scheme D using the appropriately substituted aniline for compound A.6.

JJ 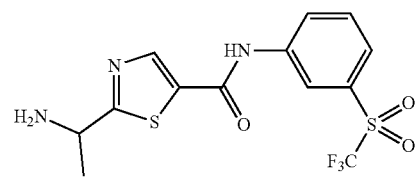
KK 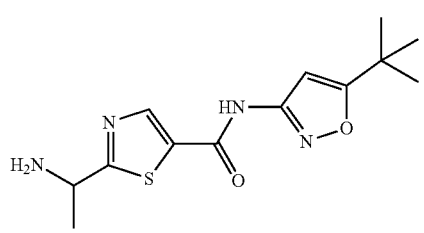
LL 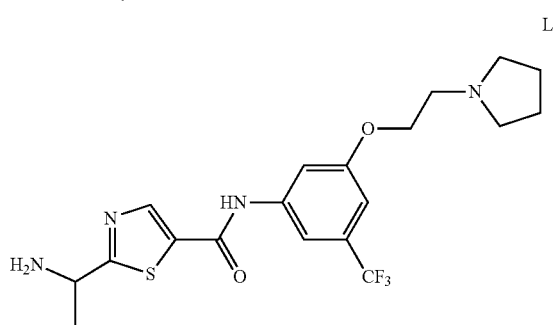
MM 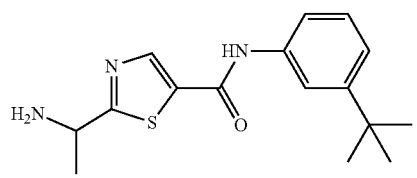 [SMILES: CC(N)c1ncc(C(=O)Nc2cccc(C(C)(C)C)c2)s1]
NN 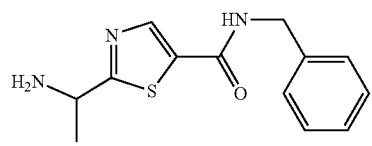
OO 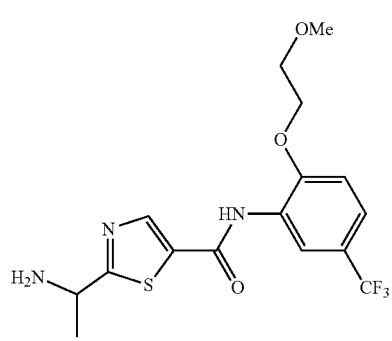
PP
QQ
RR
SS
TT
Scheme UUa.
Compound UUa can be synthesized following Scheme M substituting 3-trifluoromethylaniline for 4-methyl-3-trifluoromethyl-phenylamine.
UUa 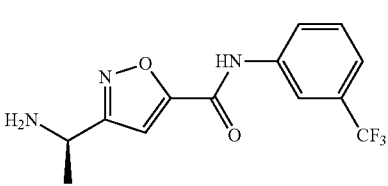 [SMILES: C[C@@H](N)c1ncc(C(=O)Nc2cccc(C(F)(F)F)c2)s1]

Scheme VV.

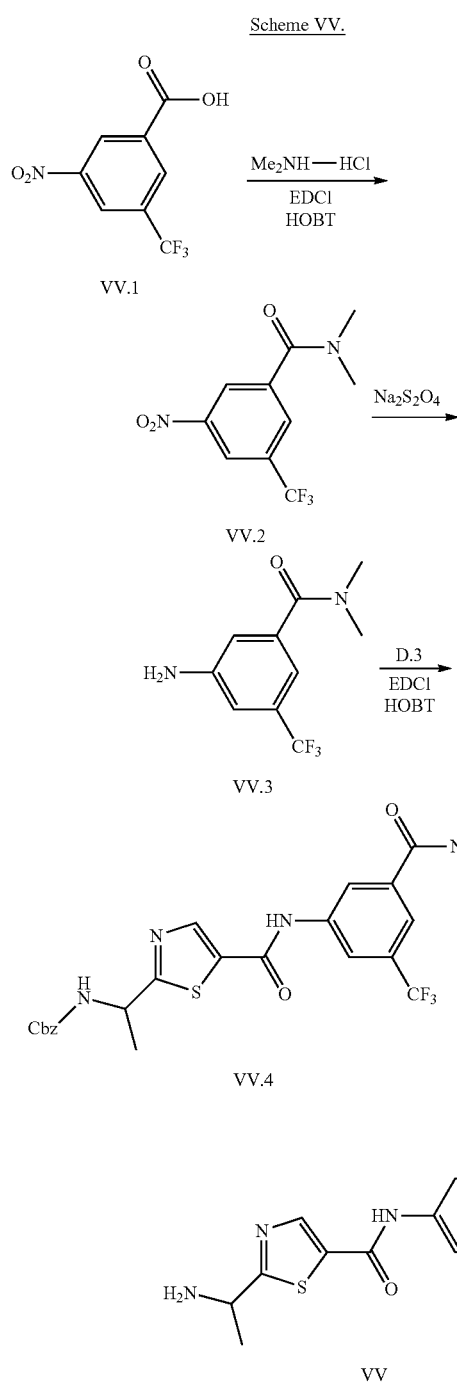

Synthesis of VV.2.

A solution of VV.1 (2 g, 0.0085 mol), dimethylamine hydrochloride (1 g, 0.0127 mol), EDCI (4.0 g, 0.0212 mol), HOBT (574 mg, 0.0042 mol) and DIPEA (1.4 g, 0.0110 mol) in DMF (20 ml) was stirred at 80° C. for 16 hr. The reaction mixture was diluted with water (50 ml) and extracted with ethyl acetate (3×100 ml). The combined organic layers was washed with water (3×50 ml), dried over $Na_2SO_4$ and concentrated under reduced pressure. The resulting crude material was purified by column chromatography to give VV.2 as a brown liquid (1.4 g, 63%): $^1$H-NMR (CDCl3, 200 MHz): δ 8.61 (s, 1H), 8.58 (s, 1H); 8.11 (s, 1H), 3.23 (s, 3H), 3.13 (s, 3H); m/z: 263 [M+1]$^+$.

Synthesis of VV.3

A solution of VV.2 (1.3 g, 0.0049 mol), sodium dithionite (3.4 g, 0.0198 mol), sodium carbonate (1 g, 0.0099 mol) in MeOH (13 ml) and water (13 ml) was stirred at RT for 2 hr. The volatiles were removed under reduced pressure and extracted with ethyl acetate (3×100 ml). The combined organic layers was dried over $Na_2SO_4$ and concentrated under reduced pressure to obtain VV.3 as a light yellow solid (600 mg, 54.5%). $^1$H-NMR (CDCl$_3$, 200 MHz) δ 7.0 (s, 1H), 6.90 (s, 1H), 6.80 (s, 1H), 3.23 (s, 3H), 3.13 (s, 3H); m/z: 233 [M+1]$^+$.

Synthesis of VV.4

Compound VV.4 was synthesized as described in Scheme D for compound D.4. m/z: 521 [M+1]$^+$.

Synthesis of VV.

Compound VV was synthesized as described in Scheme D for compound D. $^1$H-NMR (CD$_3$OD, 200 MHz): δ 8.58 (s, 1H), 8.21 (s, 1H), 8.0 (s, 1H), 7.56 (s, 1H), 5.40-5.38 (m, 1H), 3.23 (s, 3H), 3.13 (s, 3H), 1.80 (d, J=7.0 Hz, 2H); m/z: 387 [M+1]$^+$.

Compounds WW-YY.

Using the appropriate amine, the following amines could be synthesized as exemplified in Scheme VV.

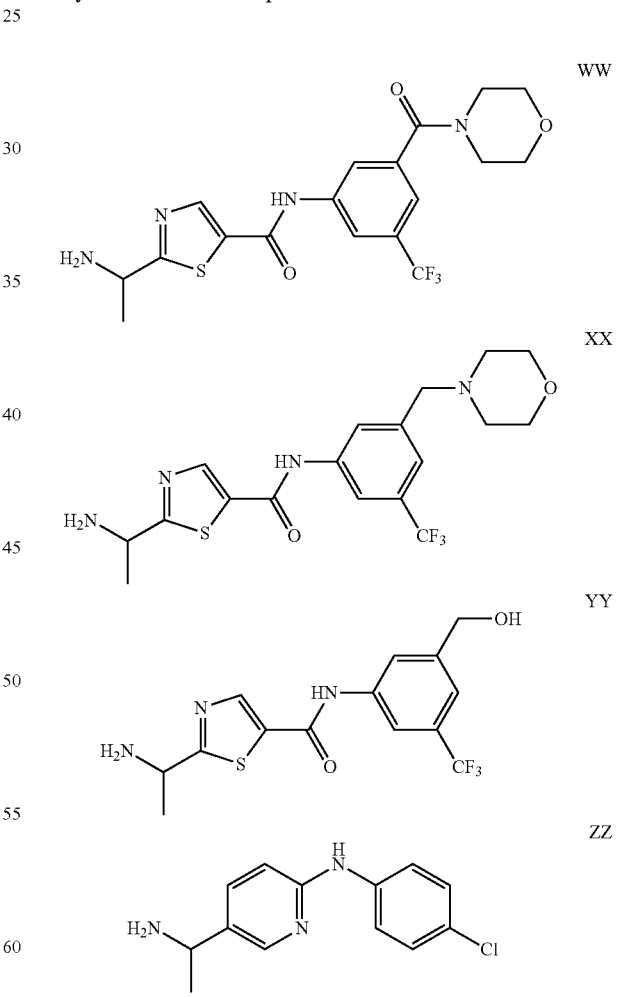

Synthesis of Compound ZZ.

The synthesis of compound ZZ was accomplished following Scheme X substituting 4-chloroaniline for 4-trifluoromethylaniline. MS m/z 248.1 [M+1]$^+$.

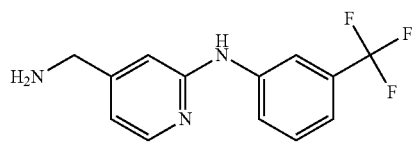 [SMILES: NCc1ccnc(Nc2cccc(C(F)(F)F)c2)c1]

AAA

Synthesis of Compound AAA.

The synthesis of compound AAA was accomplished following Scheme DD substituting 2-chloroisonicotinamide for compound DD.1 and 3-trifluoromethylaniline for 4-t-butylaniline. MS m/z 268 [M+1]$^+$.

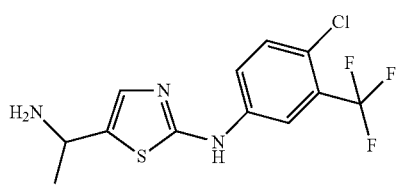 [SMILES: CC(N)c1cnc(Nc2ccc(Cl)c(C(F)(F)F)c2)s1]

Synthesis of Compound BBB.

The synthesis of compound BBB was accomplished following Scheme U substituting 4-chloro-3-(trifluoromethyl)aniline for 4-trifluoromethylaniline. MS m/z 322 [M+1]$^+$.

In certain embodiments, the compound of formula —NH$_2$-L$^1$-Cy$^1$-L$^2$-Cy$^2$ for use in preparing compounds of the present invention is selected from those set forth in Table 2, below.

TABLE 2

Exemplary —NH$_2$—L$^1$—Cy$^1$—L$^2$—Cy$^2$ Moieties (Structures labeled A, B, C, D, Da, Db, E, Ea, Eb, F, G, H, I, J, K)

TABLE 2-continued
Exemplary —NH$_2$—L$^1$—Cy$^1$—L$^2$—Cy$^2$ Moieties
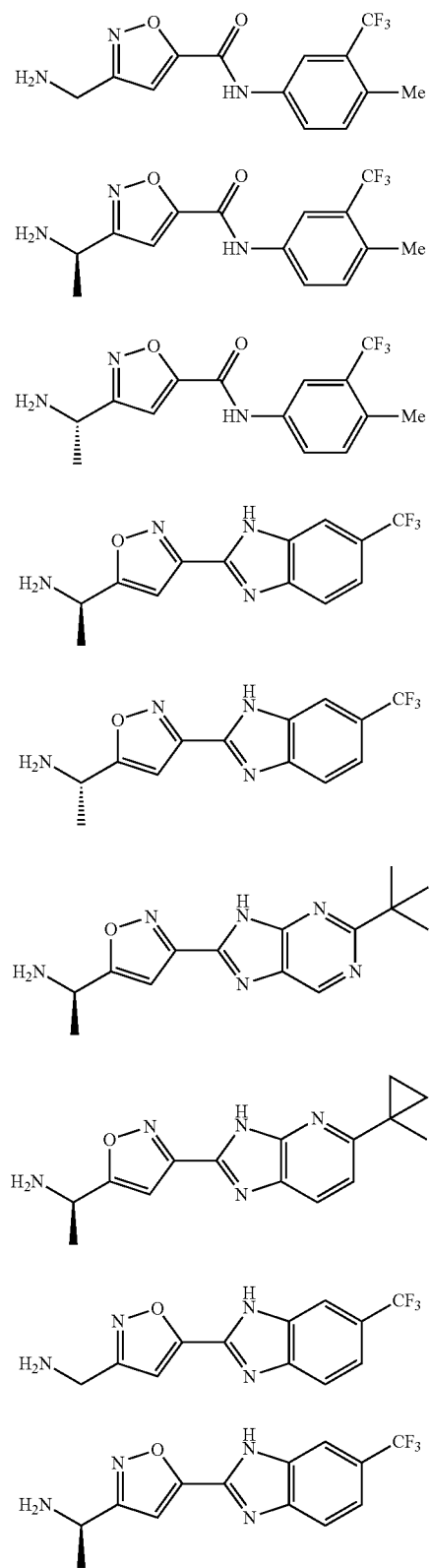
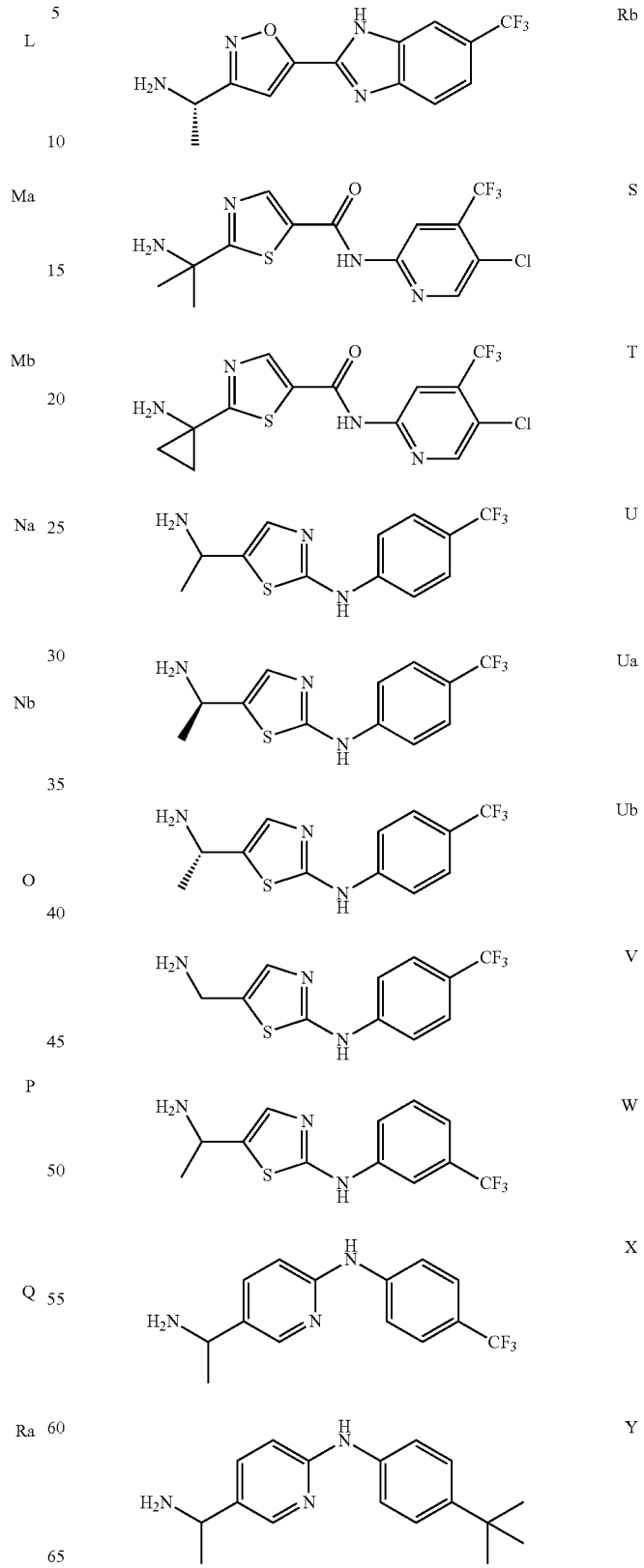

TABLE 2-continued
Exemplary —NH$_2$—L$^1$—Cy$^1$—L$^2$—Cy$^2$ Moieties
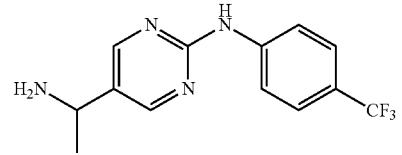 Z
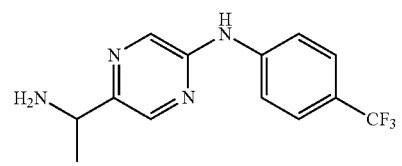 AA
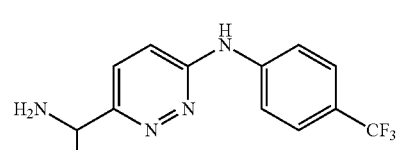 BB
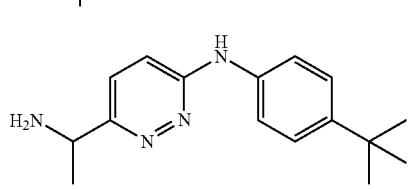 CC
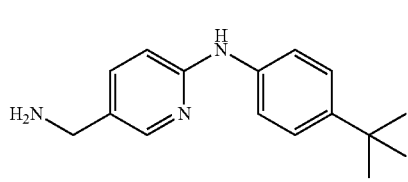 DD
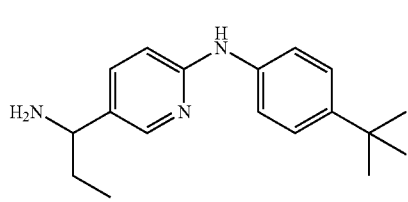 EE
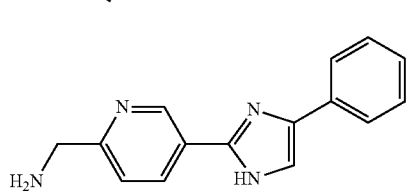 FF
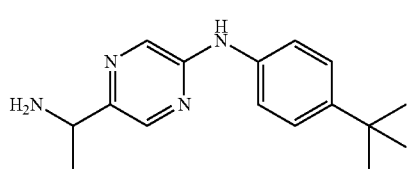 GG
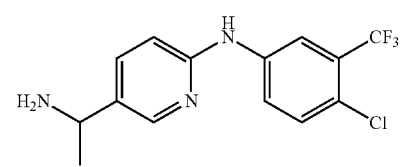 HH
TABLE 2-continued
Exemplary —NH$_2$—L$^1$—Cy$^1$—L$^2$—Cy$^2$ Moieties
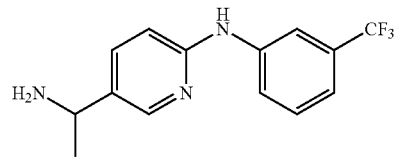 II
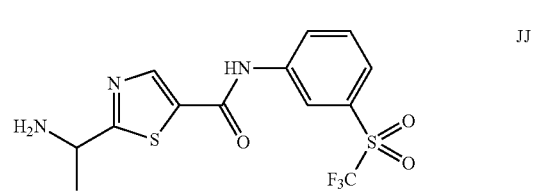 JJ
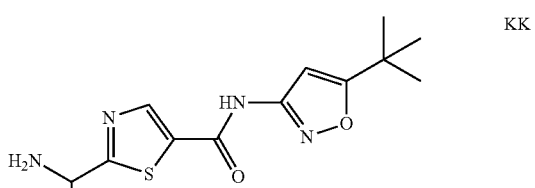 KK
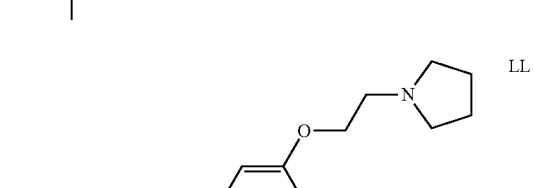 LL
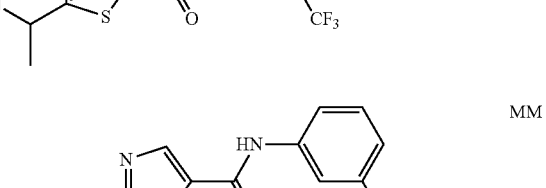 MM
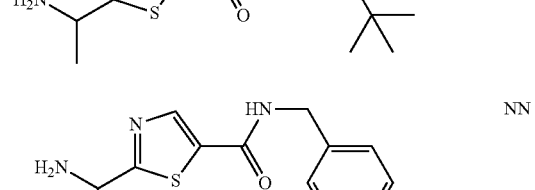 NN
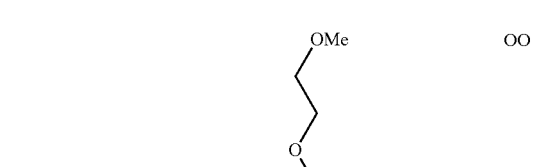 OO
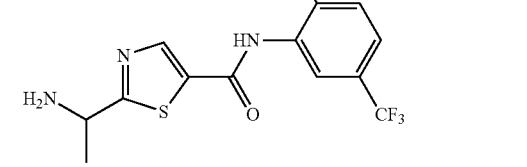

TABLE 2-continued
Exemplary —NH$_2$—L$^1$—Cy$^1$—L$^2$—Cy$^2$ Moieties
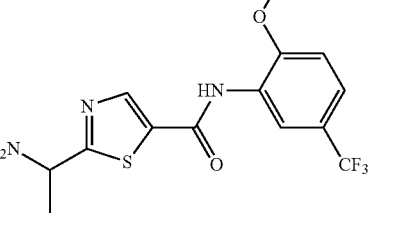

General Coupling of the Pyrimidine ("Left-Side") and -L¹-Cy¹-L²-Cy² Moieties Scheme ZZ.

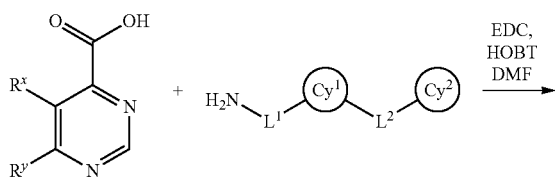

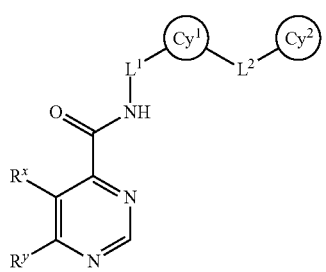

To a solution of the acid (1.3-1.6 equiv), the amine (1 equiv), and HOBT (0.3 equiv) in DMF (50 equiv) was added N-(3-dimethylaminopropyl)-N'-ethylcarbodiimide hydrochloride (1.5 eq.) and diisopropylethylamine (1.0 equiv). If the amine was used as a salt at least one additional equivalent of diisopropylamine was added. The reaction mixture was stirred at RT for 3-16 hr, monitored by LCMS. After the reaction is completed, the solution was diluted with EtOAc, washed with water and brine. The solvent was removed from the organic phase, and the residue purified on flash column chromatography (EtOAc/Hexanes or MeOH/CH₂Cl₂ as eluents) or reverse phase preparative HPLC (mobile phase: acetonitrile/water, buffered with 0.1% TFA or 0.1% formic acid) to give the desired product. In the case of a chiral final product, the chiral purity was monitored by chiral HPLC using Chiralcel OC or OJ-H column (mobile phase: ethanol/hexane buffered with 0.1% diethylamine).

In an alternative method, a clean dry flask was charged with the acid (1.05 equiv), the amine (1.00 equiv), and HOBT (0.20 equiv) under a nitrogen atmosphere. To the flask was then added DMF (22.65 equiv) and the mixture was stirred at 25° C. until all solids dissolved, or 30 minutes. To the solution/slurry was then added 1-ethyl-3-(3-dimethylaminopropyl)carbodiimide hydrochloride (EDC) (1.05-1.15 equiv) as a solid in portions to keep the internal temperature of the flask below 35° C. The reaction mixture was stirred at 25° C. for 2-3 hr, and monitored by LCMS. After the reaction is completed, the solution was diluted with 1-butanol (9.59 equiv) and the contents of the flask were heated to 60° C. To the hot solution was then added water (486.7 eq) dropwise to initiate crystallization. The solids were then collected by filtration and washed 3 times with water. The wet cake was then charged back to a clean dry flask under nitrogen. To the solids was added water (194 to 292 equiv) with stirring. The solids were slurried for 3 hr, and then collected by filtration. The wet cake was washed with water 3 times, and dried at 50° C. under vacuum to constant weight. (In the case of a chiral final product, the chiral purity was monitored by chiral HPLC using Chiralcel OC, OC—H or OJ-H column (mobile phase: ethanol/hexane buffered with 0.1% diethylamine).

In some instances, an additional chemical transformation(s) was performed after amide formation. In those instances the following procedures were utilized.

General THP Deprotection Conditions.

To a 0° C. solution of the THP protected alcohol in MeOH was added catalytic p-toluenesolfonic acid and the reaction mixture was stirred for 1 hr. Solid NaHCO₃ was added and MeOH was removed under reduced pressure. The reaction mixture was diluted with water and extracted with CH₂Cl₂. The combined organic layers were dried over Na₂SO₄, concentrated under reduced pressure to provide the desired alcohol.

General Azole Cyclization Conditions.

Procedure used in the preparation of benzimidazoles and similar derivatives. A solution of the amino amide (0.1 mmol) and acetic acid (2 mL, 40.0 mmol) was heated in the microwave for 30 minutes at 170° C. The solvent was removed and the solid was triturated with MeOH to afford the desired azole which could be purified by crystallization or column chromatography.

The following compounds of the present invention, set forth in Table 3, below, were prepared by general coupling Scheme ZZ described above.

TABLE 3

Exemplary Compounds of Formula I

| # | Structure | Characterization Data |
|---|-----------|----------------------|
| 1aD | (structure shown) | m/z 550 [M + 1]⁺; ¹H NMR (200 MHz, DMSO-d₆): δ 11.78 (bs, N—H), 9.53 (s, 1H), 9.49 (s, 1H), 8.77 (s, 1H), 8.74 (s, 1H) 8.56 (s, 1H), 8.43 (s, 1H), 7.63 (bs, 1H), 5.33 (q, J = 7.6 Hz, 1H), 3.50-3.41 (m, 4H), 1.57 (d, J = 6.8 Hz, 3H). |

TABLE 3-continued

Exemplary Compounds of Formula I

| # | Structure | Characterization Data |
|---|---|---|
| 1bD | 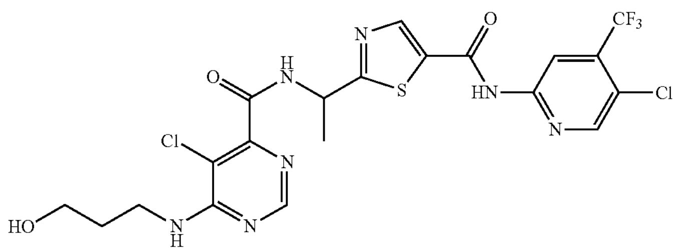 [SMILES: CC(NC(=O)c1ncnc(NCCCO)c1Cl)c1ncc(C(=O)Nc2cc(C(F)(F)F)c(Cl)cn2)s1] | m/z 564 [M + 1]+ |
| 1cD | 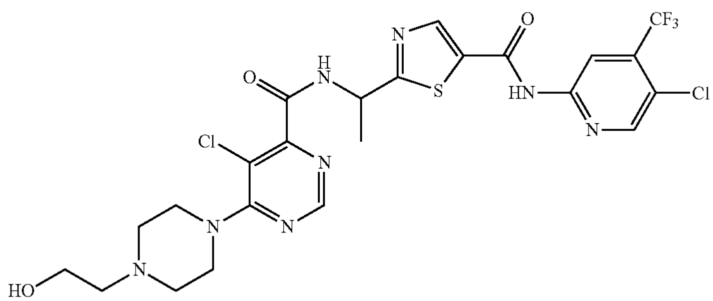 [SMILES: CC(NC(=O)c1ncnc(N2CCN(CCO)CC2)c1Cl)c1ncc(C(=O)Nc2cc(C(F)(F)F)c(Cl)cn2)s1] | m/z 619 [M + 1]+ |
| 1dD | 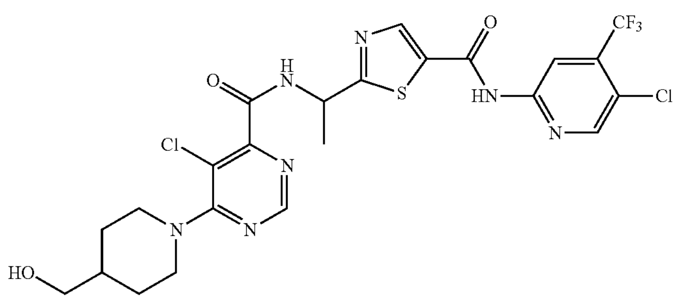 [SMILES: CC(NC(=O)c1ncnc(N2CCC(CO)CC2)c1Cl)c1ncc(C(=O)Nc2cc(C(F)(F)F)c(Cl)cn2)s1] | m/z 604 [M + 1]+ |
| 1eB | 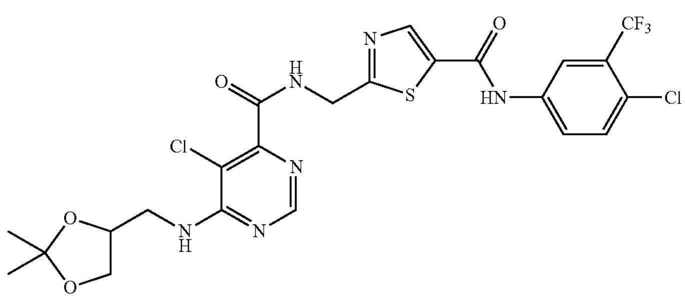 | m/z 620 [M + 1]+ |
| 1fB | 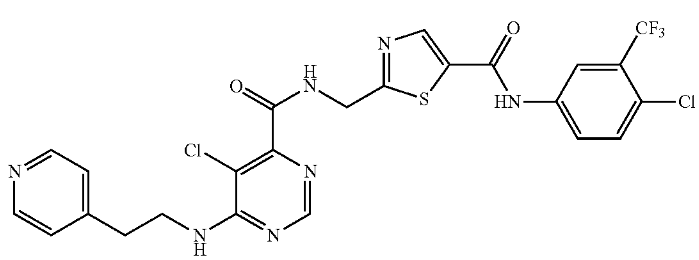 [SMILES: O=C(Nc1ccc(Cl)c(C(F)(F)F)c1)c1cnc(CNC(=O)c2ncnc(NCCc3ccncc3)c2Cl)s1] | m/z 596 [M + 1]+ |

TABLE 3-continued

Exemplary Compounds of Formula I

| # | Structure | Characterization Data |
|---|---|---|
| 1gB | 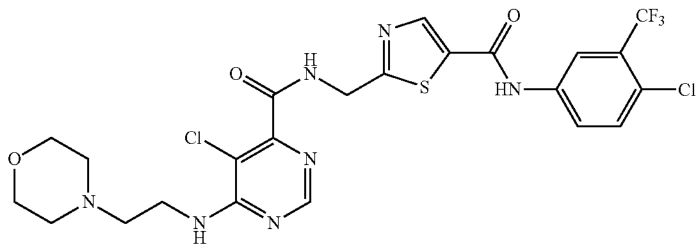 [SMILES: O=C(Nc1ccc(Cl)c(C(F)(F)F)c1)c1cnc(CNC(=O)c2ncnc(NCCN3CCOCC3)c2Cl)s1] | m/z 604 [M + 1]⁺; ¹H NMR (400 MHz, methanol-d4): δ 8.53 (s, 1H), 8.45 (s, 1H), 8.22 (d, J = 2.6 Hz, 1H), 7.95 (dd, J = 9.0, 2.6 Hz, 1H), 7.60 (d, J = 9.0 Hz, 1H), 4.08 (brs, 2H), 4.00-3.96 (m, 2H), 3.82-3.67 (m, 6H), 3.51-3.47 (m, 2H), 3.28-3.20 (m, 2H). |
| 1hB | 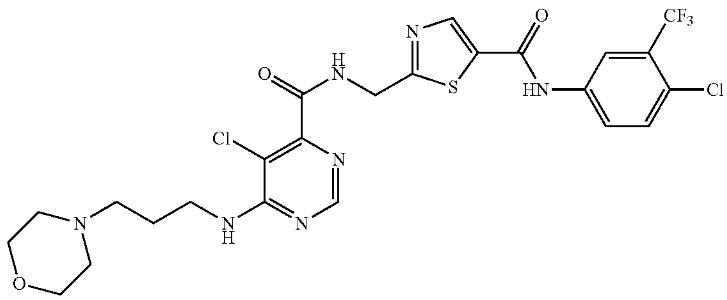 [SMILES: O=C(Nc1ccc(Cl)c(C(F)(F)F)c1)c1cnc(CNC(=O)c2ncnc(NCCCN3CCOCC3)c2Cl)s1] | m/z 618 [M + 1]⁺ |
| 1iD | 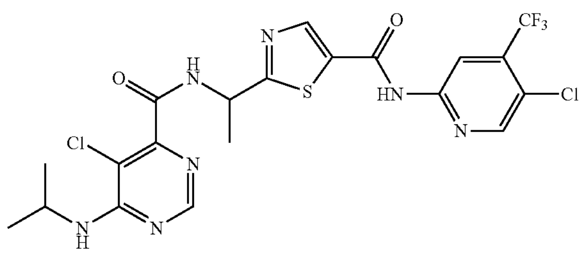 | m/z 548 [M + 1]⁺ |
| 1jD | 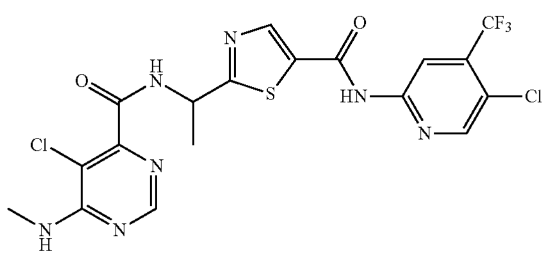 [SMILES: CNc1ncnc(C(=O)NC(C)c2ncc(C(=O)Nc3cc(C(F)(F)F)c(Cl)cn3)s2)c1Cl] | m/z 520 [M + 1]⁺ |
| 1jDa | 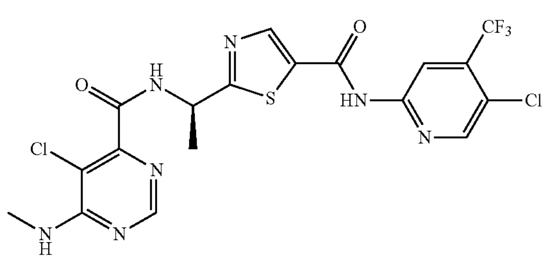 [SMILES: CNc1ncnc(C(=O)N[C@H](C)c2ncc(C(=O)Nc3cc(C(F)(F)F)c(Cl)cn3)s2)c1Cl] | m/z 520 [M⁺ + 1]; ¹HNMR: (DMSO-d₆, 400 MHz) δ: 11.8 (s, 1H, NH), 9.5 (d, J = 7.9 Hz, 1H), 8.79 (s, 1H), 8.77 (s, 1H), 8.59 (s, 1H), 8.48 (s, 1H), 7.79-7.75 (m, 1H), 5.40-5.32 (m, 1H), 2.94 (d, J = 4.9 Hz, 3H), 1.61 (d, J = 6.9 Hz, 3H). |
| 1kD | 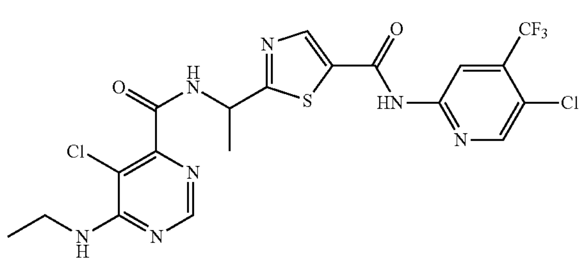 [SMILES: CCNc1ncnc(C(=O)NC(C)c2ncc(C(=O)Nc3cc(C(F)(F)F)c(Cl)cn3)s2)c1Cl] | m/z 534 [M + 1]⁺ |

TABLE 3-continued

Exemplary Compounds of Formula I

| # | Structure | Characterization Data |
|---|-----------|----------------------|
| 1lB | 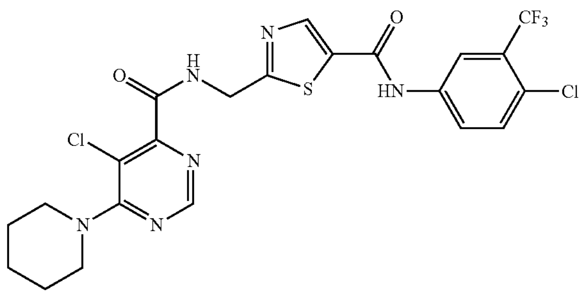 [SMILES: O=C(Nc1ccc(Cl)c(C(F)(F)F)c1)c1cnc(CNC(=O)c2ncnc(N3CCCCC3)c2Cl)s1] | m/z 559 [M + 1]+ |
| 1mB | 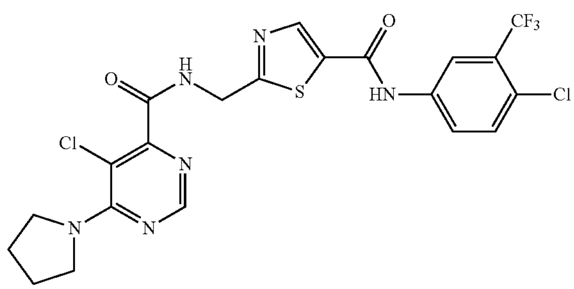 [SMILES: O=C(Nc1ccc(Cl)c(C(F)(F)F)c1)c1cnc(CNC(=O)c2ncnc(N3CCCC3)c2Cl)s1] | m/z 545 [M + 1]+ |
| 1nB | 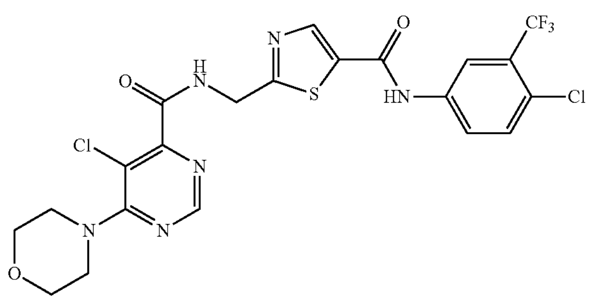 [SMILES: O=C(Nc1ccc(Cl)c(C(F)(F)F)c1)c1cnc(CNC(=O)c2ncnc(N3CCOCC3)c2Cl)s1] | m/z 561 [M + 1]+ |
| 1oD | 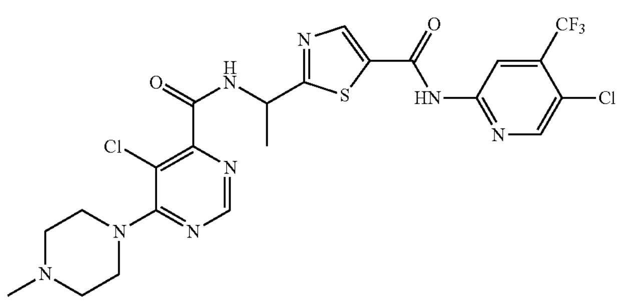 [SMILES: CC(NC(=O)c1ncnc(N2CCN(C)CC2)c1Cl)c1ncc(C(=O)Nc2cc(C(F)(F)F)c(Cl)cn2)s1] | m/z 589 [M + 1]+ |
| 1pD | 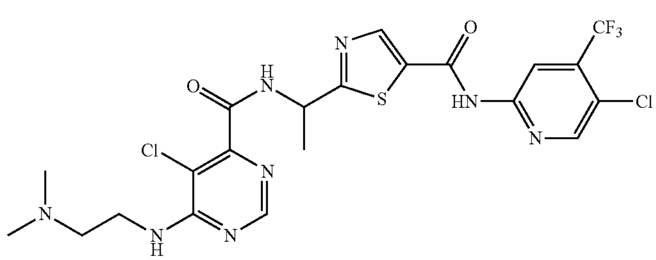 [SMILES: CC(NC(=O)c1ncnc(NCCN(C)C)c1Cl)c1ncc(C(=O)Nc2cc(C(F)(F)F)c(Cl)cn2)s1] | m/z 577 [M + 1]+ |

TABLE 3-continued

Exemplary Compounds of Formula I

| # | Structure | Characterization Data |
|---|-----------|----------------------|
| 1qD | 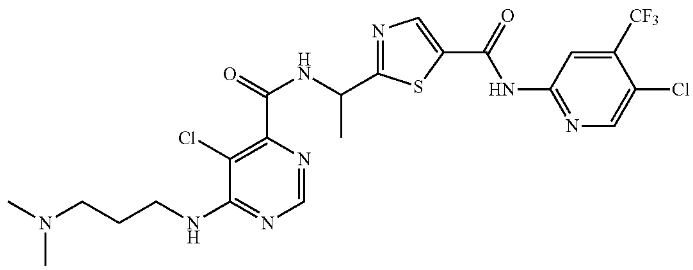 | m/z 591 [M + 1]+ |
| 1rB | 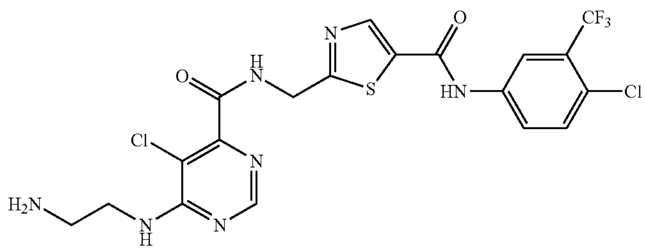 [SMILES: NCCNc1ncnc(C(=O)NCc2ncc(C(=O)Nc3ccc(Cl)c(C(F)(F)F)c3)s2)c1Cl] | m/z 534 [M + 1]+ |
| 1rD | 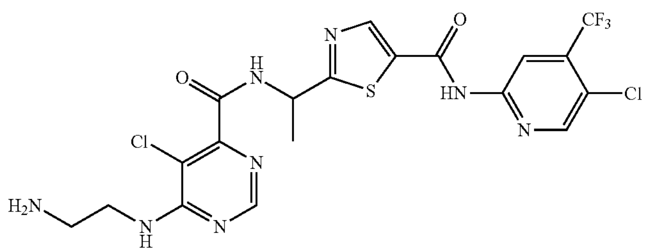 [SMILES: CC(NC(=O)c1ncnc(NCCN)c1Cl)c1ncc(C(=O)Nc2cc(C(F)(F)F)c(Cl)cn2)s1] | m/z 549 [M + 1]+ |
| 1rNa | 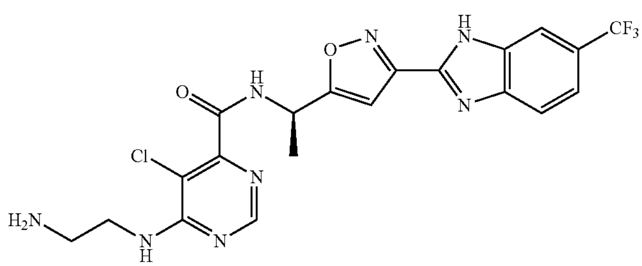 | m/z 595 [M + 1]+ |
| 2aD | 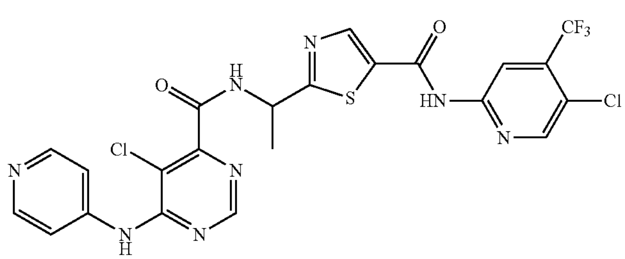 | m/z 583 [M + 1]+; $^1$H NMR δ 9.66 (d, NH), 8.77 (s, 1H), 8.76 (d, J = 9.0 Hz, 2H), 8.57 (s, 1H), 8.48 (s, 1H), 8.47 (s, 1H), 7.83 (s, 1H), 7.82 (s, 1H), 5.39 (q, J = 7.5 Hz, 1H), 1.60 (d, J = 7.0 Hz, 3H) |
| 2bD | 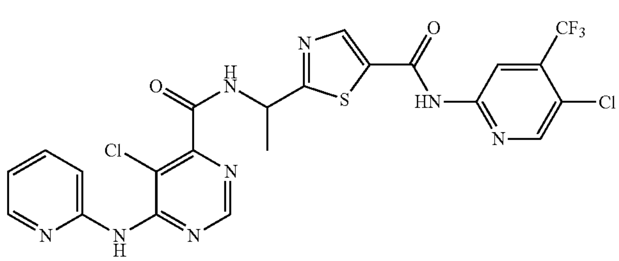 [SMILES: CC(NC(=O)c1ncnc(Nc2ccccn2)c1Cl)c1ncc(C(=O)Nc2cc(C(F)(F)F)c(Cl)cn2)s1] | m/z 583 [M + 1]+ |

TABLE 3-continued

Exemplary Compounds of Formula I

| # | Structure | Characterization Data |
|---|-----------|----------------------|
| 2cD | 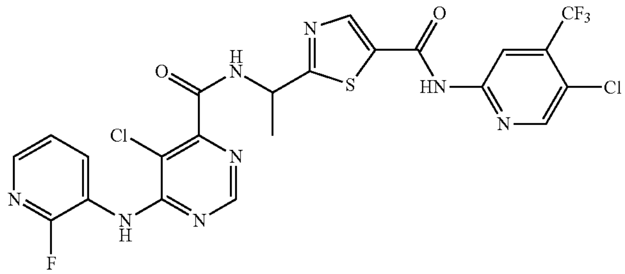 [SMILES: CC(NC(=O)c1ncnc(Nc2cccnc2F)c1Cl)c1ncc(C(=O)Nc2cc(C(F)(F)F)c(Cl)cn2)s1] | m/z 601 [M + 1]+ |
| 2dD | 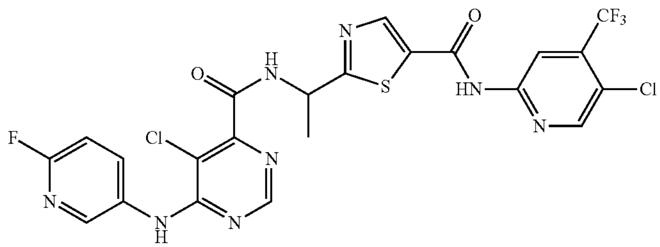 [SMILES: CC(NC(=O)c1ncnc(Nc2ccc(F)nc2)c1Cl)c1ncc(C(=O)Nc2cc(C(F)(F)F)c(Cl)cn2)s1] | m/z 601 [M + 1]+ |
| 2eD | 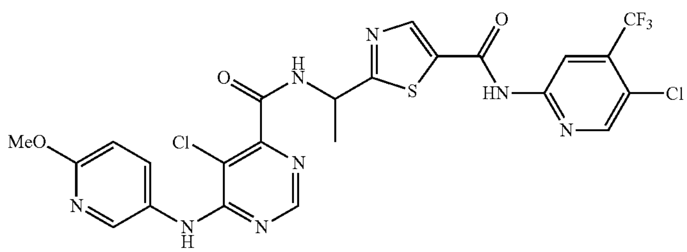 [SMILES: COc1ccc(Nc2ncnc(C(=O)NC(C)c3ncc(C(=O)Nc4cc(C(F)(F)F)c(Cl)cn4)s3)c2Cl)cn1] | m/z 613 [M + 1]+ |
| 2fD | 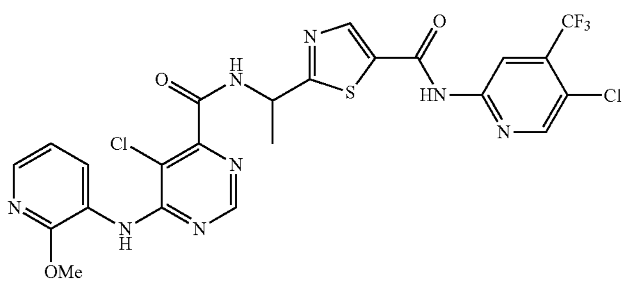 [SMILES: COc1ncccc1Nc1ncnc(C(=O)NC(C)c2ncc(C(=O)Nc3cc(C(F)(F)F)c(Cl)cn3)s2)c1Cl] | m/z 613 [M + 1]+ |
| 3aD | 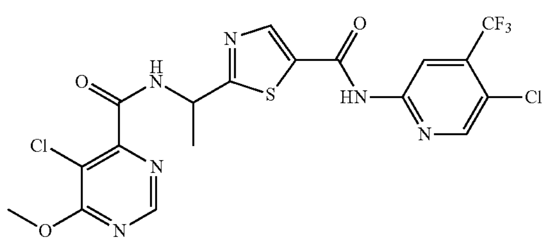 | m/z 521 [M + 1]+; $^1$H NMR δ 8.72 (s, 1H), 8.64 (s, 1H), 8.59 (s, 1H), 8.54 (s, 1H), 5.50 (q, J = 7.0 Hz, 1H) 4.15 (s, 3H), 1.70 (d, J = 7.0 Hz, 2H). |
| 3bD | 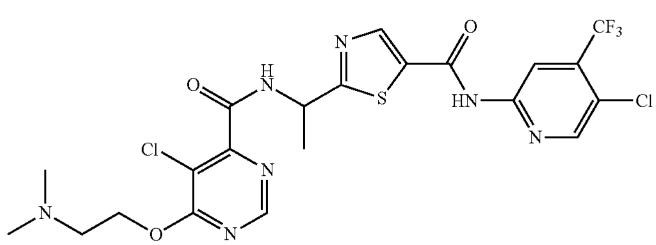 [SMILES: CC(NC(=O)c1ncnc(OCCN(C)C)c1Cl)c1ncc(C(=O)Nc2cc(C(F)(F)F)c(Cl)cn2)s1] | m/z 578 [M + 1]+ |

TABLE 3-continued

Exemplary Compounds of Formula I

| # | Structure | Characterization Data |
|---|-----------|----------------------|
| 3cD | 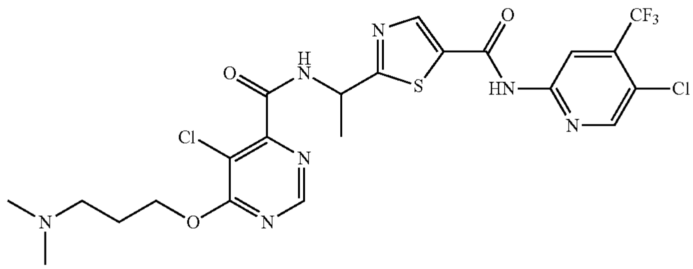 [SMILES: CC(NC(=O)c1ncnc(OCCCN(C)C)c1Cl)c1ncc(C(=O)Nc2cc(C(F)(F)F)c(Cl)cn2)s1] | m/z 592 [M + 1]+ |
| 4aD | 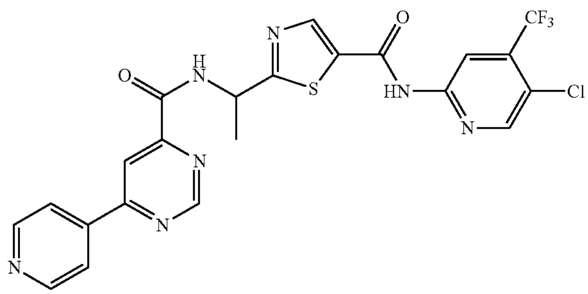 | m/z 534 [M + 1]+ |
| 4aDa | 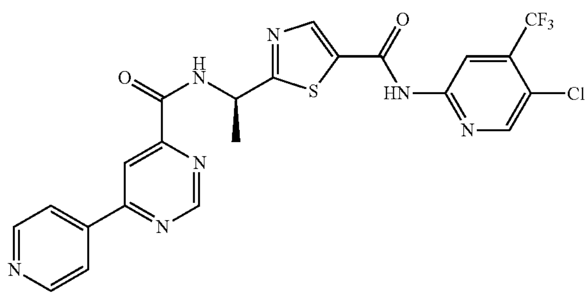 | m/z 534 [M + 1]+; ¹H NMR (400 MHz, methanol-d4): δ 9.37 (bs, 1H), 8.70 (d, J = 8 Hz, 2H), 8.61 (s, 1H), 8.51 (s, 1H), 8.47 (s, 1H), 8.43 (s, 1H), 8.21 (d, J = 8 Hz, 2H), 5.53 (q, J = 8 Hz, 1H), 1.71 (d, J = 8 Hz, 1H). |
| 4aNa | 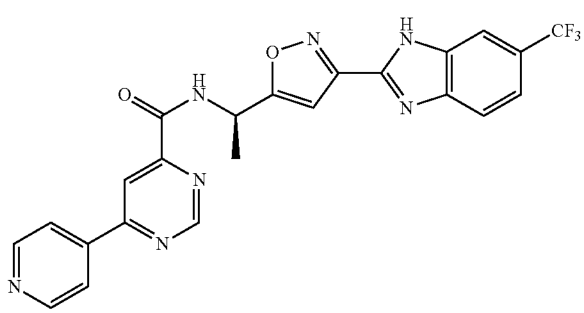 [SMILES: C[C@@H](NC(=O)c1cc(-c2ccncc2)ncn1)c1cc(-c2nc3ccc(C(F)(F)F)cc3[nH]2)no1] | m/z 480 [M + 1]+; ¹H NMR (400 MHz, Methanol-d4): δ 9.52 (s, 1H), 8.94 (brs, 2H), 8.72 (s, 1H), 8.62 (brs, 2H), 7.98 (s, 1H), 7.82 (d, J = 8.5 Hz, 1H), 7.62 (dd, J = 8.5, 1.5 Hz, 1H), 7.02 (s, 1H), 5.65 (q, J = 7.0 Hz, 1H), 1.82 (d, J = 7.0 Hz, 3H). |
| 4bD | 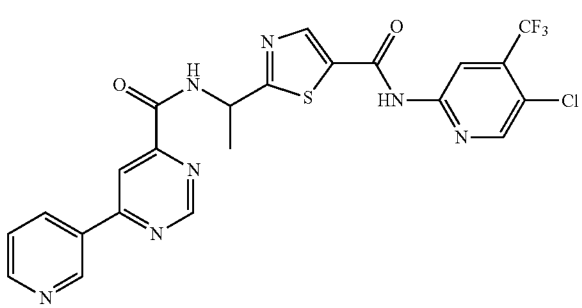 [SMILES: CC(NC(=O)c1cc(-c2cccnc2)ncn1)c1ncc(C(=O)Nc2cc(C(F)(F)F)c(Cl)cn2)s1] | m/z 534 [M + 1]+ |

TABLE 3-continued

Exemplary Compounds of Formula I

| # | Structure | Characterization Data |
|---|-----------|----------------------|
| 4bDa | 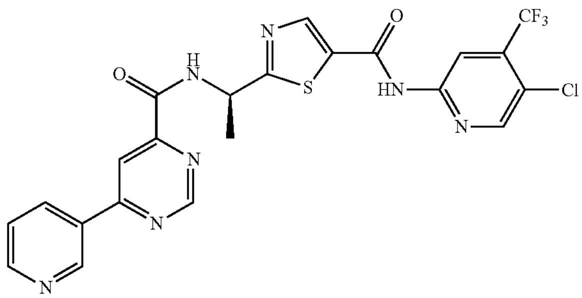 [SMILES: C[C@@H](NC(=O)c1cc(-c2cccnc2)ncn1)c1ncc(C(=O)Nc2cc(C(F)(F)F)c(Cl)cn2)s1] | m/z 534 [M + 1]+; 1H NMR (400 MHz, methanol-d4): δ 9.55 (s, 1H), 9.47 (s, 1H), 8.96 (d, J = 8.0 Hz, 1H), 8.86 (d, J = 8.0 Hz, 1H), 8.73 (s, 1H), 8.62 (s, 1H), 8.59 (s, 1H), 8.55 (s, 1H), 7.88 (m, 1H), 5.64 (q, J = 8.0 Hz, 1H), 1.83 (d, J = 8.0 Hz, 1H) |
| 4bO | 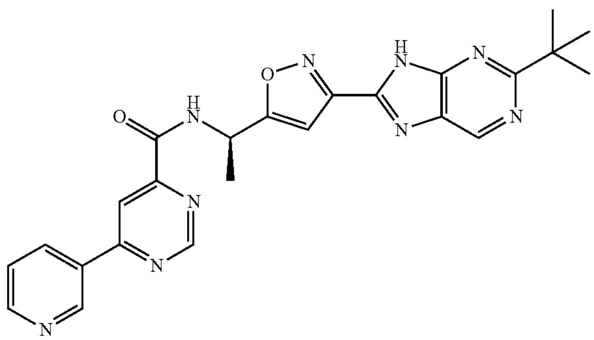 [SMILES: C[C@@H](NC(=O)c1cc(-c2cccnc2)ncn1)c1cc(-c2nc3cnc(C(C)(C)C)nc3[nH]2)no1] | m/z 470 [M + 1]+; 1H NMR (400 MHz, DMSO-d6): δ 9.80 (s, 1H), 9.49 (s, 1H), 9.48 (s, 1H), 9.16 (s, 1H), 8.84 (d, J = 4.0 Hz, 1H), 8.75 (dd, J = 8.0, 1.5 Hz, 1H), 8.66 (s, 1H), 7.70 (dd, J = 8.0, 4.0 Hz, 1H), 7.08 (s, 1H), 5.65 (q, J = 7.0 Hz, 1H), 1.82 (d, J = 7.0 Hz, 3H), 1.42 (s, 9H) |
| 4eD | 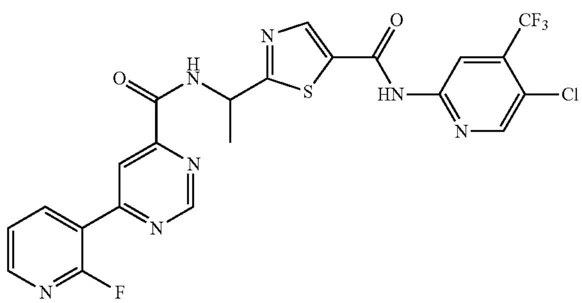 [SMILES: CC(NC(=O)c1cc(-c2cccnc2F)ncn1)c1ncc(C(=O)Nc2cc(C(F)(F)F)c(Cl)cn2)s1] | m/z 552 [M + 1]+ |
| 4eDa | 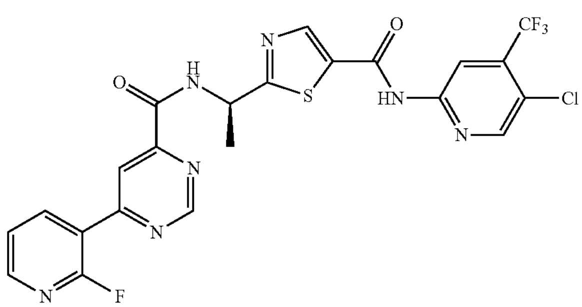 [SMILES: C[C@@H](NC(=O)c1cc(-c2cccnc2F)ncn1)c1ncc(C(=O)Nc2cc(C(F)(F)F)c(Cl)cn2)s1] | m/z 551 [M + 1]+; 1H NMR (400 MHz, CDCl3-d4): δ 9.43 (s, 1H), 8.74 (m, 2H), 8.71 (s, 1H), 8.67 (s, 1H), 8.41 (s, 1H), 8.34 (s, 1H), 7.44 (m, 1H), 5.67 (m, 1H), 1.84 (d, J = 8.0 Hz, 1H) |
| 4dD | 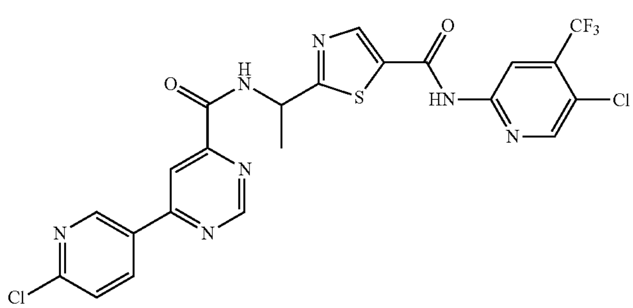 [SMILES: CC(NC(=O)c1cc(-c2ccc(Cl)nc2)ncn1)c1ncc(C(=O)Nc2cc(C(F)(F)F)c(Cl)cn2)s1] | m/z 568 [M + 1]+ |

TABLE 3-continued

Exemplary Compounds of Formula I

| # | Structure | Characterization Data |
|---|-----------|----------------------|
| 4cD | 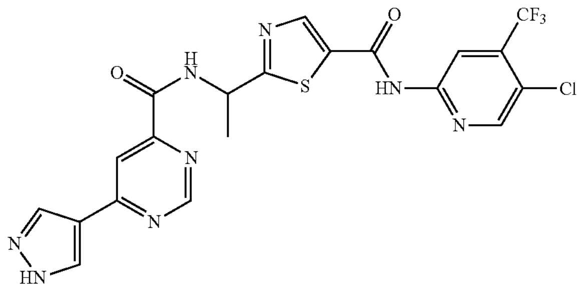 [SMILES: CC(NC(=O)c1cc(-c2cn[nH]c2)ncn1)c1ncc(C(=O)Nc2cc(C(F)(F)F)c(Cl)cn2)s1] | m/z 523 [M + 1]+ |
| 4fD | 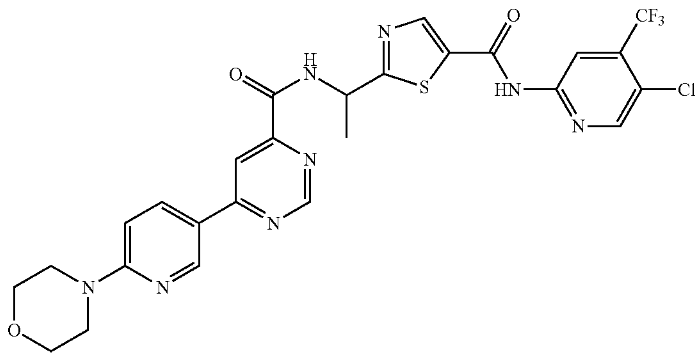 [SMILES: CC(NC(=O)c1cc(-c2ccc(N3CCOCC3)nc2)ncn1)c1ncc(C(=O)Nc2cc(C(F)(F)F)c(Cl)cn2)s1] | m/z 619 [M + 1]+ |
| 4gD | 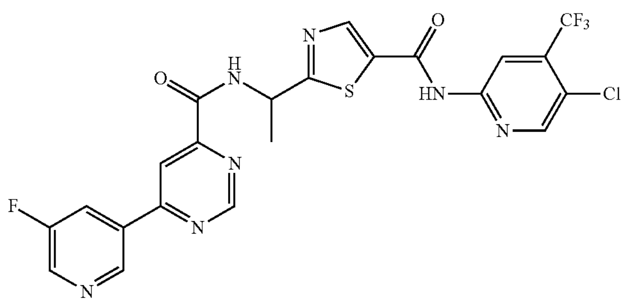 [SMILES: CC(NC(=O)c1cc(-c2cncc(F)c2)ncn1)c1ncc(C(=O)Nc2cc(C(F)(F)F)c(Cl)cn2)s1] | m/z 551 [M + 1]+ |
| 4hD | 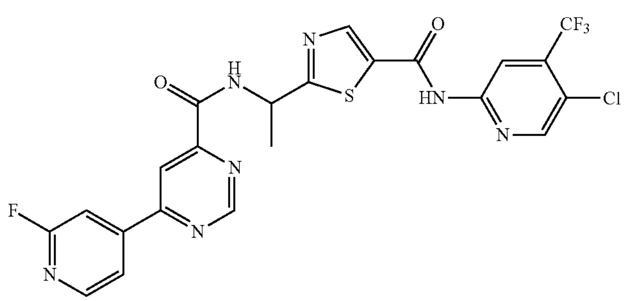 [SMILES: CC(NC(=O)c1cc(-c2ccnc(F)c2)ncn1)c1ncc(C(=O)Nc2cc(C(F)(F)F)c(Cl)cn2)s1] | m/z 552 [M + 1]+ |
| 4iD | 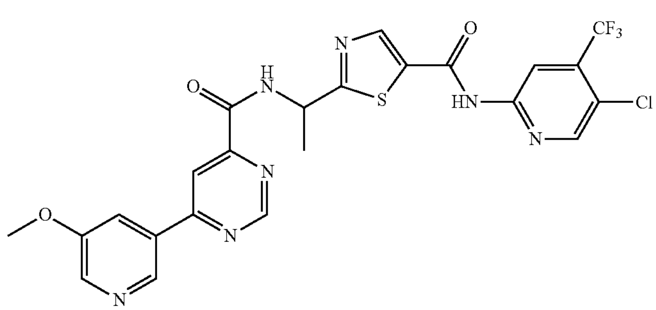 [SMILES: COc1cncc(-c2cc(C(=O)NC(C)c3ncc(C(=O)Nc4cc(C(F)(F)F)c(Cl)cn4)s3)ncn2)c1] | m/z 564 [M + 1]+ |

TABLE 3-continued

Exemplary Compounds of Formula I

| # | Structure | Characterization Data |
|---|-----------|----------------------|
| 4jD | 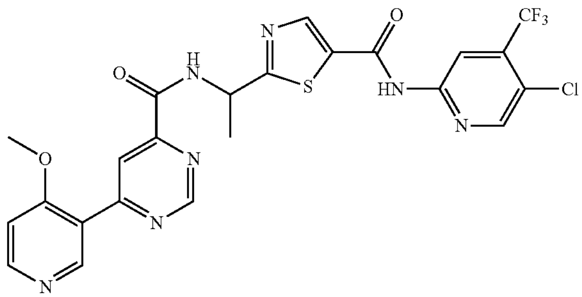 [SMILES: COc1ccncc1-c1cc(C(=O)NC(C)c2ncc(C(=O)Nc3cc(C(F)(F)F)c(Cl)cn3)s2)ncn1] | m/z 564 [M + 1]+ |
| 4kD | 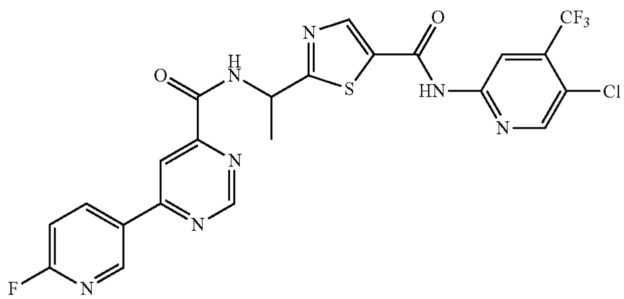 [SMILES: CC(NC(=O)c1cc(-c2ccc(F)nc2)ncn1)c1ncc(C(=O)Nc2cc(C(F)(F)F)c(Cl)cn2)s1] | m/z 552 [M + 1]+ |
| 4lD | 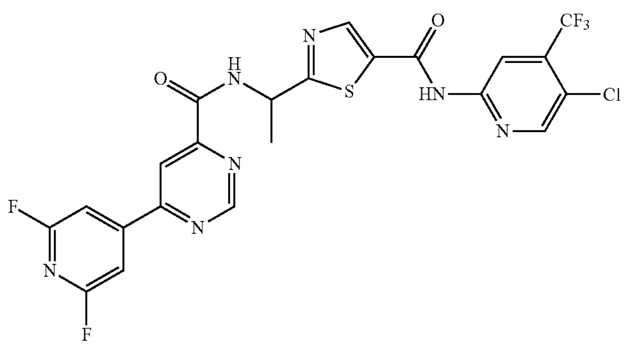 [SMILES: CC(NC(=O)c1cc(-c2cc(F)nc(F)c2)ncn1)c1ncc(C(=O)Nc2cc(C(F)(F)F)c(Cl)cn2)s1] | m/z 570 [M + 1]+ |
| 4mD | 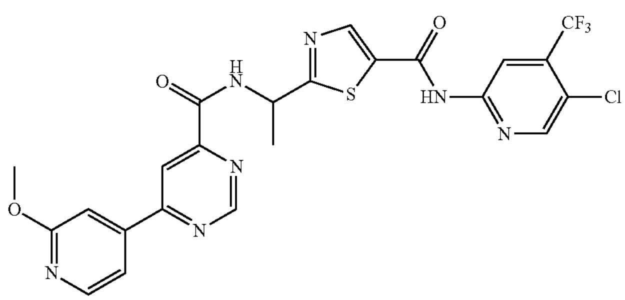 [SMILES: COc1cc(-c2cc(C(=O)NC(C)c3ncc(C(=O)Nc4cc(C(F)(F)F)c(Cl)cn4)s3)ncn2)ccn1] | m/z 564 [M + 1]+ |
| 4nD | 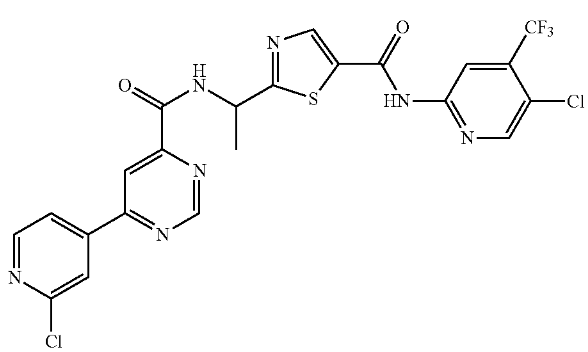 [SMILES: CC(NC(=O)c1cc(-c2ccnc(Cl)c2)ncn1)c1ncc(C(=O)Nc2cc(C(F)(F)F)c(Cl)cn2)s1] | m/z 569 [M + 1]+ |

TABLE 3-continued

Exemplary Compounds of Formula I

| # | Structure | Characterization Data |
|---|-----------|----------------------|
| 4oD | 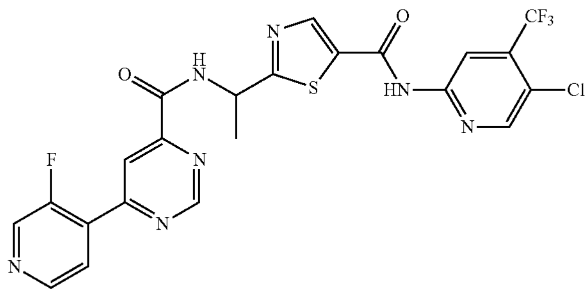 [SMILES: CC(NC(=O)c1cc(-c2ccncc2F)ncn1)c1ncc(C(=O)Nc2cc(C(F)(F)F)c(Cl)cn2)s1] | m/z 552 [M + 1]+ |
| 4pD | 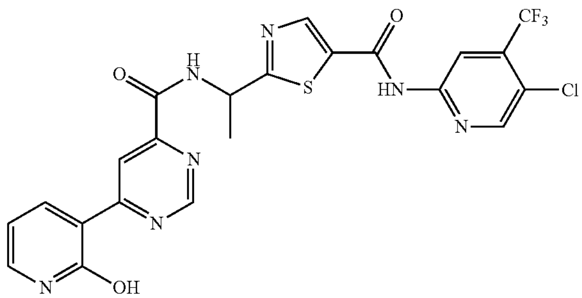 [SMILES: CC(NC(=O)c1cc(-c2cccnc2O)ncn1)c1ncc(C(=O)Nc2cc(C(F)(F)F)c(Cl)cn2)s1] | m/z 550 [M + 1]+ |
| 4qD | 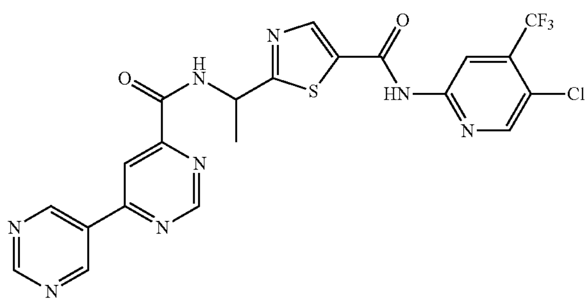 [SMILES: CC(NC(=O)c1cc(-c2cncnc2)ncn1)c1ncc(C(=O)Nc2cc(C(F)(F)F)c(Cl)cn2)s1] | m/z 535 [M + 1]+ |
| 4qDa | 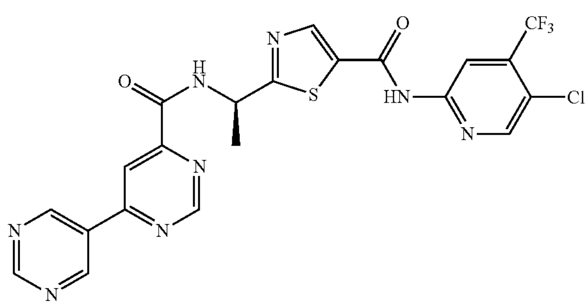 [SMILES: C[C@@H](NC(=O)c1cc(-c2cncnc2)ncn1)c1ncc(C(=O)Nc2cc(C(F)(F)F)c(Cl)cn2)s1] | m/z 535 [M + 1]+ |
| 4rD | 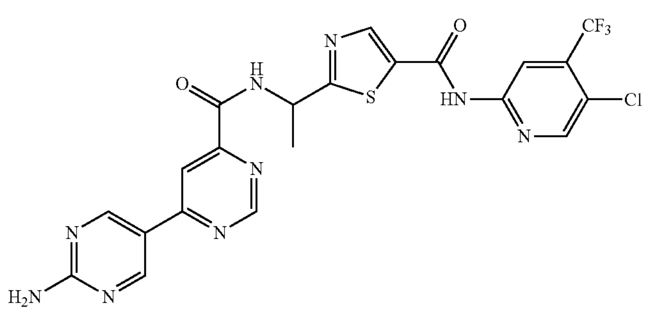 | m/z 550 [M + 1]+ |

TABLE 3-continued

Exemplary Compounds of Formula I

| # | Structure | Characterization Data |
|---|---|---|
| 4sD | 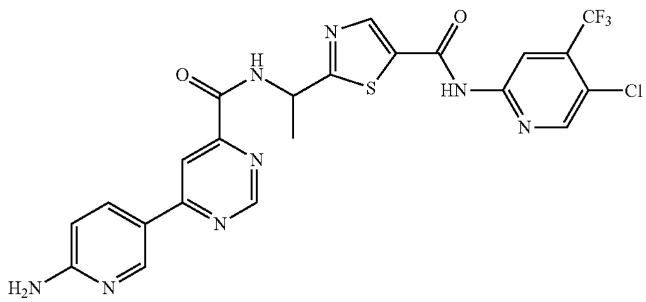 [SMILES: CC(NC(=O)c1cc(-c2ccc(N)nc2)ncn1)c1ncc(C(=O)Nc2cc(C(F)(F)F)c(Cl)cn2)s1] | m/z 549 [M + 1]+ |
| 4tD | 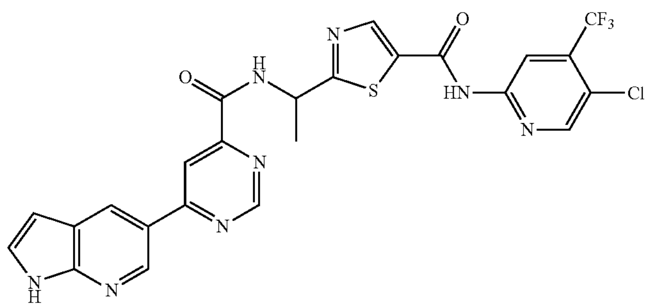 [SMILES: CC(NC(=O)c1cc(-c2cnc3[nH]ccc3c2)ncn1)c1ncc(C(=O)Nc2cc(C(F)(F)F)c(Cl)cn2)s1] | m/z 573 [M + 1]+ |
| 5aD | 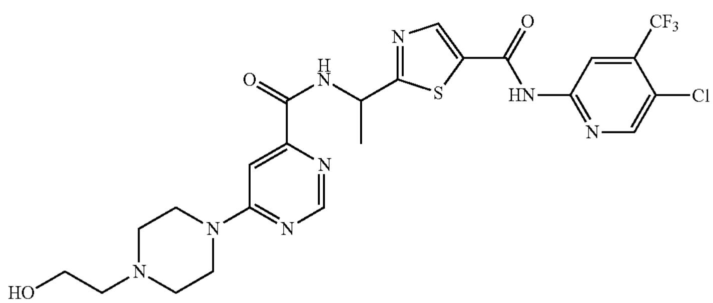 [SMILES: CC(NC(=O)c1cc(N2CCN(CCO)CC2)ncn1)c1ncc(C(=O)Nc2cc(C(F)(F)F)c(Cl)cn2)s1] | m/z 585 [M + 1]+; |
| 5aDa | 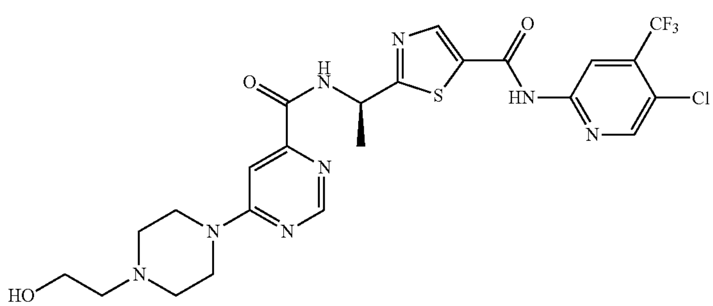 [SMILES: C[C@@H](NC(=O)c1cc(N2CCN(CCO)CC2)ncn1)c1ncc(C(=O)Nc2cc(C(F)(F)F)c(Cl)cn2)s1] | m/z 585 [M + 1]+; $^1$H NMR (400 MHz, Methanol-d$_4$): δ 8.62 (s, 1H), 8.58 (s, 1H), 8.58 (s, 1H), 8.51 (s, 1H), 7.39 (s, 1H), 5.53 (q, J = 7.4 Hz, 1H), 3.80 (brs, 4H), 3.72 (t, J = 6.0 Hz, 2H), 2.64 (t, J = 6.0 Hz, 4H), 2.60 (t, J = 6.0 Hz, 2H), 1.75 (d, J = 7.4 Hz, 3H). |
| 5bD | 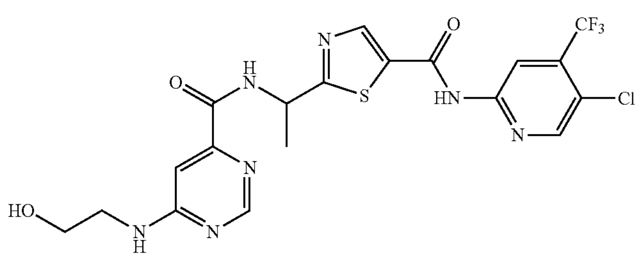 [SMILES: CC(NC(=O)c1cc(NCCO)ncn1)c1ncc(C(=O)Nc2cc(C(F)(F)F)c(Cl)cn2)s1] | m/z 516 [M + 1]+ |

TABLE 3-continued

Exemplary Compounds of Formula I

| # | Structure | Characterization Data |
|---|---|---|
| 5cD | 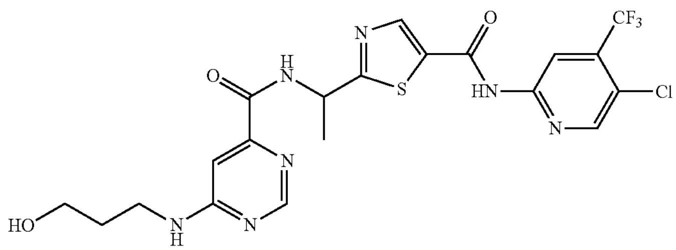 [SMILES: CC(NC(=O)c1cc(NCCCO)ncn1)c1ncc(C(=O)Nc2cc(C(F)(F)F)c(Cl)cn2)s1] | m/z 530 [M + 1]$^+$ |
| 5dD | 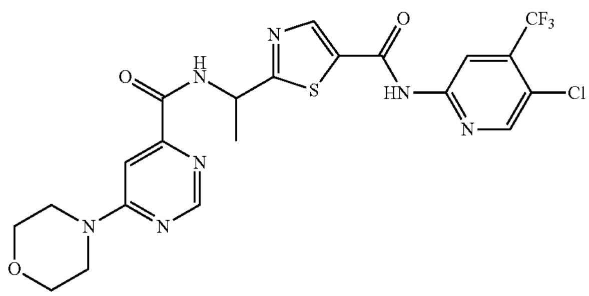 [SMILES: CC(NC(=O)c1cc(N2CCOCC2)ncn1)c1ncc(C(=O)Nc2cc(C(F)(F)F)c(Cl)cn2)s1] | m/z 542 [M + 1]$^+$ |
| 5dDa | 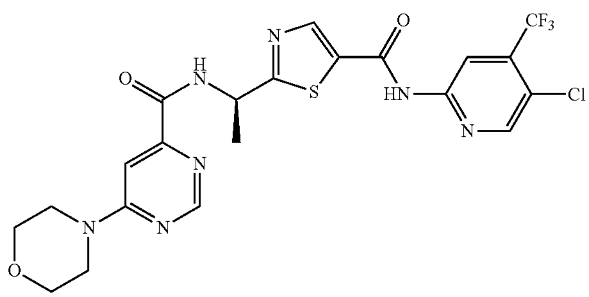 [SMILES: C[C@@H](NC(=O)c1cc(N2CCOCC2)ncn1)c1ncc(C(=O)Nc2cc(C(F)(F)F)c(Cl)cn2)s1] | m/z 542 [M + 1]$^+$ |
| 5dB | 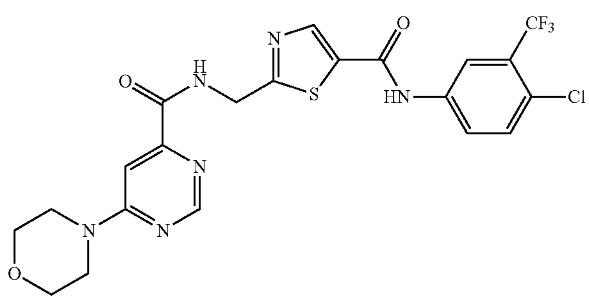 [SMILES: O=C(NCc1ncc(C(=O)Nc2ccc(Cl)c(C(F)(F)F)c2)s1)c1cc(N2CCOCC2)ncn1] | m/z 527 [M + 1]$^+$ |
| 5eD | 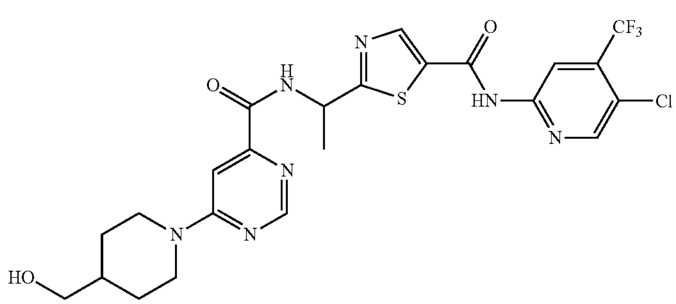 [SMILES: CC(NC(=O)c1cc(N2CCC(CO)CC2)ncn1)c1ncc(C(=O)Nc2cc(C(F)(F)F)c(Cl)cn2)s1] | m/z 570 [M + 1]$^+$ |

TABLE 3-continued

Exemplary Compounds of Formula I

| # | Structure | Characterization Data |
|---|---|---|
| 5fD | 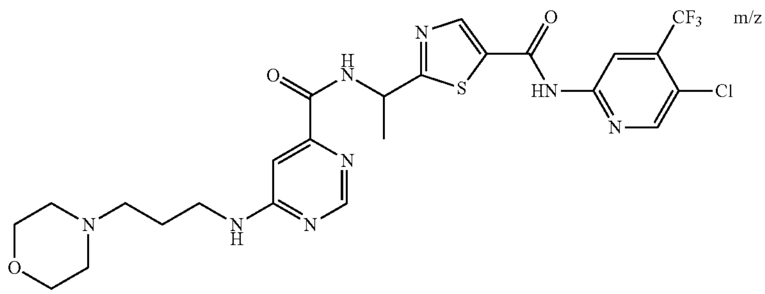 | m/z 599 [M + 1]$^+$ |
| 5gD | 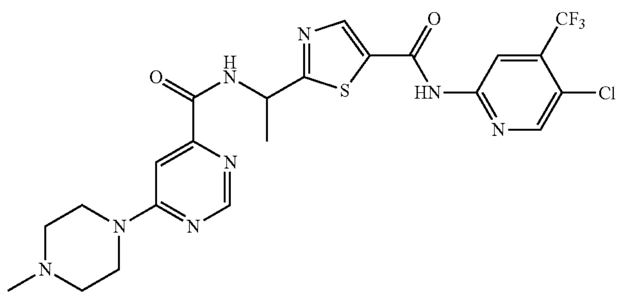 [SMILES: CC(NC(=O)c1cc(N2CCN(C)CC2)ncn1)c1ncc(C(=O)Nc2cc(C(F)(F)F)c(Cl)cn2)s1] | m/z 555 [M + 1]$^+$ |
| 5hD | 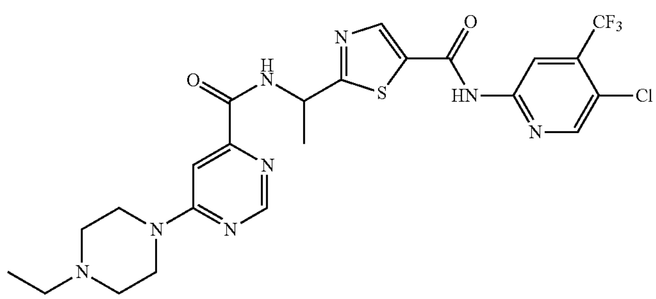 [SMILES: CCN1CCN(c2cc(C(=O)NC(C)c3ncc(C(=O)Nc4cc(C(F)(F)F)c(Cl)cn4)s3)ncn2)CC1] | m/z 569 [M + 1]$^+$ |
| 5iA | 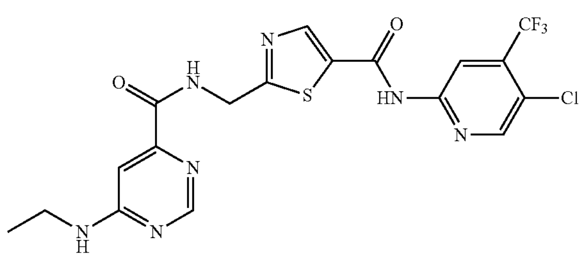 [SMILES: CCNc1cc(C(=O)NCc2ncc(C(=O)Nc3cc(C(F)(F)F)c(Cl)cn3)s2)ncn1] | m/z 486 [M + 1]$^+$ |
| 5jD | 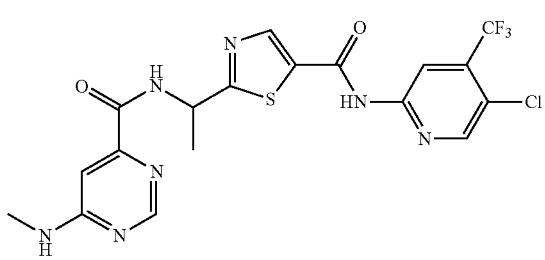 [SMILES: CNc1cc(C(=O)NC(C)c2ncc(C(=O)Nc3cc(C(F)(F)F)c(Cl)cn3)s2)ncn1] | m/z 486 [M + 1]$^+$ |

TABLE 3-continued

Exemplary Compounds of Formula I

| # | Structure | Characterization Data |
|---|---|---|
| 5jDa | 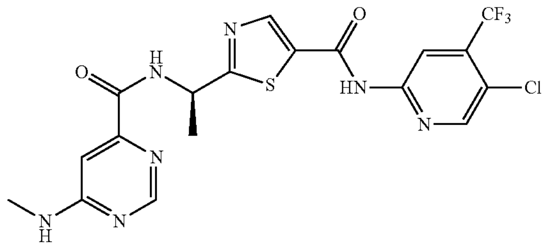 [SMILES: CNc1cc(C(=O)N[C@H](C)c2ncc(C(=O)Nc3cc(C(F)(F)F)c(Cl)cn3)s2)ncn1] | m/z 486 [M + 1]+; $^1$HNMR: (DMSO-$d_6$, 400 MHz) δ: 11.8 (s, 1H, NH), 9.5 (d, J = 7.9 Hz, 1H), 8.79 (s, 1H), 8.75 (s, 1H), 8.59-8.54 (m, 2H), 8.06-7.99 (m, 1H), 7.11 (brs, 1H), 5.42-5.38 (m, 1H), 2.89 (brs, 3H), 1.61 (d, J = 6.9 Hz, 3H). |
| 5kD | 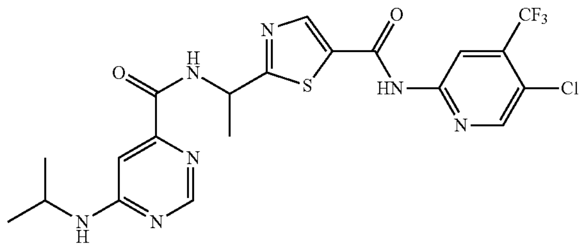 [SMILES: CC(C)Nc1cc(C(=O)NC(C)c2ncc(C(=O)Nc3cc(C(F)(F)F)c(Cl)cn3)s2)ncn1] | m/z 514 [M + 1]+ |
| 5lA | 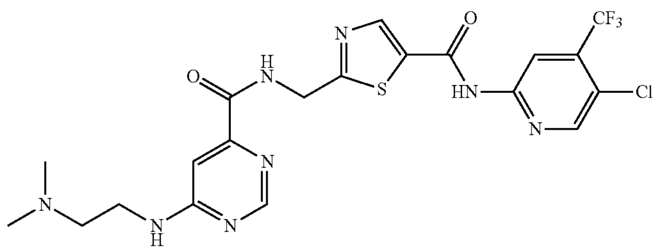 [SMILES: CN(C)CCNc1cc(C(=O)NCc2ncc(C(=O)Nc3cc(C(F)(F)F)c(Cl)cn3)s2)ncn1] | m/z 529 [M + 1]+ |
| 5lD | 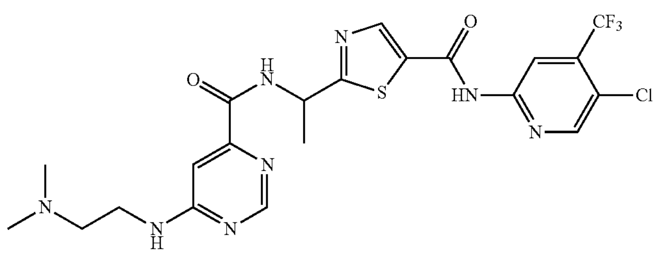 [SMILES: CC(NC(=O)c1cc(NCCN(C)C)ncn1)c1ncc(C(=O)Nc2cc(C(F)(F)F)c(Cl)cn2)s1] | m/z 543 [M + 1]+ |
| 5mD | 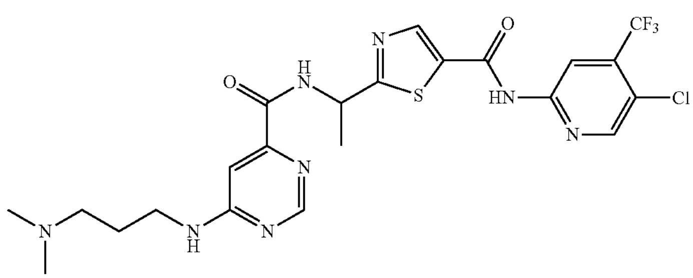 [SMILES: CC(NC(=O)c1cc(NCCCN(C)C)ncn1)c1ncc(C(=O)Nc2cc(C(F)(F)F)c(Cl)cn2)s1] | m/z 557 [M + 1]+ |
| 5nD | 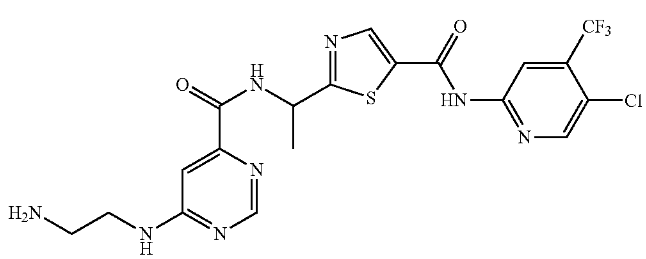 [SMILES: CC(NC(=O)c1cc(NCCN)ncn1)c1ncc(C(=O)Nc2cc(C(F)(F)F)c(Cl)cn2)s1] | m/z 515 [M + 1]+ |

TABLE 3-continued

Exemplary Compounds of Formula I

| # | Structure | Characterization Data |
|---|-----------|----------------------|
| 5oD | 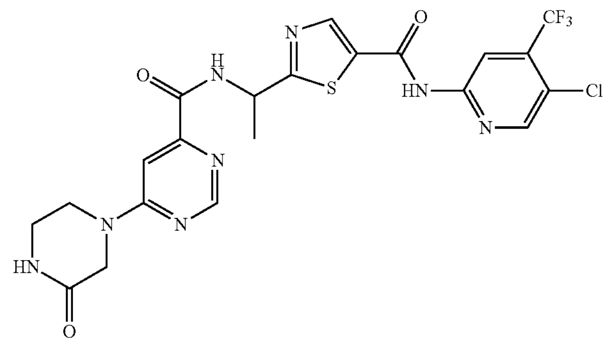 [SMILES: CC(NC(=O)c1cc(N2CCNC(=O)C2)ncn1)c1ncc(C(=O)Nc2cc(C(F)(F)F)c(Cl)cn2)s1] | m/z 555 [M + 1]+ |
| 5qD | 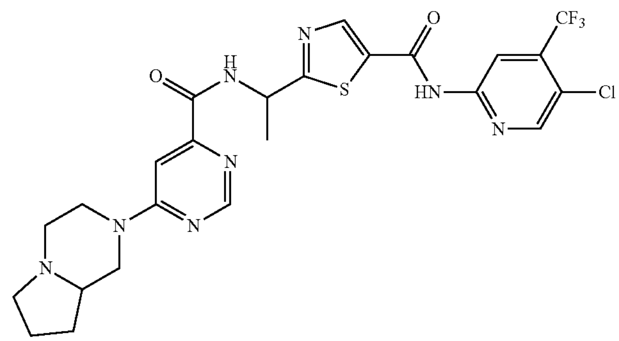 [SMILES: CC(NC(=O)c1cc(N2CCN3CCCC3C2)ncn1)c1ncc(C(=O)Nc2cc(C(F)(F)F)c(Cl)cn2)s1] | m/z 581 [M + 1]+ |
| 5pDa | 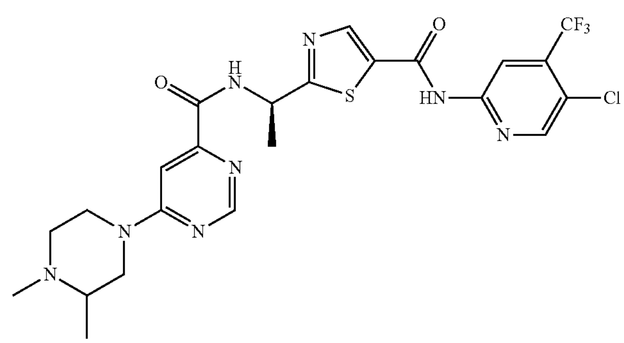 [SMILES: CC1CN(c2cc(C(=O)N[C@H](C)c3ncc(C(=O)Nc4cc(C(F)(F)F)c(Cl)cn4)s3)ncn2)CCN1C] | m/z 569 [M + 1]+ |
| 5rD | 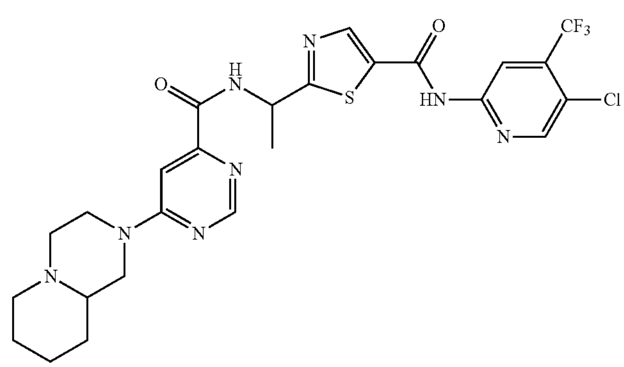 [SMILES: CC(NC(=O)c1cc(N2CCN3CCCCC3C2)ncn1)c1ncc(C(=O)Nc2cc(C(F)(F)F)c(Cl)cn2)s1] | m/z 595 [M + 1]+ |

TABLE 3-continued

Exemplary Compounds of Formula I

| # | Structure | Characterization Data |
|---|---|---|
| 5sD | 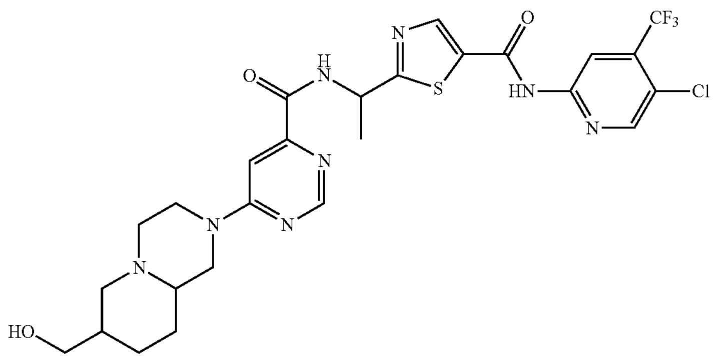 [SMILES: CC(NC(=O)c1cc(N2CCN3CC(CO)CCC3C2)ncn1)c1ncc(C(=O)Nc2cc(C(F)(F)F)c(Cl)cn2)s1] | m/z 625 [M + 1]$^+$ |
| 5tD | 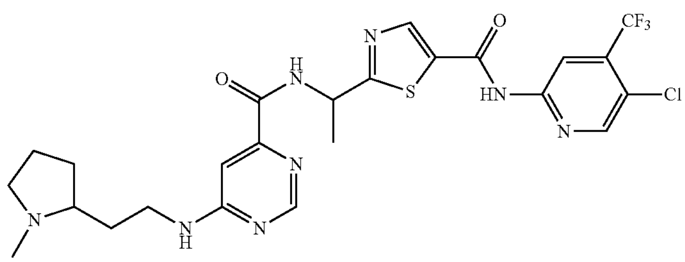 [SMILES: CC(NC(=O)c1cc(NCCC2CCCN2C)ncn1)c1ncc(C(=O)Nc2cc(C(F)(F)F)c(Cl)cn2)s1] | m/z 583 [M + 1]$^+$ |
| 5uD | 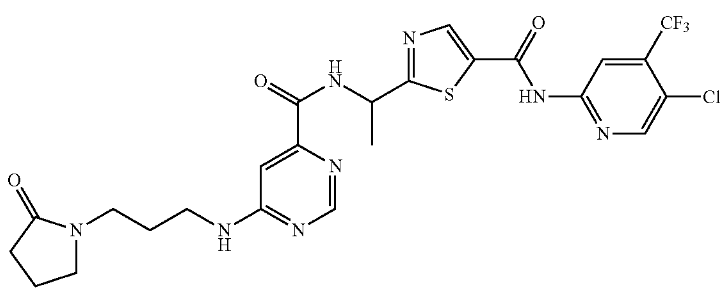 [SMILES: CC(NC(=O)c1cc(NCCCN2CCCC2=O)ncn1)c1ncc(C(=O)Nc2cc(C(F)(F)F)c(Cl)cn2)s1] | m/z 597 [M + 1]$^+$ |
| 6aD | 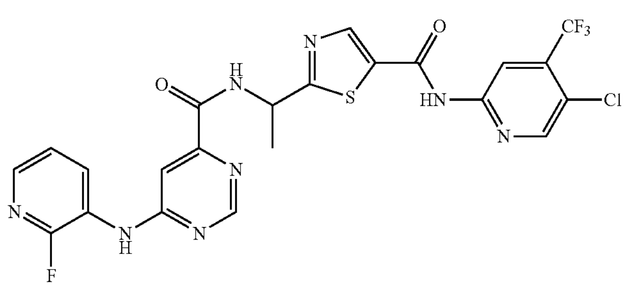 [SMILES: CC(NC(=O)c1cc(Nc2cccnc2F)ncn1)c1ncc(C(=O)Nc2cc(C(F)(F)F)c(Cl)cn2)s1] | m/z 567 [M + 1]$^+$ |
| 6bD | 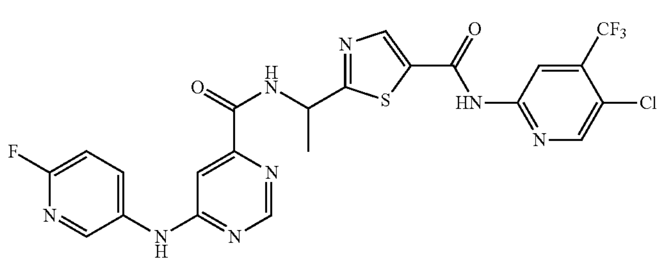 [SMILES: CC(NC(=O)c1cc(Nc2ccc(F)nc2)ncn1)c1ncc(C(=O)Nc2cc(C(F)(F)F)c(Cl)cn2)s1] | m/z 567 [M + 1]$^+$ |

TABLE 3-continued

Exemplary Compounds of Formula I

| # | Structure | Characterization Data |
|---|-----------|----------------------|
| 6cD | 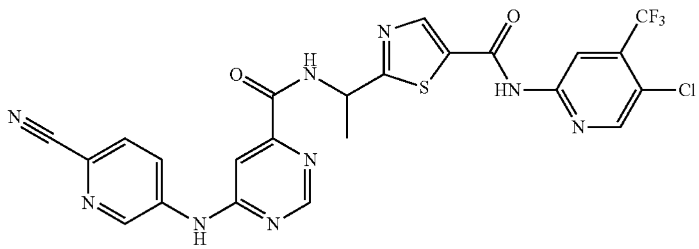 [SMILES: CC(NC(=O)c1cc(Nc2ccc(C#N)nc2)ncn1)c1ncc(C(=O)Nc2cc(C(F)(F)F)c(Cl)cn2)s1] | m/z 574 [M + 1]+ |
| 6dD | 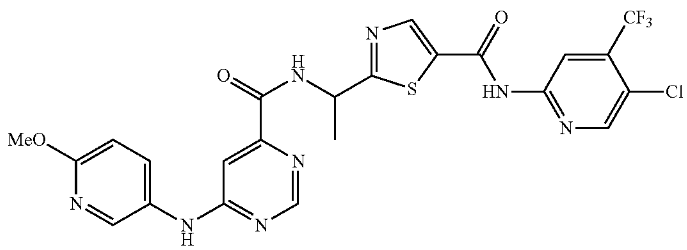 [SMILES: COc1ccc(Nc2cc(C(=O)NC(C)c3ncc(C(=O)Nc4cc(C(F)(F)F)c(Cl)cn4)s3)ncn2)cn1] | m/z 579 [M + 1]+ |
| 6eD | 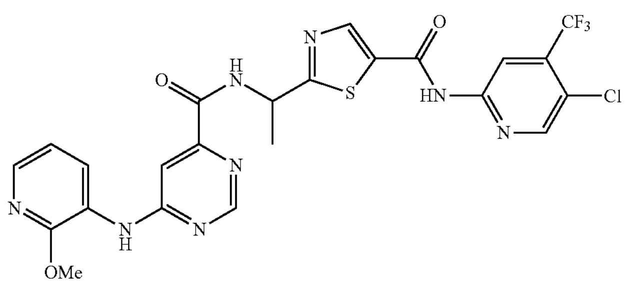 [SMILES: COc1ncccc1Nc1cc(C(=O)NC(C)c2ncc(C(=O)Nc3cc(C(F)(F)F)c(Cl)cn3)s2)ncn1] | m/z 579 [M + 1]+ |
| 6fB | 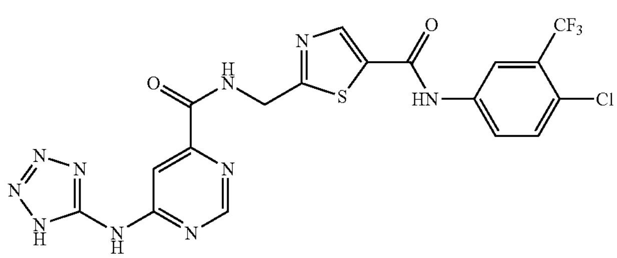 [SMILES: O=C(NCc1ncc(C(=O)Nc2ccc(Cl)c(C(F)(F)F)c2)s1)c1cc(Nc2nnn[nH]2)ncn1] | m/z 525 [M + 1]+ |
| 6gD | 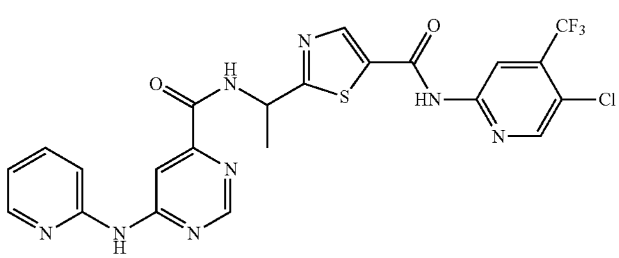 [SMILES: CC(NC(=O)c1cc(Nc2ccccn2)ncn1)c1ncc(C(=O)Nc2cc(C(F)(F)F)c(Cl)cn2)s1] | m/z 549 [M + 1]+ |
| 6hD | 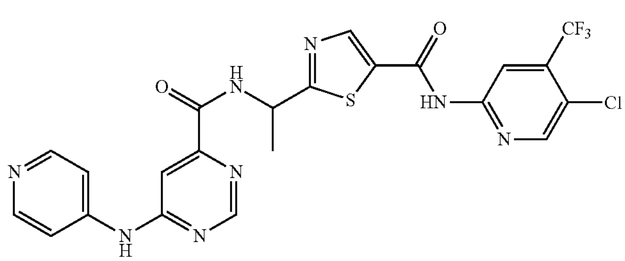 [SMILES: CC(NC(=O)c1cc(Nc2ccncc2)ncn1)c1ncc(C(=O)Nc2cc(C(F)(F)F)c(Cl)cn2)s1] | m/z 549 [M + 1 r |

TABLE 3-continued

Exemplary Compounds of Formula I

| # | Structure | Characterization Data |
|---|---|---|
| 6iD | 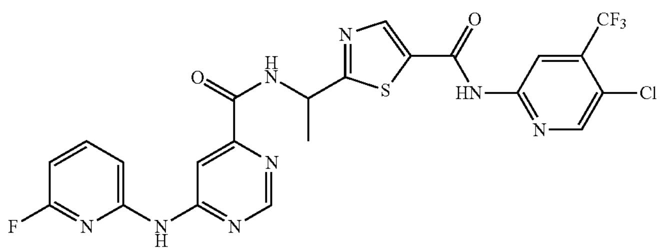 [SMILES: CC(NC(=O)c1cc(Nc2cccc(F)n2)ncn1)c1ncc(C(=O)Nc2cc(C(F)(F)F)c(Cl)cn2)s1] | m/z 567 [M + 1]+ |
| 6jD | 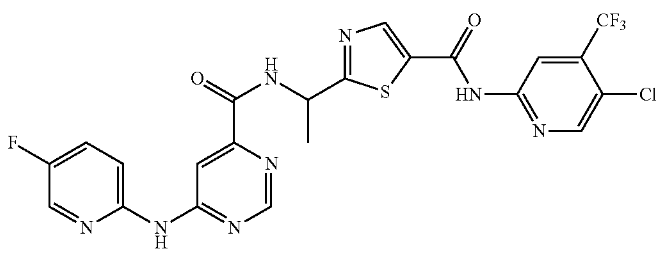 [SMILES: CC(NC(=O)c1cc(Nc2ccc(F)cn2)ncn1)c1ncc(C(=O)Nc2cc(C(F)(F)F)c(Cl)cn2)s1] | m/z 567 [M + 1]+ |
| 7aD | 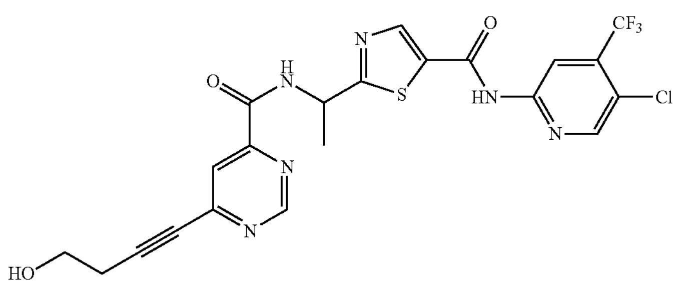 [SMILES: CC(NC(=O)c1cc(C#CCCO)ncn1)c1ncc(C(=O)Nc2cc(C(F)(F)F)c(Cl)cn2)s1] | m/z 525 [M + 1]+ |
| 8aD | 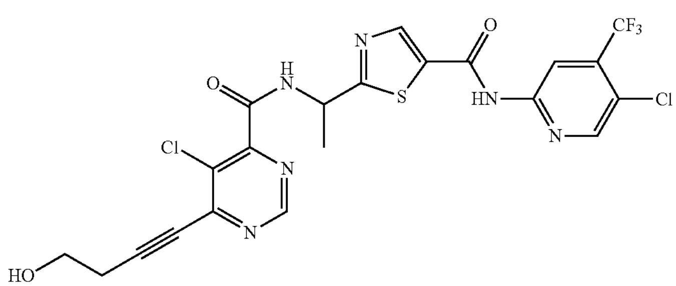 [SMILES: CC(NC(=O)c1ncnc(C#CCCO)c1Cl)c1ncc(C(=O)Nc2cc(C(F)(F)F)c(Cl)cn2)s1] | m/z 559 [M + 1]+ |
| 8bD | 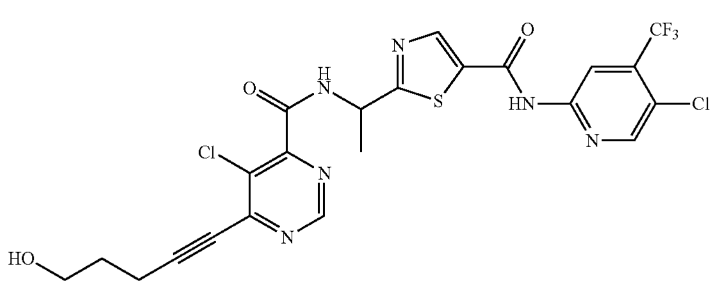 [SMILES: CC(NC(=O)c1ncnc(C#CCCCO)c1Cl)c1ncc(C(=O)Nc2cc(C(F)(F)F)c(Cl)cn2)s1] | m/z 573 [M + 1]+ |

TABLE 3-continued

Exemplary Compounds of Formula I

| # | Structure | Characterization Data |
|---|---|---|
| 9A | 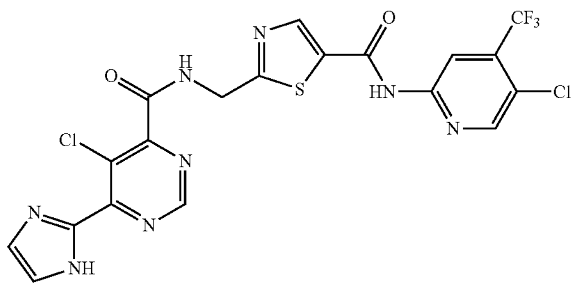 [SMILES: O=C(Nc1cc(C(F)(F)F)c(Cl)cn1)c1cnc(CNC(=O)c2ncnc(-c3ncc[nH]3)c2Cl)s1] | m/z 544 [M + 1]$^+$; $^1$H NMR (300 MHz, Methanol-d4): δ 9.20 (s, 1H), 8.54 (s, 1H), 8.50 (s, 1H), 8.43 (s, 1H), 7.59 (s, 2H), 4.85 (brs, 2H); |
| 9D | 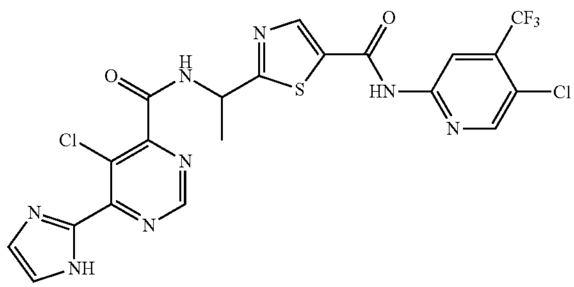 [SMILES: CC(NC(=O)c1ncnc(-c2ncc[nH]2)c1Cl)c1ncc(C(=O)Nc2cc(C(F)(F)F)c(Cl)cn2)s1] | m/z 558 [M + 1]$^+$; $^1$H NMR (400 MHz, DMSO-d$_6$): δ 9.76 (d, J = 8.0 Hz, 1H), 9.22 (s, 1H), 8.79 (s, 2H), 8.59 (s, 1H), 7.45 (s, 2H), 5.44 (q, J = 8.0 Hz, 1H), 1.62 (d, J = 8.0 Hz, 3H). |
| 10A | 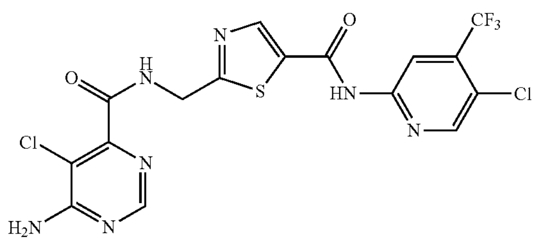 [SMILES: Nc1ncnc(C(=O)NCc2ncc(C(=O)Nc3cc(C(F)(F)F)c(Cl)cn3)s2)c1Cl] | m/z 493 [M + 1]$^+$; $^1$H NMR (400 MHz, methanol-d$_4$): δ 8.64 (s, 1H), 8.59 (s, 1H), 8.53 (s, 1H), 8.37 (s, 1H), 4.89 (d, J = 4.0 Hz). |
| 10D | 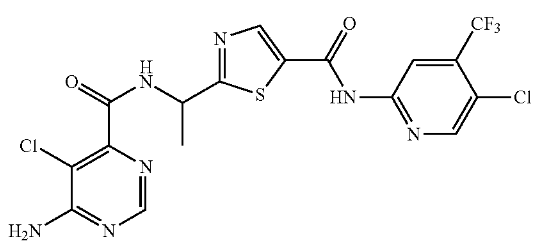 | m/z 506 [M + 1]$^+$ |
| 10Da | 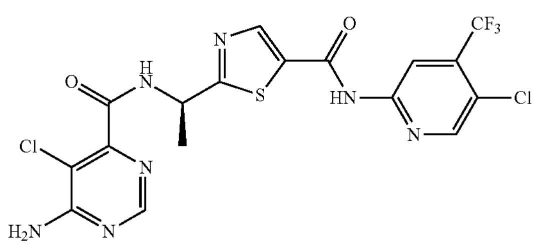 | m/z 506 [M + 1]$^+$; $^1$H NMR (400 MHz, methanol-d$_4$): δ 8.64 (s, 1H), 8.59 (s, 1H), 8.54 (s, 1H), 8.36 (s, 1H), 5.52 (q, J = 8.0 Hz), 1.74 (d, J = 8.0 Hz). |
| 10Db | 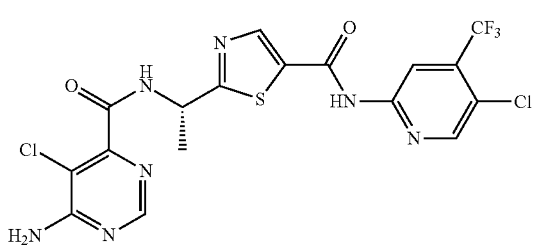 [SMILES: C[C@H](NC(=O)c1ncnc(N)c1Cl)c1ncc(C(=O)Nc2cc(C(F)(F)F)c(Cl)cn2)s1] | m/z 506 [M + 1]$^+$; $^1$H NMR (400 MHz, methanol-d$_4$): δ 8.64 (s, 1H), 8.59 (s, 1H), 8.54 (s, 1H), 8.36 (s, 1H), 5.52 (q, J = 8.0 Hz), 1.74 (d, J = 8.0 Hz). |

TABLE 3-continued
Exemplary Compounds of Formula I
| # | Structure | Characterization Data |
|---|---|---|
| 10E | 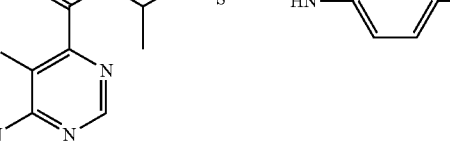 | m/z 505 [M + 1]⁺; ¹H NMR (400 MHz, Methanol-$d_4$): δ 8.44 (s, 1H), 8.34 (s, 1H), 8.20 (s, 1H), 7.96 (dd, J = 8.0, 2.0 Hz, 1H), 7.60 (d, J = 8.0 Hz, 1H), 5.50 (q, J = 7.4 Hz, 1H), 1.73 (d, J = 7.4 Hz, 3H). |
| 10F | 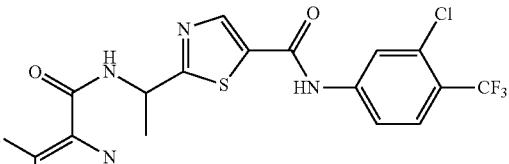 | m/z 505 [M + 1]⁺; . ¹H NMR (400 MHz, Methanol-$d_4$): δ 8.47 (s, 1H), 8.36 (s, 1H), 8.10 (s, 1H), 7.80 (dd, J = 8.0, 2.0 Hz, 1H), 7.77 (d, J = 8.0 Hz, 1H), 5.51 (q, J = 7.4 Hz, 1H), 1.74 (d, J = 7.4 Hz, 3H). |
| 10Na | 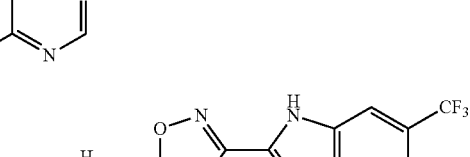 | m/z 452 [M + 1]⁺ |
| 10O | 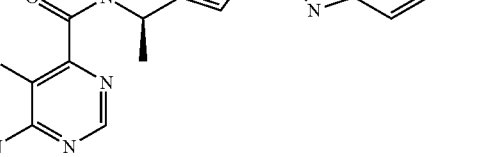 | m/z 442 [M + 1]⁺ |
| 10P | 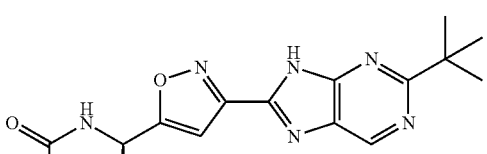 | m/z 439 [M + 1]⁺; ¹HNMR: (DMSO-$d_6$, 400 MHz) δ: 13.8 (brs, 1H, NH), 9.4 (d, J = 8.1 Hz, 1H), 8.40 (s, 1H), 8.07 (brs, 1H, NH), 7.35 (d, J = 8.1 Hz, 1H), 7.02 (d, J = 0.7 Hz, 1H), 5.44 (m, 1H), 1.63 (d, J = 7.0 Hz, 3H), 1.59 (s, 3H), 1.26 (brs, 2H), 0.90 (brs, 2H). |
| 11D | 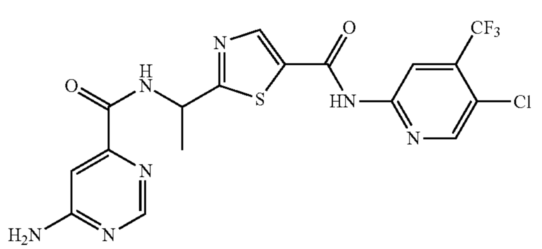 [SMILES: CC(NC(=O)c1cc(N)ncn1)c1ncc(C(=O)Nc2cc(C(F)(F)F)c(Cl)cn2)s1] | m/z 472 [M + 1]⁺ |

TABLE 3-continued

Exemplary Compounds of Formula I

| # | Structure | Characterization Data |
|---|---|---|
| 11Da | 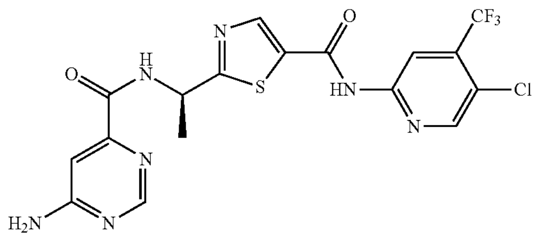 [SMILES: C[C@@H](NC(=O)c1cc(N)ncn1)c1ncc(C(=O)Nc2cc(C(F)(F)F)c(Cl)cn2)s1] | m/z 472 [M + 1]+ 1H NMR (400 MHz, CDCl3): δ 8.64 (s, 1H), 8.59 (s, 1H), 8.43 (s, 1H), 8.27 (s, 1H), 7.25 (s, 1H), 5.58 (q, J = 7.4 Hz, 1H), 5.16 (brs, 1H), 1.79 (d, J = 7.4 Hz, 3H). |
| 12aDa | 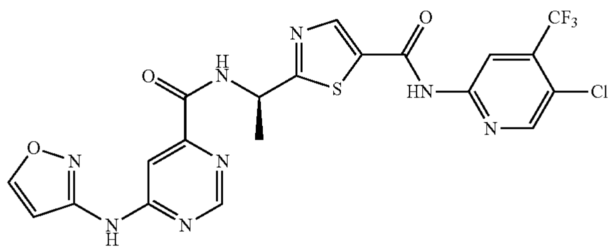 [SMILES: C[C@@H](NC(=O)c1cc(Nc2ccon2)ncn1)c1ncc(C(=O)Nc2cc(C(F)(F)F)c(Cl)cn2)s1] | m/z 540 [M + 1]+ |
| 12bDa | 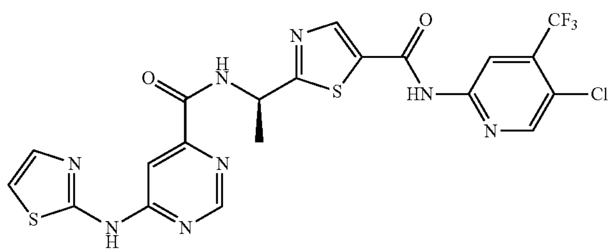 | m/z 556 [M + 1]+ |
| 12cDa | 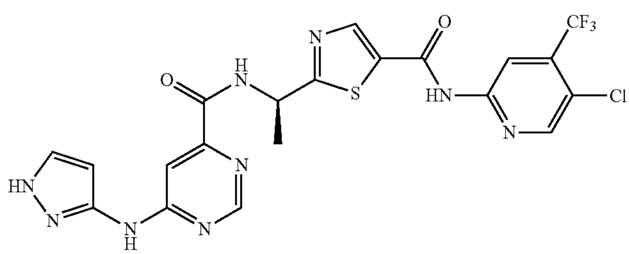 [SMILES: C[C@@H](NC(=O)c1cc(Nc2cc[nH]n2)ncn1)c1ncc(C(=O)Nc2cc(C(F)(F)F)c(Cl)cn2)s1] | m/z 538 [M + 1]+ |
| 13aD | 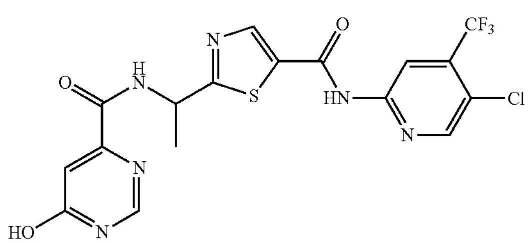 [SMILES: CC(NC(=O)c1cc(O)ncn1)c1ncc(C(=O)Nc2cc(C(F)(F)F)c(Cl)cn2)s1] | m/z 473 [M + 1]+ |
| 13bD | 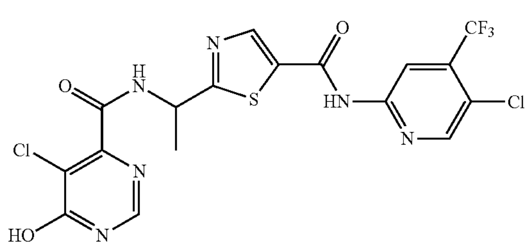 [SMILES: CC(NC(=O)c1ncnc(O)c1Cl)c1ncc(C(=O)Nc2cc(C(F)(F)F)c(Cl)cn2)s1] | m/z 507 [M + 1]+ |

TABLE 3-continued

Exemplary Compounds of Formula I

| # | Structure | Characterization Data |
|---|---|---|
| 14aD | 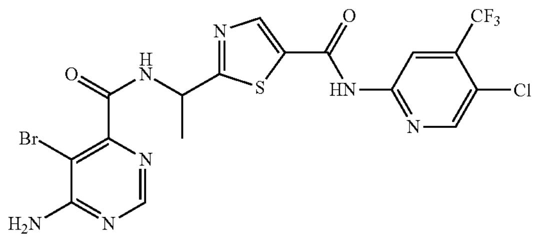 | m/z 552 [M + 1]+ |
| 14aDa | 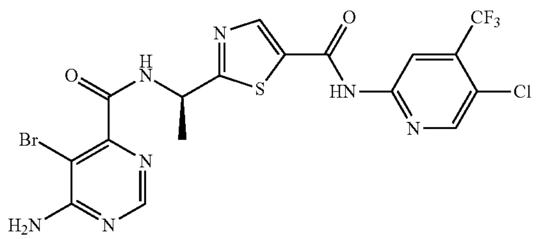 [SMILES: C[C@@H](NC(=O)c1ncnc(N)c1Br)c1ncc(C(=O)Nc2cc(C(F)(F)F)c(Cl)cn2)s1] | m/z 552 [M + 1]+; ¹HNMR: (DMSO-d$_6$, 200 MHz) δ: 11.76 (s, 1H), 9.48 (d, J = 7.8 Hz, 1H), 8.79 (s, 1H), 8.76 (s, 1H), 8.58 (s, 1H), 8.38 (s, 1H), 5.40-5.30 (m, 1H), 1.60 (d, J = 7.4 Hz, 3H). |
| 14aDb | 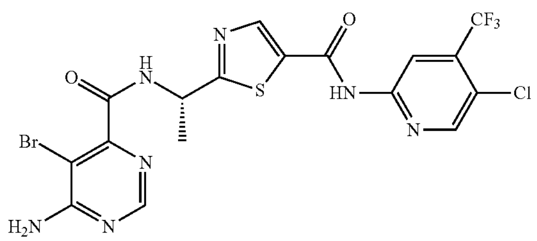 | m/z 552 [M + 1]+ |
| 14aE | 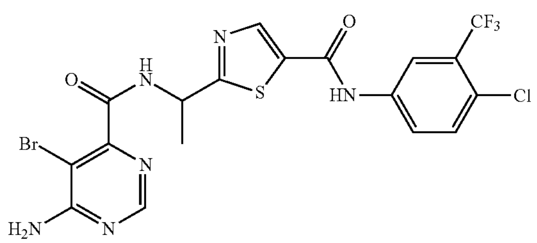 | m/z 551 [M + 1]+ |
| 14aO | 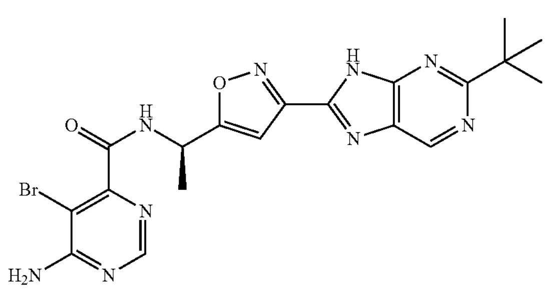 | m/z 486 [M+ + 1]; ¹H NMR (300 MHz, CDCl$_3$): δ 9.34 (d, J = 7.4 Hz, 1H), 9.15 (s, 1H), 8.35 (s, 2H), NH), 7.04 (s, 1H), 5.43-5.33 (m, 1H), 1.57 (d, J = 7.4 Hz, 1H), 1.41 (s, 9H). |
| 14bD | 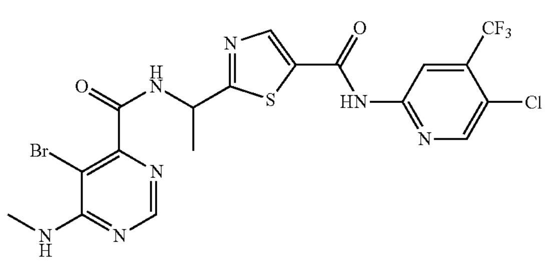 | m/z 565 [M + 1]; ¹H NMR (500 MHz, CD$_3$OD): δ 8.64 (s, 1H), 8.60 (s, 1H), 8.54 (s, 1H), 8.49 (s, 1H), 5.51 (q, J = 8.0 Hz, 1H), 3.08 (s, 3H) 1.74 (d, J = 8.0 Hz, 3H). |

TABLE 3-continued

Exemplary Compounds of Formula I

| # | Structure | Characterization Data |
|---|---|---|
| 14cD | 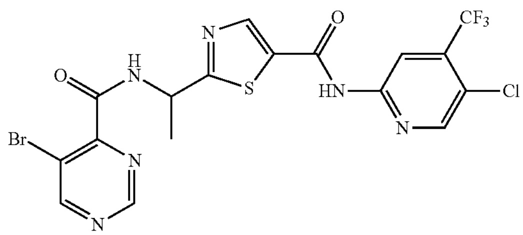 [SMILES: CC(NC(=O)c1ncncc1Br)c1ncc(C(=O)Nc2cc(C(F)(F)F)c(Cl)cn2)s1] | m/z 537 [M + 1]; 1HNMR: (DMSO-d$_6$, 200 MHz) δ: 11.79 (s, 1H), 9.75 (d, J = 7.8 Hz, 1H), 9.28 (s, 1H), 9.21 (s, 1H), 8.79 (s, 1H), 8.78 (s, 1H), 8.58 (s, 1H), 5.45-5.38 (m, 1H), 1.63 (d, J = 7.1 HZ, 3H). |
| 15aDa | 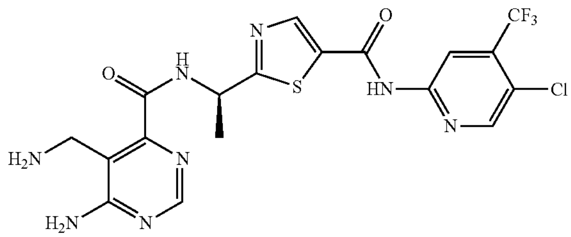 [SMILES: C[C@@H](NC(=O)c1ncnc(N)c1CN)c1ncc(C(=O)Nc2cc(C(F)(F)F)c(Cl)cn2)s1] | m/z 502 [M + 1]$^+$ |
| 15bDa | 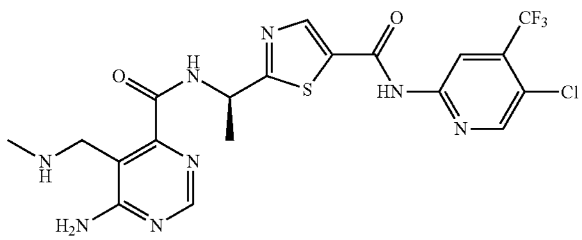 [SMILES: CNCc1c(N)ncnc1C(=O)N[C@H](C)c1ncc(C(=O)Nc2cc(C(F)(F)F)c(Cl)cn2)s1] | m/z 516 [M + 1]$^+$ |
| 15cDa | 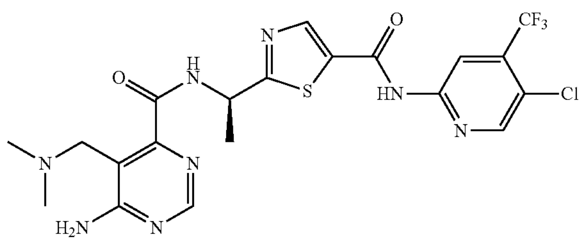 [SMILES: C[C@@H](NC(=O)c1ncnc(N)c1CN(C)C)c1ncc(C(=O)Nc2cc(C(F)(F)F)c(Cl)cn2)s1] | m/z 530 [M + 1]$^+$ |
| 15dDa | 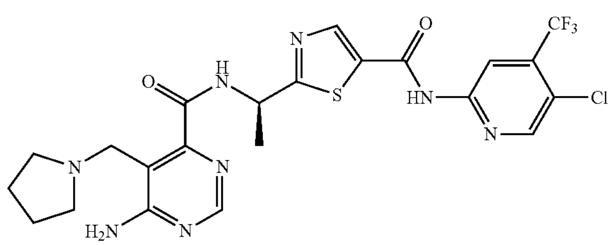 [SMILES: C[C@@H](NC(=O)c1ncnc(N)c1CN1CCCC1)c1ncc(C(=O)Nc2cc(C(F)(F)F)c(Cl)cn2)s1] | m/z 556 [M + 1]$^+$ |
| 16D | 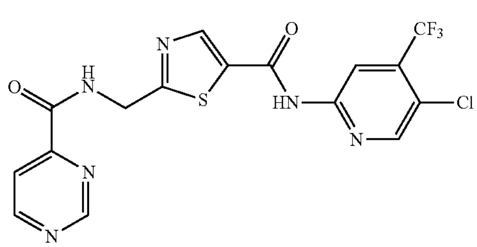 [SMILES: O=C(NCc1ncc(C(=O)Nc2cc(C(F)(F)F)c(Cl)cn2)s1)c1ccncn1] | m/z 443 [M + 1]$^+$; $^1$H NMR (300 MHz, DMSO-d$_6$): δ 11.9 (brs, 1H), 10.19 (t, J = 6.5 Hz, 1H), 9.47 (s, 1H), 9.19 (d, J = 5.1 Hz, 1H), 8.89 (s, 1H), 8.83 (s, 1H), 8.62 (s, 1H), 8.15 (d, J = 5.0 Hz, 1H), 4.88 (d, J = 6.5 Hz, 2H). |

TABLE 3-continued

Exemplary Compounds of Formula I

| # | Structure | Characterization Data |
|---|---|---|
| 16Na | 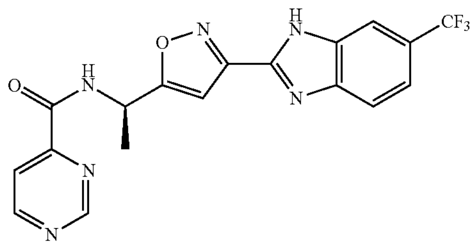 [SMILES: C[C@@H](NC(=O)c1ccncn1)c1cc(-c2nc3ccc(C(F)(F)F)cc3[nH]2)no1] | m/z 403 [M + 1]+; 1H NMR (300 MHz, DMSO-d6): δ 9.68 (d, J = 8.4 Hz, 1H), 9.33 (s, 1H), 9.05 (d, J = 5.1 Hz, 1H), 8.03 (d, J = 5.1 Hz, 1H), 7.95 (s, 1H), 7.76 (d, J = 8.4 Hz, 1H), 7.55 (d, J = 8.4 Hz, 1H), 7.00 (s, 1H), 5.48 (m, 1H), 1.63 (d, J = 8.0 Hz, 1H). |
| 17D | 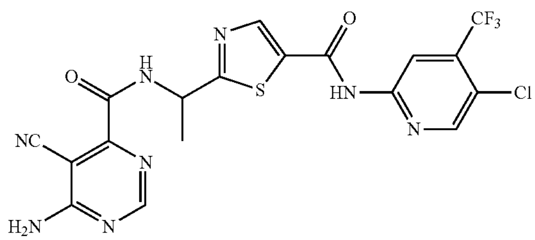 | m/z 497 [M + 1]+ |
| 18aDa | 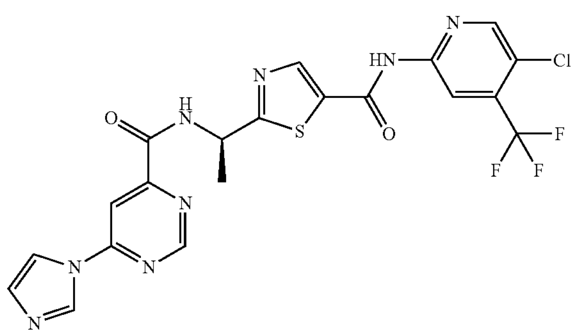 [SMILES: C[C@@H](NC(=O)c1cc(-n2ccnc2)ncn1)c1ncc(C(=O)Nc2cc(C(F)(F)F)c(Cl)cn2)s1] | m/z 523 [M + 1]+ |
| 5vDa | 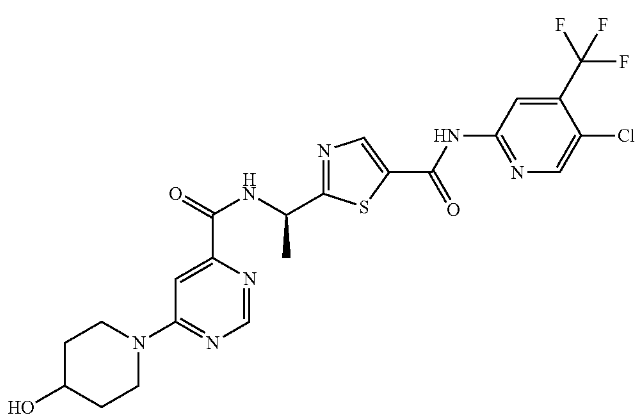 [SMILES: C[C@@H](NC(=O)c1cc(N2CCC(O)CC2)ncn1)c1ncc(C(=O)Nc2cc(C(F)(F)F)c(Cl)cn2)s1] | 1H NMR (400 MHz, DMSO-d6) δ 11.74 (s, 1 H), 9.49 (d, J = 8.1 Hz, 1 H), 8.78 (s, 1 H), 8.74 (s, 1 H), 8.60 (s, 1 H), 8.55 (s, 1 H), 7.32 (s, 1 H), 5.42 (quin, J = 7.3 Hz, 1 H), 4.79 (d, J = 4.5 Hz, 1 H), 4.08 (br. s., 1 H), 3.78 (td, J = 4.0, 8.1 Hz, 1 H), 3.37 (dd, J = 3.3, 9.3 Hz, 2 H), 1.86-1.75 (m, 2 H), 1.66 (d, J = 7.1 Hz, 3 H), 1.43-1.31 (m, 2 H); m/z 556 [M + 1]+ |

TABLE 3-continued
Exemplary Compounds of Formula I
| # | Structure | Characterization Data |
|---|---|---|
| 5wDa | 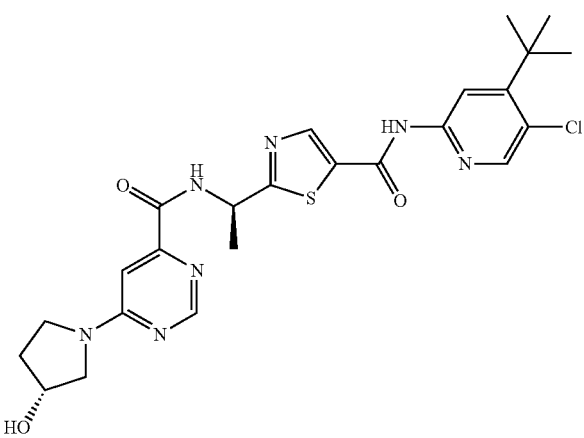 | 1H NMR (400 MHz, DMSO-d6) δ 11.75 (s, 1 H), 9.49 (d, J = 8.1 Hz, 1 H), 8.78 (s, 1 H), 8.74 (s, 1 H), 8.59 (s, 1 H), 8.55 (s, 1 H), 7.06-6.93 (m, 1 H), 5.42 (quin, J = 7.3 Hz, 1 H), 5.14-4.98 (m, 1 H), 4.51-4.32 (m, 1 H), 3.78-3.44 (m, 3 H), 2.16-1.84 (m, 2 H), 1.66 (d, J = 7.1 Hz, 3 H); m/z 542 [M + 1]⁺ |
| 5xDa | 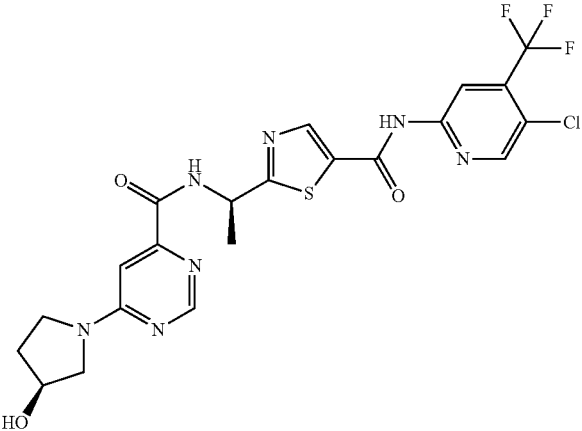 [SMILES: C[C@@H](NC(=O)c1cc(N2CC[C@H](O)C2)ncn1)c1ncc(C(=O)Nc2cc(C(F)(F)F)c(Cl)cn2)s1] | m/z 542 [M + 1]⁺ |
| 18jDa | 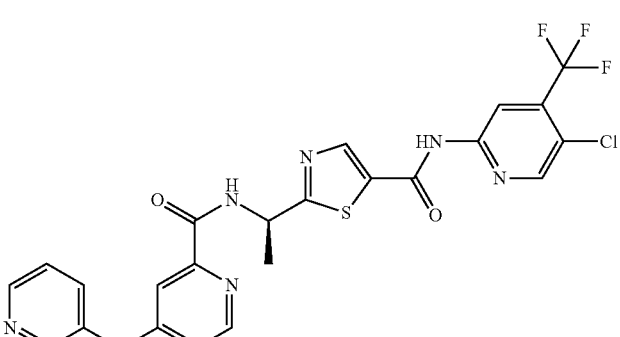 | m/z 550 [M + 1]⁺ |

TABLE 3-continued

Exemplary Compounds of Formula I

| # | Structure | Characterization Data |
|---|-----------|----------------------|
| 21 | 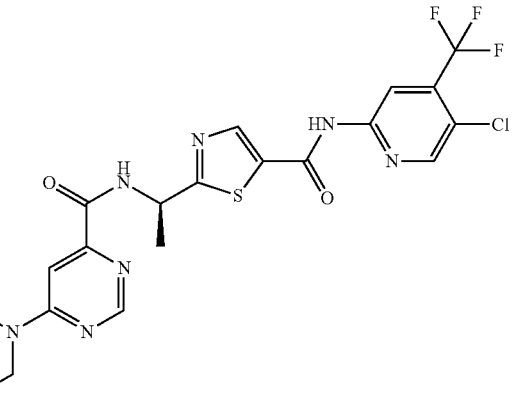 | 1H NMR (400 MHz, DMSO-d6) δ 11.75 (s, 1 H), 9.54 (d, J = 7.6 Hz, 1 H), 8.78 (s, 1 H), 8.74 (s, 1 H), 8.63 (s, 1 H), 8.56 (s, 1 H), 7.39 (br. s., 1 H), 5.43 (quin, J = 7.2 Hz, 1 H), 4.44 (dd, J = 3.5, 7.6 Hz, 1 H), 3.98 (br. s., 2 H), 3.60 (br. s., 2 H), 1.93 (br. s., 2 H), 1.73-1.57 (m, 5 H); m/z 636 [M + 1]+ |
| 18cDa | 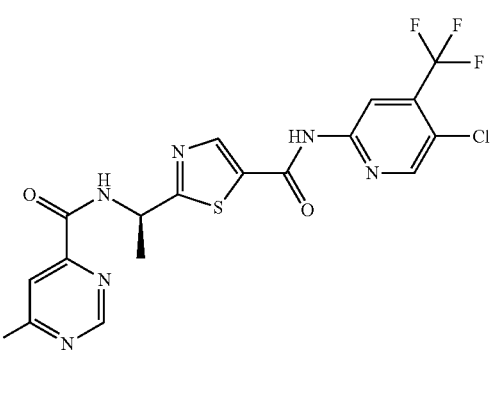 | 1H NMR (400 MHz, DMSO-d6) δ 11.76 (s, 1 H), 9.86 (d, J = 8.1 Hz, 1 H), 9.22 (s, 1 H), 8.78 (s, 1 H), 8.75 (s, 1 H), 8.73 (s, 1 H), 8.55 (s, 1 H), 8.34 (s, 1 H), 7.89 (s, 1 H), 5.49 (quin, J = 7.3 Hz, 1 H), 2.19 (s, 3 H), 1.70 (d, J = 7.1 Hz, 3 H); m/z 537 [M + 1]+ |
| 20aDa | 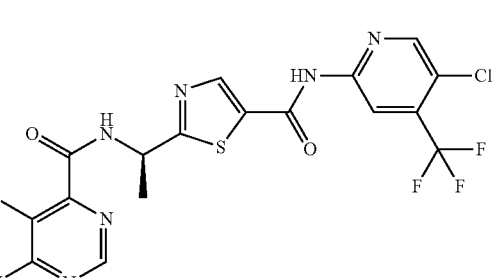 | 1H NMR (400 MHz, DMSO-d6) δ 11.76 (s, 1 H), 9.48 (d, J = 8.1 Hz, 1 H), 8.78 (s, 1 H), 8.75 (s, 1 H), 8.57 (s, 1 H), 8.25 (d, J = 2.0 Hz, 1 H), 7.64 (br. s., 2 H), 5.37 (quin, J = 7.2 Hz, 1 H), 1.62 (d, J = 7.1 Hz, 3 H); m/z 490[M + 1]+ |
| 22.1 | 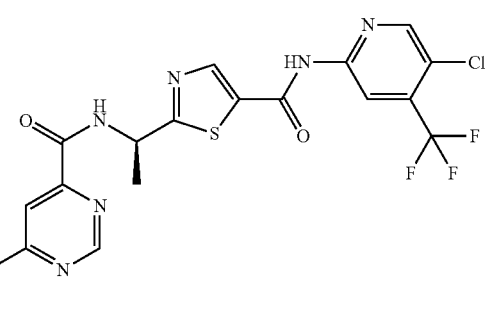 | 1H NMR (400 MHz, DMSO-d6) δ 11.76 (s, 1 H), 9.48 (d, J = 8.1 Hz, 1 H), 8.78 (s, 1 H), 8.75 (s, 1 H), 8.57 (s, 1 H), 8.25 (d, J = 2.0 Hz, 1 H), 7.64 (br. s., 2 H), 5.37 (quin, J = 7.2 Hz, 1 H), 1.62 (d, J = 7.1 Hz, 3 H); m/z 557[M + 1]+ |

TABLE 3-continued

Exemplary Compounds of Formula I

| # | Structure | Characterization Data |
|---|---|---|
| 22 | 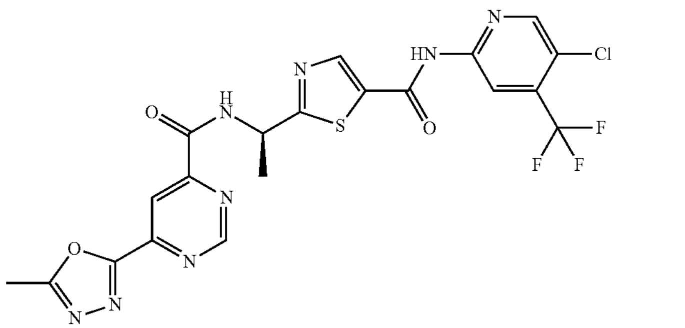 [SMILES: Cc1nnc(-c2cc(C(=O)N[C@H](C)c3ncc(C(=O)Nc4cc(C(F)(F)F)c(Cl)cn4)s3)ncn2)o1] | 1H NMR (400 MHz, DMSO-d6) δ 11.76 (s, 1 H), 10.02 (d, J = 8.1 Hz, 1 H), 9.59 (s, 1 H), 8.78 (s, 1 H), 8.76 (s, 1 H), 8.55 (s, 2 H), 5.51 (quin, J = 7.2 Hz, 1 H), 2.68 (s, 3 H), 1.71 (d, J = 7.1 Hz, 3 H); m/z 539[M + 1]+ |
| 25mDa | 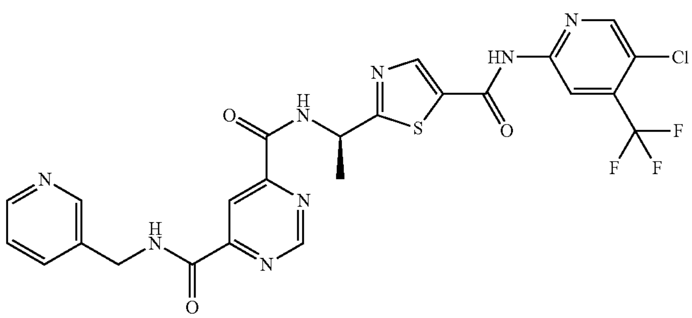 [SMILES: C[C@@H](NC(=O)c1cc(C(=O)NCc2cccnc2)ncn1)c1ncc(C(=O)Nc2cc(C(F)(F)F)c(Cl)cn2)s1] | 1H NMR (400 MHz, DMSO-d6) δ 11.75 (s, 1 H), 9.94 (d, J = 8.1 Hz, 1 H), 9.80 (t, J = 6.3 Hz, 1 H), 9.51 (s, 1 H), 8.78 (s, 1 H), 8.75 (s, 1 H), 8.57 (s, 1 H), 8.55 (s, 1 H), 8.50-8.43 (m, 2 H), 7.75 (d, J = 7.6 Hz, 1 H), 7.35 (dd, J = 4.8, 7.8 Hz, 1 H), 5.50 (quin, J = 7.2 Hz, 1 H), 4.56 (d, J = 6.1 Hz, 2 H), 1.70 (d, J = 7.1 Hz, 3 H); m/z 591 [M + 1]+ |
| 10MM | 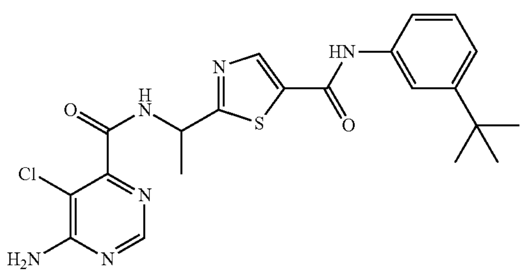 [SMILES: CC(NC(=O)c1ncnc(N)c1Cl)c1ncc(C(=O)Nc2cccc(C(C)(C)C)c2)s1] | m/z 459 [M + 1]+ |
| 10G | 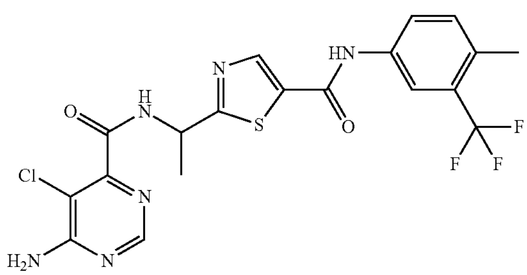 [SMILES: Cc1ccc(NC(=O)c2cnc(C(C)NC(=O)c3ncnc(N)c3Cl)s2)cc1C(F)(F)F] | m/z 485 [M + 1]+ |
| 10K | 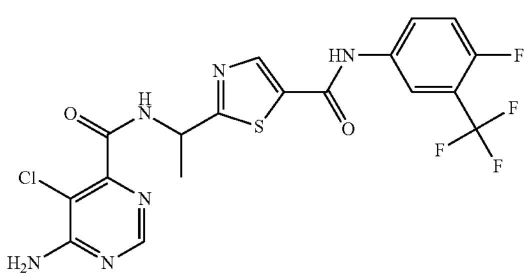 [SMILES: CC(NC(=O)c1ncnc(N)c1Cl)c1ncc(C(=O)Nc2ccc(F)c(C(F)(F)F)c2)s1] | m/z 489 [M + 1]+ |

TABLE 3-continued

Exemplary Compounds of Formula I

| # | Structure | Characterization Data |
|---|---|---|
| 10NN | 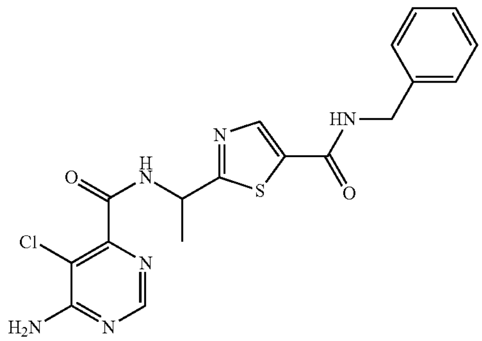 [SMILES: CC(NC(=O)c1ncnc(N)c1Cl)c1ncc(C(=O)NCc2ccccc2)s1] | m/z 417 [M + 1]⁺ |
| 10V | 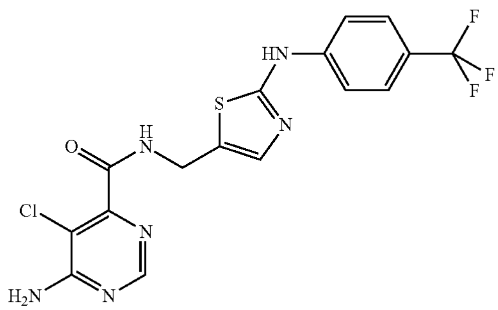 [SMILES: Nc1ncnc(C(=O)NCc2cnc(Nc3ccc(C(F)(F)F)cc3)s2)c1Cl] | m/z 429 [M + 1]⁺ |
| 33aDa | 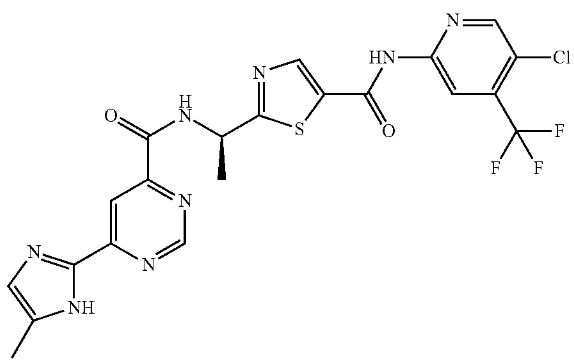 [SMILES: Cc1cnc(-c2cc(C(=O)N[C@H](C)c3ncc(C(=O)Nc4cc(C(F)(F)F)c(Cl)cn4)s3)ncn2)[nH]1] | m/z 537 [M + 1]⁺ |
| 10FF | 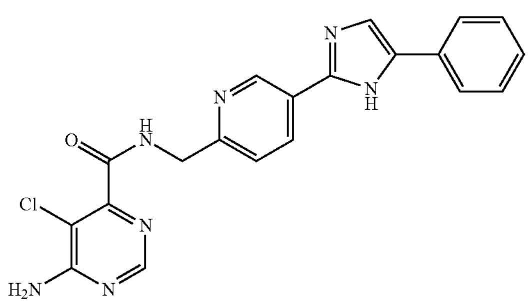 [SMILES: Nc1ncnc(C(=O)NCc2ccc(-c3ncc(-c4ccccc4)[nH]3)cn2)c1Cl] | 1H NMR (DMSO-d6) δ 9.30-9.39 (m, 1H), 9.17 (d, J = 1.8 Hz, 1H), 8.41 (dd, J = 8.3, 2.3 Hz, 1H), 8.37 (s, 1H), 8.15 (s, 1H), 7.86-7.93 (m, 2H), 7.56-7.62 (m, 1H), 7.48-7.55 (m, 2H), 7.37-7.43 (m, 1H), 4.62 (d, J = 6.0 Hz, 2H); m/z = 406 [M + 1]⁺ |
| 23.5 | 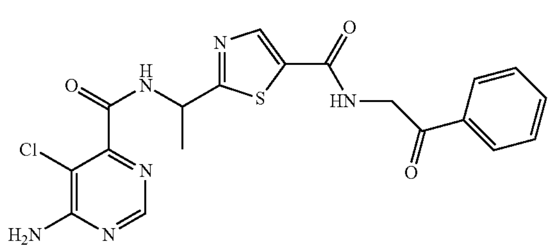 [SMILES: CC(NC(=O)c1ncnc(N)c1Cl)c1ncc(C(=O)NCC(=O)c2ccccc2)s1] | 1H NMR (MeOH-d4) δ 8.34 (d, J = 8.1 Hz, 2H), 8.07 (d, J = 7.1 Hz, 2H), 8.00 (s, 1H), 7.63-7.72 (m, 1H), 7.52-7.60 (m, 2H), 5.46-5.56 (m, 1H), 3.01 (s, 2H), 2.88 (s, 2H), 1.73 (d, J = 7.1 Hz, 3H); m/z = 445 [M + 1]⁺ |

TABLE 3-continued

Exemplary Compounds of Formula I

| # | Structure | Characterization Data |
|---|---|---|
| 23 | 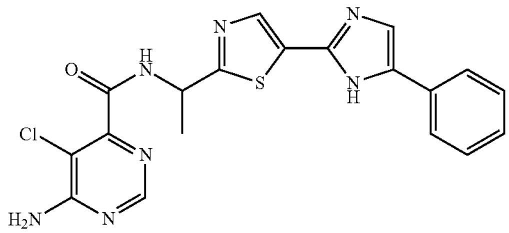 [SMILES: CC(NC(=O)c1ncnc(N)c1Cl)c1ncc(-c2ncc(-c3ccccc3)[nH]2)s1] | 1H NMR (MeOH-d4) δ 8.43 (br. s., 1H), 8.36 (br. s., 1H), 7.93 (s, 1H), 7.76-7.82 (m, 2H), 7.49-7.56 (m, 2H), 7.43-7.49 (m, 1H), 5.54 (q, J = 7.1 Hz, 1H), 2.66 (br. s., 1H), 1.77 (d, J = 7.1 Hz, 3H); m/z = 425 [M + 1]$^+$ |
| 35 | 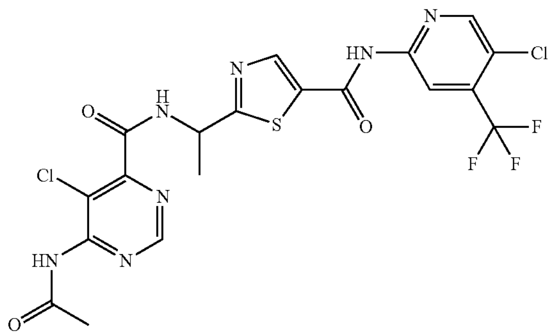 [SMILES: CC(=O)Nc1ncnc(C(=O)NC(C)c2ncc(C(=O)Nc3cc(C(F)(F)F)c(Cl)cn3)s2)c1Cl] | m/z 549 [M + 1]$^+$ |
| 5tDa | 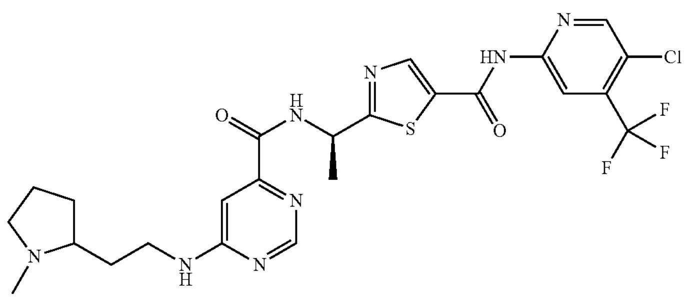 [SMILES: C[C@@H](NC(=O)c1cc(NCCC2CCCN2C)ncn1)c1ncc(C(=O)Nc2cc(C(F)(F)F)c(Cl)cn2)s1] | m/z 584 [M + 1]$^+$ |
| 36 | 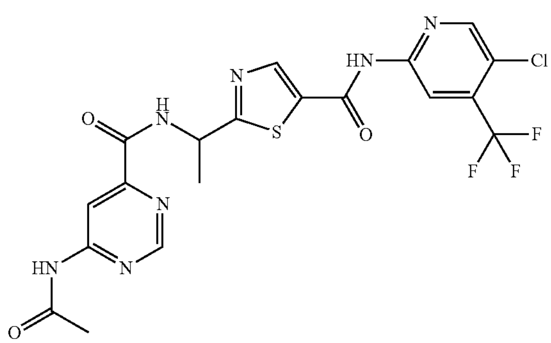 | $^1$H NMR (400 MHz, MeOD) δ = 8.93 (s, 1 H), 8.76 (s, 1 H), 8.61 (s, 1 H), 8.57 (s, 1 H), 8.51 (s, 1 H), 5.55 (q, J = 6.9 Hz, 1 H), 2.21 (s, 3 H), 1.76 (d, J = 7.1 Hz, 2 H); m/z 472 [M + 1 − Ac]$^+$ |
| 5yDa | 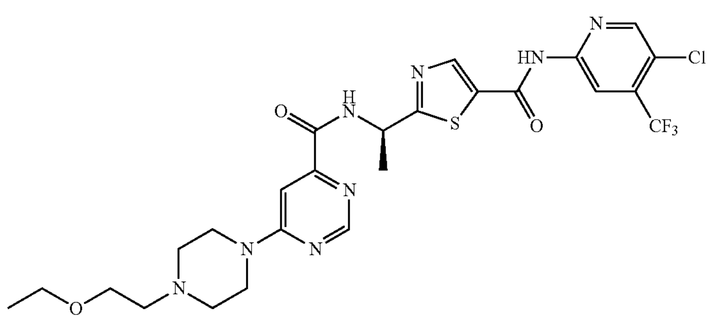 [SMILES: CCOCCN1CCN(c2cc(C(=O)N[C@H](C)c3ncc(C(=O)Nc4cc(C(F)(F)F)c(Cl)cn4)s3)ncn2)CC1] | $^1$H NMR (400 MHz, DMSO-d$_6$) δ = 11.74 (s, 1 H), 9.50 (d, J = 7.6 Hz, 1 H), 8.78 (s, 1 H), 8.74 (d, J = 2.5 Hz, 1 H), 8.62 (s, 1 H), 8.55 (s, 1 H), 7.31 (s, 1 H), 5.41 (m, 1 H), 3.76-3.62 (m, 4 H), 3.50 (t, J = 5.6 Hz, 2 H), 3.42 (q, J = 7.1 Hz, 2 H), 3.36-3.30 (m, 4 H), 1.66 (d, J = 6.6 Hz, 3 H), 1.11 (t, J = 7.1 Hz, 3 H); m/z 614 [M + 1]$^+$ |

TABLE 3-continued

Exemplary Compounds of Formula I

| # | Structure | Characterization Data |
|---|-----------|----------------------|
| 5zDa | 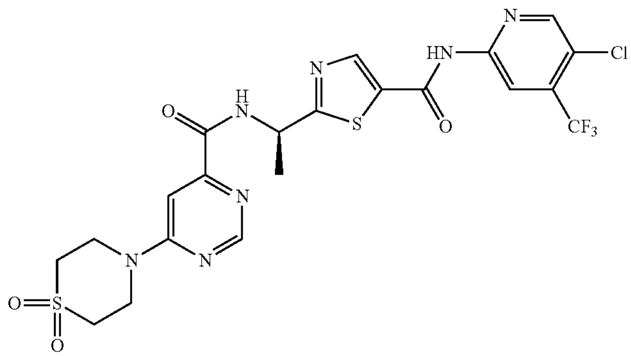 [SMILES: C[C@@H](NC(=O)c1cc(N2CCS(=O)(=O)CC2)ncn1)c1ncc(C(=O)Nc2cc(C(F)(F)F)c(Cl)cn2)s1] | $^1$H NMR (400 MHz, DMSO-$d_6$) δ = 11.75 (s, 1 H), 9.58 (d, J = 8.6 Hz, 1 H), 8.78 (s, 1 H), 8.74 (d, J = 2.5 Hz, 1 H), 8.72 (s, 1 H), 8.55 (s, 1 H), 7.52 (s, 1 H), 5.48-5.39 (m, 1 H), 4.18 (br. s., 4 H), 3.21 (br. s., 4 H), 1.67 (d, 3 H); m/z 591 [M + 1]$^+$ |
| 5aaDa | 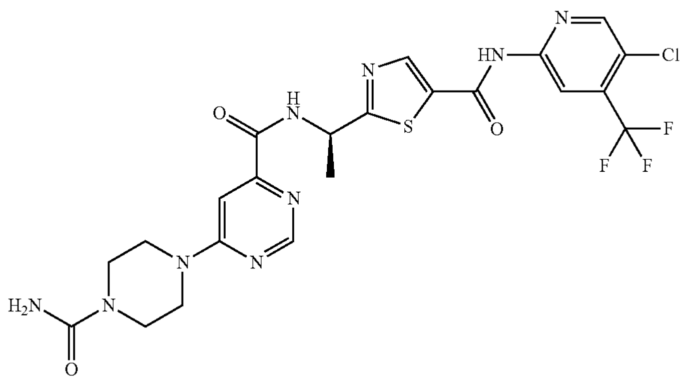 [SMILES: C[C@@H](NC(=O)c1cc(N2CCN(C(N)=O)CC2)ncn1)c1ncc(C(=O)Nc2cc(C(F)(F)F)c(Cl)cn2)s1] | m/z 584 [M + 1]$^+$ |
| 3bB | 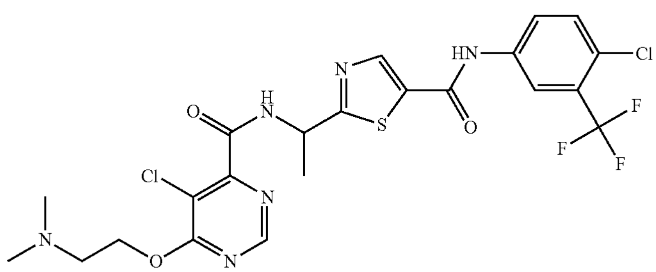 | m/z 564 [M + 1]$^+$ |
| 3bC | 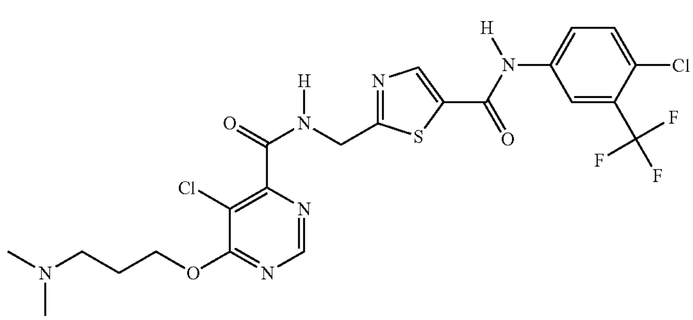 [SMILES: CN(C)CCCOc1ncnc(C(=O)NCc2ncc(C(=O)Nc3ccc(Cl)c(C(F)(F)F)c3)s2)c1Cl] | m/z 578 [M + 1]$^+$ |

TABLE 3-continued

Exemplary Compounds of Formula I

| # | Structure | Characterization Data |
|---|-----------|----------------------|
| 4dB | 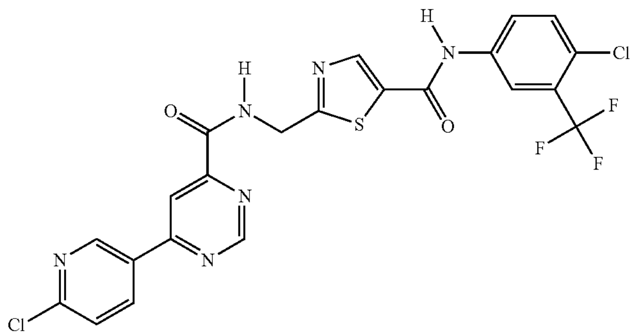 [SMILES: O=C(NCc1ncc(C(=O)Nc2ccc(Cl)c(C(F)(F)F)c2)s1)c1cc(-c2ccc(Cl)nc2)ncn1] | m/z 554 [M + 1]+ |
| 4cB | 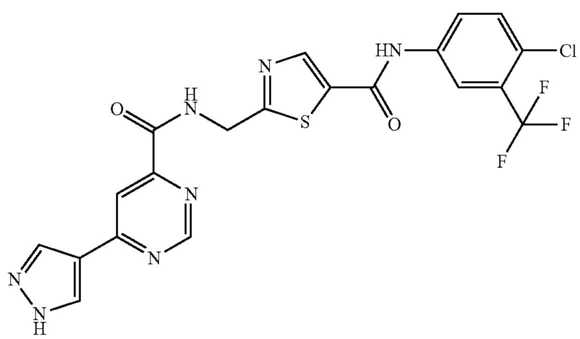 [SMILES: O=C(NCc1ncc(C(=O)Nc2ccc(Cl)c(C(F)(F)F)c2)s1)c1cc(-c2cn[nH]c2)ncn1] | m/z 508 [M + 1]+ |
| 1rA | 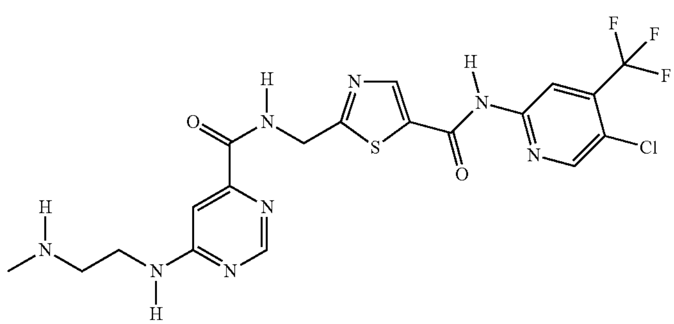 | m/z 536 [M + 1]+ |
| 14dA | 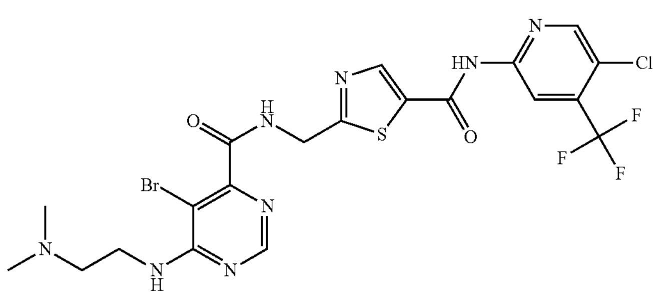 [SMILES: CN(C)CCNc1ncnc(C(=O)NCc2ncc(C(=O)Nc3cc(C(F)(F)F)c(Cl)cn3)s2)c1Br] | m/z 608 [M + 1]+ |

TABLE 3-continued

Exemplary Compounds of Formula I

| # | Structure | Characterization Data |
|---|---|---|
| 18dDa | 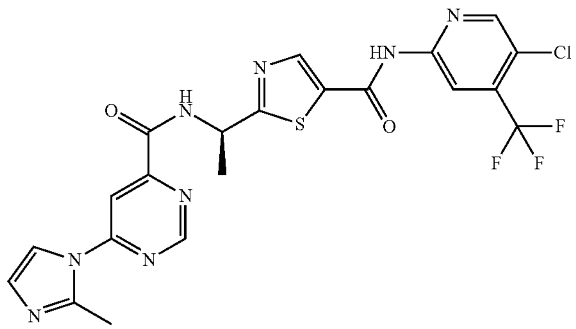 [SMILES: Cc1nccn1-c1cc(C(=O)N[C@H](C)c2ncc(C(=O)Nc3cc(C(F)(F)F)c(Cl)cn3)s2)ncn1] | $^1$H NMR (400 MHz, DMSO-$d_6$) δ = 11.76 (s, 1 H), 9.91 (d, J = 8.1 Hz, 1 H), 9.32 (s, 1 H), 8.78 (s, 1 H), 8.76 (d, J = 2.5 Hz, 1 H), 8.55 (s, 1 H), 8.21 (s, 1 H), 7.98 (s, 1 H), 7.00 (s, 1 H), 5.54-5.44 (m, 1 H), 2.69 (s, 3 H), 1.71 (d, J = 7.1 Hz, 3 H); m/z 537 [M + 1]$^+$ |
| 33bDa | 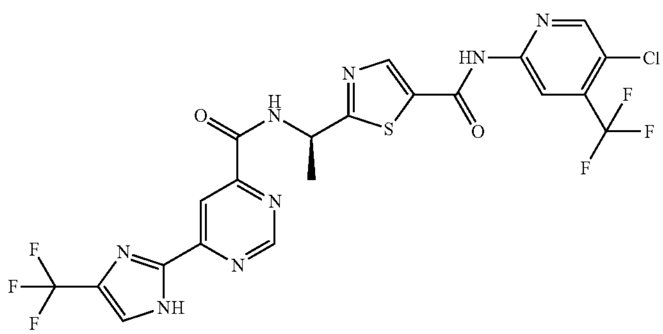 [SMILES: C[C@@H](NC(=O)c1cc(-c2nc(C(F)(F)F)c[nH]2)ncn1)c1ncc(C(=O)Nc2cc(C(F)(F)F)c(Cl)cn2)s1] | $^1$H NMR (400 MHz, DMSO-$d_6$) δ = 14.11 (br. s., 1 H), 11.76 (s, 1 H), 9.90 (d, J = 8.1 Hz, 1 H), 9.44 (s, 1 H), 8.78 (s, 1 H), 8.76 (d, J = 2.5 Hz, 1 H), 8.56 (s, 1 H), 8.53 (s, 1 H), 8.11 (s, 1 H), 5.63-5.41 (m, 1 H), 1.71 (d, J = 7.1 Hz, 3 H); m/z 591 [M + 1]$^+$ |
| 10GG | 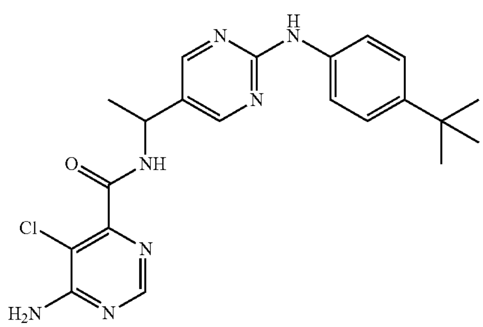 | m/z: 426 [M + 1]$^+$ |
| 10Z | 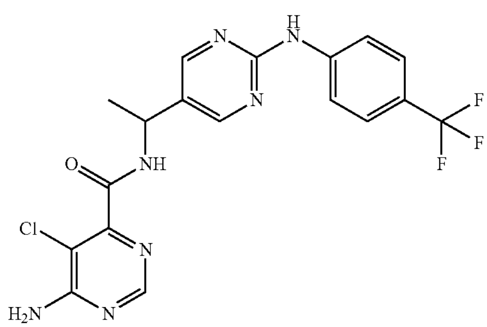 [SMILES: CC(NC(=O)c1ncnc(N)c1Cl)c1cnc(Nc2ccc(C(F)(F)F)cc2)nc1] | m/z: 438 [M + 1]$^+$ |

TABLE 3-continued

Exemplary Compounds of Formula I

| # | Structure | Characterization Data |
|---|---|---|
| 10X | 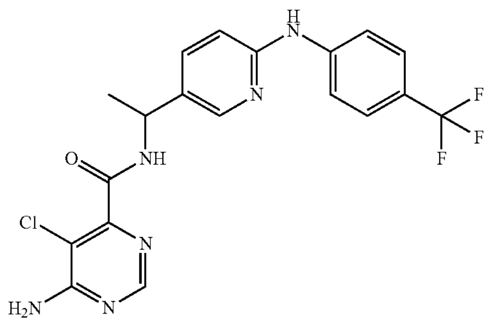 [SMILES: CC(NC(=O)c1ncnc(N)c1Cl)c1ccc(Nc2ccc(C(F)(F)F)cc2)nc1] | m/z: 437 [M + 1]+ |
| 10Y | 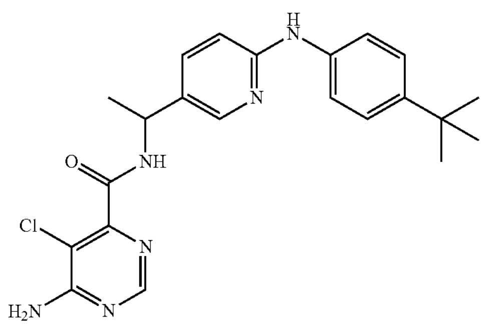 [SMILES: CC(NC(=O)c1ncnc(N)c1Cl)c1ccc(Nc2ccc(C(C)(C)C)cc2)nc1] | m/z: 425 [M + 1]+ |
| 10HH | 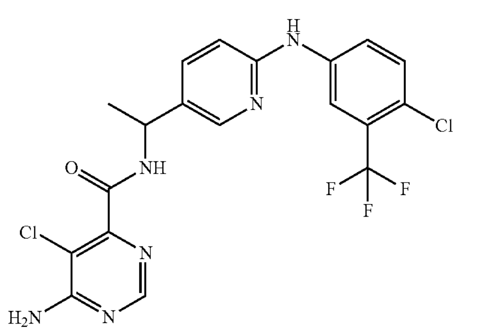 [SMILES: CC(NC(=O)c1ncnc(N)c1Cl)c1ccc(Nc2ccc(Cl)c(C(F)(F)F)c2)nc1] | m/z: 471 [M + 1]+ |
| 17Da | 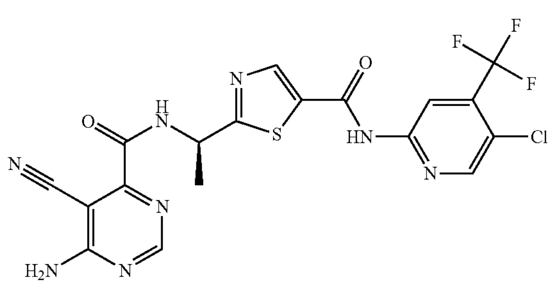 [SMILES: C[C@@H](NC(=O)c1ncnc(N)c1C#N)c1ncc(C(=O)Nc2cc(C(F)(F)F)c(Cl)cn2)s1] | 1H NMR (400 MHz, CHLOROFORM-d) δ 8.68 (s, 1H), 8.66 (s, 1H), 8.55-8.59 (m, 1H), 8.52 (br. s., 1H), 8.45 (s, 1H), 8.30 (s, 1H), 5.97 (br. s., 2H), 5.55-5.65 (m, 1H), 1.80 (d, J = 6.95 Hz, 3H); LCMS: m/z: 497 [M + 1]+ |

TABLE 3-continued

Exemplary Compounds of Formula I

| # | Structure | Characterization Data |
|---|---|---|
| 14aOO | 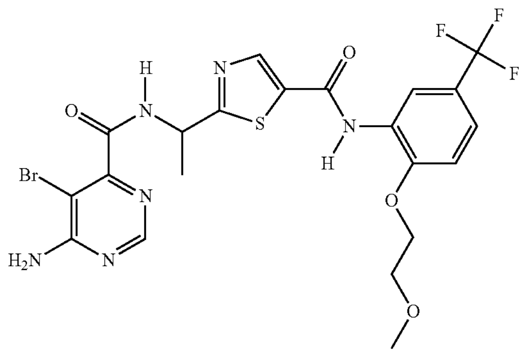 [SMILES: COCCOc1ccc(C(F)(F)F)cc1NC(=O)c1cnc(C(C)NC(=O)c2ncnc(N)c2Br)s1] | 1H NMR (400 MHz, CHLOROFORM-d) δ 8.79 (d, J = 2.02 Hz, 1H), 8.63 (d, J = 8.08 Hz, 1H), 8.50 (s, 1H), 8.44 (d, J = 3.41 Hz, 2H), 7.35 (ddd, J = 0.76, 2.18, 8.56 Hz, 1H), 6.94 (d, J = 8.59 Hz, 1H), 5.96 (br. s., 2H), 5.51-5.62 (m, 1H), 4.59 (dt, J = 2.04, 6.79 Hz, 2H), 4.31 (t, J = 4.42 Hz, 2H), 2.10 (s, 3H), 1.78 (d, 3H) |
| 14aPP | 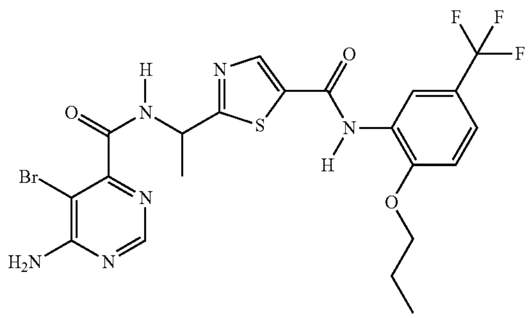 [SMILES: CCCOc1ccc(C(F)(F)F)cc1NC(=O)c1cnc(C(C)NC(=O)c2ncnc(N)c2Br)s1] | LCMS: m/z: 573 [M + 1]+ |
| 14aQQ | 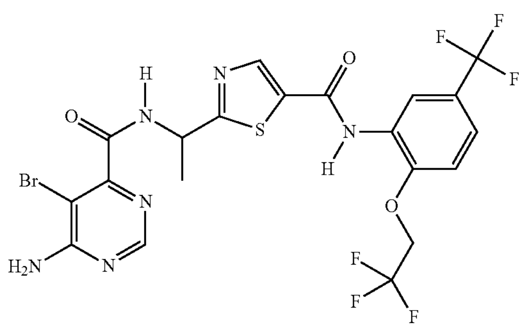 [SMILES: CC(NC(=O)c1ncnc(N)c1Br)c1ncc(C(=O)Nc2cc(C(F)(F)F)ccc2OCC(F)(F)F)s1] | LCMS: m/z: 614 [M + 1]+ |
| 14aRR | 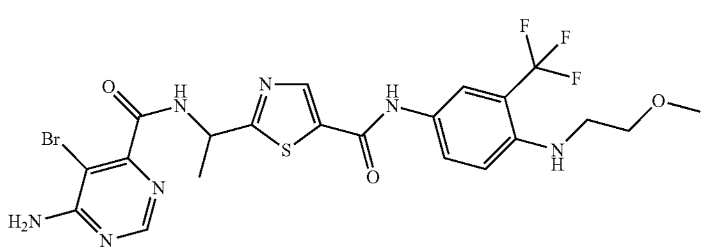 [SMILES: COCCNc1ccc(NC(=O)c2cnc(C(C)NC(=O)c3ncnc(N)c3Br)s2)cc1C(F)(F)F] | LCMS: m/z: 589 [M + 1]+ |
| 10SS | 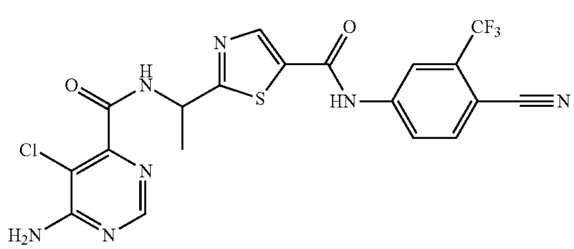 [SMILES: CC(NC(=O)c1ncnc(N)c1Cl)c1ncc(C(=O)Nc2ccc(C#N)c(C(F)(F)F)c2)s1] | LCMS: m/z: 496 [M + 1]+ |

TABLE 3-continued
Exemplary Compounds of Formula I
| # | Structure | Characterization Data |
|---|-----------|----------------------|
| 14aK | 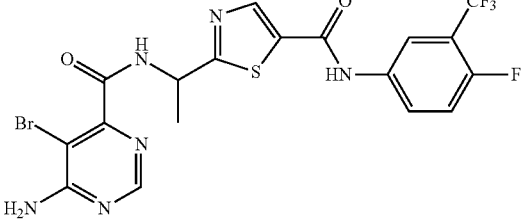 | LCMS: m/z: 534 [M + 1]+ |
| 14aTT | 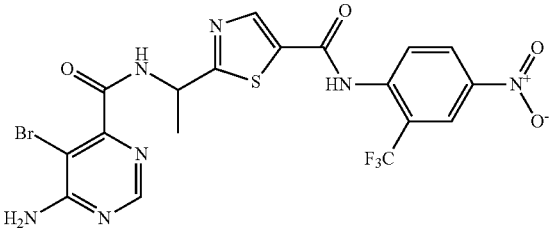 [SMILES: CC(NC(=O)c1ncnc(N)c1Br)c1ncc(C(=O)Nc2ccc([N+](=O)[O-])cc2C(F)(F)F)s1] | LCMS: m/z: 559 [M + 1]+ |
| 4uDa | 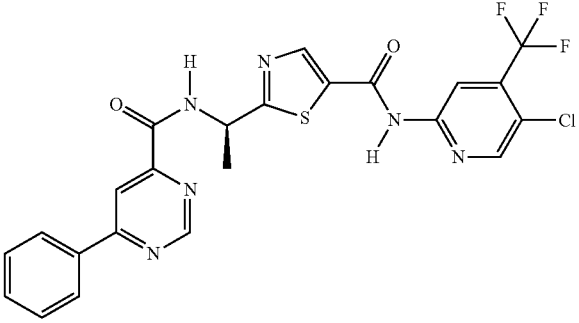 [SMILES: C[C@@H](NC(=O)c1cc(-c2ccccc2)ncn1)c1ncc(C(=O)Nc2cc(C(F)(F)F)c(Cl)cn2)s1] | LCMS: m/z: 533 [M + 1]+ |
| 25aD | 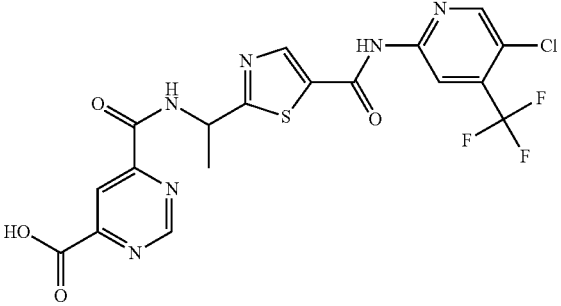 [SMILES: CC(NC(=O)c1cc(C(=O)O)ncn1)c1ncc(C(=O)Nc2cc(C(F)(F)F)c(Cl)cn2)s1] | m/z 501 [M + 1]+ |
| 25cD | 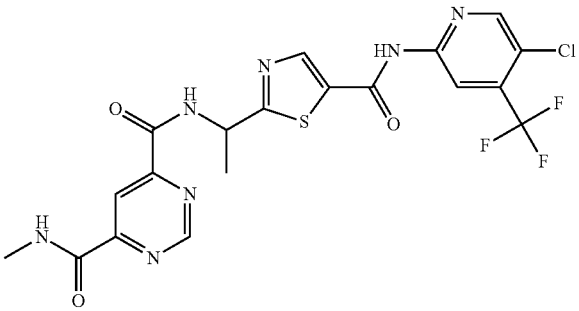 [SMILES: CNC(=O)c1cc(C(=O)NC(C)c2ncc(C(=O)Nc3cc(C(F)(F)F)c(Cl)cn3)s2)ncn1] | m/z 514 [M + 1]+ |

TABLE 3-continued

Exemplary Compounds of Formula I

| # | Structure | Characterization Data |
|---|---|---|
| 6kD | 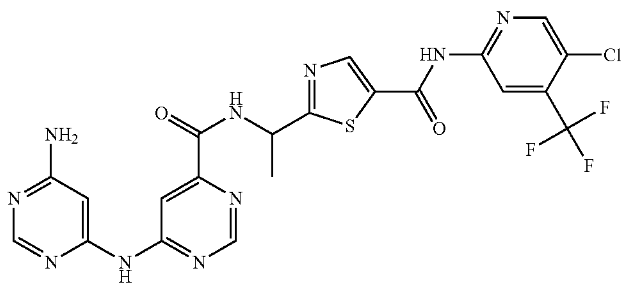 [SMILES: CC(NC(=O)c1cc(Nc2cc(N)ncn2)ncn1)c1ncc(C(=O)Nc2cc(C(F)(F)F)c(Cl)cn2)s1] | m/z 565 [M + 1]+ |
| 29b | 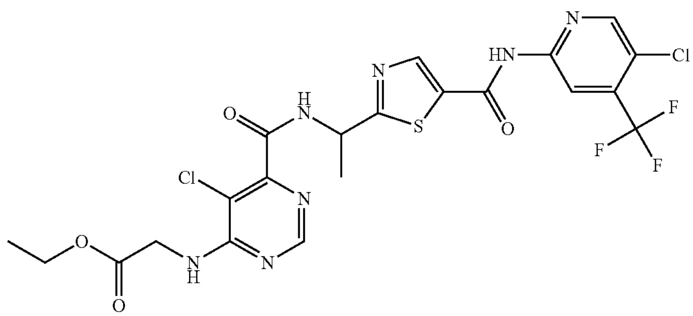 [SMILES: CCOC(=O)CNc1ncnc(C(=O)NC(C)c2ncc(C(=O)Nc3cc(C(F)(F)F)c(Cl)cn3)s2)c1Cl] | m/z 592 [M + 1]+ |
| 29a | 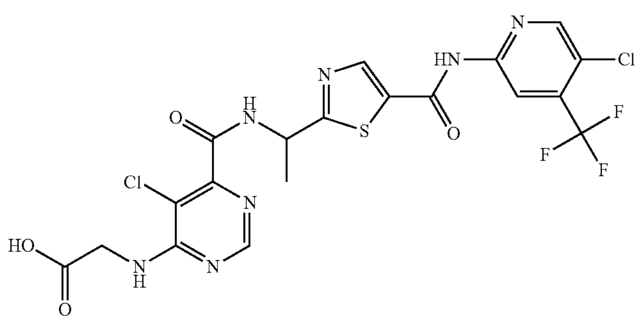 [SMILES: CC(NC(=O)c1ncnc(NCC(=O)O)c1Cl)c1ncc(C(=O)Nc2cc(C(F)(F)F)c(Cl)cn2)s1] | m/z 564 [M + 1]+ |
| 24a | 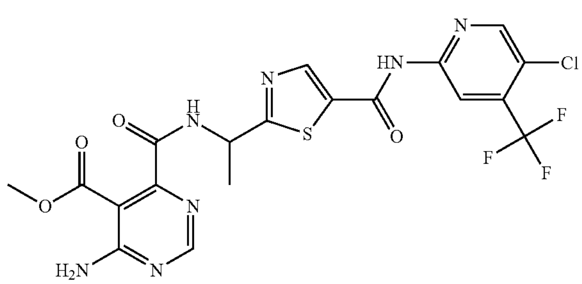 [SMILES: COC(=O)c1c(N)ncnc1C(=O)NC(C)c1ncc(C(=O)Nc2cc(C(F)(F)F)c(Cl)cn2)s1] | m/z 530 [M + 1]+ |
| 24b | 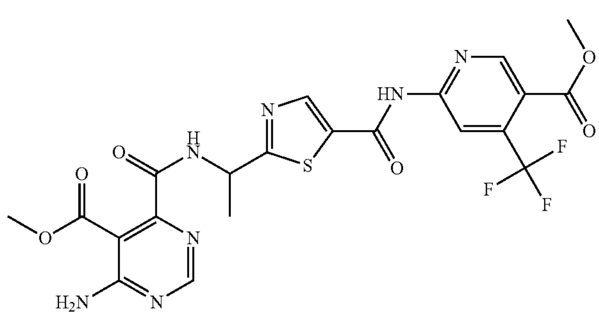 [SMILES: COC(=O)c1cnc(NC(=O)c2cnc(C(C)NC(=O)c3ncnc(N)c3C(=O)OC)s2)cc1C(F)(F)F] | m/z 554 [M + 1]+ |

TABLE 3-continued

Exemplary Compounds of Formula I

| # | Structure | Characterization Data |
|---|-----------|----------------------|
| 25dD | 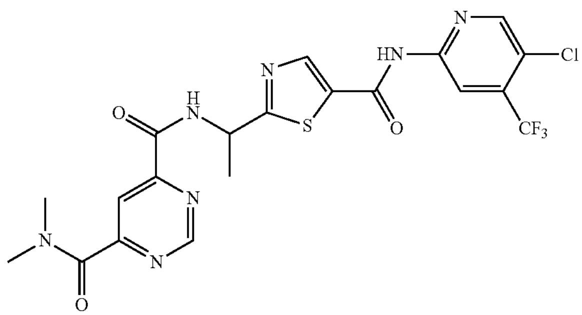 [SMILES: CC(NC(=O)c1cc(C(=O)N(C)C)ncn1)c1ncc(C(=O)Nc2cc(C(F)(F)F)c(Cl)cn2)s1] | m/z 528 [M + 1]+ |
| 37 | 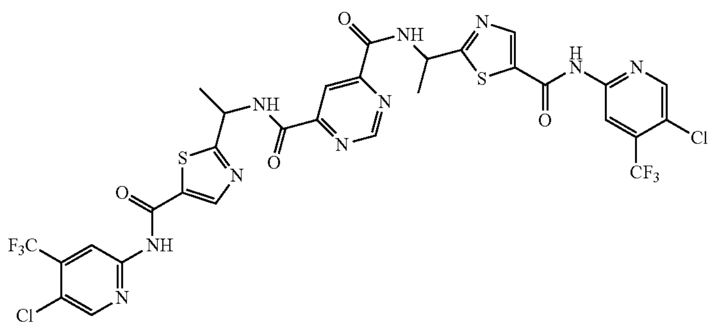 [SMILES: CC(NC(=O)c1cc(C(=O)NC(C)c2ncc(C(=O)Nc3cc(C(F)(F)F)c(Cl)cn3)s2)ncn1)c1ncc(C(=O)Nc2cc(C(F)(F)F)c(Cl)cn2)s1] | m/z 833 [M + 1]+ |
| 25eD | 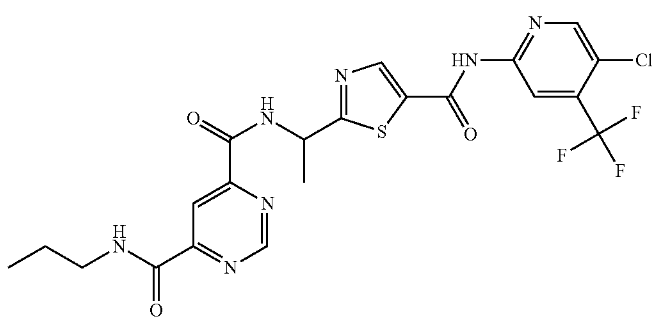 [SMILES: CCCNC(=O)c1cc(C(=O)NC(C)c2ncc(C(=O)Nc3cc(C(F)(F)F)c(Cl)cn3)s2)ncn1] | m/z 542 [M + 1]+ |
| 1tD | 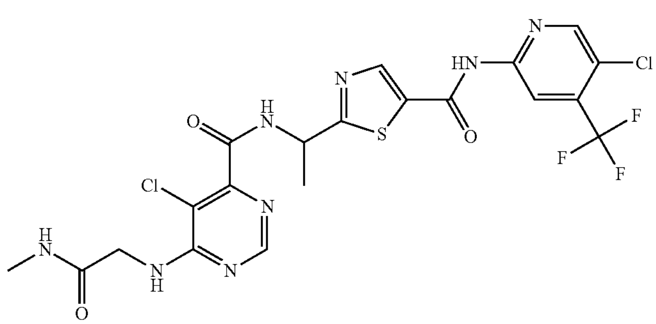 [SMILES: CNC(=O)CNc1ncnc(C(=O)NC(C)c2ncc(C(=O)Nc3cc(C(F)(F)F)c(Cl)cn3)s2)c1Cl] | m/z 577 [M + 1]+ |

TABLE 3-continued
Exemplary Compounds of Formula I
| # | Structure | Characterization Data |
|---|-----------|----------------------|
| 25fD | 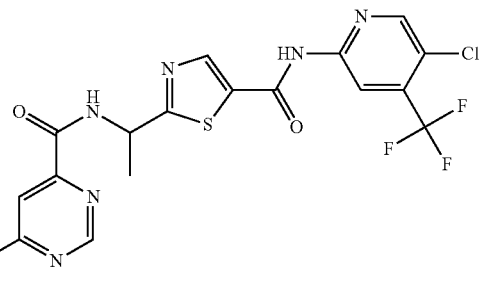 | ¹H NMR (400 MHz, DMSO-d₆) δ = 11.77 (s, 1 H), 9.96 (d, J = 8.1 Hz, 1 H), 9.54 (d, J = 1.3 Hz, 1 H), 9.33 (t, J = 6.1 Hz, 1 H), 8.78 (s, 1 H), 8.76 (s, 1 H), 8.55 (d, J = 0.6 Hz, 1 H), 8.49 (d, J = 1.3 Hz, 1 H), 8.02 - 7.66 (m, 3 H), 7.78 (br. s., 2 H), 5.80-5.30 (m, 1 H), 3.74-3.40 (m, 2 H), 3.15-2.91 (m, 2 H), 1.70 (d, J = 7.0 Hz, 3 H); m/z 543 [M + 1]⁺ |
| 25gD | 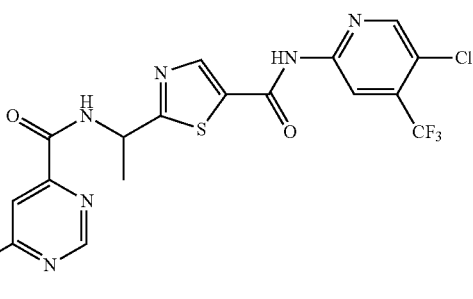 | m/z 544 [M + 1]⁺ |
| 25hD | 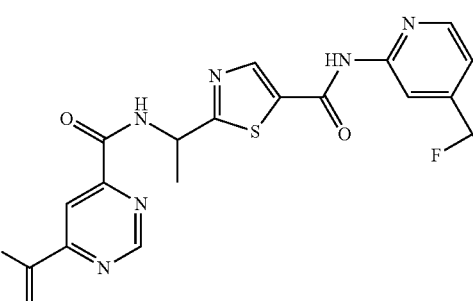 | m/z 585 [M + 1]⁺ |
| 25iD | 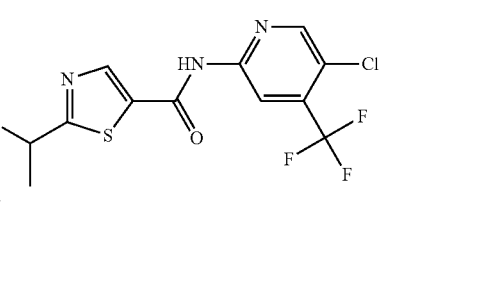 | ¹H NMR (400 MHz, DMSO-d₆) δ = 11.72 (br. s., 1 H), 9.93 (d, J = 8.6 Hz, 1 H), 9.50 (s, 1 H), 8.77 (s, 1 H), 8.75 (s, 1 H), 8.55 (s, 1 H), 8.47 (s, 1 H), 8.46-8.41 (m, 1 H), 8.10 (s, 1 H), 5.54-5.45 (m, 1 H), 1.70 (d, J = 7.1 Hz, 3 H); m/z 500 [M + 1]⁺ |

TABLE 3-continued

Exemplary Compounds of Formula I

| # | Structure | Characterization Data |
|---|---|---|
| 25jD | 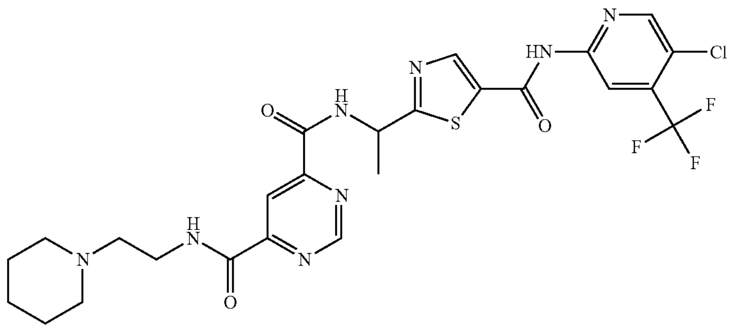 [SMILES: CC(NC(=O)c1cc(C(=O)NCCN2CCCCC2)ncn1)c1ncc(C(=O)Nc2cc(C(F)(F)F)c(Cl)cn2)s1] | m/z 611 [M + 1]+ |
| 25kD | 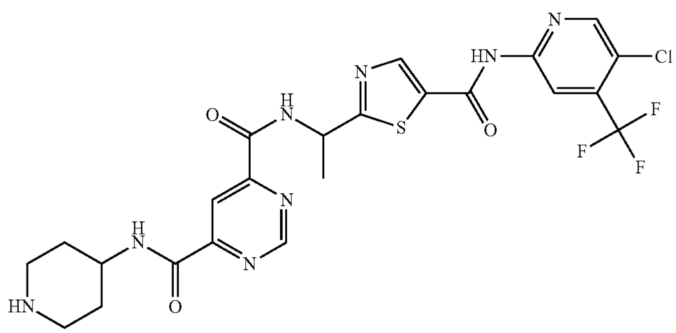 [SMILES: CC(NC(=O)c1cc(C(=O)NC2CCNCC2)ncn1)c1ncc(C(=O)Nc2cc(C(F)(F)F)c(Cl)cn2)s1] | m/z 583 [M + 1]+ |
| 25lD | 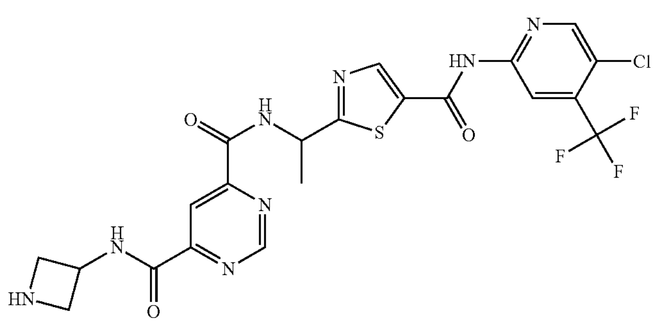 [SMILES: CC(NC(=O)c1cc(C(=O)NC2CNC2)ncn1)c1ncc(C(=O)Nc2cc(C(F)(F)F)c(Cl)cn2)s1] | ¹H NMR (400 MHz, DMSO-d₆) δ = 9.94 (d, 1 H), 9.76 (d, 1 H), 9.53 (s, 1 H), 8.77 (s, 1 H), 8.75 (s, 1 H), 8.55 (s, 1 H), 8.45 (s, 1 H), 8.37 (s, 1 H), 5.54-5.46 (m, 1 H), 4.90-4.80 (m, 1 H), 3.98-3.89 (m, 4 H), 1.70 (d, J = 7.1 Hz, 3 H); m/z 555 [M + 1]+ |
| 38 | 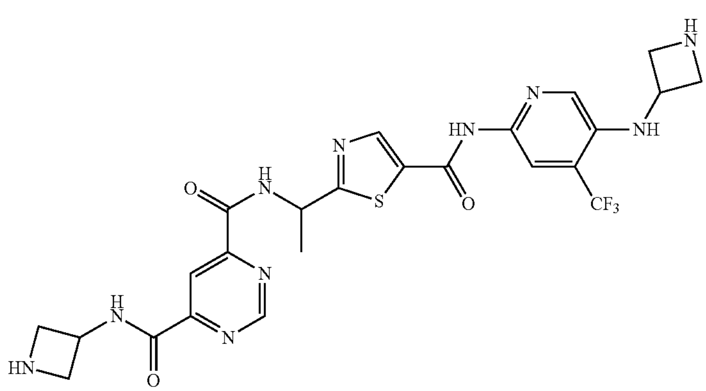 [SMILES: CC(NC(=O)c1cc(C(=O)NC2CNC2)ncn1)c1ncc(C(=O)Nc2cc(C(F)(F)F)c(NC3CNC3)cn2)s1] | m/z 591 [M + 1]+ |

TABLE 3-continued

Exemplary Compounds of Formula I

| # | Structure | Characterization Data |
|---|---|---|
| 25lDa | 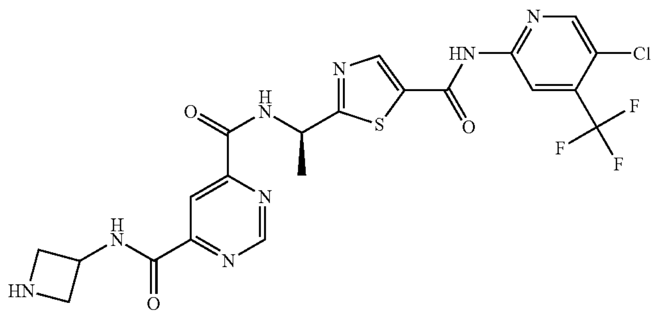 [SMILES: C[C@@H](NC(=O)c1cc(C(=O)NC2CNC2)ncn1)c1ncc(C(=O)Nc2cc(C(F)(F)F)c(Cl)cn2)s1] | $^1$H NMR (400 MHz, DMSO-d$_6$) δ = 9.94 (d, 1 H), 9.76 (d, 1 H), 9.53 (s, 1 H), 8.77 (s, 1 H), 8.75 (s, 1 H), 8.55 (s, 1 H), 8.45 (s, 1 H), 8.37 (s, 1 H), 5.54-5.46 (m, 1 H), 4.90-4.80 (m, 1 H), 3.98-3.89 (m, 4 H), 1.70 (d, J = 7.1 Hz, 3 H); m/z 555 [M + 1]$^+$ |
| 25bDa | 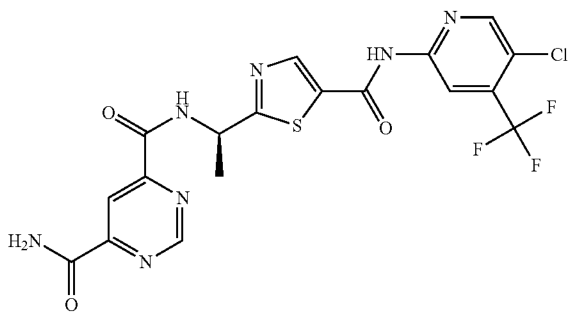 [SMILES: C[C@@H](NC(=O)c1cc(C(N)=O)ncn1)c1ncc(C(=O)Nc2cc(C(F)(F)F)c(Cl)cn2)s1] | $^1$H NMR (400 MHz, DMSO-d$_6$) δ = 11.72 (br. s., 1 H), 9.93 (d, J = 8.6 Hz, 1 H), 9.50 (s, 1 H), 8.77 (s, 1 H), 8.75 (s, 1 H), 8.55 (s, 1 H), 8.47 (s, 1 H), 8.46-8.41 (m, 1 H), 8.10 (s, 1 H), 5.54-5.45 (m, 1 H), 1.70 (d, J = 7.1 Hz, 3 H); m/z 500 [M + 1]$^+$ |
| 25nDa | 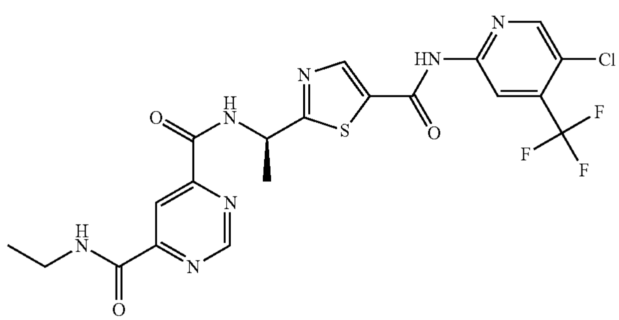 [SMILES: CCNC(=O)c1cc(C(=O)N[C@H](C)c2ncc(C(=O)Nc3cc(C(F)(F)F)c(Cl)cn3)s2)ncn1] | m/z 528 [M + 1]$^+$ |
| 1tDa | 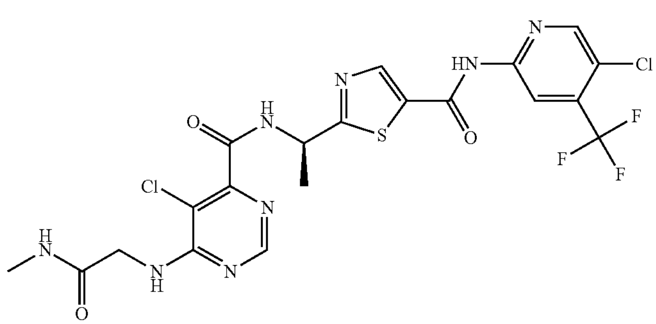 [SMILES: CNC(=O)CNc1ncnc(C(=O)N[C@H](C)c2ncc(C(=O)Nc3cc(C(F)(F)F)c(Cl)cn3)s2)c1Cl] | m/z 577 [M + 1]$^+$ |

TABLE 3-continued
Exemplary Compounds of Formula I
| # | Structure | Characterization Data |
|---|-----------|----------------------|
| 25kDa | 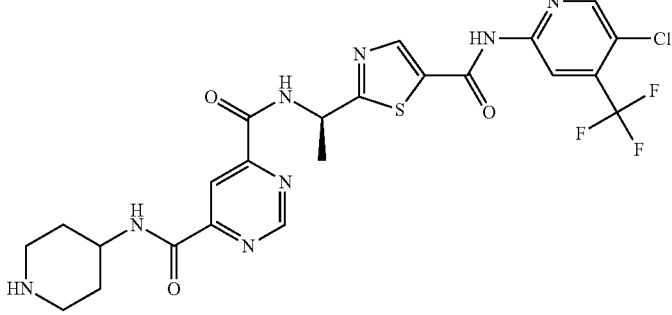 | m/z 583 [M + 1]⁺ |
| 25cDa | 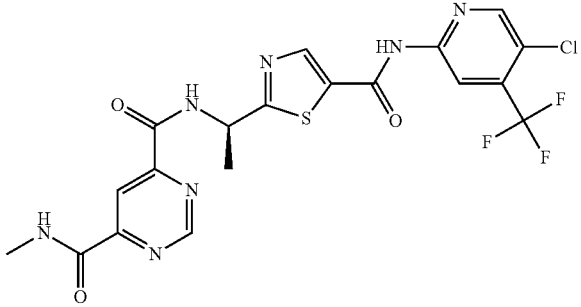 [SMILES: CNC(=O)c1cc(C(=O)N[C@H](C)c2ncc(C(=O)Nc3cc(C(F)(F)F)c(Cl)cn3)s2)ncn1] | m/z 514 [M + 1]⁺ |
| 10LL | 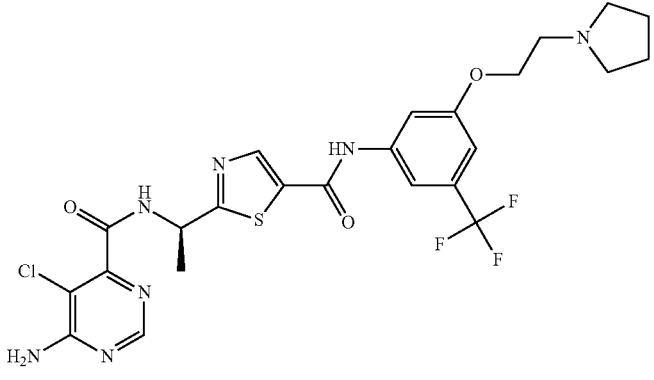 [SMILES: C[C@@H](NC(=O)c1ncnc(N)c1Cl)c1ncc(C(=O)Nc2cc(OCCN3CCCC3)cc(C(F)(F)F)c2)s1] | m/z 584 [M + 1]⁺ |
| 10EE | 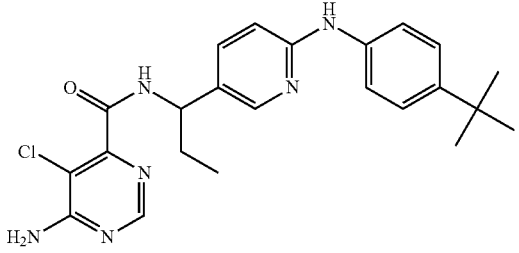 [SMILES: CCC(NC(=O)c1ncnc(N)c1Cl)c1ccc(Nc2ccc(C(C)(C)C)cc2)nc1] | m/z 439 [M + 1]⁺ |

TABLE 3-continued

Exemplary Compounds of Formula I

| # | Structure | Characterization Data |
|---|-----------|----------------------|
| 10EEa | 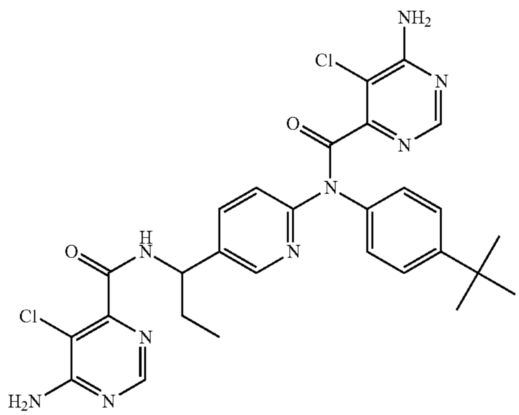 [SMILES: CCC(NC(=O)c1ncnc(N)c1Cl)c1ccc(N(C(=O)c2ncnc(N)c2Cl)c2ccc(C(C)(C)C)cc2)nc1] | m/z 594 [M + 1]+ |
| 10II | 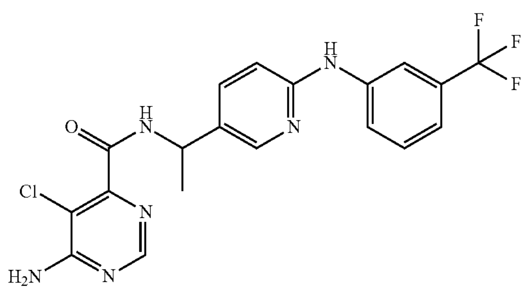 [SMILES: CC(NC(=O)c1ncnc(N)c1Cl)c1ccc(Nc2cccc(C(F)(F)F)c2)nc1] | m/z 437 [M + 1]+ |
| 10DD | 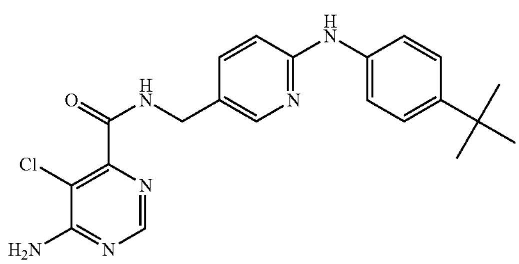 [SMILES: CC(C)(C)c1ccc(Nc2ccc(CNC(=O)c3ncnc(N)c3Cl)cn2)cc1] | m/z 411 [M + 1]+ |
| 10DDa | 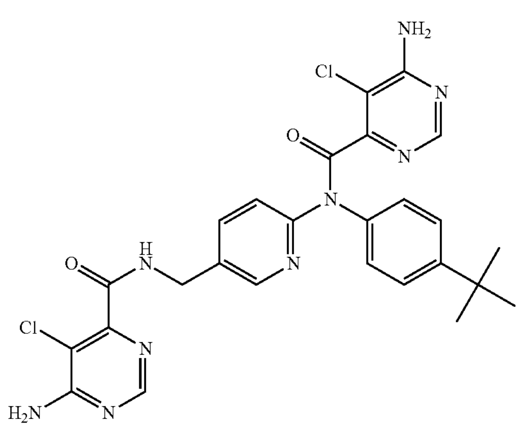 [SMILES: CC(C)(C)c1ccc(N(C(=O)c2ncnc(N)c2Cl)c2ccc(CNC(=O)c3ncnc(N)c3Cl)cn2)cc1] | m/z 566 [M + 1]+ |

TABLE 3-continued

Exemplary Compounds of Formula I

| # | Structure | Characterization Data |
|---|---|---|
| 10W | 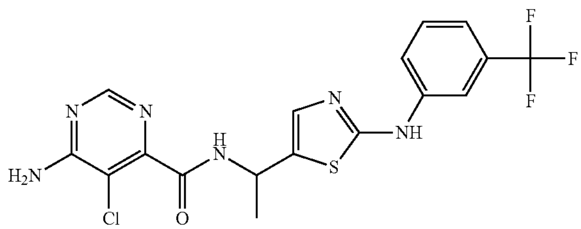 [SMILES: CC(NC(=O)c1ncnc(N)c1Cl)c1cnc(Nc2cccc(C(F)(F)F)c2)s1] | m/z 443 [M + 1]+ |
| 15eNa | 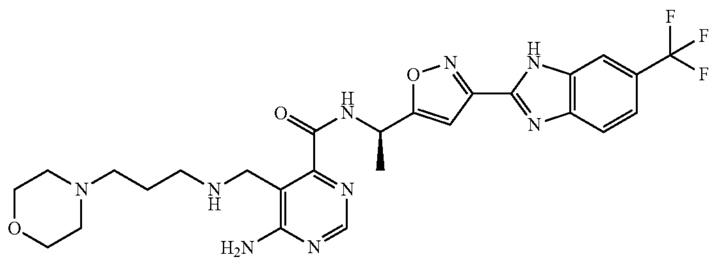 [SMILES: C[C@@H](NC(=O)c1ncnc(N)c1CNCCCN1CCOCC1)c1cc(-c2nc3ccc(C(F)(F)F)cc3[nH]2)no1] | m/z 574 [M + 1]+ |
| 15eDa | 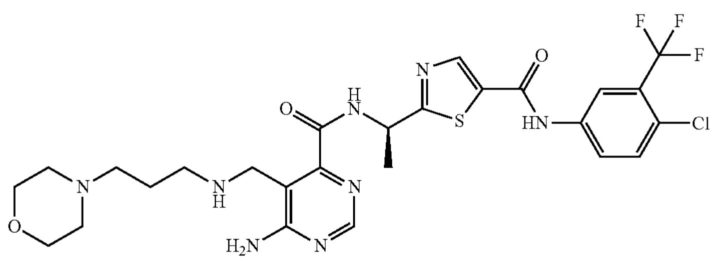 [SMILES: C[C@@H](NC(=O)c1ncnc(N)c1CNCCCN1CCOCC1)c1ncc(C(=O)Nc2ccc(Cl)c(C(F)(F)F)c2)s1] | m/z 628 [M + 1]+ |
| 39aNa | 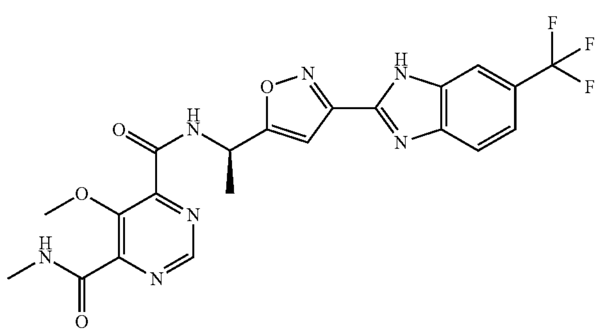 [SMILES: CNC(=O)c1ncnc(C(=O)N[C@H](C)c2cc(-c3nc4ccc(C(F)(F)F)cc4[nH]3)no2)c1OC] | m/z 490 [M + 1]+ |
| 39aEa | 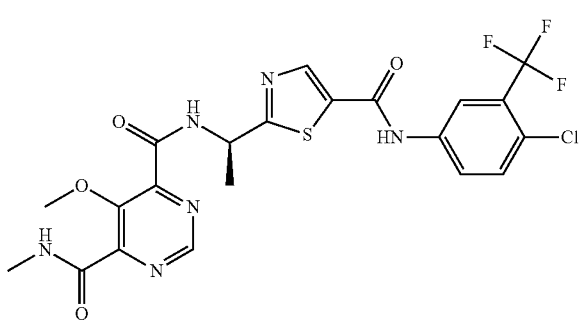 [SMILES: CNC(=O)c1ncnc(C(=O)N[C@H](C)c2ncc(C(=O)Nc3ccc(Cl)c(C(F)(F)F)c3)s2)c1OC] | m/z 544 [M + 1]+ |

TABLE 3-continued

Exemplary Compounds of Formula I

| # | Structure | Characterization Data |
|---|---|---|
| 39bNa | 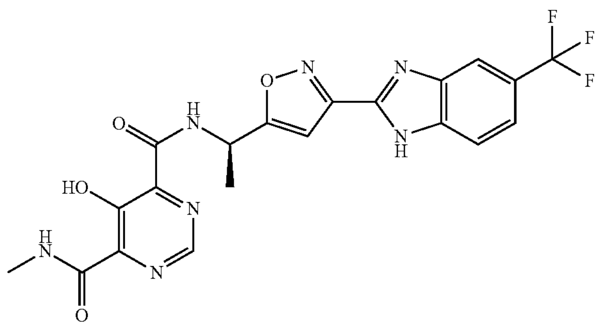 [SMILES: CNC(=O)c1ncnc(C(=O)N[C@H](C)c2cc(-c3nc4cc(C(F)(F)F)ccc4[nH]3)no2)c1O] | m/z 476 [M + 1]+ |
| 39bEa | 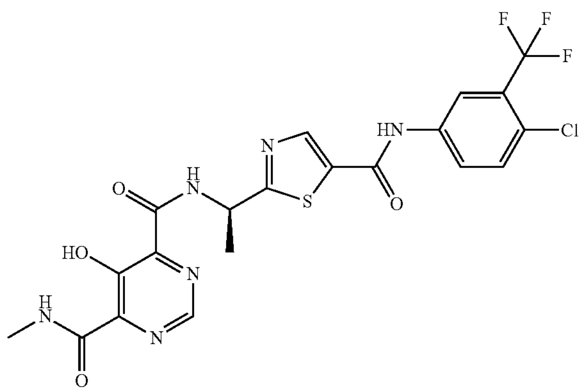 [SMILES: CNC(=O)c1ncnc(C(=O)N[C@H](C)c2ncc(C(=O)Nc3ccc(Cl)c(C(F)(F)F)c3)s2)c1O] | m/z 530 [M + 1]+ |
| 2eD | 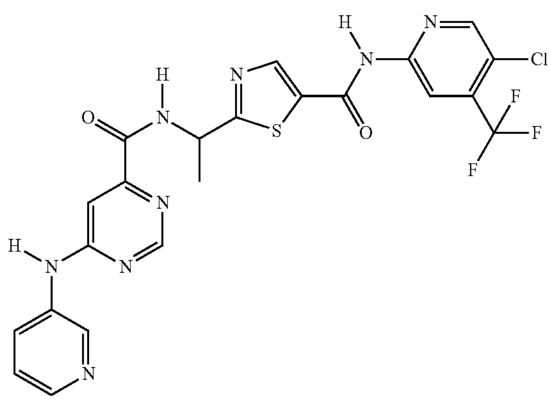 [SMILES: CC(NC(=O)c1cc(Nc2cccnc2)ncn1)c1ncc(C(=O)Nc2cc(C(F)(F)F)c(Cl)cn2)s1] | ¹H-NMR (DMSO-D6, 500 MHz): δ 11.85 (s, 1H), 9.78 (d, J = 8.5 Hz, 2H), 8.86 (d, J = 8.0 Hz, 3H), 8.58 (s, 2H), 8.38 (s, 1H), 8.01 (d, J = 8.0 Hz, 1H), 7.4 (d, J = 8.0 Hz, 1H), 5.35- 5.25 (m, 1H), 1.67 (d, J = 6.0 Hz, 3H); m/z 582.7 [M + 1]+ |
| 18iD | 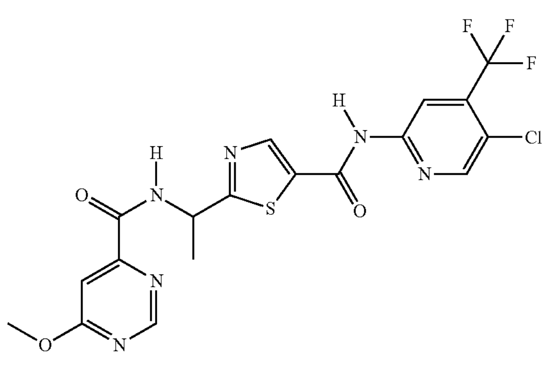 [SMILES: COc1cc(C(=O)NC(C)c2ncc(C(=O)Nc3cc(C(F)(F)F)c(Cl)cn3)s2)ncn1] | ¹H-NMR (CD3OD, 200 MHz): δ 8.95 (s, 1H), 8.64 (d, J = 8.5 Hz, 2H), 8.46 (s, 1H), 7.43 (s, 1H), 5.55- 5.45 (m, 1H), 4.01 (s, 3H), 1.77 (d, J = 6.0 Hz, 3H); m/z 486.8 [M + 1]+ |

TABLE 3-continued

Exemplary Compounds of Formula I

| # | Structure | Characterization Data |
|---|---|---|
| 6lD | 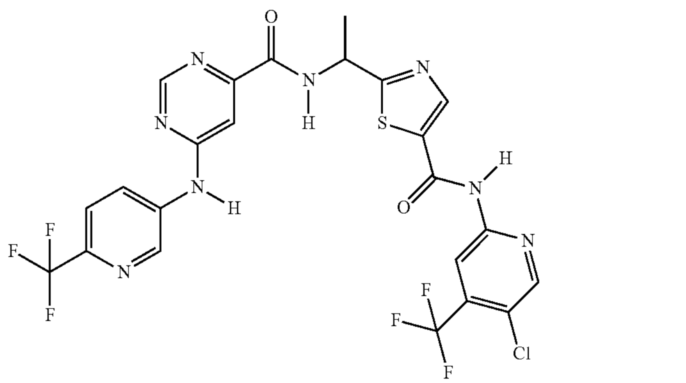 [SMILES: CC(NC(=O)c1cc(Nc2ccc(C(F)(F)F)nc2)ncn1)c1ncc(C(=O)Nc2cc(C(F)(F)F)c(Cl)cn2)s1] | $^1$H-NMR (DMSO-D6, 500 MHz): δ 11.78 (s, 1H), 10.62 (s, 1H), 9.78 (d, J = 8.5 Hz, 1H), 9.02(s, 1H), 8.95 (s, 1H), 8.76 (d, J = 14.0 Hz, 2H), 8.58 (s, 2H), 7.92 (d, J = 6.0 Hz, 1H), 7.56 (s, 1H), 5.45- 5.43 (m, 1H), 1.72 (d, J = 6.0 Hz, 3H); m/z 616.5 [M + 1]$^+$ |
| 18kD | 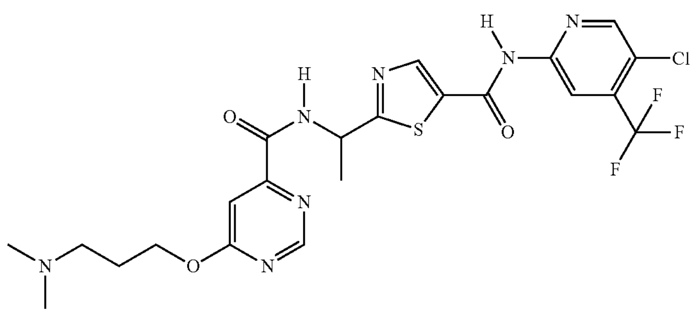 [SMILES: CC(NC(=O)c1cc(OCCCN(C)C)ncn1)c1ncc(C(=O)Nc2cc(C(F)(F)F)c(Cl)cn2)s1] | $^1$H-NMR (CD3OD, 500 MHz): δ 8.82 (s, 1H), 8.62 (s, 1H), 8.59 (s, 1H), 8.52 (s, 1H), 7.42 (s, 1H), 5.55- 5.51 (m, 1H), 4.45 (t, J = 7.5 Hz, 2H), 2.52 (t, J = 7.5 Hz, 2H), 2.25 (s, 6H), 2.04- 2.01 (m, 2H), 1.76 (d, J = 6.0 Hz, 3H); m/z 557.7 [M + 1]$^+$ |
| 4zD | 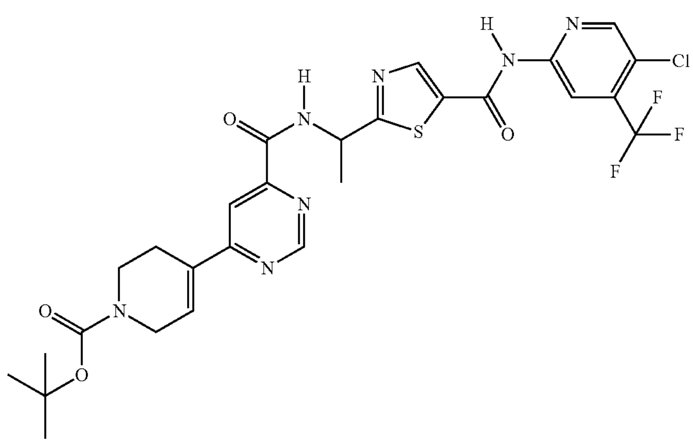 [SMILES: CC(NC(=O)c1cc(C2=CCN(C(=O)OC(C)(C)C)CC2)ncn1)c1ncc(C(=O)Nc2cc(C(F)(F)F)c(Cl)cn2)s1] | $^1$H-NMR (CDCl$_3$, 500 MHz): δ 9.18 (s, 1H), 8.62 (s, 2H),8.5(s, 1H), 8.42 (s, 1H), 8.35 (s, 1H), 8.18 (s, 1H), 7.02 (bs, 1H), 5.63- 5.61 (m, 1H), 4.20 (bs, 2H), 3.68- 3.65 (m, 2H), 2.65- 2.62 (m, 2H), 1.82 (d, J = 6.0 Hz, 3H), 1.55 (s, 9H); m/z 637.8 [M + 1]$^+$ |
| 8eD | 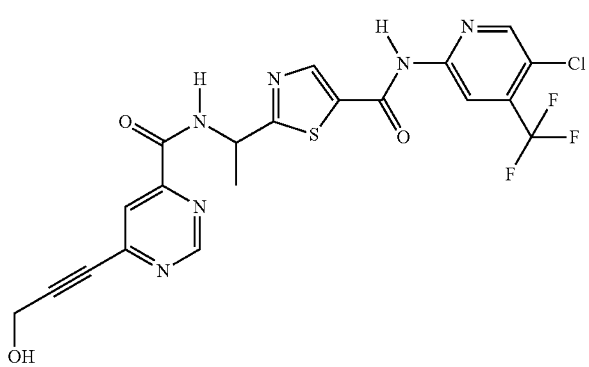 [SMILES: CC(NC(=O)c1cc(C#CCO)ncn1)c1ncc(C(=O)Nc2cc(C(F)(F)F)c(Cl)cn2)s1] | $^1$H-NMR (DMSO-D6, 500 MHz): δ 11.78 (s, 1H), 9.82 (d, J = 7.0 Hz, 1H), 9.39 (s, 1H), 8.78 (s, 1H), 8.75 (s, 1H), 8.56 (s, 1H), 7.92 (s, 1H), 5.63- 5.61 (m, 1H), 5.49- 5.42 (m, 1H), 4.39 (s, 2H), 1.63 (d, J = 7.0 Hz, 3H); m/z 510.7 [M + 1]$^+$ |

TABLE 3-continued

Exemplary Compounds of Formula I

| # | Structure | Characterization Data |
|---|-----------|----------------------|
| 18lD | 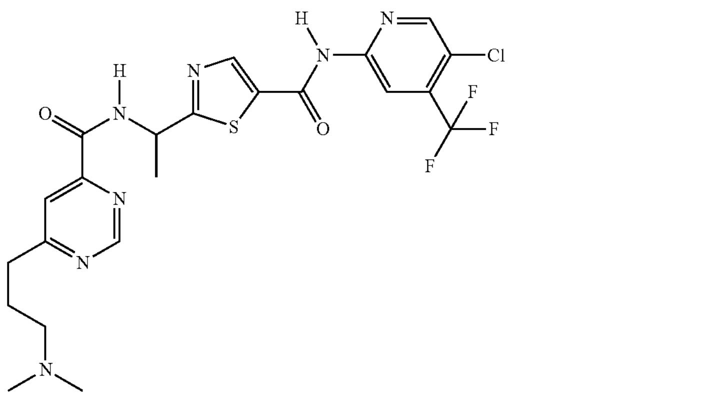 [SMILES: CC(NC(=O)c1cc(CCCN(C)C)ncn1)c1ncc(C(=O)Nc2cc(C(F)(F)F)c(Cl)cn2)s1] | ¹H-NMR (CD3OD, 500 MHz): δ 8.82 (s, 1H), 8.62 (s, 1H), 8.59 (s, 1H), 8.52 (s, 1H), 7.42 (s, 1H), 5.59- 5.56 (m, 1H), 4.60 (t, J = 7.5 Hz, 2H), 2.82 (t, J = 7.5 Hz, 2H), 2.39 (s, 6H), 1.76 (d, J = 6.0 Hz, 3H); m/z 543.9 [M + 1]⁺ |
| 8dD | 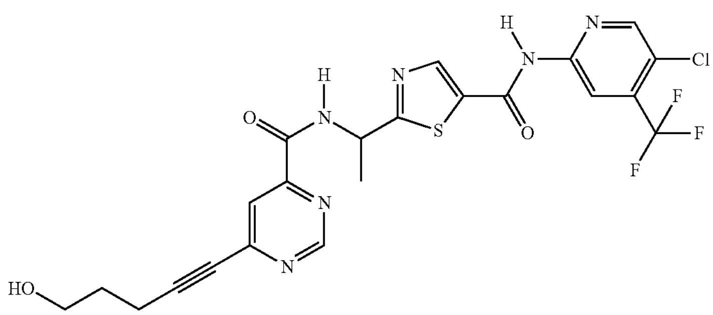 [SMILES: CC(NC(=O)c1cc(C#CCCCO)ncn1)c1ncc(C(=O)Nc2cc(C(F)(F)F)c(Cl)cn2)s1] | ¹H-NMR (DMSO-D6, 500 MHz): δ 11.76 (s, 1H), 9.84 (d, J = 7.0 Hz, 1H), 9.38 (s, 1H), 8.79 (s, 1H), 8.75 (s, 1H), 8.56 (s, 1H), 7.92 (s, 1H), 5.45- 5.41 (m, 1H), 4.58 (s, 1H), 3.54- 3.51 (m, 2H), 2.62- 2.59 (m, 2H), 1.78- 1.74 (m, 2H), 1.62 (d, J = 7.0 Hz, 3H); m/z 538.8 [M + 1]⁺ |
| 10XX | 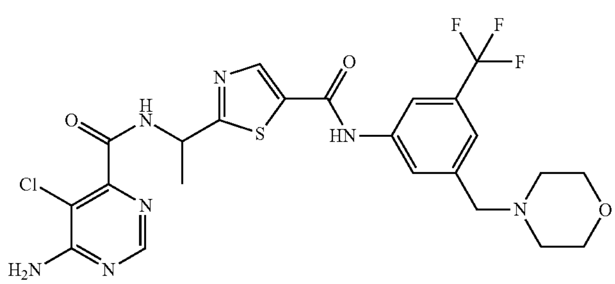 [SMILES: CC(NC(=O)c1ncnc(N)c1Cl)c1ncc(C(=O)Nc2cc(CN3CCOCC3)cc(C(F)(F)F)c2)s1] | ¹H-NMR (CD₃OD, 500 MHz): δ 8.45 (s, 1H), 8.39 (s, 1H), 8.12 (s, 1H), 7.92 (s, 1H), 7.45 (s, 1H), 5.48-5.41 (m, 1H), 3.78-3.73 (m, 4H), 3.64 (s, 2H), 2.49-2.45 (m, 4H), 1.77 (d, J = 7.0 Hz, 3H); m/z 569.9 [M + 1]⁺. |
| 10WW | 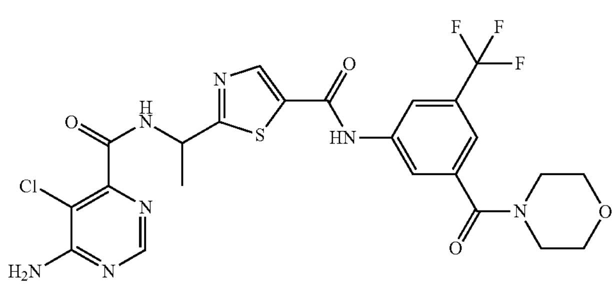 [SMILES: CC(NC(=O)c1ncnc(N)c1Cl)c1ncc(C(=O)Nc2cc(C(=O)N3CCOCC3)cc(C(F)(F)F)c2)s1] | ¹H-NMR (CD₃OD, 500 MHz): δ 8.45 (s, 1H), 8.39 (s, 1H), 8.12 (s, 1H), 8.09 (s, 1H), 7.45 (s, 1H), 5.48- 5.41 (m, 1H), 3.85-3.60 (m, 6H), 3.55-3.40 (m, 2H), 1.77 (d, J = 7.5 Hz, 3H); m/z 583.7 [M + 1]⁺. |

TABLE 3-continued

Exemplary Compounds of Formula I

| # | Structure | Characterization Data |
|---|-----------|----------------------|
| 5bbD | 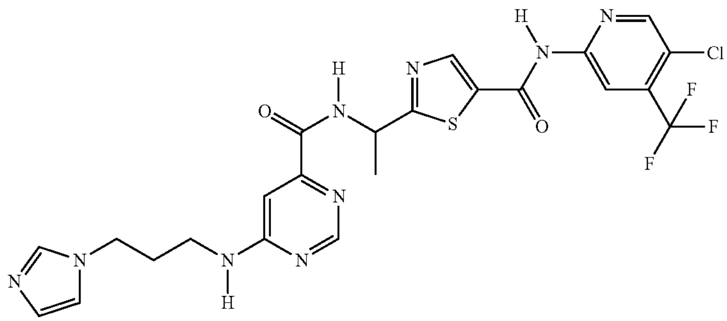 [SMILES: CC(NC(=O)c1cc(NCCCn2ccnc2)ncn1)c1ncc(C(=O)Nc2cc(C(F)(F)F)c(Cl)cn2)s1] | ¹H-NMR (CD3OD, 500 MHz): δ 8.61 (s, 1H), 8.58 (s, 1H), 8.52 (s, 1H), 7.68 (s, 1H), 7.17 (s, 1H), 7.14 (s, 1H), 6.98 (s, 1H), 5.52- 5.51 (m, 1H), 4.16 (t, J = 7.0 Hz, 2H), 3.46- 3.35 (m, 2H), 2.15- 2.12 (m, 2H), 1.77 (d, J = 6.8 Hz, 3H); m/z 579.7 [M + 1]⁺ |
| 8fD | 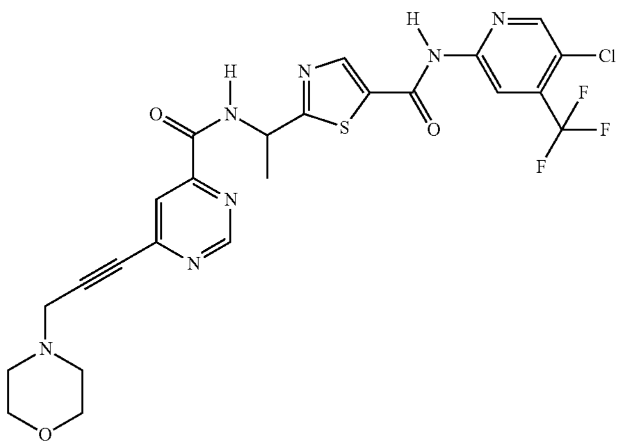 [SMILES: CC(NC(=O)c1cc(C#CCN2CCOCC2)ncn1)c1ncc(C(=O)Nc2cc(C(F)(F)F)c(Cl)cn2)s1] | ¹H-NMR (CDCl₃, 500 MHz): δ 9.20 (s, 1H), 8.63 (s, 1H), 8.57 (d, J = 7.0 Hz, 1H), 8.55 (s, 1H), 8.43 (s, 1H), 8.27 (s, 1H), 8.15 (s, 1H), 5.61- 5.58 (m, 1H), 3.77- 3.36 (m, 4H), 3.61 (s, 2H), 2.62 (bs, 4H), 1.81 (d, J = 7.0 Hz, 3H); m/z 579.9 [M + 1]⁺ |
| 27fD | 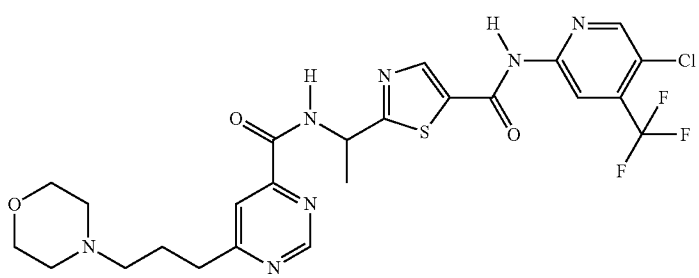 [SMILES: CC(NC(=O)c1cc(CCCN2CCOCC2)ncn1)c1ncc(C(=O)Nc2cc(C(F)(F)F)c(Cl)cn2)s1] | ¹H-NMR (CDCl3 + D2O, 200 MHz): δ 9.12 (s, 1H), 8.67 (s, 1H), 8.50 (s, 1H), 8.38 (s, 1H), 8.01 (s, 1H), 5.63- 5.61 (m, 1H), 3.88 (bs, 4H), 2.99- 2.97 (m, 2H), 2.75- 2.72 (bs, 5H), 2.15- 2.12 (m, 3H), 1.81 (d, J = 7.0 Hz, 3H); m/z 583.6 [M + 1]⁺ |
| 5ccD | 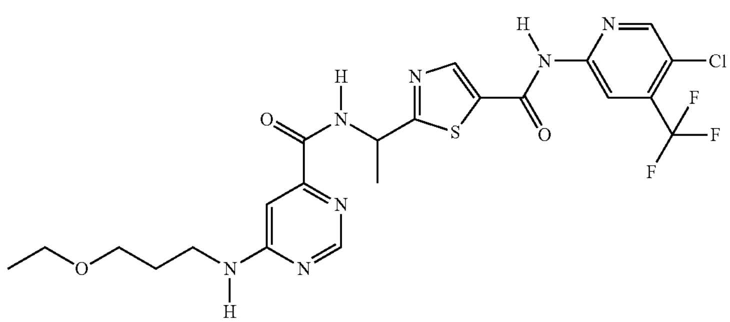 [SMILES: CCOCCCNc1cc(C(=O)NC(C)c2ncc(C(=O)Nc3cc(C(F)(F)F)c(Cl)cn3)s2)ncn1] | ¹H NMR (400 MHz, DMSO-d₆) δ = 11.74 (s, 1 H), 9.43 (d, 1 H), 8.77 (s, 1 H), 8.73 (s, 1 H), 8.55 (s, 1 H), 8.53 (br. s., 1 H), 7.97 - 7.47 (m, 1 H), 7.09 (s, 1 H), 5.73-5.14 (m, 1 H), 3.45-3.36 (m, 6 H), 1.80-1.71 (m, 2 H), 1.65 (d, J = 7.0 Hz, 3 H), 1.10 (t, J = 7.0 Hz, 3 H); m/z 558 [M + 1]⁺ |

TABLE 3-continued

Exemplary Compounds of Formula I

| # | Structure | Characterization Data |
|---|---|---|
| 5ddD | 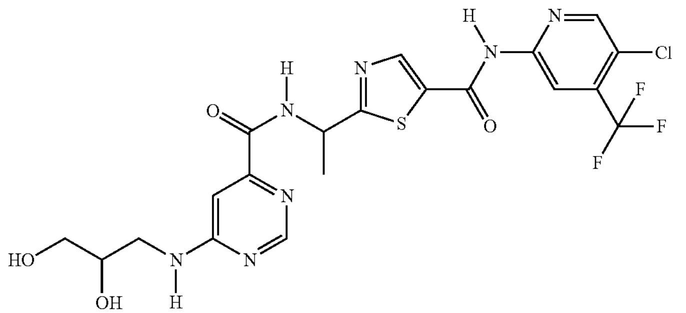 [SMILES: CC(NC(=O)c1cc(NCC(O)CO)ncn1)c1ncc(C(=O)Nc2cc(C(F)(F)F)c(Cl)cn2)s1] | ¹H-NMR (DMSO-D6, 500 MHz): δ 11.72 (s, 1H), 9.40 (d, J = 8 Hz), 1H), 8.76 (s, 1H), 8.72 (s, 1H), 8.54 (s, 1H), 8.50 (s, 1H), 7.86 (bs, 1H), 7.17 (s, 1H), 5.40- 5.37 (m, 1H), 4.85 (d, J = 4.5 Hz, 1H), 4.59 (s, 1H), 3.62- 3.60 (m, 3H), 1.64 (d, J = 7.0 Hz, 3H); m/z 545.6 [M + 1]⁺ |
| 5eeD | 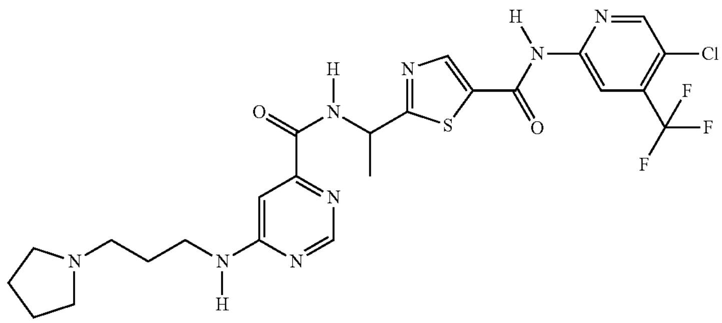 [SMILES: CC(NC(=O)c1cc(NCCCN2CCCC2)ncn1)c1ncc(C(=O)Nc2cc(C(F)(F)F)c(Cl)cn2)s1] | ¹H-NMR (DMSO-D6, 500 MHz): δ 11.76 (s, 1H), 9.39 (d, J = 7.0 Hz, 1H), 8.78 (s, 1H), 8.75 (s, 1H), 8.56 (s, 1H), 8.52 (s, 1H), 7.92 (bs, 1H), 7.12 (s, 1H), 5.39- 5.35 (m, 1H), 3.39- 3.35 (m, 4H), 2.45- 2.41(m, 4H), 1.73- 1.65 (m, 9H); m/z 582.7 [M + 1]⁺ |
| 8gD | 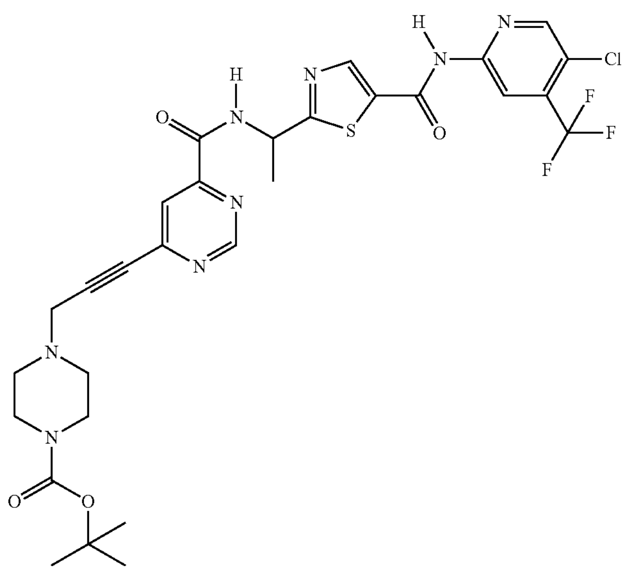 [SMILES: CC(NC(=O)c1cc(C#CCN2CCN(C(=O)OC(C)(C)C)CC2)ncn1)c1ncc(C(=O)Nc2cc(C(F)(F)F)c(Cl)cn2)s1] | ¹H-NMR (CDCl₃, 200 MHz): δ 9.20 (s, 1H), 8.63- 8.55 (s, 1H), 8.57 (d, J = 7.0 Hz, 1H), 8.43 (s, 2H), 8.28 (s, 1H), 8.14 (s, 1H), 5.65- 5.58 (m, 1H), 3.65 (s, 2H), 3.50 (bs, 4H), 2.61 (bs, 4H), 1.82 (d, J = 8.0 Hz, 3H), 1.46 (s, 9H); m/z 678.5 [M + 1]⁺ |
| 5ffD | 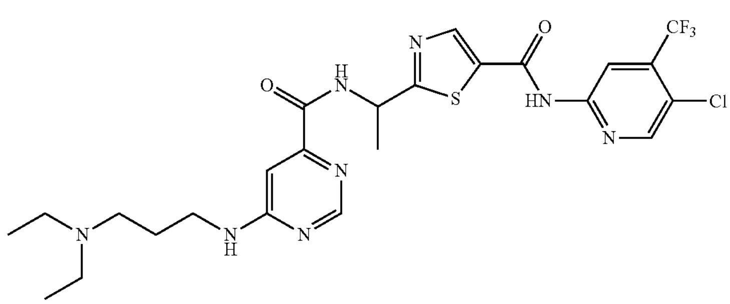 [SMILES: CCN(CC)CCCNc1cc(C(=O)NC(C)c2ncc(C(=O)Nc3cc(C(F)(F)F)c(Cl)cn3)s2)ncn1] | ¹H-NMR (CD3OD, 200 MHz): δ 8.62 (s, 1H), 8.59 (s, 1H) 8.52 (s, 1H), 7.18 (s, 1H), 5.52- 5.49 (m, 1H), 3.48- 3.42 (m, 2H), 2.78- 2.60 (m, 6H),1.90-1.82(m, 2H) 1.76 (d, J = 8.0 Hz, 3H), 1.02 (t, J = 7.5 Hz, 6H); m/z 584.9 [M + 1]⁺ |

TABLE 3-continued

Exemplary Compounds of Formula I

| # | Structure | Characterization Data |
|---|---|---|
| 27eD | 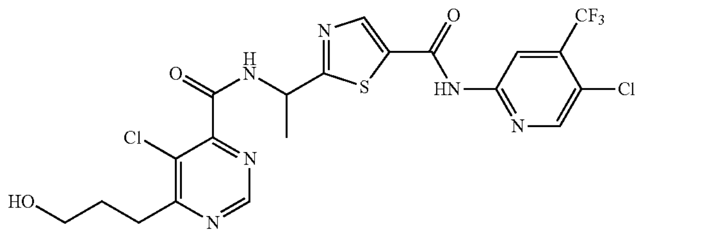 [SMILES: CC(NC(=O)c1ncnc(CCCO)c1Cl)c1ncc(C(=O)Nc2cc(C(F)(F)F)c(Cl)cn2)s1] | ¹H-NMR (DMSO-D6, 200 MHz): δ 11.78 (s, 1H), 9.75 (d, J = 7.0 Hz, 1H), 9.05 (s, 1H), 8.78 (s, 1H), 8.75 (s, 1H), 8.57 (s, 1H), 5.42- 5.39 (m, 1H), 4.61-4.55 (m, 1H), 3.55- 3.49 (m, 2H), 2.98 (t, J = 7.5 Hz, 2H), 1.95- 1.92 (m, 2H), 1.62 (d, J = 8.0 Hz, 3H); m/z 548.8 [M + 1]⁺ |
| 27gD | 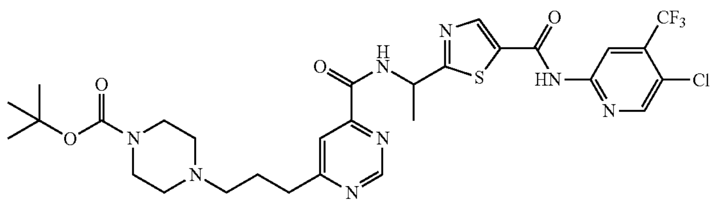 [SMILES: CC(NC(=O)c1cc(CCCN2CCN(C(=O)OC(C)(C)C)CC2)ncn1)c1ncc(C(=O)Nc2cc(C(F)(F)F)c(Cl)cn2)s1] | ¹H-NMR (CDCl₃, 200 MHz): δ 9.15 (s, 8.64 (bs, 2H), 8.57 (s, 1H), 8.43(s, 1H), 8.28 (s, 1H), 8.00 (s, 1H), 5.65- 5.58 (m, 1H), 3.39 (bs, 4H), 2.93 (t, J = 8.0 Hz, 2H), 2.38 (bs, 6H), 2.01 (bs, 2H), 1.82 (d, J = 8.0 Hz, 3H), 1.46 (s, 9H); m/z 682.9 [M + 1]⁺ |
| 10VV | 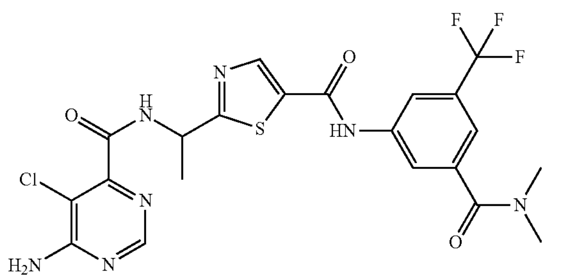 [SMILES: CC(NC(=O)c1ncnc(N)c1Cl)c1ncc(C(=O)Nc2cc(C(=O)N(C)C)cc(C(F)(F)F)c2)s1] | ¹H-NMR (CD₃OD, 500 MHz): δ 8.47 (s, 1H), 8.35 (s, 1H), 8.18 (s, 1H), 8.05 (s, 1H), 7.51 (s, 1H), 5.40-5.38 (m, 1H), 3.23 (s, 3H), 3.13 (s, 3H), 1.80 (d, J = 7.0 Hz, 2H); m/z 542 [M + 1]⁺ |
| 18aD | 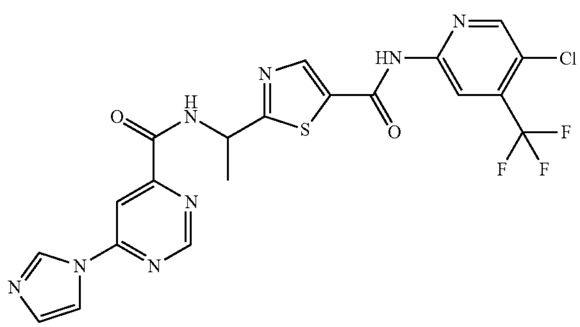 [SMILES: CC(NC(=O)c1cc(-n2ccnc2)ncn1)c1ncc(C(=O)Nc2cc(C(F)(F)F)c(Cl)cn2)s1] | ¹H-NMR (DMSO-D6, 200 MHz): δ 11.78 (s, 1H), 9.78 (d, J = 8.5 Hz, 1H), 9.25 (s, 1H), 8.85 (s, 1H), 8.76 (d, J = 12.0 Hz, 2H), 8.38 (s, 1H), 8.21 (s, 1H), 8.17 (s, 1H), 7.18 (s, 1H), 5.45- 5.43 (m, 1H), 1.72 (d, J = 6.0 Hz, 3H); m/z 523.1 [M + 1]⁺ |
| 18dD | 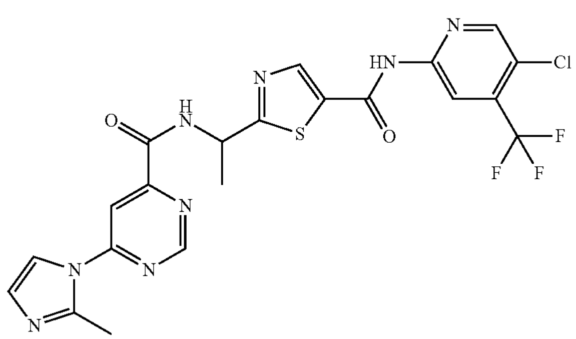 [SMILES: Cc1nccn1-c1cc(C(=O)NC(C)c2ncc(C(=O)Nc3cc(C(F)(F)F)c(Cl)cn3)s2)ncn1] | ¹H-NMR (DMSO-D6, 500 MHz): δ 11.73 (s, 1H), 9.89 (d, J = 8.0 Hz, 1H), 9.31 (s, 1H), 8.76 (s, 1H), 8.74 (s, 1H), 8.54 (s, 1H), 8.20 (s, 1H), 7.96 (s, 1H), 6.99 (s, 1H), 5.50- 5.47 (m, 1H), 2.68 (s, 3H), 1.70 (d, J = 7.0 Hz, 3H); m/z 536.9 [M + 1]⁺ |

TABLE 3-continued

Exemplary Compounds of Formula I

| # | Structure | Characterization Data |
|---|---|---|
| 5ggD | 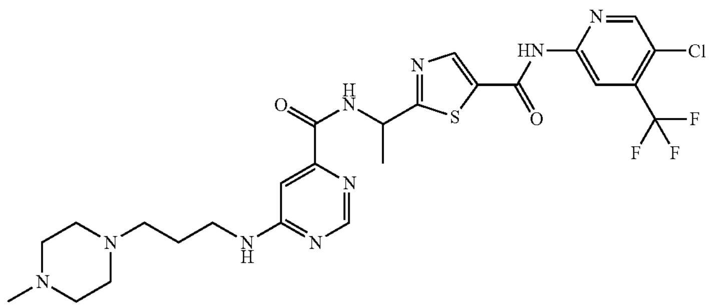 [SMILES: CC(NC(=O)c1cc(NCCCN2CCN(C)CC2)ncn1)c1ncc(C(=O)Nc2cc(C(F)(F)F)c(Cl)cn2)s1] | $^1$H-NMR (CD3OD, 200 MHz): δ 8.62 (s, 1H), 8.58 (s, 1H), 8.52 (s, 2H), 7.12 (s, 1H), 5.52- 5.51 (m, 1H), 3.59- 3.31 (m, 3H), 2.65- 2.4 (m, 9H), 2.29 (s, 3H), 1.77 (d, J = 8.0 Hz, 3H); m/z 611.6 [M + 1]$^+$ |
| 30b | 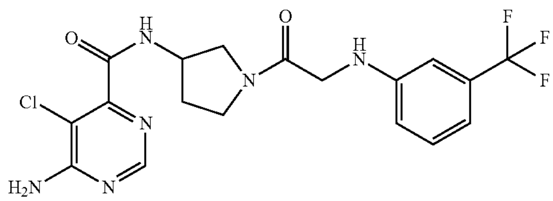 [SMILES: Nc1ncnc(C(=O)NC2CCN(C(=O)CNc3cccc(C(F)(F)F)c3)C2)c1Cl] | $^1$H-NMR (DMSO-D6, 500 MHz): 8.87 (bs, NH), 8.25 (s, 1H), 7.25 (t, J = 8 Hz, 2H), 6.95 (s, 1H), 6.88 (d, J = 8 Hz,1H), 6.83 (d, J = 8 Hz, 1H), 6.12 (s, 1H), 4.48-4.39 (m, 1H), 3.92-3.78 (m, 2H), 3.61-3.52 (m, 2H), 3.45-3.36 (m, 2H), 2.35-1.89 (m, 4H); m/z: 442 [M + 1]$^+$ |
| 5hhD | 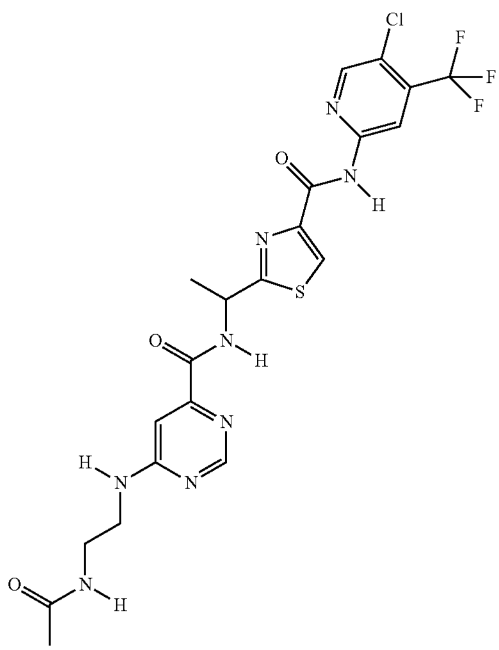 [SMILES: CC(=O)NCCNc1cc(C(=O)NC(C)c2nc(C(=O)Nc3cc(C(F)(F)F)c(Cl)cn3)cs2)ncn1] | $^1$H-NMR (DMSO-D6, 500 MHz): δ 11.78 (s, 1H), 9.46 (d, J = 8.5 Hz, 1H), 8.82 (s, 1H), 8.78 (s, 1H), 8.58 (bs, 2H), 7.95 (bs, 2H), 7.12 (s, 1H), 5.43- 5.38 (m, 1H), 3.45 (bs, 2H), 3.12 (bs, 2H), 1.82 (s, 3H), 1.65 (d, J = 7.5 Hz, 3H); m/z 556.8 [M + 1]$^+$ |
| 27hD | 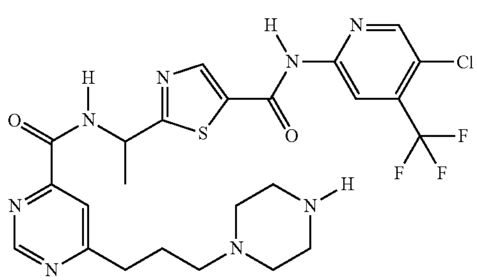 [SMILES: CC(NC(=O)c1cc(CCCN2CCNCC2)ncn1)c1ncc(C(=O)Nc2cc(C(F)(F)F)c(Cl)cn2)s1] | $^1$H-NMR (CDCl$_3$, 500 MHz): δ 9.14 (s, 1H), 8.80 (s, 1H), 8.62-8.61 (m, 2H), 8.40 (s, 1H), 8.31 (s, 1H), 7.96 (s, 1H), 5.60-5.59 (m, 1H), 3.57-3.47 (m, 8H), 3.18-10 (m, 2H), 2.98-2.97 (m, 2H), 2.26-2.25 (m, 2H), 1.79 (d, J = 7 Hz, 3H); m/z 582.8 [M + 1]$^+$ |

TABLE 3-continued

Exemplary Compounds of Formula I

| # | Structure | Characterization Data |
|---|---|---|
| 18eD | 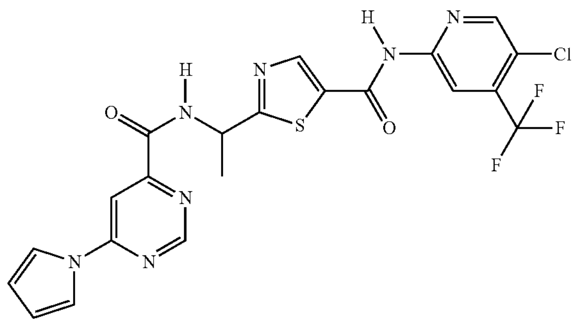 [SMILES: CC(NC(=O)c1cc(-n2cccc2)ncn1)c1ncc(C(=O)Nc2cc(C(F)(F)F)c(Cl)cn2)s1] | ¹H-NMR (DMSO-D6, 500 MHz): δ 11.71 (s, 1H), 9.76 (d, J = 8 Hz, 1H), 9.13 (s, 1H), 8.75-8.73 (m, 2H), 8.54 (s, 1H), 8.23 (s, 1H), 7.89 (m, 2H), 6.41 (s, 2H), 5.49-5.47 (m, 1H), 1.69 (d, J = 7 Hz, 3H); m/z 521.8 [M + 1]⁺ |
| 18fD | 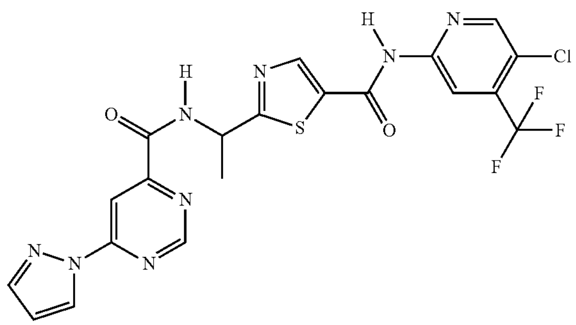 [SMILES: CC(NC(=O)c1cc(-n2cccn2)ncn1)c1ncc(C(=O)Nc2cc(C(F)(F)F)c(Cl)cn2)s1] | ¹H-NMR (DMSO-D6, 500 MHz): δ 11.72 (s, 1H), 9.85 (s, 1H), 9.23 (s, 1H), 8.75-8.73 (m, 3H), 8.53 (s, 1H), 8.37 (s, 1H), 8.01 (s, 1H), 6.71 (s, 1H), 5.50-5.49 (m, 1H), 1.69 (d, J = 7 Hz, 3H); m/z 522.8 [M + 1]⁺ |
| 5jjD | 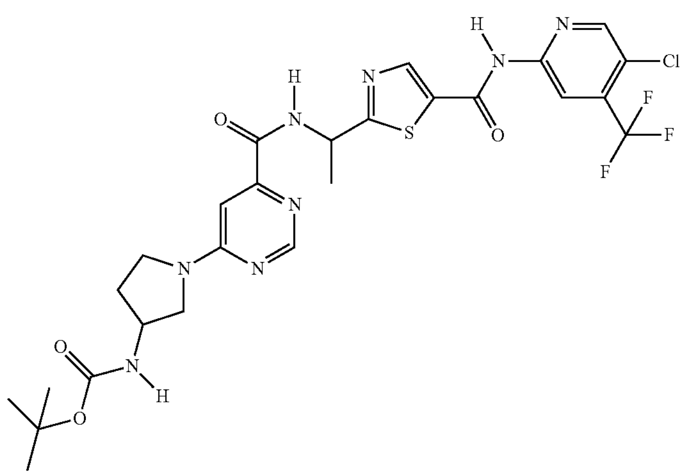 [SMILES: CC(NC(=O)c1cc(N2CCC(NC(=O)OC(C)(C)C)C2)ncn1)c1ncc(C(=O)Nc2cc(C(F)(F)F)c(Cl)cn2)s1] | ¹H-NMR (DMSO-D6, 500 MHz): δ 11.70 (s, 1H), 9.59 (d, J = 8.5 Hz, 1H), 8.75 (s, 1H), 8.72 (s, 1H), 8.58 (s, 1H), 8.54 (s, 1H), 7.22 (s, 1H), 6.97 (d, N—H), 5.43-5.42 (m, 1H), 4.15-4.09 (m, 1H), 3.79-3.29 (m, 4H), 2.15-2.08 (m, 1H), 1.98-1.90 (m, 1H), 1.65 (d, J = 7 Hz, 3H), 1.38 (s, 9H); m/z 640.7 [M + 1]⁺ |
| 5iiD | 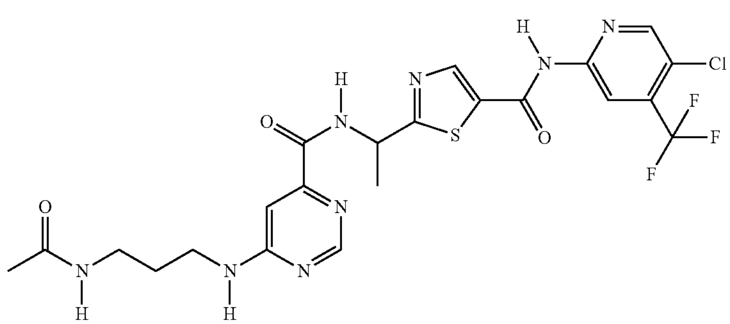 [SMILES: CC(=O)NCCCNc1cc(C(=O)NC(C)c2ncc(C(=O)Nc3cc(C(F)(F)F)c(Cl)cn3)s2)ncn1] | ¹H-NMR (DMSO-D6, 500 MHz): δ 11.73 (s, 1H), 9.41 (bs, 1H), 8.78 (s, 1H), 8.76 (s, 1H), 8.54 (s, 1H), 8.52 (s, 1H), 7.81 (bs, 2H), 7.1 (s, IH), 5.42- 5.39 (m, 1H), 3.51-3.42 (m, 2H), 3.19- 3.12 (m, 2H), 1.81 (s, 3H), 1.76 (d, J = 7.0 Hz, 3H); m/z 570.9 [M + 1]⁺ |

TABLE 3-continued

Exemplary Compounds of Formula I

| # | Structure | Characterization Data |
|---|---|---|
| 8hD | 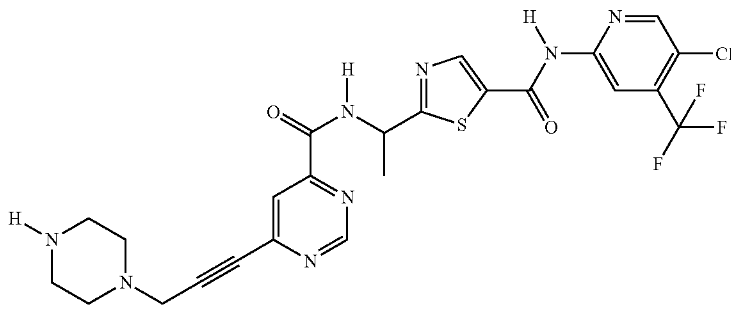 [SMILES: CC(NC(=O)c1cc(C#CCN2CCNCC2)ncn1)c1ncc(C(=O)Nc2cc(C(F)(F)F)c(Cl)cn2)s1] | $^1$H-NMR (CDCL3, 500 MHz): δ 9.70 (bs, 1H), 9.20 (s, 1H), 8.63-8.57 (m, 3H), 8.55 (s, 1H), 8.28 (s, 1H), 8.15 (s, 1H), 5.62-5.61 (m, 1H), 3.66 (s, 2H), 3.31-3.26 (m, 4H), 2.90-2.89 (m, 4H), 1.80 (d, J = 6.5 Hz, 3H); m/z 578.7 [M + 1]$^+$ |
| 19llD | 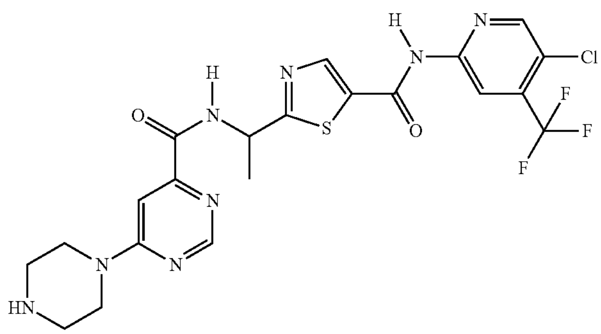 | $^1$H-NMR (DMSO-D6, 200 MHz): δ 11.73 (s, 1H), 9.52 (d, N—H), 8.76 (s, 1H), 8.72 (s, 1H), 8.64 (s, 1H), 8.53 (s, 1H), 7.33 (s, 1H), 5.44-5.36 (m, 1H), 3.78-3.58 (m, 4H), 3.54-3.35 (m, 4H), 2.03 (s, 3H), 1.67 (d, J = 7 Hz, 3H); m/z 582.8 [M + 1]$^+$ |
| 5llD | 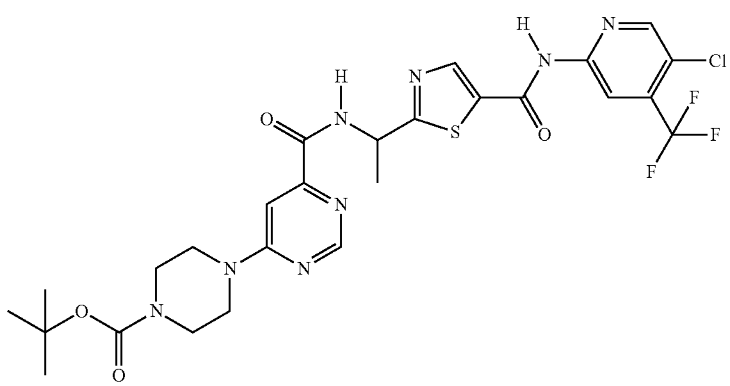 [SMILES: CC(NC(=O)c1cc(N2CCN(C(=O)OC(C)(C)C)CC2)ncn1)c1ncc(C(=O)Nc2cc(C(F)(F)F)c(Cl)cn2)s1] | $^1$H-NMR (CDCl$_3$, 200 MHz): δ 8.63-8.58 (m, 3H), 8.43 (s, 1H), 8.39 (s, 1H), 8.27 (s, 1H), 7.35 (s, 1H), 5.63-5.52 (m, 1H), 3.80-3.72 (m, 4H), 3.60-3.46 (m, 4H), 1.78 (d, J = 7 Hz, 3H), 1.49 (s, 9H); m/z 640.7 [M + 1]$^+$. |
| 18cD | 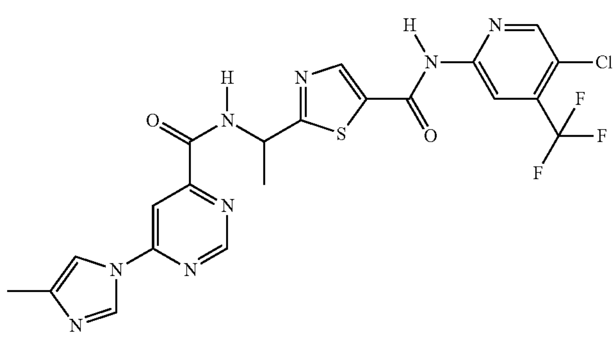 [SMILES: Cc1cn(-c2cc(C(=O)NC(C)c3ncc(C(=O)Nc4cc(C(F)(F)F)c(Cl)cn4)s3)ncn2)cn1] | $^1$H-NMR (DMSO-D6, 200 MHz): δ 11.78 (s, 1H), 9.82 (d, J = 8.5 Hz, 1H), 9.12 (s, 1H), 8.78 (t, J = 12.5 Hz, 3H), 8.48 (s, 1H), 8.34 (s, 1H), 7.18 (s, 1H), 5.45- 5.43 (m, 1H), 2.21 (s, 3H), 1.68 (d, J = 7.5 Hz, 3H); m/z 536.8 [M + 1]$^+$ |

TABLE 3-continued

Exemplary Compounds of Formula I

| # | Structure | Characterization Data |
|---|---|---|
| 18gD | 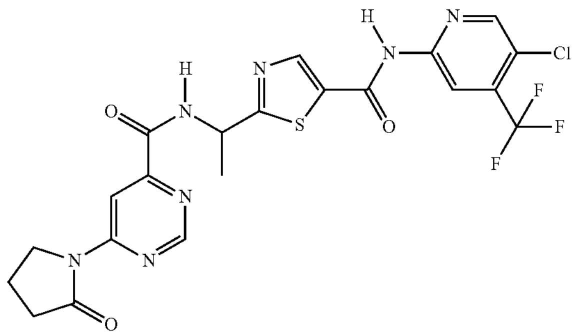 [SMILES: CC(NC(=O)c1cc(N2CCCC2=O)ncn1)c1ncc(C(=O)Nc2cc(C(F)(F)F)c(Cl)cn2)s1] | ¹H-NMR (DMSO-D6, 500 MHz): δ 11.72 (s, 1H), 9.71 (d, J = 8.5 Hz, 1H), 9.10 (s, 1H), 8.86 (s, 1H), 8.76 (s, 1H), 8.73 (s, 1H), 8.54 (s, 1H), 5.46-5.45 (m, 1H), 4.01 (t, J = 7.5 Hz, 2H), 2.64 (t, J = 7.5 Hz, 2H), 2.10 (t, J = 7.5 Hz, 2H), 1.68 (d, J = 6.5 Hz, 3H); m/z 539.7 [M + 1]⁺ |
| 19jjD | 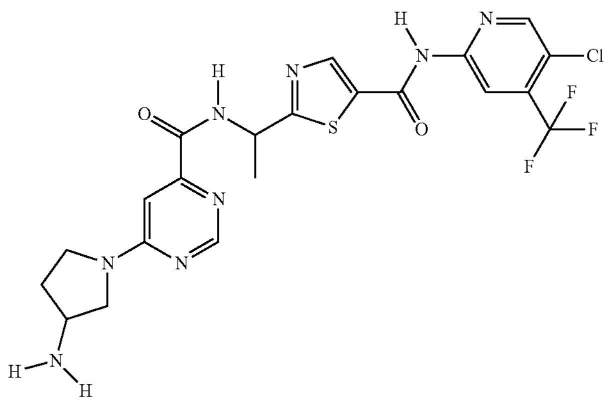 [SMILES: CC(NC(=O)c1cc(N2CCC(N)C2)ncn1)c1ncc(C(=O)Nc2cc(C(F)(F)F)c(Cl)cn2)s1] | ¹H-NMR (CD₃OD, 500 MHz): δ 8.64 (s, 1H), 8.61 (s, 1H), 8.59 (s, 1H), 8.53 (s, 1H), 7.21 (s, 1H), 5.56-5.52 (m, 1H), 4.10-4.08 (m, 1H), 3.94-3.84 (m, 1H), 3.86-3.66 (m, 3H), 2.64-2.44 (m, 1H), 2.35-2.25 (m, 1H), 1.77 (d, J = 7 Hz, 3H); m/z 540.7 [M + 1]⁺ |
| 18hD | 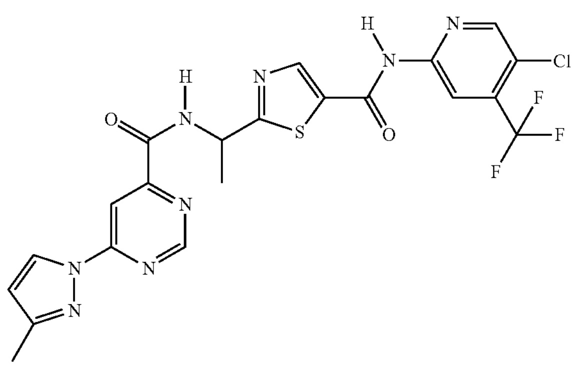 [SMILES: Cc1ccn(-c2cc(C(=O)NC(C)c3ncc(C(=O)Nc4cc(C(F)(F)F)c(Cl)cn4)s3)ncn2)n1] | ¹H-NMR (DMSO-D6, 500 MHz): δ 11.74 (s, 1H), 9.85 (d, J = 8 Hz, 1H), 9.10 (s, 1H), 8.76 (s, 1H), 8.74 (s, 1H), 8.62 (s, 1H), 8.54 (s, 1H), 8.29 (s, 1H), 6.53 (d, J = 8 Hz, 1H), 5.52-5.46 (m, 1H), 2.32 (s, 3H), 1.68 (d, J = 6.5 Hz, 3H); m/z 536.7 [M + 1]⁺ |
| 5ttD | 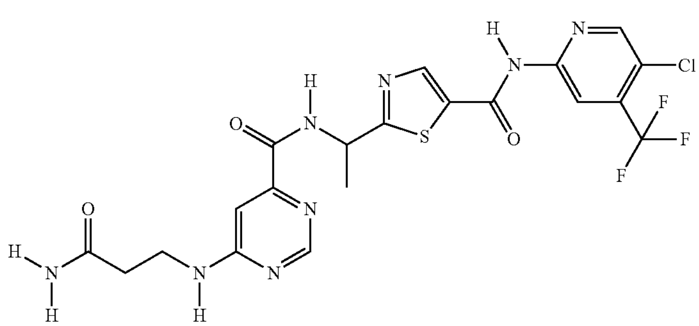 [SMILES: CC(NC(=O)c1cc(NCCC(N)=O)ncn1)c1ncc(C(=O)Nc2cc(C(F)(F)F)c(Cl)cn2)s1] | ¹H-NMR (DMSO-D6, 500 MHz): δ 11.71 (s, 1H), 9.40 (bs, 1H), 8.76 (s, 1H), 8.72 (s, 1H), 8.56 (s, 1H), 8.53 (s, 1H), 7.91 (bs, 1H), 7.32 (bs, 1H), 7.10 (s, 1H), 6.82 (bs, 1H), 5.42-5.36 (m, 1H), 3.62-3.48 (m, 2H), 2.44-2.32 (m, 2H), 1.64 (d, J = 6.5 Hz, 3H); m/z 542.7 [M + 1]⁺ |

TABLE 3-continued

Exemplary Compounds of Formula I

| # | Structure | Characterization Data |
|---|---|---|
| 26aD | 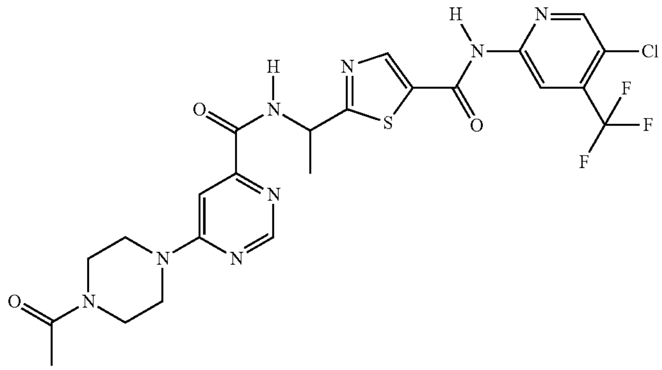 [SMILES: CC(=O)N1CCN(c2cc(C(=O)NC(C)c3ncc(C(=O)Nc4cc(C(F)(F)F)c(Cl)cn4)s3)ncn2)CC1] | ¹H-NMR (DMSO-D6, 200 MHz): δ 11.73 (s, 1H), 9.52 (d, N—H), 8.76 (s, 1H), 8.72 (s, 1H), 8.64 (s, 1H), 8.53 (s, 1H), 7.33 (s, 1H), 5.44-5.36 (m, 1H), 3.78-3.58 (m, 4H), 3.54-3.35 (m, 4H), 2.49 (s, 3H), 1.64 (d, J = 7 Hz, 3H); m/z 582.8 [M + 1]⁺ |
| 5ssD | 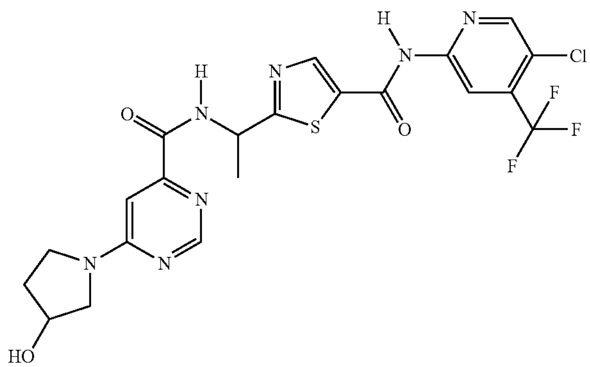 [SMILES: CC(NC(=O)c1cc(N2CCC(O)C2)ncn1)c1ncc(C(=O)Nc2cc(C(F)(F)F)c(Cl)cn2)s1] | ¹H-NMR (DMSO-D6, 500 MHz): δ 11.71 (s, 1H), 9.45 (d, N—H), 8.75 (s, 1H), 8.72 (s, 1H), 8.57 (s, 1H), 8.54 (s, 1H), 7.01 (s, 0.5H) 6.96 (s, 0.5H), 5.42-5.39 (m, 1H), 5.06 (s, 0.5H), 4.99 (s, 0.5H), 4.43 (s, 0.5H), 4.37 (s, 0.5H), 3.68-3.50 (m, 3H), 2.04-1.90 (m, 2H), 1.65 (d, J = 7 Hz, 3H); m/z 541.7 [M + 1]⁺ |
| 5mmD | 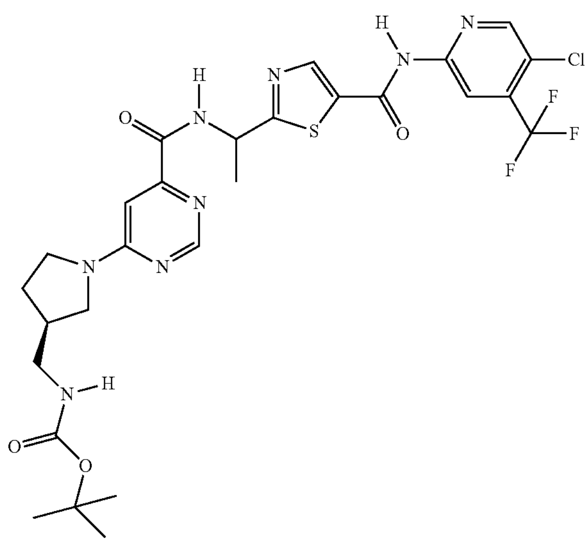 [SMILES: CC(NC(=O)c1cc(N2CC[C@H](CNC(=O)OC(C)(C)C)C2)ncn1)c1ncc(C(=O)Nc2cc(C(F)(F)F)c(Cl)cn2)s1] | ¹H-NMR (DMSO-D6, 500 MHz): δ 11.70 (s, 1H), 9.45 (d, N—H), 8.75 (s, 1H), 8.72 (s, 1H), 8.56 (s, 1H), 8.54 (s, 1H), 7.00 (s, 1H) 6.97 (s, 1H), 5.42-5.39 (m, 1H), 3.65-2.99 (m, 6H), 2.45-2.09 (m, 3H), 1.65 (d, J = 7 Hz, 3H), 1.36 (s, 9H); m/z 654.8 [M + 1]⁺ |
| 30a | 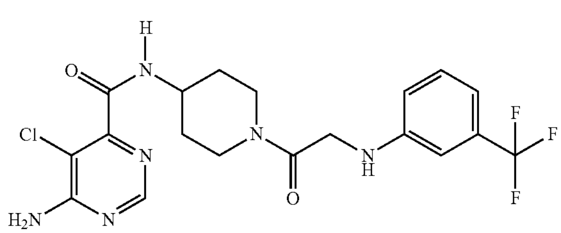 [SMILES: Nc1ncnc(C(=O)NC2CCN(C(=O)CNc3cccc(C(F)(F)F)c3)CC2)c1Cl] | ¹H-NMR (DMSO-D6, 500 MHz): 8.59 (d, J = 7.5 Hz, 1H), 8.29 (s, 1H), 7.35 (t , J = 8 Hz,1H), 6.96 (s, 1H), 6.93 (d, J = 8 Hz, 1H), 6.82 (d, J = 7.5 Hz, 1H), 6.07 (t, J = 5 Hz, 1H), 4.25 (d, N—H), 4.02-3.89 (m, 4H), 3.20-3.15 (m, 2H), 2.86 (t, J = 11 Hz, 2H), 1.85-1.80 (m, 2H), 1.60-1.49 (m, 2H); m/z 456.8 [M + 1]⁺ |

TABLE 3-continued
Exemplary Compounds of Formula I
| # | Structure | Characterization Data |
|---|---|---|
| 5nnD | 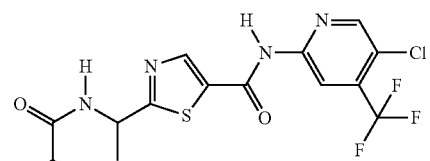 | ¹H-NMR (DMSO-D6, 200 MHz): δ 11.71 (s, 1H), 9.45 (d, N—H), 8.75 (s, 1H), 8.72 (s, 1H), 8.56 (s, 1H), 8.54 (s, 1H), 7.30 (s, 1H) 6.95 (t, N—H), 5.42-5.39 (m, 1H), 4.45-4.39 (m, 2H), 3.13-2.84 (m, 4H), 1.92-0.9 (m, 4H), 1.65 (d, J = 7 Hz, 3H), 1.36 (s, 9H); m/z 668.8 [M + 1]⁺ |
| 28a | 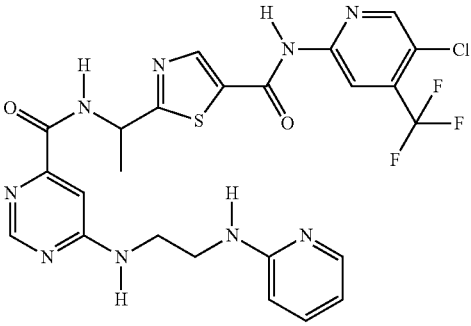 [SMILES: CC(NC(=O)c1cc(NCCNc2ccccn2)ncn1)c1ncc(C(=O)Nc2cc(C(F)(F)F)c(Cl)cn2)s1] | ¹H-NMR (DMSO-D6, 200 MHz): δ 11.74 (s, 1H), 9.45 (d, N—H), 8.76 (s, 1H), 8.72 (s, 1H), 8.56-8.53 (m, 2H), 7.97-7.95 (m, 2H), 7.36 (t, J = 6.8 Hz, 1H), 7.08 (s, 1H), 6.61-6.43 (m, 3H), 5.37-5.35 (m, 1H), 3.49-3.23 (m, 4H), 1.65 (d, J = 7 Hz, 3H); m/z 591.8 [M + 1]⁺ |
| 28b | 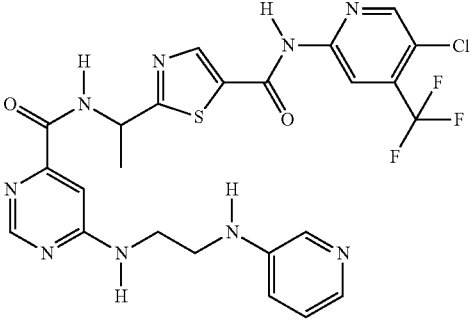 [SMILES: CC(NC(=O)c1cc(NCCNc2cccnc2)ncn1)c1ncc(C(=O)Nc2cc(C(F)(F)F)c(Cl)cn2)s1] | ¹H-NMR (DMSO-D6, 200 MHz): δ 11.70 (s, 1H), 9.39 (s, N—H), 8.76 (s, 1H), 8.72 (s, 1H), 8.56-8.53 (m, 2H), 8.00-7.75 (m, 3H), 7.11-6.97 (m, 3H), 5.91 (s, 1H), 5.40-5.35 (m, 1H), 3.51-3.28 (m, 4H), 1.65 (d, J = 7 Hz, 3H); m/z 591.8 [M + 1]⁺ |
| 5ooD | 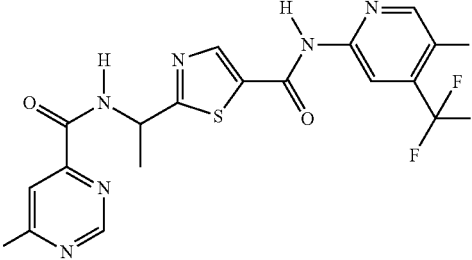 | ¹H-NMR (CD₃OD, 500 MHz): δ 8.62 (s, 1H), 8.58 (s, 1H), 8.57 (s, 1H), 8.52 (s, 1H), 7.42 (s, 1H), 5.55-5.51 (m, 1H), 4.57 (s, 1H), 4.51-4.46 (m, 1H), 3.68 (s, 1H), 3.20-3.15 (m, 2H), 1.98-1.96 (m, 2H), 1.76 (d, J = 7 Hz, 3H), 1.37-1.30 (m, 2H), 1.45 (s, 9H); m/z 654.7 [M + 1]⁺ |

TABLE 3-continued

Exemplary Compounds of Formula I

| # | Structure | Characterization Data |
|---|---|---|
| 19nnD | 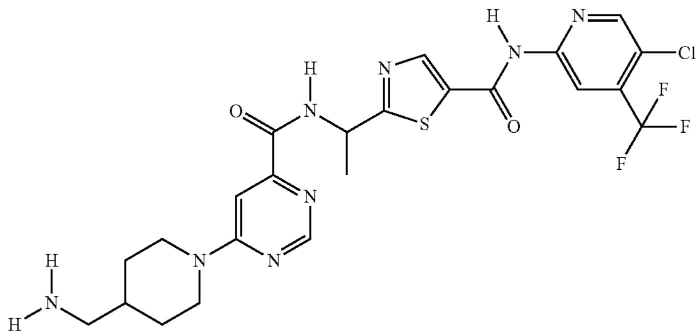 [SMILES: CC(NC(=O)c1cc(N2CCC(CN)CC2)ncn1)c1ncc(C(=O)Nc2cc(C(F)(F)F)c(Cl)cn2)s1] | ¹H-NMR (DMSO-D6, 200 MHz): δ 11.75 (s, 1H), 9.55 (d, N—H), 8.77 (s, 1H), 8.73 (s, 1H), 8.61 (s, 1H), 8.53 (s, 1H), 7.73 (bs, 2H), 7.36 (s, 1H), 5.44-5.37 (m, 1H), 4.47-4.45 (m, 2H), 3.06-2.93 (m, 2H), 2.73-2.60 (m, 2H), 1.97-1.12 (m, 5H), 1.65 (d, J = 7 Hz, 3H); m/z 568.7 [M + 1]⁺ |
| 19mmD | 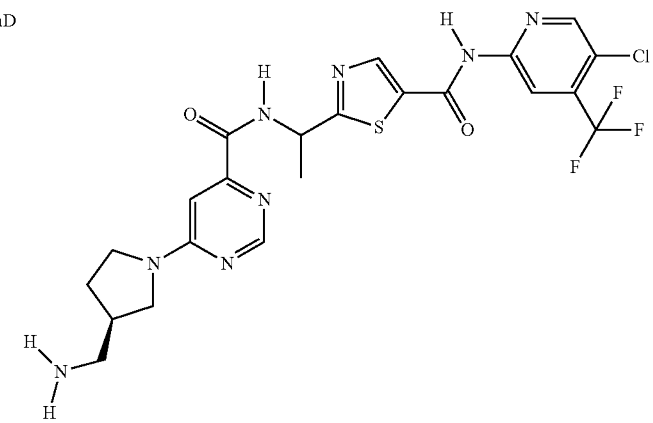 | ¹H-NMR (DMSO-D6, 500 MHz): δ 11.71 (s, 1H), 9.48 (s, 1H), 8.76 (s, 1H), 8.73 (s, 1H), 8.59 (s, 1H), 8.53 (s, 1H), 7.78 (bs, 2H), 7.01 (bs, 1H), 5.42- 5.39 (m, 1H), 3.02-2.85 (m, 6H), 2.16- 2.02 (m, 3H), 1.66 (d, J = 6.0 Hz, 3H); m/z 554.8 [M + 1]⁺ |
| 5ppD | 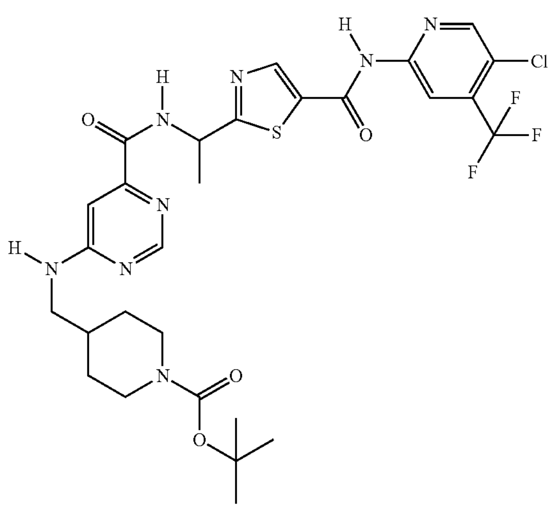 [SMILES: CC(NC(=O)c1cc(NCC2CCN(C(=O)OC(C)(C)C)CC2)ncn1)c1ncc(C(=O)Nc2cc(C(F)(F)F)c(Cl)cn2)s1] | ¹H-NMR (DMSO-D6, 500 MHz): δ 11.70 (s, 1H), 9.38 (d, J = 7.5 Hz, 1H), 8.76 (s, 1H), 8.72 (s, 1H), 8.54 (s, 1H), 8.50 (s, 1H), 7.88 (s, 1H), 7.11 (s, 1H ), 5.41- 5.37 (m, 1H), 3.983.90 (m, 2H), 2.70-2.60 (m, 3H), 1.79-1.68 (m, 4H), 1.61 (d, J = 6.5 Hz, 3H), 1.38 (s, 9H), 1.03 (d, J = 9.5 Hz, 2H); m/z 568.9 [M − Boc]. |

TABLE 3-continued
Exemplary Compounds of Formula I
| # | Structure | Characterization Data |
|---|---|---|
| 19rrD | 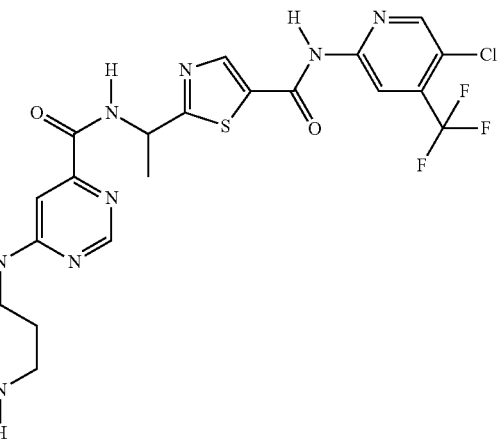 | $^1$H-NMR (DMSO-D6, 500 MHz): δ 11.71 (s, 1H), 9.42 (s, 1H), 8.76 (s, 1H), 8.72 (s, 1H), 8.54 (s, 1H), 8.47 (s, 1H), 7.93 (bs, 2H), 7.11 (s, 1H), 5.40- 5.37 (m, 1H), 4.20 (bs, 1H), 3.05- 3.03 (m, 4H), 2.04- 2.02 (m, 4H), 1.65 (d, J = 6.0 Hz, 3H); m/z 554.8 [M + 1]$^+$ |
| 31b | 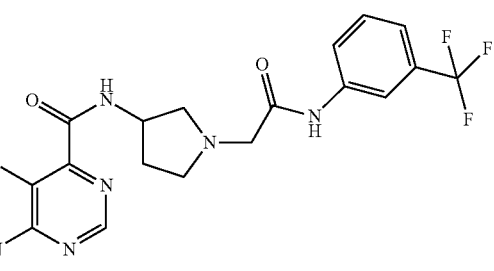 | $^1$H-NMR (DMSO-D6 500 MHz): δ 10.01 (s, 1H), 8.75 (d, J = 6.0 Hz, 1H), 8.29 (s, 1H), 8.10 (s, 1H), 7.86 (d, J = 8.0 Hz, 1H), 7.55-7.52 (m, 1H), 7.40 (d, J = 7.0 Hz, 1H), 4.42-4.19 (bs, 1H), 2.90-2.79 (m, 2H), 2.61-2.58 (m, 2H), 2.25-2.18 (m, 1H), 1.82-1.75 (m, 1H); 443 [M + 1]$^+$ |
| 19qqD | 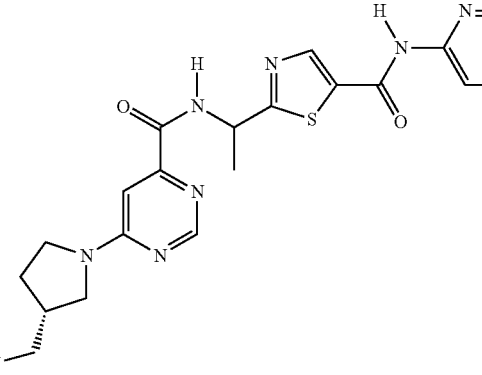 | $^1$H-NMR (DMSO-d$_6$, 500 MHz): δ 11.72 (s, 1H), 9.48 (s, 1H), 8.76 (s, 1H), 8.73 (s, 1H), 8.60 (s, 1H), 8.53 (s, 1H), 7.78 (bs, 2H), 7.01 (bs, 1H), 5.42- 5.39 (m, 1H), 3.84-3.78 (m, 2H), 3.34-3.30 (m, 2H), 2.95-2.90 (m, 3H), 2.16- 2.02 (m, 1H), 1.88-1.70 (m, 1H), 1.66 (d, J = 7.0 Hz, 3H); m/z 554.8 [M + 1]$^+$ |

TABLE 3-continued

Exemplary Compounds of Formula I

| # | Structure | Characterization Data |
|---|-----------|----------------------|
| 5qqD | 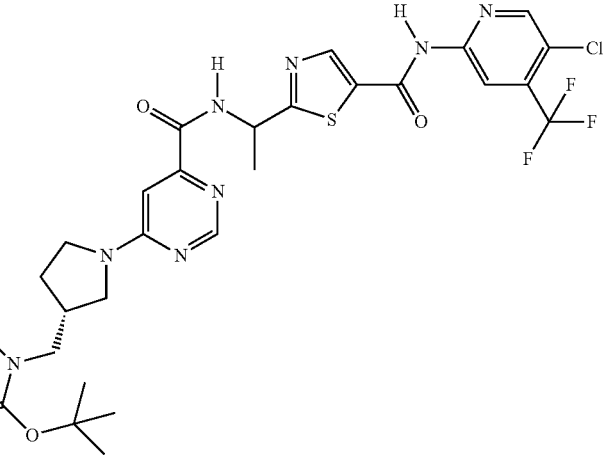 | $^1$H-NMR (DMSO-D6, 500 MHz): δ 11.71 (s, 1H), 9.46 (s, 1H), 8.75 (s, 1H), 8.72 (s, 1H), 8.56 (s, 1H), 8.54 (s, 1H), 7.00 (s, 1H), 6.97 (s, 1H), 5.41- 5.39 (m, 1H), 3.65-3.51 (m, 1H), 3.50-3.40 (m, 2H), 3.00-2.82 (m, 3H), 2.42-2.37 (m, 1H), 2.10-1.98 (m, 1H), 1.69-1.66 (m, 1H), 1.64 (d, J = 6.0 Hz, 3H), 1.36 (s, 9H); m/z 654.7 [M + 1]$^+$ |
| 19ooD | 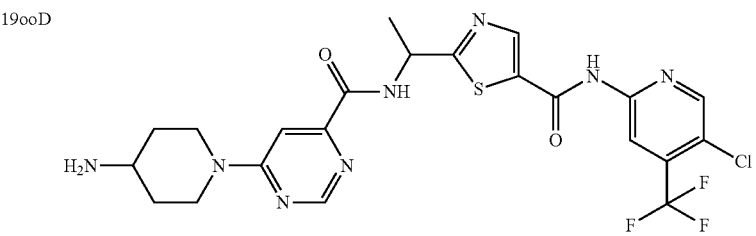 | $^1$H-NMR (CD$_3$OD-D4$_4$, 500 MHz): δ 8.60 (s, 2H), 8.58 (s, 1H), 8.52 (s, 1H), 7.44 (s, 1H), 5.54- 5.51 (m, 1H), 4.66-4.62 (m, 2H), 4.53 (bs, 1H), 3.13- 3.08 (m, 2H), 2.09-1.92 (m, 2H), 1.79 (d, J = 5.0 Hz, 3H) 1.52-1.50 (m, 2H); m/z 555.0 [M + 1]$^+$ |
| 19uuD | 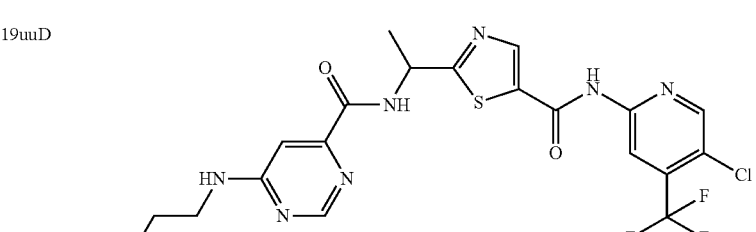 | $^1$H-NMR (CD$_3$OD-D4, 500 MHz): δ 8.60 (s, 1H), 8.58 (s, 1H), 8.56 (s, 1H), 8.52 (s, 1H), 7.18 (s, 1H), 5.53- 5.50 (m, 1H), 3.57 (bs, 2H), 3.03- 3.00 (m, 2H), 2.04- 1.99 (m, 2H), 1.77 (d, J = 5.0 Hz, 3H); m/z 528.8 [M + 1]$^+$ |
| 5vvD | 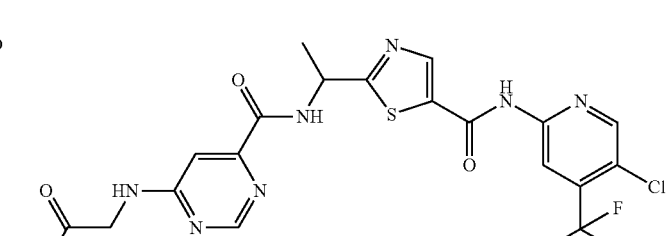 | $^1$H-NMR (DMSO-D6, 500 MHz): δ 11.68 (s, 1H), 9.38 (s, 1H), 8.75 (s, 1H), 8.71 (s, 1H), 8.53 (s, 1H), 8.52 (s, 1H), 8.03 (s, 1H), 7.39 (bs, 1H), 7.22 (bs, 1H), 7.00 (bs, 1H), 5.41- 5.37 (m, 1H), 3.93 (bs, 2H), 1.65 (d, J = 5.0 Hz, 3H); m/z 528.7 [M + 1]$^+$ |

TABLE 3-continued

Exemplary Compounds of Formula I

| # | Structure | Characterization Data |
|---|---|---|
| 5rrD | 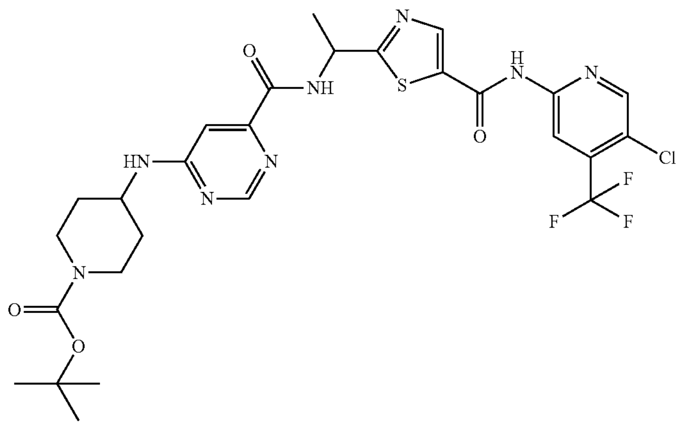 [SMILES: CC(NC(=O)c1cc(NC2CCN(C(=O)OC(C)(C)C)CC2)ncn1)c1ncc(C(=O)Nc2cc(C(F)(F)F)c(Cl)cn2)s1] | ¹H-NMR (DMSO-D6, 500 MHz): δ 11.81 (bs, 1H), 9.39 (s, 1H), 8.75 (s, 1H), 8.71 (s, 1H), 8.53 (s, 1H), 8.52 (s, 1H), 7.80 (bs, 1H), 7.08 (s, 1H), 5.40- 5.37 (m, 1H), 4.06 (bs, 1H), 3.87 (bs, 2H), 2.92 (bs, 2H), 1.86 (bs, 2H), 1.64 (d, J = 5.0 Hz, 3H), 1.40 (s, 9H), 1.29- 1.22 (m, 2H); m/z 654.9 [M + 1]⁺ |
| 28c | 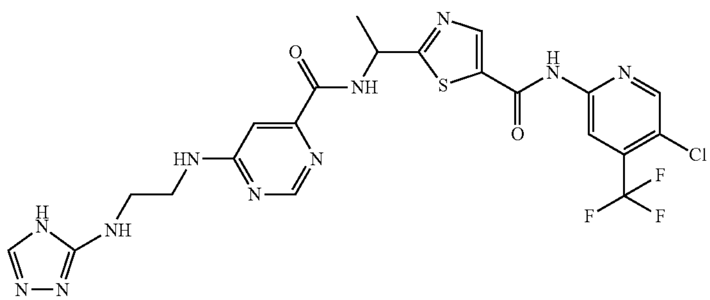 [SMILES: CC(NC(=O)c1cc(NCCNc2nnc[nH]2)ncn1)c1ncc(C(=O)Nc2cc(C(F)(F)F)c(Cl)cn2)s1] | ¹H-NMR (DMSO-D6, 200 MHz): δ 11.74 (s, 1H), 9.47 (d, J = 8.2 Hz, 1H), 8.77 (s, 1H), 8.73 (s, 1H), 8.53 (s, 1H), 8.50 (s, 1H), 8.24 (s, 1H), 7.99-7.97(m, 1H), 7.11 (s, 1H), 5.41-5.33 (m, 1H), 3.24-3.16 (m, 4H), 1.63 (d, J = 7 Hz, 3H); m/z 581.96 [M + 1]⁺ |
| 28d | 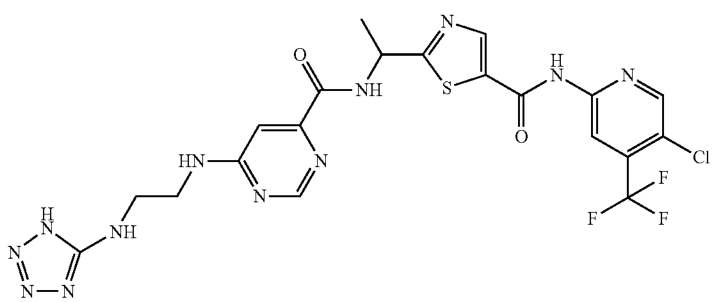 [SMILES: CC(NC(=O)c1cc(NCCNc2nnn[nH]2)ncn1)c1ncc(C(=O)Nc2cc(C(F)(F)F)c(Cl)cn2)s1] | ¹H-NMR (DMSO-D6, 500 MHz): δ 11.73 (bs, 1H), 9.46 (d, J = 8.0 Hz, 1H), 8.76 (s, 1H), 8.72 (s, 1H), 8.54 (s, 1H), 8.52 (s, 1H), 7.96 (bs, 1H), 7.08 (s, 1H), 7.05 (s, 1H), 5.42- 5.34 (m, 1H), 3.53- 3.23 (m, 4H), 1.65 (d, J = 5.0 Hz, 3H); m/z 582.8 [M + 1]⁺ |
| 28e | 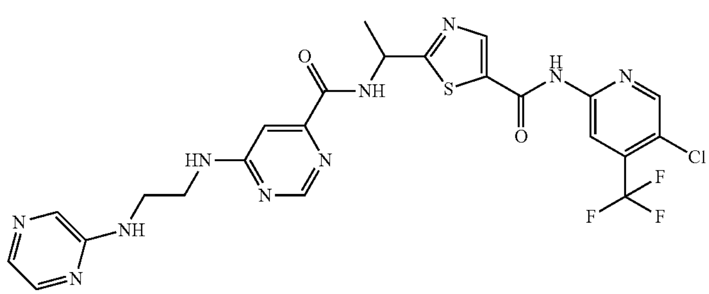 [SMILES: CC(NC(=O)c1cc(NCCNc2cnccn2)ncn1)c1ncc(C(=O)Nc2cc(C(F)(F)F)c(Cl)cn2)s1] | ¹H-NMR (DMSO-D6, 500 MHz): δ 11.74 (bs, 1H), 9.46 (d, J = 8.0 Hz, 1H), 8.76 (s, 1H), 8.72 (s, 1H), 8.54 (s, 2H), 7.98 (s, 1H), 7.90 (s, 2H), 7.64 (s, 1H), 7.18- 7.10 (bs, 2H), 5.42- 5.35 (m, 1H), 3.46- 3.41 (m, 4H), 1.65 (d, J = 5.0 Hz, 3H); m/z 592.8 [M + 1]⁺ |
| 20aD | 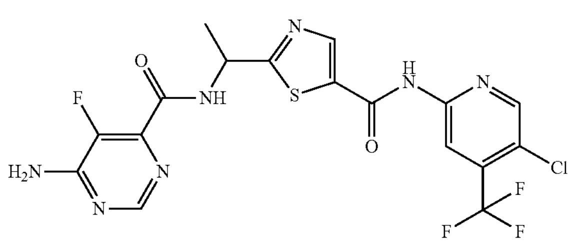 [SMILES: CC(NC(=O)c1ncnc(N)c1F)c1ncc(C(=O)Nc2cc(C(F)(F)F)c(Cl)cn2)s1] | ¹H-NMR (DMSO-D6, 500 MHz): δ 11.71 (bs, N—H), 9.44 (bs, N—H), 8.76 (s, 1H), 8.73 (s, 1H), 8.55 (s, 1H), 8.24 (s, 1H), 7.59 (s, 2H), 5.36 (m, 1H), 1.62 (d, J = 7.0 Hz, 3H); m/z 489.9 [M + 1]⁺ |

TABLE 3-continued

Exemplary Compounds of Formula I

| # | Structure | Characterization Data |
|---|---|---|
| 30c | 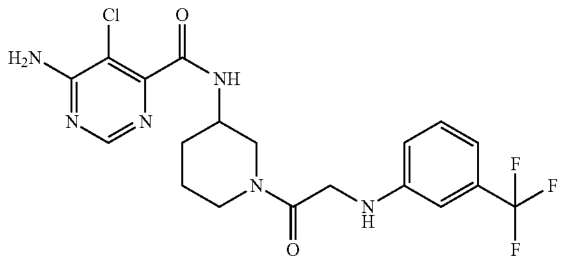 [SMILES: Nc1ncnc(C(=O)NC2CCCN(C(=O)CNc3cccc(C(F)(F)F)c3)C2)c1Cl] | $^1$H-NMR (DMSO-D6, 500 MHz): δ 8.71 (d, J = 7.0 Hz, 1H), 8.58 (d, J = 8.0 Hz, 1H), 8.27 (s, 2H), 7.85-7.35 (bs, 2N—H), 6.97-6.81 (m, 2H), 6.08 (d, J = 4.0 Hz, 1H), 6.18 (d, J = 4.0 Hz, 1H), 4.22 (d, J = 10 Hz, 1H), 4.01-3.85 (m, 2H), 3.82-3.66 (m, 2H), 3.07-3.00 (m, 2H), 2.78 (q, J = 11 Hz, 1H), 1.92-1.85 (m, 3H); m/z: 456.8 [M + 1]$^+$ |
| 28f | 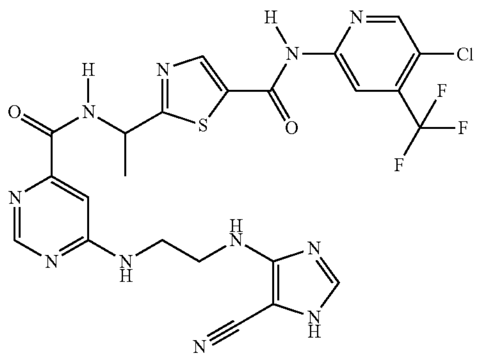 [SMILES: CC(NC(=O)c1cc(NCCNc2nc[nH]c2C#N)ncn1)c1ncc(C(=O)Nc2cc(C(F)(F)F)c(Cl)cn2)s1] | $^1$H-NMR (DMSO-D6, 200 MHz, Rotamers): δ 12.41 (s, 1H), 11.83 (s, 1H), 11.73 (s, 2H), 9.44 (d, J = 8.6 Hz, 2H), 8.76 (s, 2H), 8.76 (s, 2H), 8.72 (s, 2H), 8.54 (s, 4H), 7.96 (bs, 2H), 7.50 (s, 1H), 7.18 (s, 1H), 7.09 (m, 2H), 6.57 (bs, 1H), 6.34 (bs, 1H), 5.41-5.32 (m, 2H), 3.51-3.20 (m, 8H), 1.64 (d, J = 6.8 Hz, 6H); m/z 605.8 [M + 1]$^+$ |
| 26cD | 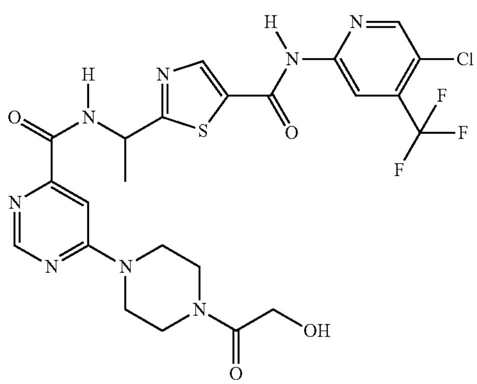 [SMILES: CC(NC(=O)c1cc(N2CCN(C(=O)CO)CC2)ncn1)c1ncc(C(=O)Nc2cc(C(F)(F)F)c(Cl)cn2)s1] | $^1$H-NMR (DMSO-D6, 200 MHz): δ 11.73 (s, 1H), 9.53 (d, J = 8.0 Hz, 1H), 8.76 (s, 1H), 8.72 (s, 1H), 8.64 (s, 1H), 8.53 (s, 1H), 7.33 (s, 1H), 5.45-5.37 (m, 1H), 4.66 (t, J = 5.4 Hz, 1H), 4.12 (d, J = 5.4 Hz, 1H), 3.80-3.40 (m, 8H), 1.64 (d, J = 6.8 Hz, 3H); m/z 598.7 [M + 1]$^+$ |
| 5wwD | 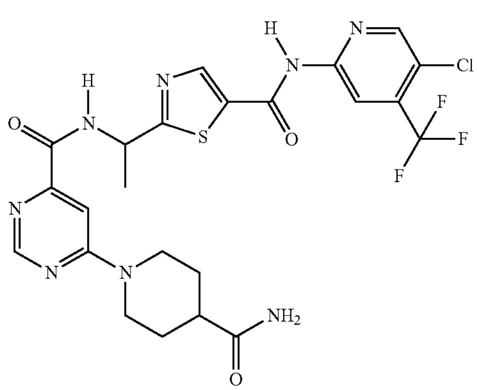 [SMILES: CC(NC(=O)c1cc(N2CCC(C(N)=O)CC2)ncn1)c1ncc(C(=O)Nc2cc(C(F)(F)F)c(Cl)cn2)s1] | $^1$H-NMR (DMSO-D6, 500 MHz): δ 11.70 (s, 1H), 9.44 (d, J = 7.0 Hz, 1H), 8.75 (s, 1H), 8.72 (s, 1H), 8.59 (s, 1H), 8.54 (s, 1H), 7.30 (s, 1H), 7.27 (s, 1H), 6.77 (s, 1H), 5.40-5.35 (m, 1H), 4.43 (bs, 2H), 3.04-3.02 (m, 2H), 2.46-2.42 (m, 1H), 1.80-1.76 (m, 2H), 1.64 (d, J = 7.5 Hz, 3H), 1.49-1.46 (m, 2H); m/z 582.7 [M + 1]$^+$ |

TABLE 3-continued

Exemplary Compounds of Formula I

| # | Structure | Characterization Data |
|---|---|---|
| 39a | 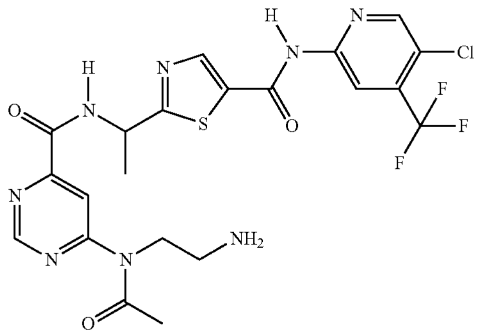 [SMILES: CC(=O)N(CCN)c1cc(C(=O)NC(C)c2ncc(C(=O)Nc3cc(C(F)(F)F)c(Cl)cn3)s2)ncn1] | $^1$H-NMR (DMSO-D6, 500 MHz): δ 11.20 (bs, 1H), 9.39 (d, J = 7.5 Hz, 1H), 8.74 (s, 1H), 8.70 (s, 1H), 8.54 (s, 1H), 8.52 (s, 1H), 7.91 (bs, 2H), 7.07 (s, 1H), 5.40-5.36 (m, 1H), 3.40-3.39 (m, 2H), 3.22-3.18 (m, 2H), 1.78 (s, 3H), 1.64 (d, J = 7.5 Hz, 3H); m/z 556.8 [M + 1]$^+$ |
| 5xxD | 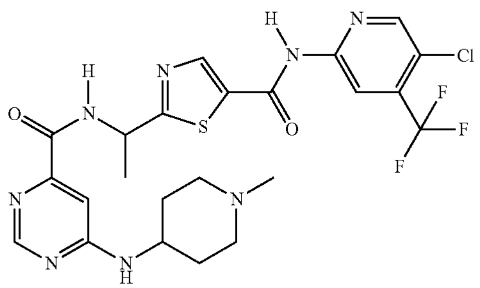 [SMILES: CC(NC(=O)c1cc(NC2CCN(C)CC2)ncn1)c1ncc(C(=O)Nc2cc(C(F)(F)F)c(Cl)cn2)s1] | $^1$H-NMR (DMSO-D6, 500 MHz): δ 11.70 (s, 1H), 9.37 (d, J = 7.5 Hz, 1H), 8.75 (s, 1H), 8.71 (s, 1H), 8.54 (s, 1H), 8.51 (s, 1H), 7.76 (d, J = 6.5 Hz, 1H), 7.08 (s, 1H), 5.40-5.35 (m, 1H), 3.83-3.82 (m, 1H), 2.73-2.70 (m, 2H), 2.15 (s, 3H), 2.00-1.95 (m, 4H), 1.86-1.84 (m, 2H), 1.64 (d, J = 7.5 Hz, 3H); m/z 568.8 [M + 1] |
| 26bD | 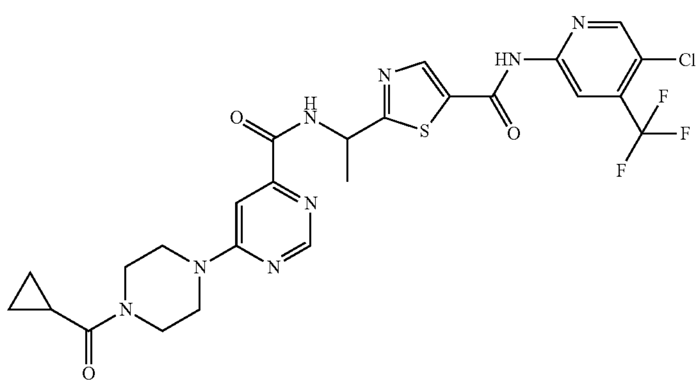 [SMILES: CC(NC(=O)c1cc(N2CCN(C(=O)C3CC3)CC2)ncn1)c1ncc(C(=O)Nc2cc(C(F)(F)F)c(Cl)cn2)s1] | $^1$H-NMR (CD$_3$OD, 500 MHz): δ 8.63 (s, 1H), 8.61 (s, 1H), 8.58 (s, 1H), 8.52 (s, 1H), 7.43 (s, 1H), 5.56-5.52 (m, 1H), 4.55 (s, 1H), 3.93-3.82 (m, 4H), 3.81-3.70 (m, 4H), 2.03-2.00 (m, 1H), 1.78 (d, J = 7.5 Hz, 3H) 0.94-0.85 (m, 4H); m/z 608.7 [M + 1]$^+$ |
| 5aaaD | 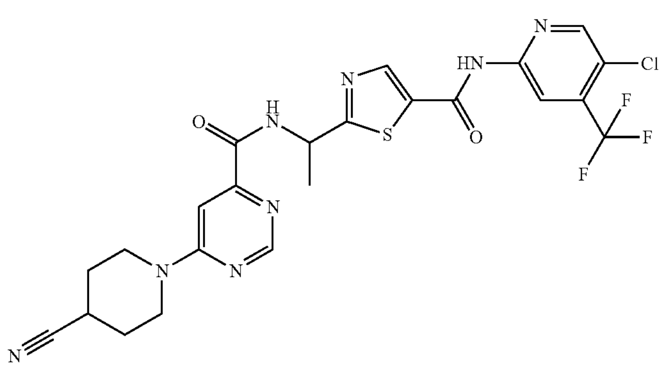 [SMILES: CC(NC(=O)c1cc(N2CCC(C#N)CC2)ncn1)c1ncc(C(=O)Nc2cc(C(F)(F)F)c(Cl)cn2)s1] | $^1$H-NMR (DMSO-D6, 500 MHz): δ 11.71 (s, 1H), 9.47 (d, J = 8.0 Hz, 1H), 8.75 (s, 1H), 8.72 (s, 1H), 8.61 (s, 1H), 8.54 (s, 1H), 7.34 (s, 1H), 5.41-5.38 (m, 1H), 4.00-3.98 (m, 2H), 3.54-3.52 (m, 2H), 3.16-3.12 (m, 2H), 1.97-1.93 (m, 2H), 1.72 (d, J = 7.5 Hz, 3H); m/z 564.8 [M + 1]$^+$ |

TABLE 3-continued

Exemplary Compounds of Formula I

| # | Structure | Characterization Data |
|---|---|---|
| 26eD | 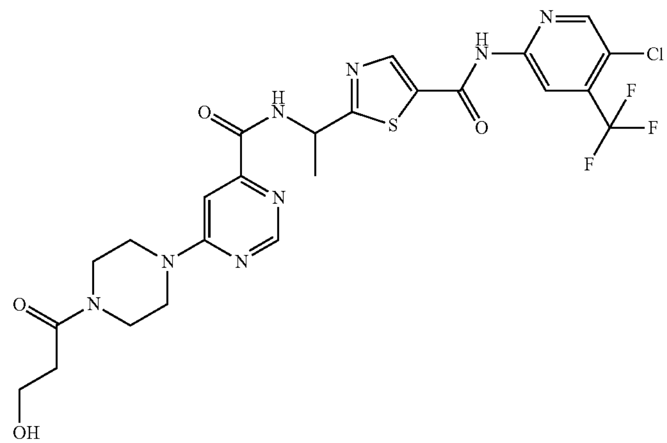 [SMILES: CC(NC(=O)c1cc(N2CCN(C(=O)CCO)CC2)ncn1)c1ncc(C(=O)Nc2cc(C(F)(F)F)c(Cl)cn2)s1] | $^1$H-NMR (Acetone-D6, 500 MHz): δ 10.34 (s, 1H), 8.90 (d, J = 8.0 Hz, 1H), 8.68 (s, 1H), 8.63 (s, 1H), 8.55 (s, 1H), 8.53 (s, 1H), 7.34 (s, 1H), 5.53-5.49 (m, 1H), 3.85-3.81 (m, 2H), 3.77-3.60 (m, 9H), 2.60-2.57 (m, 2H), 1.75 (d, J = 7.5 Hz, 3H); m/z 613.3 [M + 1]$^+$ |
| 5yyD | 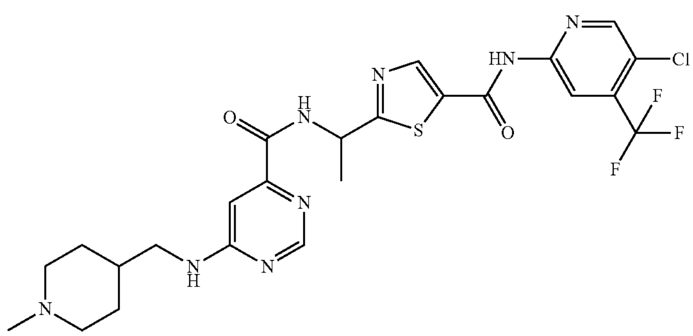 [SMILES: CC(NC(=O)c1cc(NCC2CCN(C)CC2)ncn1)c1ncc(C(=O)Nc2cc(C(F)(F)F)c(Cl)cn2)s1] | $^1$H-NMR (DMSO-D6, 500 MHz): δ 11.71 (s, 1H), 9.38 (d, J = 8.0 Hz, 1H), 8.76 (s, 1H), 8.72 (s, 1H), 8.54 (s, 1H), 8.51 (s, 1H), 7.90 (s, 1H), 7.11 (s, 1H), 5.40-5.37 (m, 1H), 1.63-1.47 (m, 6H), 1.34 (d, J = 7.5 Hz, 3H), 1.33-1.22 (m, 4H); m/z 582.9 [M + 1]$^+$ |
| 31c | 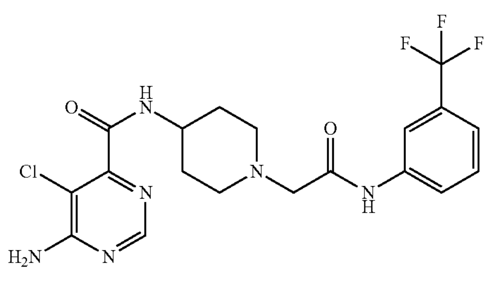 [SMILES: Nc1ncnc(C(=O)NC2CCN(CC(=O)Nc3cccc(C(F)(F)F)c3)CC2)c1Cl] | $^1$H-NMR (DMSO-D6, 500 MHz): δ 10.04 (s, 1H), 8.49 (d, J = 8.0 Hz, 1H), 8.28 (s, 1H), 8.15 (s, 1H), 7.87 (d, J = 9.0 Hz, 1H), 7.53 (t, J = 8.0 Hz, 1H), 7.40 (d, J = 8.0 Hz, 1H), 3.71 (bs, 1H), 3.14 (s, 2H), 2.88-2.83 (m, 2H), 2.28-2.24 (m, 2H), 1.80-1.78 (m, 2H), 1.63-1.61 (m, 2H); m/z 457 [M + 1]$^+$ |
| 31a | 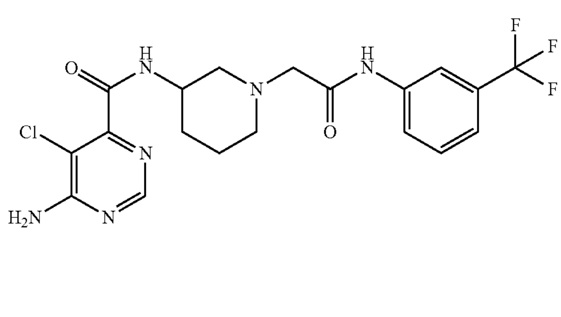 [SMILES: Nc1ncnc(C(=O)NC2CCCN(CC(=O)Nc3cccc(C(F)(F)F)c3)C2)c1Cl] | $^1$H-NMR (DMSO-D6, 500 MHz): δ 9.99 (s, 1H), 8.57 (d, J = 8.0 Hz, 1H), 8.28 (s, 1H), 8.10 (s, 1H), 7.82 (d, J = 7.5 Hz, 1H), 7.54-7.51 (m, 1H), 7.39 (d, J = 7.5 Hz, 1H), 4.03-3.98 (m, 1H), 3.20-3.06 (m, 2H), 2.69 (d, J = 9.5 Hz, 1H), 2.49-2.30 (m, 2H), 1.68-1.59 (m, 3H), 1.42-1.34 (m, 1H); m/z 456.9 [M + 1]$^+$ |

TABLE 3-continued
Exemplary Compounds of Formula I
| # | Structure | Characterization Data |
|---|-----------|----------------------|
| 40b | 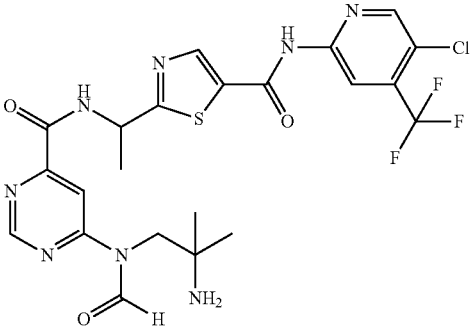 [SMILES: CC(NC(=O)c1cc(N(C=O)CC(C)(C)N)ncn1)c1ncc(C(=O)Nc2cc(C(F)(F)F)c(Cl)cn2)s1] | ¹H-NMR (DMSO-D6, 500 MHz): δ 11.71 (s, 1H), 9.40 (s, 1H ), 8.75 (s, 1H), 8.72 (s, 1H), 8.54 (s, 1H), 8.50 (s, 1H), 7.89 (s, 1H), 7.21 (s, 1H), 5.40-5.37 (m, 1H), 3.69-3.67 (m, 1H), 3.48-3.47 (m, 1H), 1.64 (d, J = 6.5 Hz, 3H), 1.24 (s, 6H); m/z 570.9 [M + 1]⁺ |
| 20bDa | 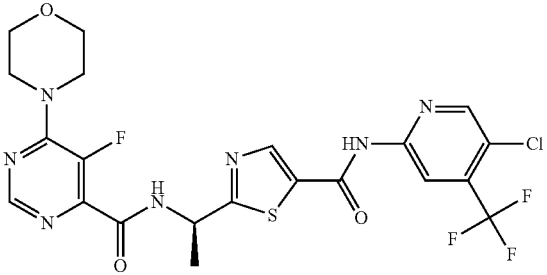 [SMILES: C[C@@H](NC(=O)c1ncnc(N2CCOCC2)c1F)c1ncc(C(=O)Nc2cc(C(F)(F)F)c(Cl)cn2)s1] | ¹H-NMR (DMSO-D6, 500 MHz): δ 11.75 (s, 1H), 9.46 (d, J = 8.5 Hz, 1H), 8.75 (s, 1H), 8.72 (s, 1H), 8.48 (bs, 1H), 8.12 (s, 1H), 5.41- 5.39 (m, 1H), 378-3.65 (m, 8H), 1.67 (d, J = 8.0 Hz, 3H); m/z 559.6 [M + 1]⁺ |
| 26dD | 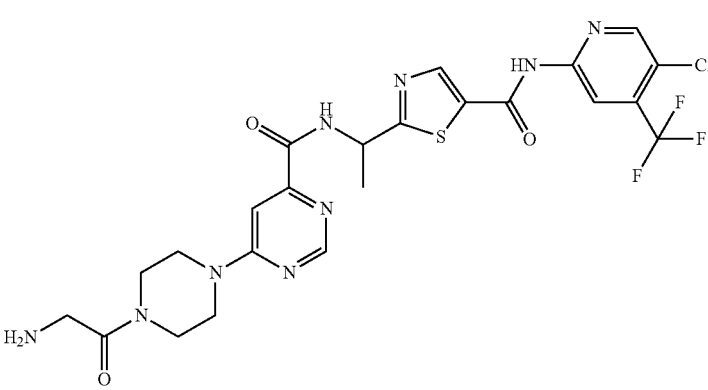 [SMILES: CC(NC(=O)c1cc(N2CCN(C(=O)CN)CC2)ncn1)c1ncc(C(=O)Nc2cc(C(F)(F)F)c(Cl)cn2)s1] | ¹H-NMR (CD₃OD, 500 MHz): δ 8.65 (s, 1H), 8.61 (s, 1H ), 8.59 (s, 1H), 8.53 (s, 1H), 7.45 (s, 1H), 5.55-5.53 (m, 1H), 4.02 (s, 2H), 3.92- 3.84 (m, 4H), 3.80-3.76 (m, 2H), 3.63-3.59 (m, 2H), 1.78 (d, J = 7.0 Hz, 3H); m/z 598.2 [M + 1]⁺ |
| 18mD | 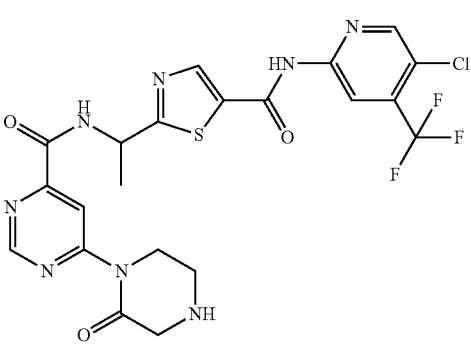 [SMILES: CC(NC(=O)c1cc(N2CCNCC2=O)ncn1)c1ncc(C(=O)Nc2cc(C(F)(F)F)c(Cl)cn2)s1] | ¹H-NMR (DMSO-D6, 200 MHz): δ 11.77 (s, 1H), 9.81 (d, J = 8.5 Hz, 1H), 9.13 (s, 1H), 8.78 (s, 1H), 8.76 (s, 1H), 8.75 (s, 1H), 8.46 (s, 1H), 5.47- 5.43 (m, 1H), 4.23-4.13 (m, 2H), 3.98 (s, 2H), 3.57-3.54 (m, 2H), 1.64 (d, J = 6.5 Hz, 3H); m/z 554.8 [M + 1]⁺ |

TABLE 3-continued

Exemplary Compounds of Formula I

| # | Structure | Characterization Data |
|---|-----------|----------------------|
| 28g | 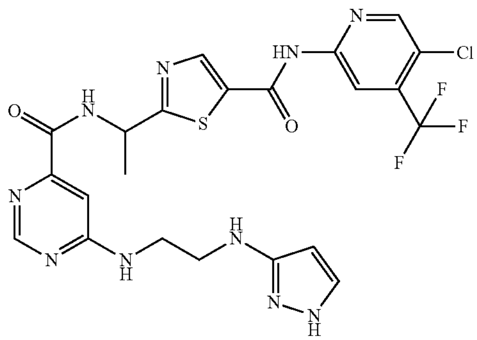 [SMILES: CC(NC(=O)c1cc(NCCNc2cc[nH]n2)ncn1)c1ncc(C(=O)Nc2cc(C(F)(F)F)c(Cl)cn2)s1] | ¹H-NMR (Acetone-D6, 500 MHz): δ 10.74 (bs, 1H), 8.89 (s, 1H), 8.67 (s, 1H), 8.63 (s, 1H), 8.55 (s, 1H), 8.47 (s, 1H), 7.20- 7.16 (m, 3H), 5.49-5.40 (m, 1H), 3.57- 3.48 (m, 6H), 1.74 (d, J = 6.5 Hz, 3H); m/z 580.7 [M + 1]⁺ |
| 28h | 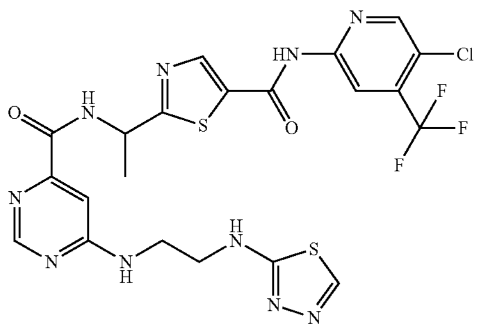 [SMILES: CC(NC(=O)c1cc(NCCNc2nncs2)ncn1)c1ncc(C(=O)Nc2cc(C(F)(F)F)c(Cl)cn2)s1] | ¹H-NMR (DMSO-D6, 500 MHz): δ 11.74 (s, 1H), 9.45 (s, 1H), 8.76 (s, 1H), 8.72 (s, 1H), 8.61 (s, 1H), 8.54 (s, 1H), 8.02 (s, 1H), 7.86 (s, 1H), 7.09 (s, 1H), 5.40-5.37 (m, 1H), 3.80-3.60 (m, 1H), 1.64 (d, J = 7 Hz, 3H); m/z 598.7 [M + 1]⁺ |
| 5bbbDa | 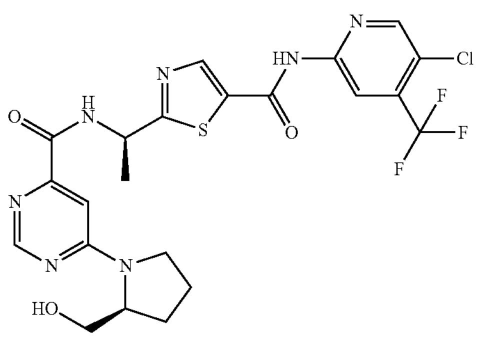 [SMILES: C[C@@H](NC(=O)c1cc(N2CCC[C@H]2CO)ncn1)c1ncc(C(=O)Nc2cc(C(F)(F)F)c(Cl)cn2)s1] | ¹H-NMR (DMSO-D6, 500 MHz): δ 11.74 (s, 1H), 9.49 (s, 1H ), 8.76 (s, 1H), 8.72 (s, 1H), 8.57 (s, 1H), 8.54 (s, 1H), 7.20 (s, 0.5H), 6.97 (s, 0.5H), 5.41-5.38 (m, 1H), 4.99 (s, 0.5H), 4.80 (s, 0.5H), 4.25 (s, 0.5H), 3.95 (s, 0.5H), 3.63-3.49 (m, 3H), 2.04-1.93 (m, 4H), 1.65 (d, J = 6.5 Hz, 3H); m/z 555.7 [M + 1]⁺ |
| 41 | 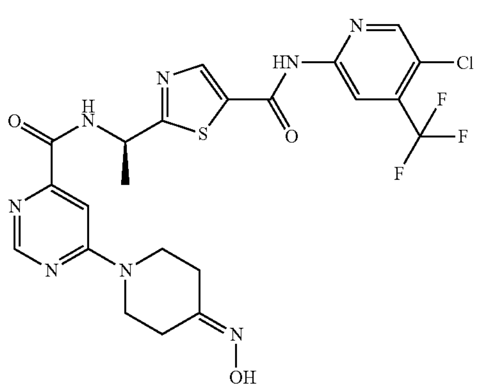 [SMILES: C[C@@H](NC(=O)c1cc(N2CCC(=NO)CC2)ncn1)c1ncc(C(=O)Nc2cc(C(F)(F)F)c(Cl)cn2)s1] | ¹H-NMR (DMSO-D6, 500 MHz): δ 11.74 (s, 1H), 10.50 (s, 1H), 9.52 (s, 1H), 8.76 (s, 1H), 8.72 (s, 1H), 8.63 (s, 1H), 8.54 (s, 1H), 7.31 (s, 1H), 5.42-5.39 (m, 1H), 3.81-3.70 (m, 4H), 2.49-2.41 (m, 4H), 1.66 (d, J = 7 Hz, 3H), m/z 568.7 [M + 1]⁺ |

TABLE 3-continued

Exemplary Compounds of Formula I

| # | Structure | Characterization Data |
|---|---|---|
| 28i | 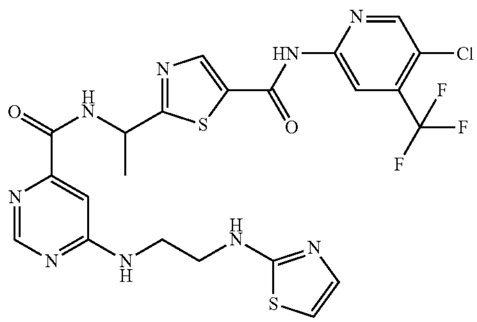 [SMILES: CC(NC(=O)c1cc(NCCNc2nccs2)ncn1)c1ncc(C(=O)Nc2cc(C(F)(F)F)c(Cl)cn2)s1] | $^1$H-NMR (DMSO-D6, 500 MHz): δ 11.9 (s, 1H), 9.45 (s, 1H ), 8.76 (s, 1H), 8.72 (s, 1H), 8.54 (s, 2H), 7.97 (s, 1H), 7.09 (s, 1H), 5.40-5.37 (m, 1H), 3.85-3.82 (m, 2H), 3.50 (bs, 2H), 3.36-3.31 (m, 2H), 1.64 (d, J = 7 Hz, 3H), m/z 599.7 [M + 1]$^+$ |
| 28j | 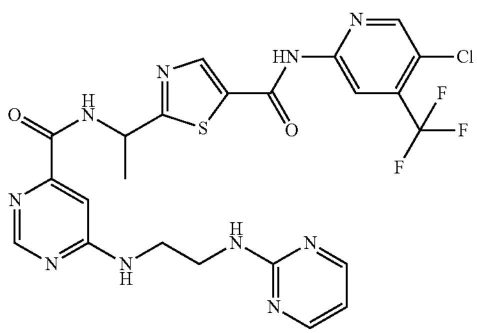 [SMILES: CC(NC(=O)c1cc(NCCNc2ncccn2)ncn1)c1ncc(C(=O)Nc2cc(C(F)(F)F)c(Cl)cn2)s1] | $^1$H-NMR (DMSO-D6, 500 MHz): δ 11.74 (s, 1H), 9.44 (d, J = 7.5 Hz, 1H ), 8.76 (s, 1H), 8.72 (s, 1H), 8.54 (s, 2H), 8.26 (s, 2H), 7.98 (s, 1H), 7.20 (s, 1H), 7.07 (s, 1H), 6.56 (s, 1H), 5.42-5.39 (m, 1H), 3.53-3.44 (m, 4H), 1.64 (d, J = 6.5 Hz, 3H), m/z 592.6 [M + 1]$^+$ |
| 28k | 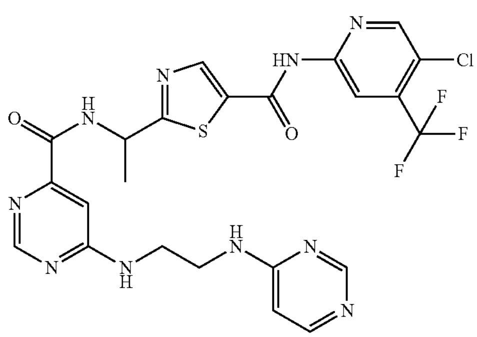 [SMILES: CC(NC(=O)c1cc(NCCNc2ccncn2)ncn1)c1ncc(C(=O)Nc2cc(C(F)(F)F)c(Cl)cn2)s1] | $^1$H-NMR (DMSO-D6, 500 MHz): δ 11.82 (s, 1H), 9.44 (d, NH ), 8.75 (s, 1H), 8.70 (s, 1H), 8.55 (s, 1H), 8.53 (s, 1H), 8.39 (s, 1H), 8.00 (bs, 2H), 7.49 (s, 1H), 7.08 (s, 1H), 6.45 (s, 1H), 5.39-5.37 (m, 1H), 3.52-3.46 (m, 4H), 1.64 (d, J = 7.5 Hz, 3H), m/z 592.6 [M + 1]$^+$ |
| 5dddDa | 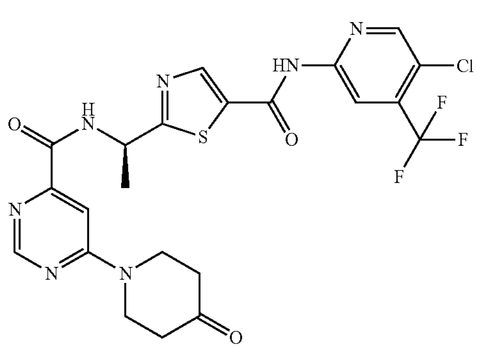 [SMILES: C[C@@H](NC(=O)c1cc(N2CCC(=O)CC2)ncn1)c1ncc(C(=O)Nc2cc(C(F)(F)F)c(Cl)cn2)s1] | $^1$H-NMR (DMSO-D6, 500 MHz): δ 11.74 (s, 1H), 9.55 (s, 1H), 8.76 (s, 1H), 8.73 (s, 1H), 8.67 (s, 1H), 8.54 (s, 1H), 7.39 (s, 1H), 5.43-5.40 (m, 1H), 4.10-4.00 (m, 4H), 3.31-3.29 (m, 4H), 1.66 (d, J = 7 Hz, 3H); m/z 553.7 [M + 1]$^+$ |

TABLE 3-continued

Exemplary Compounds of Formula I

| # | Structure | Characterization Data |
|---|---|---|
| 5vvDa | 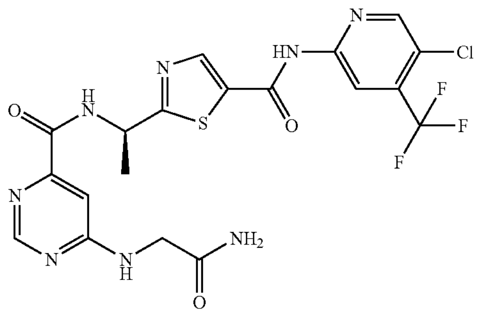 [SMILES: C[C@@H](NC(=O)c1cc(NCC(N)=O)ncn1)c1ncc(C(=O)Nc2cc(C(F)(F)F)c(Cl)cn2)s1] | $^1$H-NMR (DMSO-D6, 500 MHz): δ 11.74 (s, 1H), 9.45 (d, J = 7 Hz, 1H), 8.76 (s, 1H), 8.72 (s, 1H), 8.54 (s, 1H), 8.53 (s, 1H), 8.08 (s, 1H), 7.43 (s, 1H), 7.22 (s, 1H), 7.05 (s, 1H), 5.40-5.37 (m, 1H), 3.93 (s, 2H), 1.64 (d, J = 7 Hz, 3H); m/z 528.7 [M + 1]$^+$ |
| 26cDa | 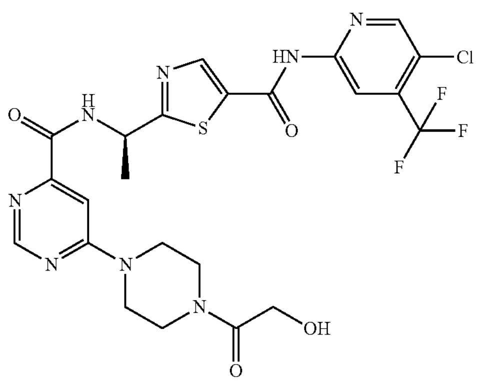 [SMILES: C[C@@H](NC(=O)c1cc(N2CCN(C(=O)CO)CC2)ncn1)c1ncc(C(=O)Nc2cc(C(F)(F)F)c(Cl)cn2)s1] | $^1$H-NMR (DMSO-D6, 500 MHz): δ 11.73 (s, 1H), 9.53 (d, J = 9 Hz, 1H), 8.76 (s, 1H), 8.71 (s, 1H), 8.64 (s, 1H), 8.54 (s, 1H), 7.34 (s, 1H), 5.42-5.39 (m, 1H), 4.69-4.68 (m, 1H), 4.12 (d, J = 5.5 Hz, 2H), 3.80-3.64 (m, 4H), 3.60-3.55 (m, 2H), 3.52-3.46 (m, 2H), 1.65 (d, J = 6.5 Hz, 3H); m/z 598.7 [M + 1]$^+$ |
| 18fDa | 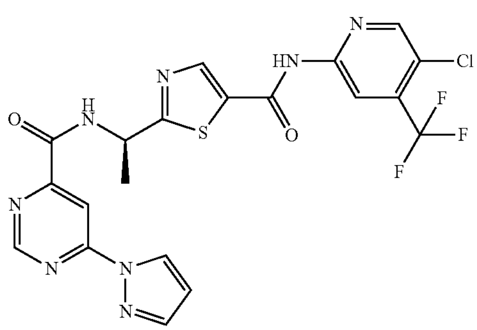 [SMILES: C[C@@H](NC(=O)c1cc(-n2cccn2)ncn1)c1ncc(C(=O)Nc2cc(C(F)(F)F)c(Cl)cn2)s1] | $^1$H-NMR (DMSO-D6, 500 MHz): δ 11.74 (s, 1H), 9.88 (d, J = 7.5 Hz, 1H), 9.24 (s, 1H), 8.76-8.74 (m, 3H), 8.54 (s, 1H), 8.37 (s, 1H), 8.02 (s, 1H), 6.72 (s, 1H), 5.52-5.47 (m, 1H), 1.69 (d, J = 6.5 Hz, 3H); m/z 522.8 [M + 1]$^+$ |
| 42a | 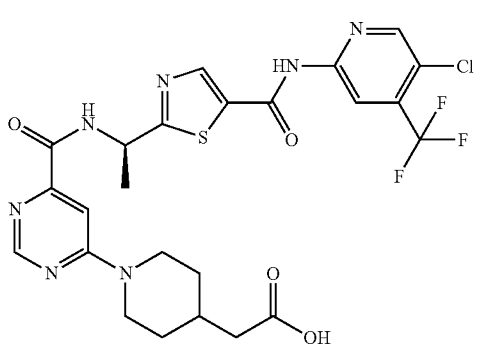 [SMILES: C[C@@H](NC(=O)c1cc(N2CCC(CC(=O)O)CC2)ncn1)c1ncc(C(=O)Nc2cc(C(F)(F)F)c(Cl)cn2)s1] | $^1$H-NMR (DMSO-D6, 500 MHz): δ 11.75 (s, 1H), 9.58 (s, 1H), 8.77 (s, 1H), 8.73 (s, 1H), 8.60 (s, 1H), 8.54 (s, 1H), 7.38 (s, 1H), 5.43-5.40 (m, 1H), 4.60-4.40 (m, 2H), 3.08-2.97 (m, 2H), 2.18 (d, J = 6.5 Hz, 2H), 2.10-1.98 (m, 1H), 1.78 (d, J = 11 Hz, 2H), 1.65 (d, J = 7.5 Hz, 3H), 1.22-1.14 (m, 2H); m/z 597.7 [M + 1]$^+$ |

TABLE 3-continued

Exemplary Compounds of Formula I

| # | Structure | Characterization Data |
|---|---|---|
| 42b | 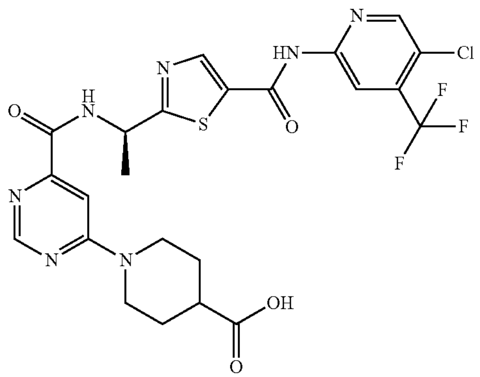 [SMILES: C[C@@H](NC(=O)c1cc(N2CCC(C(=O)O)CC2)ncn1)c1ncc(C(=O)Nc2cc(C(F)(F)F)c(Cl)cn2)s1] | ¹H-NMR (DMSO-D6, 500 MHz): δ 11.75 (s, 1H), 9.64 (bs, 1H), 8.77 (s, 1H), 8.74 (s, 1H), 8.63 (s, 1H), 8.54 (s, 1H), 7.45 (bs, 1H), 5.44-5.41 (m, 1H), 4.44-4.24 (m, 2H), 3.24-3.18 (m, 2H), 2.65-2.60 (m, 1H), 1.93 (d, J = 11 Hz, 2H), 1.66 (d, J = 7.5 Hz, 3H), 1.53 (d, J = 11.5 Hz, 2H); m/z 583.7 [M + 1]⁺ |
| 32b | 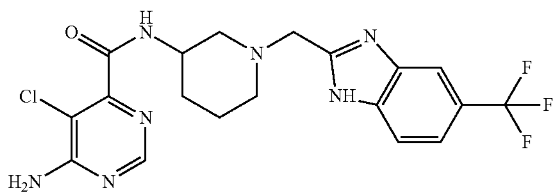 [SMILES: Nc1ncnc(C(=O)NC2CCCN(Cc3nc4cc(C(F)(F)F)ccc4[nH]3)C2)c1Cl] | ¹H-NMR (Acetone-D6, 500 MHz): 11.95-11.89 (bs, 1N—H), 8.56 (bs, 1N—H), 8.25 (s, 1H), 8.00 (s, 1H), 7.52 (d, J = 8.0 Hz, 1H), 7.23 (d, J = 8.0 Hz, 1H), 4.62-4.55 (bs, 2H), 4.02-3.99 (m, 1H), 3.18-3.09 (m, 2H), 2.39-2.36 (m, 2H), 2.22-2.15 (m, 2H), 2.02-1.98 (m, 2H), 1.69-1.58 (m, 2H); m/z 453.8 [M + 1]⁺ |
| 5eeeDa | 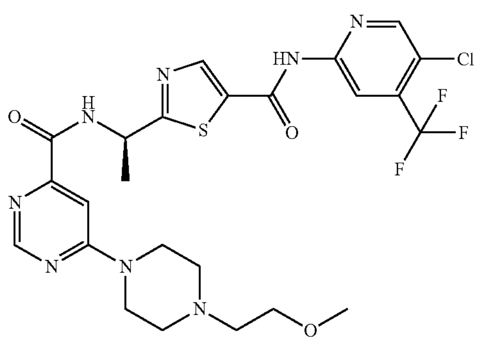 [SMILES: COCCN1CCN(c2cc(C(=O)N[C@H](C)c3ncc(C(=O)Nc4cc(C(F)(F)F)c(Cl)cn4)s3)ncn2)CC1] | ¹H-NMR (DMSO-D6, 500 MHz): δ 11.74 (s, 1H), 9.51 (d, NH ), 8.76 (s, 1H), 8.72 (s, 1H), 8.60 (s, 1H), 8.54 (s, 1H), 7.30 (s, 1H), 5.41-5.38 (m, 1H), 3.67- 3.58 (m, 4H), 3.48- 3.43 (m, 4H), 3.31 (s, 3H), 3.29- 3.22 (m, 4H), 1.65 (d, J = 7 Hz, 3H); m/z 598.7 [M + 1]⁺ |
| 32a | 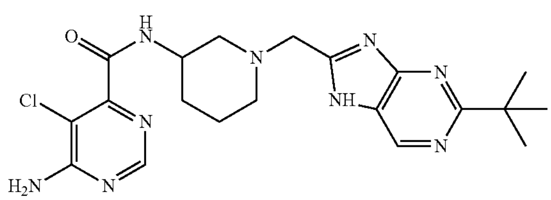 [SMILES: CC(C)(C)c1ncc2[nH]c(CN3CCCC(NC(=O)c4ncnc(N)c4Cl)C3)nc2n1] | ¹H-NMR (DMSO-D6, 500 MHz): δ 9.08 (s, 1N—H), 8.56 (bs, 1N—H), 8.25 (s, 1H), 8.00 (s, 1H), 4.62-4.55 (bs, 2H), 4.02-3.99 (m, 1H), 3.18-3.09 (m, 2H), 2.39-2.36 (m, 2H), 2.22-2.15 (m, 2H), 2.02-1.98 (m, 2H), 1.69-1.58 (m, 2H), 1.22 (s, 9H); m/z 443.9 [M + 1]⁺ |
| 4vDa | 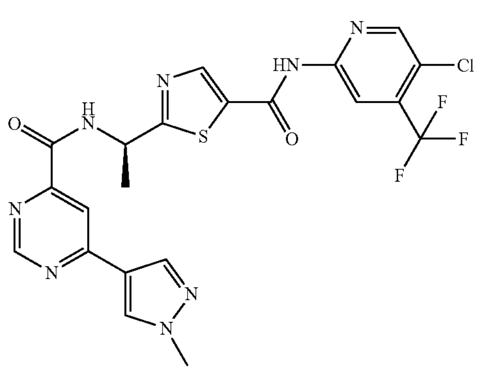 [SMILES: C[C@@H](NC(=O)c1cc(-c2cnn(C)c2)ncn1)c1ncc(C(=O)Nc2cc(C(F)(F)F)c(Cl)cn2)s1] | ¹H-NMR (DMSO-D6, 200 MHz): δ 11.78 (s, 1H), 9.82 (d, J = 8.5 Hz, 1H), 9.12 (s, 1H), 8.78 (s, 1H), 8.76 (s, 1H), 8.68 (s, 1H), 8.54 (s, 1H), 8.25 (s, 1H), 8.21 (s, 1H), 5.46- 5.43 (m, 1H), 3.92 (s, 3H), 1.67 (d, J = 7.5 Hz, 3H); m/z 536.8 [M + 1]⁺ |

TABLE 3-continued

Exemplary Compounds of Formula I

| # | Structure | Characterization Data |
|---|---|---|
| 4vD | 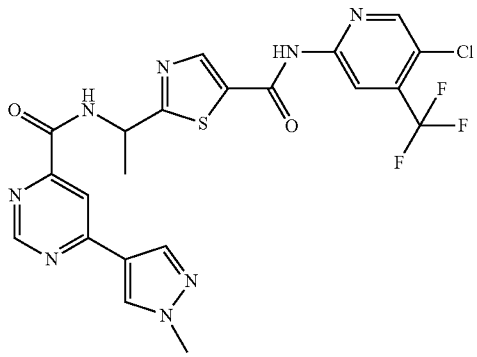 [SMILES: CC(NC(=O)c1cc(-c2cnn(C)c2)ncn1)c1ncc(C(=O)Nc2cc(C(F)(F)F)c(Cl)cn2)s1] | $^1$H-NMR (DMSO-D6, 500 MHz): δ 11.74 (s, 1H), 9.77 (d, NH), 9.19 (s, 1H), 8.76 (s, 1H), 8.74 (s, 1H), 8.65 (s, 1H), 8.54 (s, 1H), 8.25 (s, 1H), 8.20 (s, 1H), 5.48-5.45 (m, 1H), 3.92 (s, 3H), 1.68 (d, J = 6.5 Hz, 3H), m/z 536.7 [M + 1]$^+$ |
| 5ttDa | 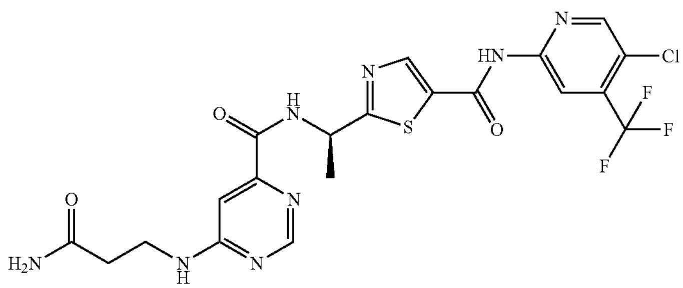 [SMILES: C[C@@H](NC(=O)c1cc(NCCC(N)=O)ncn1)c1ncc(C(=O)Nc2cc(C(F)(F)F)c(Cl)cn2)s1] | $^1$H-NMR (DMSO-D6, 500 MHz): δ 11.74 (bs, 1H), 9.43 (bs, 1H), 8.73 (s, 1H), 8.71 (s, 1H), 8.39 (s, 2H), 7.92 (s, 1H), 7.39 (s, 1H), 7.15 (s, 1H), 6.99 (s, 1H), 5.39-5.34 (m, 1H), 3.47-3.44 (m, 2H), 2.41-2.38 (m, 2H), 1.69 (d, J = 6.5 Hz, 3H); m/z 542.6 [M + 1]$^+$ |
| 28I | 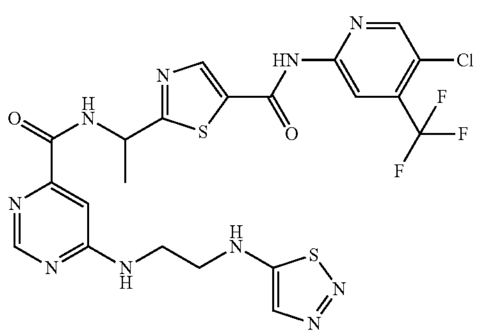 | $^1$H-NMR (DMSO-D6, 500 MHz): δ 11.74 (s, 1H), 9.45 (s, 1H), 8.77 (s, 1H), 8.72 (s, 1H), 8.56 (s, 1H), 8.54 (s, 1H), 8.02 (bs, 1H), 7.92 (s, 1H), 7.90 (s, 1H), 7.09 (s, 1H), 5.42-5.39 (m, 1H), 3.57- 3.45 (m, 4H), 1.64 (d, J = 6.5 Hz, 3H); m/z 598.6 [M + 1]$^+$ |
| 4WD | 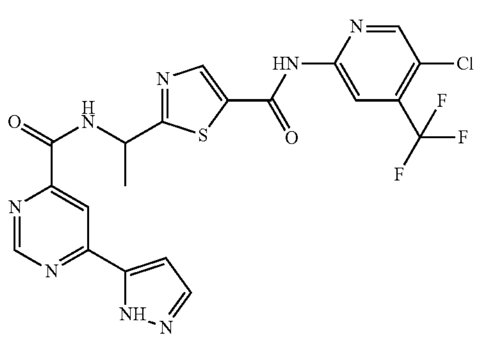 [SMILES: CC(NC(=O)c1cc(-c2ccn[nH]2)ncn1)c1ncc(C(=O)Nc2cc(C(F)(F)F)c(Cl)cn2)s1] | $^1$H-NMR (CD3OD, 500 MHz): δ 9.28 (s, 1H), 8.65 (s, 1H ), 8.62 (s, 1H ), 8.59 (s, 1H), 8.54 (s, 1H), 7.83 (s, 1H), 7.13 (s, 1H), 5.62- 5.61 (m, 1H), 1.82 (d, J = 7 Hz, 3H); m/z 522.6 [M + 1]$^+$ |

TABLE 3-continued

Exemplary Compounds of Formula I

| # | Structure | Characterization Data |
|---|---|---|
| 4cD | 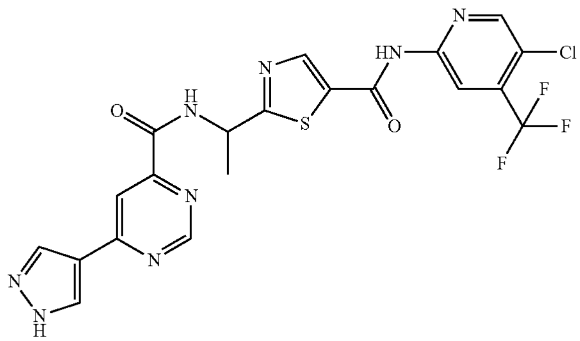 [SMILES: CC(NC(=O)c1cc(-c2cn[nH]c2)ncn1)c1ncc(C(=O)Nc2cc(C(F)(F)F)c(Cl)cn2)s1] | $^1$H-NMR (DMSO-D6, 500 MHz): δ 13.41 (s, 1H), 11.74 (s, 1H ), 9.76 (d, J = 7.0 Hz, 1H), 9.20 (s, 1H), 8.76 (s, 1H), 8.74 (s, 1H), 8.72 (s, 1H), 8.54 (s, 1H), 8.29 (s, 1H), 8.27 (s, 1H), 5.48-5.45 (m, 1H), 1.69 (d, J = 7 Hz, 3H), m/z 522.9 [M + 1]$^+$ |
| 28m | 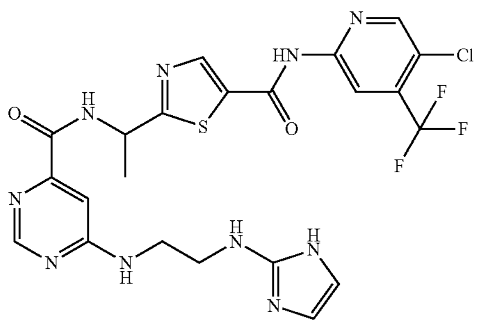 [SMILES: CC(NC(=O)c1cc(NCCNc2ncc[nH]2)ncn1)c1ncc(C(=O)Nc2cc(C(F)(F)F)c(Cl)cn2)s1] | $^1$H-NMR (DMSO-D6, 500 MHz): δ 12.12 (s, 1H), 11.74 (s, 1H), 9.54 (s, 1H), 8.77 (s, 1H), 8.73 (s, 1H), 8.54 (s, 1H), 8.51 (s, 1H), 7.98 (bs, 1H ), 7.14 (s, 1H), 6.97 (s, 1H), 5.45-5.37 (m, 1H), 3.49 (bs, 4H), 2.82 (bs, 2H), 1.65 (d, J = 7.0 Hz, 3H); m/z 580.8 [M + 1]$^+$ |
| 1nDa | 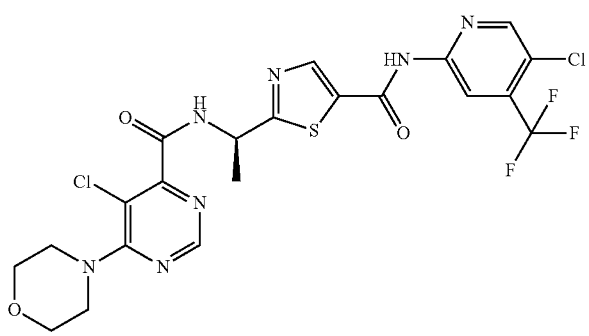 [SMILES: C[C@@H](NC(=O)c1ncnc(N2CCOCC2)c1Cl)c1ncc(C(=O)Nc2cc(C(F)(F)F)c(Cl)cn2)s1] | $^1$H-NMR (DMSO-D6, 500 MHz): δ 11.76 (s, 1H), 9.56 (d, J = 7.0, 1H), 8.77 (s, 1H), 8.75 (s, 1H), 8.63 (s, 1H), 8.57 (s, 1H), 5.36- 5.33 (m, 1H), 3.71-3.68 (m, 8H), 1.58 (d, J = 7.5 Hz, 3H); m/z 575.7 [M + 1]$^+$ |
| 5zzD | 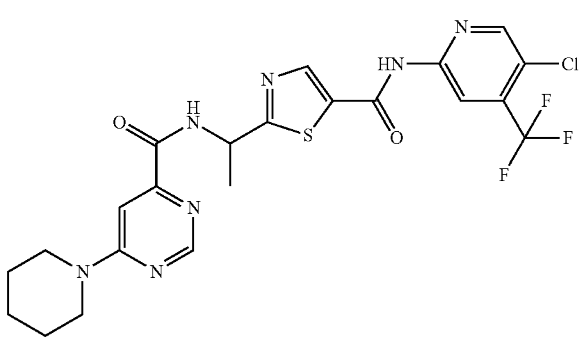 [SMILES: CC(NC(=O)c1cc(N2CCCCC2)ncn1)c1ncc(C(=O)Nc2cc(C(F)(F)F)c(Cl)cn2)s1] | $^1$H-NMR (DMSO-D6, 500 MHz): δ 11.78 (s, 1H), 9.46 (d, J = 8.5 Hz, 1H), 8.78 (s, 1H), 8.76 (s, 1H), 8.58 (s, 1H), 8.56 (s, 1H), 7.25 (s, 1H), 5.43- 5.38 (m, 1H), 3.65 (bs, 4H),1.67 (d, J = 7.5 Hz, 3H), 1.57 (bs, 6H); m/z 539.7 [M + 1]$^+$ |

TABLE 3-continued

Exemplary Compounds of Formula I

| # | Structure | Characterization Data |
|---|---|---|
| 10U | 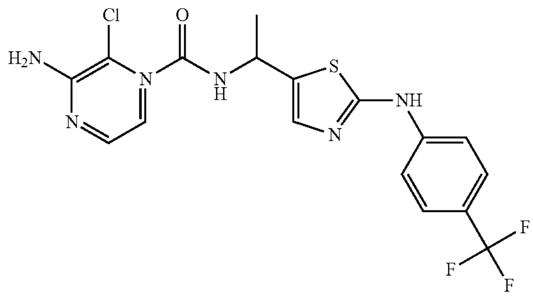 | ¹HNMR: (DMSO-D6, 500 MHz) δ: 10.50 (s, 1H), 9.10 (d, NH), 8.31 (s, 1H), 7.82 (d, J = 8 Hz, 2H), 7.62 (d, J = 8 Hz, 2H), 7.21 (s, 1H), 5.29-5.31 (m, 1H), 1.52 (d, J = 7 Hz, 3H); m/z 442.7 [M + 1]⁺ |
| 4qU | 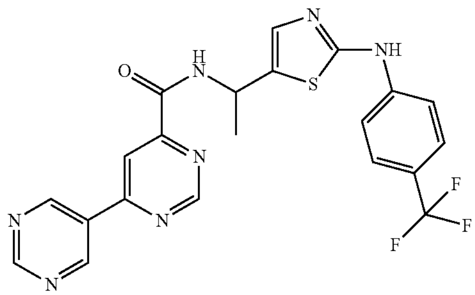 [SMILES: CC(NC(=O)c1cc(-c2cncnc2)ncn1)c1cnc(Nc2ccc(C(F)(F)F)cc2)s1] | ¹H-NMR (DMSO-D6, 500 MHz): δ 10.48 (s, 1H), 9.60 (s, 2H), 9.52 (d, J = 7.0 Hz, 2H), 9.37 (s, 1H), 8.70 (s, 1H), 7.77 (d, J = 8.0 Hz, 2H), 7.62 (d, J = 8.0 Hz, 2H), 7.22 (s, 1H), 5.40-5.37 (m, 1H), 1.64 (d, J = 7.0 Hz, 3H); m/z 471.7 [M + 1]⁺ |
| 4qV | 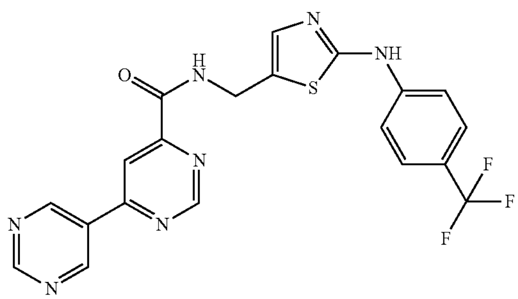 [SMILES: O=C(NCc1cnc(Nc2ccc(C(F)(F)F)cc2)s1)c1cc(-c2cncnc2)ncn1] | ¹H-NMR (DMSO-D6, 500 MHz): δ 10.48 (s, 1H), 9.60 (s, 2H), 9.52 (d, J = 7.0 Hz, 2H), 9.37 (s, 1H), 8.70 (s, 1H), 7.77 (d, J = 8.0 Hz, 2H), 7.62 (d, J = 8.0 Hz, 2H), 7.22 (s, 1H), 4.51 (d, J = 3.0 Hz, 2H); m/z 457.9 [M + 1]⁺ |
| 5dV | 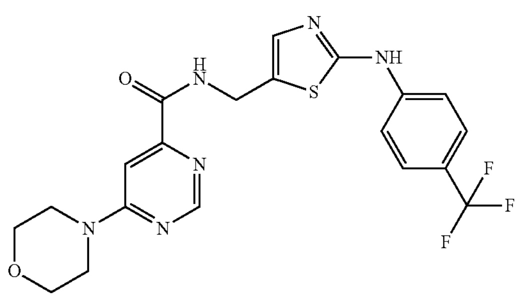 [SMILES: O=C(NCc1cnc(Nc2ccc(C(F)(F)F)cc2)s1)c1cc(N2CCOCC2)ncn1] | ¹H-NMR (DMSO-D6, 500 MHz): δ 10.45 (s, 1H), 9.31 (s, 1H), 8.57 (s, 1H), 7.77 (d, J = 8 Hz, 2H), 7.62 (d, J = 8.0 Hz, 2H), 7.30 (s, 1H), 7.16 (s, 1H), 4.50 (d, J = 3.0 Hz, 2H), 3.63-3.60 (m, 8H); m/z 464.9 [M + 1]⁺ |
| 18dV | 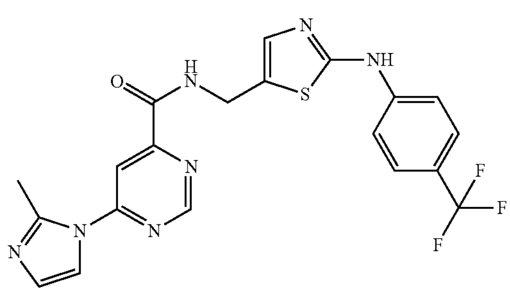 [SMILES: Cc1nccn1-c1cc(C(=O)NCc2cnc(Nc3ccc(C(F)(F)F)cc3)s2)ncn1] | ¹H-NMR (DMSO-D6, 500 MHz): δ 10.49 (s, 1H), 9.69 (s, 1H), 9.25 (s, 1H), 8.17 (s, 1H), 7.95 (s, 1H), 7.77 (d, J = 8.0 Hz, 2H), 7.62 (d, J = 8.0 Hz, 2H), 7.21 (s, 1H), 6.99 (s, 1H), 4.56 (d, J = 6.0 Hz, 2H), 2.66 (s, 3H); m/z 459.9 [M + 1]⁺ |

TABLE 3-continued

Exemplary Compounds of Formula I

| # | Structure | Characterization Data |
|---|---|---|
| 5vV | 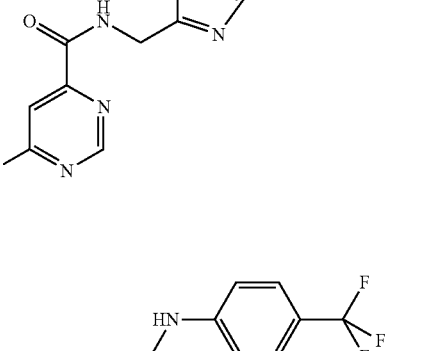 | ¹H-NMR (DMSO-D6, 500 MHz): δ 10.47 (s, 1H), 9.25 (d, J = 8.5 Hz, 1H), 8.46 (s, 1H), 7.69 (d, J = 8.5 Hz, 2H), 7.59 (d, J = 8.0 Hz, 2H), 7.24 (s, 1H), 7.16 (s, 1H), 4.47 (s, 2H), 3.77-3.73 (m, 1H), 3.25-3.21 (m, 2H), 1.79-1.77 (m, 2H), 1.40-1.39 (m, 2H); m/z 478.9 [M + 1]⁺ |
| 25iU | 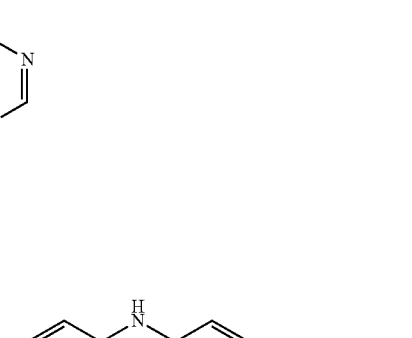 | ¹H-NMR (DMSO-D6, 500 MHz): δ 10.48 (s, 1H), 9.57 (d, J = 8.0 Hz, 1H), 9.48 (s, 1H), 8.39 (s, 1H), 7.77 (d, J = 8.5 Hz, 2H), 7.62 (d, J = 8.0 Hz, 2H), 7.20 (s, 1H), 5.37-5.36 (m, 1H), 1.62 (d, J = 7.0 Hz, 3H); m/z 437.7 [M + 1]⁺ |
| 10CC | 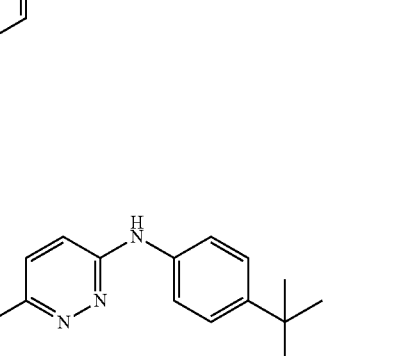 | ¹H-NMR (DMSO-D6-500 MHz) δ 9.12 (s, 1H), 9.10 (d, NH) 8.25 (s, 1H), 7.62 (d, J = 8.5 Hz, 2H), 7.42 (d, J = 6.5 Hz, 1H), 7.32 (d, J = 8.5 Hz, 2H), 7.12 (d, J = 6.5 Hz, 1H), 5.23-5.19 (m, 1H), 1.45 (d, J = 8 Hz, 3H), 1.21 (s, 9H); m/z 425.9 [M + 1]⁺ |
| 5vU | 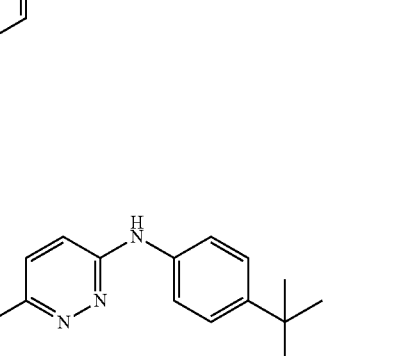 | ¹H-NMR (DMSO-D6, 500 MHz): δ 10.47 (s, 1H), 9.05 (d, J = 8.5 Hz, 1H), 8.53 (s, 1H), 7.77 (d, J = 8.5 Hz, 2H), 7.62 (d, J = 8.0 Hz, 2H), 7.28 (s, 1H), 7.17 (s, 1H), 5.30-5.27 (m, 1H), 4.79 (bs, 1H), 4.02 (bs, 1H), 3.77-3.75 (m, 2H), 3.25- 3.21 (m, 2H), 1.78 (bs, 2H), 1.59 (d, J = 7.0 Hz , 3H), 1.35- 1.21 (m, 2H); m/z 493.2 [M + 1]⁺ |

TABLE 3-continued

Exemplary Compounds of Formula I

| # | Structure | Characterization Data |
|---|---|---|
| 18dU | 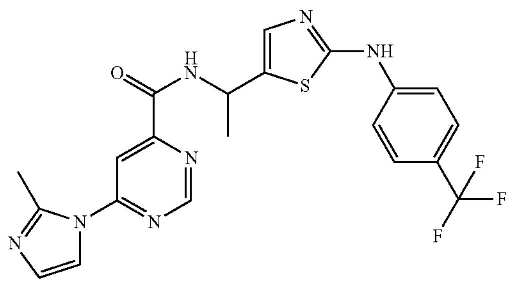 [SMILES: Cc1nccn1-c1cc(C(=O)NC(C)c2cnc(Nc3ccc(C(F)(F)F)cc3)s2)ncn1] | ¹H-NMR (DMSO-D6, 500 MHz): δ 10.49 (s, 1H), 9.52 (d, J = 8.0 Hz, 1H), 9.25 (s, 1H), 8.17 (s, 1H), 7.95 (s, 1H), 7.77 (d, J = 8.0 Hz, 2H), 7.63 (d, J = 8.0 Hz, 2H), 7.21 (s, 1H), 6.99 (s, 1H), 5.37-5.35 (m, 1H), 2.66 (s, 3H), 1.63 (d, J = 7.0 Hz, 3H); m/z 474.1 [M + 1]⁺ |
| 25iV | 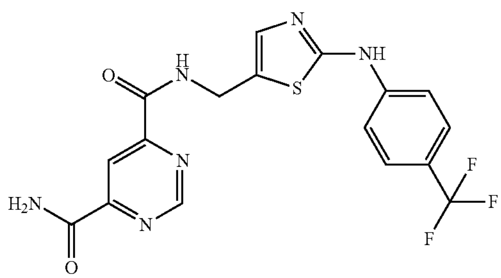 [SMILES: NC(=O)c1cc(C(=O)NCc2cnc(Nc3ccc(C(F)(F)F)cc3)s2)ncn1] | ¹H-NMR (DMSO-D6, 500 MHz): δ 10.48 (s, 1H), 9.70 (s, 1H), 9.48 (s, 1H), 8.44 (s, 1H), 8.41 (s, 1H), 7.77 (d, J = 8.5 Hz, 2H), 7.62 (d, J = 8.0 Hz, 2H), 7.20 (s, 1H), 4.56 (d, J = 7.0 Hz, 3H); m/z 423.0 [M + 1]⁺ |
| 10BB | 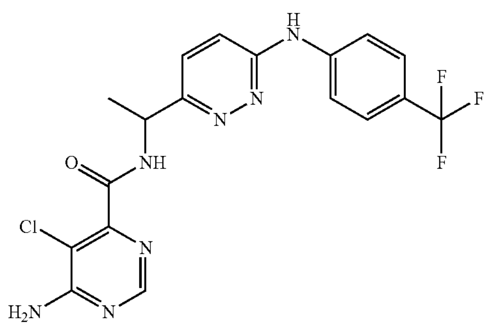 [SMILES: CC(NC(=O)c1ncnc(N)c1Cl)c1ccc(Nc2ccc(C(F)(F)F)cc2)nn1] | ¹H NMR (DMSO-D6, 500 MHz) δ 8.3 (s, 1H), 7.9 (d, J = 10 Hz, 2H), 7.6 (d, J = 10 Hz, 2H), 7.5 (d, J = 10 Hz, 1H), 7.2 (d, J = 10 Hz, 1H), 5.19-5.23 (m, 1H), 1.30 (s, 3H); m/z 438 [M + 1]⁺ |
| 10AA | 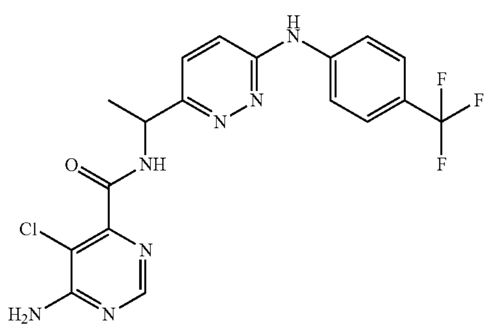 [SMILES: CC(NC(=O)c1ncnc(N)c1Cl)c1ccc(Nc2ccc(C(F)(F)F)cc2)nn1] | ¹H-NMR (DMSO-D6, 500 MHz): δ 9.92 (s, 1H), 9.03 (d, J = 4 Hz, 1H), 8.31 (s, 1H), 8.27 (d, J = 4 Hz, 2H), 7.89 (d, J = 4 Hz, 2H), 7.64 (d, J = 4 Hz, 2H), 5.10 (m, 1H), 1.47 (d, J = 4 Hz, 3H); m/z 438 [M + 1]⁺ |
| 5dJJ | 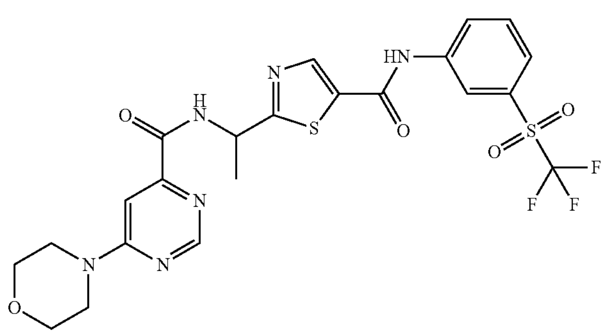 [SMILES: CC(NC(=O)c1cc(N2CCOCC2)ncn1)c1ncc(C(=O)Nc2cccc(S(=O)(=O)C(F)(F)F)c2)s1] | ¹H-NMR (DMSO-D6, 500 MHz): δ 10.88 (s, 1H), 9.53 (d, J = 8.0 Hz, 2H), 8.64 (s, 1H), 8.53 (s, 2H), 8.31 (d, J = 7.0 Hz, 1H), 7.85 (d, J = 7.0 Hz, 2H), 7.32 (s, 1H), 5.44-5.41 (m, 1H), 3.67 (s, 8H), 3.30 (s, 3H), 1.64 (d, J = 7.0, 3H); m/z 570.9 [M + 1]⁺ |

TABLE 3-continued

Exemplary Compounds of Formula I

| # | Structure | Characterization Data |
|---|---|---|
| 5vJJ | 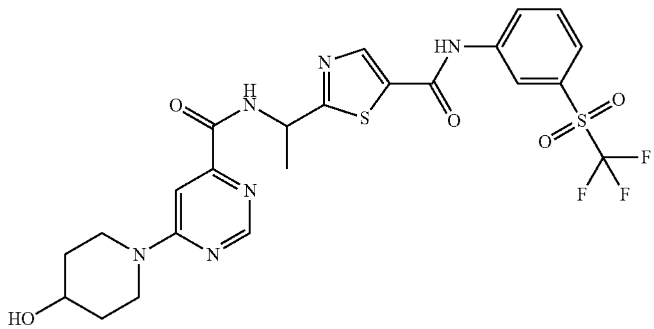 [SMILES: CC(NC(=O)c1cc(N2CCC(O)CC2)ncn1)c1ncc(C(=O)Nc2cccc(S(=O)(=O)C(F)(F)F)c2)s1] | $^1$H-NMR (DMSO-D6 500 MHz): δ 10.87 (s, 1H), 9.50 (d, J = 8.0 Hz, 2H), 8.59 (s, 1H), 8.52 (s, 2H), 8.31 (d, J = 5 Hz, 1H), 7.85 (d, J = 5 Hz, 2H), 7.31 (s, 1H), 5.42-5.34 (m, 1H), 4.78 (d, J = 5 Hz, 1H), 4.05 (bs, 1H), 3.8 (bs, 1H), 1.77 (s, 2H), 1.67 (d, J = 7.0, 3H), 1.35 ( m, 4H); m/z 584.8 [M + 1]$^+$ |
| 33aJJ | 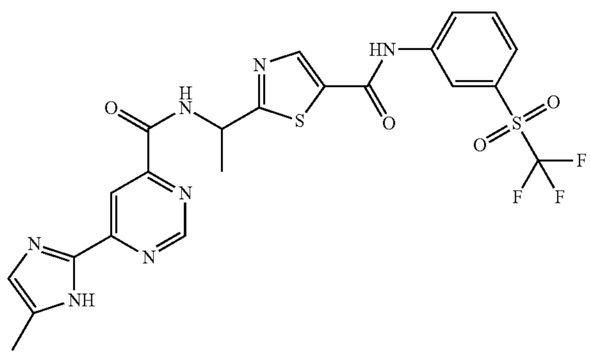 [SMILES: Cc1cnc(-c2cc(C(=O)NC(C)c3ncc(C(=O)Nc4cccc(S(=O)(=O)C(F)(F)F)c4)s3)ncn2)[nH]1] | $^1$H-NMR (DMSO-D6, 500 MHz): δ 13.17 (s, 1H), 10.89 (s, 1H), 9.82 (s, 1H), 9.28 (s, 1H), 8.54 (d, J = 10 Hz, 2H), 8.42 (s, 1H), 8.31 (d, J = 5 Hz, 1H), 7.85 (d, J = 5 Hz, 2H), 6.98 (s, 1H), 5.45- 5.41 (m, 1H), 2.25 (d, J = 10 Hz, 3H), 1.69 (d, J = 7.0, 3H); m/z 565.8 [M + 1]$^+$ |
| 4qJJ | 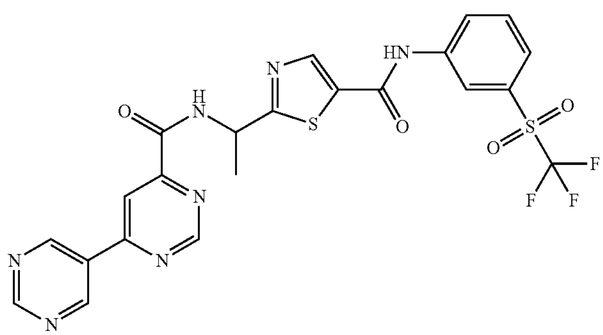 [SMILES: CC(NC(=O)c1cc(-c2cncnc2)ncn1)c1ncc(C(=O)Nc2cccc(S(=O)(=O)C(F)(F)F)c2)s1] | $^1$H-NMR (DMSO-D6, 500 MHz): δ 10.90 (s, 1H), 9.95 (d, J = 10 Hz, 1H), 9.62 (d, J = 10 Hz, 2H), 9.52 (s, 1H), 9.37 (s, 1H), 8.74 (s, 1H), 8.55 (d, J = 15 Hz, 3H), 8.31 (d, J = 5 Hz, 1H), 7.85 (d, J = 5 Hz, 2H), 5.51-5.55 (m, 1H), 3.28 (s, 3H), 1.72 (d, J = 5 Hz, 3H); m/z 563.9 [M + 1]$^+$ |
| 4bU | 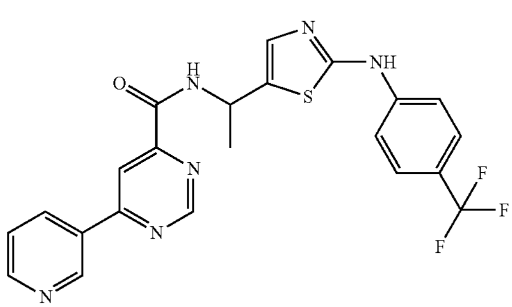 [SMILES: CC(NC(=O)c1cc(-c2cccnc2)ncn1)c1cnc(Nc2ccc(C(F)(F)F)cc2)s1] | $^1$H-NMR (DMSO-D6, 500 MHz): δ 10.46 (s, 1H), 9.44-9.38 (m, 3H), 8.76 (d, J = 4 Hz, 1H), 8.63 (d, J = 3 Hz, 1H), 8.58 (s, 1H), 7.78-7.75 (m, 2H), 7.62-7.59 (m, 3H), 7.22 (s, 1H), 5.40-5.37 (m, 1H), 1.54 (d, J = 7 Hz, 3H); m/z 470.7 [M + 1]$^+$ |

TABLE 3-continued

Exemplary Compounds of Formula I

| # | Structure | Characterization Data |
|---|---|---|
| 4eU | 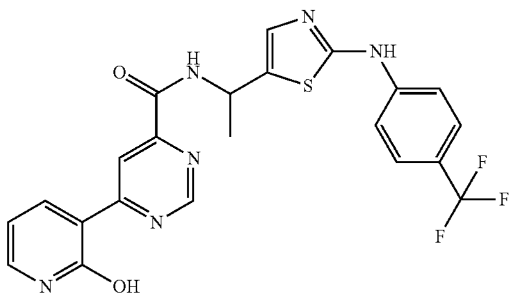 [SMILES: CC(NC(=O)c1cc(-c2cccnc2O)ncn1)c1cnc(Nc2ccc(C(F)(F)F)cc2)s1] | ¹H-NMR (DMSO-D6, 500 MHz): δ 12.32 (s, 1H), 10.47 (s, 1H), 9.34 (d, J = 9 Hz, 1H), 9.27 (s, 1H), 9.25 (s, 1H), 8.70- 8.68 (m, 1H), 7.76 (d, J = 9 Hz, 2H), 7.71 (d, J = 5 Hz, 1H), 7.61 (d, J = 9 Hz, 2H), 6.47 (t, J = 13.5 Hz, 1H), 5.36-5.33 (m, 1H), 1.62 (d, J = 10 Hz, 3H); m/z 486.9 [M + 1]⁺ |
| 6gU | 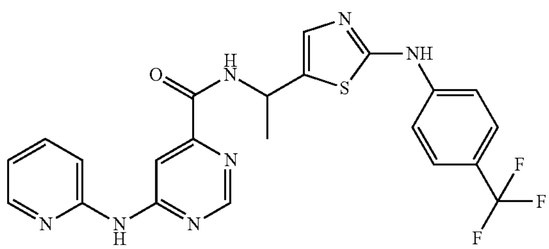 [SMILES: CC(NC(=O)c1cc(Nc2ccccn2)ncn1)c1cnc(Nc2ccc(C(F)(F)F)cc2)s1] | ¹H-NMR (DMSO-D6, 500 MHz): δ 10.54 (s, 1H), 10.47 (s, 1H), 9.16 (d, J = 8.5 Hz, 1H), 8.78 (s, 1H), 8.34 (d, J = 4.5 Hz, 1H), 8.29 (s, 1H), 7.78-7.75 (m, 4H), 7.64-7.61 (m, 2H), 7.19 (s, 1H), 7.05 (s, 1H), 5.34-531 (m, 1H), 1.61 (d, J = 4.2 Hz, 3H); m/z 486 [M + 1]⁺ |
| 5dKK | 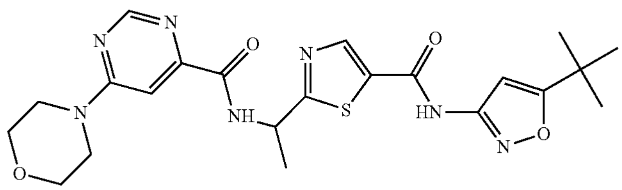 [SMILES: CC(NC(=O)c1cc(N2CCOCC2)ncn1)c1ncc(C(=O)Nc2cc(C(C)(C)C)on2)s1] | ¹H-NMR (CD₃OD, 500 MHz): δ 8.62 (s, 1H), 8.45 (s, 1H), 7.40 (s, 1H), 6.62 (s, 1H), 5.58- 5.52 (m, 1H), 3.84- 3.75 (m, 8H), 1.77 (d, J = 7.0 Hz, 3H), 1.38 (s, 9H); m/z 485.9 [M + 1]⁺ |
| 10KK | 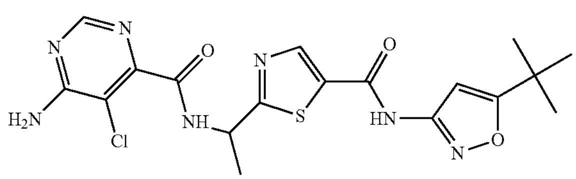 [SMILES: CC(NC(=O)c1ncnc(N)c1Cl)c1ncc(C(=O)Nc2cc(C(C)(C)C)on2)s1] | ¹H-NMR (CD₃OD, 500 MHz): δ 8.45 (s, 1H), 8.35 (s, 1H), 6.63 (s, 1H), 5.50- 5.48 (m, 1H), 1.73 (d, J = 7.0 Hz, 3H), 1.38 (s, 9H); m/z 449.8 [M+30[M + 1]⁺ |
| 5dU | 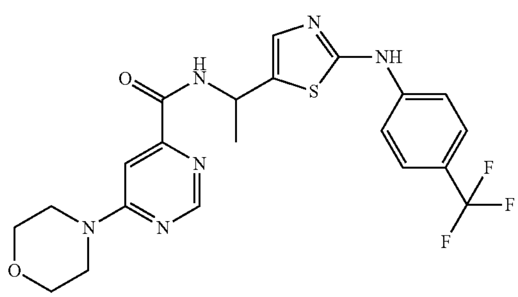 [SMILES: CC(NC(=O)c1cc(N2CCOCC2)ncn1)c1cnc(Nc2ccc(C(F)(F)F)cc2)s1] | ¹H-NMR (DMSO-D6, 500 MHz): δ 10.44 (s, 1H), 9.08 (d, J = 7.0, 1H), 8.61 (s, 1H), 7.78 (d, J = 8.5 Hz, 2H), 7.58 (d, J = 8.5 Hz, 2H), 7.31 (s, 1H), 7.21 (s, 1H), 5.23-5.22 (m, 1H), 3.65- 3.60 (m, 8H), 1.65 (d, J = 7.0 Hz, 3H); m/z 479 [M + 1]⁺ |
| 5vvU | 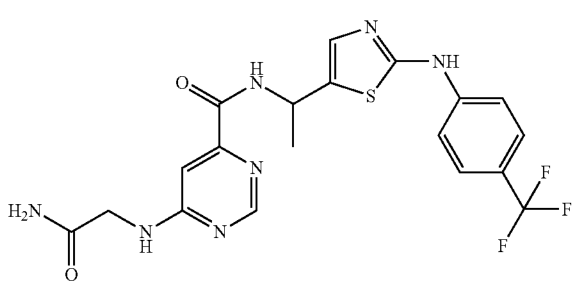 [SMILES: CC(NC(=O)c1cc(NCC(N)=O)ncn1)c1cnc(Nc2ccc(C(F)(F)F)cc2)s1] | ¹H-NMR (DMSO-D6, 500 MHz): δ 10.45 (s,1H), 8.98 (d, J = 7.0, 1H), 8.45 (s, 1H), 8.04 (bs, 1H), 7.78 (d, J = 8.5 Hz, 2H), 7.59 (d, J = 8.5 Hz, 2H),7.43 (bs, 1H), 7.15 (s, 2H), 7.07 (s, 1H), 5.24- 5.22 (m, 1H), 3.89 (s, 2H), 1.56 (d, J = 7.0 Hz, 3H); m/z 465.7 [M + 1]⁺ |

TABLE 3-continued

Exemplary Compounds of Formula I

| # | Structure | Characterization Data |
|---|---|---|
| 5vKK | 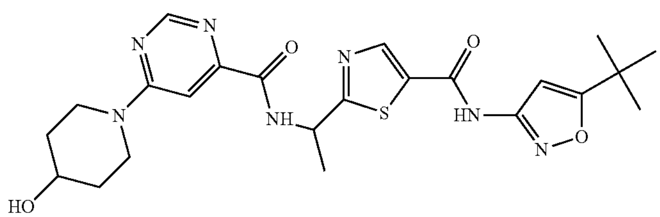 [SMILES: CC(NC(=O)c1cc(N2CCC(O)CC2)ncn1)c1ncc(C(=O)Nc2cc(C(C)(C)C)on2)s1] | $^1$H-NMR (CD$_3$OD, 500 MHz): δ 8.55 (s, 1H), 8.43 (s, 1H), 7.39 (s, 1H), 6.61 (s, 1H), 5.52- 5.49 (m, 1H), 4.26- 4.18 (m, 2H), 3.98- 3.87 (m, 1H), 3.41- 3.36 (m, 2H), 1.95- 1.93 (m, 2H), 1.74 (d, J = 7.0 Hz, 3H), 1.52- 1.50 (m, 2H), 1.36 (s, 9H); m/z 499.8 [M + 1]$^+$ |
| 26cU | 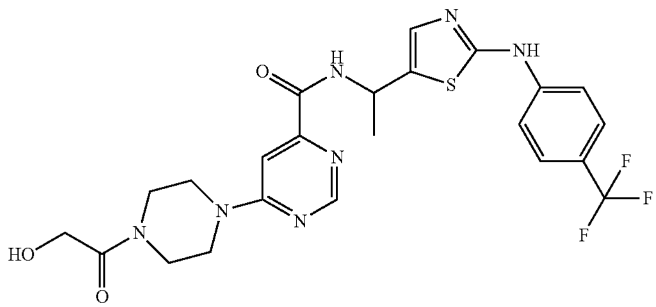 [SMILES: CC(NC(=O)c1cc(N2CCN(C(=O)CO)CC2)ncn1)c1cnc(Nc2ccc(C(F)(F)F)cc2)s1] | $^1$H-NMR (DMSO-D6, 500 MHz): δ 10.46 (s, 1H), 9.07 (d, J = 8.5 Hz, 1H), 8.58 (s, 1H), 7.76 (d, J = 9 Hz, 2H), 7.61 (d, J = 9 Hz, 2H), 7.31 (s, 1H), 7.17 (s, 1H), 5.31- 5.28 (m, 1H), 4.66 (t, J = 11.5 Hz, 1H), 4.12 (d, J = 6 Hz, 2H), 3.78- 3.65 (m, 4H), 3.60- 3.50 (m, 2H), 3.48- 3.40 (m, 2H), 1.59 (d, J = 7 Hz, 3H); m/z = 536 [M + 1]$^+$ |
| 5ccU | 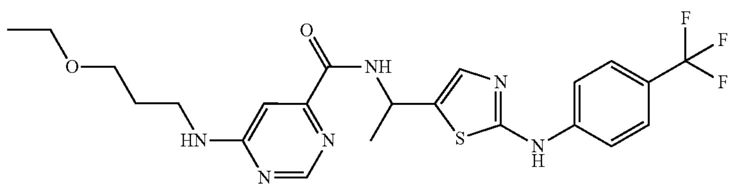 [SMILES: CCOCCCNc1cc(C(=O)NC(C)c2cnc(Nc3ccc(C(F)(F)F)cc3)s2)ncn1] | $^1$H-NMR (DMSO-D6, 500 MHz): δ 10.44 (s, 1H), 8.95 (d, J = 7.0, 1H), 8.40 (s, 1H), 7.80 (s, 1H), 7.68 (d, J = 8.5 Hz, 2H), 7.58 (d, J = 8 Hz$^+$, 2H), 7.14 (s, 1H), 6.99 (s, 1H), 5.25- 5.11 (m, 1H), 3.40- 3.38 (m, 6H), 1.72-1.64 ( m, 2H), 1.54 (d, J = 7.5 Hz, 3H), 1.04 (t, J = 7 Hz, 3H); m/z 495.1 [M + 1]$^+$ |
| 43 | 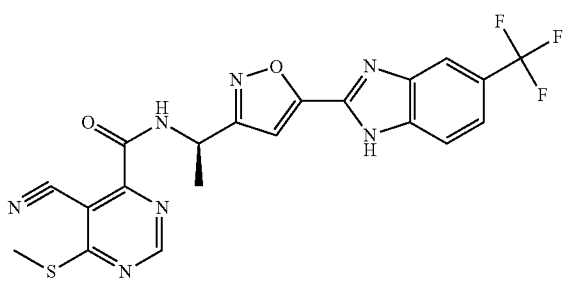 [SMILES: CSc1ncnc(C(=O)N[C@H](C)c2cc(-c3nc4cc(C(F)(F)F)ccc4[nH]3)on2)c1C#N] | $^1$HNMR (CDCl$_3$) δ = 8.25 (s, 1H), 8.0 (s, 1H), 7.78 (d, 1H), 7.58 (d, 1H), 6.22 (q, 1H), 2.56 (s, 3H), 1.88 (d, 3H)- |
| 34a | 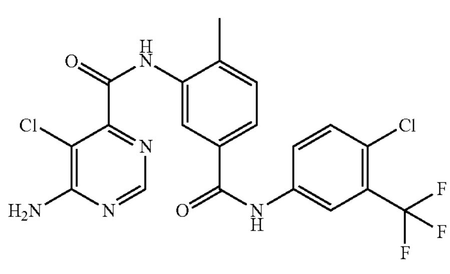 [SMILES: Cc1ccc(C(=O)Nc2ccc(Cl)c(C(F)(F)F)c2)cc1NC(=O)c1ncnc(N)c1Cl] | $^1$H NMR (DMSO-D6, 500 MHz) δ 10.6 (s, 1H, D2O exchangeable), 10.3 (s, 1H, D2O exchangeable), 8.4 (2s, 2H), 8.15 (m, 2H), 7.8 (m,1H), 7.75 (m,1H), 7.5 (m, 1H), 2.3 (s,3H); MS: m/z 484.26 [M + 1]$^+$. |
| 34b | 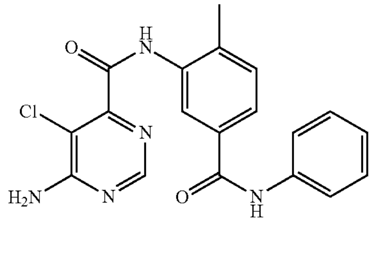 [SMILES: Cc1ccc(C(=O)Nc2ccccc2)cc1NC(=O)c1ncnc(N)c1Cl] | $^1$H-NMR (ACETONE-D6, 500 MHz): δ 9.95 (bs, 1H), 9.60 (bs, 1H), 8.54 (s, 1H), 8.38 (s, 1H), 7.82 (d, J = 8.5 Hz, 2H), 7.72 (d, 1NH), 7.38- 7.28 (m, 3H), 7.07- 7.044 (m, 2H), 2.39 (s, 3H); m/z 381.9 [M + 1]$^+$. |

TABLE 3-continued

Exemplary Compounds of Formula I

| # | Structure | Characterization Data |
|---|---|---|
| 34c | 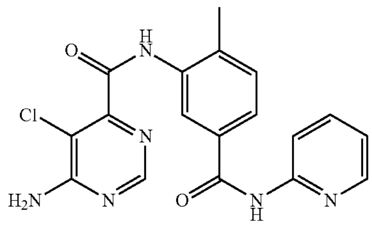 | ¹H-NMR (DMSO-D6, 500 MHz): δ 10.77 (s, 1H), 10.26 (s, 1H), 8.40-8.38 (m, 2H), 8.18-8.15 (m, 2H), 7.87-7.82 (m, 2H), 7.40 (d, J = 8.5 Hz, 1H), 7.17-7.15 (m, 1H), 2.33 (s, 3H); m/z 382.9 [M + 1]⁺. |
| 34d | 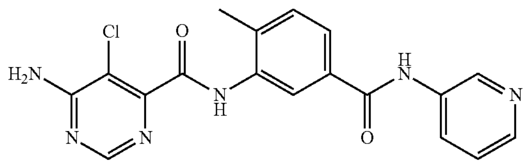 [SMILES: Cc1ccc(C(=O)Nc2cccnc2)cc1NC(=O)c1ncnc(N)c1Cl] | ¹H-NMR (DMSO-D6, 500 MHz): δ 10.48 (s, 1H), 10.33 (s, 1H), 8.94 (s, 1H), 8.42 (s, 1H), 8.32 (s, 1H), 8.21-8.12 (m, 2H), 7.84 (d, J = 8.5 Hz, 1H), 7.48-7.41 (m, 3H), 2.36 (s, 3H); m/z 382.8 [M + 1]⁺. |
| 34e | 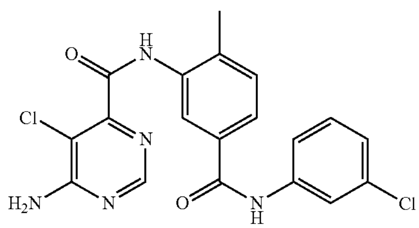 [SMILES: Cc1ccc(C(=O)Nc2cccc(Cl)c2)cc1NC(=O)c1ncnc(N)c1Cl] | ¹H-NMR (DMSO-D6, 500 MHz): δ 10.40 (s, 1H), 10.30 (s, 1H), 8.40 (s, 1H), 8.07 (s, 1H), 7.96 (s, 1H), 7.79 (d, J = 8.5 Hz, 1H), 7.72 (d, J = 8.5 Hz, 1H), 7.44-7.36 (m, 3H), 7.16 (d, J = 8.5 Hz, 1H), 2.33 (s, 3H); m/z 415.7 [M + 1]⁺. |
| 34f | 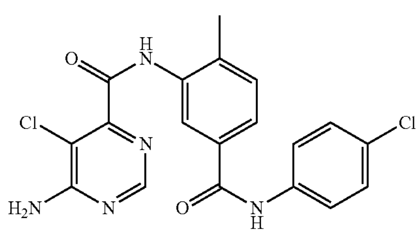 [SMILES: Cc1ccc(C(=O)Nc2ccc(Cl)cc2)cc1NC(=O)c1ncnc(N)c1Cl] | ¹H-NMR (DMSO-D6, 500 MHz): δ 10.37 (s, 1H), 10.30 (s, 1H), 8.40 (s, 1H), 8.07 (s, 1H), 7.82-7.77 (m, 3H), 7.44-7.39 (m, 3H), 2.33 (s, 3H); m/z 415.8 [M + 1]⁺. |
| 34g | 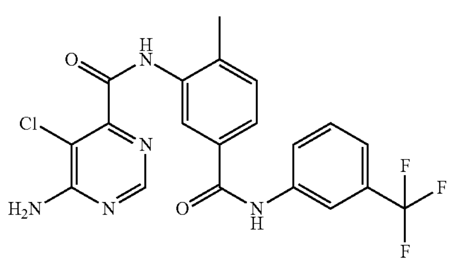 [SMILES: Cc1ccc(C(=O)Nc2cccc(C(F)(F)F)c2)cc1NC(=O)c1ncnc(N)c1Cl] | ¹H-NMR (DMSO-D6, 500 MHz): δ 10.55 (s, 1H), 10.31 (s, 1H), 8.40 (s, 1H), 8.24 (s, 1H), 8.10-8.05 (m, 2H), 7.82 (d, J = 8.5 Hz, 1H), 7.61-7.58 (m, 1H), 7.45 (d, J = 8.5 Hz, 3H), 2.34 (s, 3H); m/z 449.8 [M + 1]⁺. |
| 34h | 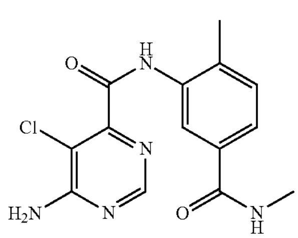 [SMILES: CNC(=O)c1ccc(C)c(NC(=O)c2ncnc(N)c2Cl)c1] | ¹H-NMR (DMSO-D6, 500 MHz): ): δ 10.22 (bs, 1H), 8.43 (s, 1H), 8.39 (s, 1H), 7.94 (s, 1H), 7.62 (d, J = 8.5 Hz, 1H), 7.34 (d, J = 8.5 Hz, 1H), 2.76 (s, 3H), 2.28 (s, 3H); m/z 319.9 [M + 1]⁺. |

TABLE 3-continued

Exemplary Compounds of Formula I

| # | Structure | Characterization Data |
|---|---|---|
| 34i | 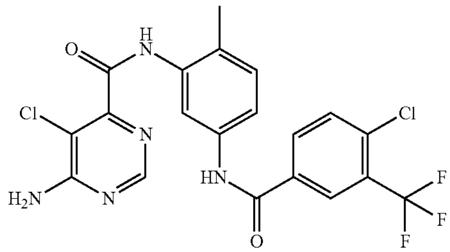 [SMILES: Cc1ccc(NC(=O)c2ccc(Cl)c(C(F)(F)F)c2)cc1NC(=O)c1ncnc(N)c1Cl] | ¹H NMR (DMSO-D6, 500 MHz) δ 10.6 (s, 1H, D2O exchangeable), 10.1 (s, 1H, D2O exchangeable), 8.4 (s, 2H), 8.2-8.25 (d, 1H), 7.9-8.0 (d,2H), 7.6-7.7 (d 1H), 7.2-7.3 (d, 1H), 2.3 (s,3H); MS: m/z 483.7 [M + 1]⁺. |
| 34j | 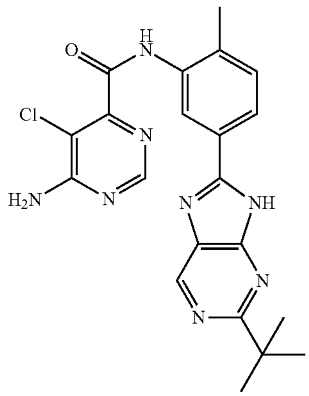 [SMILES: Cc1ccc(-c2nc3cnc(C(C)(C)C)nc3[nH]2)cc1NC(=O)c1ncnc(N)c1Cl] | ¹H-NMR (CD3OD, 500 MHz): δ 8.83 (s, 1H), 8.33 (s, 1H), 8.32 (s, 1H), 7.89 (bs, 1H), 7.43 (d, J = 8.5 Hz, 1H), 2.36 (s, 3H), 1.38 (s, 9H); m/z 436.8 [M + 1]⁺. |
| 34k | 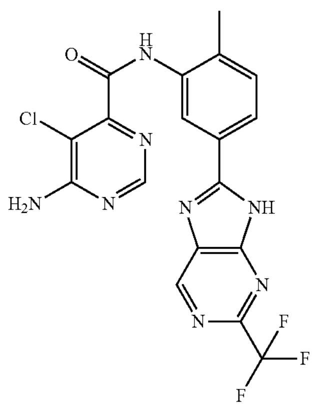 [SMILES: Cc1ccc(-c2nc3cnc(C(F)(F)F)nc3[nH]2)cc1NC(=O)c1ncnc(N)c1Cl] | ¹H-NMR (CD3OD, 500 MHz): δ 8.32 (s, 2H), 7.88 (d, J = 8.0 Hz, 1H), 7.83 (s, 1H), 7.67 (d, J = 8.0 Hz, 1H), 7.47 (d, J = 8.0 Hz, 1H), 2.36 (s, 3H); m/z 446.8 [M + 1]⁺. |

Additional compounds of the present invention may be prepared according to general Scheme ZZ. Such compounds are set forth in Table 4, below.

TABLE 4

Exemplary Compounds of Formula I
Additional compounds

| 1aA |
|---|

TABLE 4-continued
Exemplary Compounds of Formula I
Additional compounds
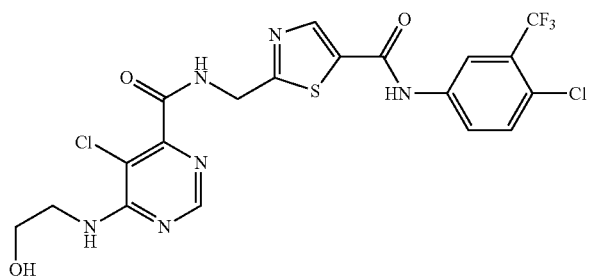 [SMILES: O=C(Nc1ccc(Cl)c(C(F)(F)F)c1)c1cnc(CNC(=O)c2ncnc(NCCO)c2Cl)s1]  1aB
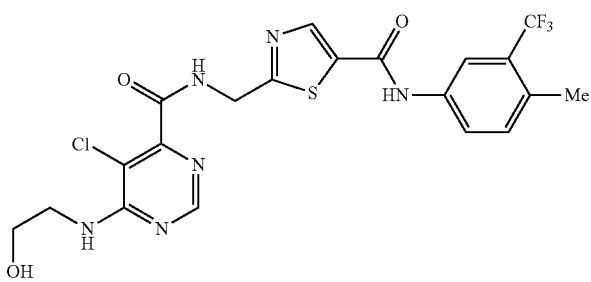 [SMILES: Cc1ccc(NC(=O)c2cnc(CNC(=O)c3ncnc(NCCO)c3Cl)s2)cc1C(F)(F)F]  1aC
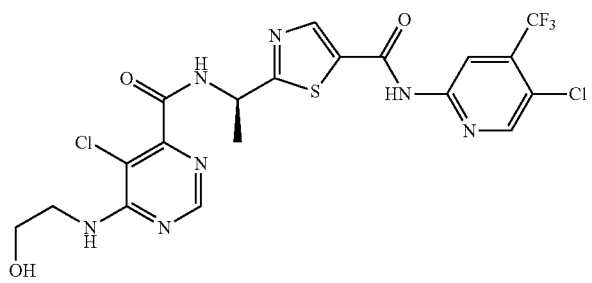  1aDa
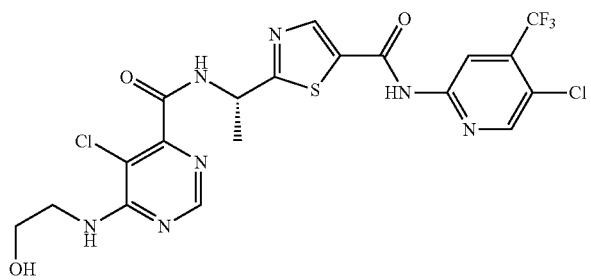  1aDb
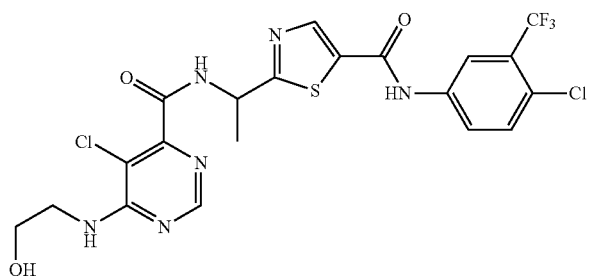 [SMILES: C[C@H](NC(=O)c1ncnc(NCCO)c1Cl)c1ncc(C(=O)Nc2cc(C(F)(F)F)c(Cl)cn2)s1]  1aE TABLE 4-continued
Exemplary Compounds of Formula I
Additional compounds
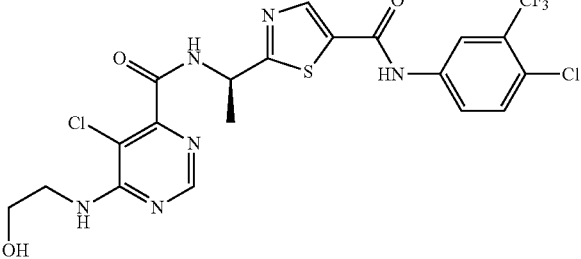 1aEa
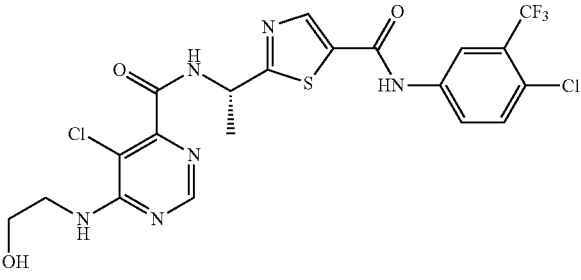 [SMILES: C[C@H](NC(=O)c1ncnc(NCCO)c1Cl)c1ncc(C(=O)Nc2ccc(Cl)c(C(F)(F)F)c2)s1] 1aEb
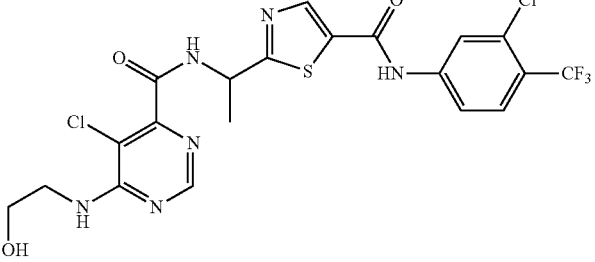 1aF
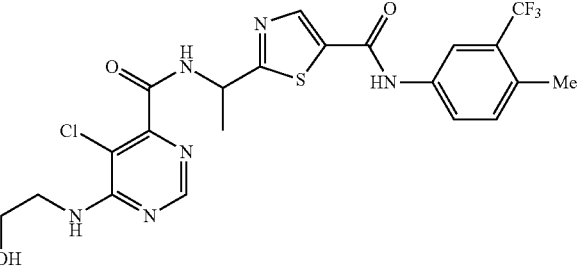 [SMILES: CC(NC(=O)c1ncnc(NCCO)c1Cl)c1ncc(C(=O)Nc2ccc(C(F)(F)F)c(Cl)c2)s1] 1aG
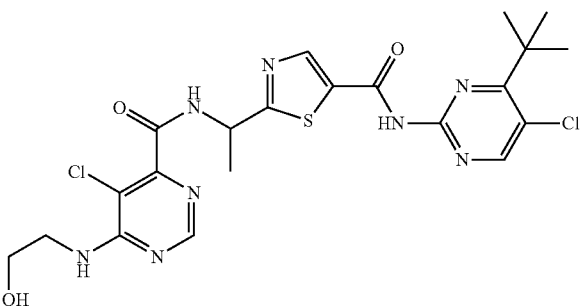 [SMILES: CC(NC(=O)c1ncnc(NCCO)c1Cl)c1ncc(C(=O)Nc2ncc(Cl)c(C(C)(C)C)n2)s1] 1aH TABLE 4-continued
Exemplary Compounds of Formula I
Additional compounds
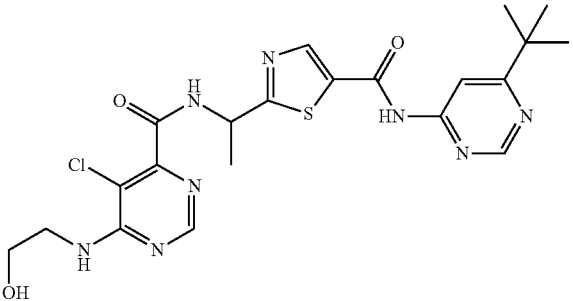 [SMILES: CC(NC(=O)c1ncnc(NCCO)c1Cl)c1ncc(C(=O)Nc2cc(C(C)(C)C)ncn2)s1]
1aI
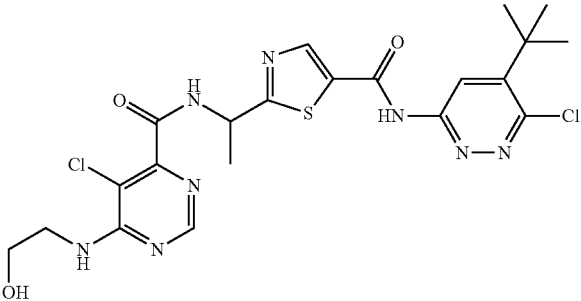 [SMILES: CC(NC(=O)c1ncnc(NCCO)c1Cl)c1ncc(C(=O)Nc2cc(C(C)(C)C)c(Cl)nn2)s1]
1aJ
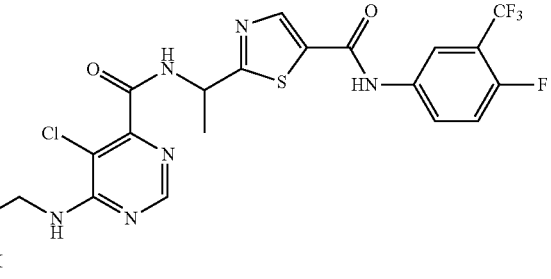
1aK
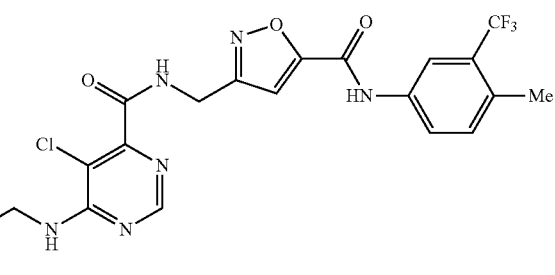
1aL
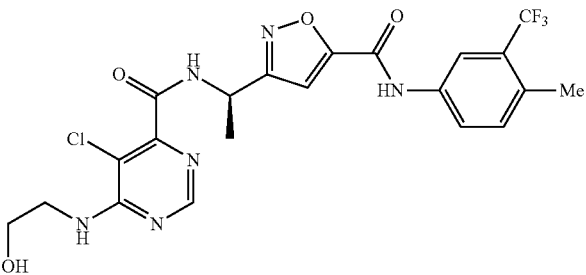 [SMILES: Cc1ccc(NC(=O)c2cc([C@@H](C)NC(=O)c3ncnc(NCCO)c3Cl)no2)cc1C(F)(F)F]
1aMa TABLE 4-continued
Exemplary Compounds of Formula I
Additional compounds
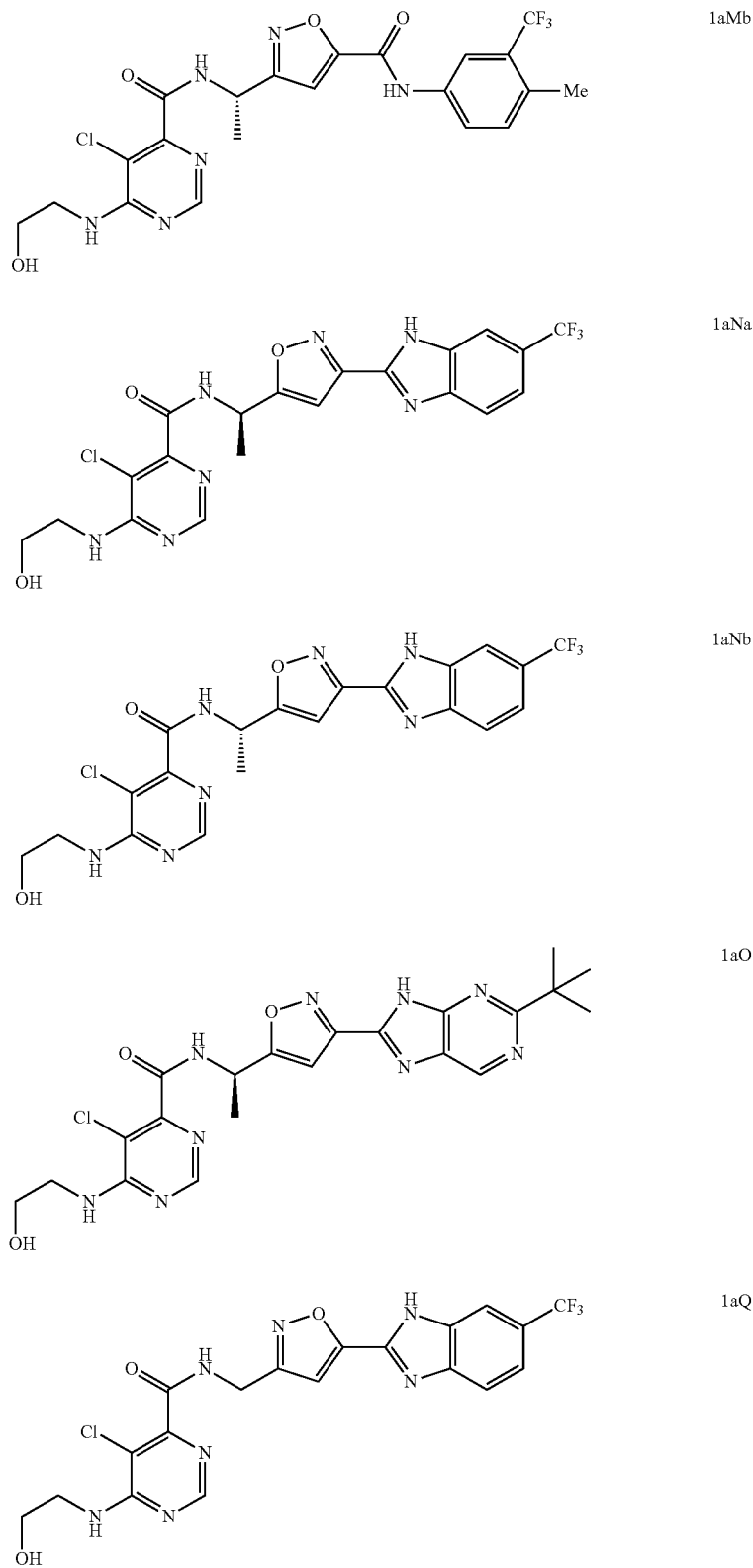

TABLE 4-continued

Exemplary Compounds of Formula I
Additional compounds

| Structure | ID |
|---|---|
| (structure) | 1aRa |
| (structure) | 1aRb |
| (structure) | 2aA |
| (structure) | 2aB |
| (structure) | 2aC |
| (structure) | 2aDa |

TABLE 4-continued
Exemplary Compounds of Formula I
Additional compounds
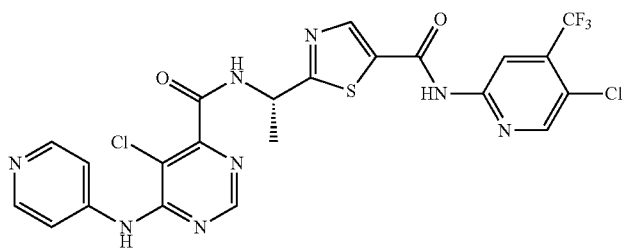 [SMILES: C[C@H](NC(=O)c1ncnc(Nc2ccncc2)c1Cl)c1ncc(C(=O)Nc2cc(C(F)(F)F)c(Cl)cn2)s1] 2aDb
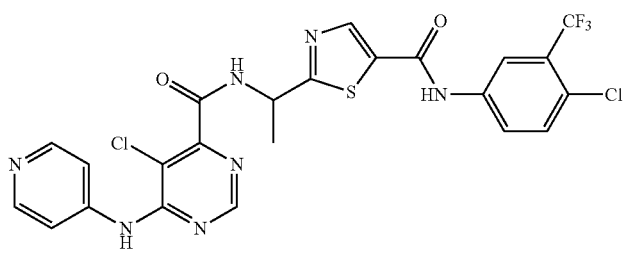 [SMILES: CC(NC(=O)c1ncnc(Nc2ccncc2)c1Cl)c1ncc(C(=O)Nc2ccc(Cl)c(C(F)(F)F)c2)s1] 2aE
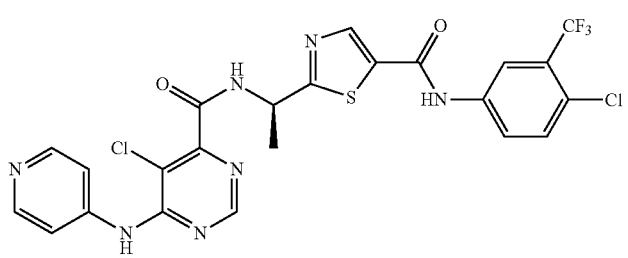 [SMILES: C[C@@H](NC(=O)c1ncnc(Nc2ccncc2)c1Cl)c1ncc(C(=O)Nc2ccc(Cl)c(C(F)(F)F)c2)s1] 2aEa
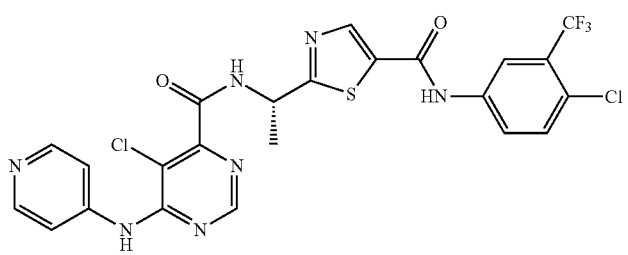 [SMILES: C[C@H](NC(=O)c1ncnc(Nc2ccncc2)c1Cl)c1ncc(C(=O)Nc2ccc(Cl)c(C(F)(F)F)c2)s1] 2aEb
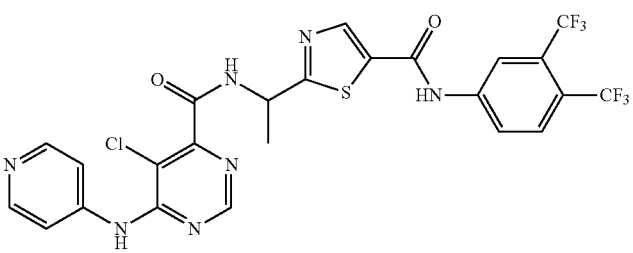 [SMILES: CC(NC(=O)c1ncnc(Nc2ccncc2)c1Cl)c1ncc(C(=O)Nc2ccc(C(F)(F)F)c(C(F)(F)F)c2)s1] 2aF
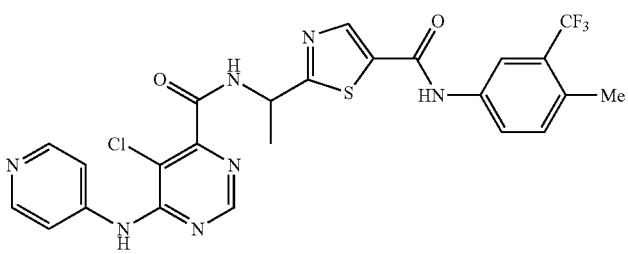 [SMILES: Cc1ccc(NC(=O)c2cnc(C(C)NC(=O)c3ncnc(Nc4ccncc4)c3Cl)s2)cc1C(F)(F)F] 2aG TABLE 4-continued
Exemplary Compounds of Formula I
Additional compounds
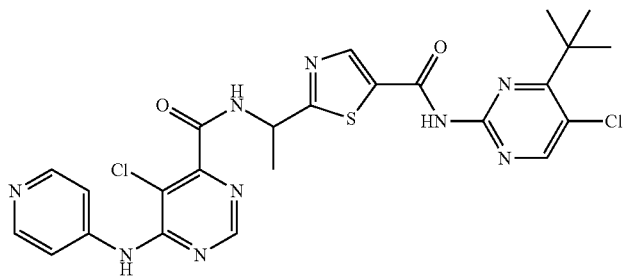 [SMILES: CC(NC(=O)c1ncnc(Nc2ccncc2)c1Cl)c1ncc(C(=O)Nc2ncc(Cl)c(C(C)(C)C)n2)s1] 2aH
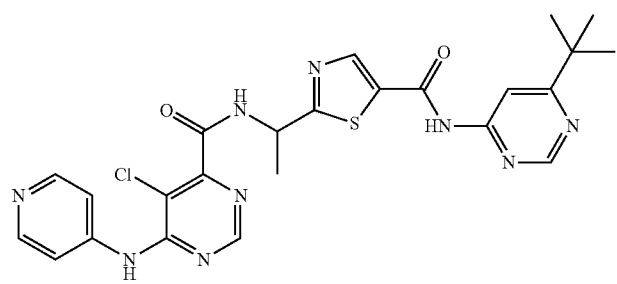 [SMILES: CC(NC(=O)c1ncnc(Nc2ccncc2)c1Cl)c1ncc(C(=O)Nc2cc(C(C)(C)C)ncn2)s1] 2aI
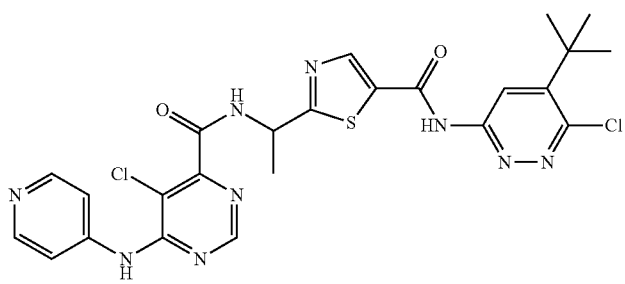 2aJ
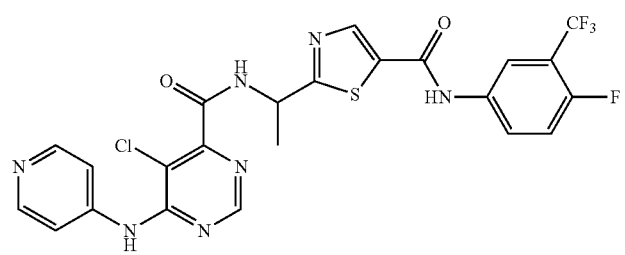 [SMILES: CC(NC(=O)c1ncnc(Nc2ccncc2)c1Cl)c1ncc(C(=O)Nc2ccc(F)c(C(F)(F)F)c2)s1] 2aK
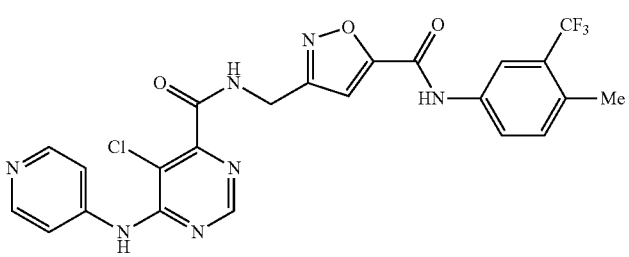 [SMILES: Cc1ccc(NC(=O)c2cc(CNC(=O)c3ncnc(Nc4ccncc4)c3Cl)no2)cc1C(F)(F)F] 2aL TABLE 4-continued
Exemplary Compounds of Formula I
Additional compounds
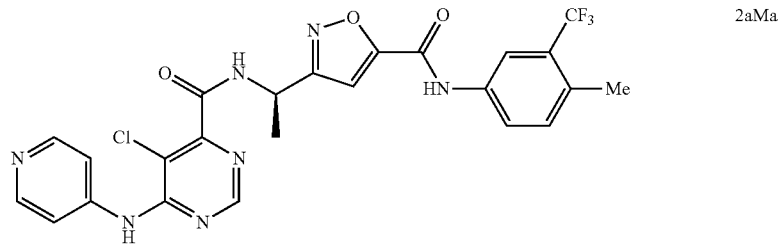 2aMa
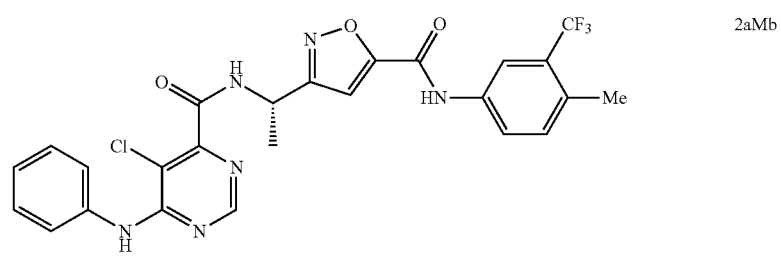 2aMb
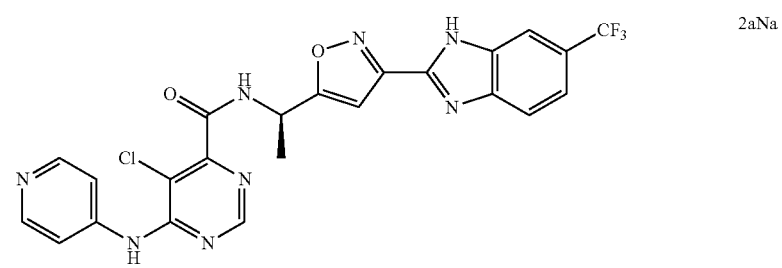 2aNa
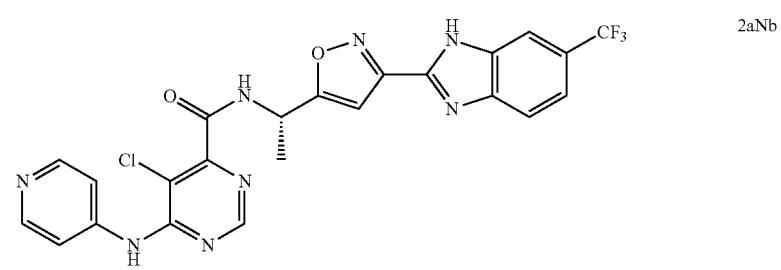 2aNb
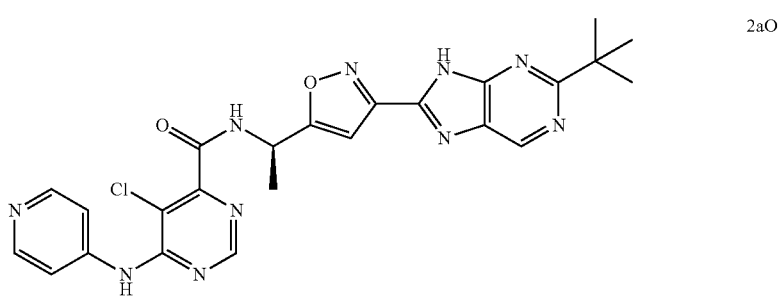 2aO TABLE 4-continued
Exemplary Compounds of Formula I
Additional compounds
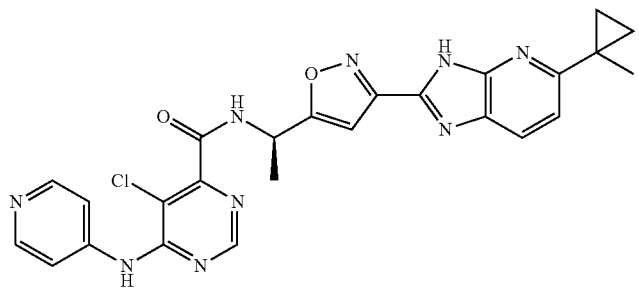 [SMILES: C[C@@H](NC(=O)c1ncnc(Nc2ccncc2)c1Cl)c1cc(-c2nc3ccc(C4(C)CC4)nc3[nH]2)no1] 2aP
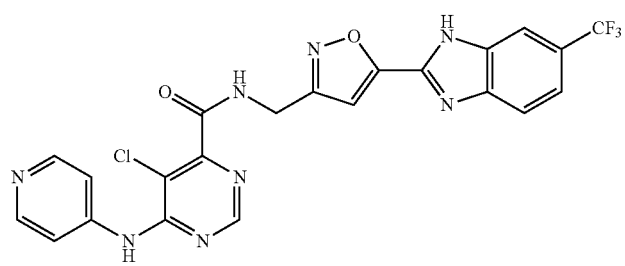 [SMILES: O=C(NCc1cc(-c2nc3ccc(C(F)(F)F)cc3[nH]2)on1)c1ncnc(Nc2ccncc2)c1Cl] 2aQ
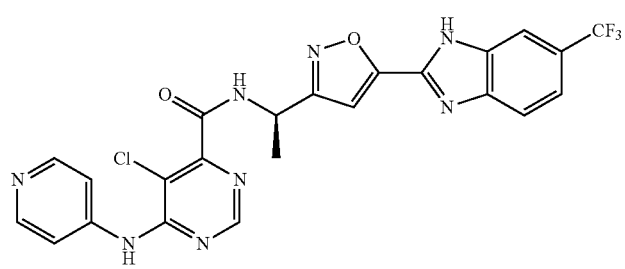 [SMILES: C[C@@H](NC(=O)c1ncnc(Nc2ccncc2)c1Cl)c1cc(-c2nc3ccc(C(F)(F)F)cc3[nH]2)on1] 2aRa
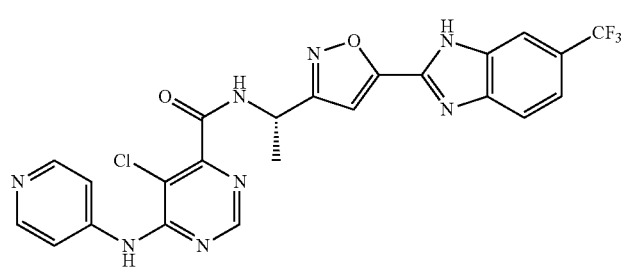 [SMILES: C[C@H](NC(=O)c1ncnc(Nc2ccncc2)c1Cl)c1cc(-c2nc3ccc(C(F)(F)F)cc3[nH]2)on1] 2aRb
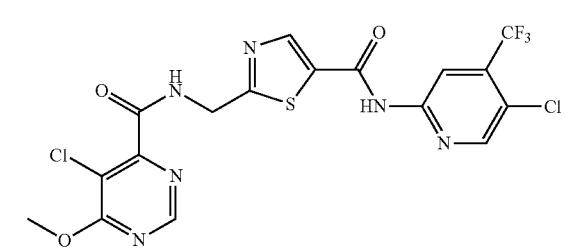 [SMILES: COc1ncnc(C(=O)NCc2ncc(C(=O)Nc3cc(C(F)(F)F)c(Cl)cn3)s2)c1Cl] 3aA
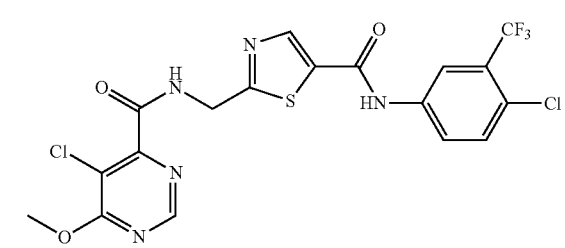 [SMILES: COc1ncnc(C(=O)NCc2ncc(C(=O)Nc3ccc(Cl)c(C(F)(F)F)c3)s2)c1Cl] 3aB TABLE 4-continued
Exemplary Compounds of Formula I
Additional compounds
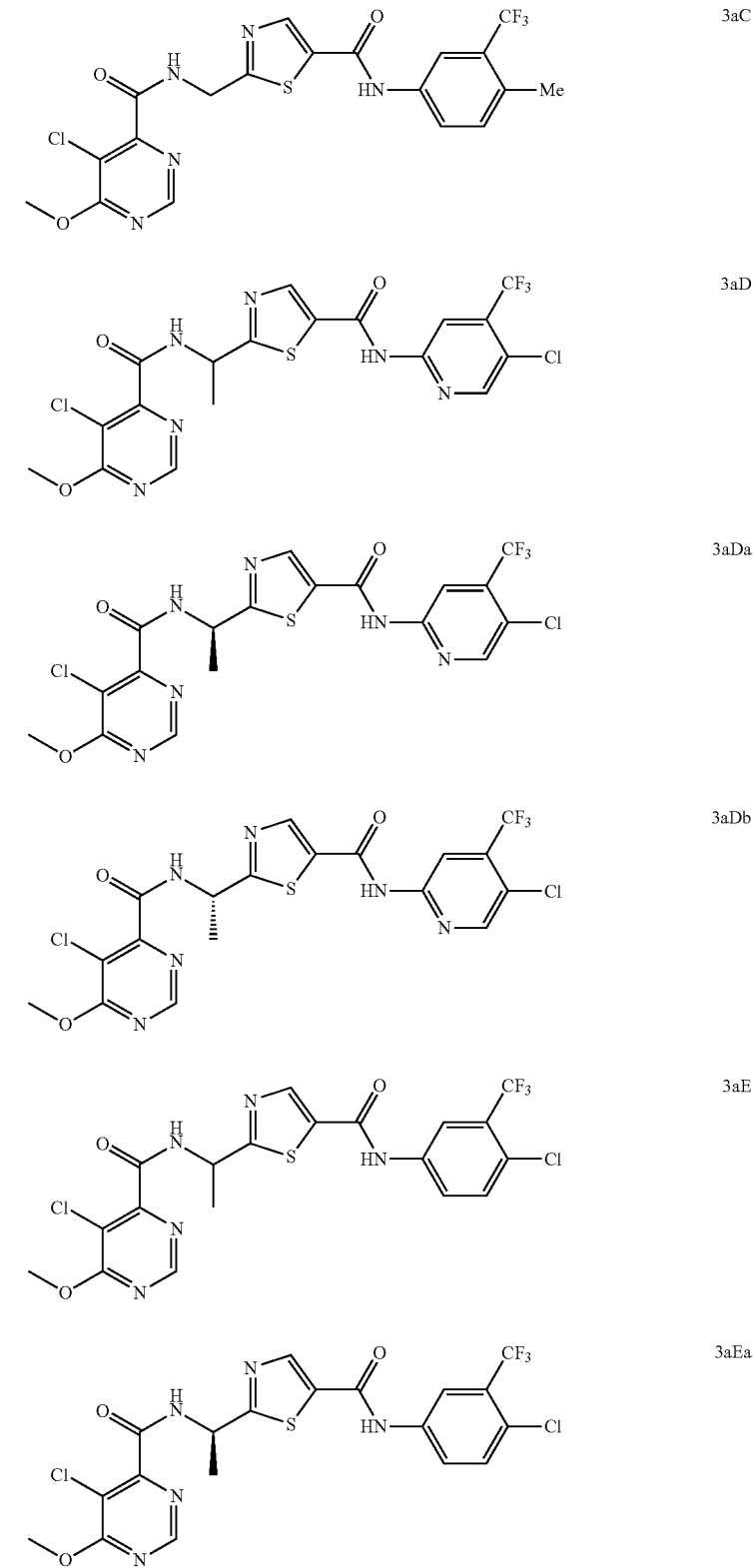
3aC
3aD
3aDa
3aDb
3aE
3aEa TABLE 4-continued
Exemplary Compounds of Formula I
Additional compounds
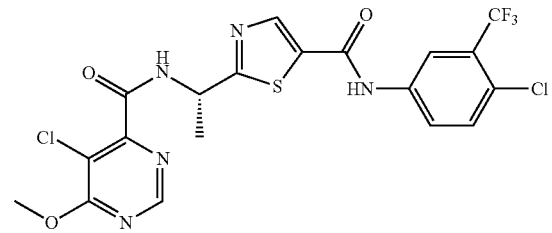 [SMILES: COc1ncnc(C(=O)N[C@@H](C)c2ncc(C(=O)Nc3cc(C(F)(F)F)c(Cl)cn3)s2)c1Cl] 3aEb
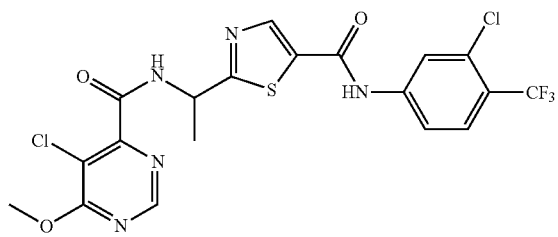 [SMILES: COc1ncnc(C(=O)NC(C)c2ncc(C(=O)Nc3ccc(C(F)(F)F)c(Cl)c3)s2)c1Cl] 3aF
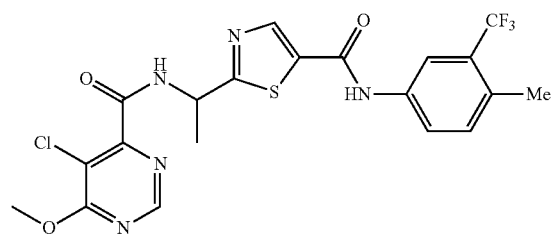 [SMILES: COc1ncnc(C(=O)NC(C)c2ncc(C(=O)Nc3ccc(C)c(C(F)(F)F)c3)s2)c1Cl] 3aG
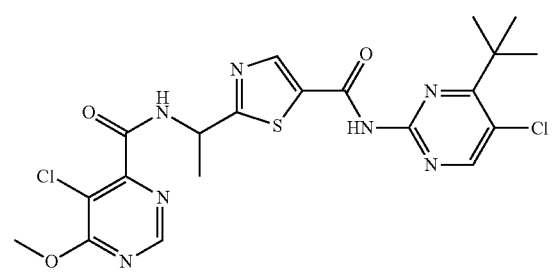 [SMILES: COc1ncnc(C(=O)NC(C)c2ncc(C(=O)Nc3ncc(Cl)c(C(C)(C)C)n3)s2)c1Cl] 3aH
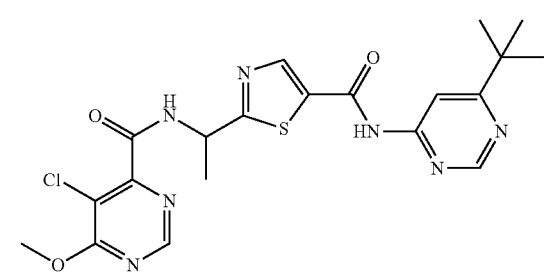 [SMILES: COc1ncnc(C(=O)NC(C)c2ncc(C(=O)Nc3cc(C(C)(C)C)ncn3)s2)c1Cl] 3aI
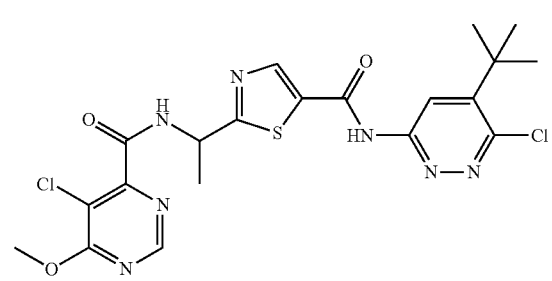 [SMILES: COc1ncnc(C(=O)NC(C)c2ncc(C(=O)Nc3cc(C(C)(C)C)c(Cl)nn3)s2)c1Cl] 3aJ TABLE 4-continued Exemplary Compounds of Formula I
Additional compounds

| | |
|---|---|
| (structure) | 3aK |
| (structure) | 3aL |
| (structure) | 3aMa |
| (structure) | 3aMb |
| (structure) | 3aNa |
| (structure) | 3aNb |

TABLE 4-continued
Exemplary Compounds of Formula I
Additional compounds
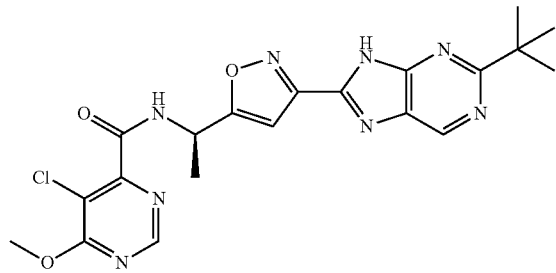 [SMILES: COc1ncnc(C(=O)N[C@H](C)c2cc(-c3nc4cnc(C(C)(C)C)nc4[nH]3)no2)c1Cl]
3aO
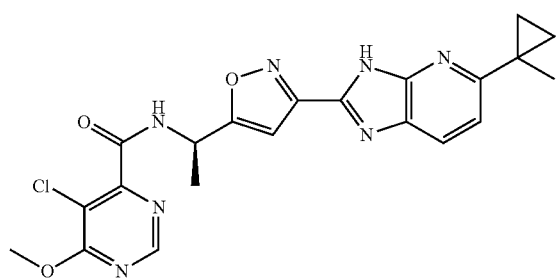 [SMILES: COc1ncnc(C(=O)N[C@H](C)c2cc(-c3nc4ccc(C5(C)CC5)nc4[nH]3)no2)c1Cl]
3aP
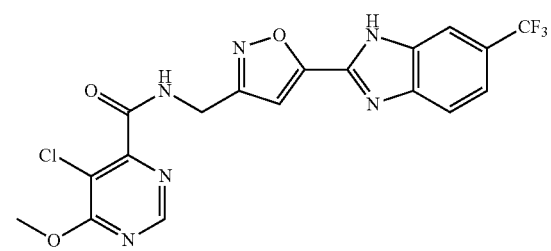 [SMILES: COc1ncnc(C(=O)NCc2cc(-c3nc4ccc(C(F)(F)F)cc4[nH]3)on2)c1Cl]
3aQ
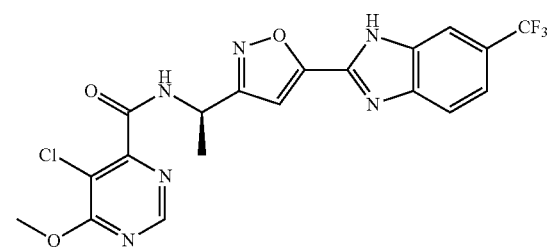 [SMILES: COc1ncnc(C(=O)N[C@H](C)c2cc(-c3nc4ccc(C(F)(F)F)cc4[nH]3)on2)c1Cl]
3aRa
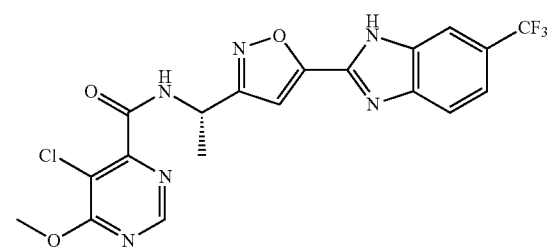 [SMILES: COc1ncnc(C(=O)N[C@@H](C)c2cc(-c3nc4ccc(C(F)(F)F)cc4[nH]3)on2)c1Cl]
3aRb TABLE 4-continued
Exemplary Compounds of Formula I
Additional compounds
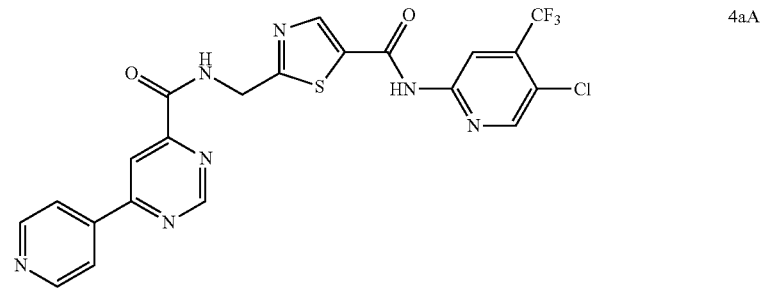
4aA
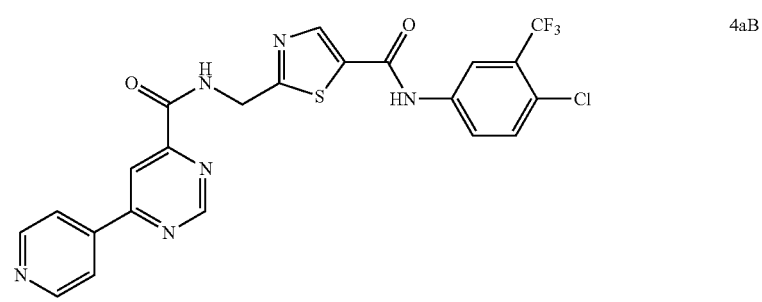
4aB
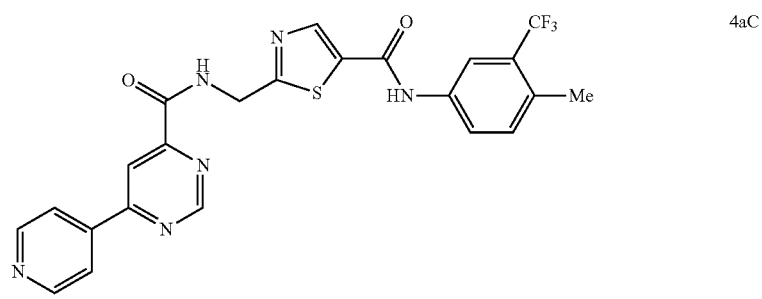
4aC
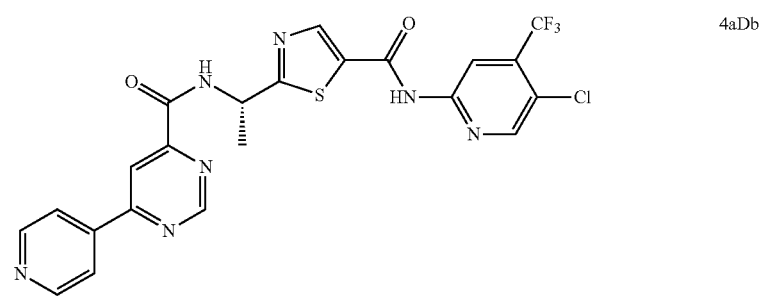
4aDb
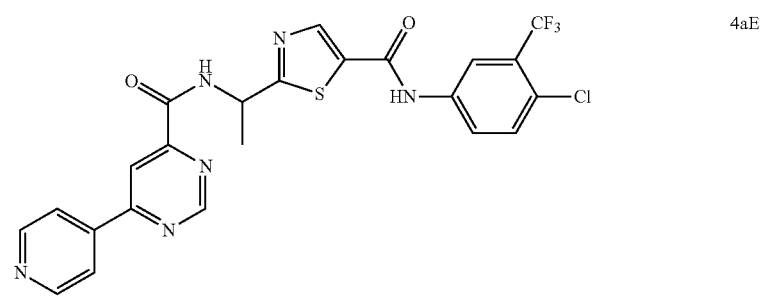
4aE TABLE 4-continued
Exemplary Compounds of Formula I
Additional compounds
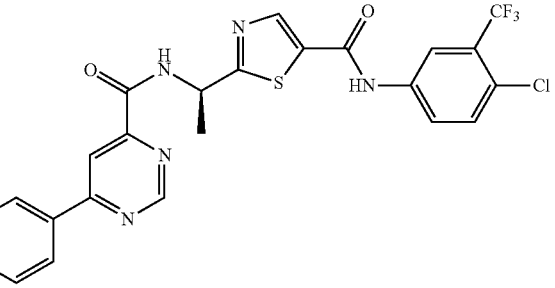 4aEa
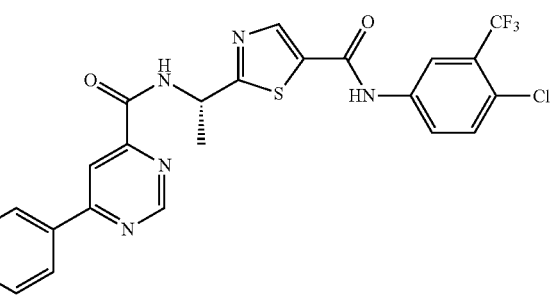 4aEb
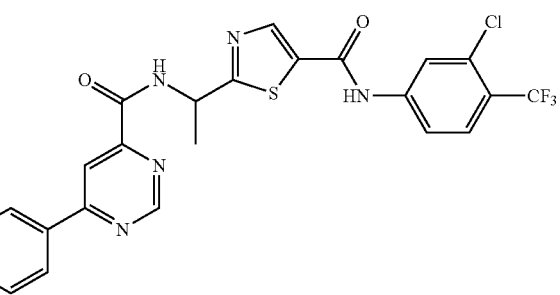 4aF
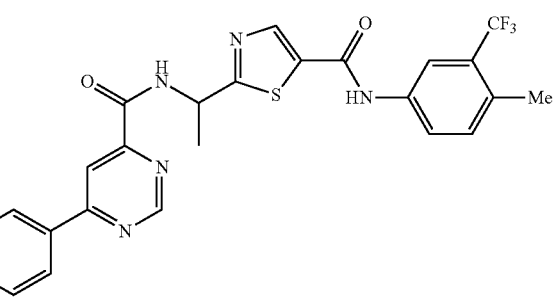 4aG
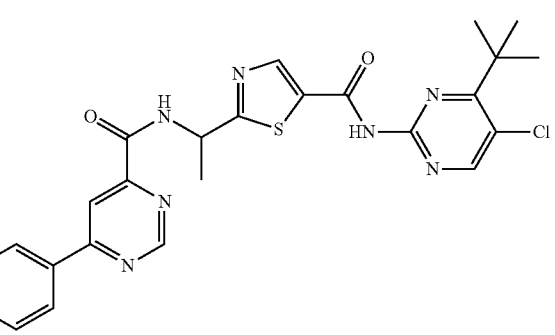 4aH TABLE 4-continued
Exemplary Compounds of Formula I
Additional compounds
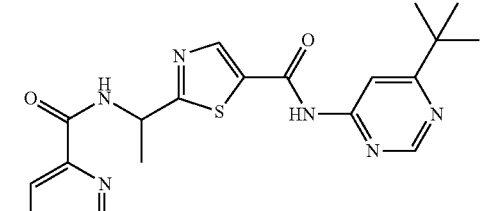
4aI
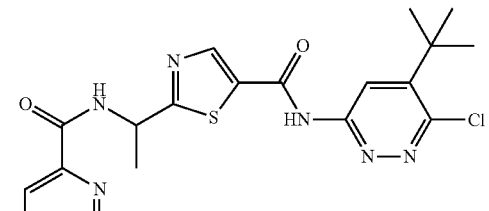
4aJ
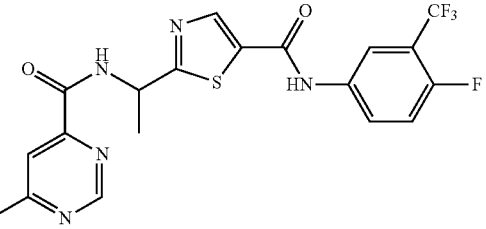
4aK
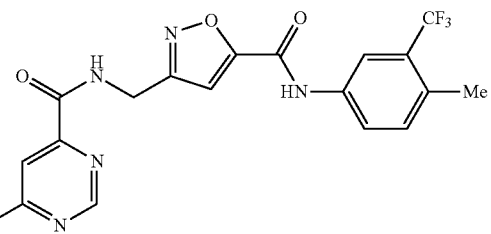
4aL
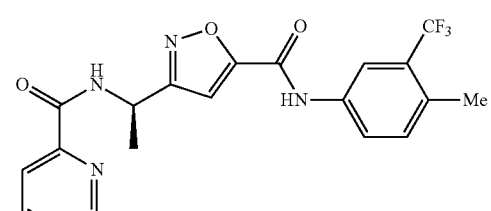
4aMa TABLE 4-continued
Exemplary Compounds of Formula I
Additional compounds
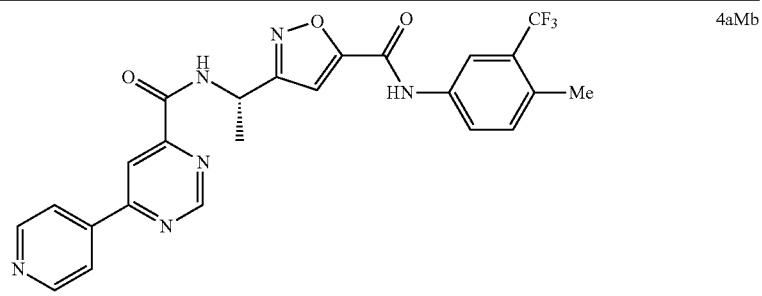 4aMb
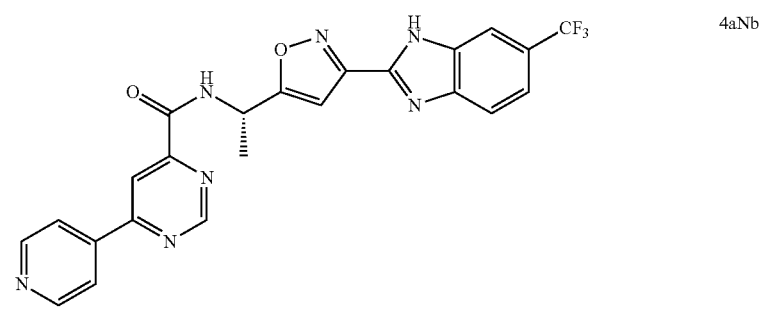 4aNb
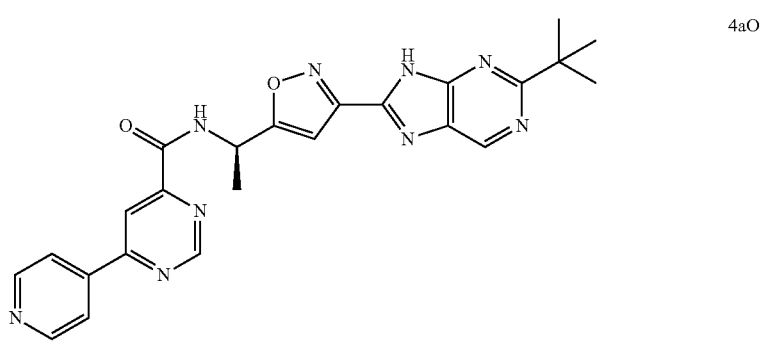 4aO
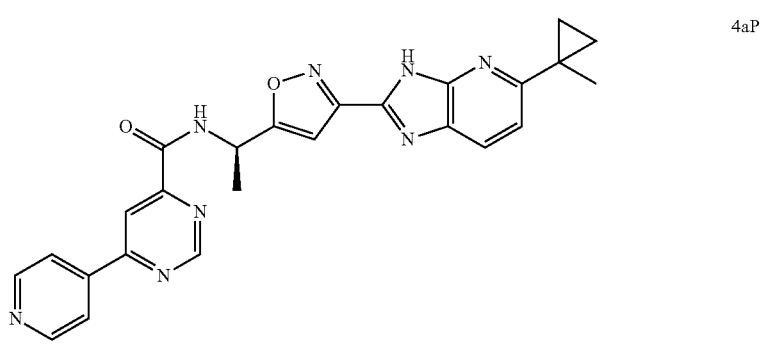 4aP
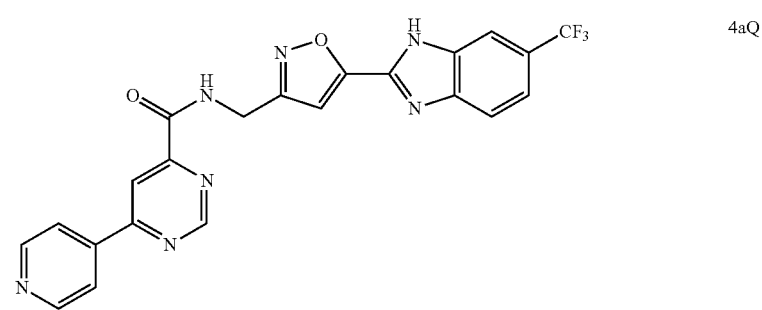 4aQ TABLE 4-continued
Exemplary Compounds of Formula I
Additional compounds
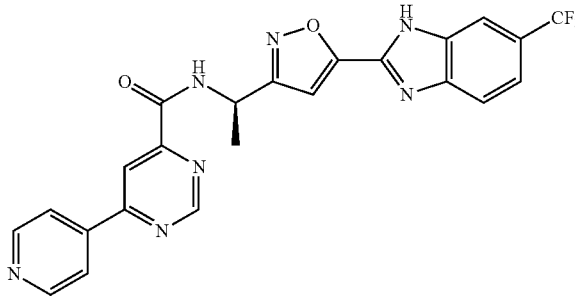 4aRa
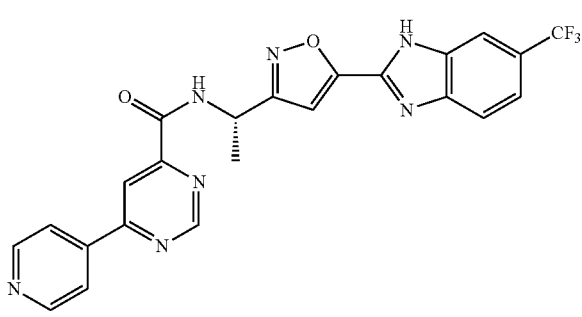 [SMILES: C[C@H](NC(=O)c1cc(-c2ccncc2)ncn1)c1cc(-c2nc3ccc(C(F)(F)F)cc3[nH]2)on1] 4aRb
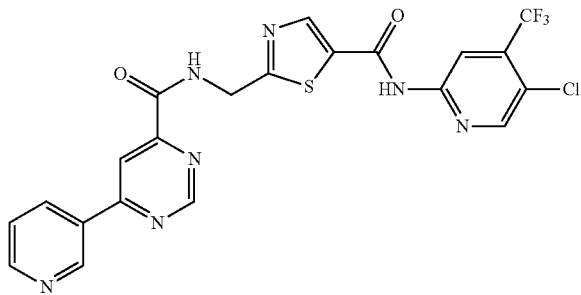 [SMILES: O=C(NCc1ncc(C(=O)Nc2cc(C(F)(F)F)c(Cl)cn2)s1)c1cc(-c2cccnc2)ncn1] 4ba
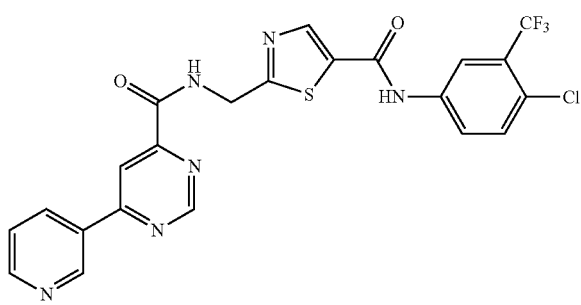 [SMILES: O=C(NCc1ncc(C(=O)Nc2ccc(Cl)c(C(F)(F)F)c2)s1)c1cc(-c2cccnc2)ncn1] 4bB
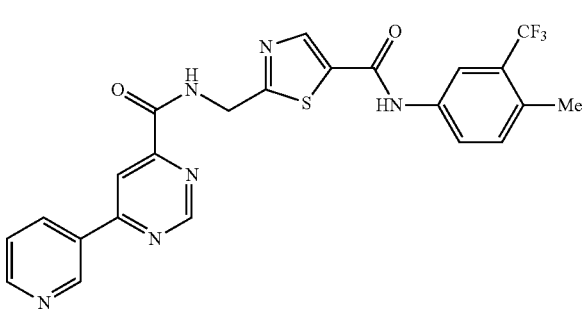 [SMILES: Cc1ccc(NC(=O)c2cnc(CNC(=O)c3cc(-c4cccnc4)ncn3)s2)cc1C(F)(F)F] 4bC TABLE 4-continued
Exemplary Compounds of Formula I
Additional compounds
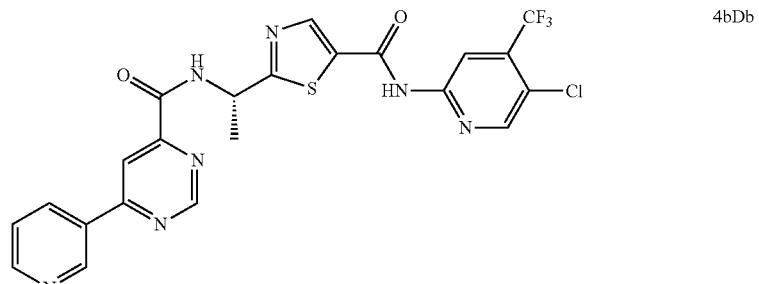
4bDb
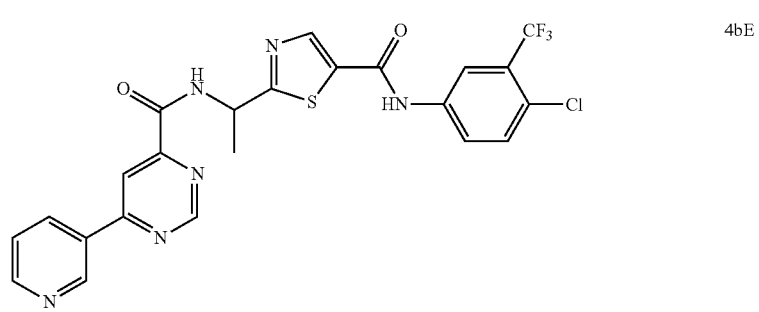
4bE
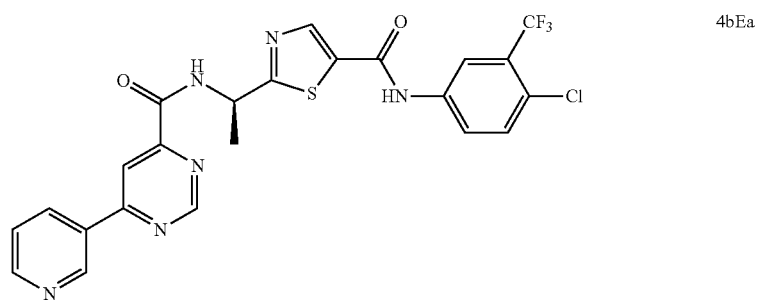
4bEa
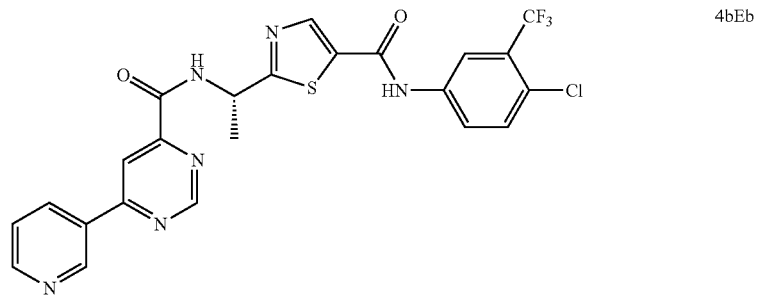
4bEb
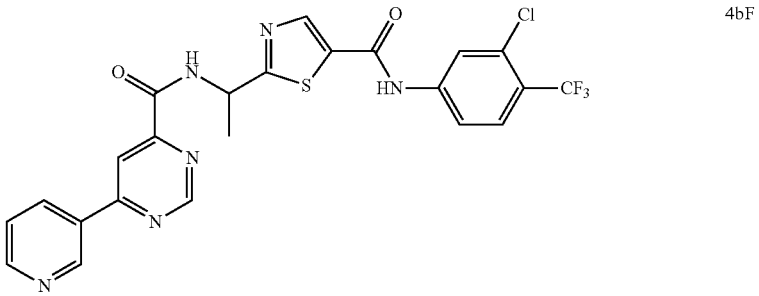
4bF TABLE 4-continued
Exemplary Compounds of Formula I
Additional compounds
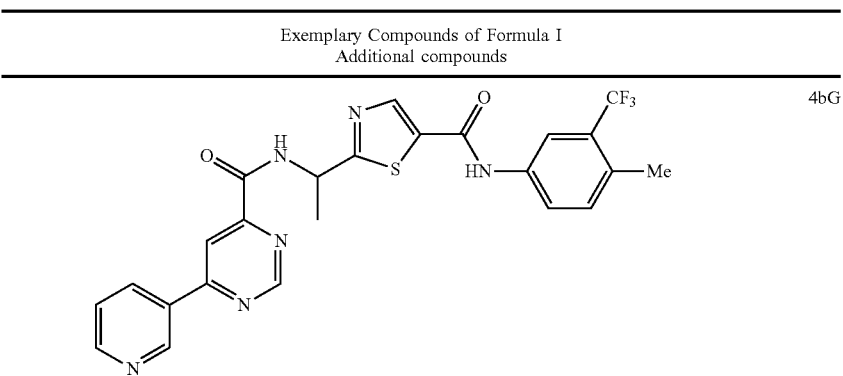 4bG
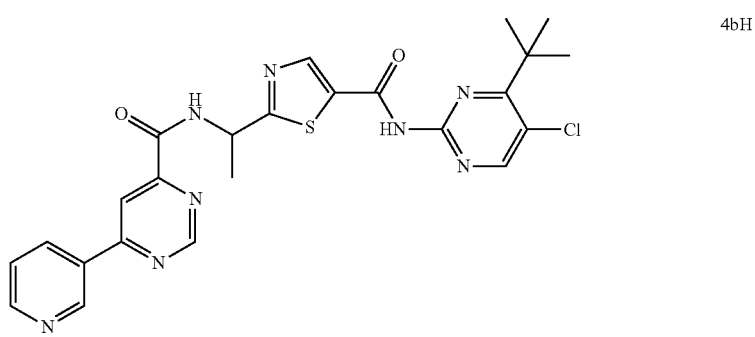 4bH
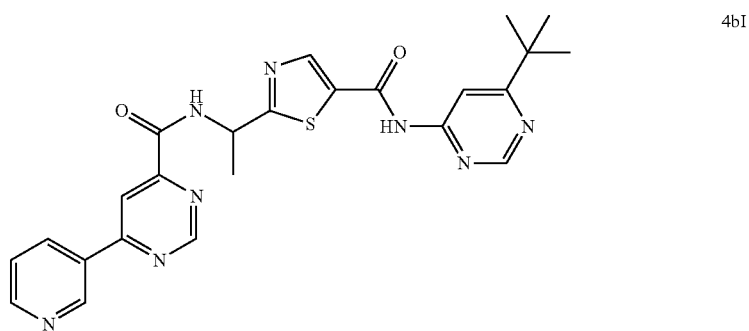 4bI
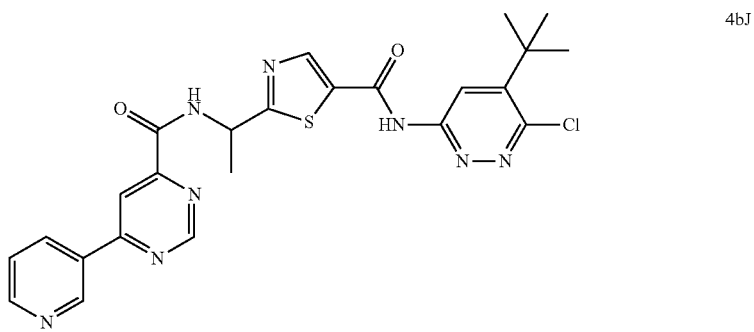 4bJ TABLE 4-continued
Exemplary Compounds of Formula I
Additional compounds
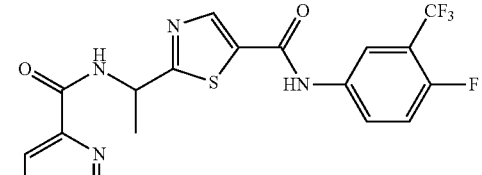 4bK
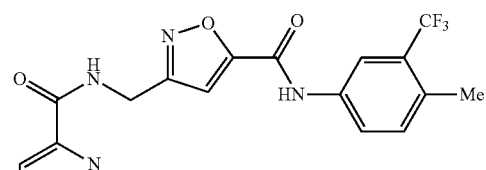 4bL
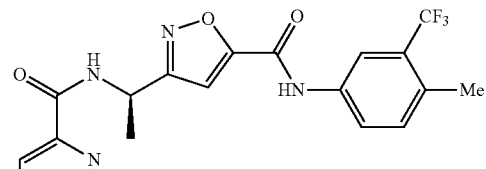 4bMa
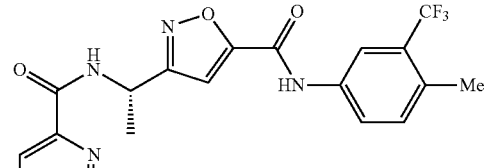 4bMb
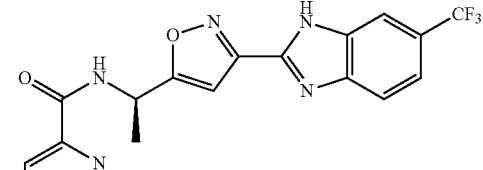 4bNa TABLE 4-continued
Exemplary Compounds of Formula I
Additional compounds
| | |
|---|---|
| 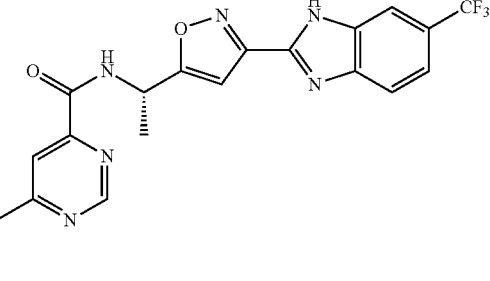 | 4bNb |
| | 4bP |
| | 4bQ |
| | 4bRa |
| | 4bRb |

TABLE 4-continued
Exemplary Compounds of Formula I
Additional compounds
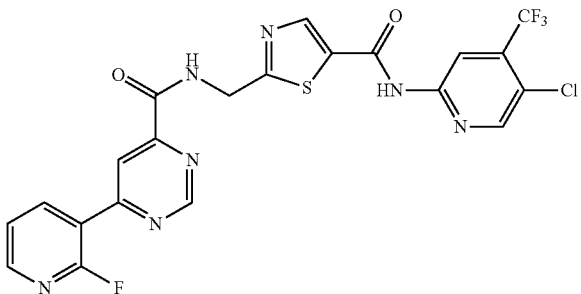 [SMILES: O=C(NCc1ncc(C(=O)Nc2cc(C(F)(F)F)c(Cl)cn2)s1)c1cc(-c2cccnc2F)ncn1] 4eA
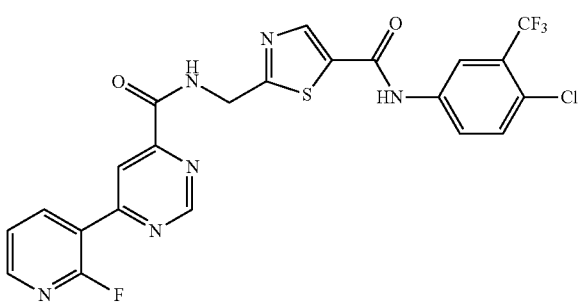 [SMILES: O=C(NCc1ncc(C(=O)Nc2ccc(Cl)c(C(F)(F)F)c2)s1)c1cc(-c2cccnc2F)ncn1] 4eB
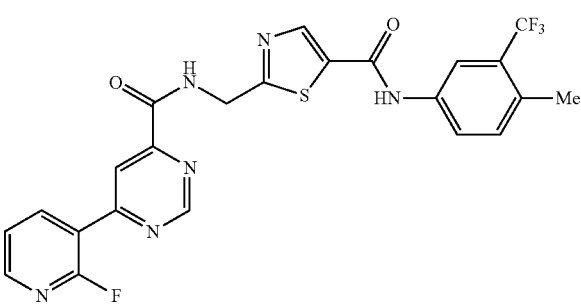 [SMILES: Cc1ccc(NC(=O)c2cnc(CNC(=O)c3cc(-c4cccnc4F)ncn3)s2)cc1C(F)(F)F] 4eC
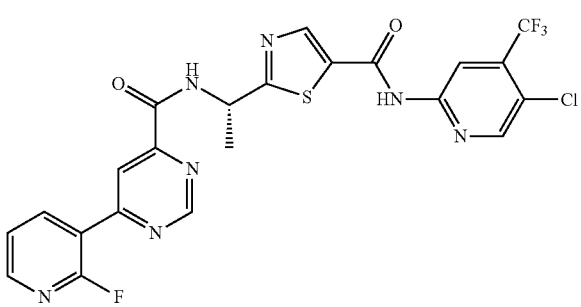 4eDb
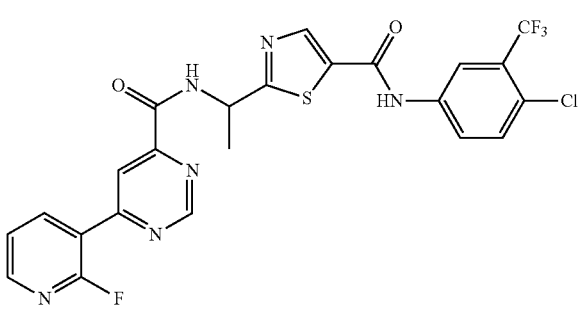 [SMILES: CC(NC(=O)c1cc(-c2cccnc2F)ncn1)c1ncc(C(=O)Nc2ccc(Cl)c(C(F)(F)F)c2)s1] 4eE TABLE 4-continued
Exemplary Compounds of Formula I
Additional compounds
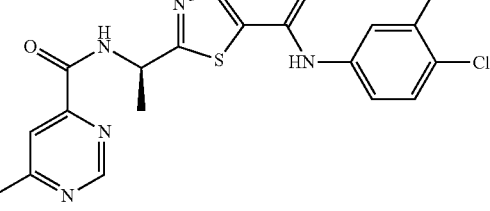 4eEa
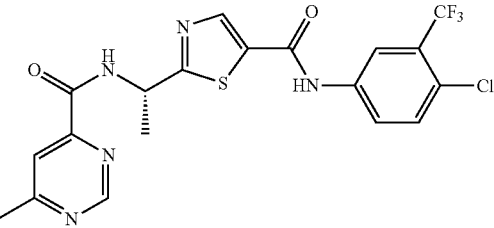 4eEb
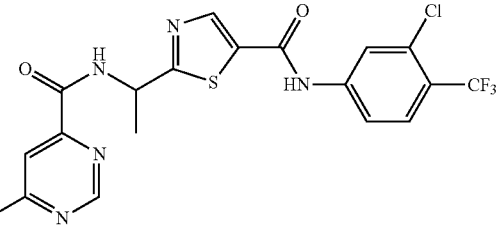 4eF
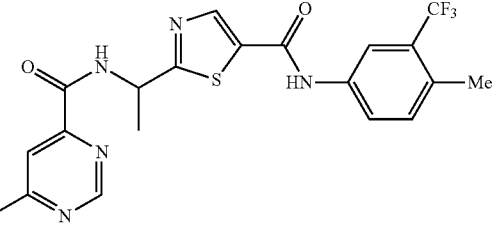 4eG
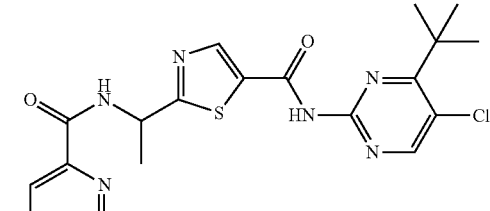 4eH TABLE 4-continued
Exemplary Compounds of Formula I
Additional compounds
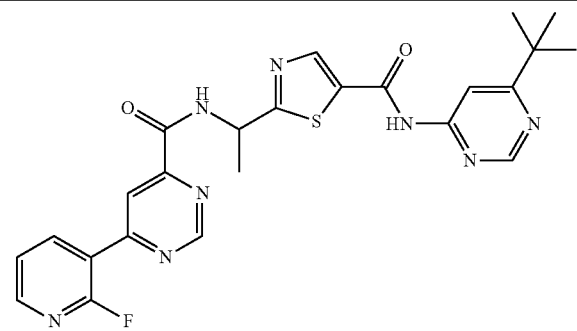
4eI
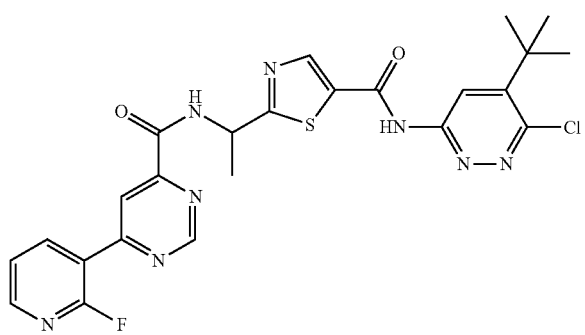 [SMILES: CC(NC(=O)c1cc(-c2cccnc2F)ncn1)c1ncc(C(=O)Nc2cc(C(C)(C)C)c(Cl)nn2)s1]
4eJ
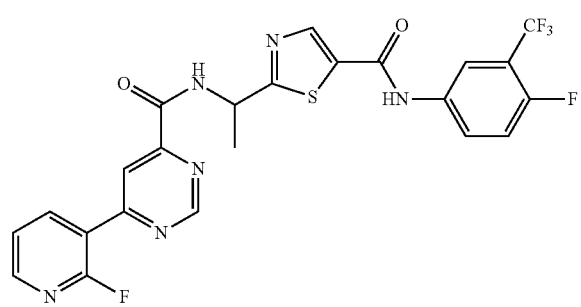 [SMILES: CC(NC(=O)c1cc(-c2cccnc2F)ncn1)c1ncc(C(=O)Nc2ccc(F)c(C(F)(F)F)c2)s1]
4eK
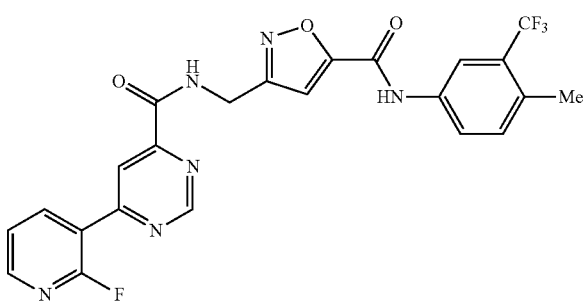 [SMILES: Cc1ccc(NC(=O)c2cc(CNC(=O)c3cc(-c4cccnc4F)ncn3)no2)cc1C(F)(F)F]
4eL
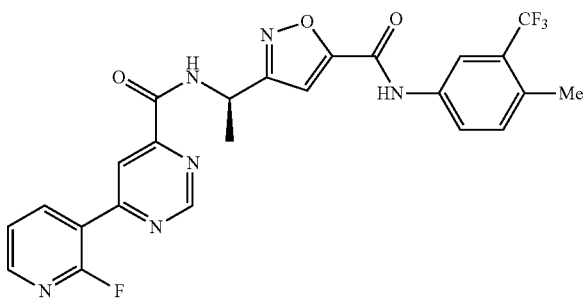 [SMILES: Cc1ccc(NC(=O)c2cc([C@@H](C)NC(=O)c3cc(-c4cccnc4F)ncn3)no2)cc1C(F)(F)F]
4eMa TABLE 4-continued
Exemplary Compounds of Formula I
Additional compounds
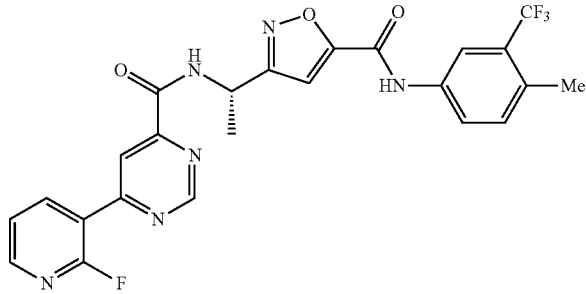 [SMILES: Cc1ccc(NC(=O)c2cc([C@H](C)NC(=O)c3cc(-c4cccnc4F)ncn3)no2)cc1C(F)(F)F] 4eMb
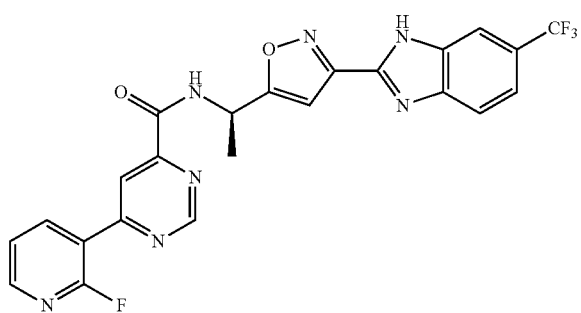 [SMILES: C[C@@H](NC(=O)c1cc(-c2cccnc2F)ncn1)c1cc(-c2nc3ccc(C(F)(F)F)cc3[nH]2)no1] 4eNa
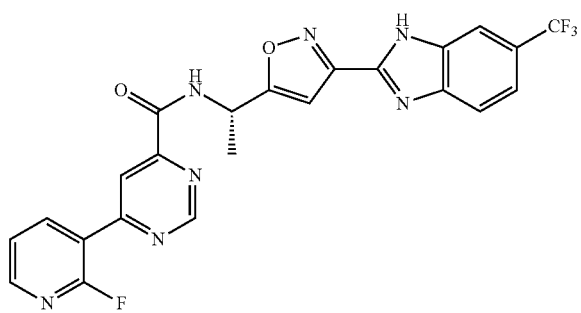 [SMILES: C[C@H](NC(=O)c1cc(-c2cccnc2F)ncn1)c1cc(-c2nc3ccc(C(F)(F)F)cc3[nH]2)no1] 4eNb
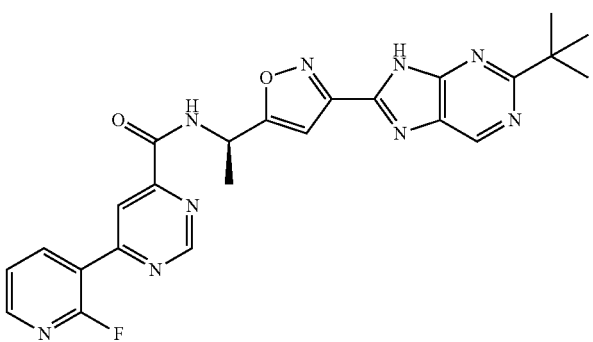 [SMILES: C[C@@H](NC(=O)c1cc(-c2cccnc2F)ncn1)c1cc(-c2nc3cnc(C(C)(C)C)nc3[nH]2)no1] 4eO TABLE 4-continued
Exemplary Compounds of Formula I
Additional compounds
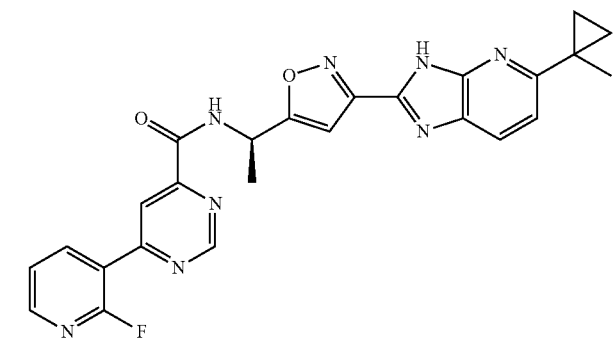 [SMILES: C[C@@H](NC(=O)c1cc(-c2cccnc2F)ncn1)c1cc(-c2nc3ccc(C4(C)CC4)nc3[nH]2)no1]
4eP
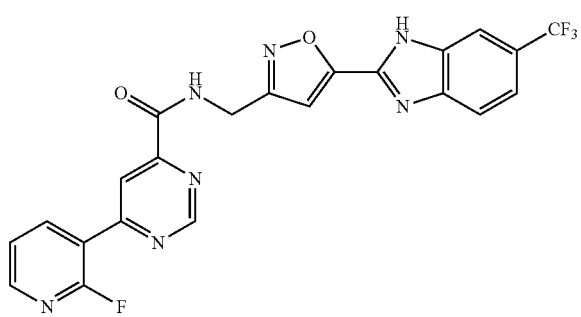 [SMILES: O=C(NCc1cc(-c2nc3ccc(C(F)(F)F)cc3[nH]2)on1)c1cc(-c2cccnc2F)ncn1]
4eQ
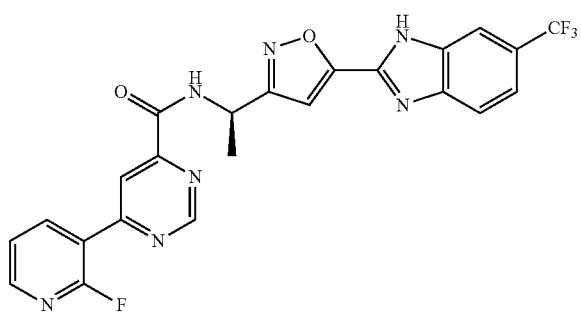 [SMILES: C[C@@H](NC(=O)c1cc(-c2cccnc2F)ncn1)c1cc(-c2nc3ccc(C(F)(F)F)cc3[nH]2)on1]
4eRa
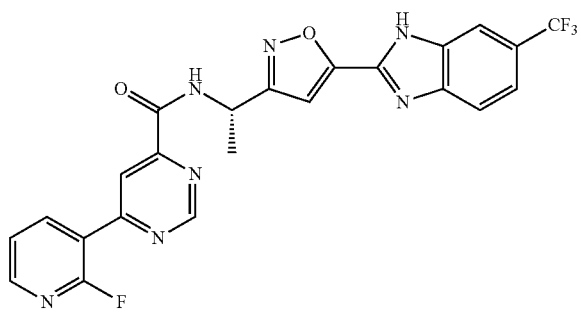 [SMILES: C[C@H](NC(=O)c1cc(-c2cccnc2F)ncn1)c1cc(-c2nc3ccc(C(F)(F)F)cc3[nH]2)on1]
4eRb
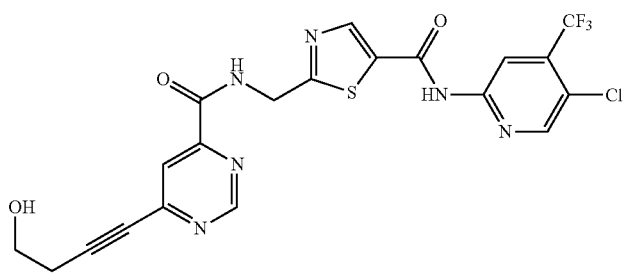 [SMILES: O=C(NCc1ncc(C(=O)Nc2cc(C(F)(F)F)c(Cl)cn2)s1)c1cc(C#CCCO)ncn1]
7aA TABLE 4-continued
Exemplary Compounds of Formula I
Additional compounds
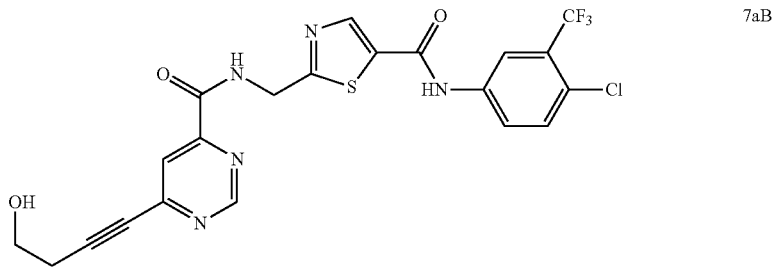 7aB
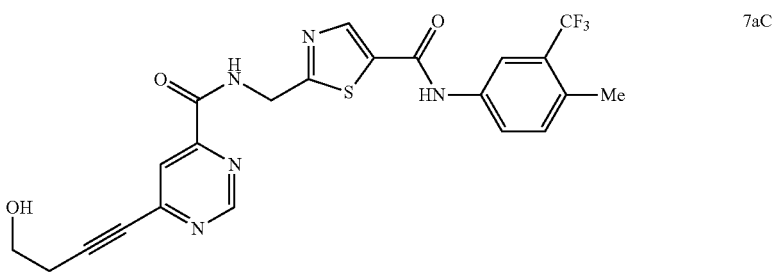 7aC
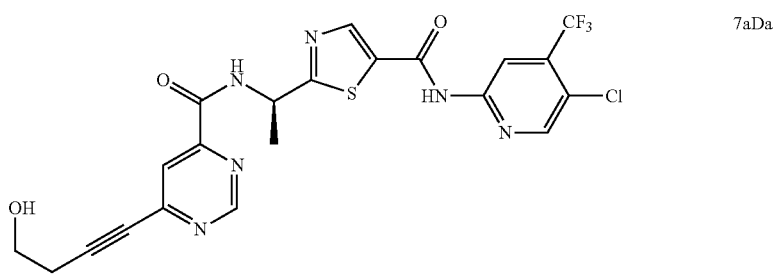 7aDa
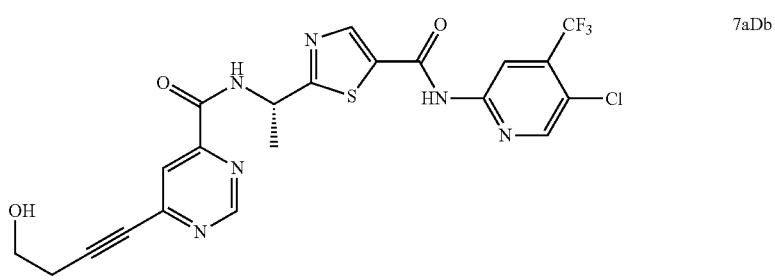 7aDb
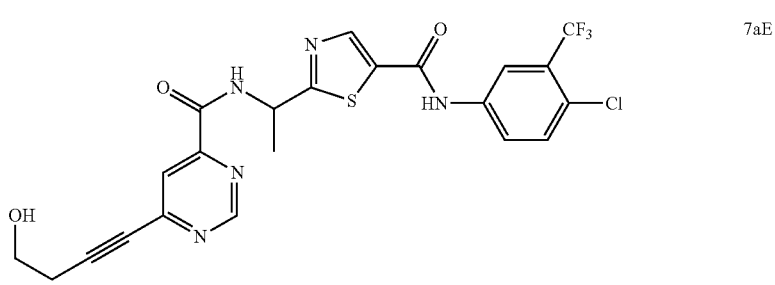 7aE TABLE 4-continued
Exemplary Compounds of Formula I
Additional compounds
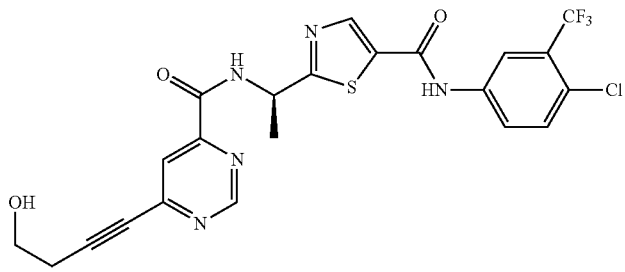 [SMILES: C[C@@H](NC(=O)c1cc(C#CCCO)ncn1)c1ncc(C(=O)Nc2ccc(Cl)c(C(F)(F)F)c2)s1]
7aEa
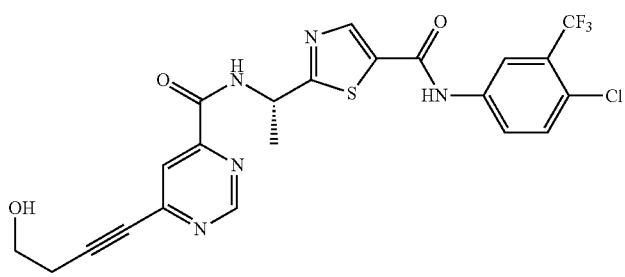 [SMILES: C[C@H](NC(=O)c1cc(C#CCCO)ncn1)c1ncc(C(=O)Nc2ccc(Cl)c(C(F)(F)F)c2)s1]
7aEb
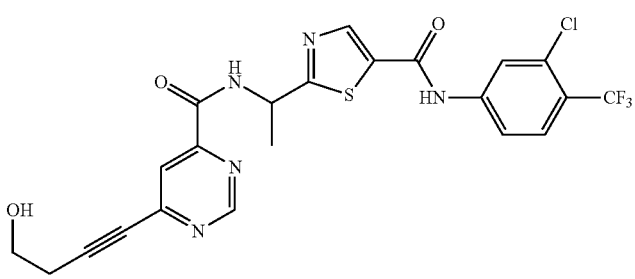 [SMILES: CC(NC(=O)c1cc(C#CCCO)ncn1)c1ncc(C(=O)Nc2ccc(C(F)(F)F)c(Cl)c2)s1]
7aF
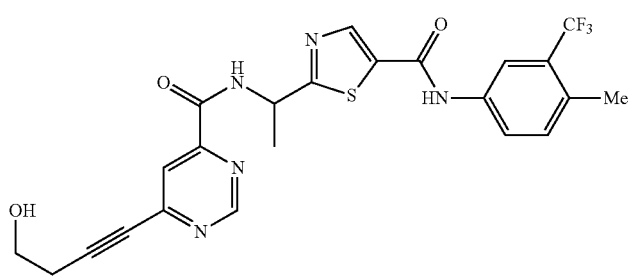
7aG
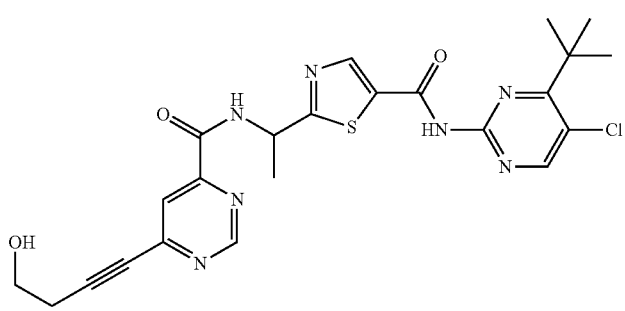 [SMILES: CC(NC(=O)c1cc(C#CCCO)ncn1)c1ncc(C(=O)Nc2ncc(Cl)c(C(C)(C)C)n2)s1]
7aH TABLE 4-continued
Exemplary Compounds of Formula I
Additional compounds
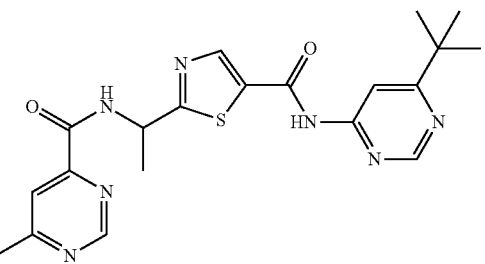 7aI
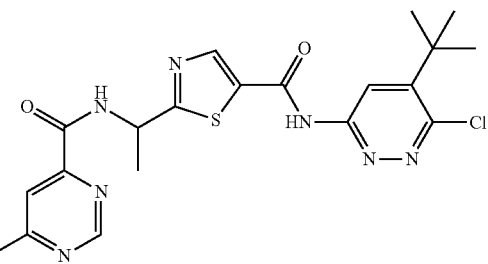 7aJ
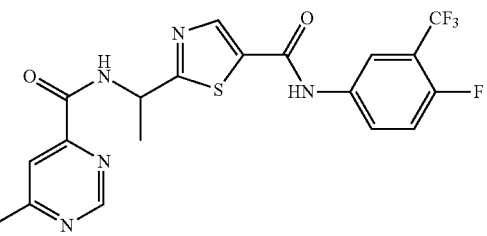 7aK
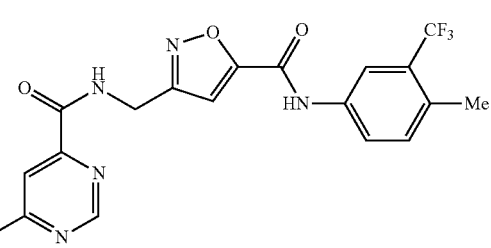 7aL
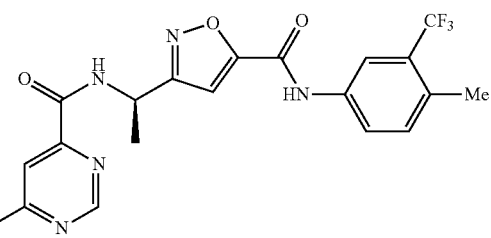 7aMa TABLE 4-continued
Exemplary Compounds of Formula I
Additional compounds
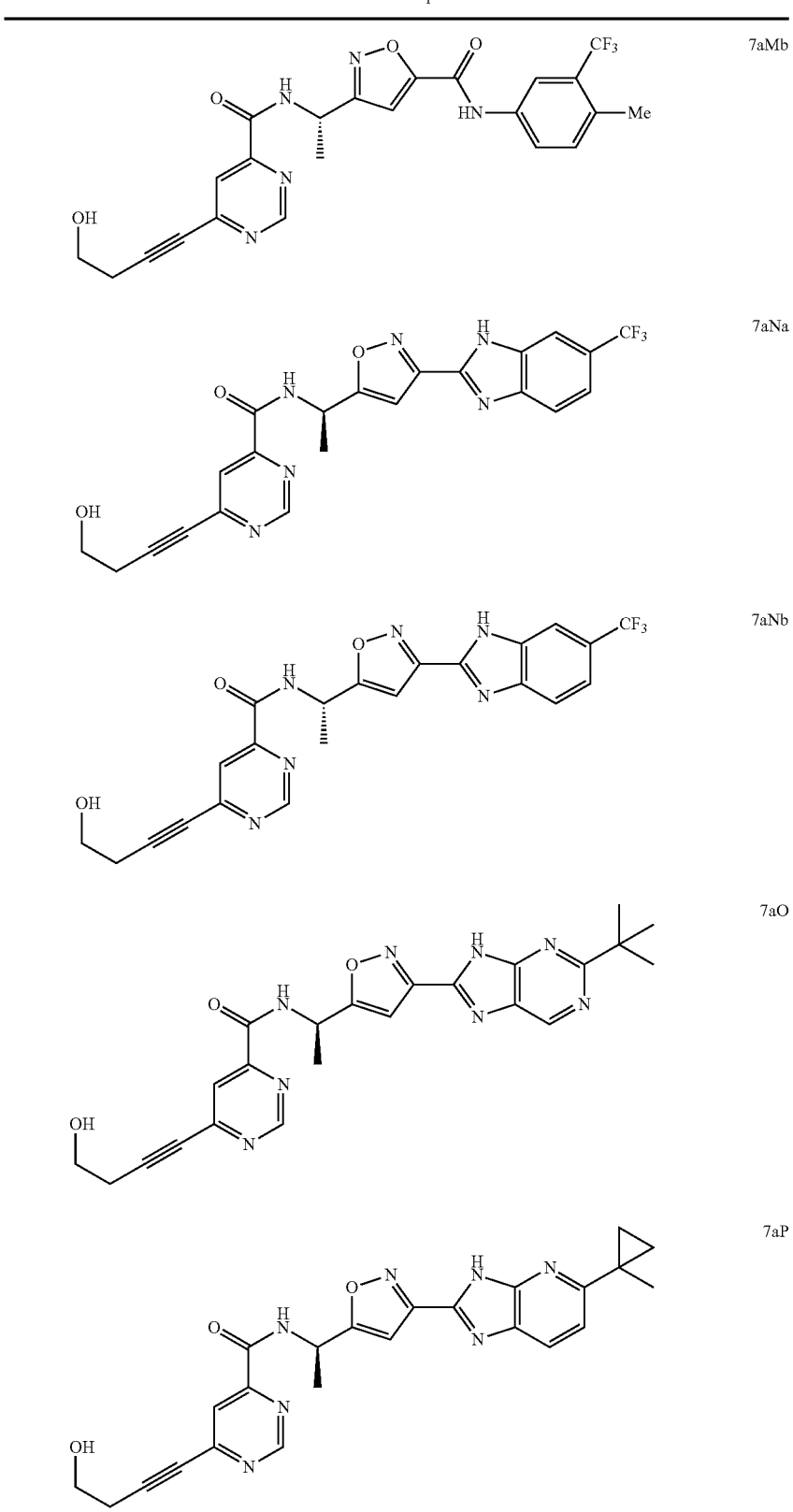
7aMb
7aNa
7aNb
7aO
7aP TABLE 4-continued
Exemplary Compounds of Formula I
Additional compounds
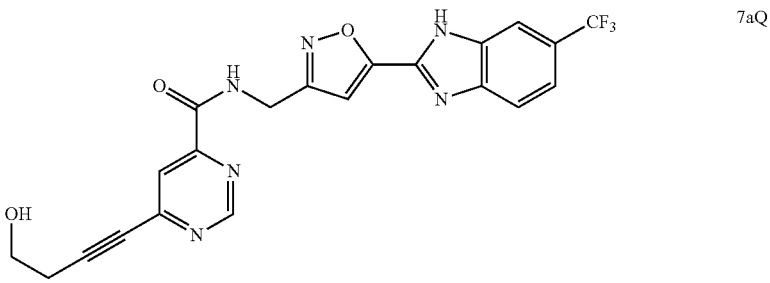
7aQ
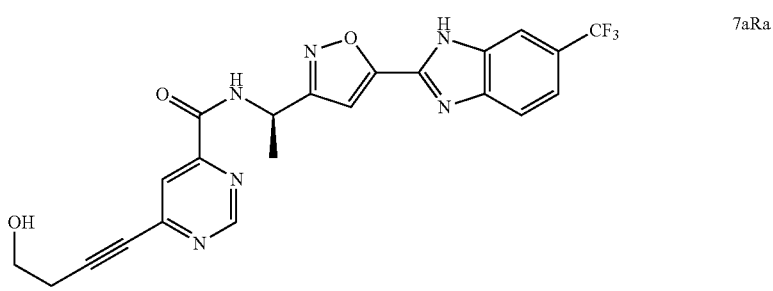
7aRa
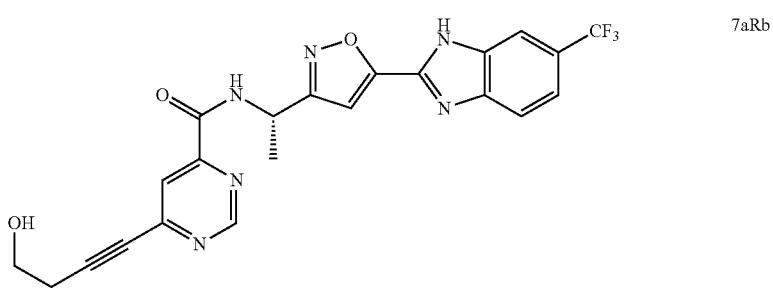
7aRb
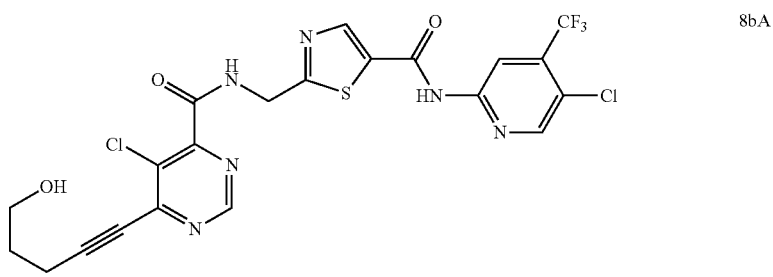
8bA
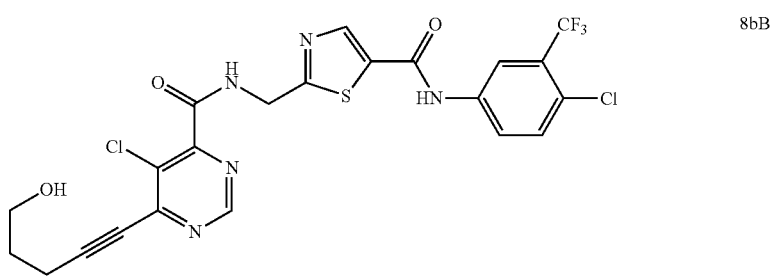
8bB TABLE 4-continued
Exemplary Compounds of Formula I
Additional compounds
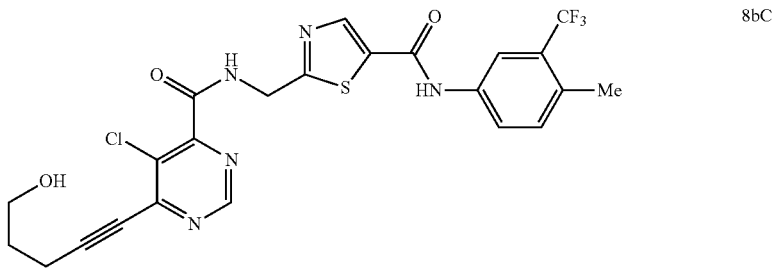
8bC
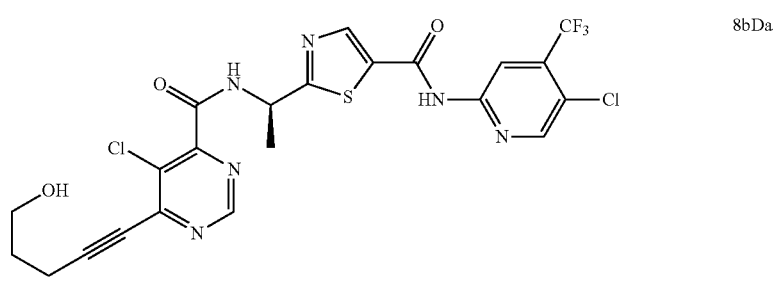
8bDa
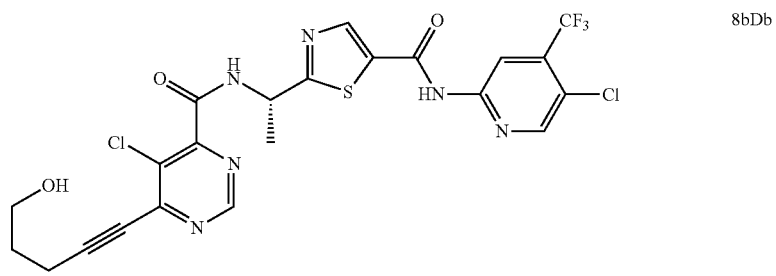
8bDb
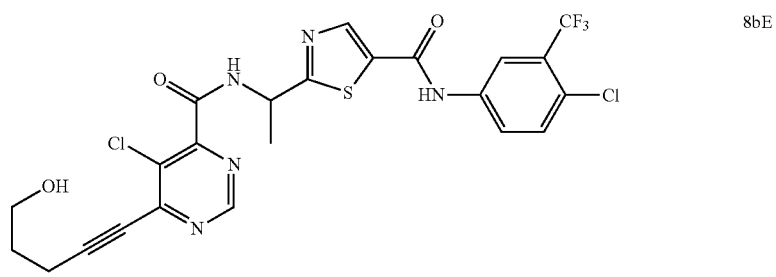
8bE
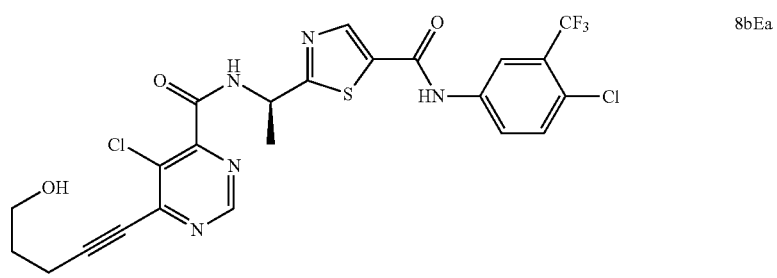
8bEa TABLE 4-continued
Exemplary Compounds of Formula I
Additional compounds
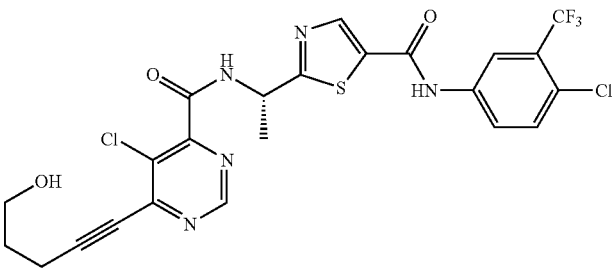 [SMILES: C[C@H](NC(=O)c1ncnc(C#CCCCO)c1Cl)c1ncc(C(=O)Nc2ccc(Cl)c(C(F)(F)F)c2)s1] 8bEb
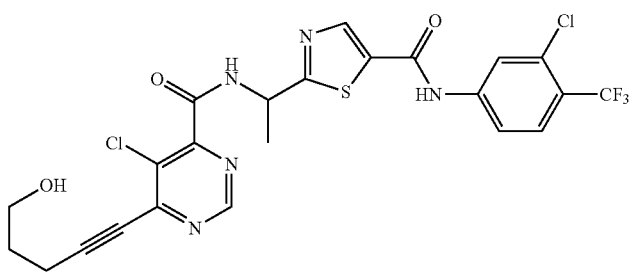 [SMILES: CC(NC(=O)c1ncnc(C#CCCCO)c1Cl)c1ncc(C(=O)Nc2ccc(C(F)(F)F)c(Cl)c2)s1] 8bF
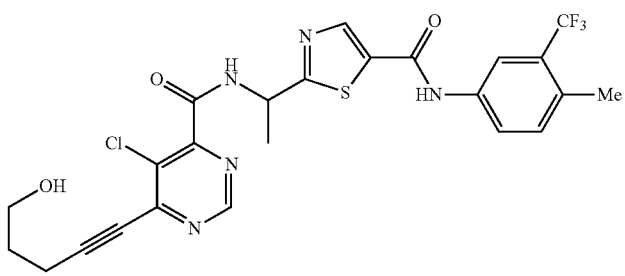 [SMILES: Cc1ccc(NC(=O)c2cnc(C(C)NC(=O)c3ncnc(C#CCCCO)c3Cl)s2)cc1C(F)(F)F] 8bG
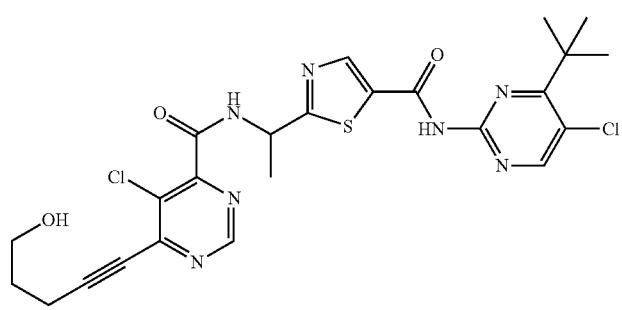 [SMILES: CC(NC(=O)c1ncnc(C#CCCCO)c1Cl)c1ncc(C(=O)Nc2ncc(Cl)c(C(C)(C)C)n2)s1] 8bH
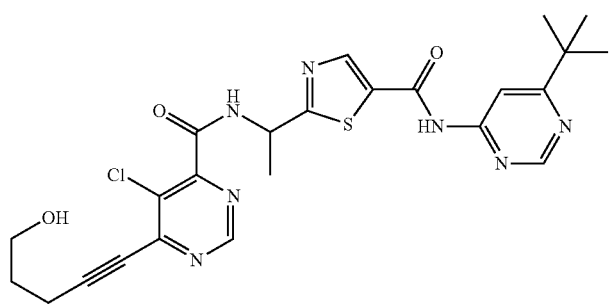 [SMILES: CC(NC(=O)c1ncnc(C#CCCCO)c1Cl)c1ncc(C(=O)Nc2cc(C(C)(C)C)ncn2)s1] 8bI TABLE 4-continued
Exemplary Compounds of Formula I
Additional compounds
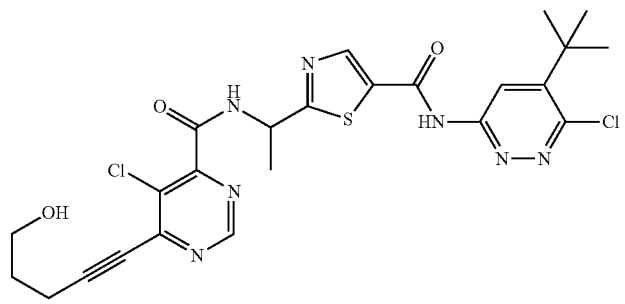 [SMILES: CC(NC(=O)c1ncnc(C#CCCCO)c1Cl)c1ncc(C(=O)Nc2cc(C(C)(C)C)c(Cl)nn2)s1] 8bJ
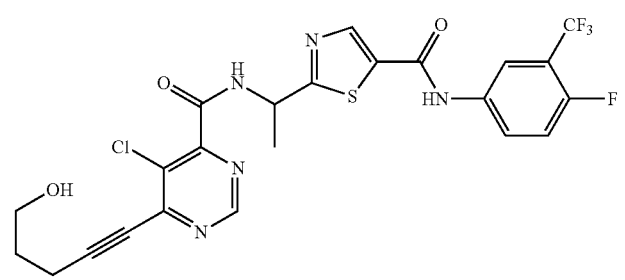 [SMILES: CC(NC(=O)c1ncnc(C#CCCCO)c1Cl)c1ncc(C(=O)Nc2ccc(F)c(C(F)(F)F)c2)s1] 8bK
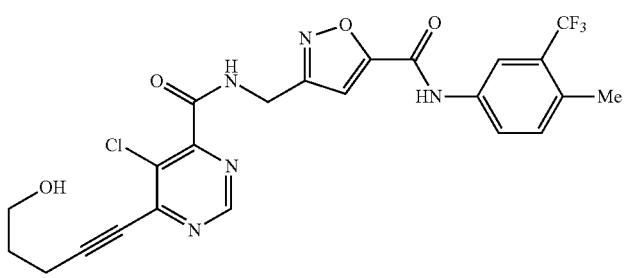 8bL
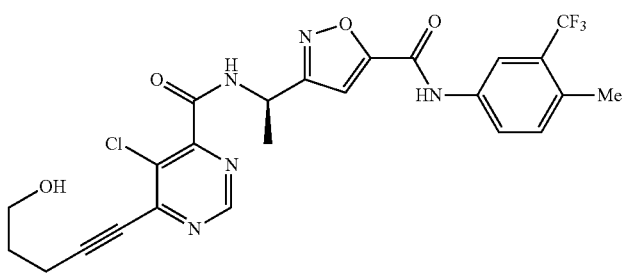 [SMILES: Cc1ccc(NC(=O)c2cc([C@@H](C)NC(=O)c3ncnc(C#CCCCO)c3Cl)no2)cc1C(F)(F)F] 8bMa
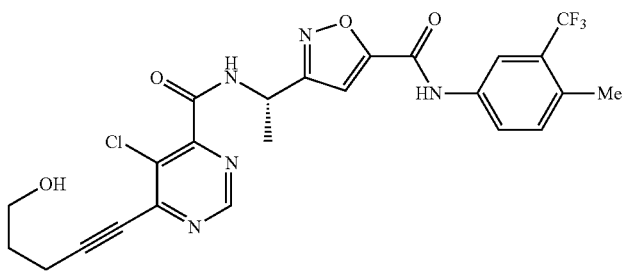 [SMILES: Cc1ccc(NC(=O)c2cc([C@H](C)NC(=O)c3ncnc(C#CCCCO)c3Cl)no2)cc1C(F)(F)F] 8bMb TABLE 4-continued
Exemplary Compounds of Formula I
Additional compounds
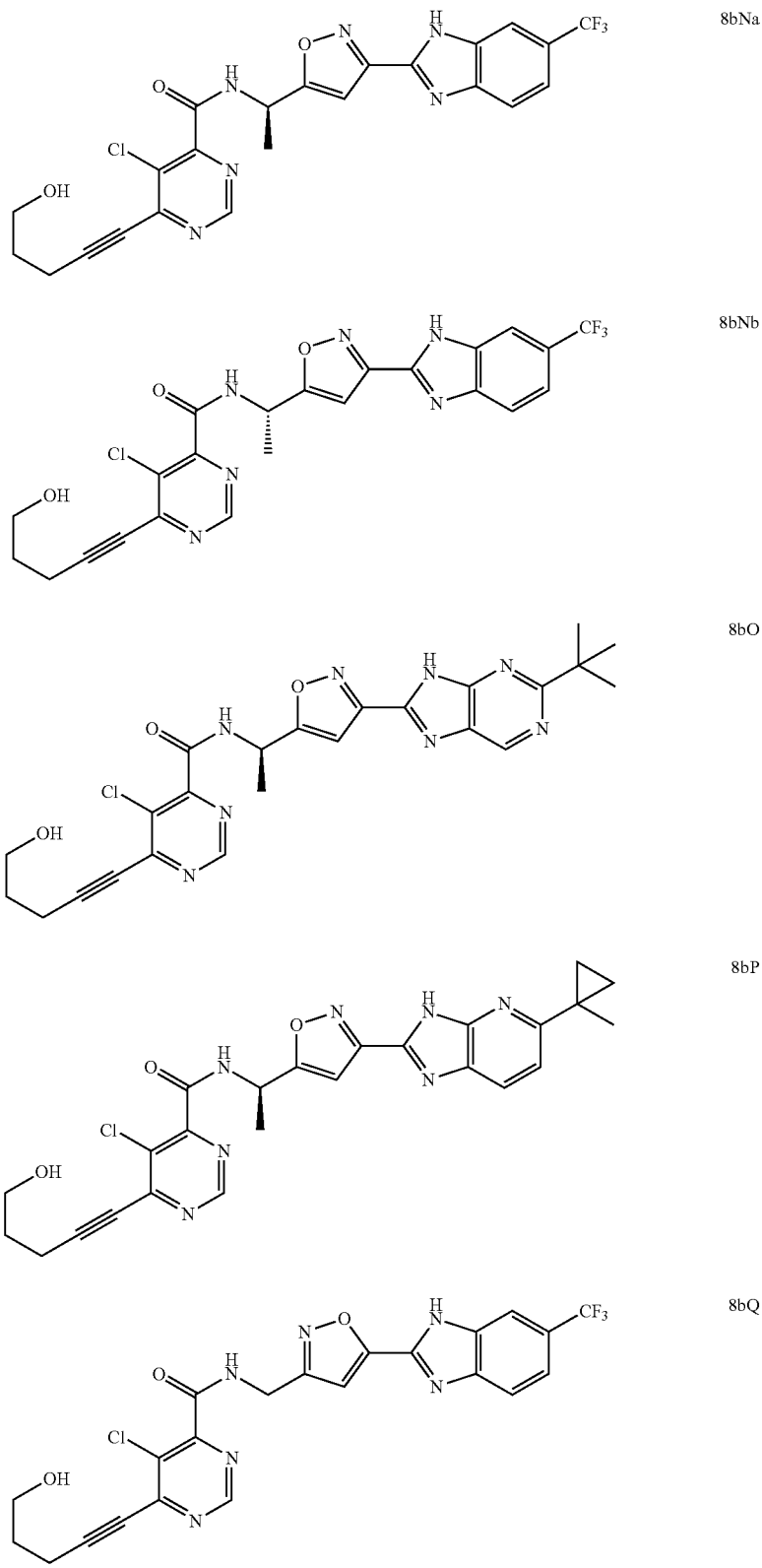
8bNa
8bNb
8bO
8bP
8bQ TABLE 4-continued
Exemplary Compounds of Formula I
Additional compounds
| | |
|---|---|
| 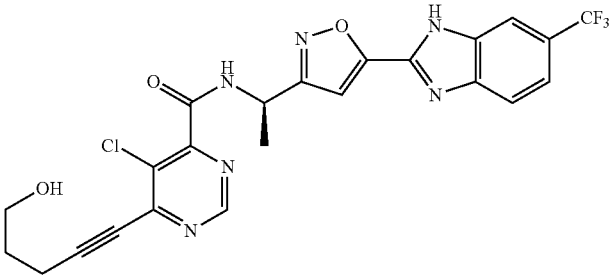 [SMILES: C[C@@H](NC(=O)c1ncnc(C#CCCCO)c1Cl)c1cc(-c2nc3ccc(C(F)(F)F)cc3[nH]2)on1] | 8bRa |
| 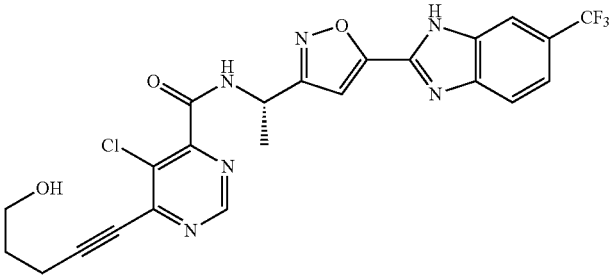 [SMILES: C[C@H](NC(=O)c1ncnc(C#CCCCO)c1Cl)c1cc(-c2nc3ccc(C(F)(F)F)cc3[nH]2)on1] | 8bRb |
| 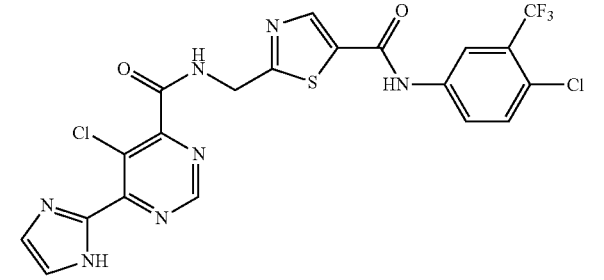 | 9B |
| 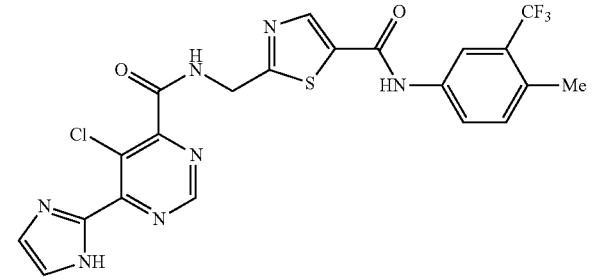 [SMILES: Cc1ccc(NC(=O)c2cnc(CNC(=O)c3ncnc(-c4ncc[nH]4)c3Cl)s2)cc1C(F)(F)F] | 9C |
| 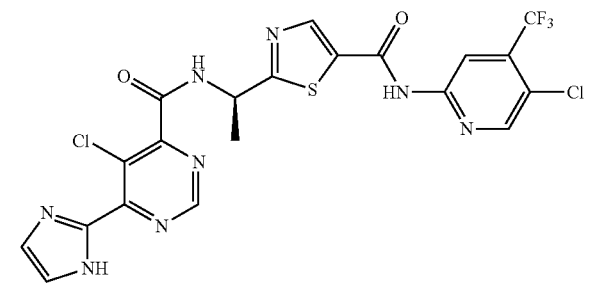 [SMILES: C[C@@H](NC(=O)c1ncnc(-c2ncc[nH]2)c1Cl)c1ncc(C(=O)Nc2cc(C(F)(F)F)c(Cl)cn2)s1] | 9Da |

TABLE 4-continued

Exemplary Compounds of Formula I
Additional compounds

| | |
|---|---|
| (structure) | 9Db |
| (structure) | 9E |
| (structure) | 9Ea |
| (structure) | 9Eb |
| (structure) | 9F |

TABLE 4-continued
Exemplary Compounds of Formula I
Additional compounds
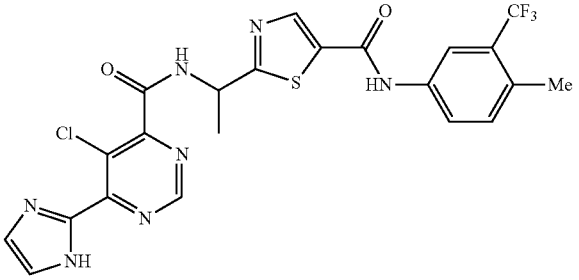 [SMILES: Cc1ccc(NC(=O)c2cnc(C(C)NC(=O)c3ncnc(-c4ncc[nH]4)c3Cl)s2)cc1C(F)(F)F]
9G
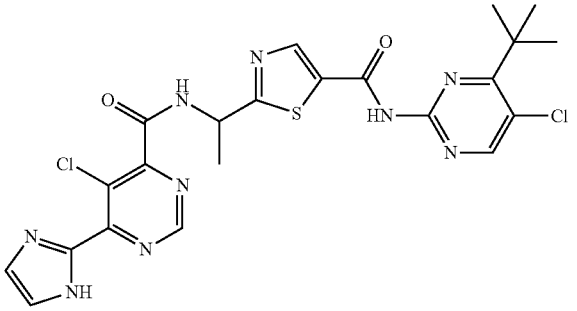 [SMILES: CC(NC(=O)c1ncnc(-c2ncc[nH]2)c1Cl)c1ncc(C(=O)Nc2ncc(Cl)c(C(C)(C)C)n2)s1]
9H
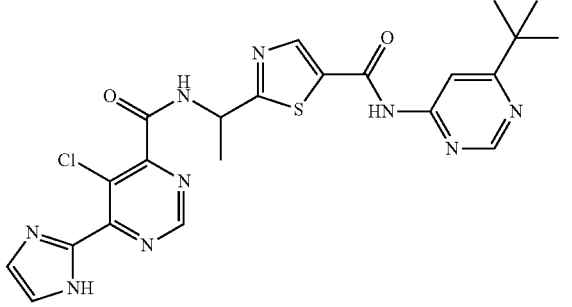 [SMILES: CC(NC(=O)c1ncnc(-c2ncc[nH]2)c1Cl)c1ncc(C(=O)Nc2cc(C(C)(C)C)ncn2)s1]
9I
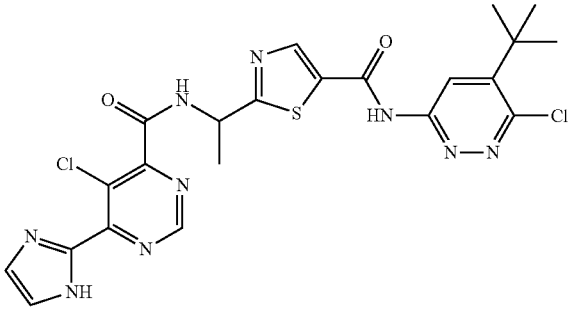 [SMILES: CC(NC(=O)c1ncnc(-c2ncc[nH]2)c1Cl)c1ncc(C(=O)Nc2cc(C(C)(C)C)c(Cl)nn2)s1]
9J
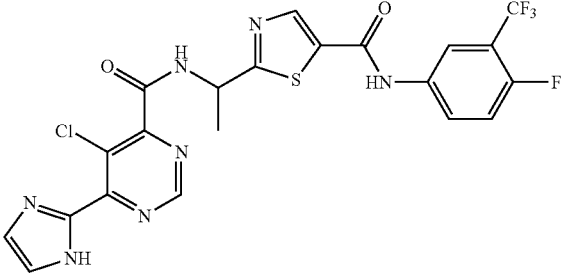 [SMILES: CC(NC(=O)c1ncnc(-c2ncc[nH]2)c1Cl)c1ncc(C(=O)Nc2ccc(F)c(C(F)(F)F)c2)s1]
9K TABLE 4-continued Exemplary Compounds of Formula I
Additional compounds

| | |
|---|---|
| (structure) | 9L |
| (structure) | 9Ma |
| (structure) | 9Mb |
| (structure) | 9Na |
| (structure) | 9Nb |

TABLE 4-continued
Exemplary Compounds of Formula I
Additional compounds
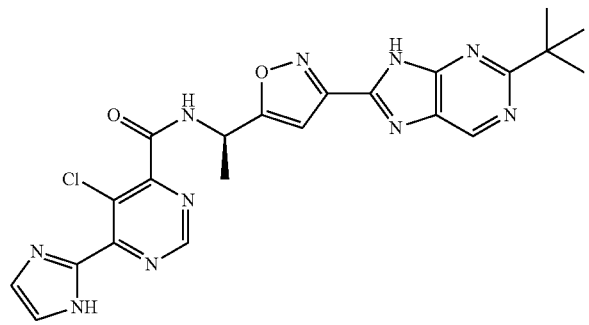 [SMILES: C[C@@H](NC(=O)c1ncnc(-c2ncc[nH]2)c1Cl)c1cc(-c2nc3cnc(C(C)(C)C)nc3[nH]2)no1]
9O
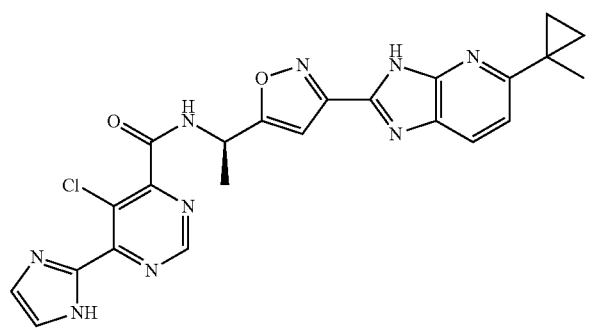 [SMILES: C[C@@H](NC(=O)c1ncnc(-c2ncc[nH]2)c1Cl)c1cc(-c2nc3ccc(C4(C)CC4)nc3[nH]2)no1]
9P
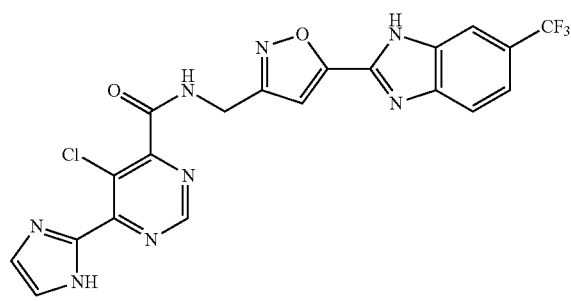 [SMILES: O=C(NCc1cc(-c2nc3ccc(C(F)(F)F)cc3[nH]2)on1)c1ncnc(-c2ncc[nH]2)c1Cl]
9Q
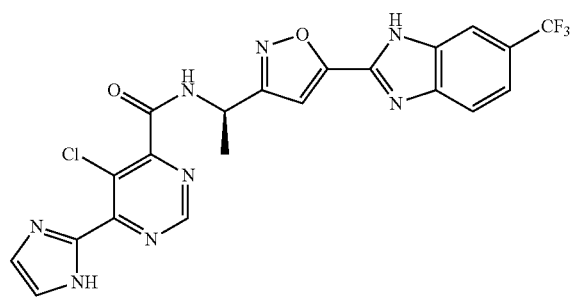 [SMILES: C[C@@H](NC(=O)c1ncnc(-c2ncc[nH]2)c1Cl)c1cc(-c2nc3ccc(C(F)(F)F)cc3[nH]2)on1]
9Ra
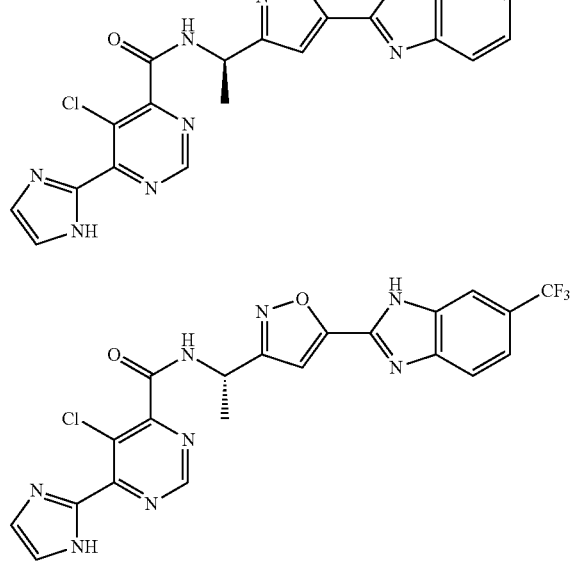
9Rb TABLE 4-continued
Exemplary Compounds of Formula I
Additional compounds
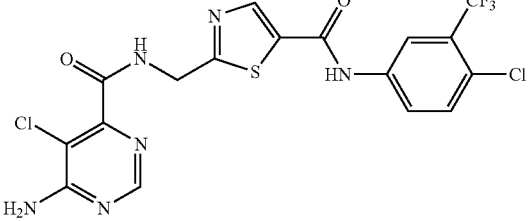 10B
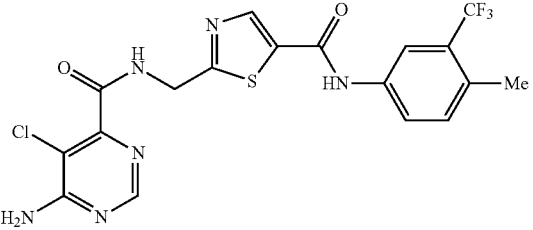 [SMILES: Cc1ccc(NC(=O)c2cnc(CNC(=O)c3ncnc(N)c3Cl)s2)cc1C(F)(F)F] 10C
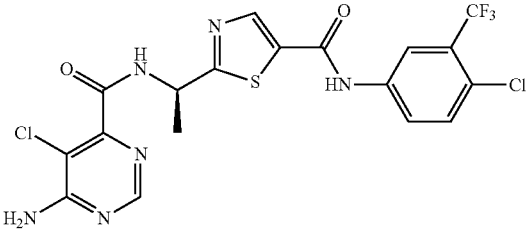 10Ea
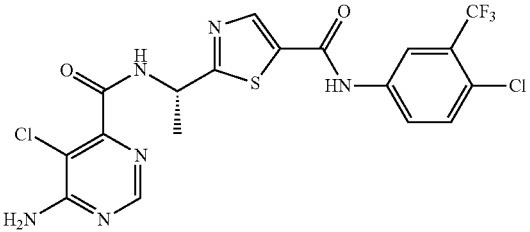 10Eb
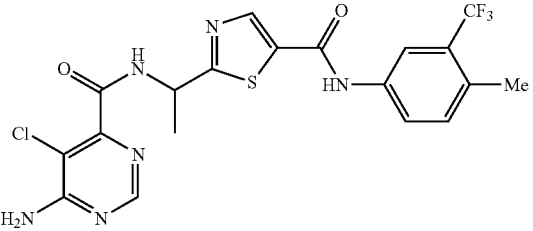 [SMILES: Cc1ccc(NC(=O)c2cnc(C(C)NC(=O)c3ncnc(N)c3Cl)s2)cc1C(F)(F)F] 10G
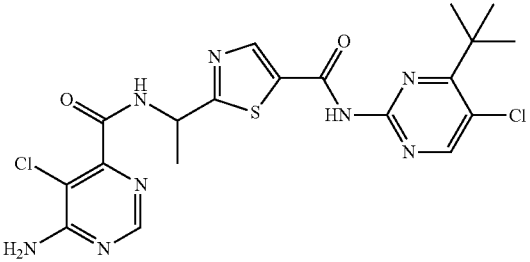 [SMILES: CC(NC(=O)c1ncnc(N)c1Cl)c1ncc(C(=O)Nc2ncc(Cl)c(C(C)(C)C)n2)s1] 10H TABLE 4-continued
Exemplary Compounds of Formula I
Additional compounds
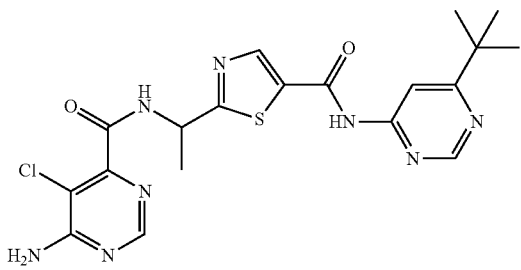 [SMILES: CC(NC(=O)c1ncnc(N)c1Cl)c1ncc(C(=O)Nc2cc(C(C)(C)C)ncn2)s1]
10I
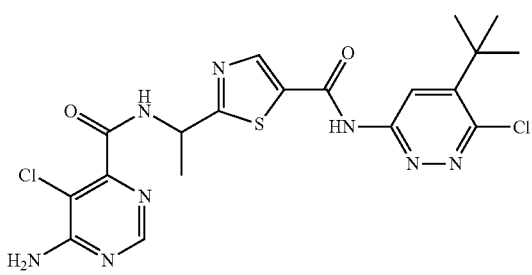 [SMILES: CC(NC(=O)c1ncnc(N)c1Cl)c1ncc(C(=O)Nc2cc(C(C)(C)C)c(Cl)nn2)s1]
10J
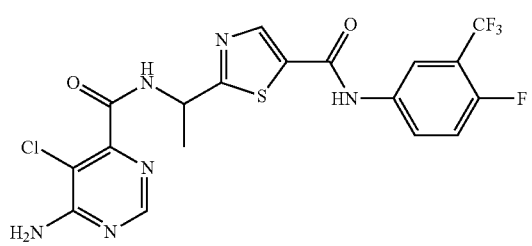 [SMILES: CC(NC(=O)c1ncnc(N)c1Cl)c1ncc(C(=O)Nc2ccc(F)c(C(F)(F)F)c2)s1]
10K
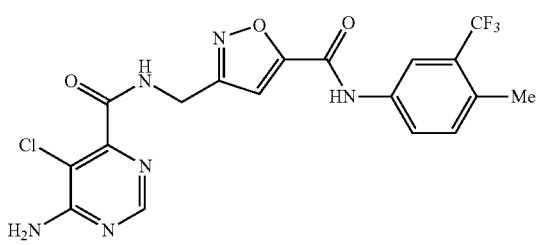 [SMILES: Cc1ccc(NC(=O)c2cc(CNC(=O)c3ncnc(N)c3Cl)no2)cc1C(F)(F)F]
10L
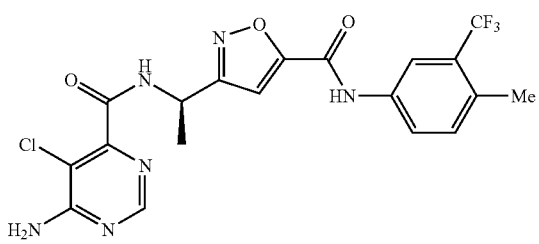 [SMILES: Cc1ccc(NC(=O)c2cc([C@@H](C)NC(=O)c3ncnc(N)c3Cl)no2)cc1C(F)(F)F]
10Ma
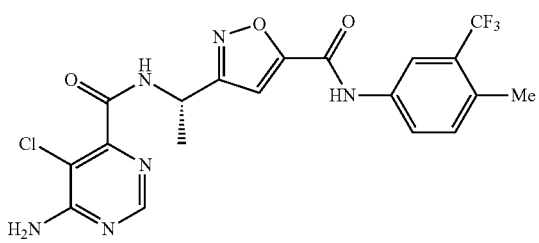 [SMILES: Cc1ccc(NC(=O)c2cc([C@H](C)NC(=O)c3ncnc(N)c3Cl)no2)cc1C(F)(F)F]
10Mb TABLE 4-continued
Exemplary Compounds of Formula I
Additional compounds
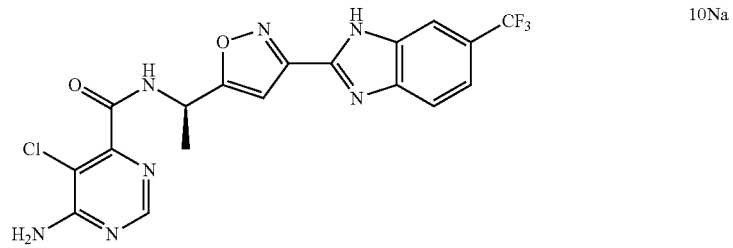 10Na
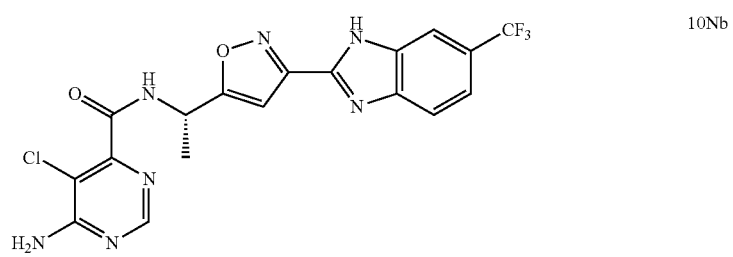 10Nb
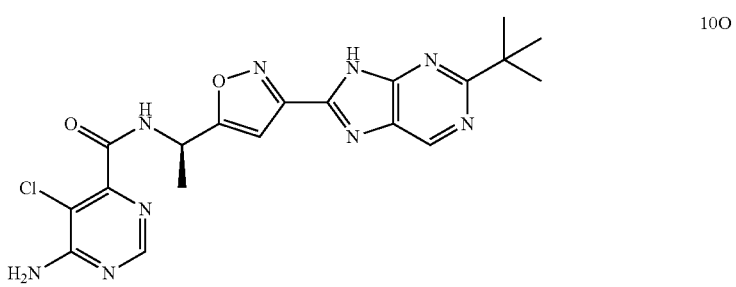 10O
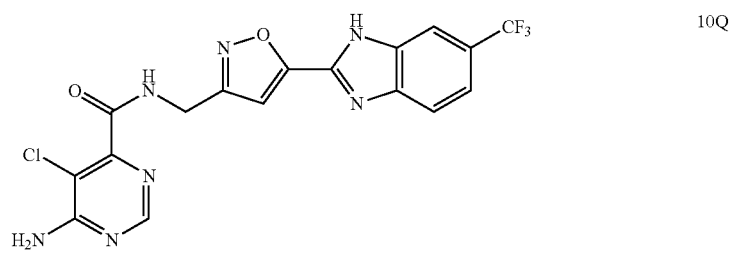 10Q
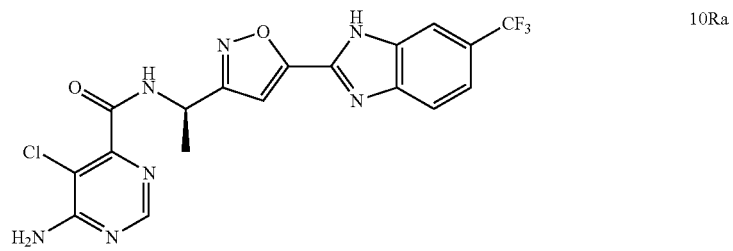 10Ra
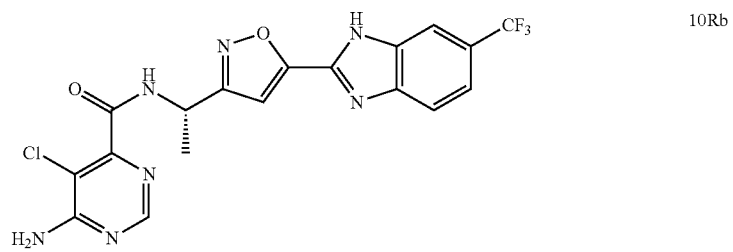 10Rb TABLE 4-continued
Exemplary Compounds of Formula I
Additional compounds
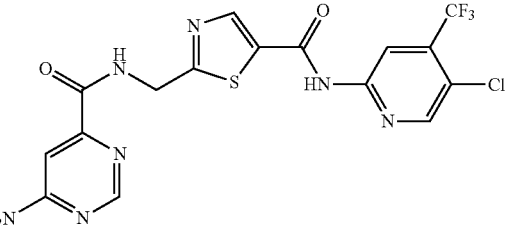 11A
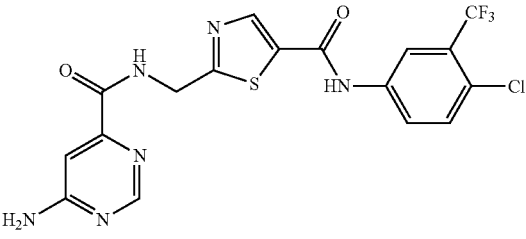 [SMILES: Nc1cc(C(=O)NCc2ncc(C(=O)Nc3ccc(Cl)c(C(F)(F)F)c3)s2)ncn1] 11B
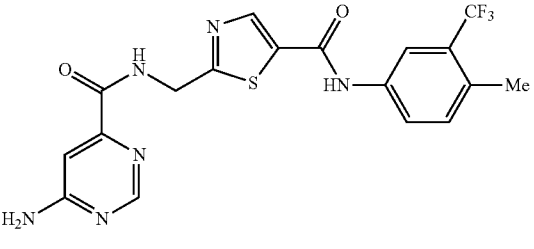 [SMILES: Cc1ccc(NC(=O)c2cnc(CNC(=O)c3cc(N)ncn3)s2)cc1C(F)(F)F] 11C
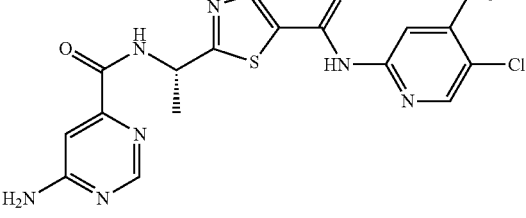 11Db
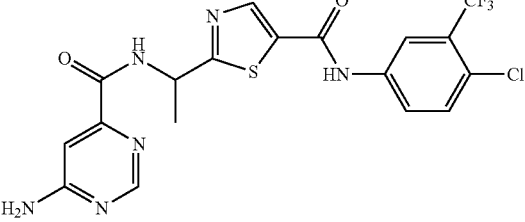 11E
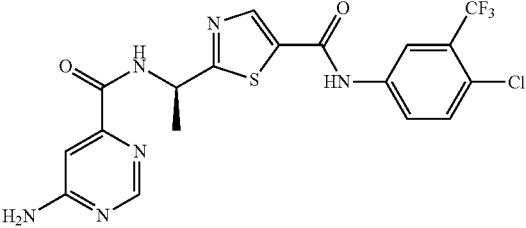 11Ea TABLE 4-continued
Exemplary Compounds of Formula I
Additional compounds
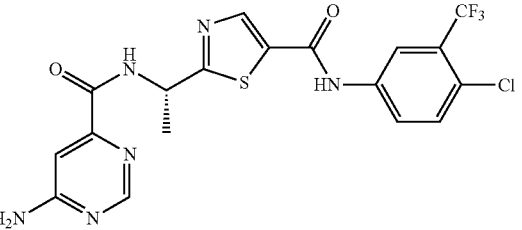 11Eb
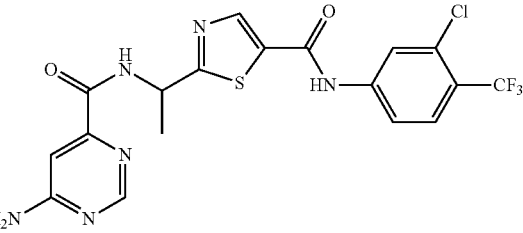 11F
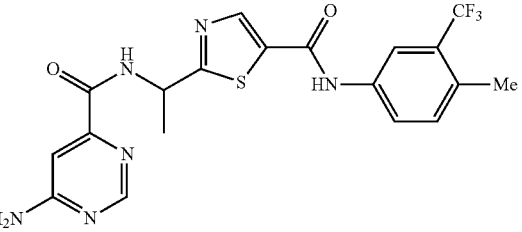 11G
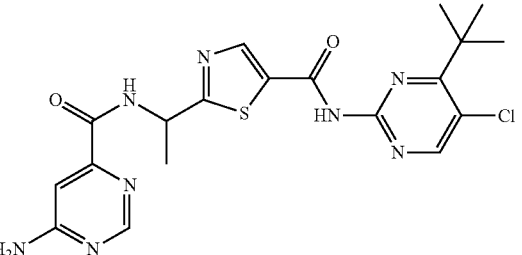 11H
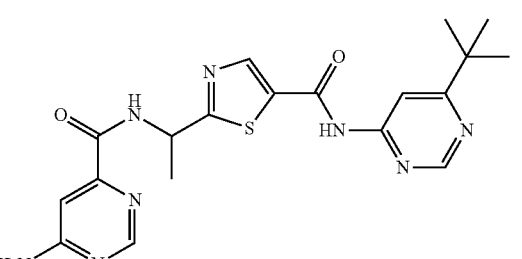 11I
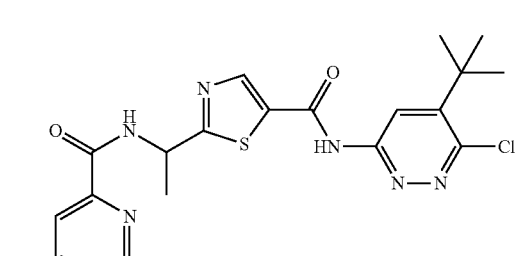 11J TABLE 4-continued
Exemplary Compounds of Formula I
Additional compounds
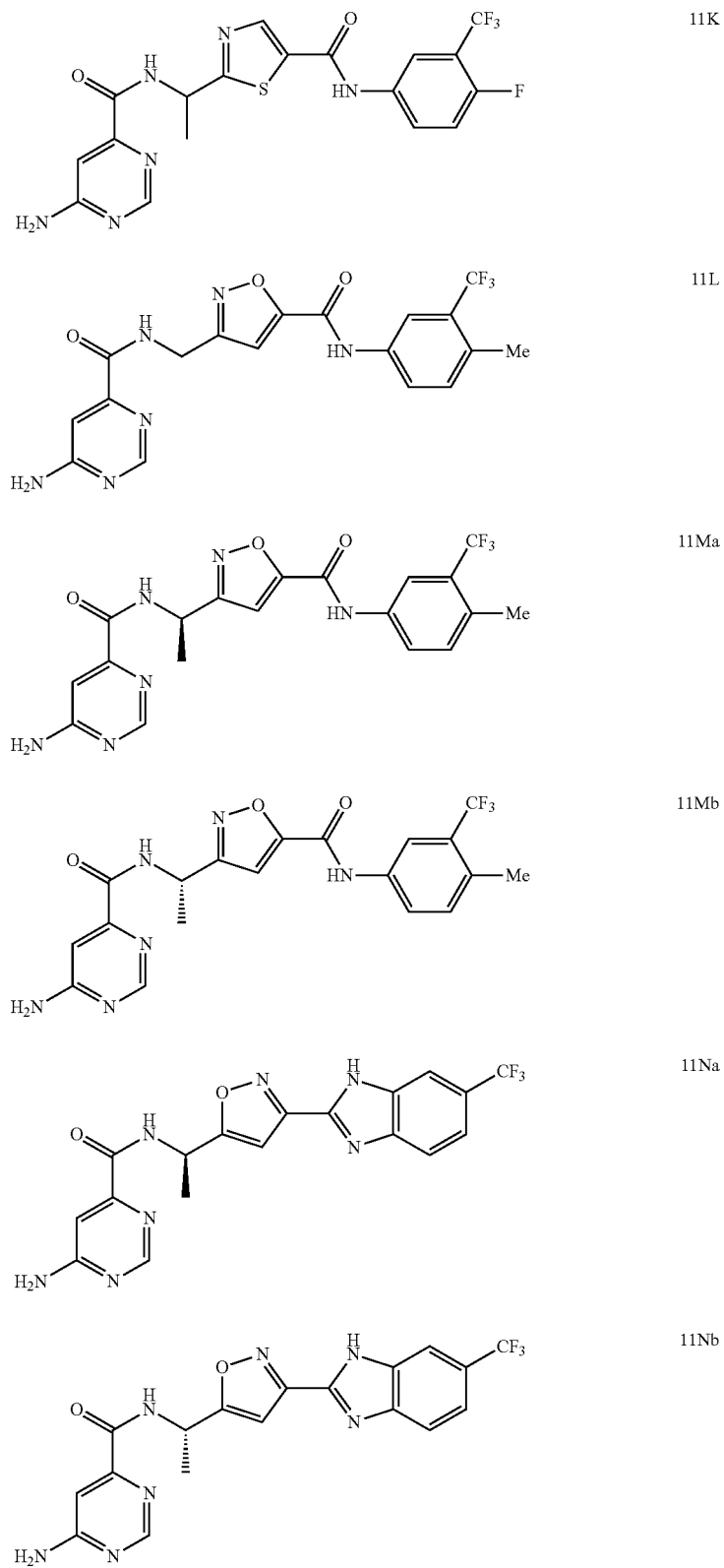

TABLE 4-continued
Exemplary Compounds of Formula I
Additional compounds
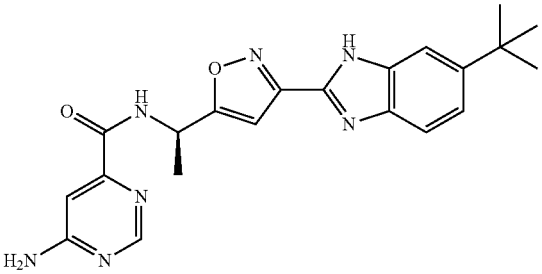 [SMILES: C[C@@H](NC(=O)c1cc(N)ncn1)c1cc(-c2nc3ccc(C(C)(C)C)cc3[nH]2)no1]
11O
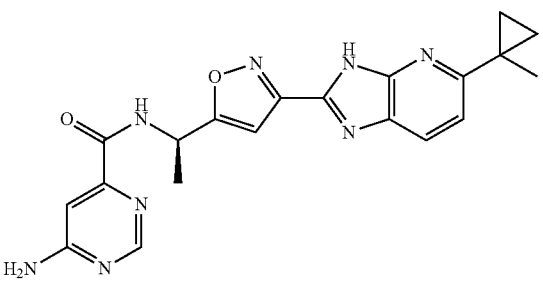 [SMILES: C[C@@H](NC(=O)c1cc(N)ncn1)c1cc(-c2nc3ccc(C4(C)CC4)nc3[nH]2)no1]
11P
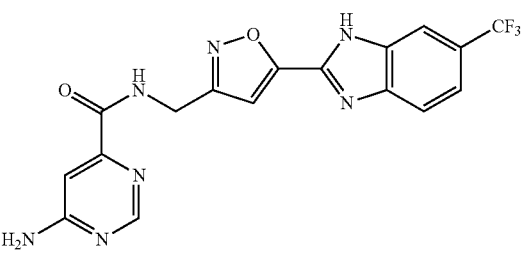 [SMILES: Nc1cc(C(=O)NCc2cc(-c3nc4ccc(C(F)(F)F)cc4[nH]3)on2)ncn1]
11Q
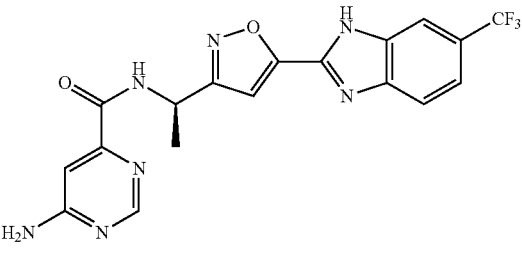 [SMILES: C[C@@H](NC(=O)c1cc(N)ncn1)c1cc(-c2nc3ccc(C(F)(F)F)cc3[nH]2)on1]
11Ra
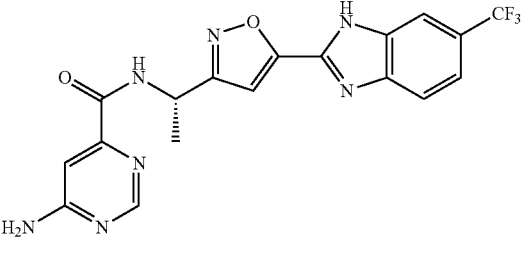 [SMILES: C[C@H](NC(=O)c1cc(N)ncn1)c1cc(-c2nc3ccc(C(F)(F)F)cc3[nH]2)on1]
11Rb
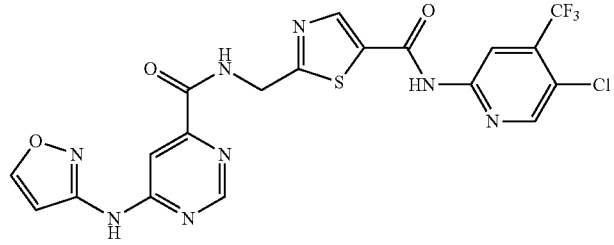 [SMILES: O=C(NCc1ncc(C(=O)Nc2cc(C(F)(F)F)c(Cl)cn2)s1)c1cc(Nc2ccon2)ncn1]
12aA TABLE 4-continued
Exemplary Compounds of Formula I
Additional compounds
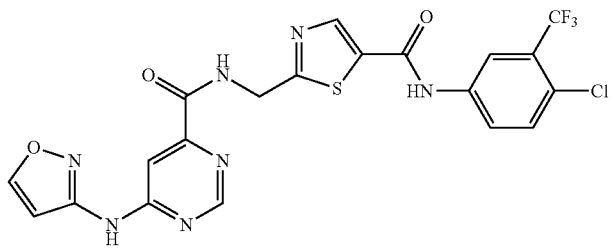 [SMILES: O=C(NCc1ncc(C(=O)Nc2ccc(Cl)c(C(F)(F)F)c2)s1)c1cc(Nc2ccon2)ncn1] 12aB
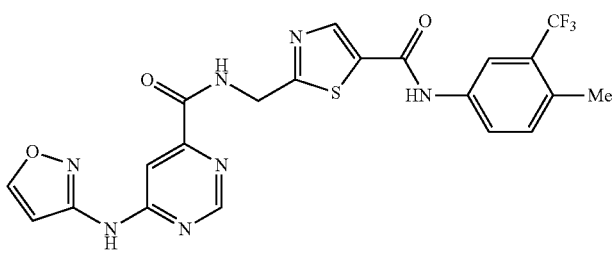 12aC
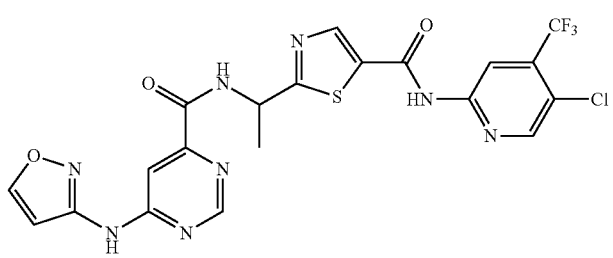 12aD
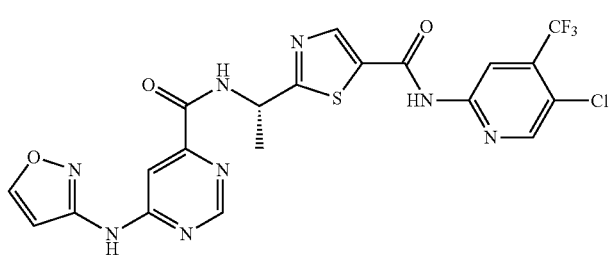 [SMILES: CC(NC(=O)c1cc(Nc2ccon2)ncn1)c1ncc(C(=O)Nc2cc(C(F)(F)F)c(Cl)cn2)s1] 12aDb
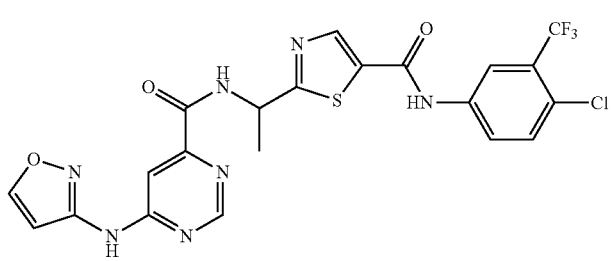 [SMILES: CC(NC(=O)c1cc(Nc2ccon2)ncn1)c1ncc(C(=O)Nc2ccc(Cl)c(C(F)(F)F)c2)s1] 12aE
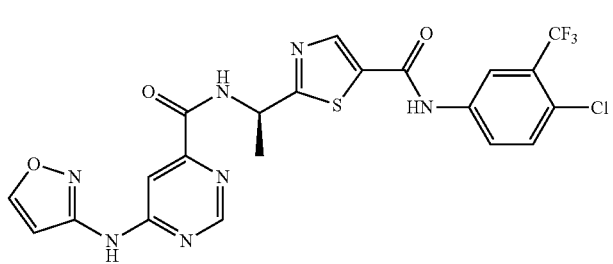 12aEa TABLE 4-continued
Exemplary Compounds of Formula I
Additional compounds
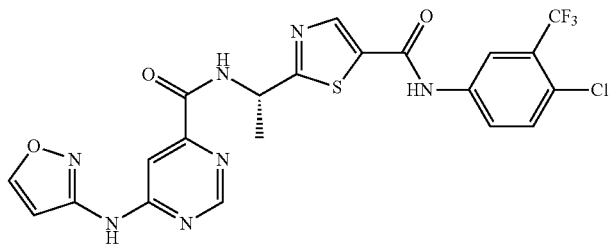 [SMILES: C[C@H](NC(=O)c1cc(Nc2ccon2)ncn1)c1ncc(C(=O)Nc2ccc(Cl)c(C(F)(F)F)c2)s1] 12aEb
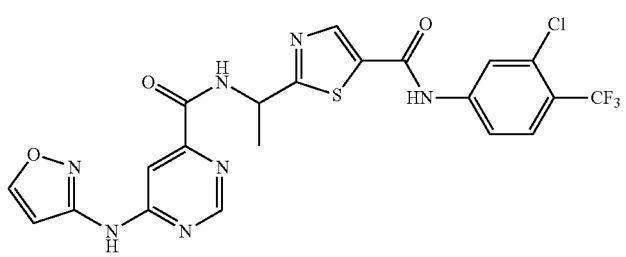 [SMILES: CC(NC(=O)c1cc(Nc2ccon2)ncn1)c1ncc(C(=O)Nc2ccc(C(F)(F)F)c(Cl)c2)s1] 12aF
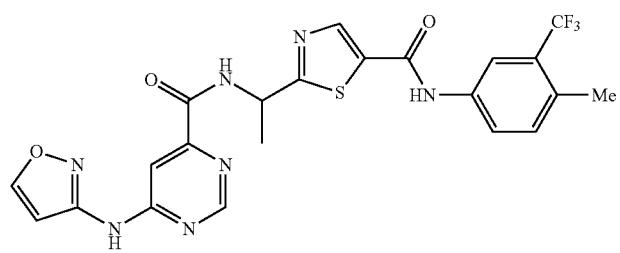 [SMILES: Cc1ccc(NC(=O)c2cnc(C(C)NC(=O)c3cc(Nc4ccon4)ncn3)s2)cc1C(F)(F)F] 12aG
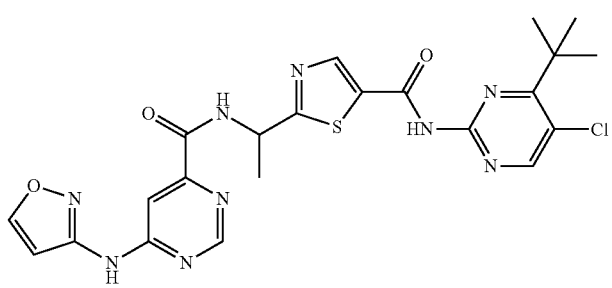 [SMILES: CC(NC(=O)c1cc(Nc2ccon2)ncn1)c1ncc(C(=O)Nc2ncc(Cl)c(C(C)(C)C)n2)s1] 12aH
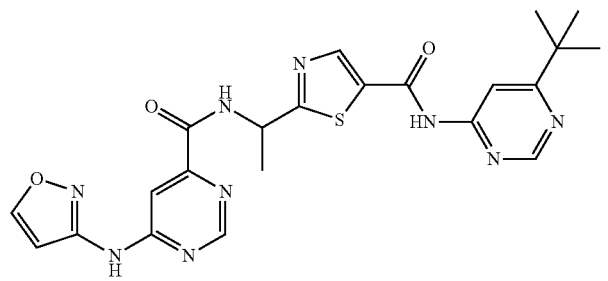 [SMILES: CC(NC(=O)c1cc(Nc2ccon2)ncn1)c1ncc(C(=O)Nc2cc(C(C)(C)C)ncn2)s1] 12aI TABLE 4-continued
Exemplary Compounds of Formula I
Additional compounds
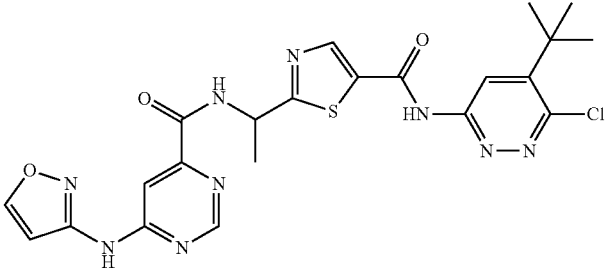 [SMILES: CC(NC(=O)c1cc(Nc2ccon2)ncn1)c1ncc(C(=O)Nc2cc(C(C)(C)C)c(Cl)nn2)s1] 12aJ
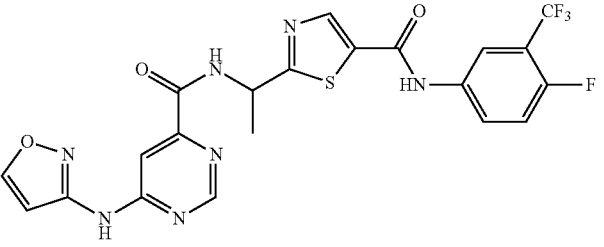 [SMILES: CC(NC(=O)c1cc(Nc2ccon2)ncn1)c1ncc(C(=O)Nc2ccc(F)c(C(F)(F)F)c2)s1] 12aK
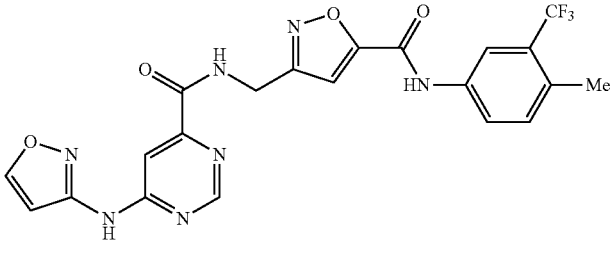 [SMILES: Cc1ccc(NC(=O)c2cc(CNC(=O)c3cc(Nc4ccon4)ncn3)no2)cc1C(F)(F)F] 12aL
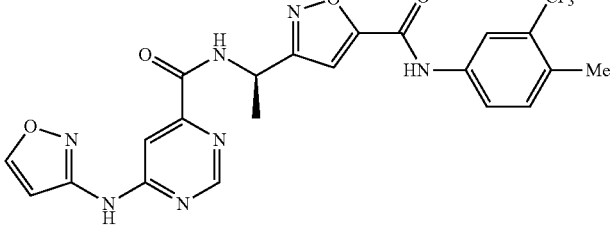 12aMa
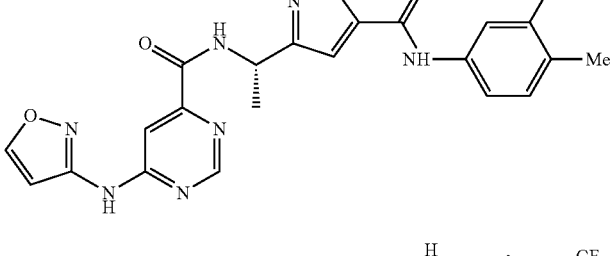 12aMb
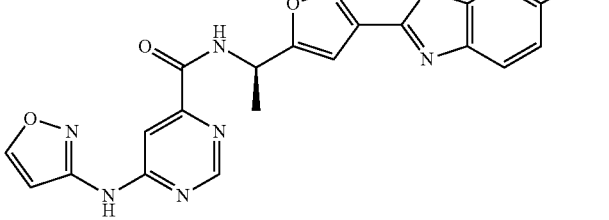 12aNa TABLE 4-continued
Exemplary Compounds of Formula I
Additional compounds
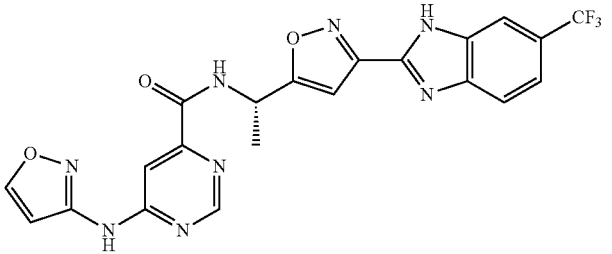 [SMILES: C[C@H](NC(=O)c1cc(Nc2ccon2)ncn1)c1cc(-c2nc3ccc(C(F)(F)F)cc3[nH]2)no1] 12aNb
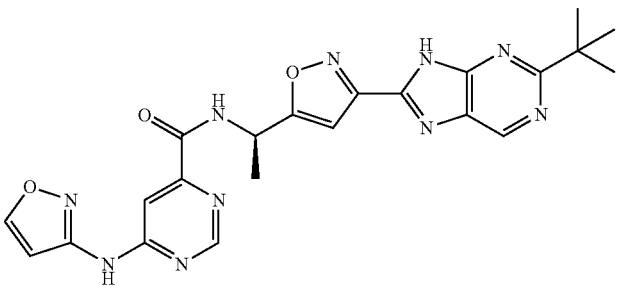 [SMILES: C[C@@H](NC(=O)c1cc(Nc2ccon2)ncn1)c1cc(-c2nc3cnc(C(C)(C)C)nc3[nH]2)no1] 12aO
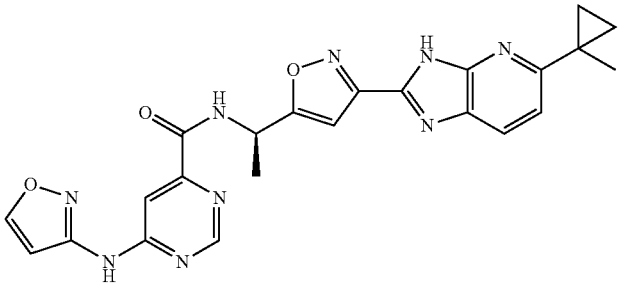 [SMILES: C[C@@H](NC(=O)c1cc(Nc2ccon2)ncn1)c1cc(-c2nc3ccc(C4(C)CC4)nc3[nH]2)no1] 12aP
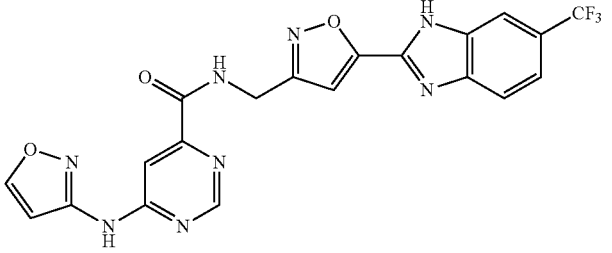 [SMILES: O=C(NCc1cc(-c2nc3ccc(C(F)(F)F)cc3[nH]2)on1)c1cc(Nc2ccon2)ncn1] 12aQ
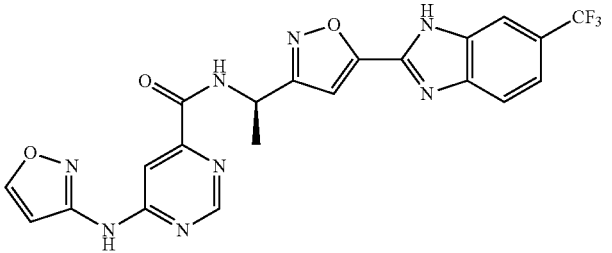 [SMILES: C[C@@H](NC(=O)c1cc(Nc2ccon2)ncn1)c1cc(-c2nc3ccc(C(F)(F)F)cc3[nH]2)on1] 12aRa TABLE 4-continued
Exemplary Compounds of Formula I
Additional compounds
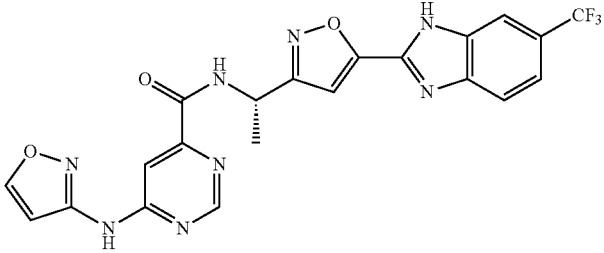 [SMILES: C[C@H](NC(=O)c1cc(Nc2ccon2)ncn1)c1cc(-c2nc3ccc(C(F)(F)F)cc3[nH]2)on1] 12aRb
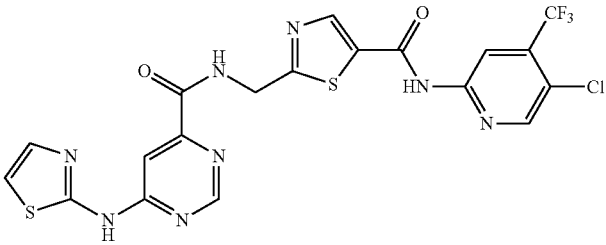 [SMILES: CC(NC(=O)c1cc(Nc2nccs2)ncn1)c1ncc(C(=O)Nc2cc(C(F)(F)F)c(Cl)cn2)s1] 12bA
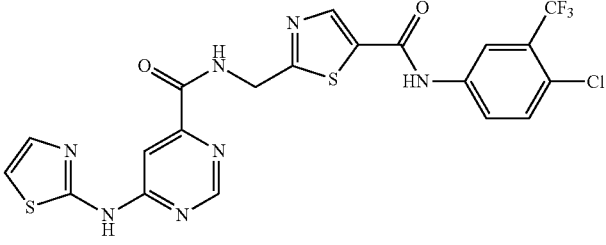 [SMILES: CC(NC(=O)c1cc(Nc2nccs2)ncn1)c1ncc(C(=O)Nc2ccc(Cl)c(C(F)(F)F)c2)s1] 12bB
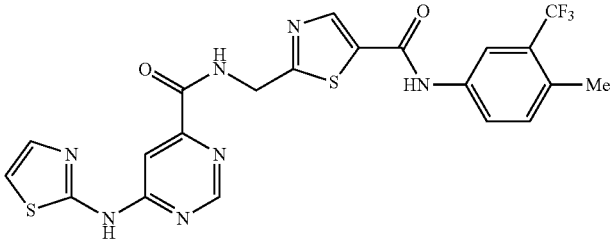 12bC
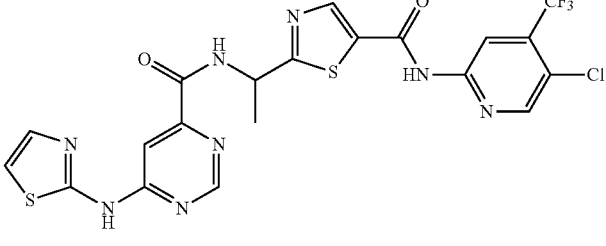 12bD
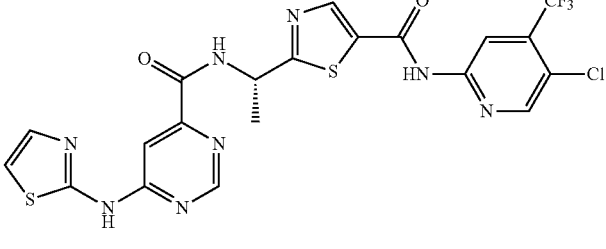 12bDb TABLE 4-continued
Exemplary Compounds of Formula I
Additional compounds
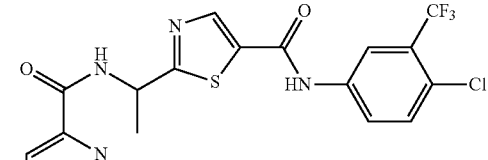 12bE
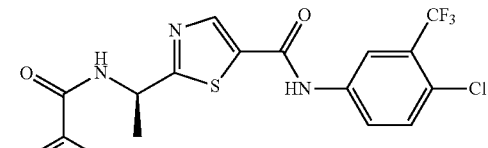 12bEa
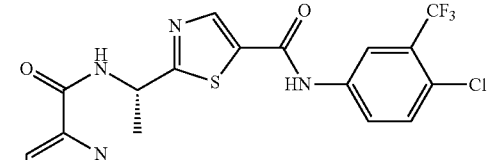 12bEb
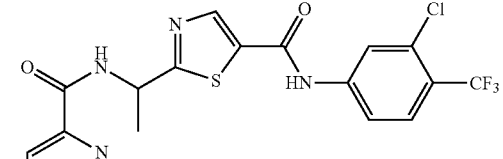 12bF
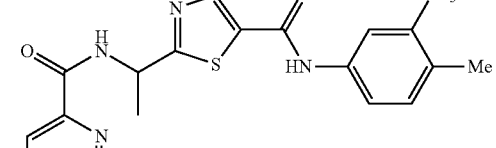 12bG
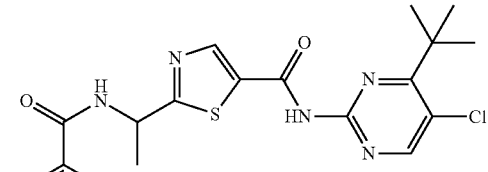 12bH TABLE 4-continued
Exemplary Compounds of Formula I
Additional compounds
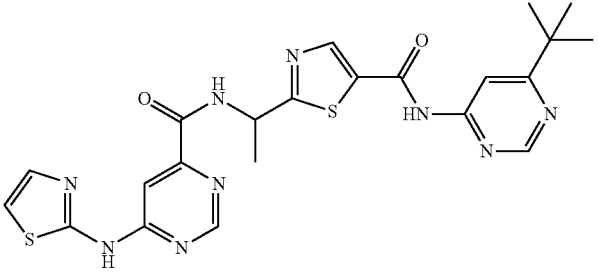 [SMILES: CC(NC(=O)c1cc(Nc2nccs2)ncn1)c1ncc(C(=O)Nc2cc(C(C)(C)C)ncn2)s1]
12bI
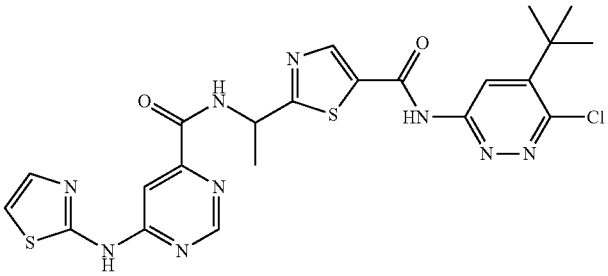 [SMILES: CC(NC(=O)c1cc(Nc2nccs2)ncn1)c1ncc(C(=O)Nc2cc(C(C)(C)C)c(Cl)nn2)s1]
12bJ
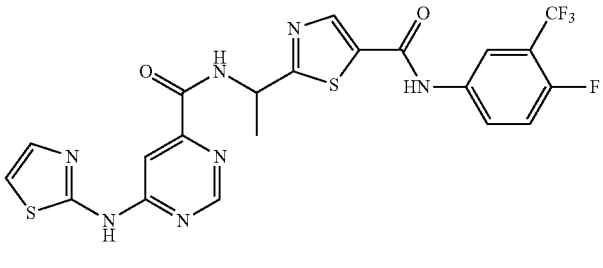 [SMILES: CC(NC(=O)c1cc(Nc2nccs2)ncn1)c1ncc(C(=O)Nc2ccc(F)c(C(F)(F)F)c2)s1]
12bK
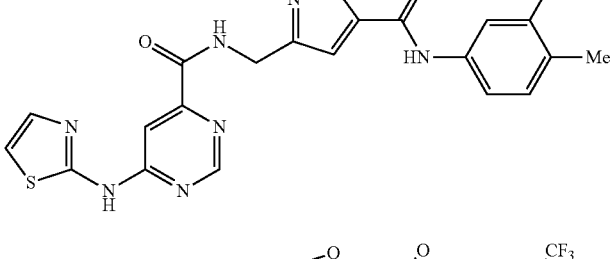
12bL
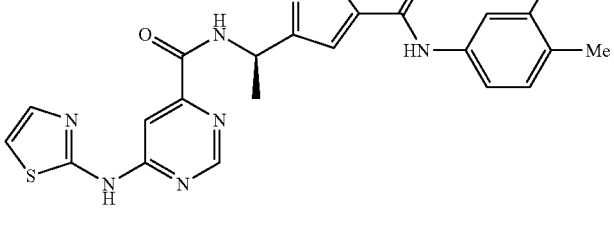
12bMa
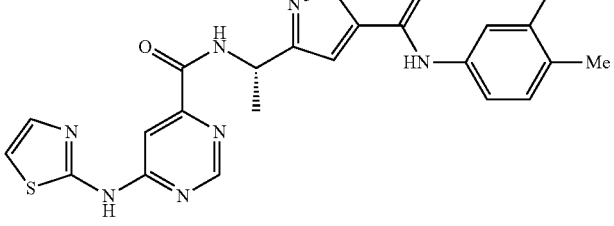
12bMb TABLE 4-continued
Exemplary Compounds of Formula I
Additional compounds
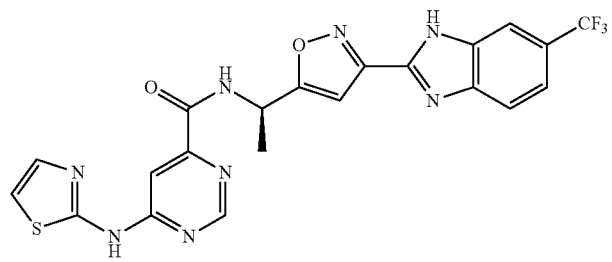 [SMILES: C[C@@H](NC(=O)c1cc(Nc2nccs2)ncn1)c1cc(-c2nc3ccc(C(F)(F)F)cc3[nH]2)no1] 12bNa
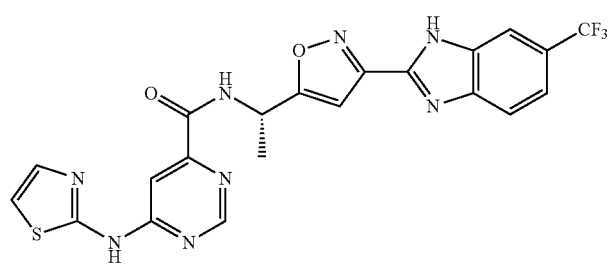 [SMILES: C[C@H](NC(=O)c1cc(Nc2nccs2)ncn1)c1cc(-c2nc3ccc(C(F)(F)F)cc3[nH]2)no1] 12bNb
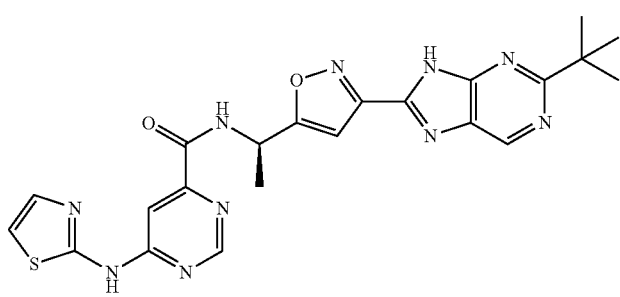 [SMILES: C[C@@H](NC(=O)c1cc(Nc2nccs2)ncn1)c1cc(-c2nc3cnc(C(C)(C)C)nc3[nH]2)no1] 12bO
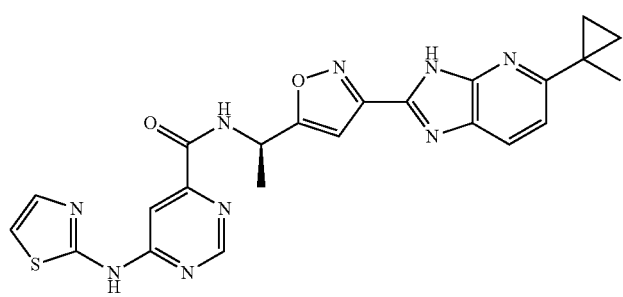 [SMILES: C[C@@H](NC(=O)c1cc(Nc2nccs2)ncn1)c1cc(-c2nc3ccc(C4(C)CC4)nc3[nH]2)no1] 12bP
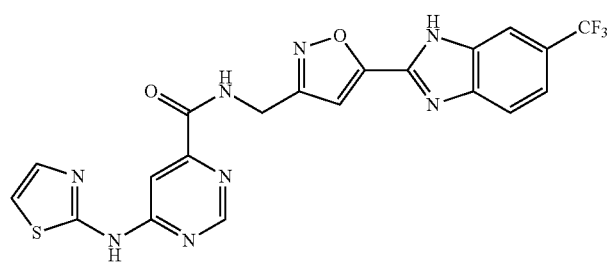 [SMILES: O=C(NCc1cc(-c2nc3ccc(C(F)(F)F)cc3[nH]2)on1)c1cc(Nc2nccs2)ncn1] 12bQ TABLE 4-continued
Exemplary Compounds of Formula I
Additional compounds
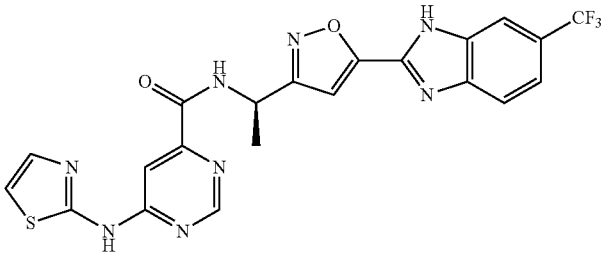 [SMILES: C[C@@H](NC(=O)c1cc(Nc2nccs2)ncn1)c1cc(-c2nc3ccc(C(F)(F)F)cc3[nH]2)on1] 12bRa
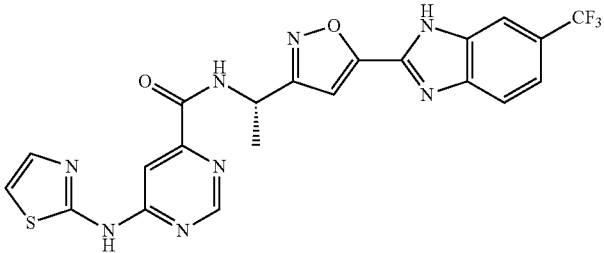 [SMILES: C[C@H](NC(=O)c1cc(Nc2nccs2)ncn1)c1cc(-c2nc3ccc(C(F)(F)F)cc3[nH]2)on1] 12bRb
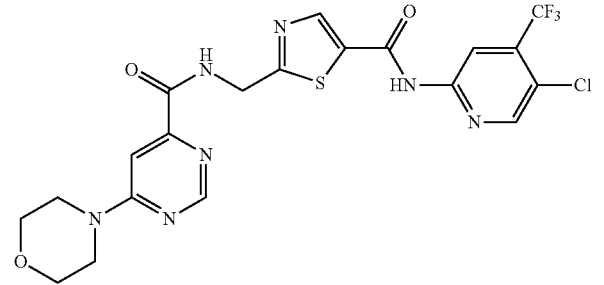 [SMILES: O=C(NCc1ncc(C(=O)Nc2cc(C(F)(F)F)c(Cl)cn2)s1)c1cc(N2CCOCC2)ncn1] 5dA
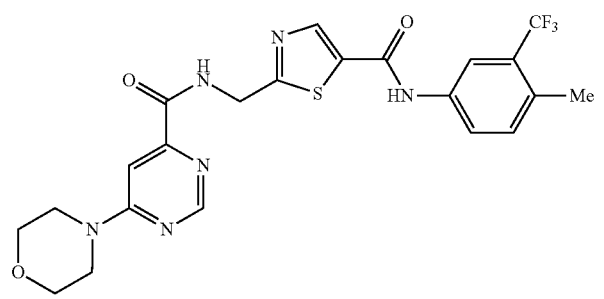 [SMILES: Cc1ccc(NC(=O)c2cnc(CNC(=O)c3cc(N4CCOCC4)ncn3)s2)cc1C(F)(F)F] 5dC
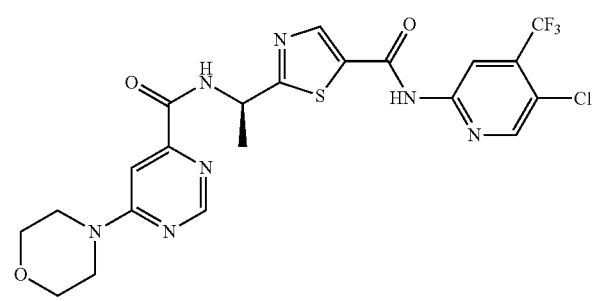 [SMILES: C[C@@H](NC(=O)c1cc(N2CCOCC2)ncn1)c1ncc(C(=O)Nc2cc(C(F)(F)F)c(Cl)cn2)s1] 5dDa TABLE 4-continued
Exemplary Compounds of Formula I
Additional compounds
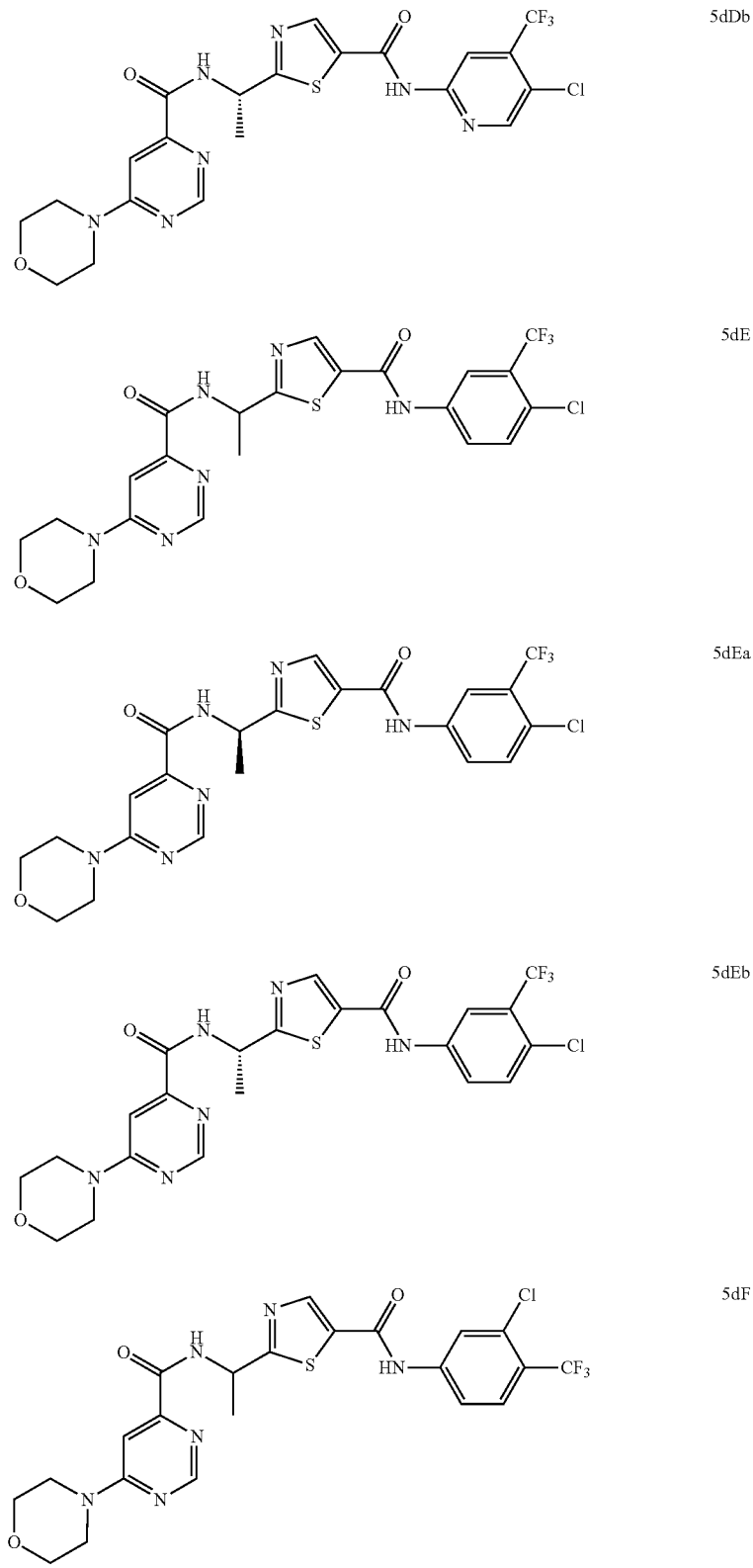
5dDb
5dE
5dEa
5dEb
5dF TABLE 4-continued
Exemplary Compounds of Formula I
Additional compounds
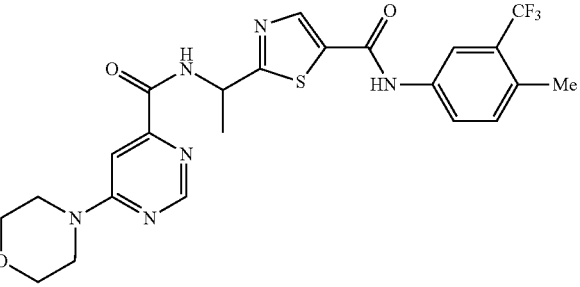 [SMILES: CC(NC(=O)c1cc(N2CCOCC2)ncn1)c1ncc(C(=O)Nc2ccc(C(F)(F)F)c(Cl)c2)s1] 5dG
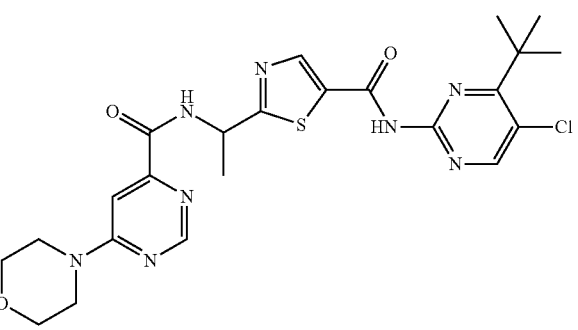 [SMILES: CC(NC(=O)c1cc(N2CCOCC2)ncn1)c1ncc(C(=O)Nc2ncc(Cl)c(C(C)(C)C)n2)s1] 5dH
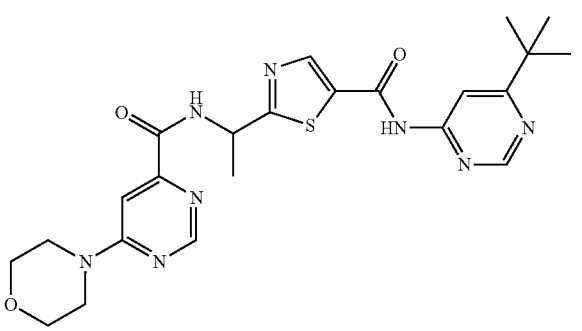 [SMILES: CC(NC(=O)c1cc(N2CCOCC2)ncn1)c1ncc(C(=O)Nc2cc(C(C)(C)C)ncn2)s1] 5dI
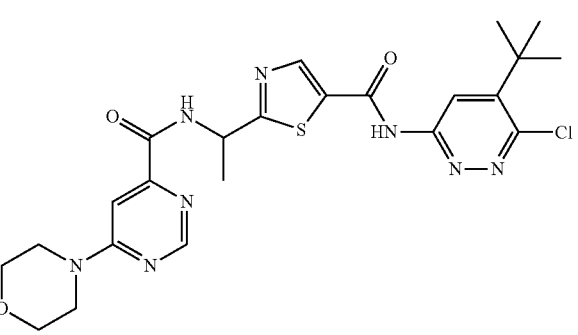 [SMILES: CC(NC(=O)c1cc(N2CCOCC2)ncn1)c1ncc(C(=O)Nc2cc(C(C)(C)C)c(Cl)nn2)s1] 5dJ
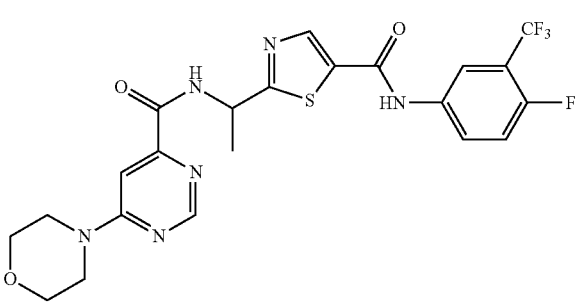 [SMILES: CC(NC(=O)c1cc(N2CCOCC2)ncn1)c1ncc(C(=O)Nc2ccc(F)c(C(F)(F)F)c2)s1] 5dK TABLE 4-continued
Exemplary Compounds of Formula I
Additional compounds
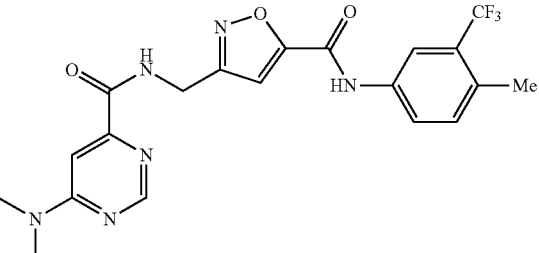 5dL
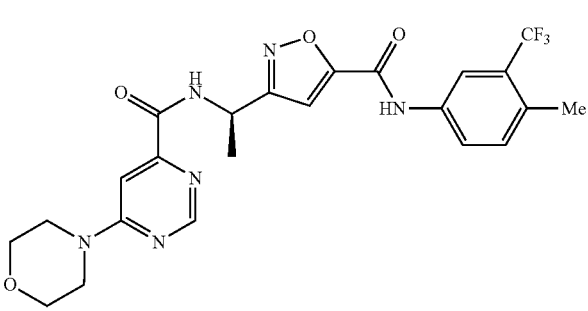 [SMILES: Cc1ccc(NC(=O)c2cc([C@@H](C)NC(=O)c3cc(N4CCOCC4)ncn3)no2)cc1C(F)(F)F] 5dMa
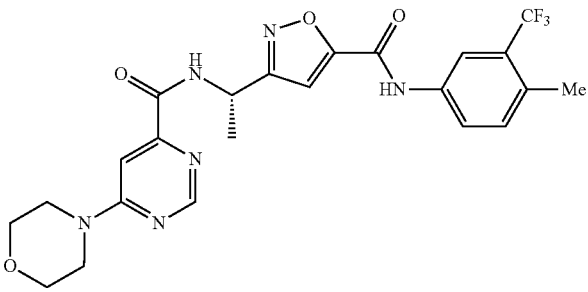 [SMILES: Cc1ccc(NC(=O)c2cc([C@H](C)NC(=O)c3cc(N4CCOCC4)ncn3)no2)cc1C(F)(F)F] 5dMb
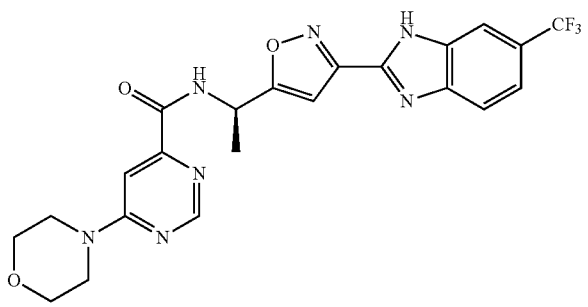 [SMILES: C[C@@H](NC(=O)c1cc(N2CCOCC2)ncn1)c1cc(-c2nc3ccc(C(F)(F)F)cc3[nH]2)no1] 5dNa
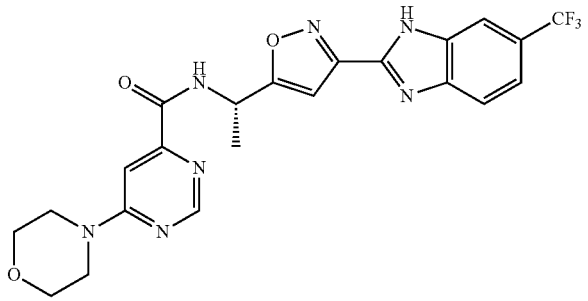 [SMILES: C[C@H](NC(=O)c1cc(N2CCOCC2)ncn1)c1cc(-c2nc3ccc(C(F)(F)F)cc3[nH]2)no1] 5dNb TABLE 4-continued
Exemplary Compounds of Formula I
Additional compounds
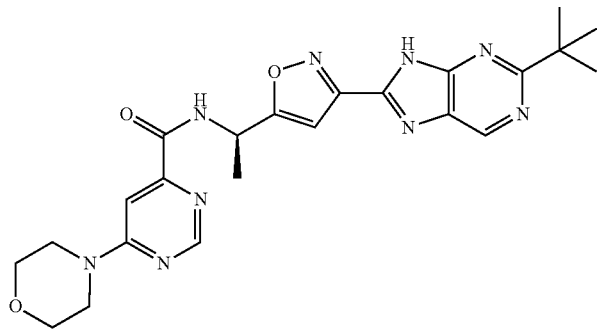 [SMILES: C[C@@H](NC(=O)c1cc(N2CCOCC2)ncn1)c1cc(-c2nc3cnc(C(C)(C)C)nc3[nH]2)no1]
5dO
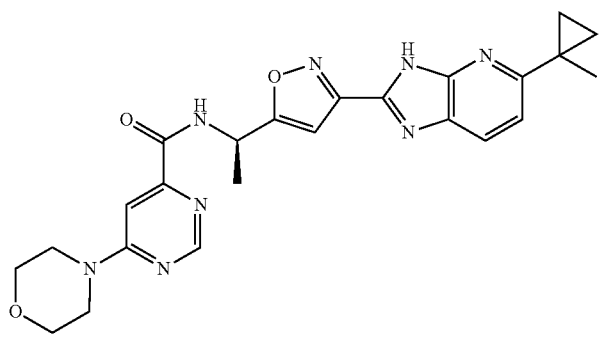 [SMILES: C[C@@H](NC(=O)c1cc(N2CCOCC2)ncn1)c1cc(-c2nc3ccc(C4(C)CC4)nc3[nH]2)no1]
5dP
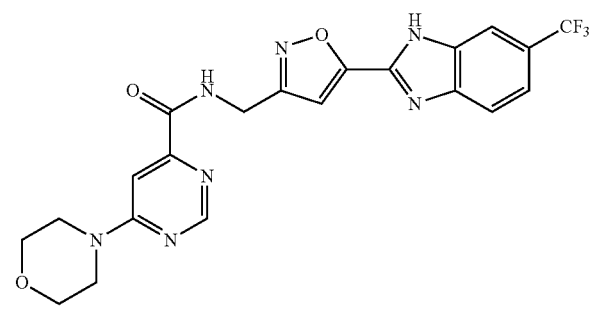 [SMILES: O=C(NCc1cc(-c2nc3ccc(C(F)(F)F)cc3[nH]2)on1)c1cc(N2CCOCC2)ncn1]
5dQ
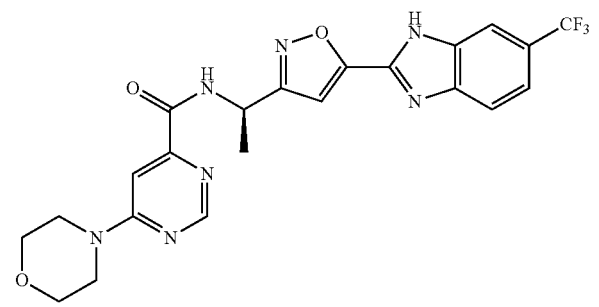 [SMILES: C[C@@H](NC(=O)c1cc(N2CCOCC2)ncn1)c1cc(-c2nc3ccc(C(F)(F)F)cc3[nH]2)on1]
5dRa
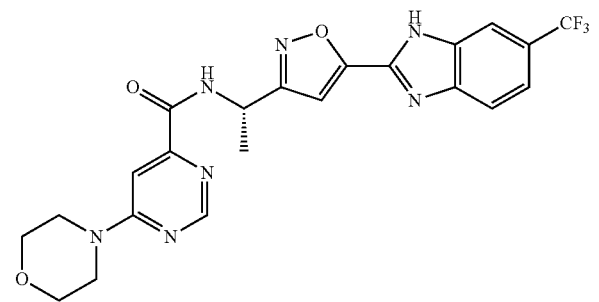 [SMILES: C[C@H](NC(=O)c1cc(N2CCOCC2)ncn1)c1cc(-c2nc3ccc(C(F)(F)F)cc3[nH]2)on1]
5dRb TABLE 4-continued
Exemplary Compounds of Formula I
Additional compounds
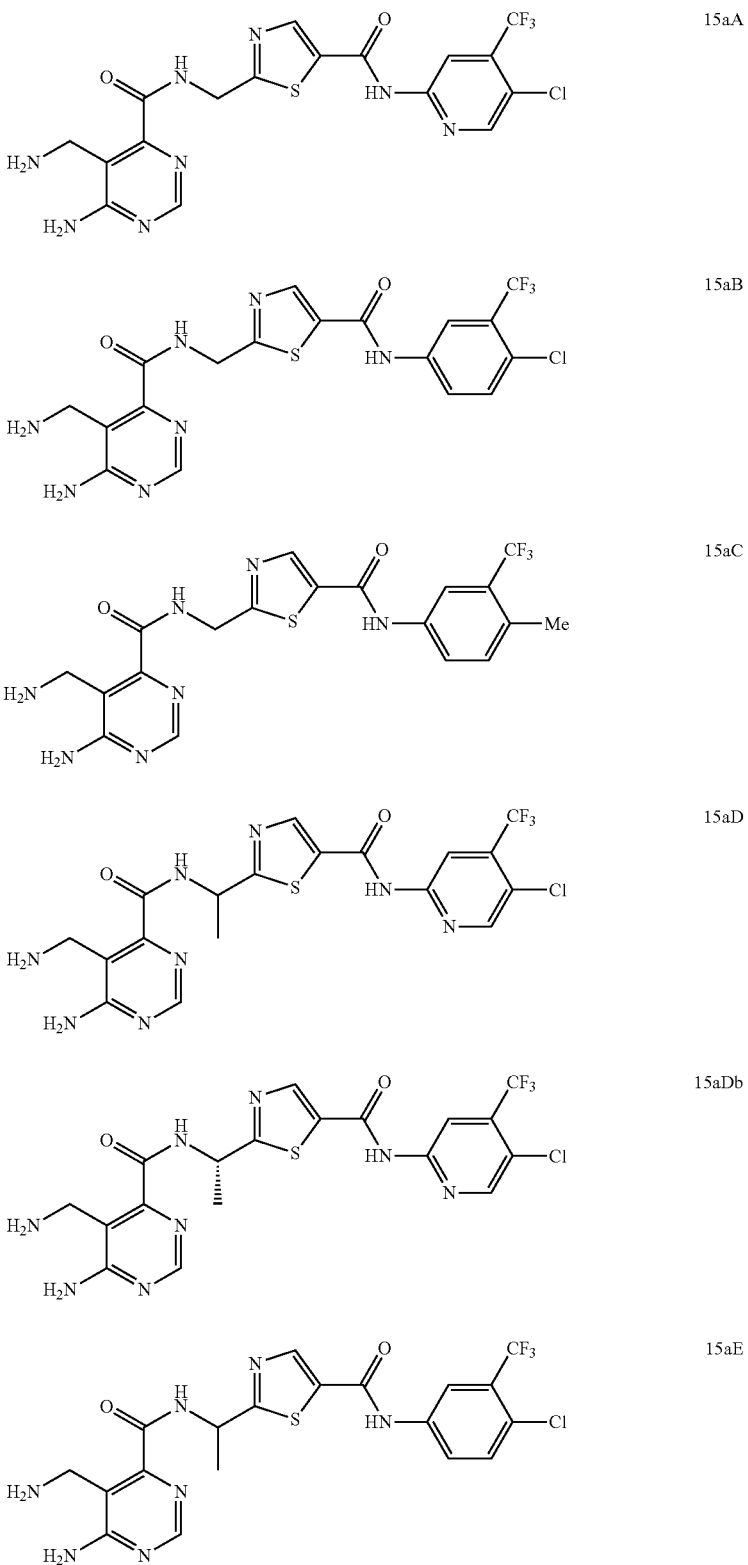

TABLE 4-continued
Exemplary Compounds of Formula I
Additional compounds
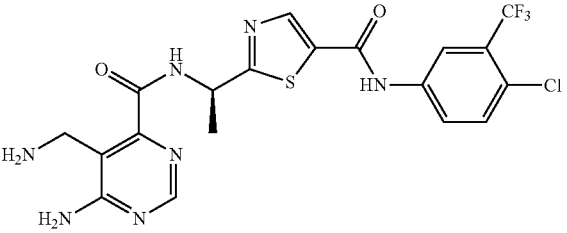 [SMILES: C[C@@H](NC(=O)c1ncnc(N)c1CN)c1ncc(C(=O)Nc2ccc(Cl)c(C(F)(F)F)c2)s1] 15aEa
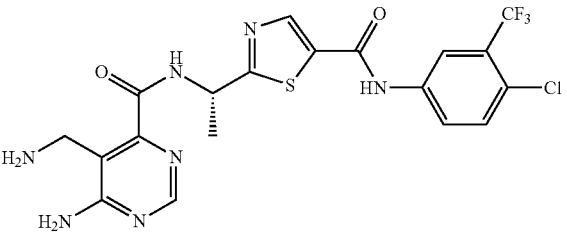 [SMILES: C[C@H](NC(=O)c1ncnc(N)c1CN)c1ncc(C(=O)Nc2ccc(Cl)c(C(F)(F)F)c2)s1] 15aEb
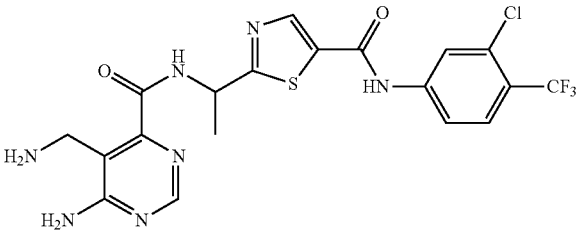 [SMILES: CC(NC(=O)c1ncnc(N)c1CN)c1ncc(C(=O)Nc2ccc(C(F)(F)F)c(Cl)c2)s1] 15aF
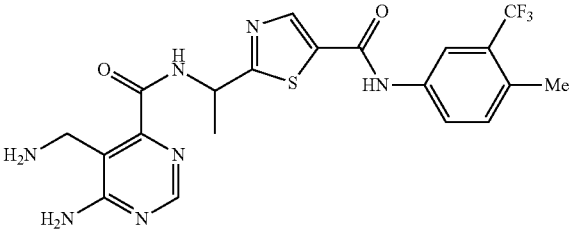 [SMILES: Cc1ccc(NC(=O)c2cnc(C(C)NC(=O)c3ncnc(N)c3CN)s2)cc1C(F)(F)F] 15aG
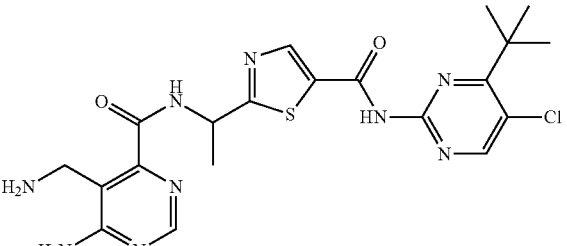 15aH
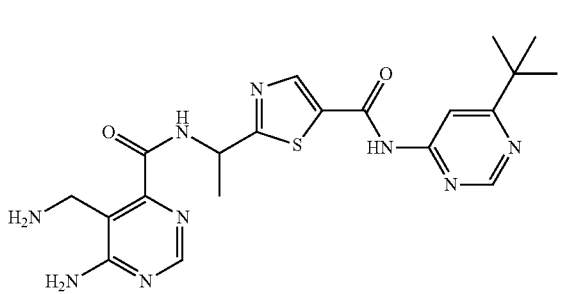 [SMILES: CC(NC(=O)c1ncnc(N)c1CN)c1ncc(C(=O)Nc2cc(C(C)(C)C)ncn2)s1] 15aI TABLE 4-continued
Exemplary Compounds of Formula I
Additional compounds
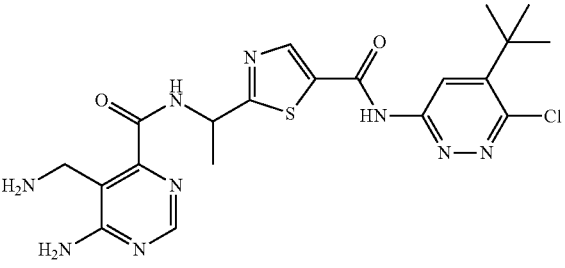 [SMILES: CC(NC(=O)c1ncnc(N)c1CN)c1ncc(C(=O)Nc2cc(C(C)(C)C)c(Cl)nn2)s1]
15aJ
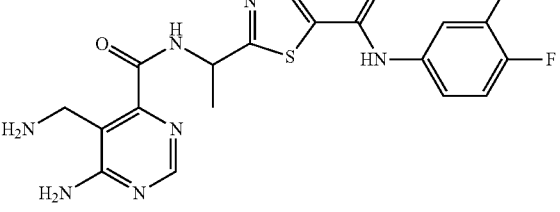
15aK
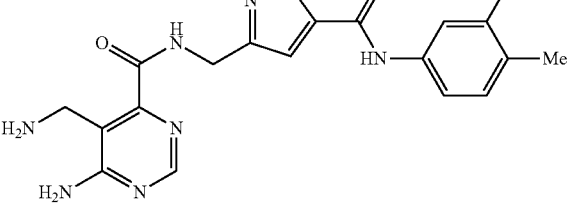
15aL
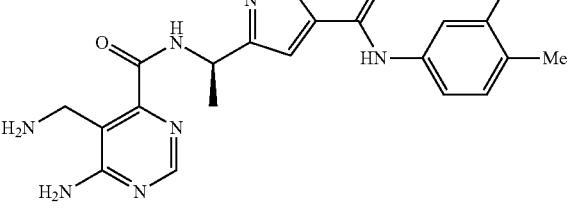
15aMa
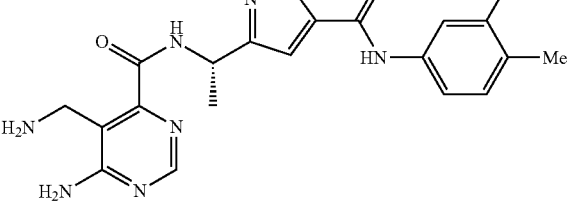
15aMb
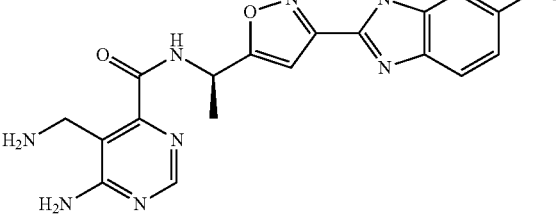
15aNa TABLE 4-continued
Exemplary Compounds of Formula I
Additional compounds
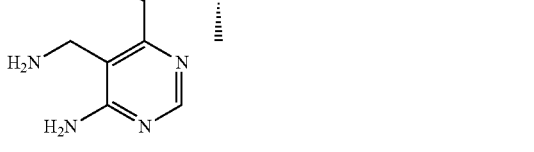 15aNb
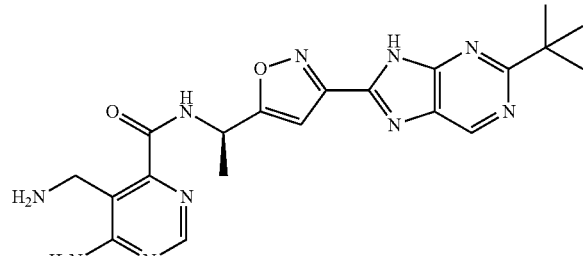 15aO
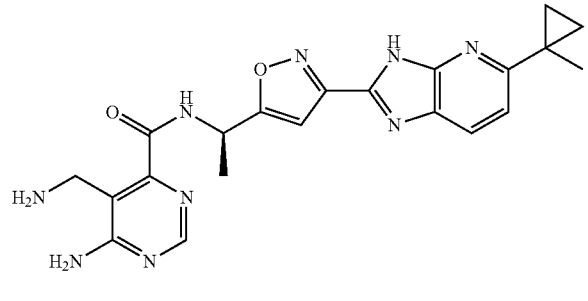 [SMILES: C[C@@H](NC(=O)c1ncnc(N)c1CN)c1cc(-c2nc3ccc(C4(C)CC4)nc3[nH]2)no1] 15aP
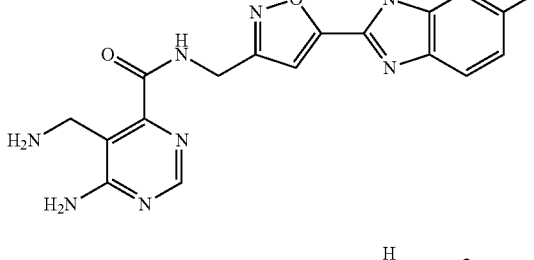 15aQ
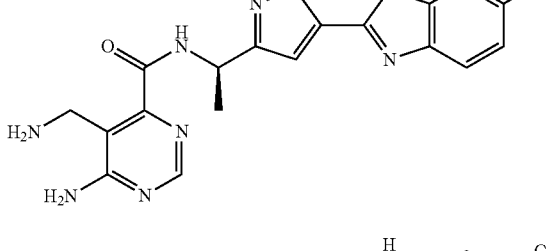 15aRa
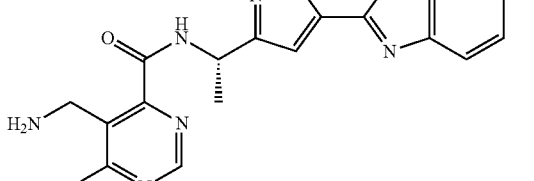 15aRb TABLE 4-continued
Exemplary Compounds of Formula I
Additional compounds
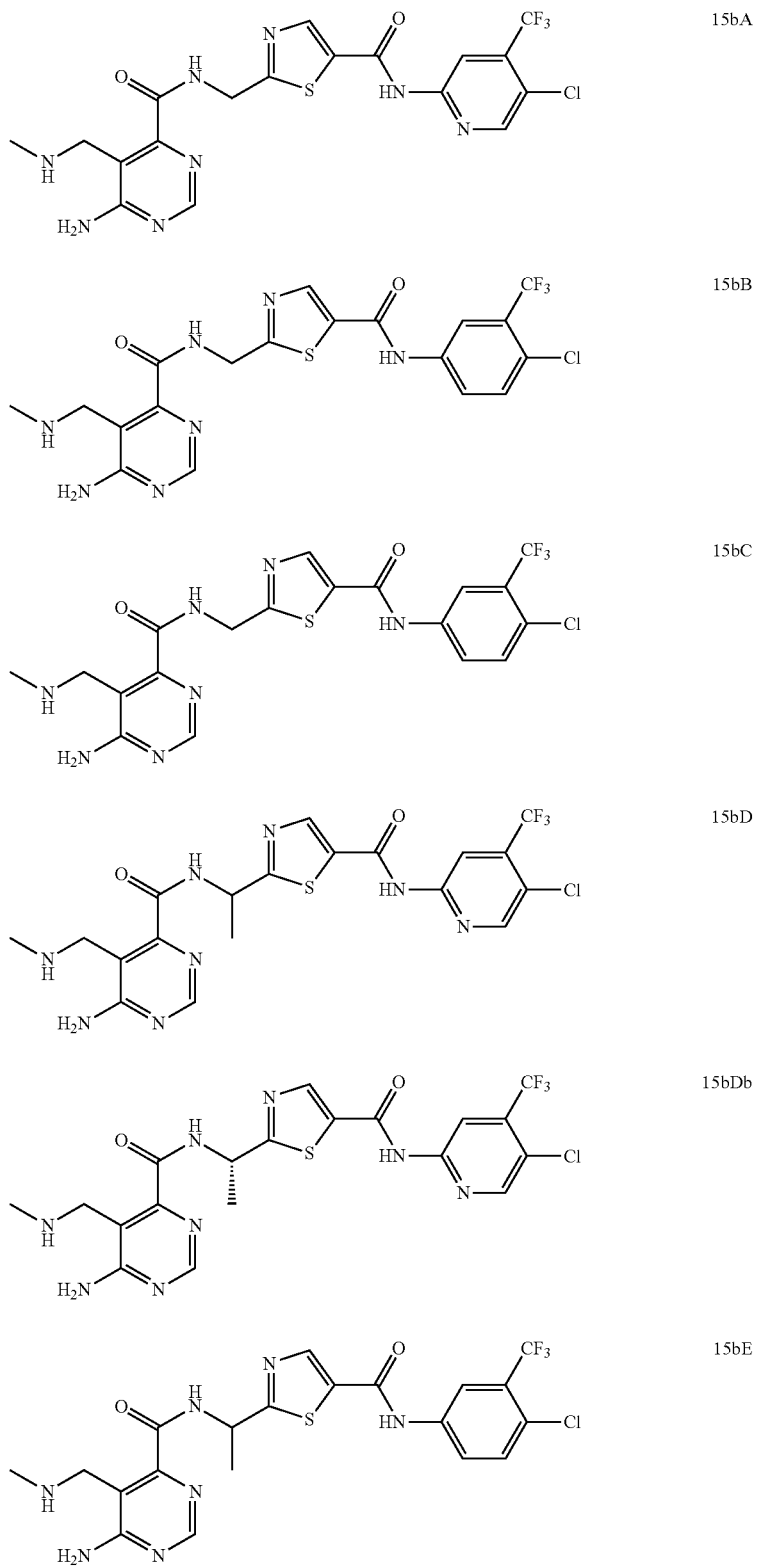

TABLE 4-continued
Exemplary Compounds of Formula I
Additional compounds
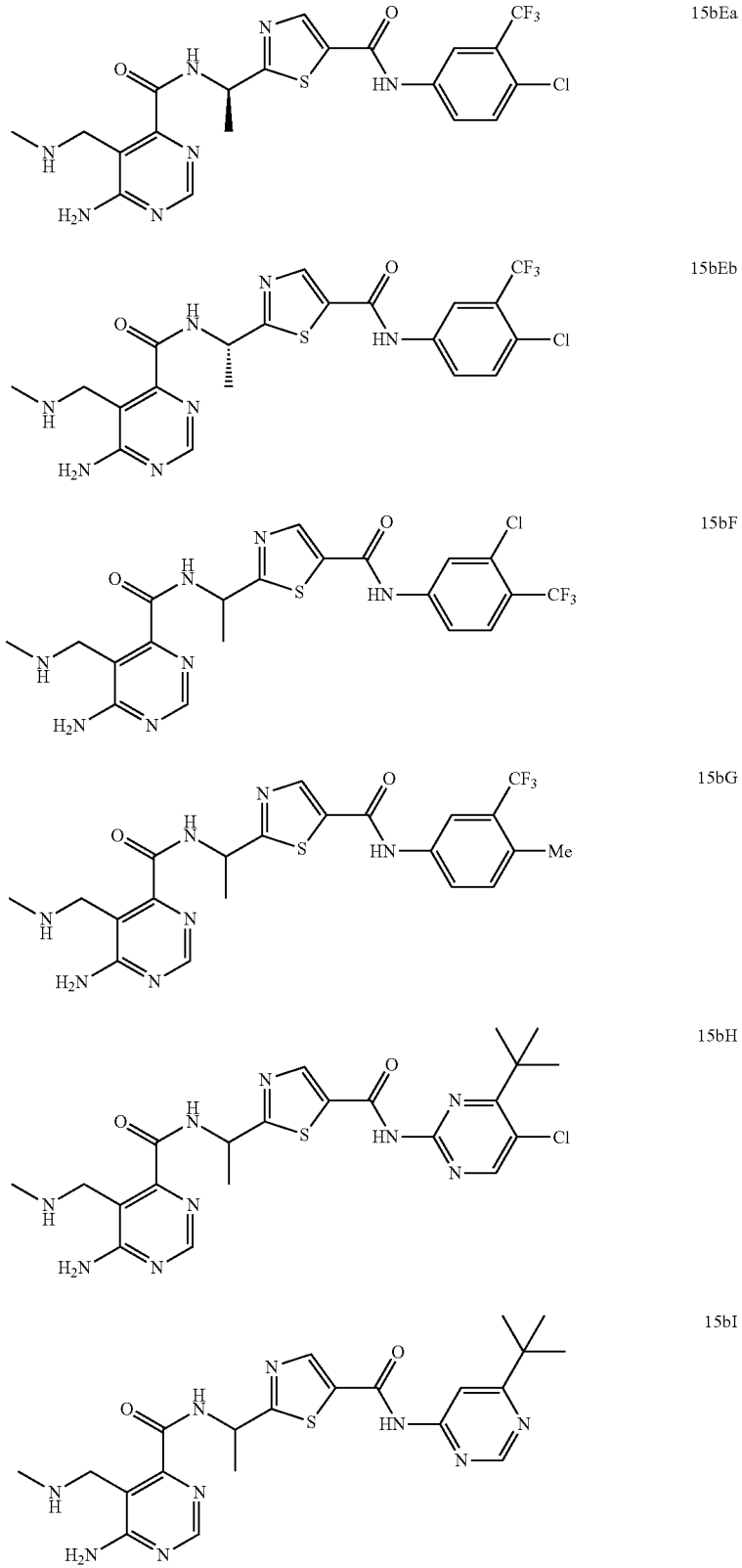

TABLE 4-continued
Exemplary Compounds of Formula I
Additional compounds
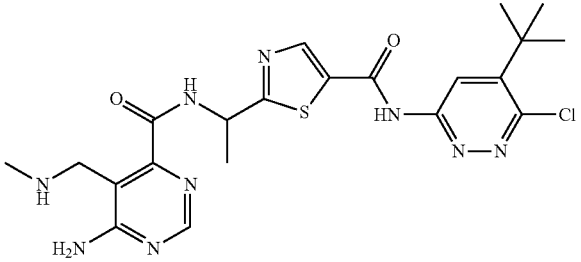 [SMILES: CNCc1c(N)ncnc1C(=O)NC(C)c1ncc(C(=O)Nc2cc(C(C)(C)C)c(Cl)nn2)s1] 15bJ
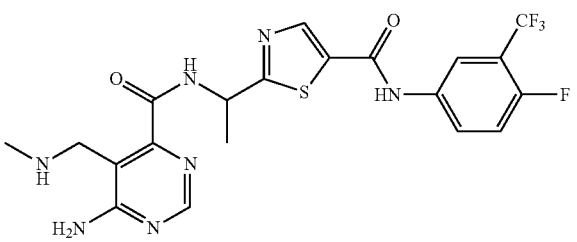 [SMILES: CNCc1c(N)ncnc1C(=O)NC(C)c1ncc(C(=O)Nc2ccc(F)c(C(F)(F)F)c2)s1] 15bK
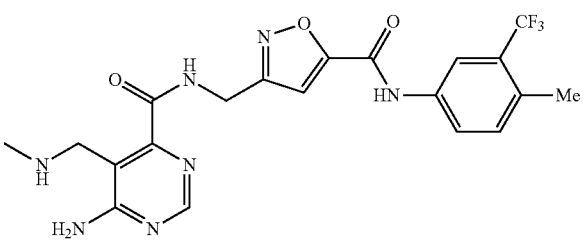 [SMILES: CNCc1c(N)ncnc1C(=O)NCc1cc(C(=O)Nc2ccc(C)c(C(F)(F)F)c2)on1] 15bL
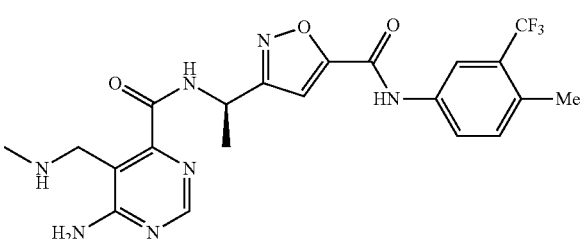 15bMa
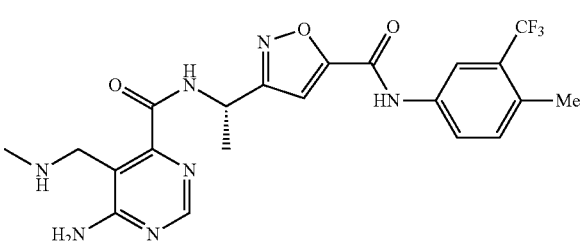 15bMb
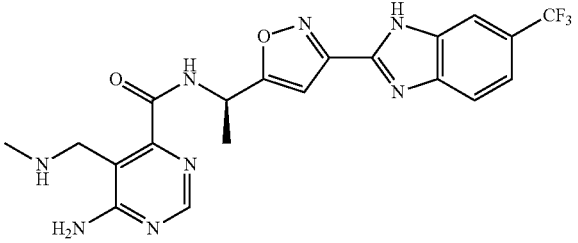 [SMILES: CNCc1c(N)ncnc1C(=O)N[C@H](C)c1cc(-c2nc3ccc(C(F)(F)F)cc3[nH]2)no1] 15bNa TABLE 4-continued Exemplary Compounds of Formula I
Additional compounds

| Compound | ID |
|---|---|
| (structure) | 15bNb |
| (structure) | 15bO |
| (structure) | 15bP |
| (structure) | 15bQ |
| (structure) | 15bRa |
| (structure) | 15bRb |

TABLE 4-continued
Exemplary Compounds of Formula I
Additional compounds
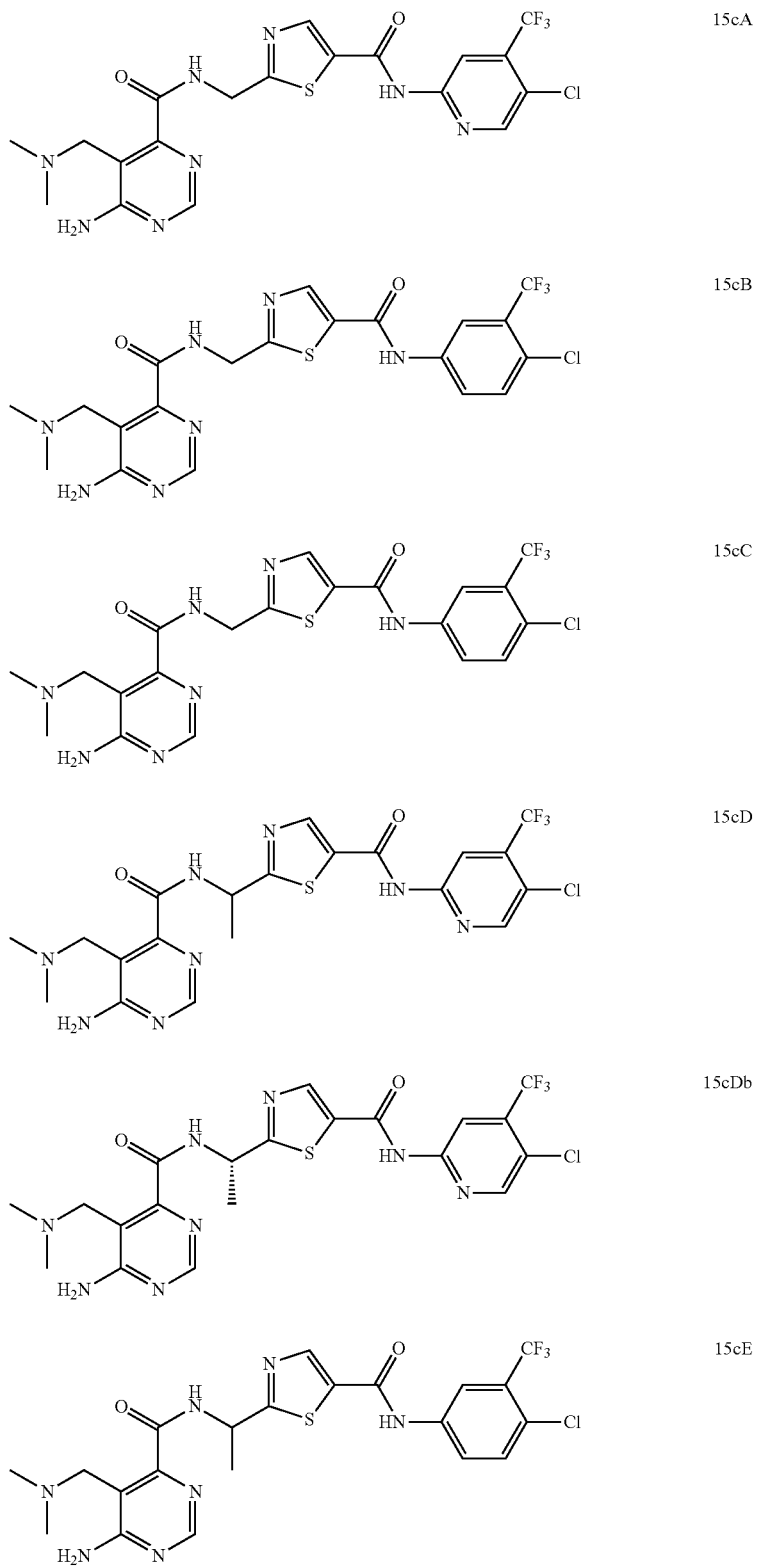

TABLE 4-continued
Exemplary Compounds of Formula I
Additional compounds
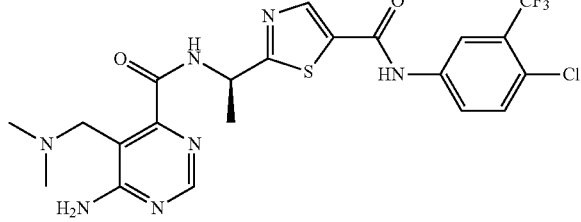 15cEa
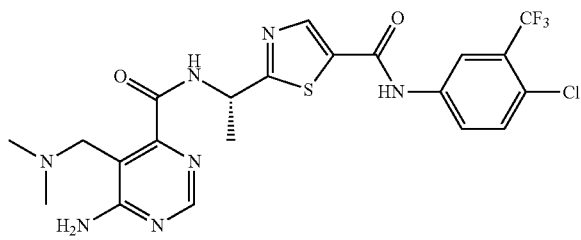 [SMILES: CC(NC(=O)c1ncnc(N)c1CN(C)C)c1ncc(C(=O)Nc2cc(C(F)(F)F)c(Cl)cn2)s1] 15cEb
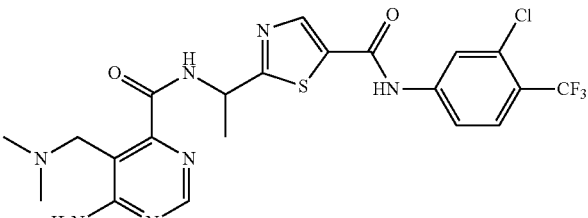 15cF
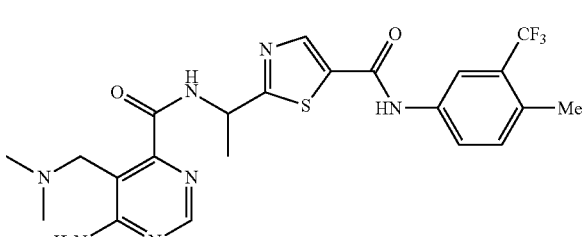 15cG
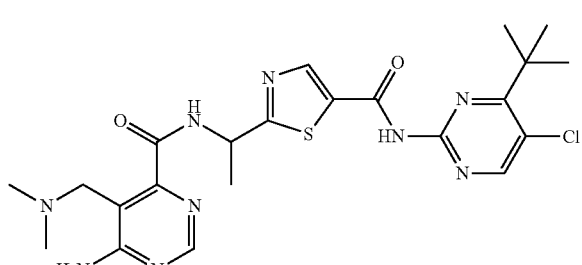 15cH
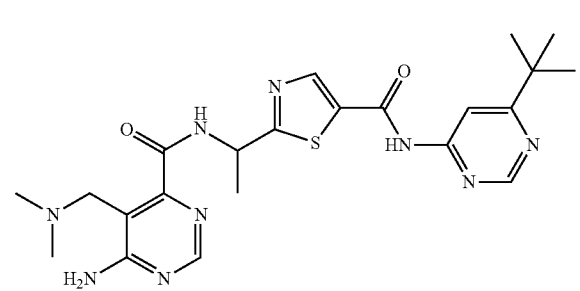 [SMILES: CC(NC(=O)c1ncnc(N)c1CN(C)C)c1ncc(C(=O)Nc2cc(C(C)(C)C)ncn2)s1] 15cI TABLE 4-continued
Exemplary Compounds of Formula I
Additional compounds
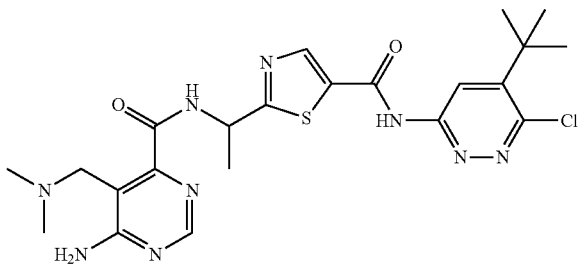 [SMILES: CC(NC(=O)c1ncnc(N)c1CN(C)C)c1ncc(C(=O)Nc2cc(C(C)(C)C)c(Cl)nn2)s1]
15cJ
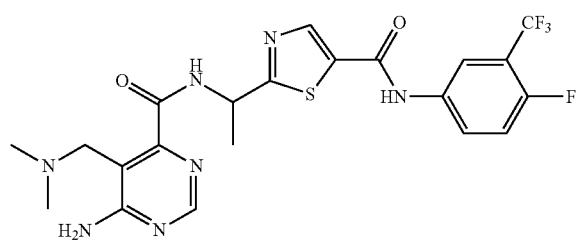 [SMILES: CC(NC(=O)c1ncnc(N)c1CN(C)C)c1ncc(C(=O)Nc2ccc(F)c(C(F)(F)F)c2)s1]
15cK
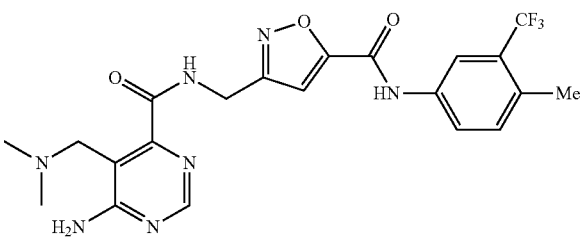 [SMILES: Cc1ccc(NC(=O)c2cc(CNC(=O)c3ncnc(N)c3CN(C)C)no2)cc1C(F)(F)F]
15cL
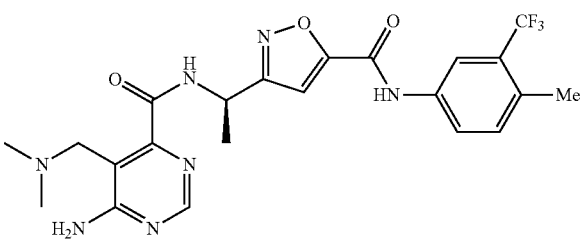 [SMILES: Cc1ccc(NC(=O)c2cc([C@@H](C)NC(=O)c3ncnc(N)c3CN(C)C)no2)cc1C(F)(F)F]
15cMa
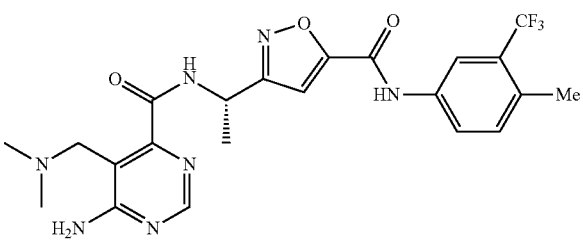
15cMb
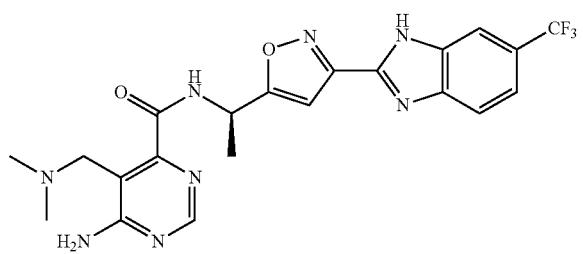 [SMILES: C[C@@H](NC(=O)c1ncnc(N)c1CN(C)C)c1cc(-c2nc3ccc(C(F)(F)F)cc3[nH]2)no1]
15cNa TABLE 4-continued Exemplary Compounds of Formula I
Additional compounds

| Structure | ID |
|---|---|
| | 15cNb |
| | 15cO |
| | 15cP |
| | 15cQ |
| | 15cRa |
| | 15cRb |

TABLE 4-continued
Exemplary Compounds of Formula I
Additional compounds
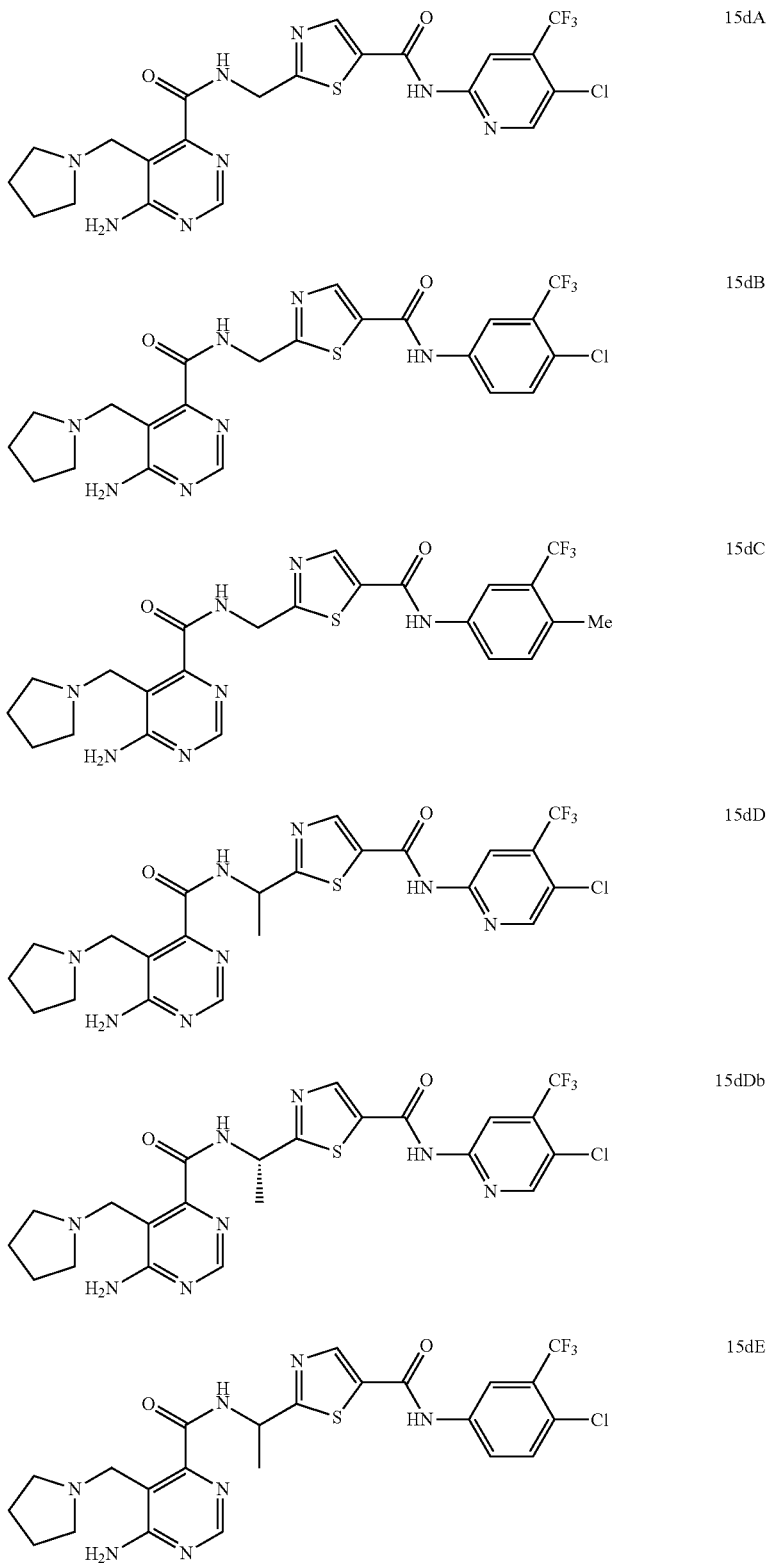
15dA
15dB
15dC
15dD
15dDb
15dE TABLE 4-continued
Exemplary Compounds of Formula I
Additional compounds
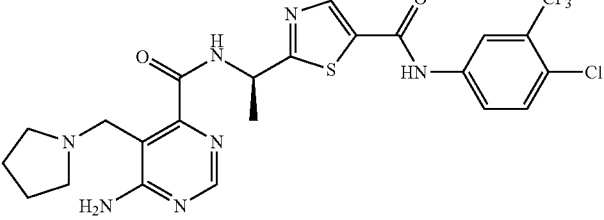 15dEa
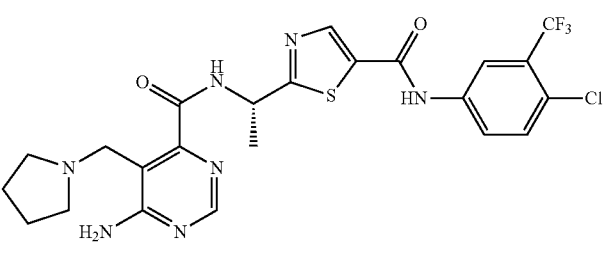 15dEb
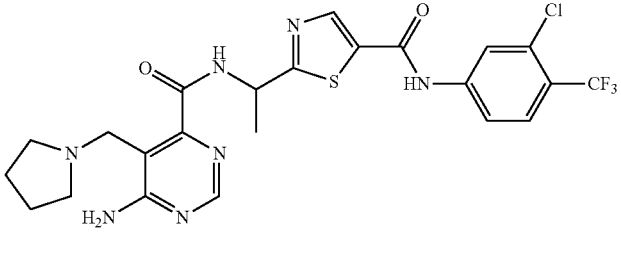 [SMILES: CC(NC(=O)c1ncnc(N)c1CN1CCCC1)c1ncc(C(=O)Nc2ccc(C(F)(F)F)c(Cl)c2)s1] 15dF
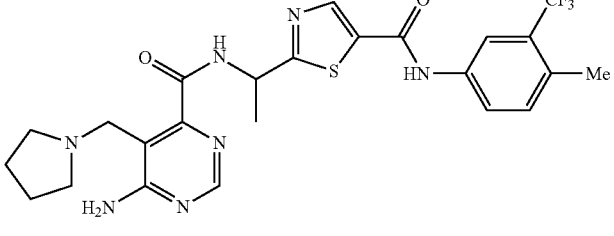 15dG
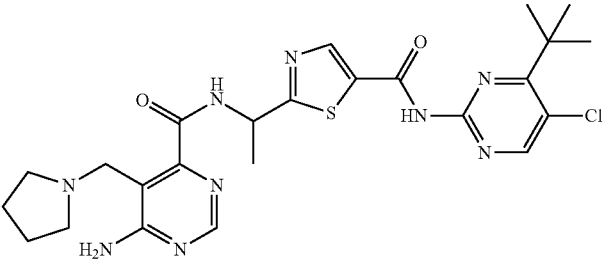 [SMILES: CC(NC(=O)c1ncnc(N)c1CN1CCCC1)c1ncc(C(=O)Nc2ncc(Cl)c(C(C)(C)C)n2)s1] 15dH
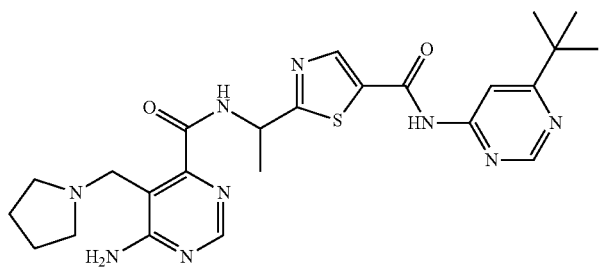 [SMILES: CC(NC(=O)c1ncnc(N)c1CN1CCCC1)c1ncc(C(=O)Nc2cc(C(C)(C)C)ncn2)s1] 15dI TABLE 4-continued
Exemplary Compounds of Formula I
Additional compounds
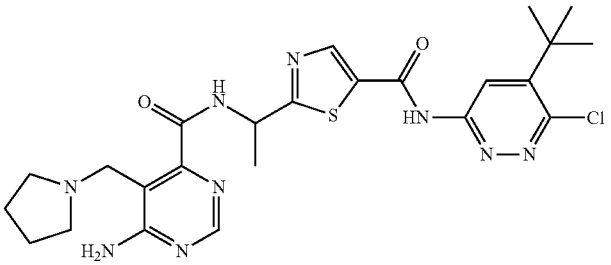 [SMILES: CC(NC(=O)c1ncnc(N)c1CN1CCCC1)c1ncc(C(=O)Nc2cc(C(C)(C)C)c(Cl)nn2)s1] 15dJ
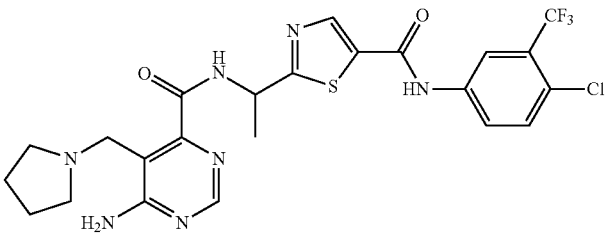 [SMILES: CC(NC(=O)c1ncnc(N)c1CN1CCCC1)c1ncc(C(=O)Nc2ccc(Cl)c(C(F)(F)F)c2)s1] 15dK
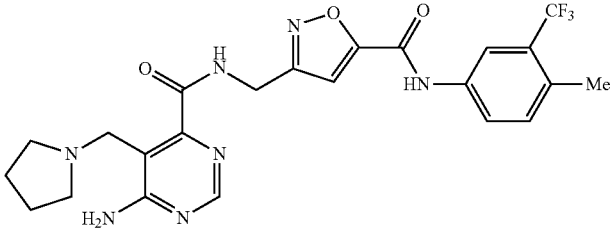 [SMILES: Cc1ccc(NC(=O)c2cc(CNC(=O)c3ncnc(N)c3CN3CCCC3)no2)cc1C(F)(F)F] 15dL
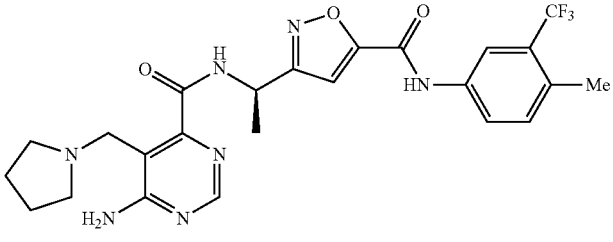 [SMILES: Cc1ccc(NC(=O)c2cc([C@@H](C)NC(=O)c3ncnc(N)c3CN3CCCC3)no2)cc1C(F)(F)F] 15dMa
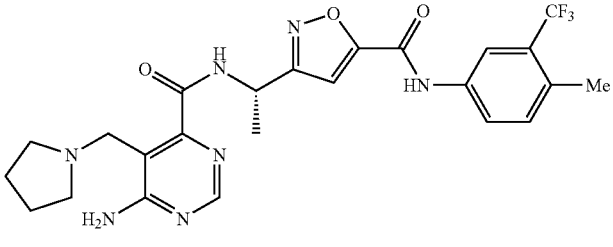 [SMILES: Cc1ccc(NC(=O)c2cc([C@H](C)NC(=O)c3ncnc(N)c3CN3CCCC3)no2)cc1C(F)(F)F] 15dMb
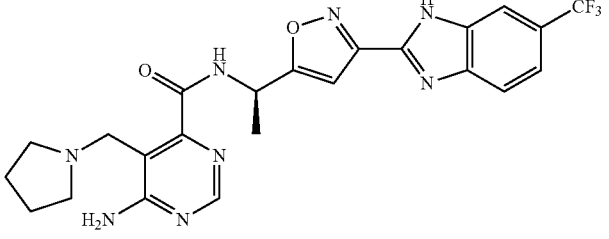 15dNa TABLE 4-continued Exemplary Compounds of Formula I
Additional compounds

| Compound ID |
|---|
| 15dNb |
| 15dO |
| 15dP |
| 15dQ |
| 15dRa |
| 15dRb |

TABLE 4-continued
Exemplary Compounds of Formula I
Additional compounds
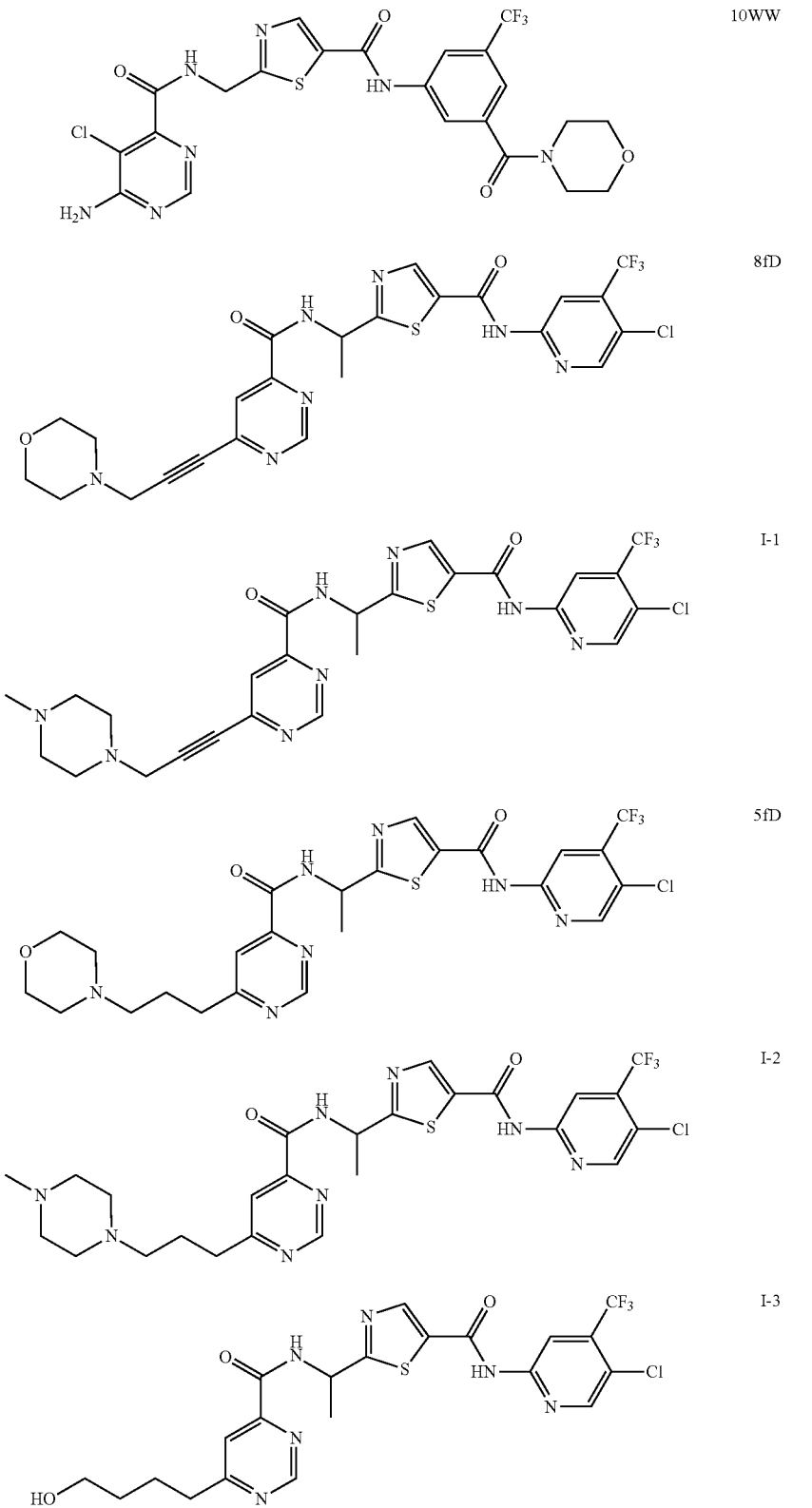

TABLE 4-continued
Exemplary Compounds of Formula I
Additional compounds
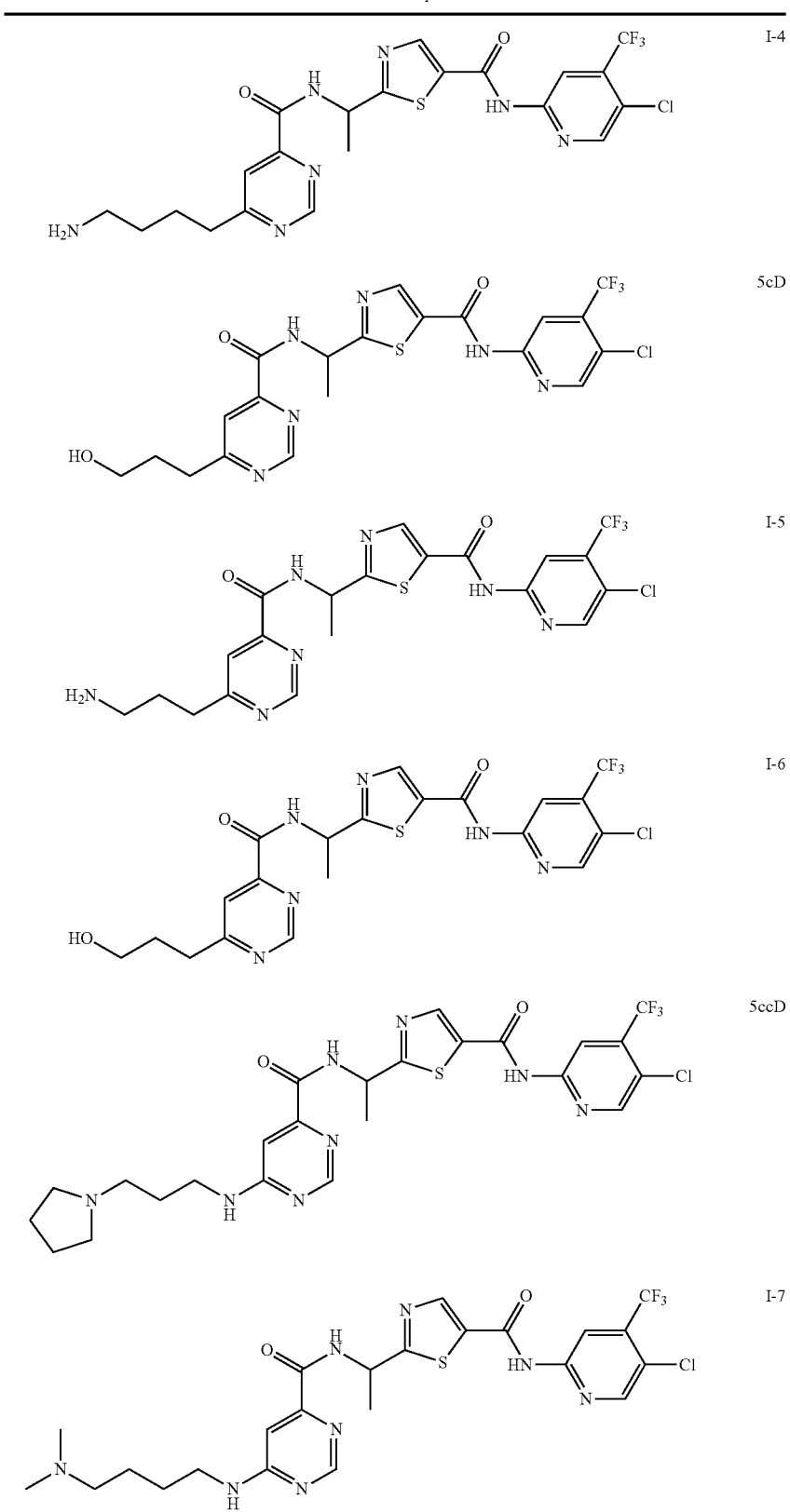

TABLE 4-continued
Exemplary Compounds of Formula I
Additional compounds
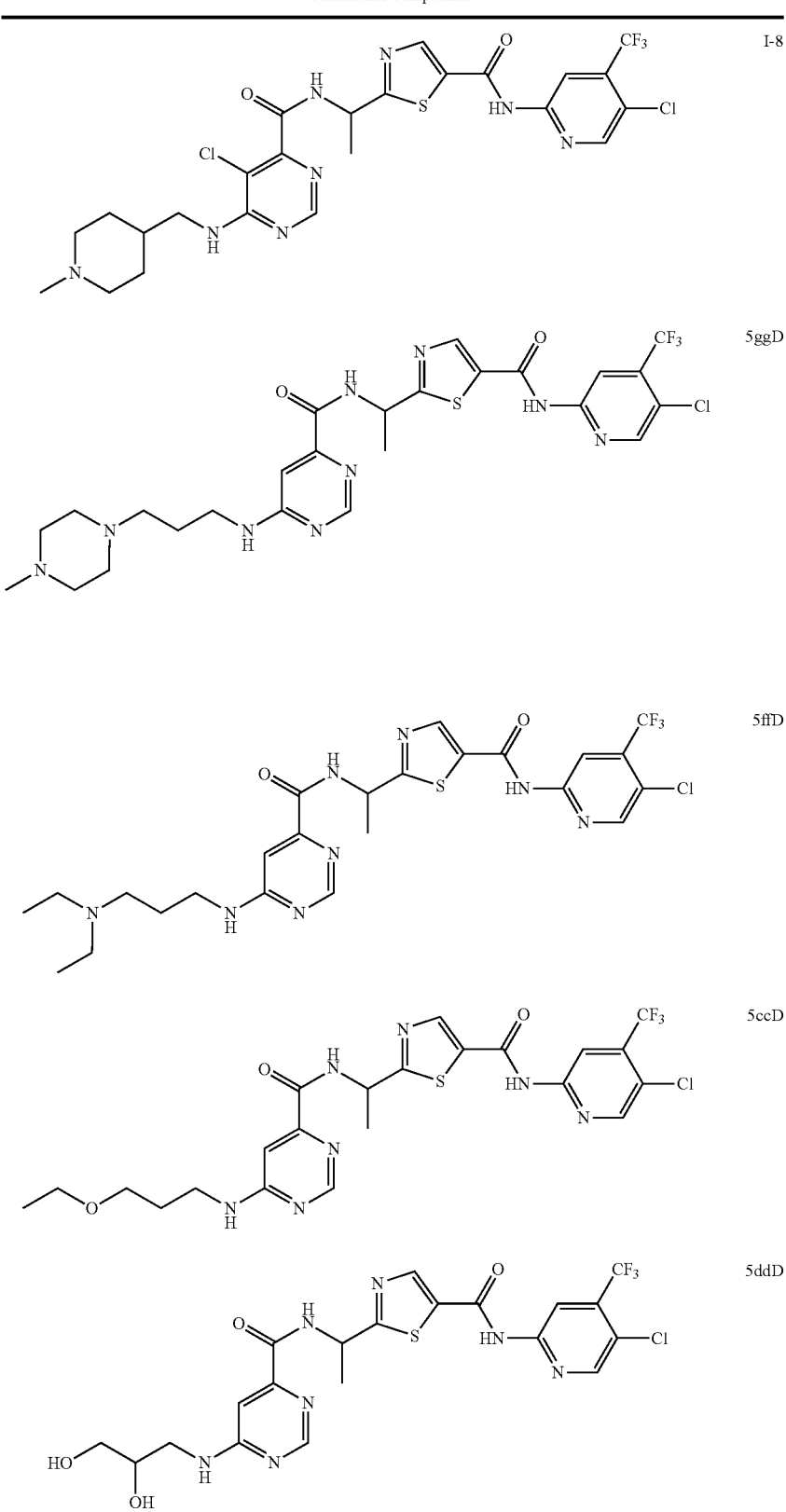
I-8
5ggD
5ffD
5ccD
5ddD TABLE 4-continued
Exemplary Compounds of Formula I
Additional compounds
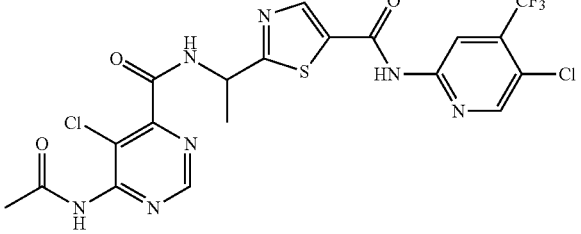 I-9
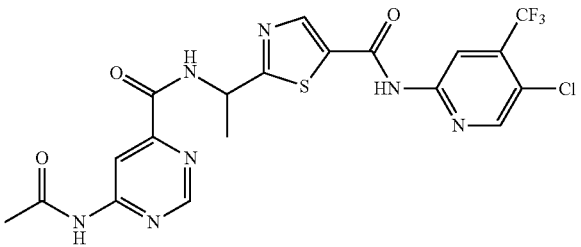 [SMILES: CC(=O)Nc1cc(C(=O)NC(C)c2ncc(C(=O)Nc3cc(C(F)(F)F)c(Cl)cn3)s2)ncn1] I-10
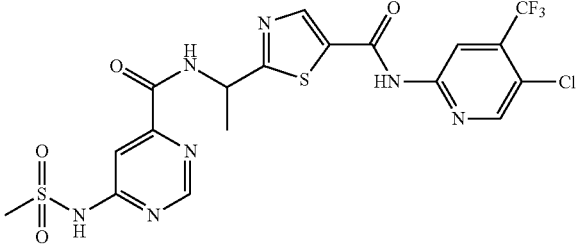 [SMILES: CC(NC(=O)c1cc(NS(C)(=O)=O)ncn1)c1ncc(C(=O)Nc2cc(C(F)(F)F)c(Cl)cn2)s1] I-11
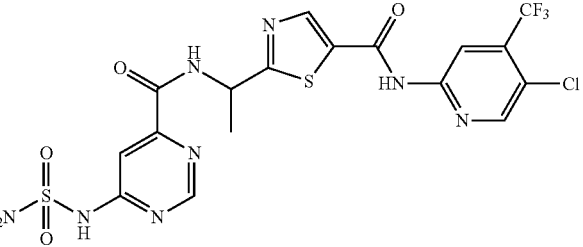 I-12
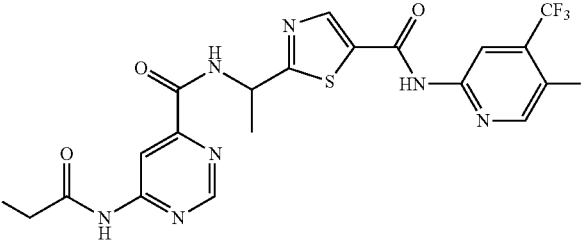 I-13
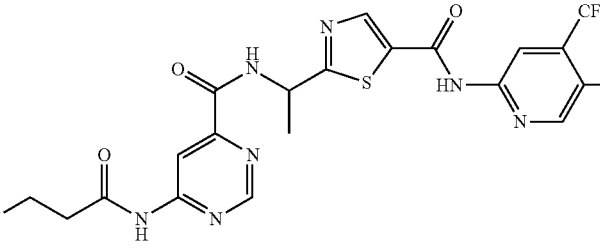 I-14

TABLE 4-continued
Exemplary Compounds of Formula I
Additional compounds
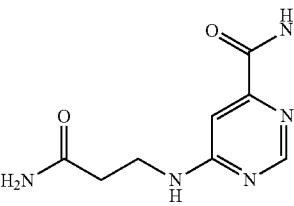
5ttD
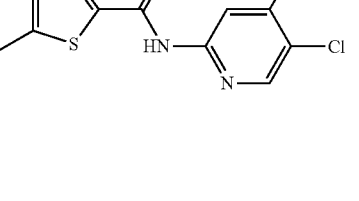
5iiD
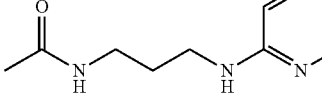
5vvD
5hhD
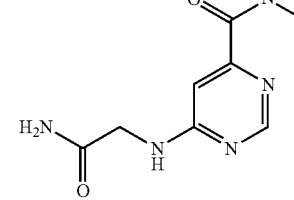
I-15

TABLE 4-continued
Exemplary Compounds of Formula I
Additional compounds
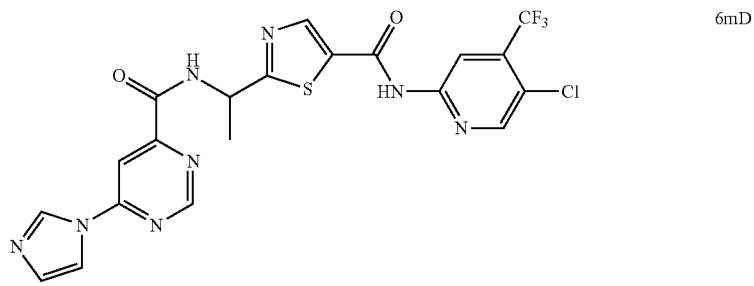 6mD
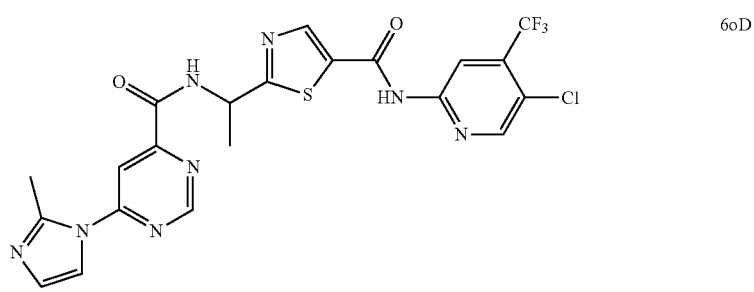 6oD
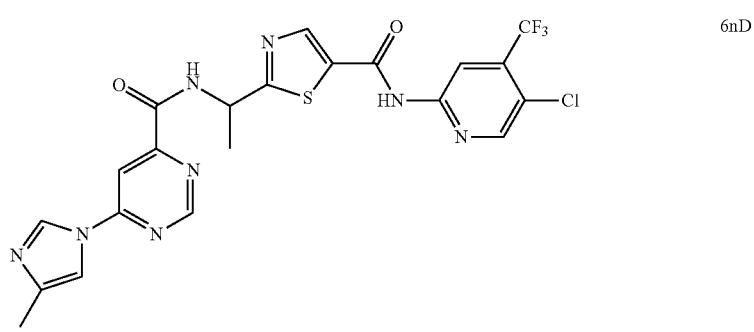 6nD
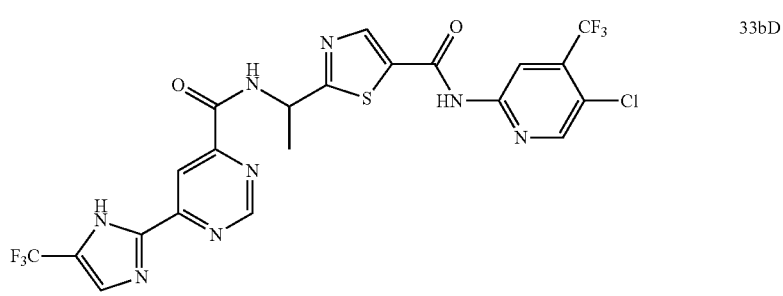 33bD
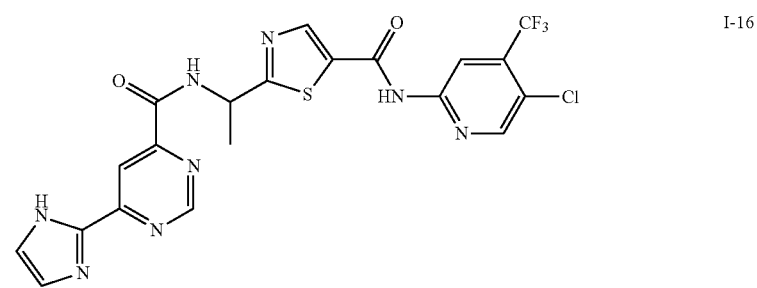 I-16

TABLE 4-continued
Exemplary Compounds of Formula I
Additional compounds
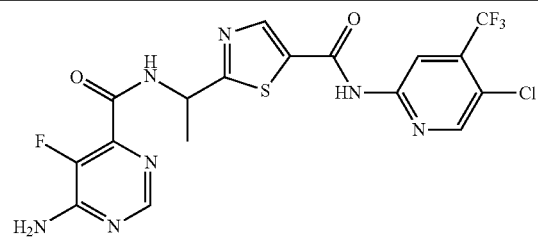
20aD
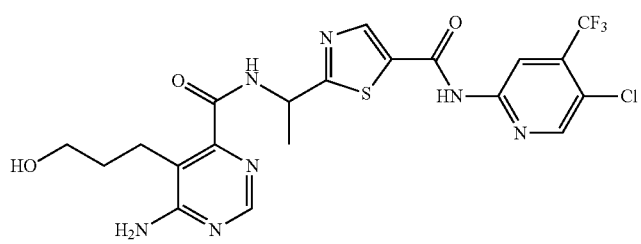 [SMILES: CC(NC(=O)c1ncnc(N)c1CCCO)c1ncc(C(=O)Nc2cc(C(F)(F)F)c(Cl)cn2)s1]
I-17
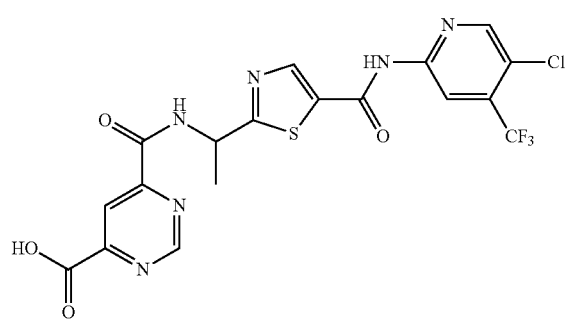 [SMILES: CC(NC(=O)c1cc(C(=O)O)ncn1)c1ncc(C(=O)Nc2cc(C(F)(F)F)c(Cl)cn2)s1]
I-18
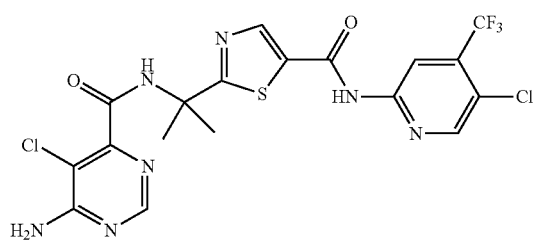 [SMILES: CC(C)(NC(=O)c1ncnc(N)c1Cl)c1ncc(C(=O)Nc2cc(C(F)(F)F)c(Cl)cn2)s1]
10S
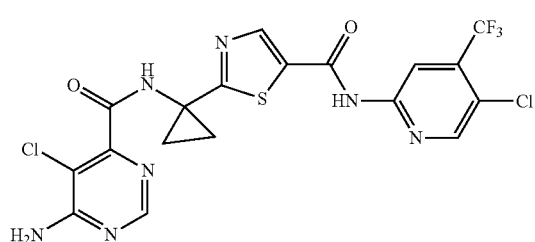
10T In certain embodiments, the present invention provides a compound selected from those set forth in Table 5, below, where each compound # corresponds to a compound number as recited in Table 3 or Table 4, supra.

TABLE 5

Selected Compounds of Formula I

| # | Structure | Name |
|---|-----------|------|
| 33bDa | 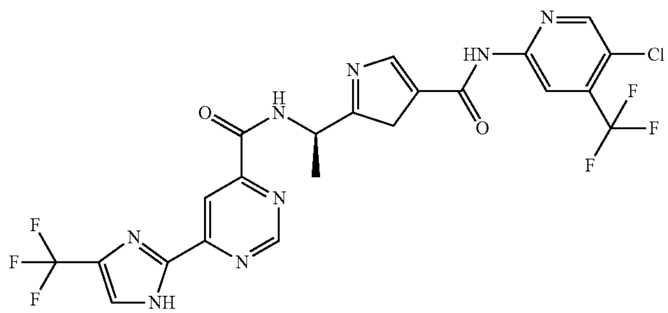 [SMILES: C[C@@H](NC(=O)c1cc(-c2nc(C(F)(F)F)c[nH]2)ncn1)C1=NC=C(C(=O)Nc2cc(C(F)(F)F)c(Cl)cn2)C1] | (R)-N-(5-chloro-4-(trifluoromethyl)pyridin-2-yl)-2-(1-(6-(4-(trifluoromethyl)-1H-imidazol-2-yl)pyrimidine-4-carboxamido)ethyl)thiazole-5-carboxamide |
| 26cD | 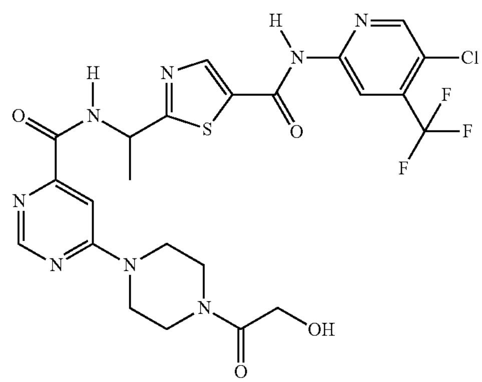 [SMILES: CC(NC(=O)c1cc(N2CCN(C(=O)CO)CC2)ncn1)c1ncc(C(=O)Nc2cc(C(F)(F)F)c(Cl)cn2)s1] | N-(5-chloro-4-(trifluoromethyl)pyridin-2-yl)-2-(1-(6-(4-(2-hydroxyacetyl)piperazin-1-yl)pyrimidine-4-carboxamido)ethyl)thiazole-5-carboxamide |
| 5vvD | 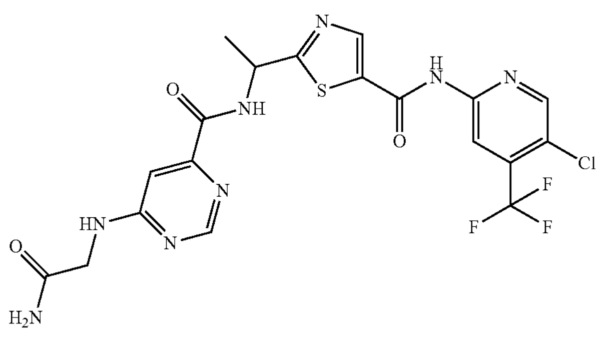 [SMILES: CC(NC(=O)c1cc(NCC(N)=O)ncn1)c1ncc(C(=O)Nc2cc(C(F)(F)F)c(Cl)cn2)s1] | 2-(1-(6-(2-amino-2-oxoethylamino)pyrimidine-4-carboxamido)ethyl)-N-(5-chloro-4-(trifluoromethyl)pyridin-2-yl)thiazole-5-carboxamide |
| 18cDa | 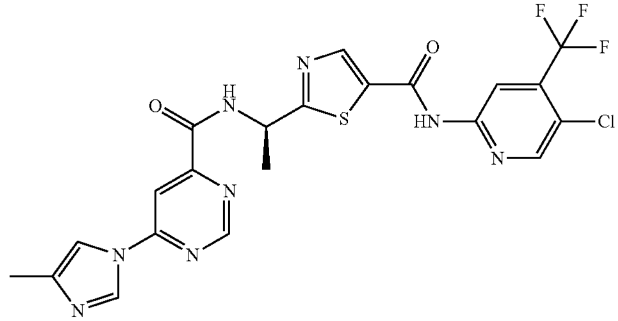 [SMILES: Cc1cn(-c2cc(C(=O)N[C@H](C)c3ncc(C(=O)Nc4cc(C(F)(F)F)c(Cl)cn4)s3)ncn2)cn1] | (R)-N-(5-chloro-4-(trifluoromethyl)pyridin-2-yl)-2-(1-(6-(4-methyl-1H-imidazol-1-yl)pyrimidine-4-carboxamido)ethyl)thiazole-5-carboxamide |

TABLE 5-continued

Selected Compounds of Formula I

| # | Structure | Name |
|---|-----------|------|
| 25bDa | 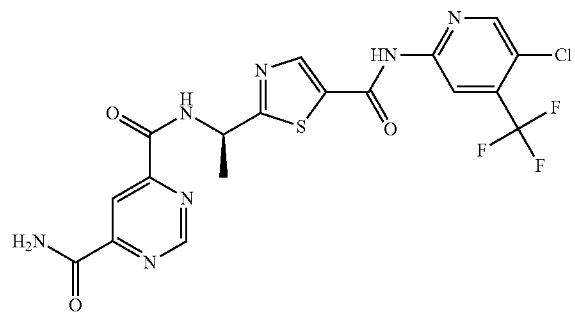 [SMILES: C[C@@H](NC(=O)c1cc(C(N)=O)ncn1)c1ncc(C(=O)Nc2cc(C(F)(F)F)c(Cl)cn2)s1] | (R)-N4-(1-(5-(5-chloro-4-(trifluoromethyl)pyridin-2-ylcarbamoyl)thiazol-2-yl)ethyl)pyrimidine-4,6-dicarboxamide |
| 25lDa | 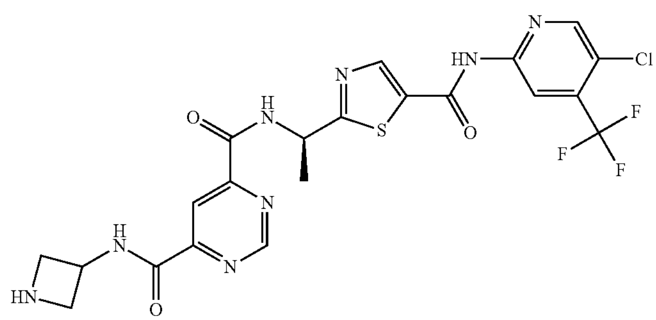 [SMILES: C[C@@H](NC(=O)c1cc(C(=O)NC2CNC2)ncn1)c1ncc(C(=O)Nc2cc(C(F)(F)F)c(Cl)cn2)s1] | (R)-N4-(azetidin-3-yl)-N6-(1-(5-(5-chloro-4-(trifluoromethyl)pyridin-2-ylcarbamoyl)thiazol-2-yl)ethyl)pyrimidine-4,6-dicarboxamide |
| 5vDa | 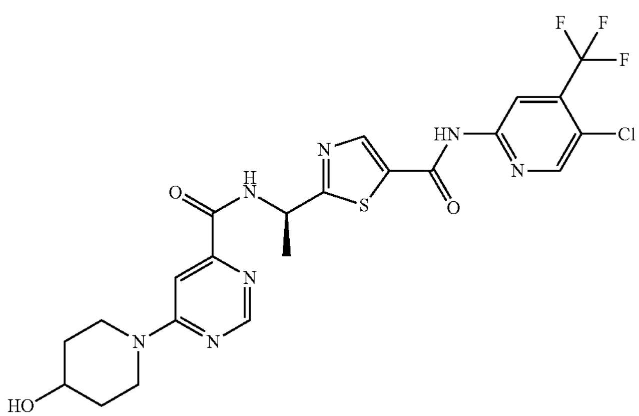 [SMILES: C[C@@H](NC(=O)c1cc(N2CCC(O)CC2)ncn1)c1ncc(C(=O)Nc2cc(C(F)(F)F)c(Cl)cn2)s1] | (R)-N-(5-chloro-4-(trifluoromethyl)pyridin-2-yl)-2-(1-(6-(4-hydroxypiperidin-1-yl)pyrimidine-4-carboxamido)ethyl)thiazole-5-carboxamide |
| 21 | 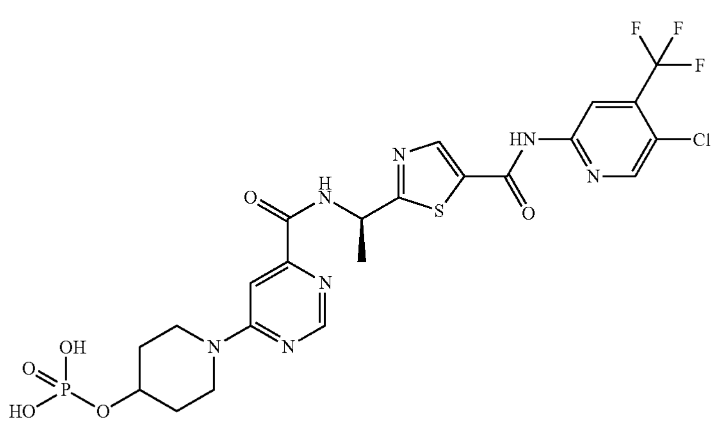 [SMILES: C[C@@H](NC(=O)c1cc(N2CCC(OP(=O)(O)O)CC2)ncn1)c1ncc(C(=O)Nc2cc(C(F)(F)F)c(Cl)cn2)s1] | (R)-1-(6-(1-(5-(5-chloro-4-(trifluoromethyl)pyridin-2-ylcarbamoyl)thiazol-2-yl)ethylcarbamoyl)pyrimidin-4-yl)piperidin-4-yl dihydrogen phosphate |

TABLE 5-continued

Selected Compounds of Formula I

| # | Structure | Name |
|---|-----------|------|
| 19mmD | 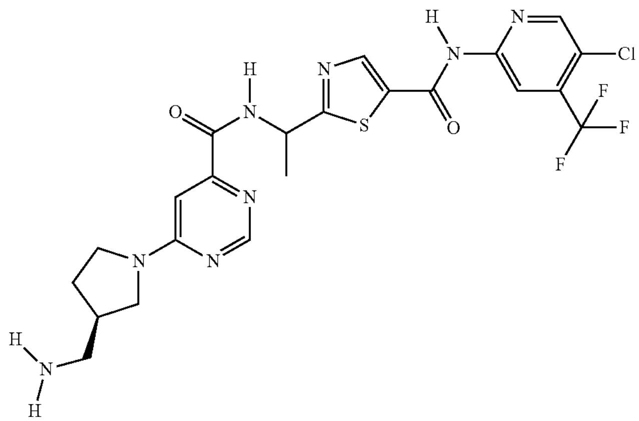 [SMILES: CC(NC(=O)c1cc(N2CC[C@H](CN)C2)ncn1)c1ncc(C(=O)Nc2cc(C(F)(F)F)c(Cl)cn2)s1] | 2-(1-(6-((R)-3-(aminomethyl)pyrrolidin-1-yl)pyrimidine-4-carboxamido)ethyl)-N-(5-chloro-4-(trifluoromethyl)pyridin-2-yl)thiazole-5-carboxamide |
| 5wDa | 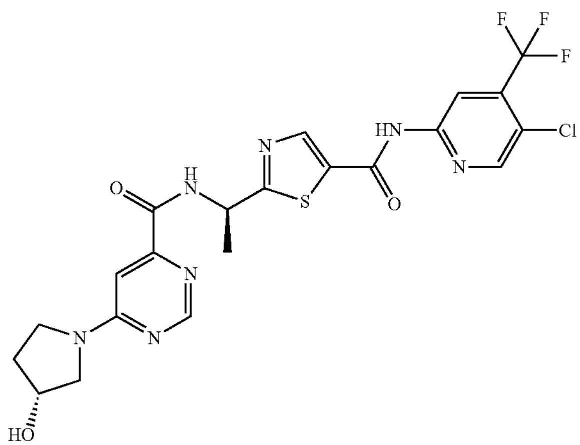 [SMILES: C[C@@H](NC(=O)c1cc(N2CC[C@@H](O)C2)ncn1)c1ncc(C(=O)Nc2cc(C(F)(F)F)c(Cl)cn2)s1] | N-(5-chloro-4-(trifluoromethyl)pyridin-2-yl)-2-((R)-1-(6-((R)-3-hydroxypyrrolidin-1-yl)pyrimidine-4-carboxamido)ethyl)thiazole-5-carboxamide |
| 18fD | 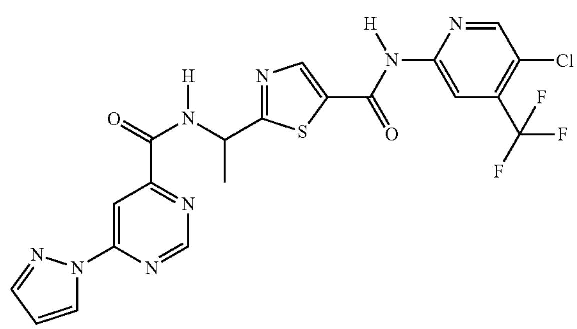 [SMILES: CC(NC(=O)c1cc(-n2cccn2)ncn1)c1ncc(C(=O)Nc2cc(C(F)(F)F)c(Cl)cn2)s1] | 2-(1-(6-(1H-pyrazol-1-yl)pyrimidine-4-carboxamido)ethyl)-N-(5-chloro-4-(trifluoromethyl)pyridin-2-yl)thiazole-5-carboxamide |
| 25fD | 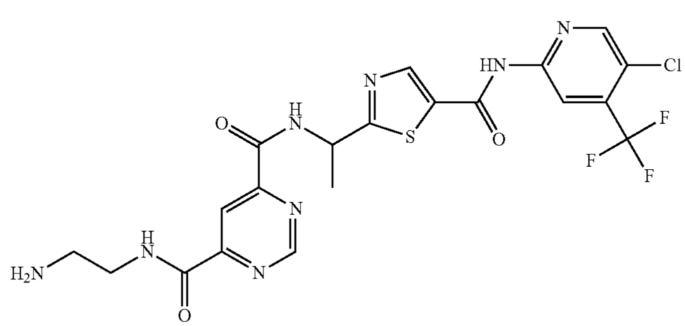 [SMILES: CC(NC(=O)c1cc(C(=O)NCCN)ncn1)c1ncc(C(=O)Nc2cc(C(F)(F)F)c(Cl)cn2)s1] | N4-(2-aminoethyl)-N6-(1-(5-(5-chloro-4-(trifluoromethyl)pyridin-2-ylcarbamoyl)thiazol-2-yl)ethyl)pyrimidine-4,6-dicarboxamide |

TABLE 5-continued

Selected Compounds of Formula I

| # | Structure | Name |
|---|---|---|
| 18dDa | 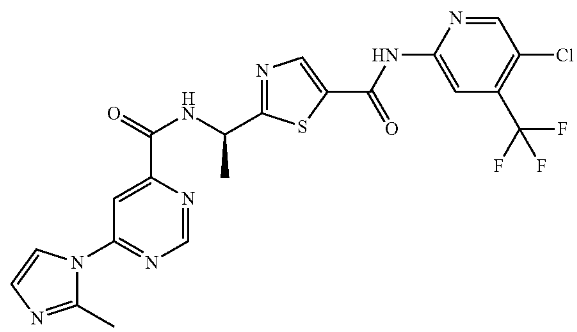 [SMILES: Cc1nccn1-c1cc(C(=O)N[C@H](C)c2ncc(C(=O)Nc3cc(C(F)(F)F)c(Cl)cn3)s2)ncn1] | (R)-N-(5-chloro-4-(trifluoromethyl)pyridin-2-yl)-2-(1-(6-(2-methyl-1H-imidazol-1-yl)pyrimidine-4-carboxamido)ethyl)thiazole-5-carboxamide |
| 5dDa | 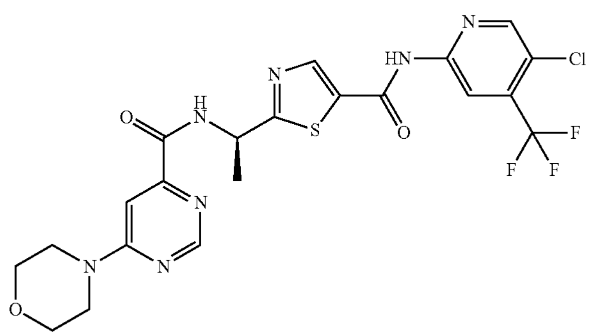 [SMILES: C[C@@H](NC(=O)c1cc(N2CCOCC2)ncn1)c1ncc(C(=O)Nc2cc(C(F)(F)F)c(Cl)cn2)s1] | (R)-N-(5-chloro-4-(trifluoromethyl)pyridin-2-yl)-2-(1-(6-morpholinopyrimidine-4-carboxamido)ethyl)thiazole-5-carboxamide |
| 4qDa | 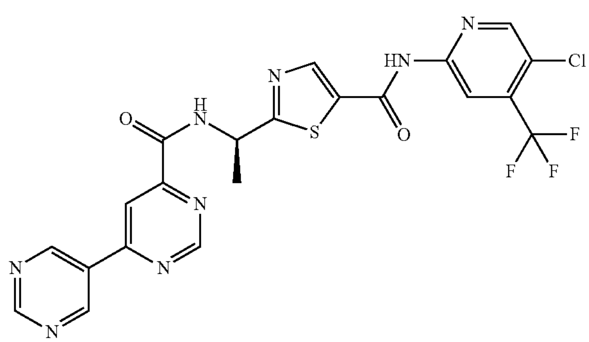 [SMILES: C[C@@H](NC(=O)c1cc(-c2cncnc2)ncn1)c1ncc(C(=O)Nc2cc(C(F)(F)F)c(Cl)cn2)s1] | (R)-2-(1-(4,5'-bipyrimidine-6-carboxamido)ethyl)-N-(5-chloro-4-(trifluoromethyl)pyridin-2-yl)thiazole-5-carboxamide |
| 5aDa | 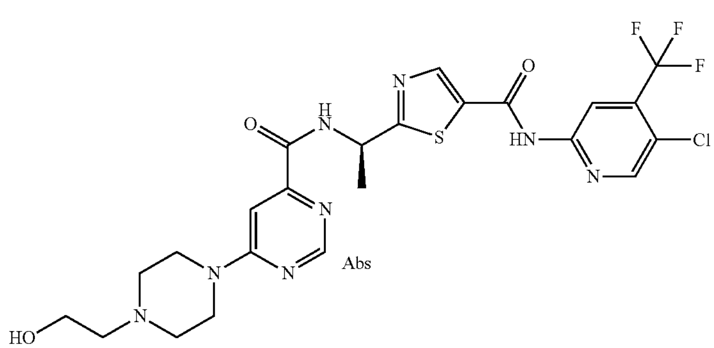 [SMILES: C[C@@H](NC(=O)c1cc(N2CCN(CCO)CC2)ncn1)c1ncc(C(=O)Nc2cc(C(F)(F)F)c(Cl)cn2)s1] | (R)-N-(5-chloro-4-(trifluoromethyl)pyridin-2-yl)-2-(1-(6-(4-(2-hydroxyethyl)piperazin-1-yl)pyrimidine-4-carboxamido)ethyl)thiazole-5-carboxamide |

TABLE 5-continued

Selected Compounds of Formula I

| # | Structure | Name |
|---|-----------|------|
| 15dDa | 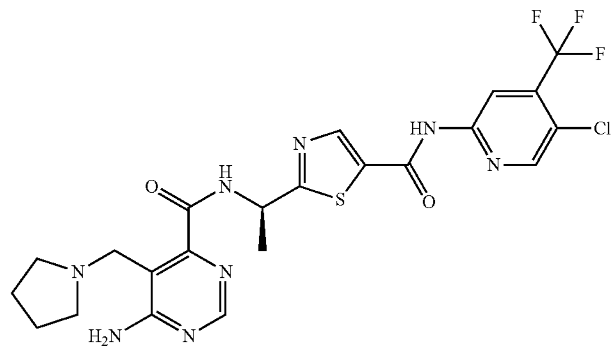 [SMILES: C[C@@H](NC(=O)c1ncnc(N)c1CN1CCCC1)c1ncc(C(=O)Nc2cc(C(F)(F)F)c(Cl)cn2)s1] | (R)-2-(1-(6-amino-5-(pyrrolidin-1-ylmethyl)pyrimidine-4-carboxamido)ethyl)-N-(5-chloro-4-(trifluoromethyl)pyridin-2-yl)thiazole-5-carboxamide |
| 5zDa | 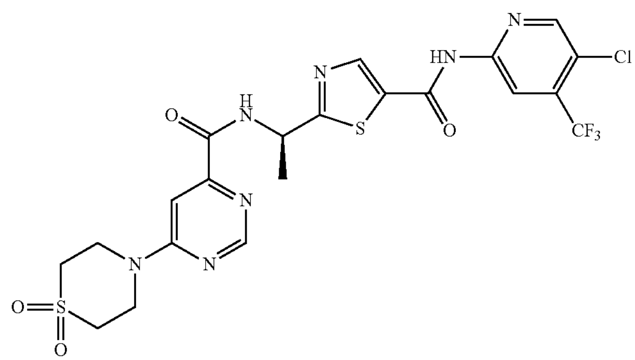 [SMILES: C[C@@H](NC(=O)c1cc(N2CCS(=O)(=O)CC2)ncn1)c1ncc(C(=O)Nc2cc(C(F)(F)F)c(Cl)cn2)s1] | (R)-N-(5-chloro-4-(trifluoromethyl)pyridin-2-yl)-2-(1-(6-(4,4-Dioxothiomorpholin-1-yl)-pyrimidine-4-carboxamido)ethyl)thiazole-5-carboxamide |
| 35 | 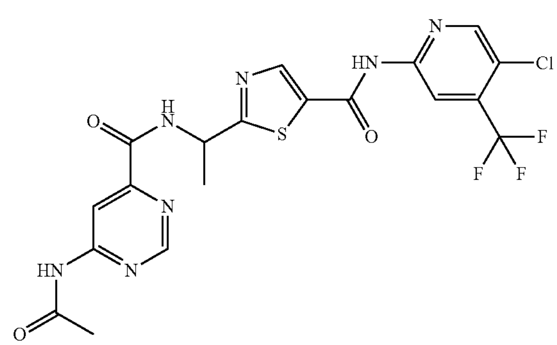 [SMILES: CC(=O)Nc1cc(C(=O)NC(C)c2ncc(C(=O)Nc3cc(C(F)(F)F)c(Cl)cn3)s2)ncn1] | 2-(1-(6-acetamidopyrimidine-4-carboxamido)ethyl)-N-(5-chloro-4-(trifluoromethyl)pyridin-2-yl)thiazole-5-carboxamide |
| 18aDa | 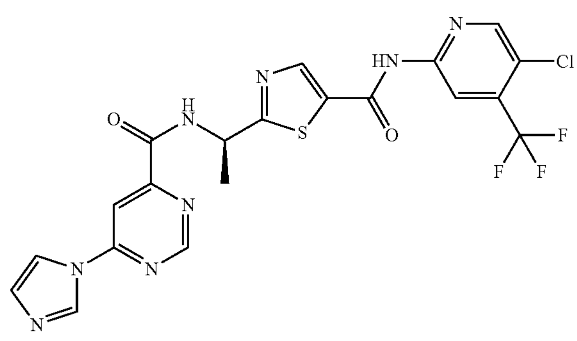 [SMILES: C[C@@H](NC(=O)c1cc(-n2ccnc2)ncn1)c1ncc(C(=O)Nc2cc(C(F)(F)F)c(Cl)cn2)s1] | (R)-2-(1-(6-(1H-imidazol-1-yl)pyrimidine-4-carboxamido)ethyl)-N-(5-chloro-4-(trifluoromethyl)pyridin-2-yl)thiazole-5-carboxamide |

TABLE 5-continued

Selected Compounds of Formula I

| # | Name |
|---|---|
| 5yDa | (R)-N-(5-chloro-4-(trifluoromethyl)pyridin-2-yl)-2-(1-(6-(4-(2-ethoxyethyl)piperazin-1-yl)pyrimidine-4-carboxamido)ethyl)thiazole-5-carboxamide |
| 10E | 2-(1-(6-amino-5-chloropyrimidine-4-carboxamido)ethyl)-N-(4-chloro-3-(trifluoromethyl)phenyl)thiazole-5-carboxamide |
| 10Da | (R)-2-(1-(6-amino-5-chloropyrimidine-4-carboxamido)ethyl)-N-(5-chloro-4-(trifluoromethyl)pyridin-2-yl)thiazole-5-carboxamide |
| 10Db | (S)-2-(1-(6-amino-5-chloropyrimidine-4-carboxamido)ethyl)-N-(5-chloro-4-(trifluoromethyl)pyridin-2-yl)thiazole-5-carboxamide |
| 1jDa | (R)-N-(5-chloro-4-(trifluoromethyl)pyridin-2-yl)-2-(1-(5-chloro-6-(methylamino)pyrimidine-4-carboxamido)ethyl)thiazole-5-carboxamide |

TABLE 5-continued

Selected Compounds of Formula I

| # | Structure | Name |
|---|---|---|
| 5jDa | 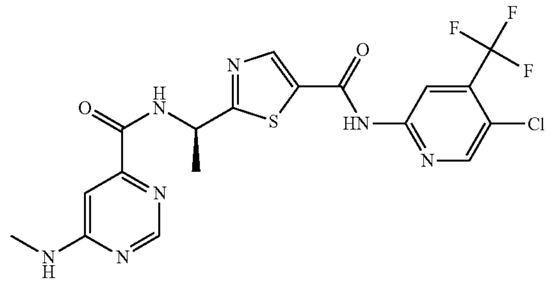 [SMILES: CNc1cc(C(=O)N[C@H](C)c2ncc(C(=O)Nc3cc(C(F)(F)F)c(Cl)cn3)s2)ncn1] | (R)-N-(5-chloro-4-(trifluoromethyl)pyridin-2-yl)-2-(1-(6-(methylamino)pyrimidine-4-carboxamido)ethyl)thiazole-5-carboxamide |
| 17D | 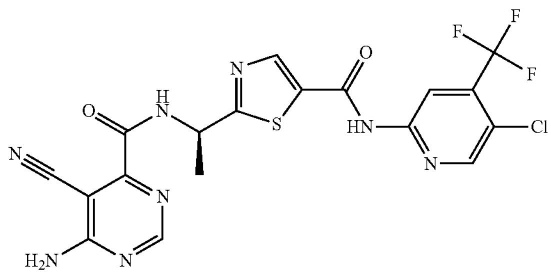 [SMILES: C[C@@H](NC(=O)c1ncnc(N)c1C#N)c1ncc(C(=O)Nc2cc(C(F)(F)F)c(Cl)cn2)s1] | (R)-2-(1-(6-amino-5-cyanopyrimidine-4-carboxamido)ethyl)-N-(5-chloro-4-(trifluoromethyl)pyridin-2-yl)thiazole-5-carboxamide |
| 11Da | 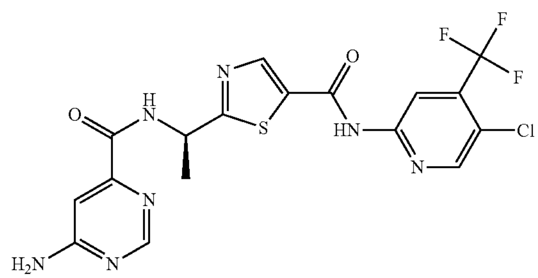 [SMILES: C[C@@H](NC(=O)c1cc(N)ncn1)c1ncc(C(=O)Nc2cc(C(F)(F)F)c(Cl)cn2)s1] | (R)-2-(1-(6-amino-pyrimidine-4-carboxamido)ethyl)-N-(5-chloro-4-(trifluoromethyl)pyridin-2-yl)thiazole-5-carboxamide |
| 4eDa | 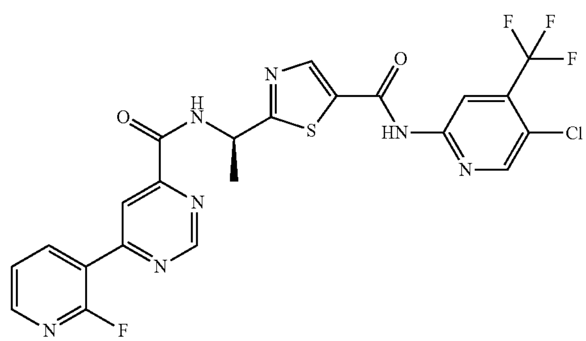 [SMILES: C[C@@H](NC(=O)c1cc(-c2cccnc2F)ncn1)c1ncc(C(=O)Nc2cc(C(F)(F)F)c(Cl)cn2)s1] | (R)-N-(5-chloro-4-(trifluoromethyl)pyridin-2-yl)-2-(1-(6-(2-fluoropyridin-3-yl)pyrimidine-4-carboxamido)ethyl)thiazole-5-carboxamide |
| 4bD | 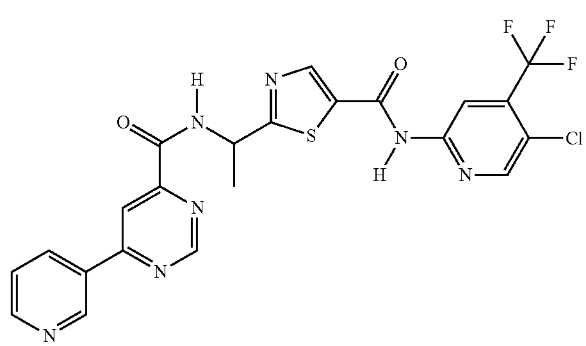 [SMILES: CC(NC(=O)c1cc(-c2cccnc2)ncn1)c1ncc(C(=O)Nc2cc(C(F)(F)F)c(Cl)cn2)s1] | N-(5-chloro-4-(trifluoromethyl)pyridin-2-yl)-2-(1-(6-(pyridin-3-yl)pyrimidine-4-carboxamido)ethyl)thiazole-5-carboxamide |

TABLE 5-continued

Selected Compounds of Formula I

| # | Structure | Name |
|---|-----------|------|
| 10D | 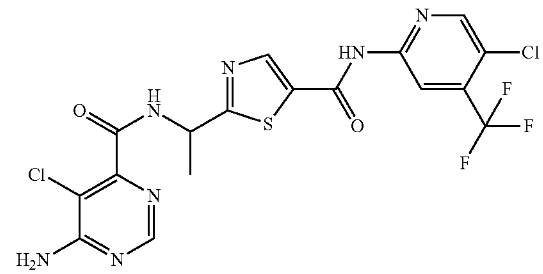 | 2-(1-(6-amino-5-chloropyrimidine-4-carboxamido)ethyl)-N-(5-chloro-4-(trifluoromethyl)pyridin-2-yl)thiazole-5-carboxamide |
| 10U | 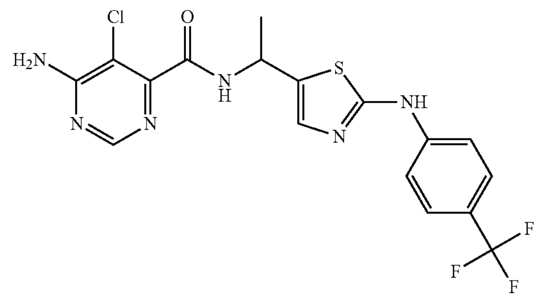 [SMILES: CC(NC(=O)c1ncnc(N)c1Cl)c1cnc(Nc2ccc(C(F)(F)F)cc2)s1] | 6-amino-5-chloro-N-(1-(2-(4-(trifluoromethyl)phenylamino)thiazol-5-yl)ethyl)pyrimidine-4-carboxamide |
| 5aD | 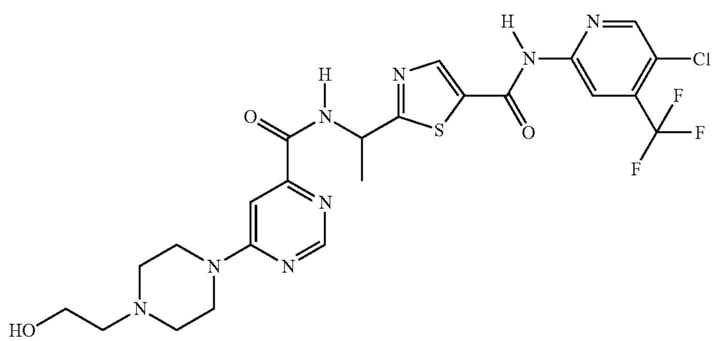 [SMILES: CC(NC(=O)c1cc(N2CCN(CCO)CC2)ncn1)c1ncc(C(=O)Nc2cc(C(F)(F)F)c(Cl)cn2)s1] | N-(5-chloro-4-(trifluoromethyl)pyridin-2-yl)-2-(1-(6-(4-hydroxypiperidin-1-yl)pyrimidine-4-carboxamido)ethyl)thiazole-5-carboxamide |

Biological Assays (1) Biochemical FRET Assay

Method utilized for measuring the phosphorylation of MEK by wild-type (WT) B-Raf as a method for quantifying the ability of molecules to inhibit the enzymatic activity of WT-B-Raf.

In the assay methods described below, the following definitions apply:

"HEPES" refers to 4-(2-hydroxyethyl)-1-piperazineethanesulfonic acid;

"MEK" refers to mitogen activated extracellular signal-related kinase kinase;

"DTT" refers to dithiothreitol;

"APC" refers to allophycocyanin;

"TR-FRET" refers to time resolved fluorescence energy transfer;

"PBS" refers to phosphate buffered saline;

"PMSF" refers ti phenyl methyl sulfonamide; and

"BSA" refers to bovine serum albumin.

TABLE 6

Reagents

| Name | Units/Amount | Source | Catalog Number | Storage |
|------|--------------|--------|----------------|---------|
| Biotin-MEK1 (15:1) | DB021505 767 µg/mL (10.8 µM) | Biogen Idec. | In house | −80° C. |
| ATP | 10 mM, 500 µl | Gibco BRL | 8330-019 | −20° C. |
| B-Raf (WT) | 12 µg/480 µl 54% Pure (2.1 µM) | Upstate | 14-530M | −80° C. |
| DMSO | 100% | Fisher | D128-500 | RT |
| Streptavidin Allophycocyanin (SA-APC) | 14.8 uM SA (2.20 mg/ml) | Prozyme | PJ25S | 4° C., in the dark |

TABLE 6-continued

| Reagents | | | | |
|---|---|---|---|---|
| Name | Units/Amount | Source | Catalog Number | Storage |
| Polyclonal Antiphospho MEK1/2(Ser 217/221) Antibody | 265 µg/ml (1.8 uM) | Cell Signaling Technologies Inc. | 9121 | −20° C. |
| Lance Eu-W1024 Anti Rabbit IgG | 880 µg/ml (5.5 µM) | Perkin Elmer | AD083 | 4° C. |
| LANCE 10X Detection Buffer | N/A | Perkin Elmer | CR97-100 | 4° C. |
| SuperBlock in TBS | N/A | Pierce | 37535 | 4° C. |

TABLE 7

| Buffers | |
|---|---|
| Master Buffer | Storage |
| 50 mM HEPES, 60 mM NaCl, 3 mM MgCl$_2$ | 4° C. |
| 1M Dithiothreitol(DTT) | −20° C. in aliquots of 150 µl |
| 1M MnCl$_2$ | 4° C. |
| 20% BSA, 0.002% Sodium Azide. | 4° C. |
| 20% Tween-20 | room temperature (~25° C.) |
| 1M EDTA in dH$_2$O | room temperature (~25° C.) |

Equipment and Materials:

Analyst AD, LJL BioSystems, ID1615; 96 well ½ Area Black Polystyrene plates. Costar 3694.

TABLE 8

| Reagents |
|---|
| Reagents used for Kinase reaction: |
| 50 µM ATP |
| 0.125 nM B-Raf (WT) |
| 12.5 nM Biotin-MEK (15:1) |
| 1% DMSO |
| 50 mM Hepes, 60 mM NaCl, 3 mM MgCl$_2$, 2 mM DTT, 0.25 mM MnCl2, 0.01% BSA, 0.01% Tween-20 |
| Reagents used for Detection Reaction |
| 20 nM SA-APC |
| 2.5 nM Polyclonal Anti p-MEK1/2 (Ser217/221) |
| 2.5 nM Eu-AntiRabbit IgG |
| 1X Lance Detection Buffer |
| 10% Superblock in TBS |

WT Raf

Inhibitors were diluted 4-fold in 100% DMSO and added to a final concentration of 10 µM to 40 pM to a solution containing 12.5 nM biotin-MEK, 0.125 nM WT Raf in 50 mM HEPES, pH 7.4, 60 mM NaCl, 3 mM MgCl$_2$, 2 mM DTT, 0.25 mM MnCl$_2$, 0.01% BSA, and 0.01% Tween-20 and incubated for 2 hours at room temperature. The kinase reaction was started by the addition of 50 µM ATP to a final volume of 45 µl and allowed to progress for 60 minutes. The reaction was stopped with 15 mM EDTA and 20 nM Streptavidin-APC, 2.5 nM Polyclonal anti p-MEK1/2 (Ser217/221), 2.5 nM Eu-labeled anti-rabbit IgG were added in Lance detection buffer and 5% Superblock in PBS for a final volume of 100 µl. The detection reaction was incubated for 90 minutes at room temperature and then read on an Analyst plate reader using standard TR-FRET (time resolved fluorescence resonance energy transfer) settings for Eu and APC.

Mutant Raf

Inhibitors were diluted 4-fold in 100% DMSO and added to a final concentration of 10 µM to 40 pM to a solution containing 100 nM biotin-MEK, 0.125 nM V599E Raf in 50 mM HEPES, pH 7.4, 60 mM NaCl, 3 mM MgCl$_2$, 2 mM DTT, 0.25 mM MnCl$_2$, 0.01% BSA, and 0.01% Tween-20 and incubated for 20 minutes at room temperature. The kinase reaction was started by the addition of 25 µM ATP to a final volume of 45 µl and allowed to progress for 60 minutes. The reaction was stopped with 15 mM EDTA and 20 nM Streptavidin-APC, 2.5 nM Polyclonal anti p-MEK1/2 (Ser217/221), 2.5 nM Eu-labeled anti-rabbit IgG were added in Lance detection buffer and 5% Superblock in PBS for a final volume of 100 µl. The detection reaction was incubated for 90 minutes at room temperature and then read on an Analyst plate reader using standard TR-FRET (time resolved fluorescence resonance energy transfer) settings for Eu and APC.

C-Raf

Inhibitors were diluted 4-fold in 100% DMSO and added to a final concentration of 10 µM to 40 pM to a solution containing 50 nM biotin-MEK, 0.075 nM C-Raf in 50 mM HEPES, pH 7.4, 60 mM NaCl, 3 mM MgCl$_2$, 2 mM DTT, 0.25 mM MnCl$_2$, 0.01% BSA, and 0.01% Tween-20 and incubated for 20 minutes at room temperature. The kinase reaction was started by the addition of 10 µM ATP to a final volume of 45 µl and allowed to progress for 60 minutes. The reaction was stopped with 15 mM EDTA and 20 nM Streptavidin-APC, 2.5 nM Polyclonal anti p-MEK1/2 (Ser217/221), 2.5 nM Eu-labeled anti-rabbit IgG were added in Lance detection buffer and 5% Superblock in PBS for a final volume of 100 µl. The detection reaction was incubated for 90 minutes at room temperature and then read on an Analyst plate reader using standard TR-FRET (time resolved fluorescence resonance energy transfer) settings for Eu and APC.

Certain compounds of the present invention were assayed using the above Biochemical FRET assays and were found to be inhibitors of Raf kinase.

(2) Mechanistic Cellular Assay for Raf Kinase Activity

The following method was utilized for quantifying the amount of phospho-ERK in melanoma derived WM-266-4 cells (one allele each of wild type BRaf and mutant BRaf (V600D) as an indicator of Raf kinase activity in cells treated with various kinase inhibitors.

TABLE 9

Cellular Assay

| Materials Needed | Catalog Number |
|---|---|
| WM-266-4 cells | (ATCC number: CRL-1676) |
| RPMI 1640 cell culture medium | |
| Fetal Bovine Serum (FBS) | |
| Phosphate Buffered Saline (PBS) | |
| 96-well tissue culture plates | |
| Tissue culture 37° C. incubator | |
| 96-well V-bottom plates | |
| Rotary plate shaker (e.g., BELLCO GLASS Mini Orbital Shaker) | |
| Bio-Plex suspension array system | |
| Bio-Plex Cell Lysis Kit | (Bio Rad Catalog #171-304011) |
| Phenyl methyl sulphonyl fluoride (PMSF) | |
| Bio-Plex Phospho-ERK1/2 Assay Kit | (Bio Rad Catalog #171-V22238) |

Day 1: Cell Seeding (1) Detached adhered WM-266-4 cells from flask using 0.25% Trypsin. Resuspended cells in growth media (90% RPMI 1640, 10% FBS) and determine cell density.

(2) Seeded cells @ 10,000 cells/well in 96-well (flat bottom) tissue culture plates (36,000 cells/cm$^2$). Added growth media to a final volume of 200 uL/well and incubated overnight at 37° C.

Day 2: Cell Treatment (1) Prepared compound dilutions (1000× in DMSO) as follows. Starting with a stock of 5 mM compound in DMSO, diluted serially 3-fold in DMSO for a total of eight concentrations (5 mM, 1.67 mM, 0.556 mM, 0.185 mM, 0.062 mM, 0.021 mM, 0.007 mM, 0.002 mM).

(2) Prepared compound-containing media by adding 1 mL treatment media (100% RPMI 1640 without FBS) to 1 µL of compound dilution (from step 3).

(3) Removed plates (from step 2) from incubator. Aspirated media and replace with 150 µL compound-containing media. Incubate for 1-2 hr at 37° C.

(4) Removed plates (from step 5) from incubator and treated each as follows: aspirated compound-containing media and replaced with 300 µL ice-cold 1×PBS, aspirated PBS and replaced with 45 µL lysis buffer (Biorad Bio-Plex lysis buffer containing 0.4% v/v lysis buff. Factor 1, 0.2% v/v lysis buff. Factor 2, and PMSF to 2 mM final concentration), and then placed plate on ice until all plates were treated.

(5) After all plates were processed (step 6), placed plates on an orbital shaker and shook at room temperature for at least 15 min.

(6) Finally, removed plates from shaker, and transferred 40 uL/well of lysate from each to new corresponding 96-well V-bottom plates. At this point, samples may be frozen and stored @−80 C.°.

Day 2: Bioplex Assay (1) Thaw (if necessary) plates (from step 8) and added 40 µL of Phospho-Protein Assay Buffer to each 40 µL lysate for a 1:1 dilution.

(2) Prepared phospho-ERK1,2 Bioplex beads by diluting 1:50 with Bioplex Wash Buffer (mixing 49 µL Wash Buffer with 1 µL of phospho-ERK1,2 Bioplex beads for each sample to be analyzed). Protected from light by wrapping tube in aluminum foil and kept at room temperature.

(3) Prepared Filter Plate by adding 100 µL/well Bioplex Wash Buffer and removed by vacuum filtration.

(4) Add 50 µL of bead solution (from step 10) to each well of a prepared Filter Plate (from step 11) and vacuum filter. Wash/filter 2× with 100 uL/well Wash Buffer.

(5) Added 50 µL of each lysate to appropriate well of the Filter Plate (from step 12). For this and all subsequent plate incubation steps, placed plate on an inverted plate cover (reduces background), and wrapped in aluminum foil (to protect from light). Shook overnight at room temperature. Included positive (control lysate) and negative (lysis buffer) controls.

Day 3: Bioplex Assay Continued (1) Prepared detection antibody (phospho-ERK1,2 Ab) by diluting 1:25 with Detection Antibody Dilution Buffer (mixing 24 µL Detection Antibody Dilution Buffer with 1 µL of phospho-ERK1,2 Ab for each sample to be analyzed).

(2) Removed plate (from step 13) from shaker and vacuum filter. Washed/filter plate 3× with 100 µL/well Wash Buffer. Added 25 µL of diluted antibody to each well. Incubated on shaker at room temperature for 30-45 min.

(3) Prepared streptavidin-PE by diluting 1:100 with Wash Buffer (mixing 49.5 µL Wash Buffer with 0.5 µL of 100× streptavidin-PE for each sample to be analyzed). Protected from light.

(4) Removed plate (from step 15) from shaker and vacuum filter. Washed/filter plate 3× with 100 µL/well Wash Buffer. Add 50 µL of diluted streptavidin-PE solution (from step 16) to each sample well. Incubated on shaker for 10-20 min.

(5) Removed plate from shaker and vacuum filter. Wash/filter plate 3× with 100 uL/well Bead Resuspension Buffer. After last wash resuspended beads in 125 µL Bead Resuspension Buffer. Place plate on shaker for 2-3 minutes to ensure beads are well resuspended.

(6) Quantified phospho-ERK by reading plate in the Bio-Plex plate reader (run start-up and calibration programs before this step) using bead region 38 (pERK1,2) and counting 50 beads per region.

Certain compounds of the present invention were assayed using the above Cellular Assay for Raf Kinase Activity and were found to be inhibitors of Raf kinase.

WM-266-4 cells were seeded at a density of 10,000 cells/well in RPMI 1640 cell culture media containing 10% FBS in a 96-well flat bottom and incubated overnight at 37° C. Inhibitors were diluted 3-fold in DMSO, added to serum free RPMI 1640 cell culture media to a final concentration range of 5 µM to 2 nM, and used to treat the previously seeded WM-266-4 cells for 1-2 hours at 37° C. Cells were washed with ice-cold PBS, treated with 45 µl of lysis buffer (Bio-Rad Bio-Plex Lysis Buffer, Cat #171-304011, containing 0.4% v/v lysis buffer factor 1, 0.2% v/v lysis buffer Factor 2, and 2 mM PMSF) for 15 minutes on an orbital shaker at room temperature. Phosphorylated ERK was detected using a phospho-ERK Bioplex kit (Bio-Rad, Cat #171-304011) per the manufacturer's instructions and detected on a Bio-Plex plate reader counting 50 beads per region.

Certain compounds of the present invention were assayed using the above cellular assays and were found to be inhibitors of Raf kinase.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula II-vi-a:

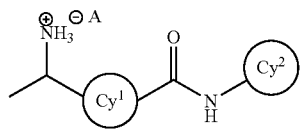

II-vi-a wherein:
A⁻ is a chiral anion of a chiral acid selected from the group consisting of camphorsulfonic acid (−), tartaric acid (+), malic acid (−), N-acetyl-L-leucine (−), ditoluoyl-L-tartaric acid (−), deoxycholic acid (+), quinic acid (−), camphoric acid (+), tert-butoxycarbonyl-alanine (−), tartaric acid (−), ditoluoyl-D-tartaric acid (+), camphorsulfonic acid (+), dibenzoyl-D-tartaric acid (+), L-citramalic (+), 5-acetyl mandelic acid (+), tert-butoxycarbonyl-isoleucine (+), (S)-mandelic acid, and (R)-mandelic acid;
Cy¹ is

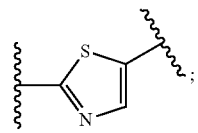 [SMILES: *c1cnc(*)s1]

and
Cy² is an unsubstituted or substituted 5-10 membered saturated, partially unsaturated, or aromatic monocyclic or bicyclic ring having 0-4 heteroatoms, independently selected from the group consisting of nitrogen, oxygen, and sulfur, wherein the substituents are selected from the group consisting of Cl, F, CF₃ and C₁₋₄ alkyl.

2. The compound of claim 1, wherein the chiral acid is (S)-mandelic acid or (R)-mandelic acid mandelic acid.

3. The compound of claim 2, wherein the chiral acid is (S)-mandelic acid.

4. The compound of claim 1, wherein the chiral acid is ditoluoyl-D-tartaric acid (+).

5. The compound of claim 1, wherein the chiral acid is ditoluoyl-L-tartaric acid (−).

6. The compound of claim 1, wherein Cy² is an unsubstituted or substituted 6 membered aromatic ring having 1-2 heteroatoms independently selected from the group consisting of nitrogen, oxygen, and sulfur, wherein the substituents are selected from the group consisting of Cl, F, CF₃, and C₁₋₄ alkyl.

7. The compound of claim 1, wherein Cy² is an unsubstituted or substituted pyridinyl, wherein the substituents are selected from the group consisting of Cl, F, CF₃, and C₁₋₄ alkyl.

8. The compound of claim 1, wherein the compound is

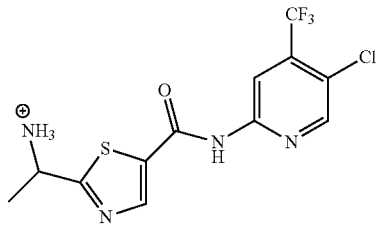

-continued

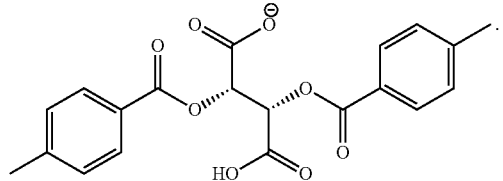

9. The compound of claim 3, wherein the compound is

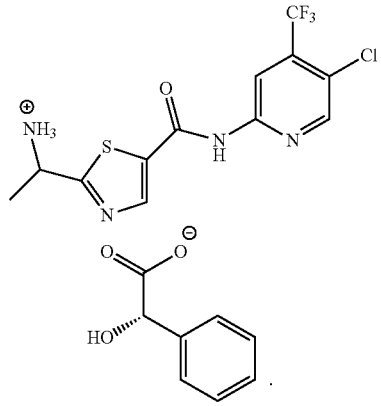 [SMILES: CC([NH3+])c1ncc(C(=O)Nc2cc(C(F)(F)F)c(Cl)cn2)s1 ; O=C([O-])[C@@H](O)c1ccccc1]

10. A compound of formula II-vi-b:

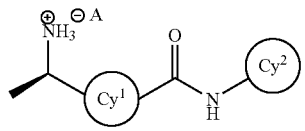

II-vi-b wherein:
A⁻ is a chiral anion of a chiral acid selected from the group consisting of camphorsulfonic acid (−), tartaric acid (+), malic acid (−), N-acetyl-L-leucine (−), ditoluoyl-L-tartaric acid (−), deoxycholic acid (+), quinic acid (−), camphoric acid (+), tert-butoxycarbonyl-alanine (−), tartaric acid (−), ditoluoyl-D-tartaric acid (+), camphorsulfonic acid (+), dibenzoyl-D-tartaric acid (+), L-citramalic (+), 5-acetyl mandelic acid (+); and tert-butoxycarbonyl-isoleucine (+), (S)-mandelic acid, and (R)-mandelic acid;
Cy¹ is

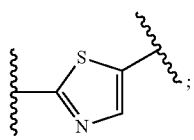 [SMILES: *c1cnc(*)s1]

and
Cy² is an unsubstituted or substituted 5-10 membered saturated, partially unsaturated, or aromatic monocyclic or bicyclic ring having 0-4 heteroatoms, independently selected from the group consisting of nitrogen, oxygen, and sulfur, wherein the substituents are selected from the group consisting of Cl, F, CF₃ and C₁₋₄ alkyl.

11. The compound of claim 10, wherein the chiral acid is (S)-mandelic acid or (R)-mandelic acid mandelic acid.

12. The compound of claim 11, wherein the chiral acid is (S)-mandelic acid.

13. The compound of claim 10, wherein the chiral acid is ditoluoyl-D-tartaric acid (+).

14. The compound of claim 10, wherein the chiral acid is ditoluoyl-L-tartaric acid (−).

15. The compound of claim 10, wherein the compound is:

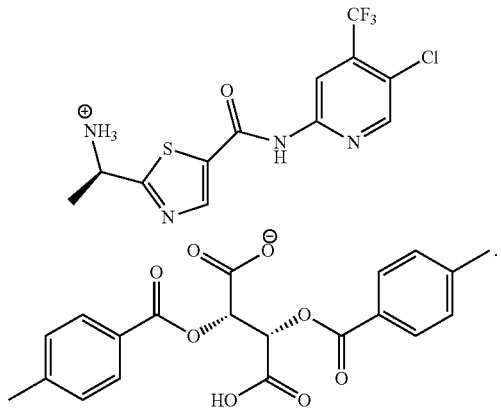

16. The compound of claim 12, wherein the compound is

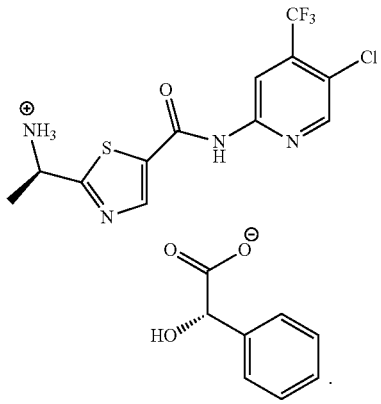 [SMILES: C[C@@H]([NH3+])c1ncc(C(=O)Nc2cc(C(F)(F)F)c(Cl)cn2)s1 ; O=C([O-])[C@@H](O)c1ccccc1]

17. A compound of formula II-iv:

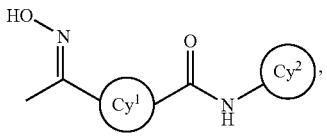

wherein

Cy¹ is

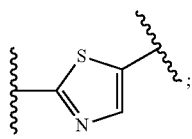 [SMILES: *c1cnc(*)s1]

and

Cy² is an unsubstituted or substituted 5-10 membered saturated, partially unsaturated, or aromatic monocyclic or bicyclic ring having 0-4 heteroatoms, independently selected from the group consisting of nitrogen, oxygen, and sulfur, wherein the substituents are selected from the group consisting of Cl, F, $CF_3$ and $C_{1-4}$ alkyl.

18. The compound of claim 17, wherein Cy² is an unsubstituted or substituted 6 membered aromatic ring having 1-2 heteroatoms independently selected from the group consisting of nitrogen, oxygen, and sulfur, wherein the substituents are selected from the group consisting of Cl, F, $CF_3$, and $C_{1-4}$ alkyl.

* * * * *

UNITED STATES PATENT AND TRADEMARK OFFICE
CERTIFICATE OF CORRECTION

PATENT NO.        : 9,556,177 B2
APPLICATION NO.   : 14/444007
DATED             : January 31, 2017
INVENTOR(S)       : Chen et al.

Page 1 of 9

It is certified that error appears in the above-identified patent and that said Letters Patent is hereby corrected as shown below:

At Column 82, 3rd structure:

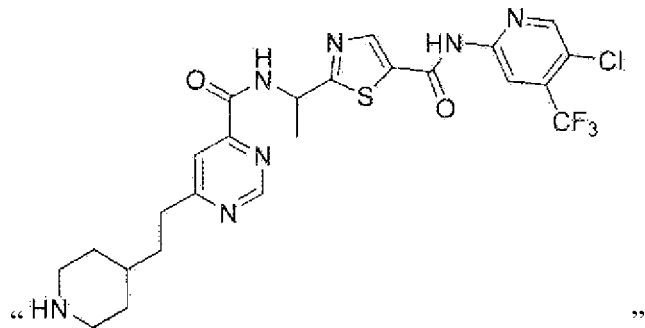

Should be deleted and replaced with the following:

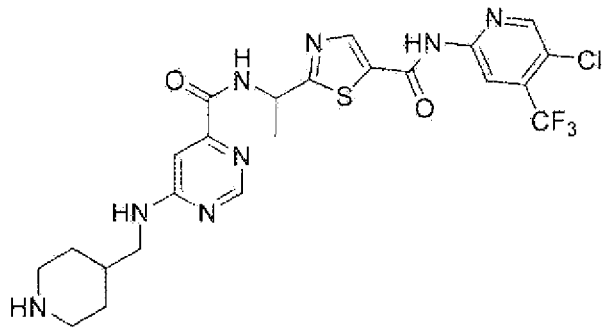

Signed and Sealed this
Twelfth Day of September, 2017

Joseph Matal
*Performing the Functions and Duties of the
Under Secretary of Commerce for Intellectual Property and
Director of the United States Patent and Trademark Office*

At Column 88, 1st structure:
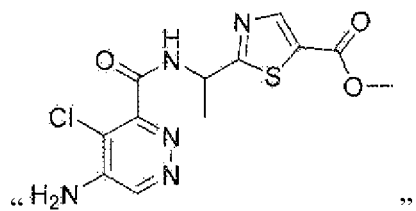
Should be deleted and replaced with the following:
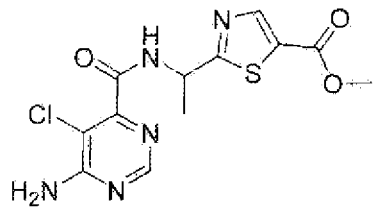
At Column 127, 5th structure:
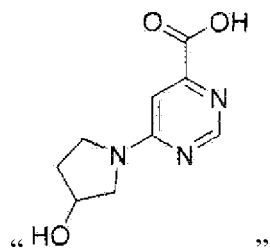
Should be deleted and replaced with the following:
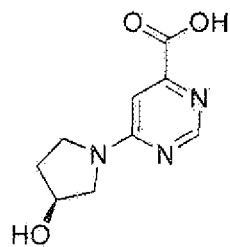
At Column 195, 8th structure:
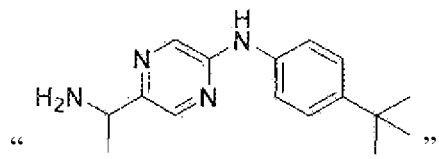
Should be deleted and replaced with the following:
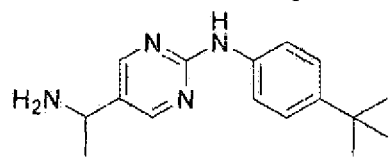

At Column 197, 6th structure:
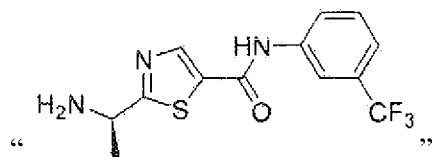
" "
Should be deleted and replaced with the following:
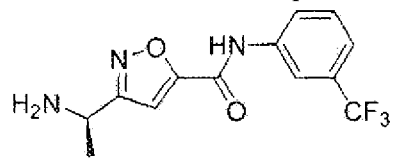
At Column 234, 6th entry, "[M + 1 r" should read -- [M + 1]$^+$ --
At Column 249, 1st structure:
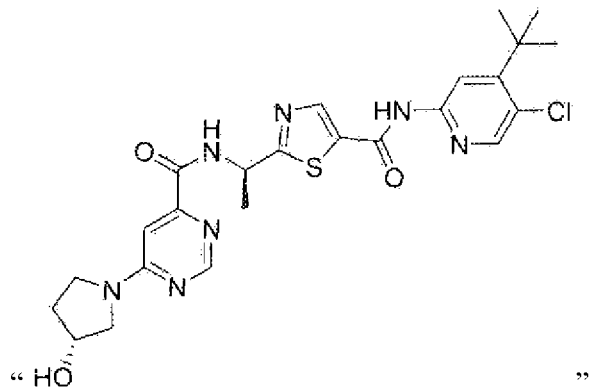
" "
Should be deleted and replaced with the following:
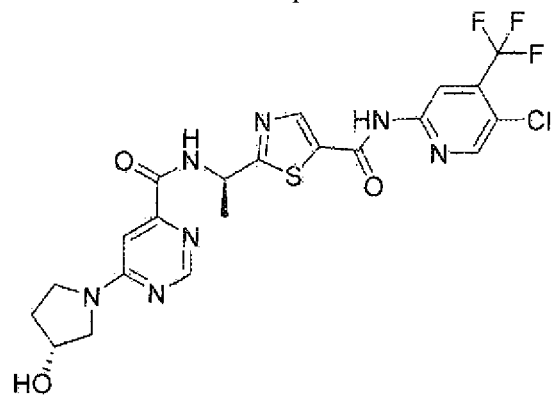

At Column 259, 3rd structure:
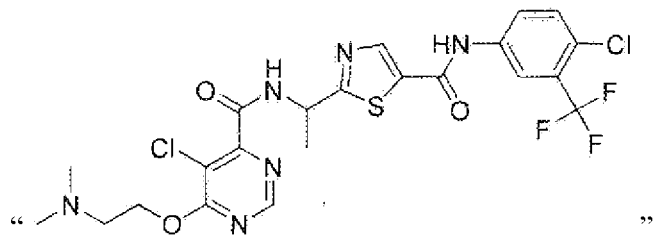
Should be deleted and replaced with the following:
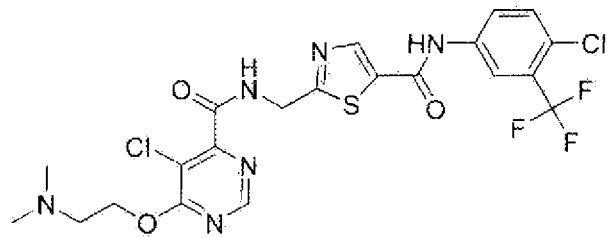
At Column 261, 3rd structure:
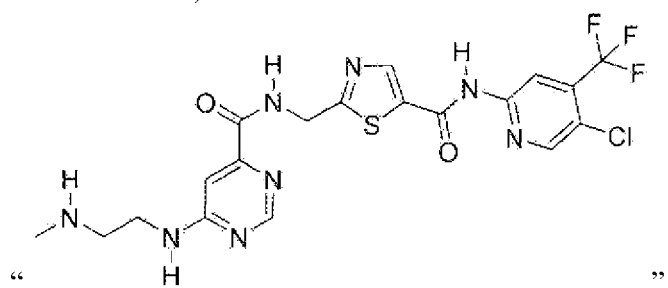
Should be deleted and replaced with the following:
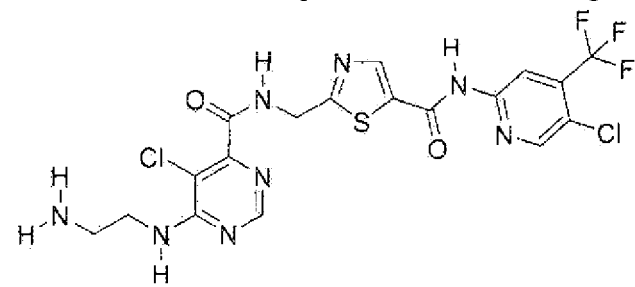

At Column 281, 3rd structure:
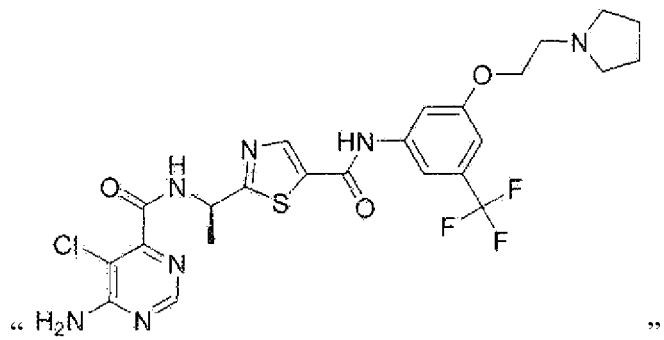
"
"
Should be deleted and replaced with the following:
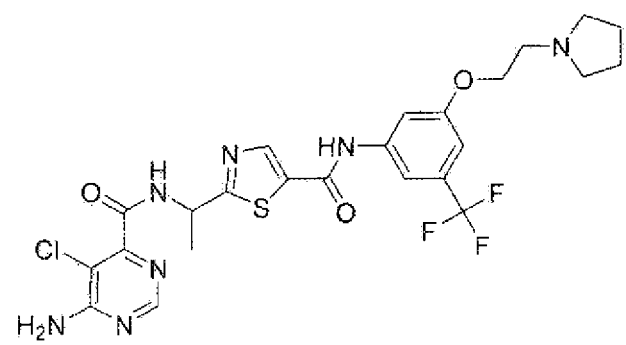
At Column 285, 4th structure:
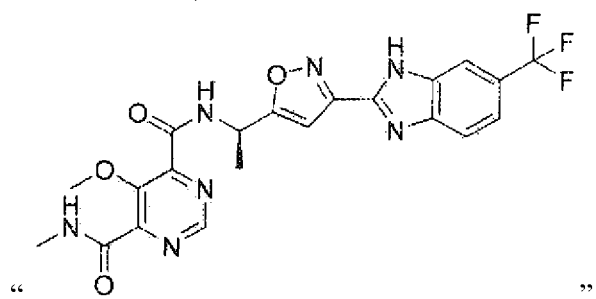
"
"
Should be deleted and replaced with the following:
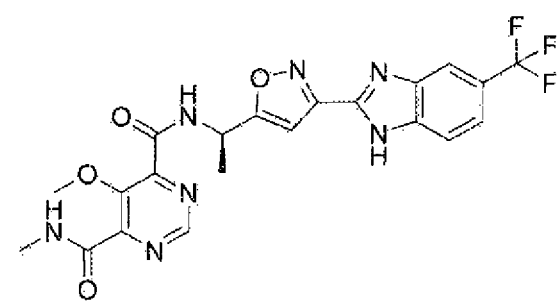

At Column 287, 3rd structure:
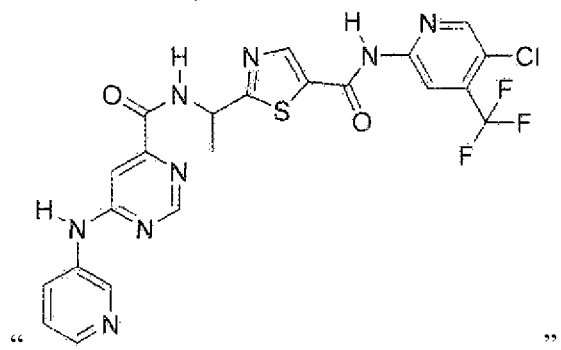
" "
Should be deleted and replaced with the following:
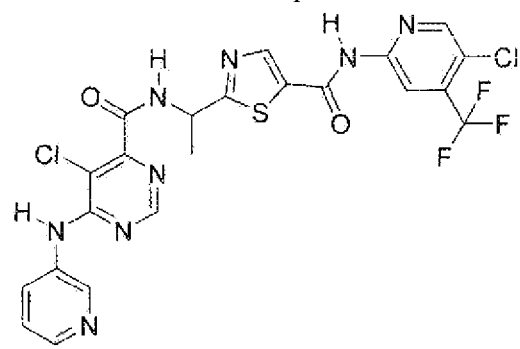
At Column 291, 1st structure:
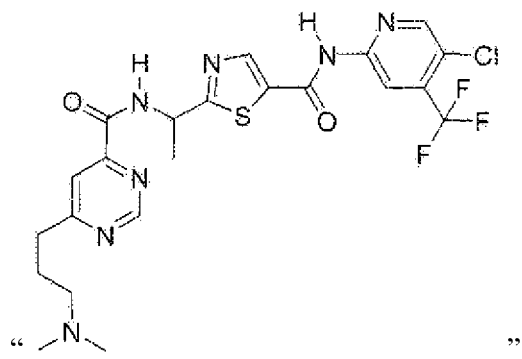
" "
Should be deleted and replaced with the following:
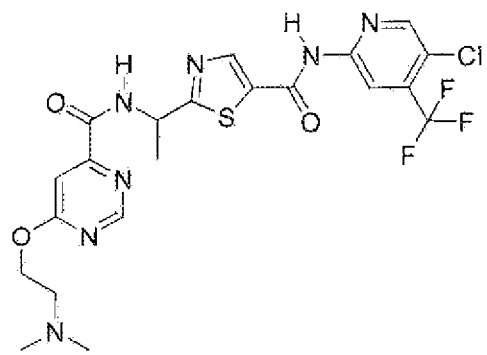

At Column 341, 1st structure:
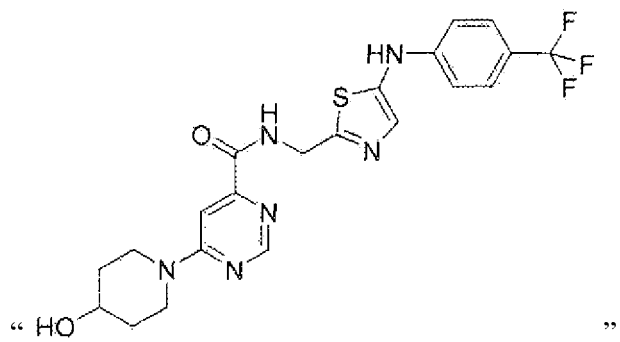
" " 
Should be deleted and replaced with the following:
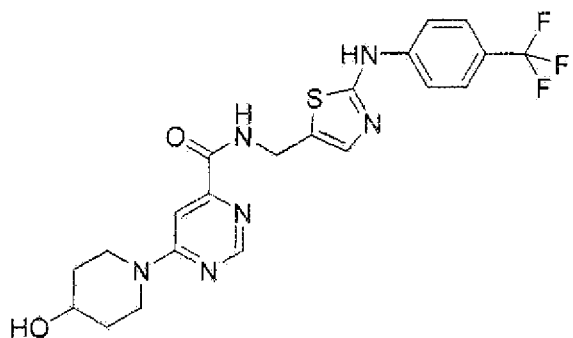
At Column 341, 2nd structure:
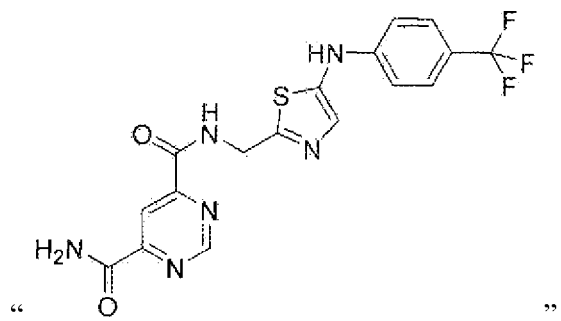
" "
Should be deleted and replaced with the following:
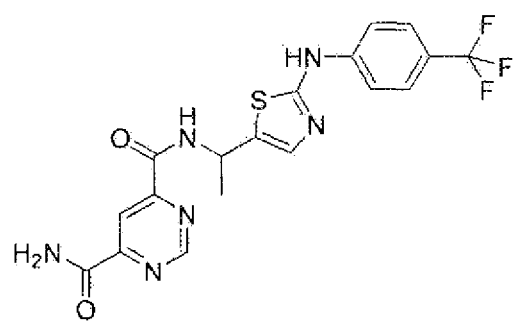

CERTIFICATE OF CORRECTION (continued)
U.S. Pat. No. 9,556,177 B2

At Column 343, 4th structure:

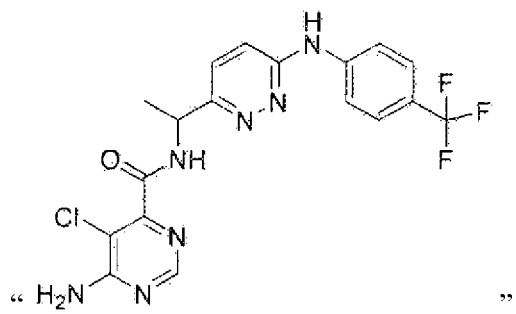

Should be deleted and replaced with the following:

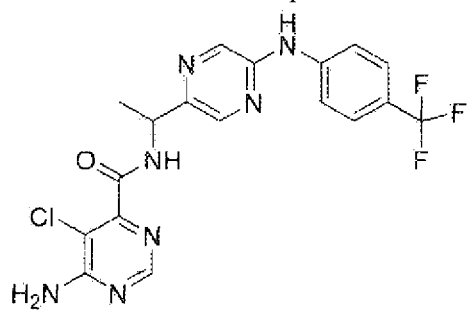

At Column 449, 1st structure:

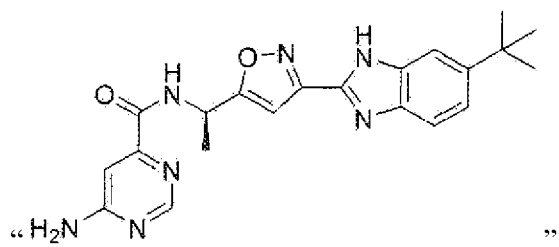

Should be deleted and replaced with the following:

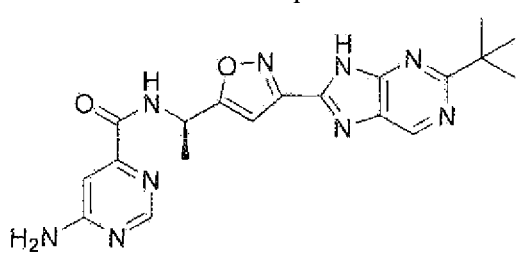

At Column 485, 3rd structure:

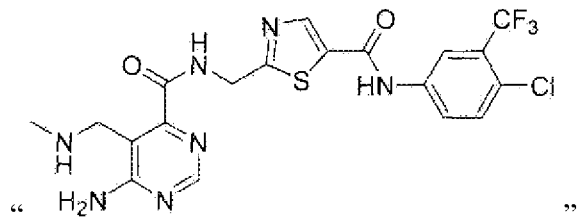

" "

Should be deleted and replaced with the following:

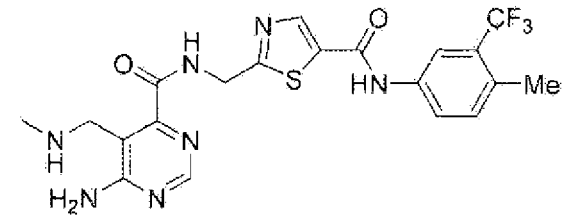

At Column 493, 3rd structure:

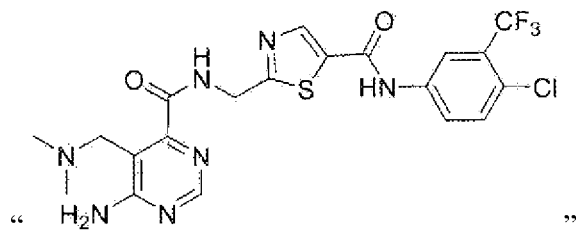

" "

Should be deleted and replaced with the following:

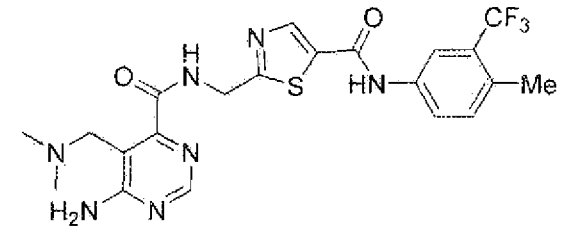

In Claim 1, at Column 543, Line 18, "5-acetyl mandelic acid (+)" should read -- S-acetyl mandelic acid (+) --

In Claim 2, at Column 543, Line 39, "(R)-mandelic acid mandelic acid." should read -- (R)-mandelic acid. --

In Claim 10, at Column 544, Line 44, "5-acetyl mandelic acid (+)" should read -- S-acetyl mandelic acid (+) --

In Claim 11, at Column 544, Line 65, "(R)-mandelic acid mandelic acid." should read -- (R)-mandelic acid. --